US010069086B2

(12) United States Patent
Kim et al.

(10) Patent No.: US 10,069,086 B2
(45) Date of Patent: Sep. 4, 2018

(54) PLURALITY OF HOST MATERIALS AND AN ORGANIC ELECTROLUMINESCENCE DEVICE COMPRISING THE SAME

(71) Applicant: Rohm and Haas Electronic Materials Korea Ltd., Cheonan (KR)

(72) Inventors: Bitnari Kim, Cheonan (KR); Nam-Kyun Kim, Yongin (KR); Hong-Yeop Na, Seoul (KR); Tae-Jin Lee, Seoul (KR); Kyung-Hoon Choi, Hwaseong (KR); Jae-Hoon Shim, Seoul (KR); Young-Jun Cho, Seongnam (KR); Hee-Ryong Kang, Seoul (KR); Young-Mook Lim, Cheonan (KR); Hyun-Ju Kang, Gwangmyeong (KR); Doo-Hyeon Moon, Hwaseong (KR); Ji-Song Jun, Hwaseong (KR); Hee-Choon Ahn, Seoul (KR); Young-Kwang Kim, Hwaseong (KR); Jin-Ri Hong, Cheonan (KR)

(73) Assignee: ROHM AND HAAS ELECTRONIC MATERIALS KOREA LTD., Cheonan (KR)

( * ) Notice: Subject to any disclaimer, the term of this patent is extended or adjusted under 35 U.S.C. 154(b) by 0 days.

(21) Appl. No.: 15/503,742

(22) PCT Filed: Aug. 20, 2015

(86) PCT No.: PCT/KR2015/008727
§ 371 (c)(1),
(2) Date: Feb. 14, 2017

(87) PCT Pub. No.: WO2016/028110
PCT Pub. Date: Feb. 25, 2016

(65) Prior Publication Data

US 2017/0279056 A1 Sep. 28, 2017

(30) Foreign Application Priority Data

Aug. 20, 2014 (KR) ........................ 10-2014-0108415
Jan. 9, 2015 (KR) ........................ 10-2015-0003430
Aug. 19, 2015 (KR) ........................ 10-2015-0116757

(51) Int. Cl.

| | |
|---|---|
| ***H01L 51/00*** | (2006.01) |
| ***C09K 11/06*** | (2006.01) |
| *H01L 51/50* | (2006.01) |
| *H01L 51/56* | (2006.01) |

(52) U.S. Cl.
CPC .......... *H01L 51/0072* (2013.01); *C09K 11/06* (2013.01); *H01L 51/0058* (2013.01); *H01L 51/0061* (2013.01); *H01L 51/0067* (2013.01); *H01L 51/0077* (2013.01); *C09K 2211/1029* (2013.01); *C09K 2211/181* (2013.01); *H01L 51/001* (2013.01); *H01L 51/0052* (2013.01); *H01L 51/5016* (2013.01); *H01L 51/5064* (2013.01); *H01L 51/5072* (2013.01); *H01L 51/5088* (2013.01); *H01L 51/5092* (2013.01); *H01L 51/56* (2013.01); *H01L 2251/5384* (2013.01); *H01L 2251/558* (2013.01)

(58) Field of Classification Search
CPC ............. H01L 51/0072; H01L 51/0058; H01L 51/0061; H01L 51/0077; C09K 11/06
See application file for complete search history.

(56) References Cited

U.S. PATENT DOCUMENTS

2013/0234119 A1* 9/2013 Mizuki ............... H01L 51/0072
257/40
2014/0100367 A1* 4/2014 Yoon .................... C07D 401/14
544/229
2014/0306207 A1 10/2014 Nishimura et al.

FOREIGN PATENT DOCUMENTS

KR 2008-0080306 A 9/2008
WO 2013/112557 A1 8/2013
WO 2015/093814 A1 6/2015

* cited by examiner

*Primary Examiner* — Nicholas Tobergte
(74) *Attorney, Agent, or Firm* — S. Matthew Cairns

(57) ABSTRACT

The present invention relates to a plurality of host materials and an organic electroluminescent device comprising the same. By comprising a specific combination of a plurality of host compounds, the organic electroluminescent device according to the present invention provides excellent lifespan characteristics while maintaining high luminous efficiency.

7 Claims, No Drawings

PLURALITY OF HOST MATERIALS AND AN ORGANIC ELECTROLUMINESCENCE DEVICE COMPRISING THE SAME

TECHNICAL FIELD

The present invention relates to a plurality of host materials and an organic electroluminescence device comprising the same.

BACKGROUND ART

An electroluminescence device (EL device) is a self-light-emitting device which has advantages in that it provides a wider viewing angle, a greater contrast ratio, and a faster response time. The first organic EL device was developed by Eastman Kodak, by using small aromatic diamine molecules, and aluminum complexes as materials for forming a light-emitting layer [Appl. Phys. Lett. 51, 913, 1987].

An organic EL device (OLED) is a device changing electrical energy to light by applying electricity to an organic electroluminescent material, and generally has a structure comprising an anode, a cathode, and an organic layer between the anode and the cathode. The organic layer of an organic EL device may be comprised of a hole injection layer, a hole transport layer, an electron blocking layer, a light-emitting layer (which comprises host and dopant materials), an electron buffer layer, a hole blocking layer, an electron transport layer, an electron injection layer, etc., and the materials used for the organic layer are categorized by their functions in hole injection material, hole transport material, electron blocking material, light-emitting material, electron buffer material, hole blocking material, electron transport material, electron injection material, etc. In the organic EL device, due to an application of a voltage, holes are injected from the anode to the light-emitting layer, electrons are injected from the cathode to the light-emitting layer, and excitons of high energies are formed by a recombination of the holes and the electrons. By this energy, luminescent organic compounds reach an excited state, and light emission occurs by emitting light from energy due to the excited state of the luminescent organic compounds returning to a ground state.

The most important factor determining luminous efficiency in an organic EL device is light-emitting materials. A light-emitting material must have high quantum efficiency, high electron and hole mobility, and the formed light-emitting material layer must be uniform and stable. Light-emitting materials are categorized into blue, green, and red light-emitting materials dependent on the color of the light emission, and additionally yellow or orange light-emitting materials. In addition, light-emitting materials can also be categorized into host and dopant materials according to their functions. Recently, the development of an organic EL device providing high efficiency and long lifespan is an urgent issue. In particular, considering EL characteristic requirements for a middle or large-sized panel of OLED, materials showing better characteristics than conventional ones must be urgently developed. The host material, which acts as a solvent in a solid state and transfers energy, needs to have high purity and a molecular weight appropriate for vacuum deposition. Furthermore, the host material needs to have high glass transition temperature and high thermal degradation temperature to achieve thermal stability, high electro-chemical stability to achieve a long lifespan, ease of forming an amorphous thin film, good adhesion to materials of adjacent layers, and non-migration to other layers.

A light-emitting material can be used as a combination of a host and a dopant to improve color purity, luminous efficiency, and stability. Generally, an EL device having excellent characteristics has a structure comprising a light-emitting layer formed by doping a dopant to a host. Since host materials greatly influence the efficiency and lifespan of the EL device when using a dopant/host material system as a light-emitting material, their selection is important.

Korean Patent Appln. Laid-Open No. 10-2008-0080306 discloses an organic electroluminescent device using a compound wherein two carbazoles are linked via an arylene as a host material, and International Publication No. WO 2013/112557 A1 discloses an organic electroluminescent device using a compound wherein a biscarbazole is linked to a carbazole directly or via an arylene as a host material. However, the references fail to disclose an organic electroluminescent device using a compound wherein a biscarbazole compound comprising an aryl and a compound wherein a dibenzocarbazole is linked to a nitrogen-containing heteroaryl directly or via an arylene as plural host materials.

DISCLOSURE OF THE INVENTION

Problems to be Solved

The objective of the present invention is to provide an organic electroluminescent device having a long lifespan while maintaining high luminous efficiency.

Solution to Problems

The present inventors found that the above objective can be achieved by an organic electroluminescent device comprising at least one light-emitting layer between an anode and a cathode, wherein the light-emitting layer comprises a host and a phosphorescent dopant, the host comprises plural host compounds, at least a first host compound of the plural host compounds is represented by the following formula 1, and a second host compound is represented by the following formula 2:

(1)

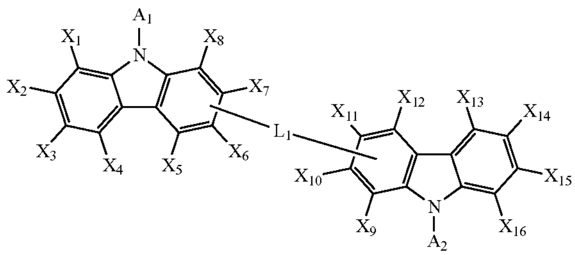

wherein $A_1$ and $A_2$ each independently represent a substituted or unsubstituted (C6-C30)aryl, provided that the substituents of $A_1$ and $A_2$ are not nitrogen-containing heteroaryls;

$L_1$ represents a single bond, or a substituted or unsubstituted (C6-C30)arylene;

$X_1$ to $X_{16}$ each independently represent hydrogen, deuterium, a halogen, a cyano, a substituted or unsubstituted (C1-C30)alkyl, a substituted or unsubstituted (C2-C30) alkenyl, a substituted or unsubstituted (C2-C30)alkynyl, a substituted or unsubstituted (C3-C30)cycloalkyl, a substituted or unsubstituted (C6-C60)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted mono- or di-(C6-C30)arylamino; or are linked to an adjacent substituent(s) to form a substituted or unsubstituted, mono- or polycyclic, (C3-C30) alicyclic or aromatic ring, whose carbon atom(s) may be replaced with at least one hetero atom selected from nitrogen, oxygen, and sulfur;

(2)

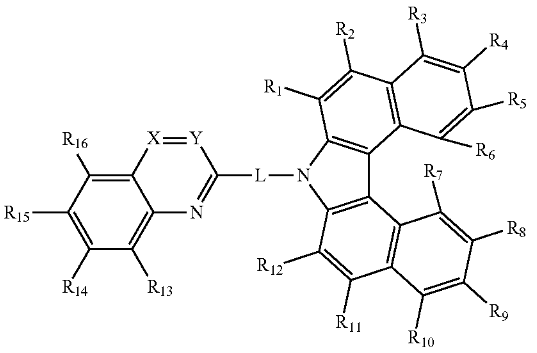

wherein

L represents a single bond, or a substituted or unsubstituted (C6-C30)arylene;

X and Y each independently represent N or $CR_{17}$;

$R_1$ to $R_{17}$ each independently represent hydrogen, deuterium, a substituted or unsubstituted (C3-C30)cycloalkyl, a substituted or unsubstituted (C6-C30)aryl, a substituted or unsubstituted 3- to 30-membered heteroaryl, a substituted or unsubstituted mono- or di-(C6-C30)arylamino, a substituted or unsubstituted (C1-C30)alkyl(C6-C30)arylamino, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, or a substituted or unsubstituted (C1-C30)alkyldi(C6-C30)arylsilyl; or are linked to an adjacent substituent(s) to form a substituted or unsubstituted, mono- or polycyclic, (C3-C30) alicyclic or aromatic ring, whose carbon atom(s) may be replaced with at least one hetero atom selected from nitrogen, oxygen, and sulfur; and the heteroaryl contains at least one hetero atom selected from B, N, O, S, Si, and P.

Effects of the Invention

According to the present invention, an organic electroluminescent device having high efficiency and long lifespan is provided, and a display device or a lighting device using the organic electroluminescent device can be manufactured.

EMBODIMENTS OF THE INVENTION

Hereinafter, the present invention will be described in detail. However, the following description is intended to explain the invention, and is not meant in any way to restrict the scope of the invention.

Hereinafter, the organic electroluminescent device comprising the organic electroluminescent compounds of formulas 1 and 2 will be described in detail.

The compound represented by formula 1 can be represented by formula 3, 4, 5, or 6:

(3)

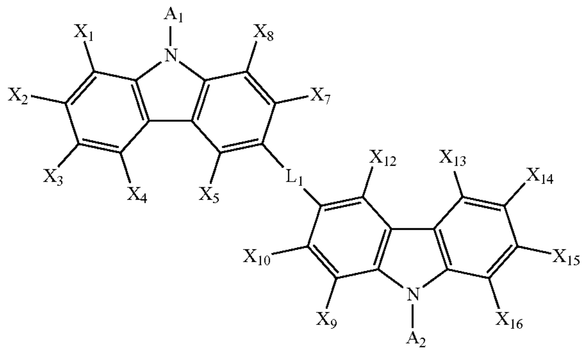

(4)

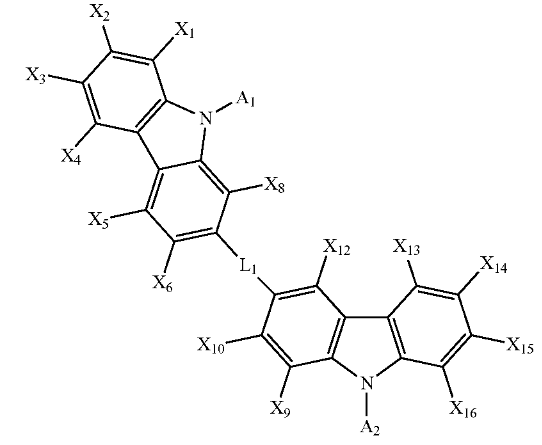

(5)

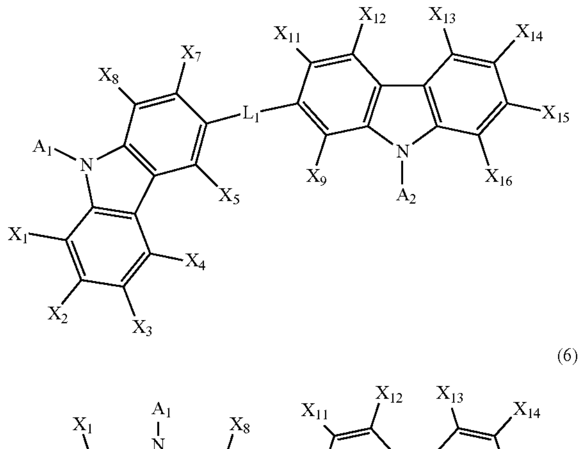

(6)

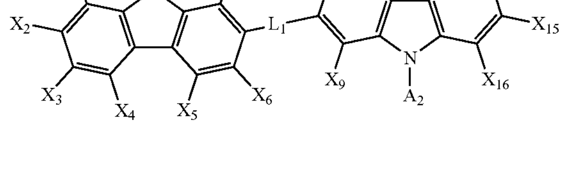

wherein $A_1$, $A_2$, $L_1$, and $X_1$ to $X_{16}$ are as defined in formula 1.

In formula 1 above, $A_1$ and $A_2$ each independently represent a substituted or unsubstituted (C6-C30)aryl, preferably each independently represent a substituted or unsubstituted (C6-C18)aryl, and more preferably each independently represent a (C6-C18)aryl unsubstituted or substituted with a cyano, a halogen, a (C1-C6)alkyl, a (C6-C12)aryl, or a tri(C6-C12)arylsilyl. Specifically, $A_1$ and $A_2$ each independently may be selected from a group consisting of a substituted or unsubstituted phenyl, a substituted or unsubstituted biphenyl, a substituted or unsubstituted terphenyl, a substituted or unsubstituted naphthyl, a substituted or unsubstituted fluorenyl, a substituted or unsubstituted benzofluorenyl, a substituted or unsubstituted phenanthrenyl, a substituted or unsubstituted anthracenyl, a substituted or unsubstituted indenyl, a substituted or unsubstituted triphenylenyl, a substituted or unsubstituted pyrenyl, a substituted or unsubstituted tetracenyl, a substituted or unsubstituted perylenyl, a substituted or unsubstituted chrysenyl, a substituted or unsubstituted phenylnaphthyl, a substituted or unsubstituted naphthylphenyl, and a substituted or unsubstituted fluoranthenyl. Herein, the substituent of the substituted phenyl, etc. may be a cyano, a halogen, a (C1-C6)alkyl, a (C6-C12)aryl, or a tri(C6-C12)arylsilyl.

In formula 1 above, $X_1$ to $X_{16}$ each independently represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted mono- or di-(C6-C30)arylamino; or are linked to an adjacent substituent(s) to form a substituted or unsubstituted, mono- or polycyclic, (C3-C30) alicyclic or aromatic ring, whose carbon atom(s) may be replaced with at least one hetero atom selected from nitrogen, oxygen, and sulfur, preferably each independently represent hydrogen, a cyano, a substituted or unsubstituted (C1-C10)alkyl, a substituted or unsubstituted (C6-C20)aryl, a substituted or unsubstituted 5- to 20-membered heteroaryl, or a substituted or unsubstituted tri(C6-C12)arylsilyl, and more preferably each independently represent hydrogen; a cyano; a (C1-C10)alkyl; a (C6-C20)aryl unsubstituted or substituted with a cyano, a (C1-C10)alkyl, or a tri(C6-C12) arylsilyl; a 5- to 20-membered heteroaryl unsubstituted or substituted with a (C1-C10)alkyl, a (C6-C15)aryl, or a tri(C6-C12)arylsilyl; or a tri(C6-C12)arylsilyl unsubstituted or substituted with a (C1-C10)alkyl. Specifically, $X_1$ to $X_{16}$ may each independently represent hydrogen; a cyano; a (C1-C6)alkyl; a phenyl, a biphenyl, a terphenyl, or a naphthyl, unsubstituted or substituted with a cyano, a (C1-C6) alkyl, or a triphenylsilyl; a dibenzothiophene or a dibenzofuran, unsubstituted or substituted with a (C1-C6)alkyl, a phenyl, a biphenyl, a naphthyl, or a triphenylsilyl; or a triphenylsilyl unsubstituted or substituted with a (C1-C6) alkyl.

In formula 1 above, $L_1$ represents a single bond, or a substituted or unsubstituted (C6-C30)arylene, preferably represents a single bond, or a substituted or unsubstituted (C6-C15)arylene, and more preferably represents a single bond; or a (C6-C15)arylene unsubstituted or substituted with a cyano, a (C1-C6)alkyl, or a tri(C6-C12)arylsilyl.

In addition, $L_1$ can be represented by one of the following formulas 7 to 19:

(7)

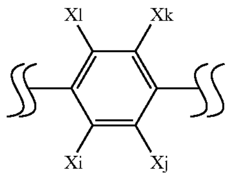

(8)

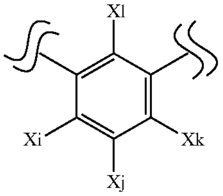

(9)

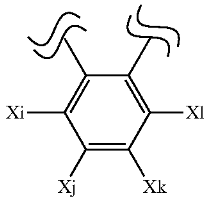

(10)

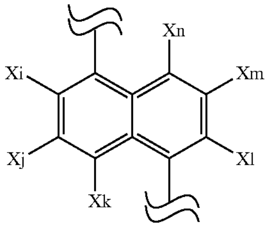

(11)

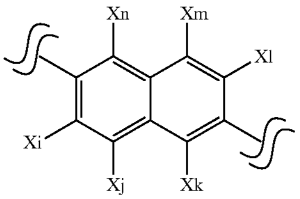

(12)

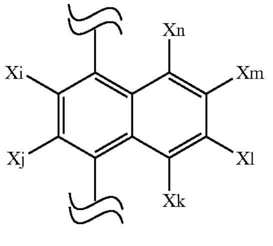

(13)

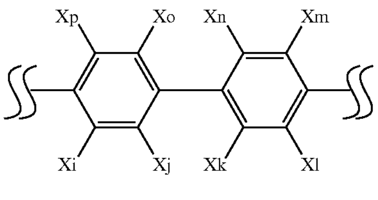

-continued (14)

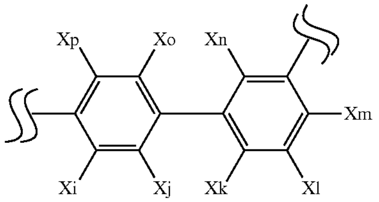

(15)

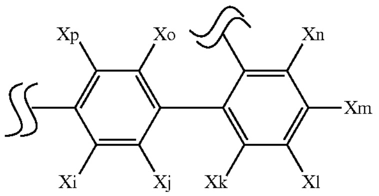

(16)

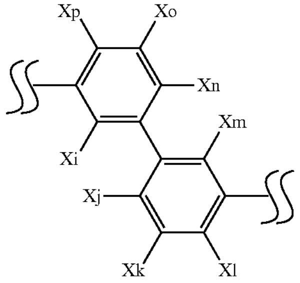

(17)

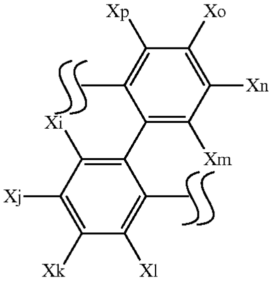

(18)

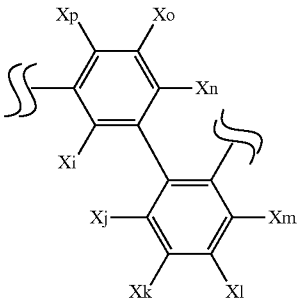

(19)

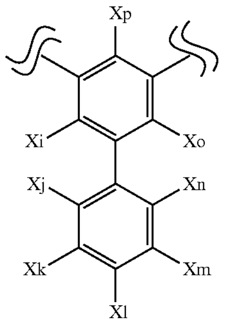

wherein

Xi to Xp each independently represent hydrogen, deuterium, a halogen, a cyano, a substituted or unsubstituted (C1-C30)alkyl, a substituted or unsubstituted (C2-C30) alkenyl, a substituted or unsubstituted (C2-C30)alkynyl, a substituted or unsubstituted (C3-C30)cycloalkyl, a substituted or unsubstituted (C6-C60)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi (C6-C30)arylsilyl, or a substituted or unsubstituted mono- or di-(C6-C30)arylamino; or are linked to an adjacent substituent(s) to form a substituted or unsubstituted, mono- or polycyclic, (C3-C30) alicyclic or aromatic ring, whose carbon atom(s) may be replaced with at least one hetero atom selected from nitrogen, oxygen, and sulfur.

Preferably, Xi to Xp may each independently represent hydrogen, a halogen, a cyano, a (C1-C10)alkyl, a (C3-C20) cycloalkyl, a (C6-C12)aryl, a (C1-C6)alkyldi(C6-C12)arylsilyl, or a tri(C6-C12)arylsilyl, and more preferably, each independently represent hydrogen, a cyano, a (C1-C6)alkyl, or a tri(C6-C12)arylsilyl.

The compound represented by formula 2 can be represented by formula 20 or 21:

(20)

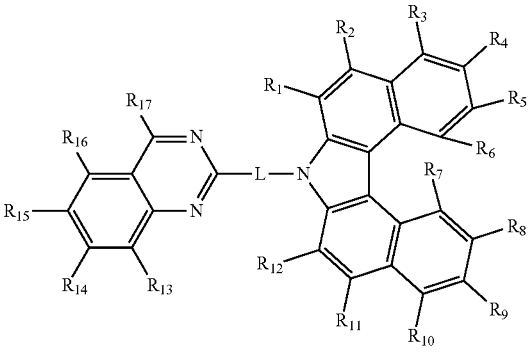

(21)

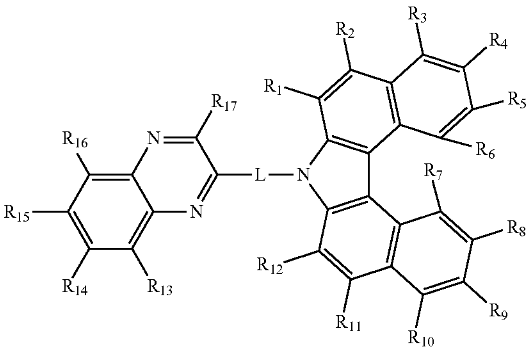

wherein

L and $R_1$ to $R_{17}$ are as defined in formula 2.

In formula 2 above, L represents a single bond, or a substituted or unsubstituted (C6-C30)arylene, preferably represents a single bond, or a substituted or unsubstituted (C6-C15)arylene, and more preferably represents a single bond, or an unsubstituted (C6-C15)arylene.

In formula 2 above, X and Y each independently represent N or $CR_{17}$.

In formula 2 above, $R_1$ to $R_{17}$ each independently represent hydrogen, deuterium, a substituted or unsubstituted (C3-C30)cycloalkyl, a substituted or unsubstituted (C6-C30)aryl, a substituted or unsubstituted 3- to 30-membered heteroaryl, a substituted or unsubstituted mono- or di-(C6-C30)arylamino, a substituted or unsubstituted (C1-C30) alkyl(C6-C30)arylamino, a substituted or unsubstituted tri (C1-C30)alkylsilyl, a substituted or unsubstituted tri(C6-C30)arylsilyl, a substituted or unsubstituted di(C1-C30) alkyl(C6-C30)arylsilyl, or a substituted or unsubstituted (C1-C30)alkyldi(C6-C30)arylsilyl; or are linked to an adjacent substituent(s) to form a substituted or unsubstituted, mono- or polycyclic, (C3-C30) alicyclic or aromatic ring, whose carbon atom(s) may be replaced with at least one hetero atom selected from nitrogen, oxygen, and sulfur.

Preferably, $R_1$ to $R_{12}$ each independently represent hydrogen, a substituted or unsubstituted (C6-C15)aryl, or a substituted or unsubstituted 5- to 15-membered heteroaryl; or are linked to an adjacent substituent(s) to form a substituted or unsubstituted, mono- or polycyclic, (C6-C15) aromatic ring, whose carbon atom(s) may be replaced with at least one hetero atom selected from nitrogen, oxygen, and sulfur. More preferably, $R_1$ to $R_{12}$ each independently represent hydrogen, an unsubstituted (C6-C15)aryl, or a 5- to 15-membered heteroaryl unsubstituted or substituted with a (C6-C12)aryl; or are linked to an adjacent substituent(s) to form a benzofuran, a benzothiophene, or an indole substituted with a phenyl.

Preferably, $R_{13}$ to $R_{16}$ each independently represent hydrogen, a substituted or unsubstituted (C6-C15)aryl, or a substituted or unsubstituted 5- to 15-membered heteroaryl. More preferably, $R_{13}$ to $R_{16}$ each independently represent hydrogen, an unsubstituted (C6-C15)aryl, or an unsubstituted 5- to 15-membered heteroaryl.

Preferably, $R_{17}$ represents a substituted or unsubstituted (C6-C25)aryl, or a substituted or unsubstituted 5- to 15-membered heteroaryl. More preferably, $R_{17}$ represents a (C6-C25)aryl unsubstituted or substituted with a (C6-C20) aryl, or a 5- to 15-membered heteroaryl unsubstituted or substituted with a (C6-C12)aryl.

Herein, "(C1-C30)alkyl" is meant to be a linear or branched alkyl having 1 to 30 carbon atoms consisting the chain, in which the number of carbon atoms is preferably 1 to 20, more preferably 1 to 10, and includes methyl, ethyl, n-propyl, isopropyl, n-butyl, isobutyl, tert-butyl, etc.; "(C2-C30)alkenyl" is meant to be a linear or branched alkenyl having 2 to 30 carbon atoms consisting the chain, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc.; "(C2-C30)alkynyl" is meant to be a linear or branched alkynyl having 2 to 30 carbon atoms consisting the chain, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc.; "(C3-C30)cycloalkyl" is a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc.; "3- to 7-membered heterocycloalkyl" is a cycloalkyl having 3 to 7 ring backbone atoms, preferably 5 to 7, including at least one heteroatom selected from B, N, O, S, Si, and P, preferably O, S, and N, and includes tetrahydrofuran, pyrrolidine, thiolan, tetrahydropyran, etc.; "(C6-C30)aryl(ene)" is a monocyclic or fused ring derived from an aromatic hydrocarbon having 6 to 30 ring backbone carbon atoms, in which the number of carbon atoms is preferably 6 to 20, more preferably 6 to 15, and includes phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, etc.; "3- to 30-membered heteroaryl" is an aryl having 3 to 30 ring backbone atoms, including at least one, preferably 1 to 4 heteroatoms selected from the group consisting of B, N, O, S, Si, and P; is a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, etc.; "nitrogen-containing 5- to 30-membered heteroaryl" is an aryl having 5 to 30 ring backbone atoms, preferably 5 to 20, and more preferably 5 to 15, including at least one heteroatom, N; is a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl including pyrrolyl, imidazolyl, pyrazolyl, triazinyl, tetrazinyl, triazolyl, tetrazolyl, pyridyl, pyrazinyl, pyrimidinyl, pyridazinyl, etc., and a fused ring-type heteroaryl including benzoimidazolyl, isoindolyl, indolyl, indazolyl, benzothiadiazolyl, quinolyl, isoquinolyl, cinnolinyl, quinazolinyl, quinoxalinyl, carbazolyl, phenanthridinyl, etc. Further, "halogen" includes F, Cl, Br, and I.

Herein, "substituted" in the expression "substituted or unsubstituted" means that a hydrogen atom in a certain functional group is replaced with another atom or group, i.e. a substituent. The substituents of the substituted alkyl, the substituted alkenyl, the substituted alkynyl, the substituted cycloalkyl, the substituted aryl(ene), the substituted heteroaryl, the substituted trialkylsilyl, the substituted triarylsilyl, the substituted dialkylarylsilyl, the substituted alkyldiarylsilyl, the substituted mono- or di-arylamino, the substituted alkylarylamino, and the substituted mono- or polycyclic, alicyclic or aromatic ring in $A_1$, $A_2$, $L_1$, $X_1$ to $X_{16}$, L, and $R_1$ to $R_{17}$ in formulas 1 and 2 each independently are at least one selected from the group consisting of deuterium; a halogen; a cyano; a carboxyl; a nitro; a hydroxyl; a (C1-C30)alkyl; a halo(C1-C30)alkyl; a (C2-C30) alkenyl; a (C2-C30) alkynyl; a (C1-C30)alkoxy; a (C1-C30)alkylthio; a (C3-C30)cycloalkyl; a (C3-C30)cycloalkenyl; a 3- to 7-membered heterocycloalkyl; a (C6-C30)aryloxy; a (C6-C30)arylthio; a 3- to 30-membered heteroaryl unsubstituted or substituted with a (C6-C30)aryl; a (C6-C30)aryl unsubstituted or substituted with a cyano, a 3- to 30-membered heteroaryl, or a tri(C6-C30)arylsilyl; a tri(C1-C30)alkylsilyl; a tri(C6-C30)arylsilyl; a di(C1-C30) alkyl(C6-C30)arylsilyl; a (C1-C30)alkyldi(C6-C30)arylsilyl; an amino; a mono- or di-(C1-C30)alkylamino; a monoor di-(C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl (C6-C30)aryl, and preferably are at least one selected from the group consisting of a halogen; a cyano; a (C1-C6)alkyl; a 5- to 15-membered heteroaryl; a (C6-C20)aryl unsubstituted or substituted with a cyano, a (C6-C12)aryl, or a tri(C6-C12)arylsilyl; a tri(C6-C12)arylsilyl; and a (C1-C6) alkyl(C6-C12)aryl.

In formula 1, the triarylsilyl of $X_1$ to $X_{16}$ is preferably a triphenylsilyl.

The first host compound represented by formula 1 includes the following compounds, but is not limited thereto:

H1-1

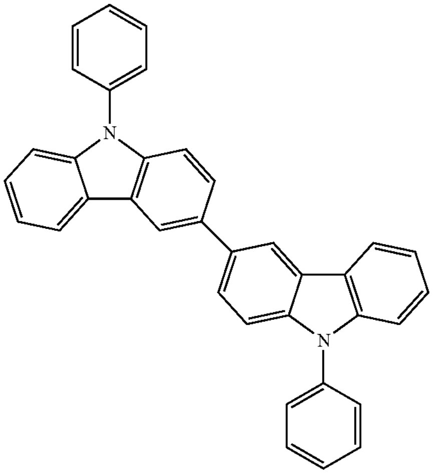

H1-2

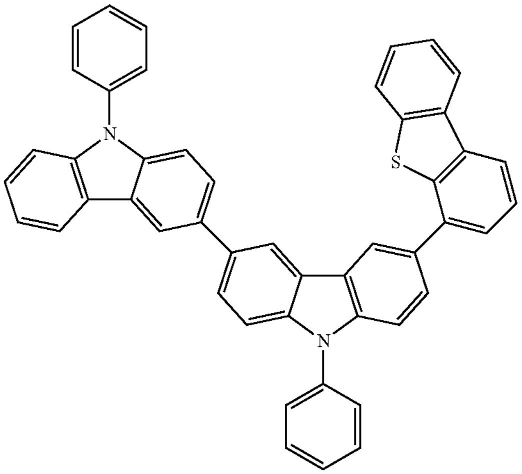

-continued

H1-3

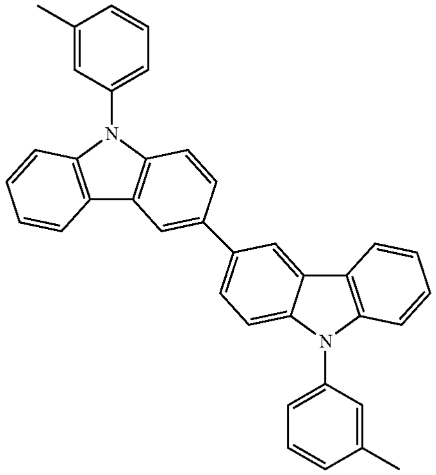

H1-4

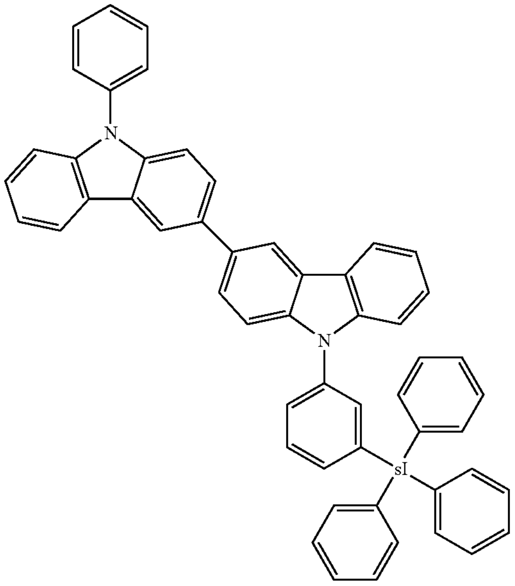

H1-5

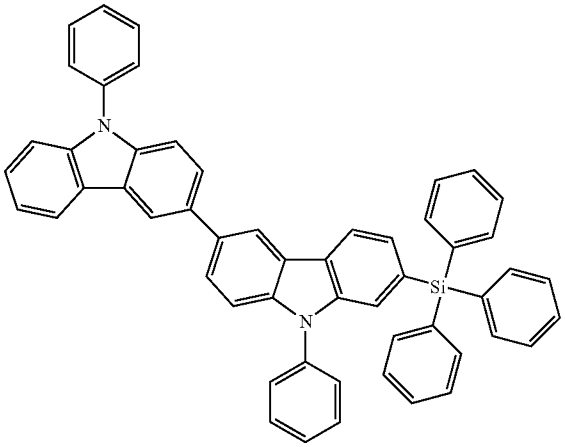

H1-6
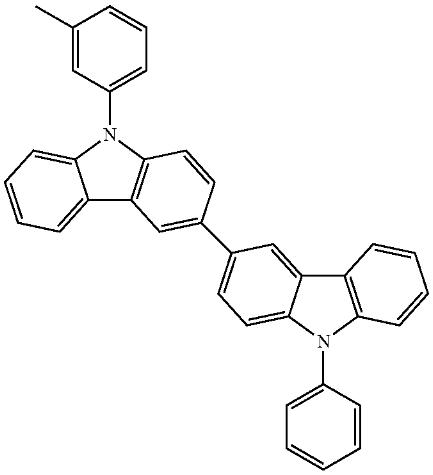
H1-7
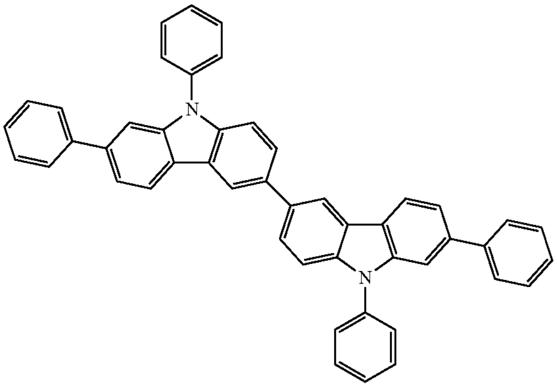
H1-8
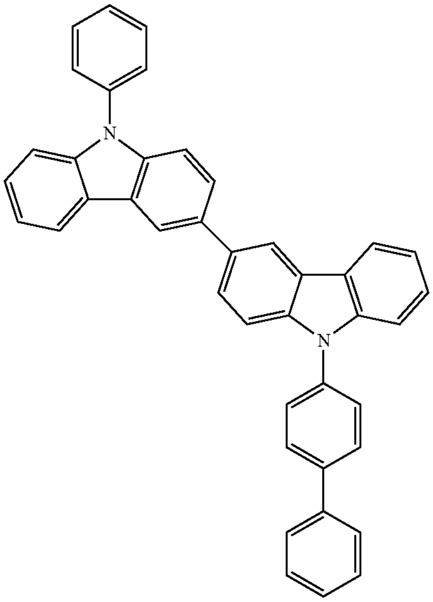
H1-9
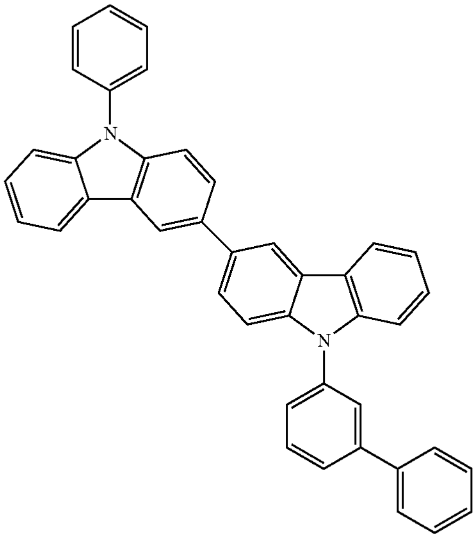
H1-10
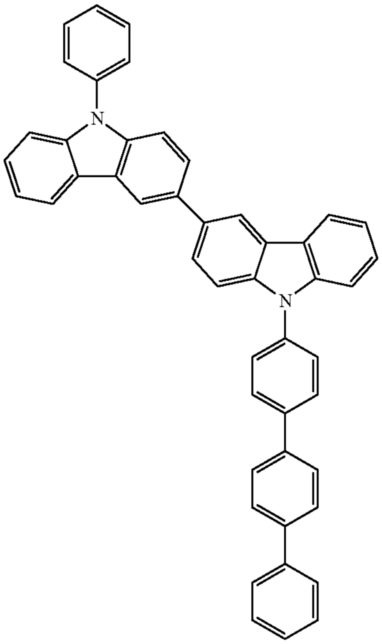

-continued
H1-11
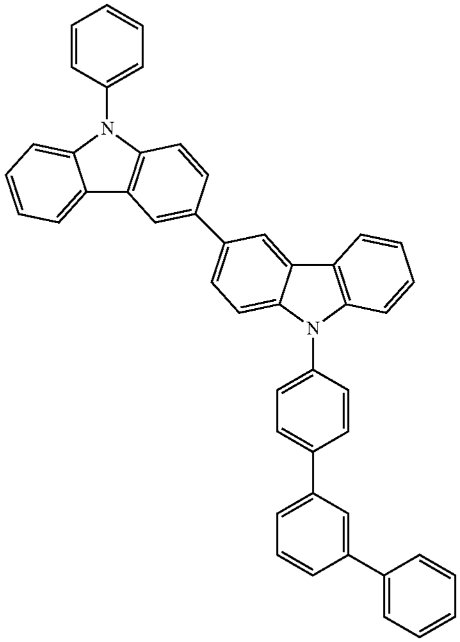
H1-12
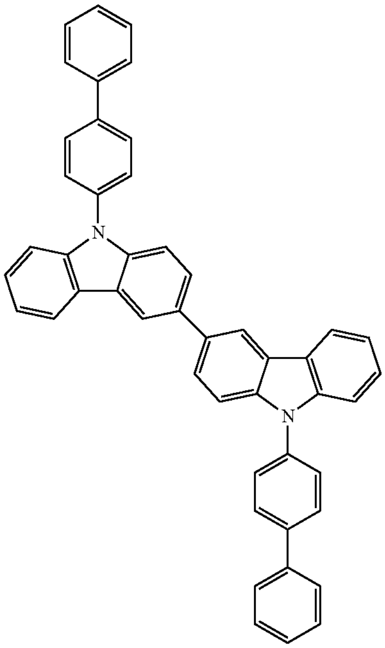
-continued
H1-13
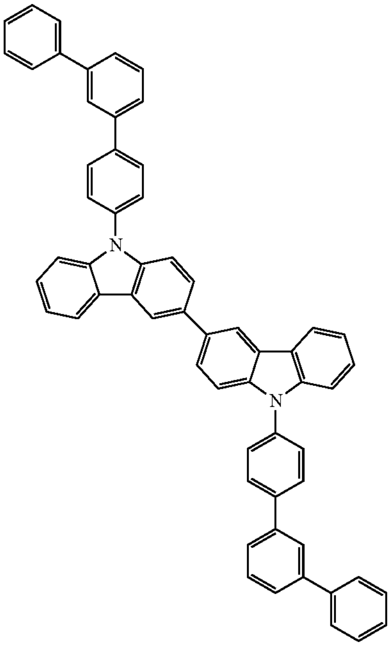
H1-14
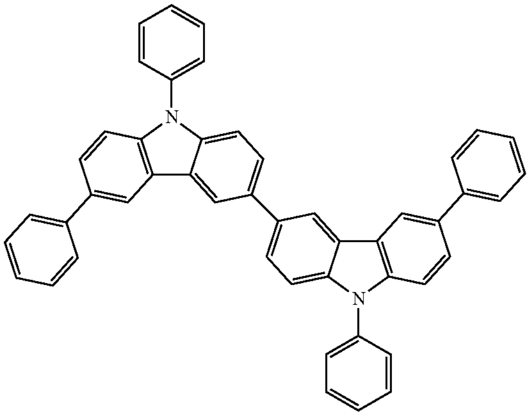
H1-15
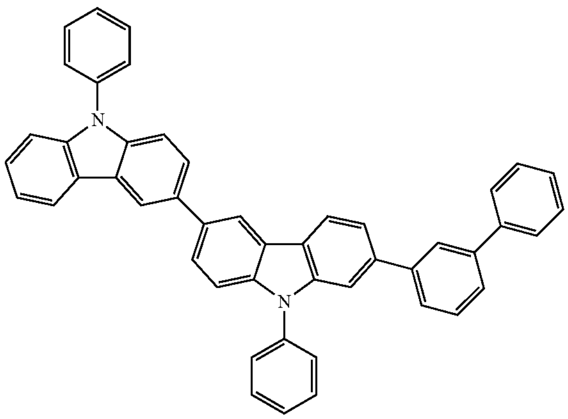

-continued
H1-16
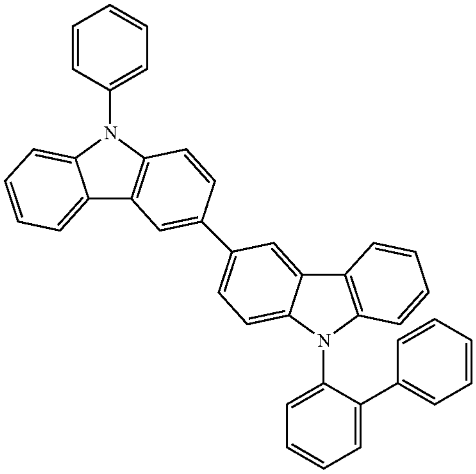
H1-17
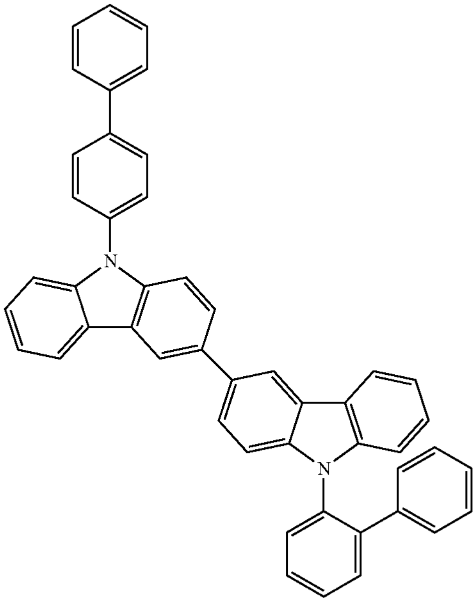
H-18
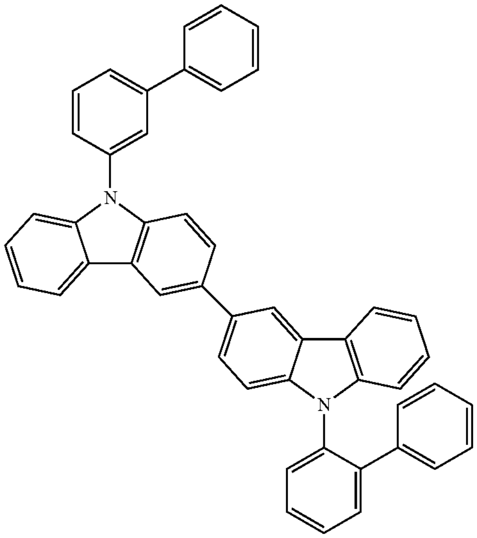
-continued
H1-19
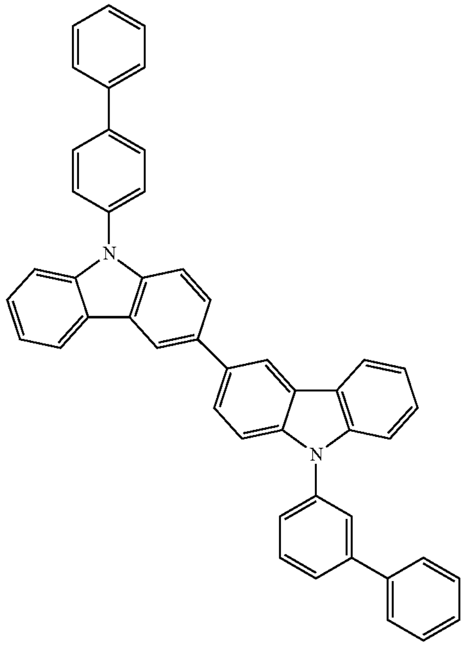
H1-20
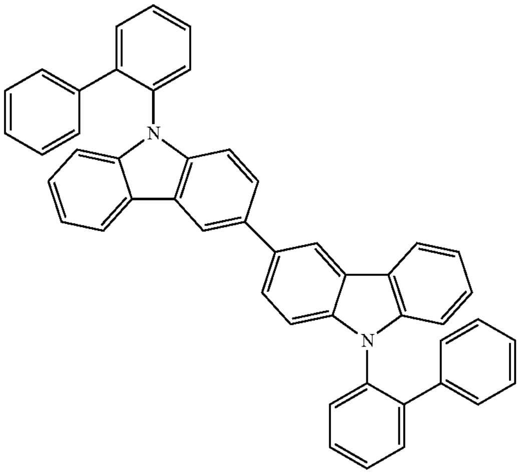
H1-21
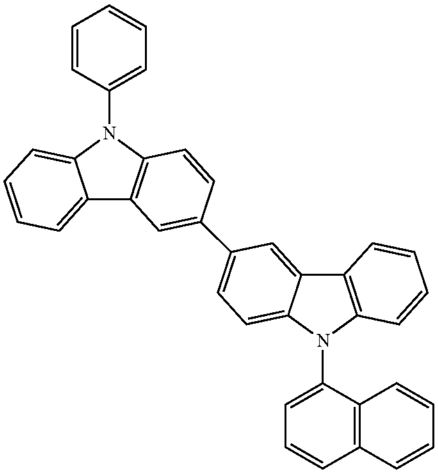

-continued
H1-22
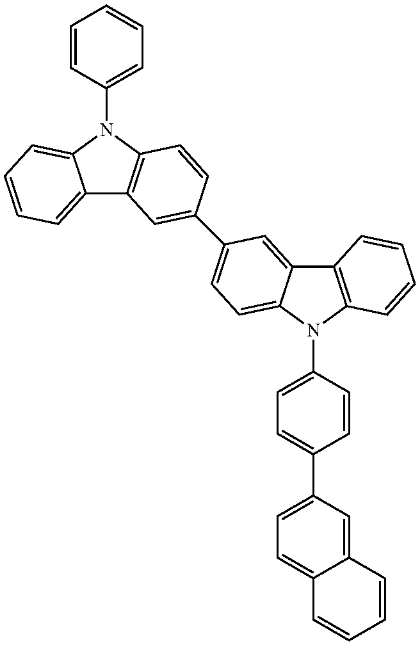
H1-23
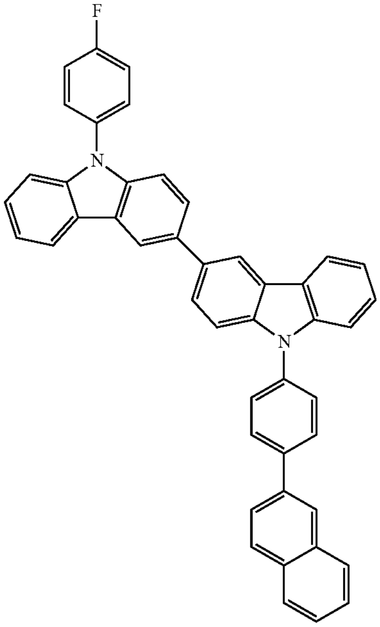
H1-24
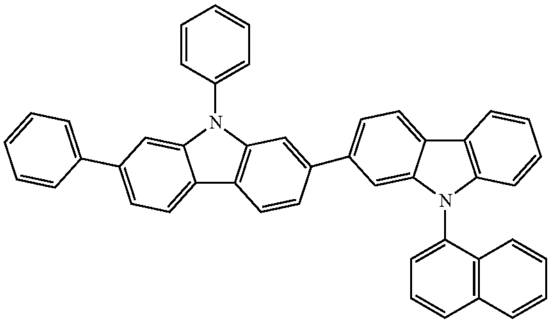
-continued
H1-25
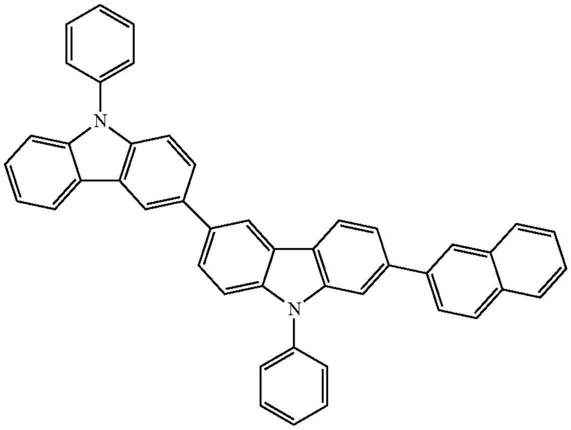
H1-26
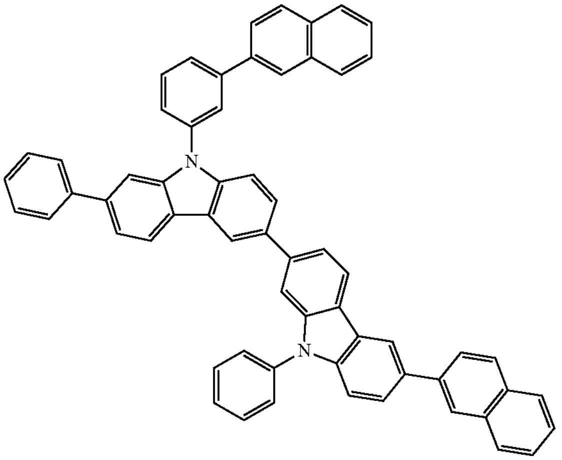
H1-27
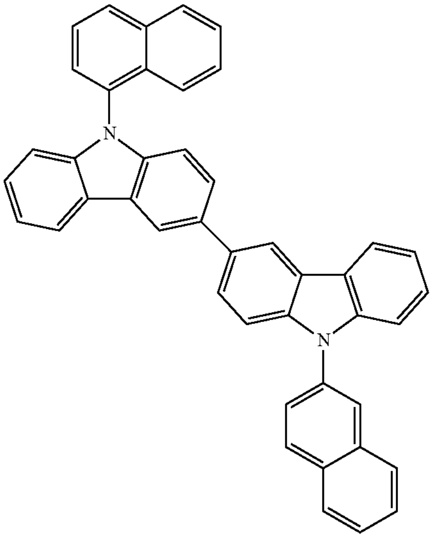

-continued
H1-28
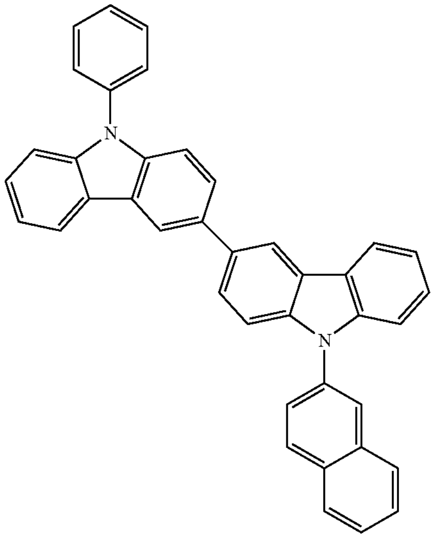
H1-29
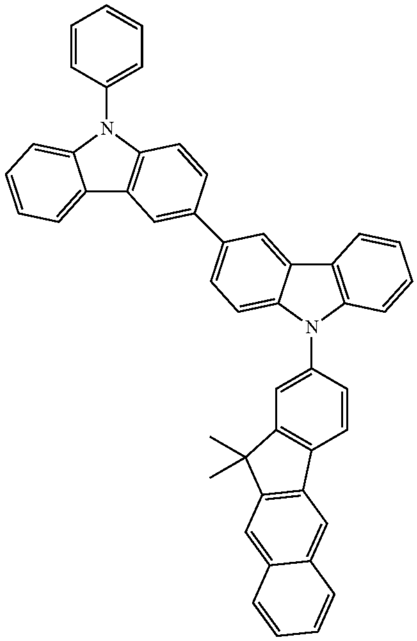
-continued
H1-30
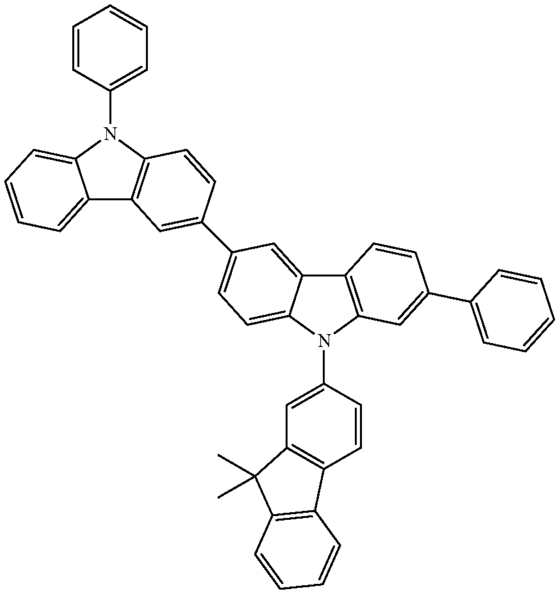
H1-31
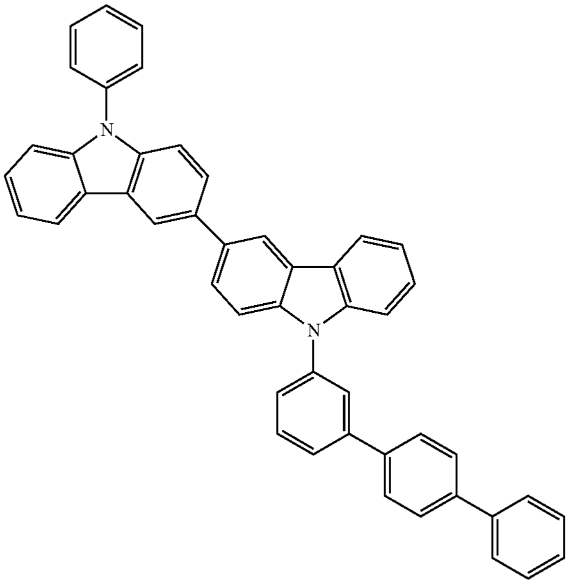
H1-32
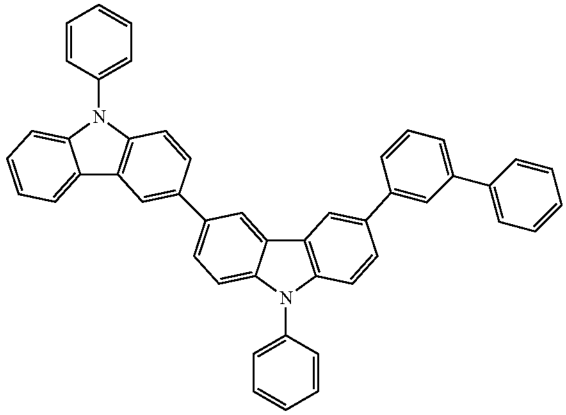

-continued
H1-33
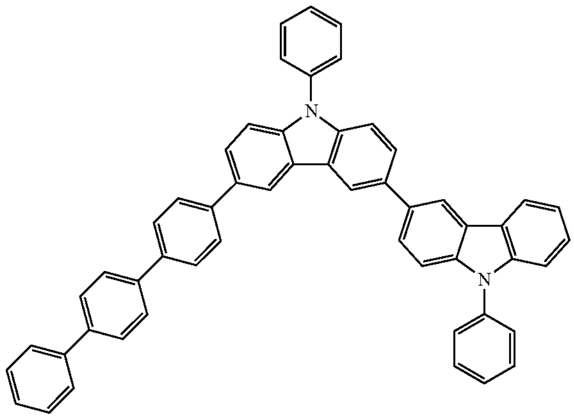
H1-34
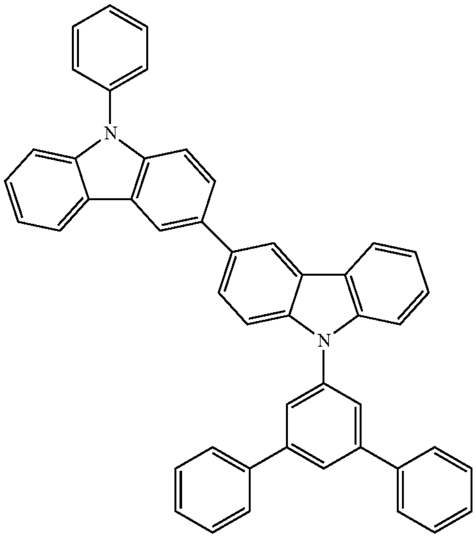
H1-35
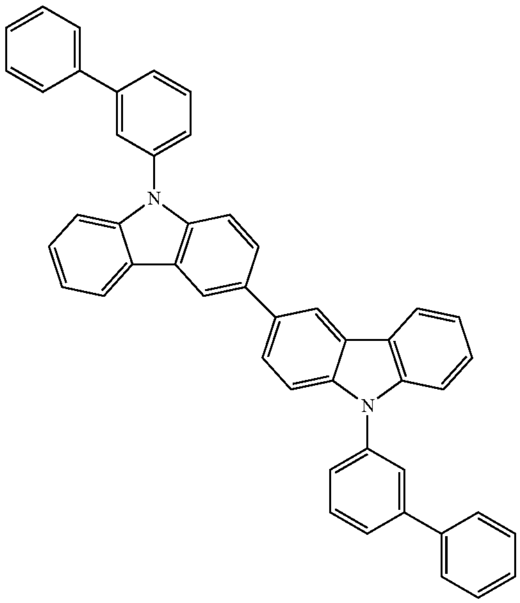
-continued
H1-36
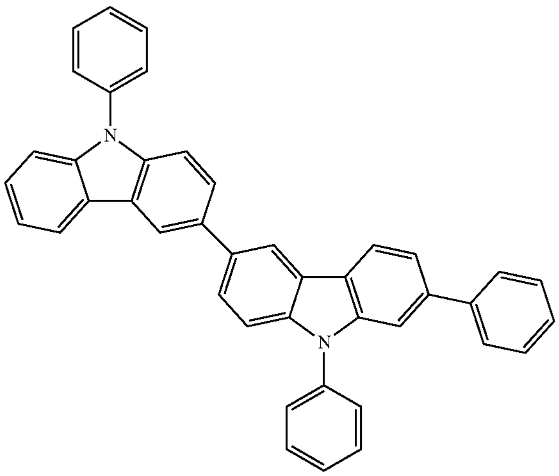
H1-37
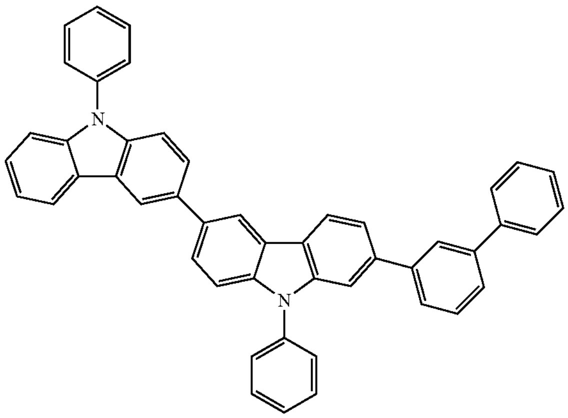
H1-38
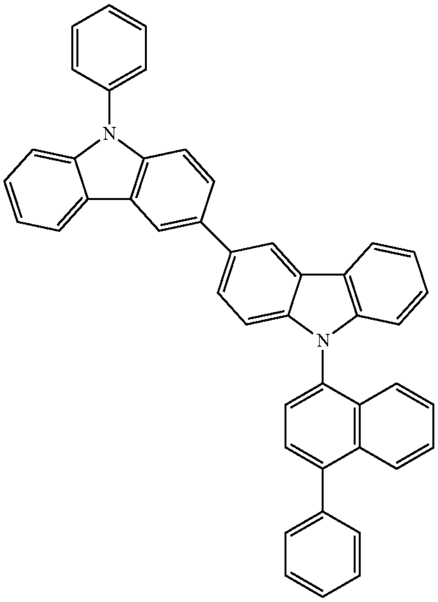

-continued
H1-39
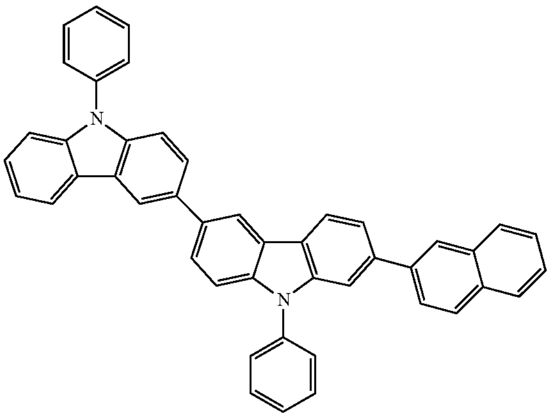
H1-40
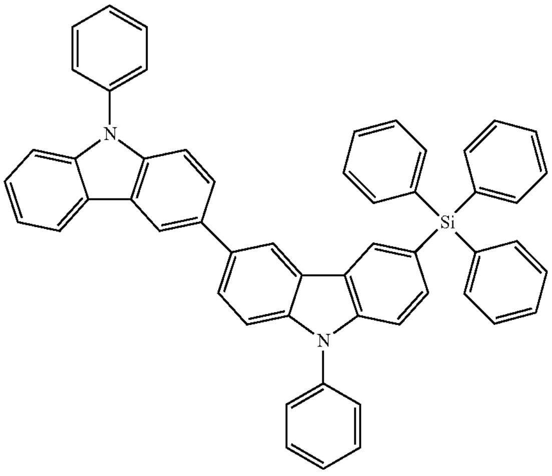
H1-41
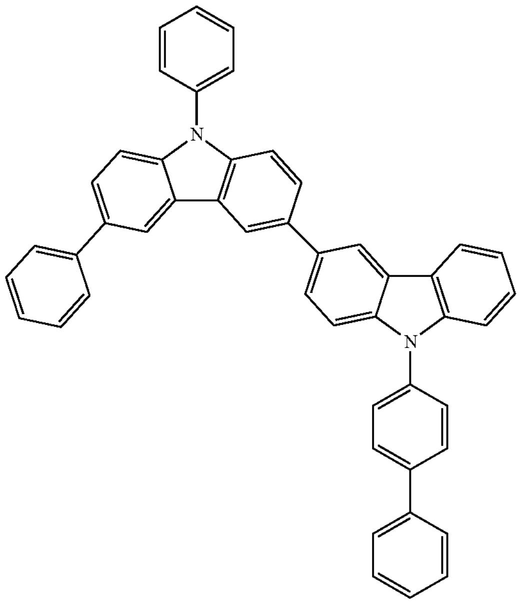
-continued
H1-42
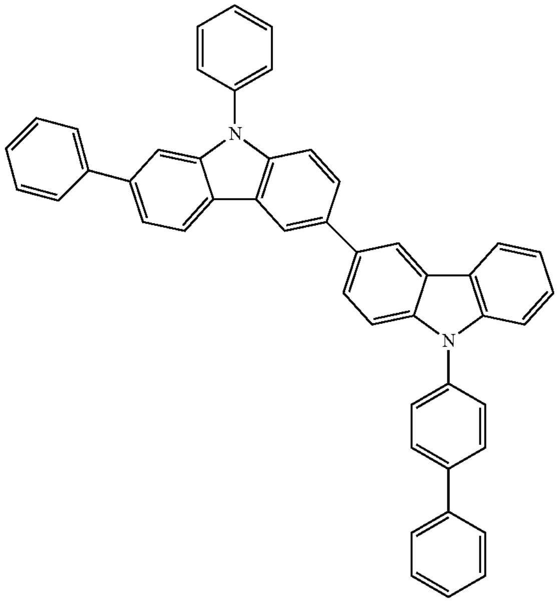
H1-43
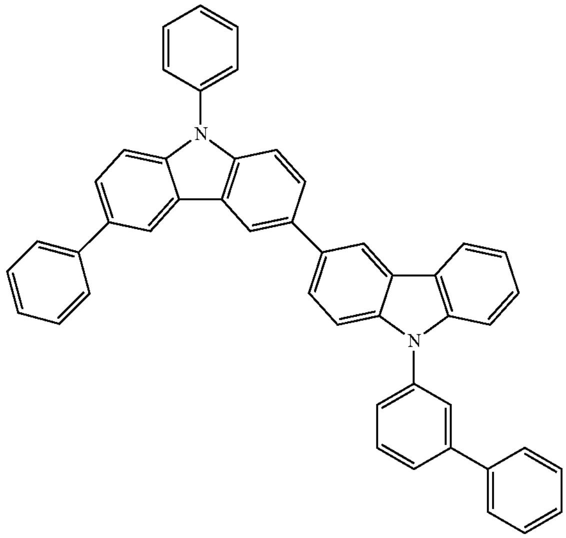

-continued
H1-44
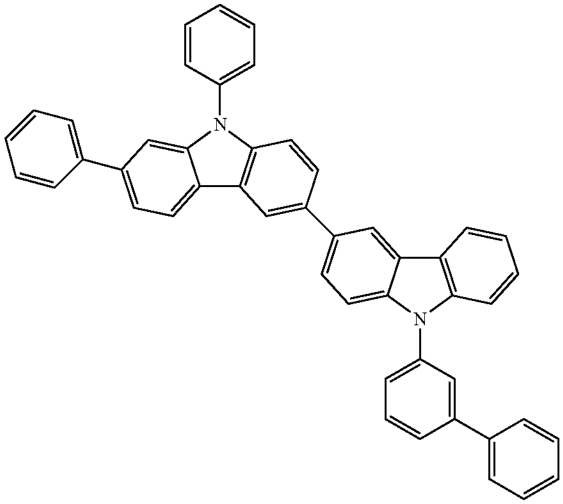
H1-45
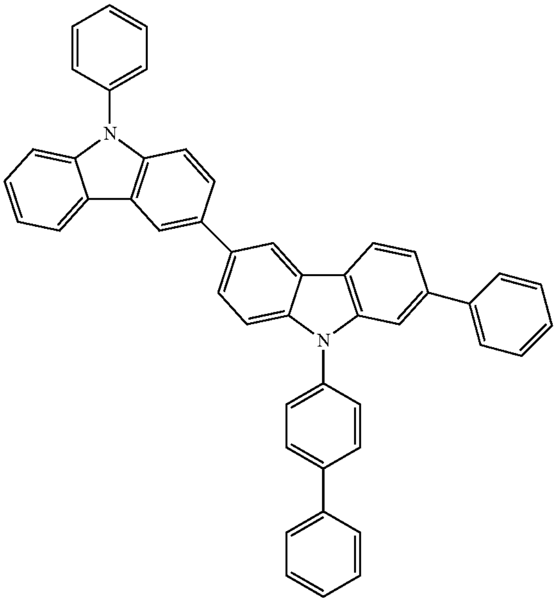
-continued
H1-46
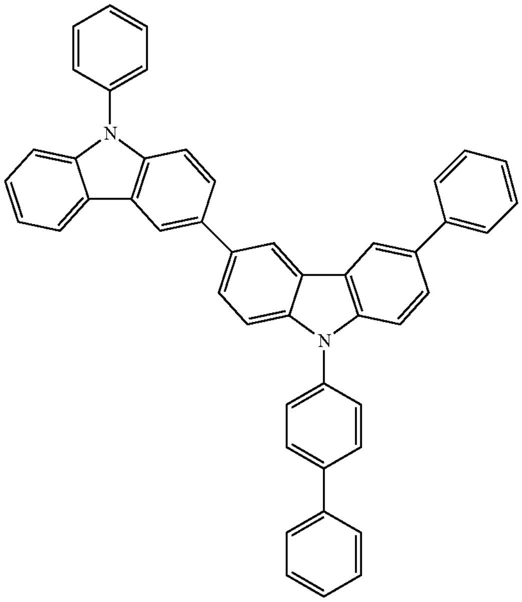
H1-47
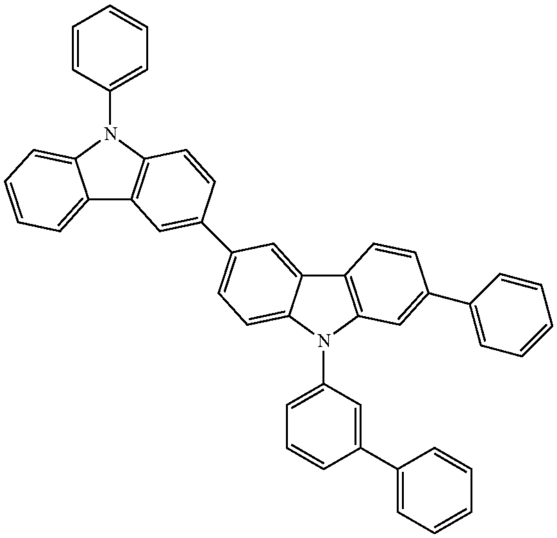

-continued
H1-48
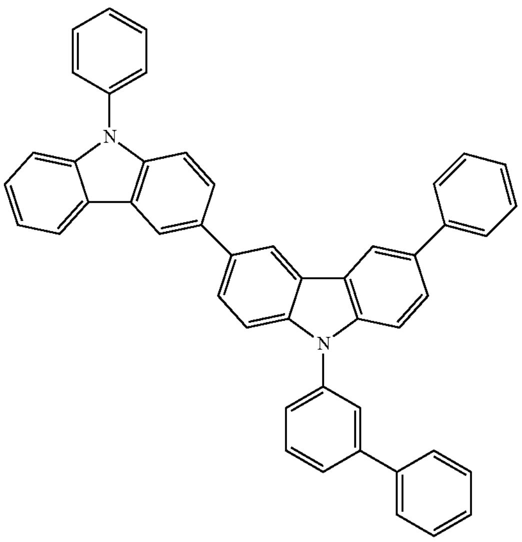
H1-49
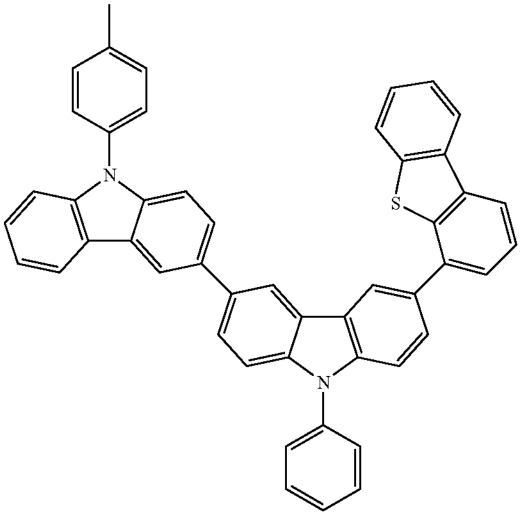
H1-50
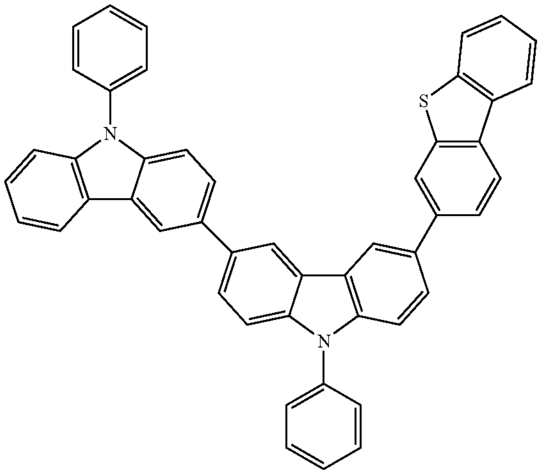
-continued
H1-51
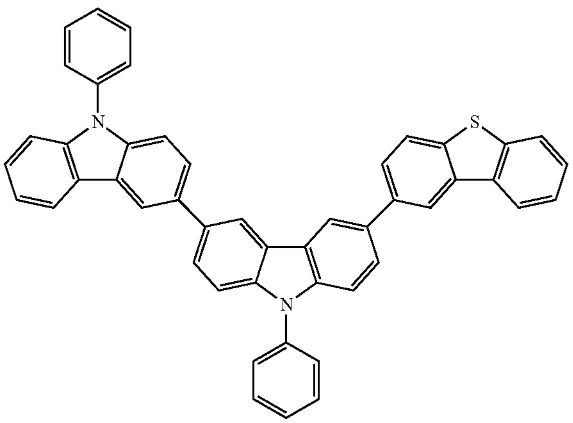
H1-52
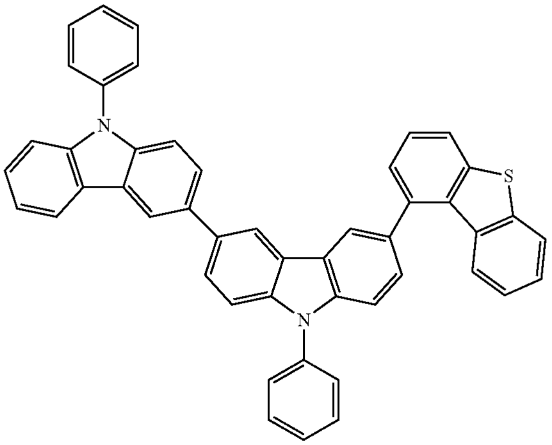
H1-53
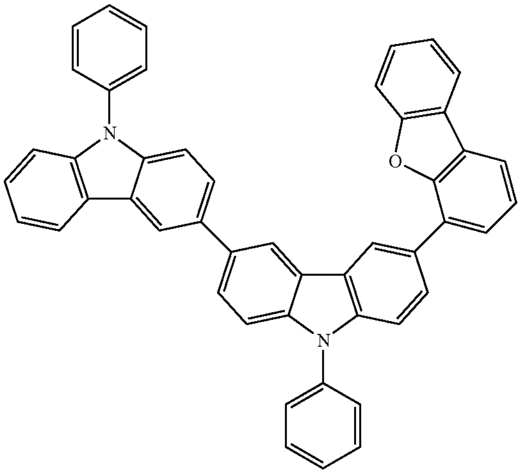

-continued
H1-54
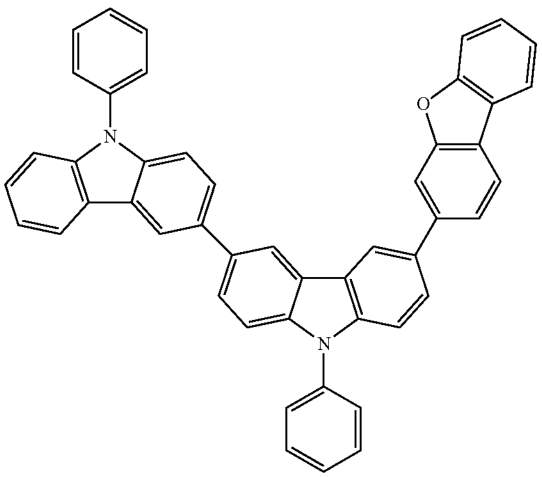
H1-55
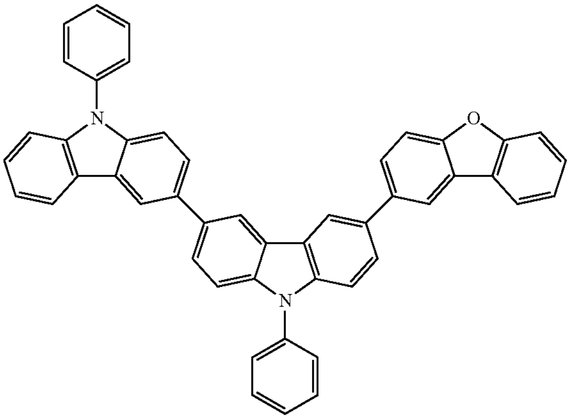
H1-56
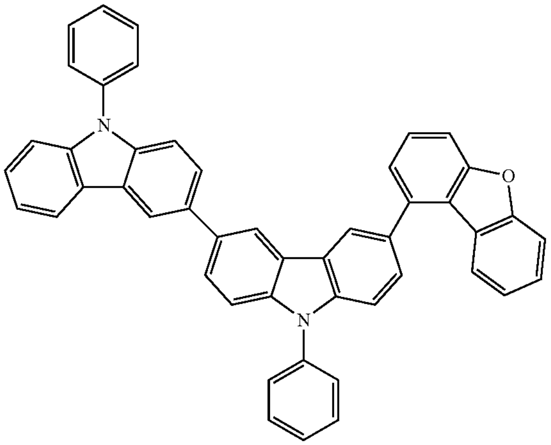
-continued
H1-57
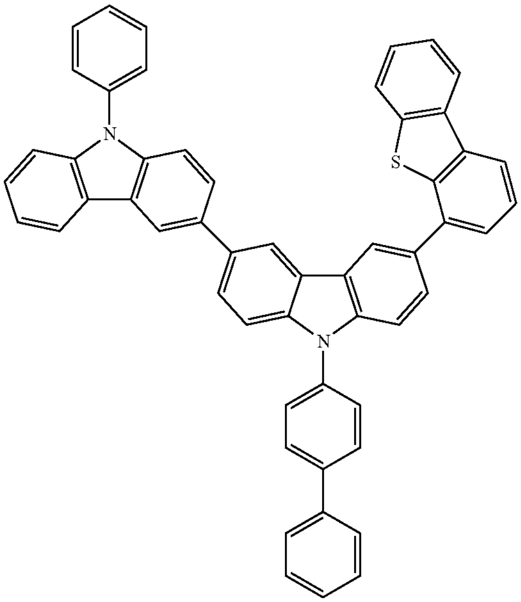
H1-58
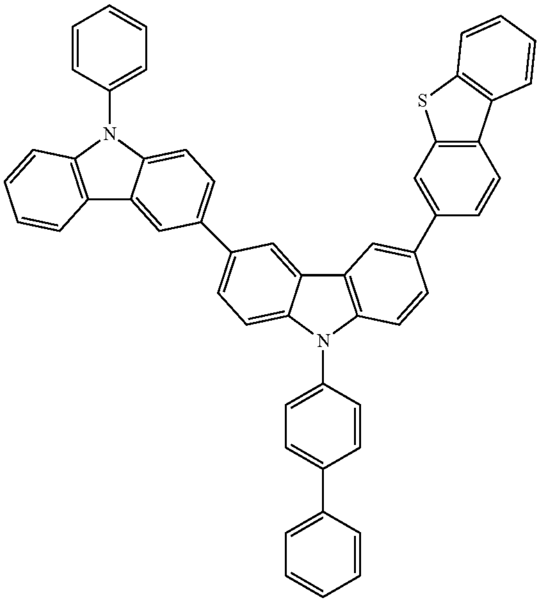

-continued
H1-59
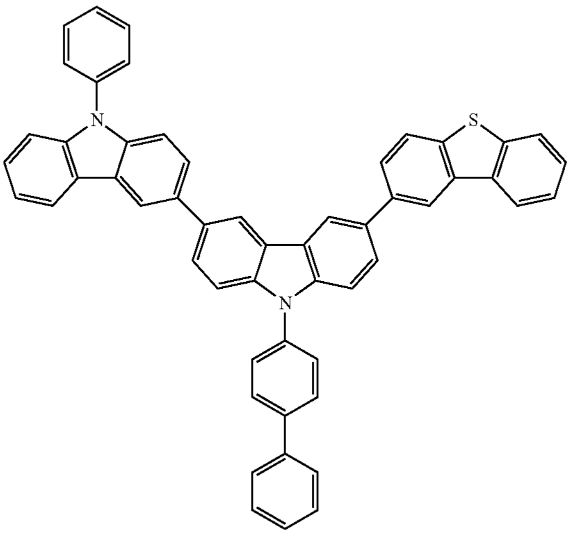
H1-60
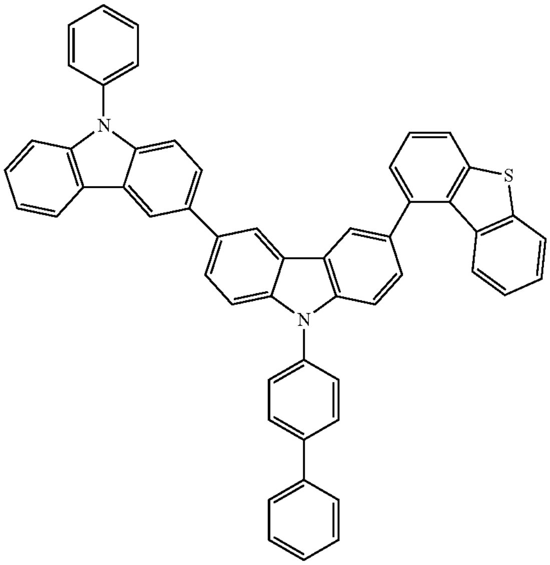
-continued
H1-61
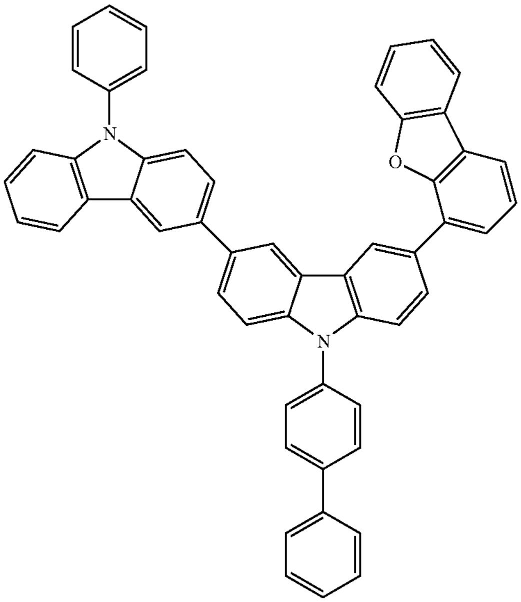
H1-62
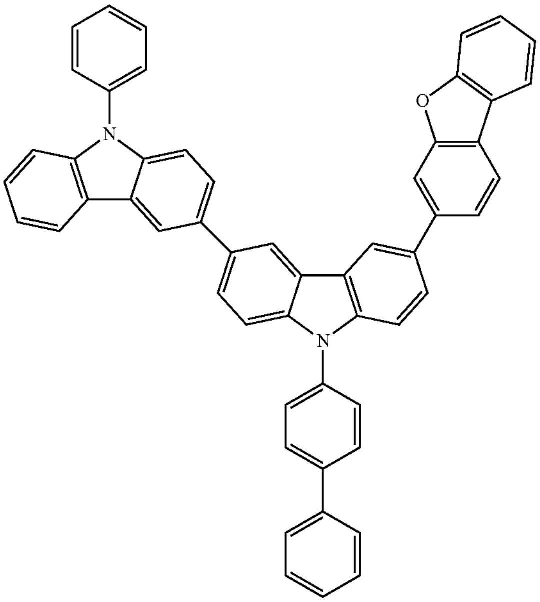

-continued
H1-63
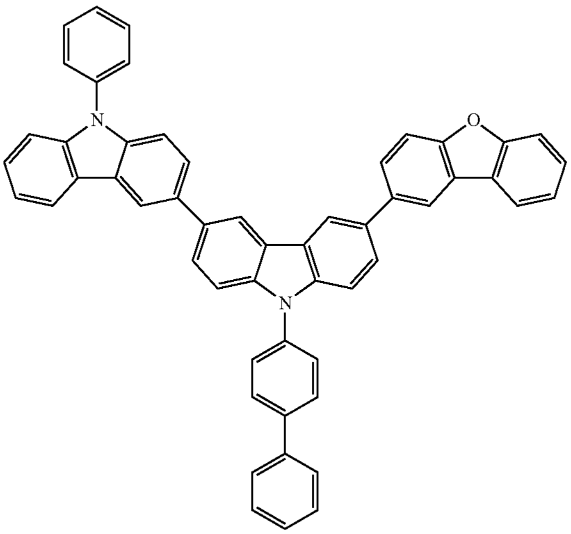
H1-64
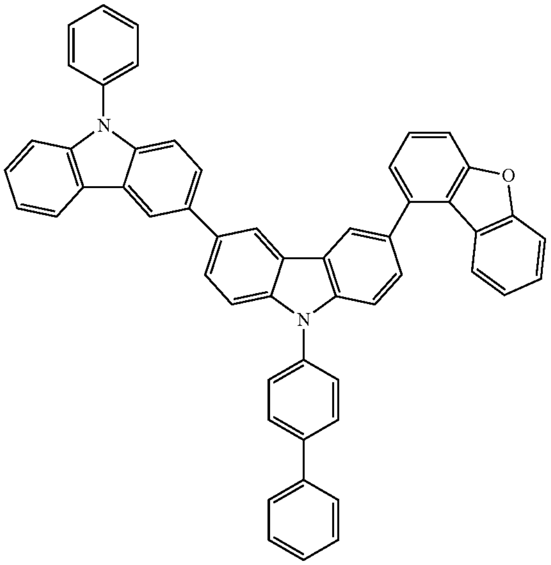
-continued
H1-65
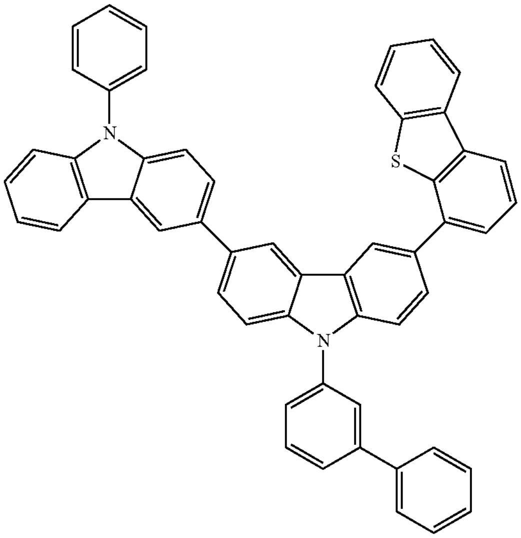
H1-66
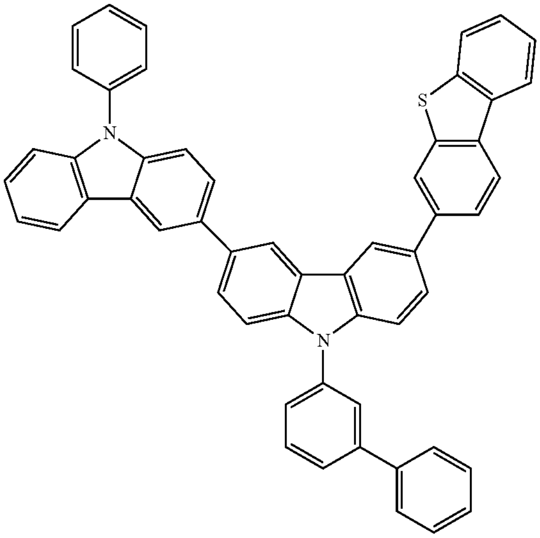
H1-67
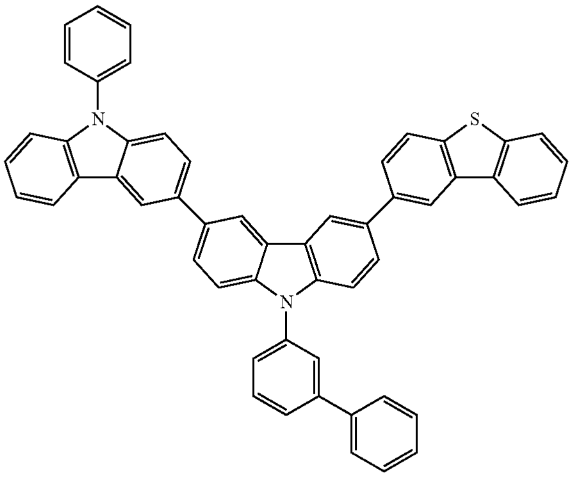

-continued
H1-68
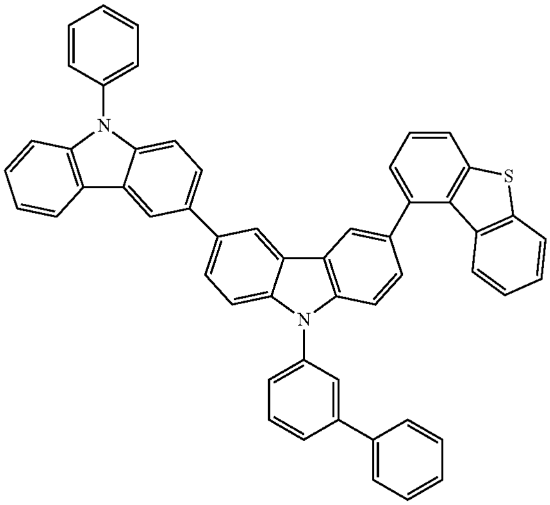
H1-69
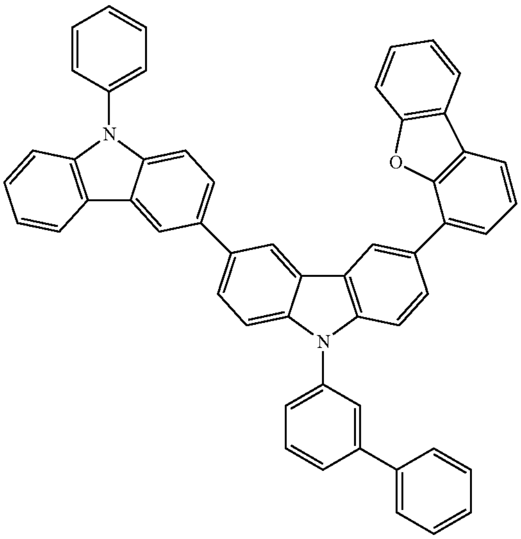
H1-70
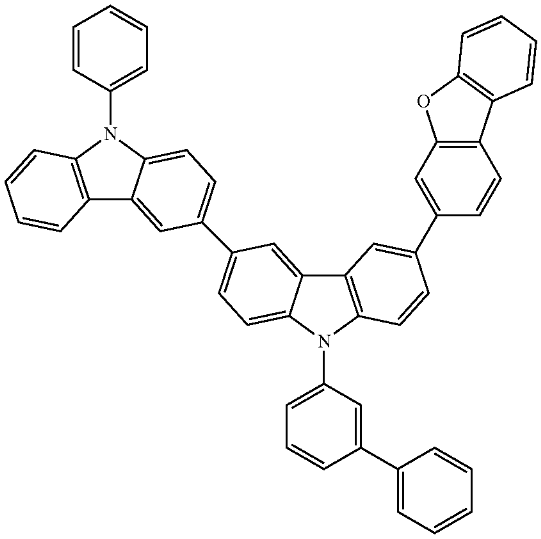
-continued
H1-71
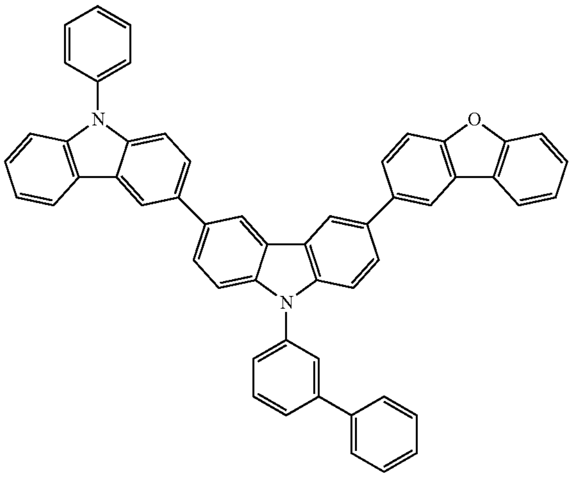
H1-72
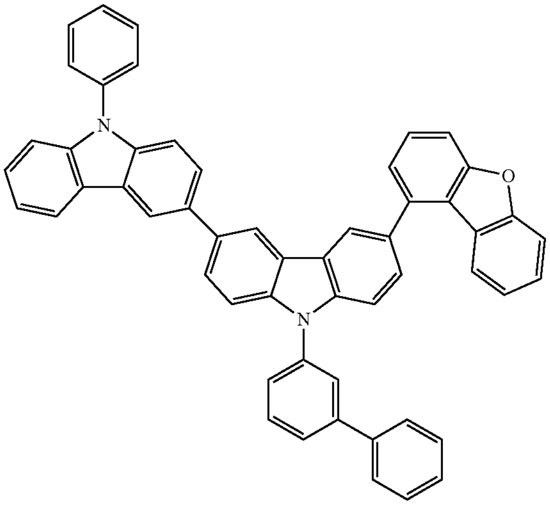
H1-73
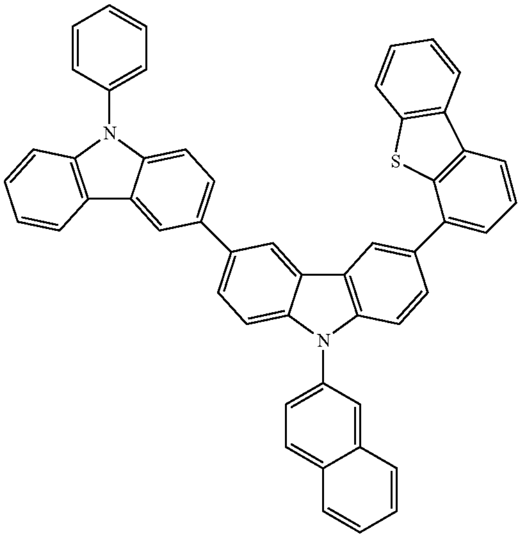

-continued
H1-74
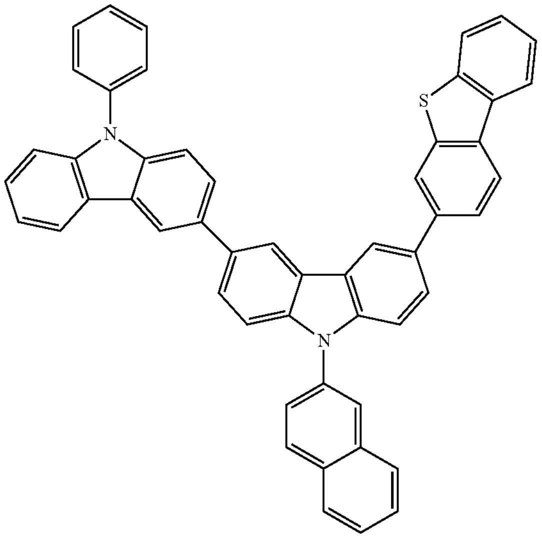
H1-75
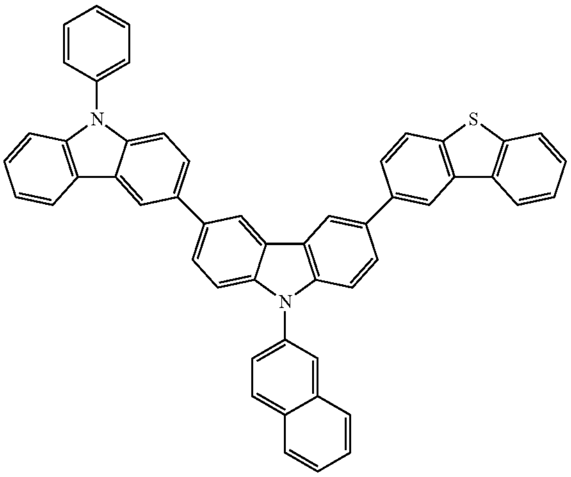
H1-76
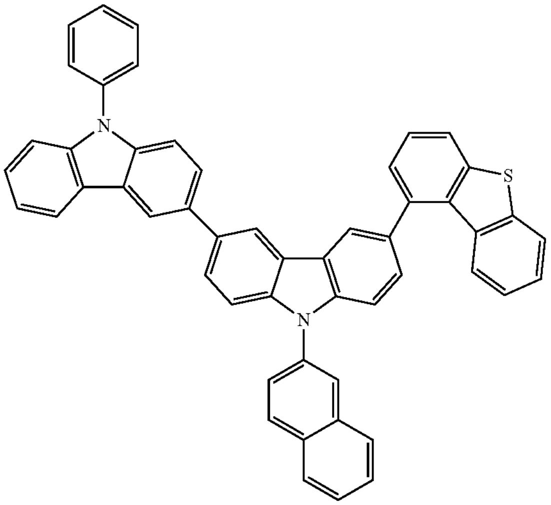
-continued
H1-77
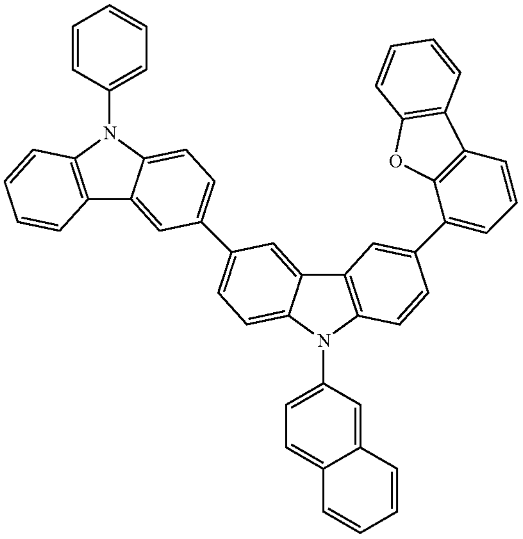
H1-78
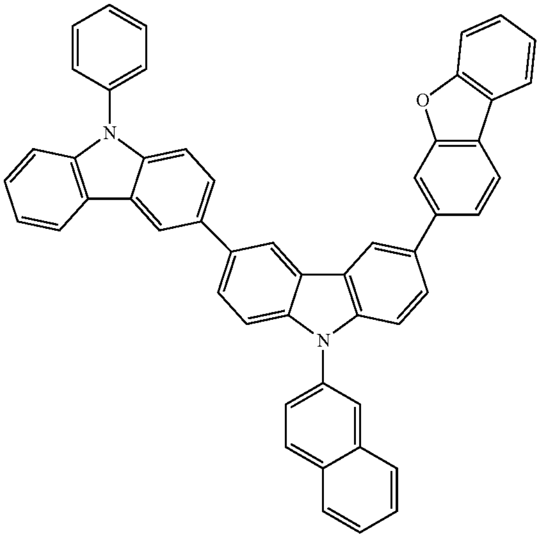
H1-79
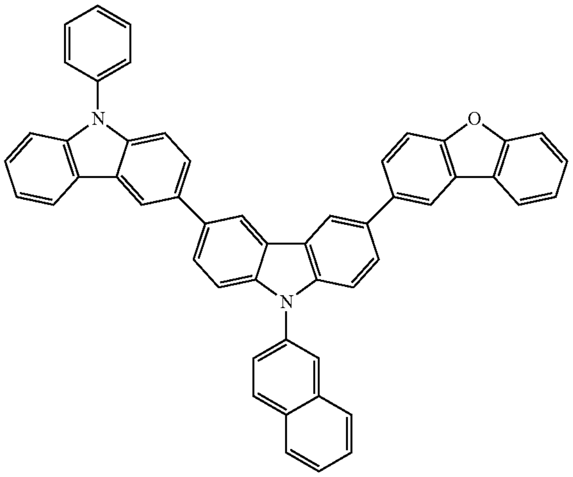

-continued
H1-80
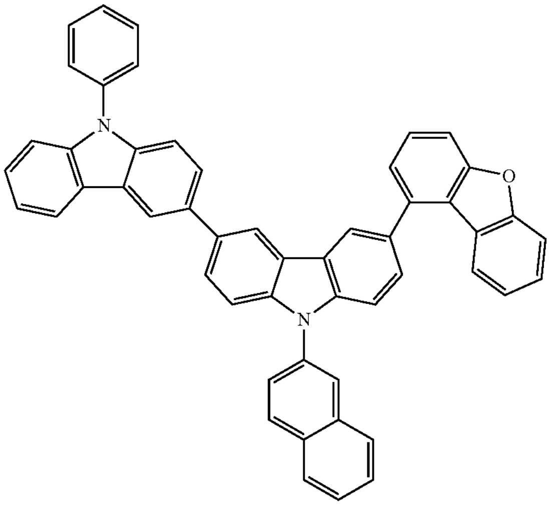
H1-81
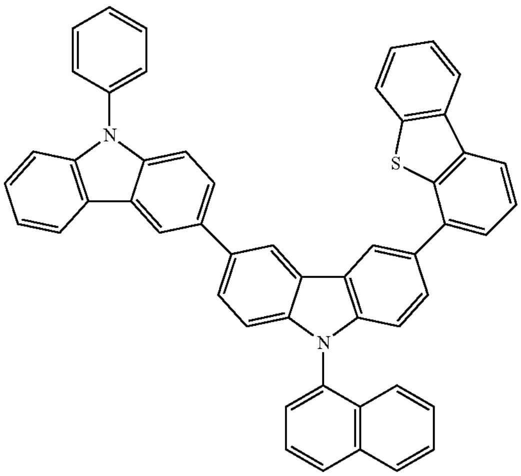
H1-82
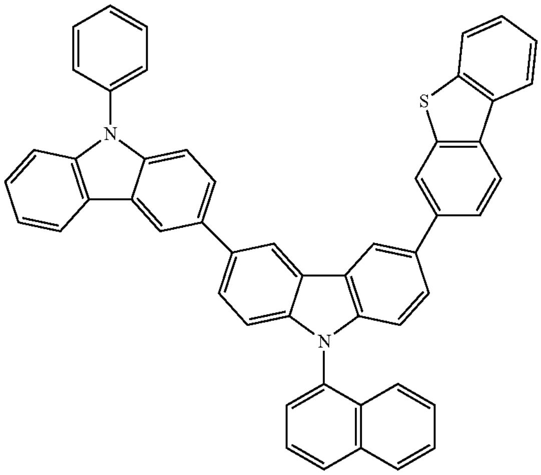
-continued
H1-83
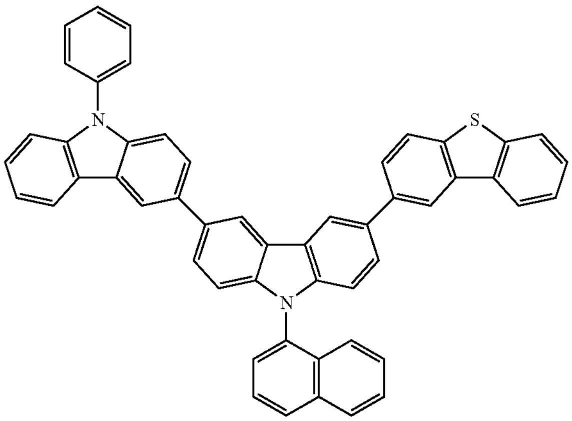
H1-84
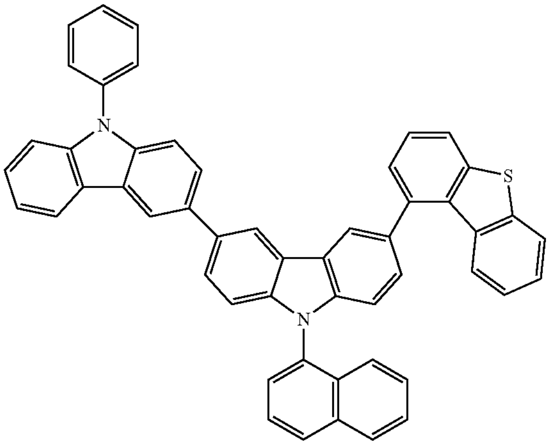
H1-85
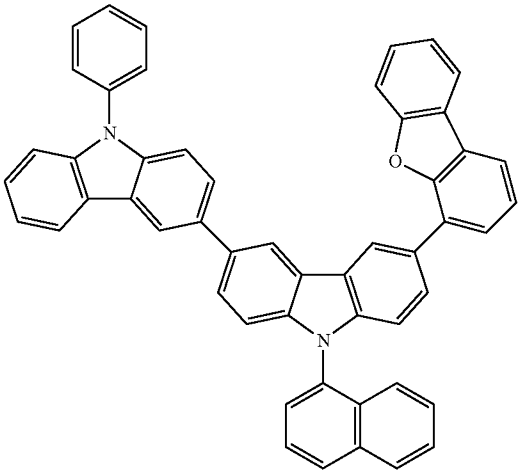

-continued
H1-86
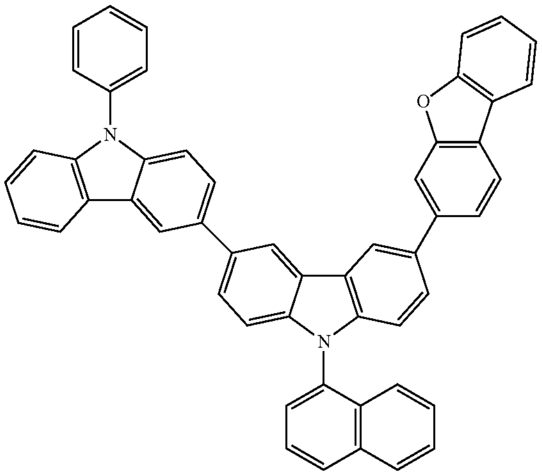
H1-87
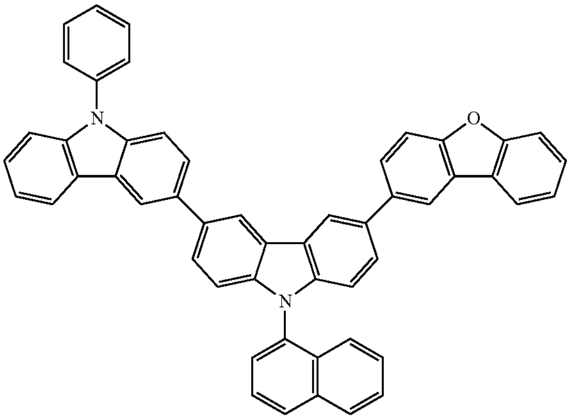
H1-88
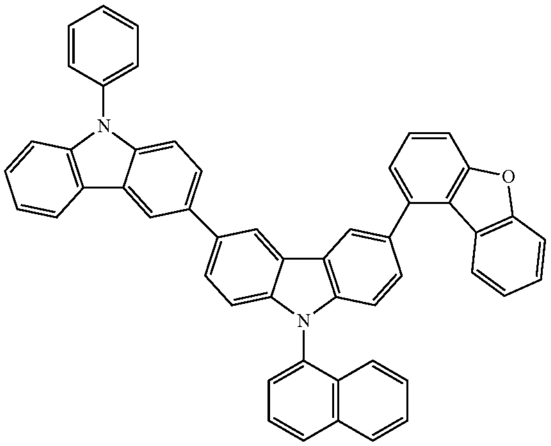
-continued
H1-89
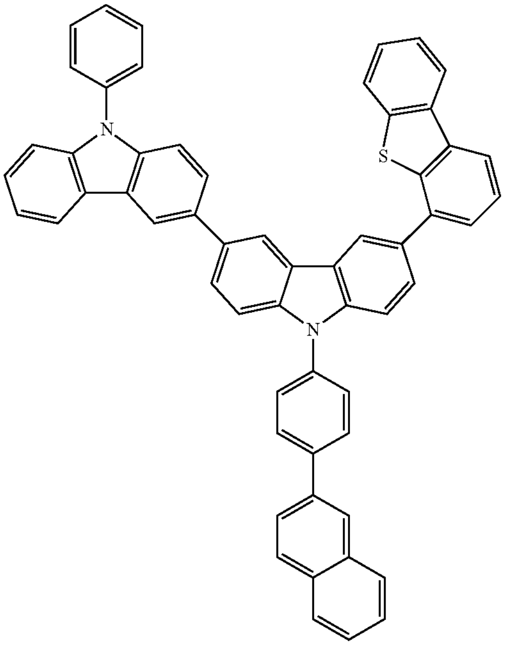
H1-90
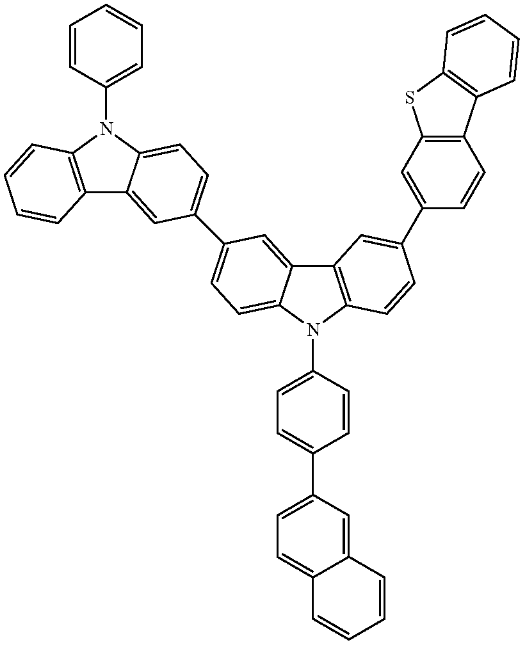

H1-91
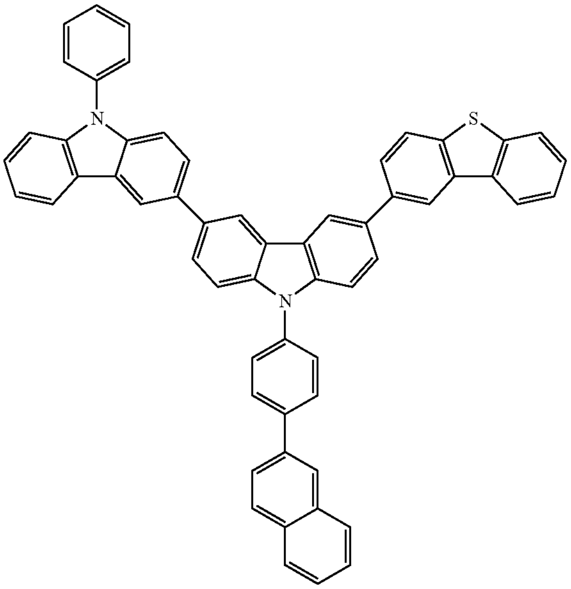
H1-92
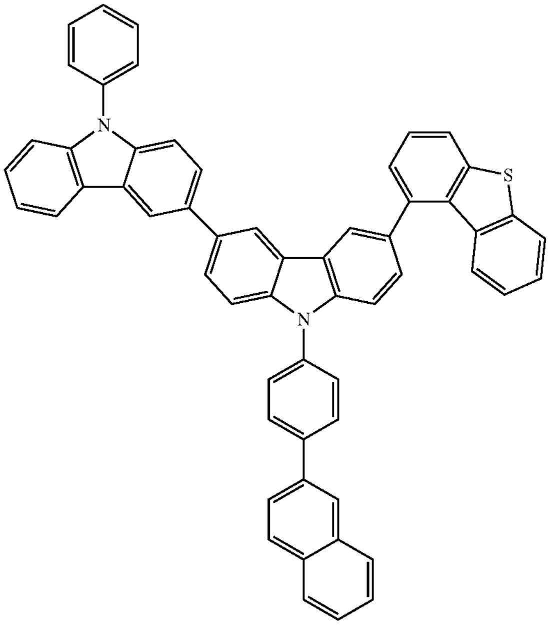
H1-93
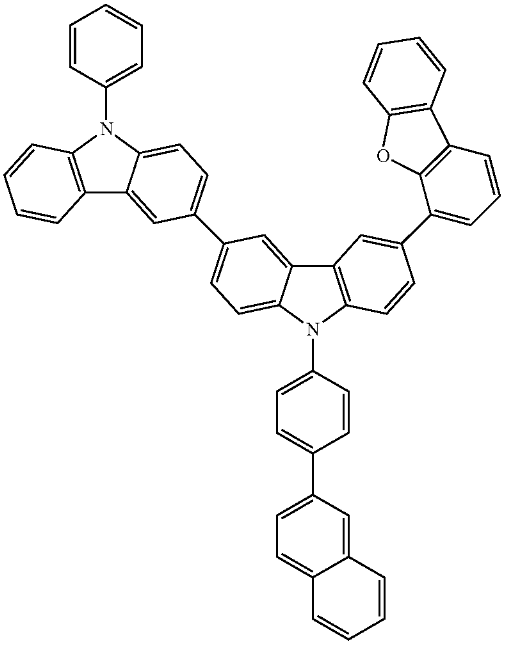
H1-94
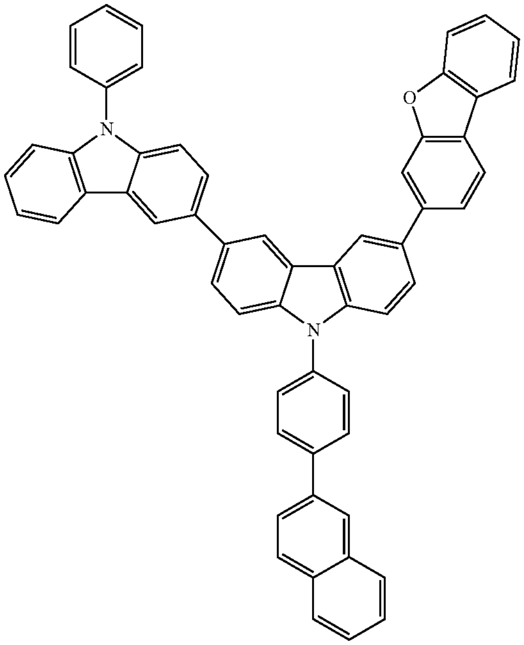

-continued
H1-95
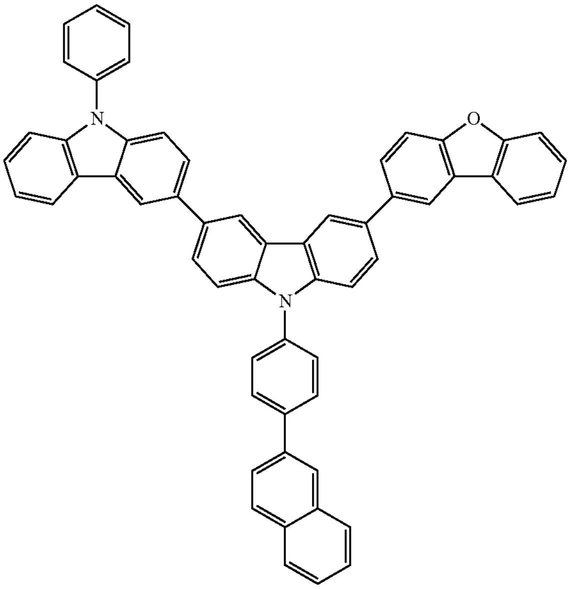
H1-96
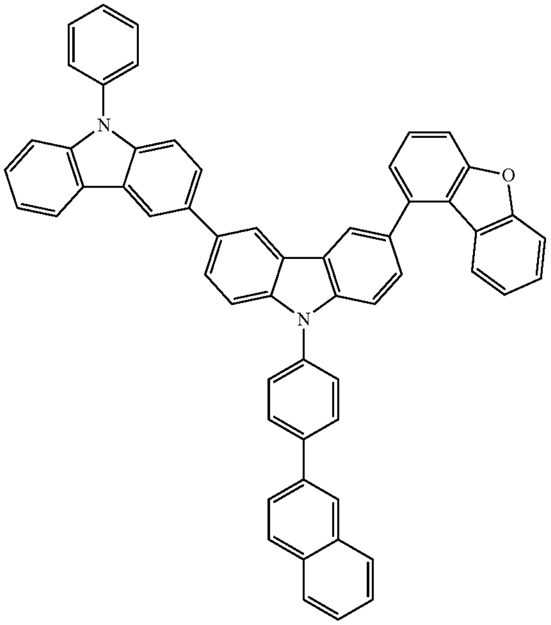
-continued
H1-97
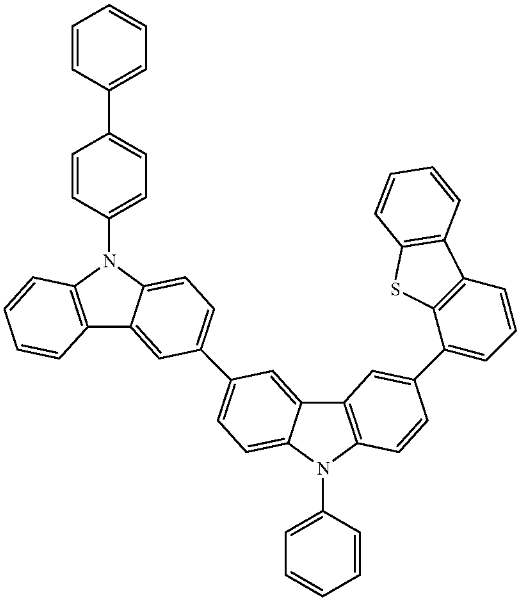
H1-98
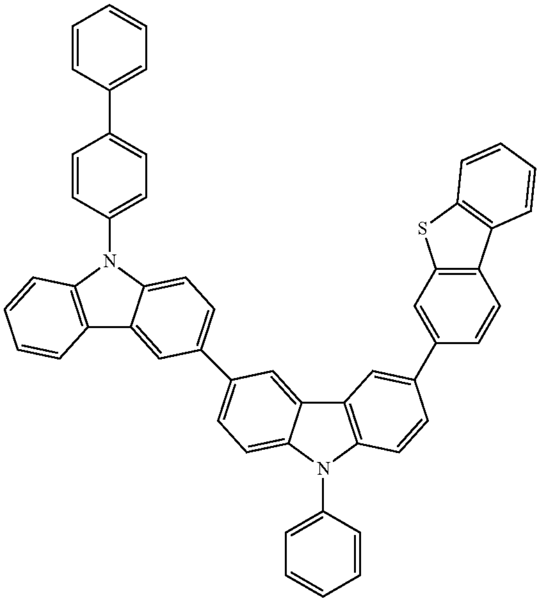

-continued
H1-99
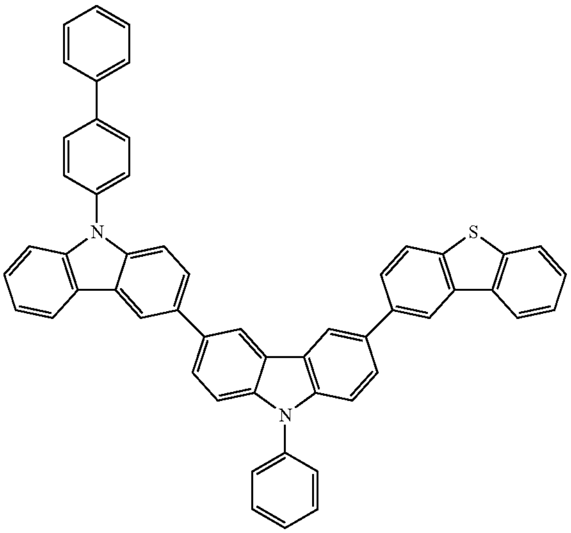
H1-100
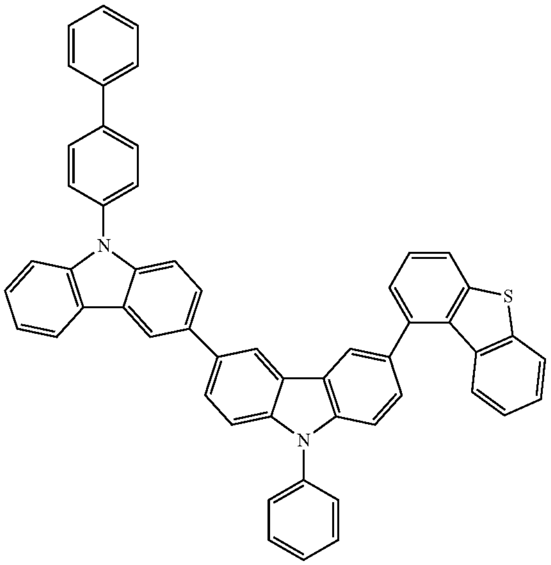
-continued
H1-101
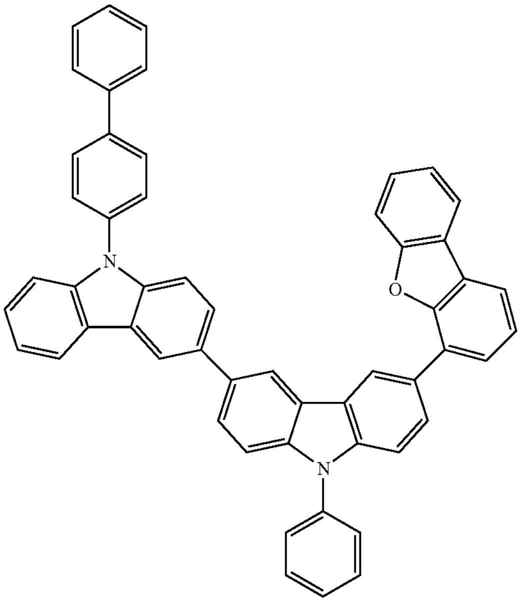
H1-102
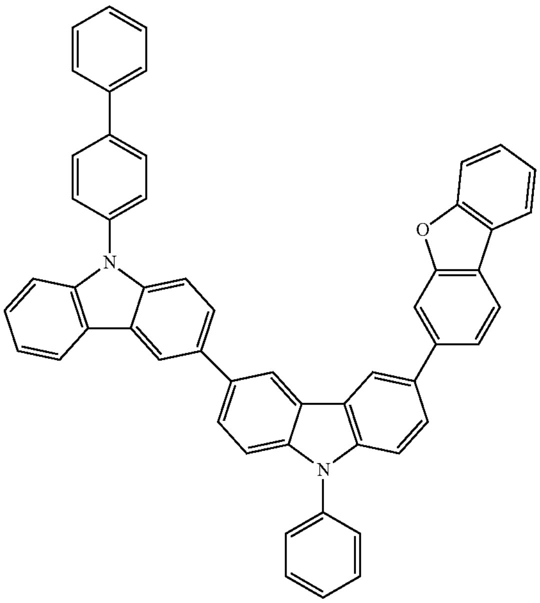

-continued
H1-103
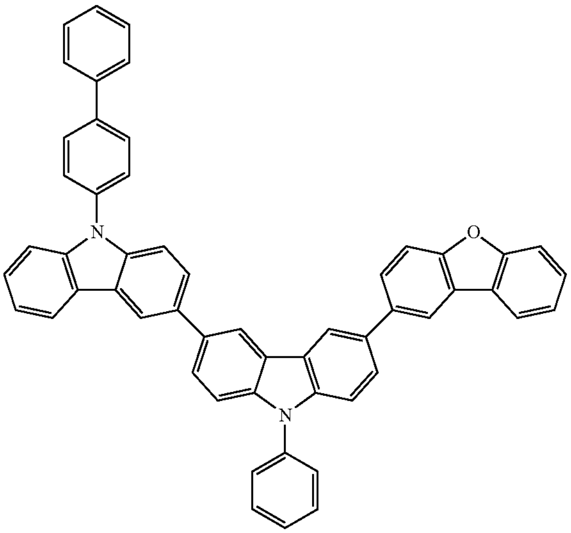
H1-104
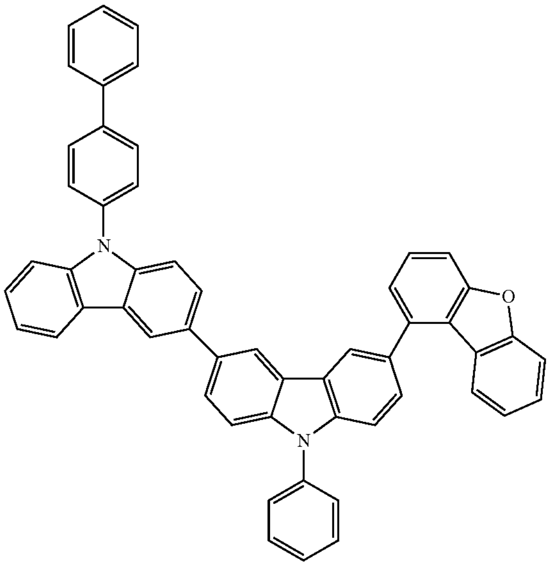
-continued
H1-105
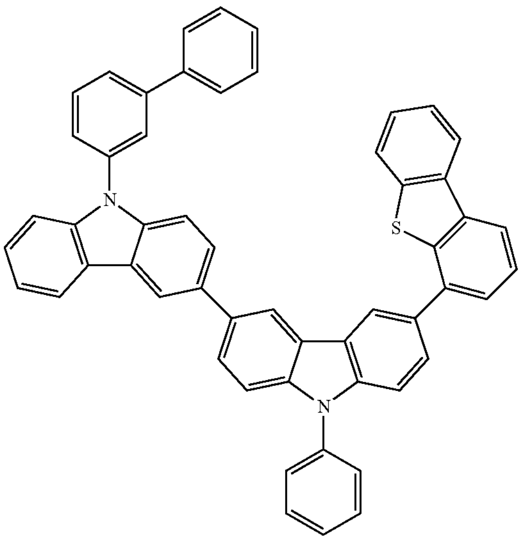
H1-106
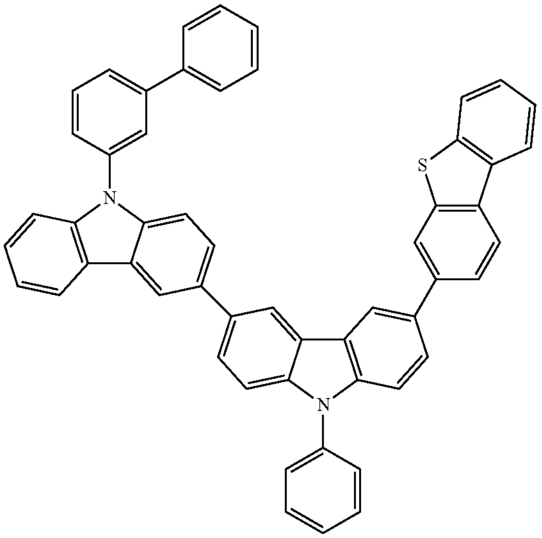
H1-107
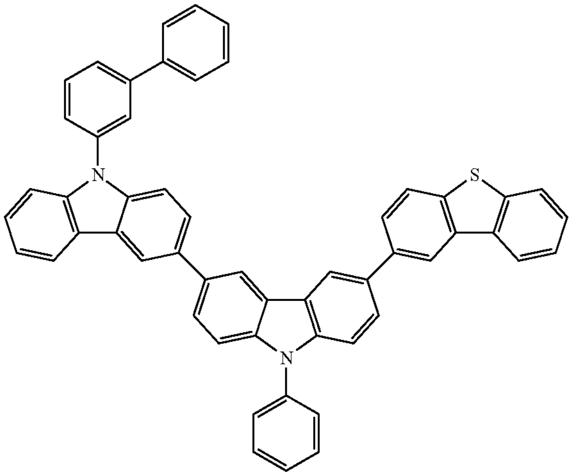

-continued
H1-108
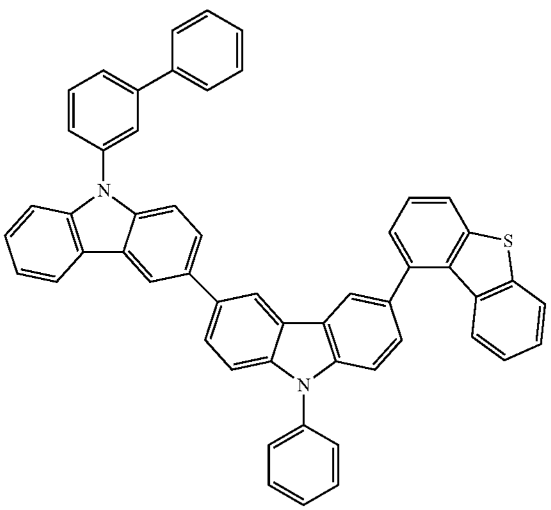
H1-109
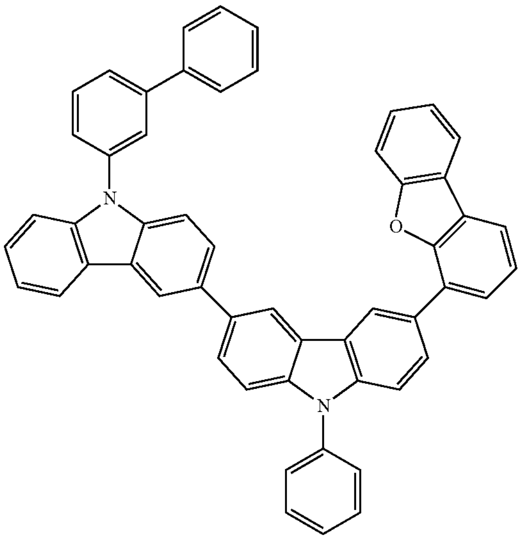
H1-110
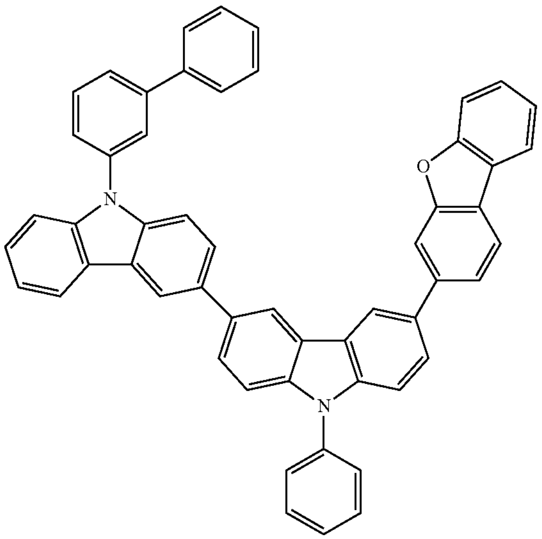
-continued
H1-111
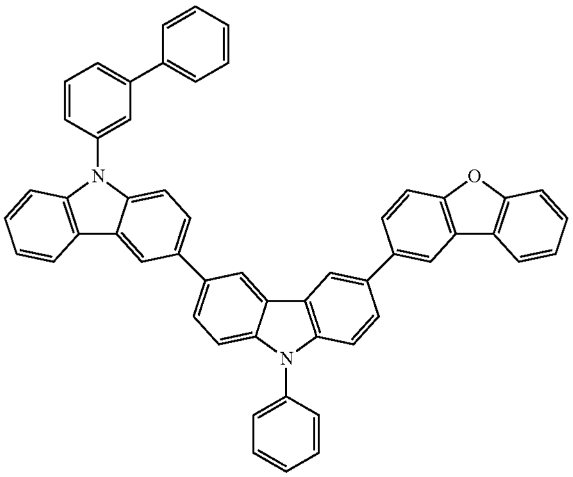
H1-112
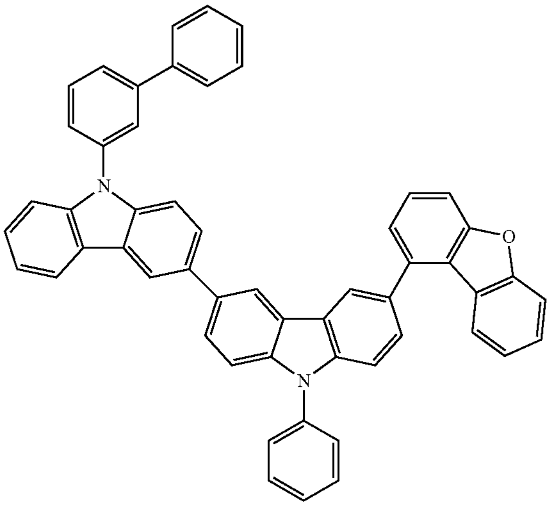
H1-113
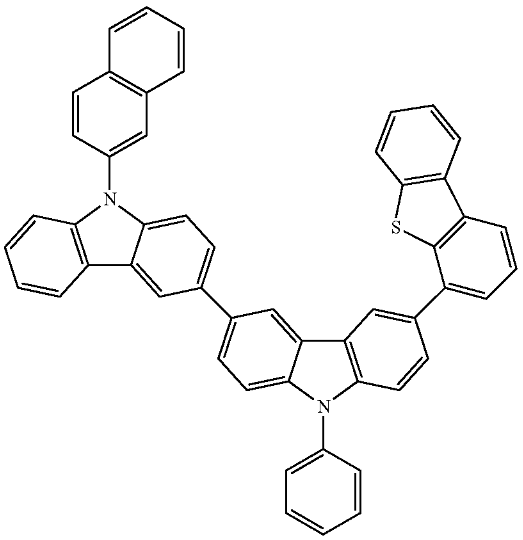

-continued
H1-114
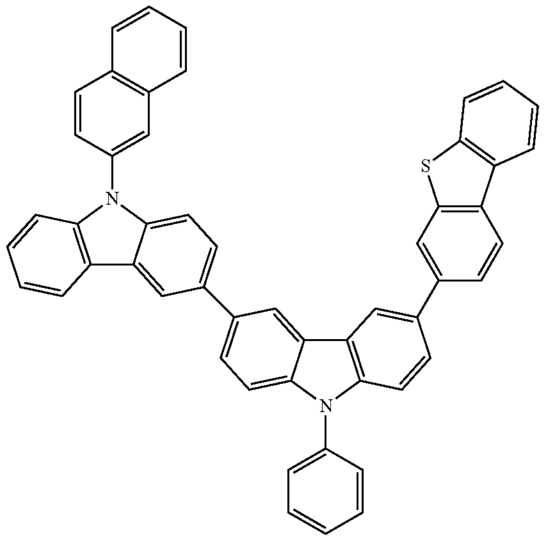
H1-115
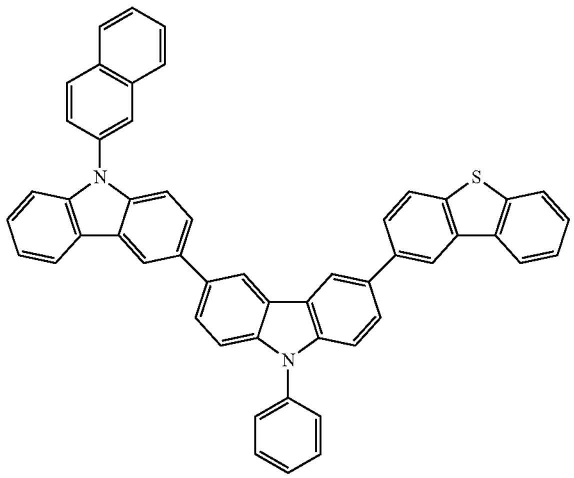
H1-116
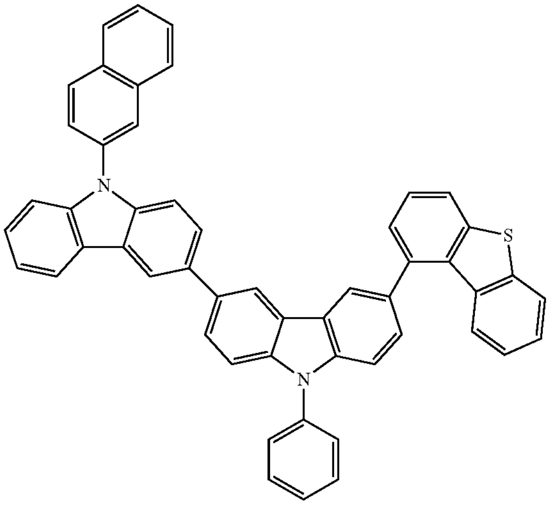
-continued
H1-117
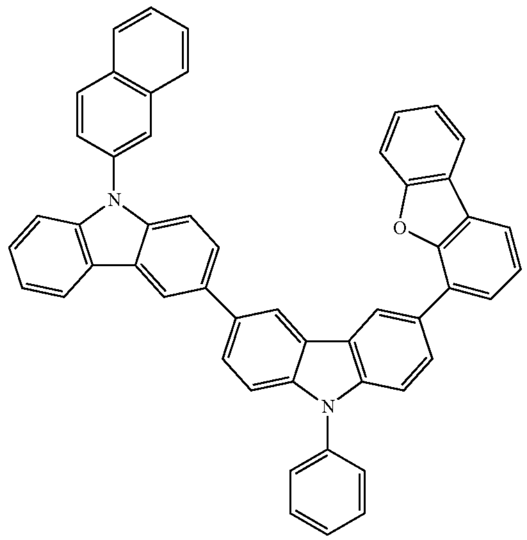
H1-118
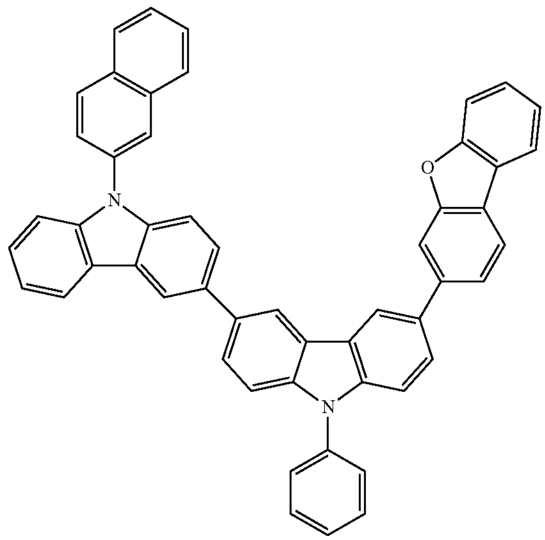
H1-119
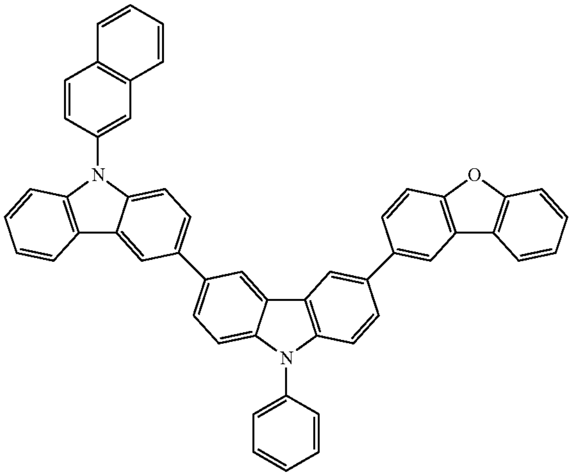

-continued
H1-120
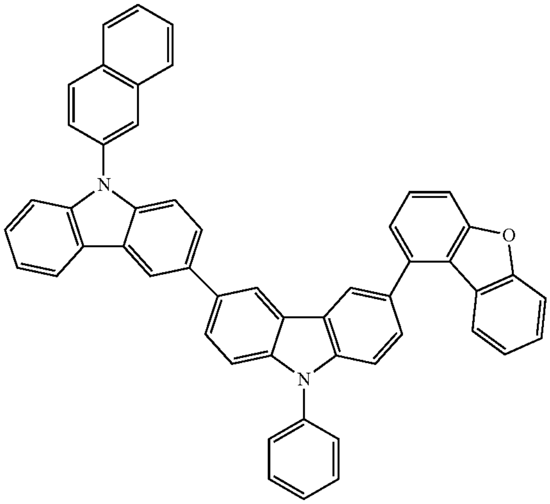
H1-121
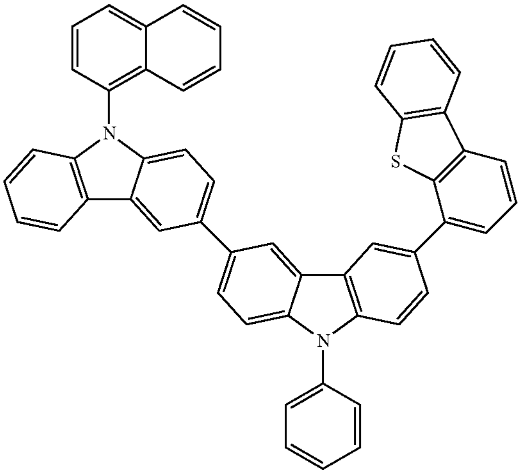
H1-122
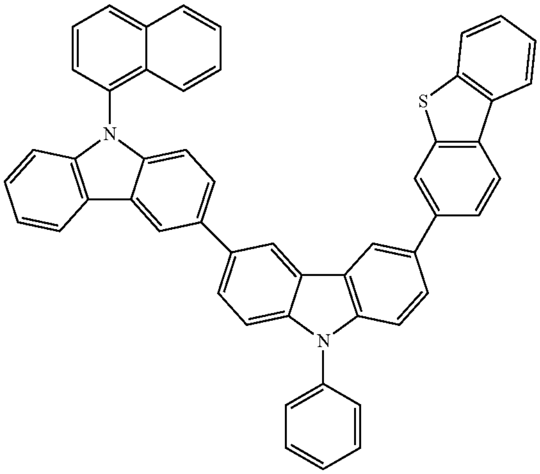
-continued
H1-123
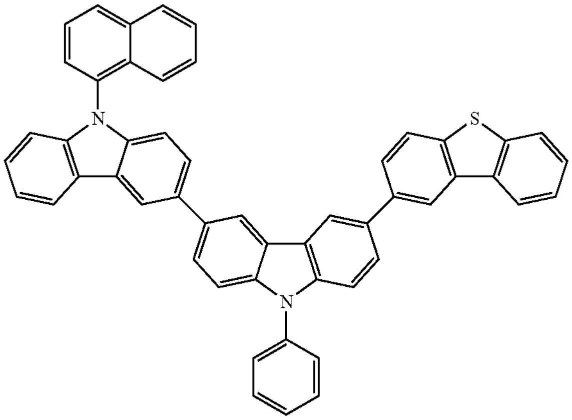
H1-124
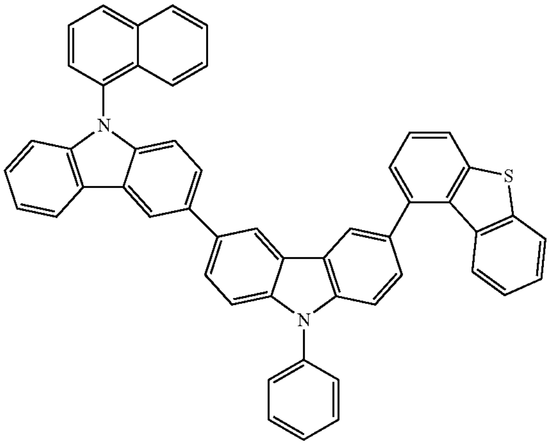
H1-125
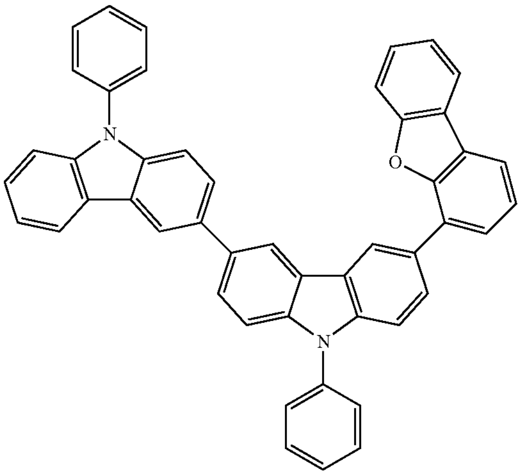

-continued
H1-126
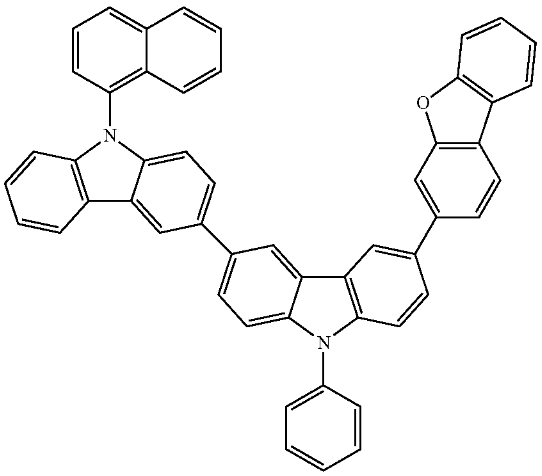
H1-127
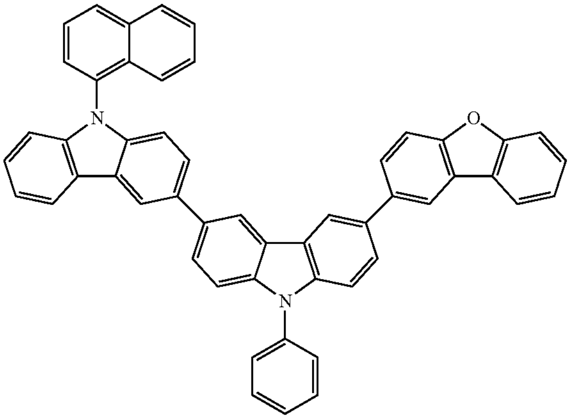
H1-128
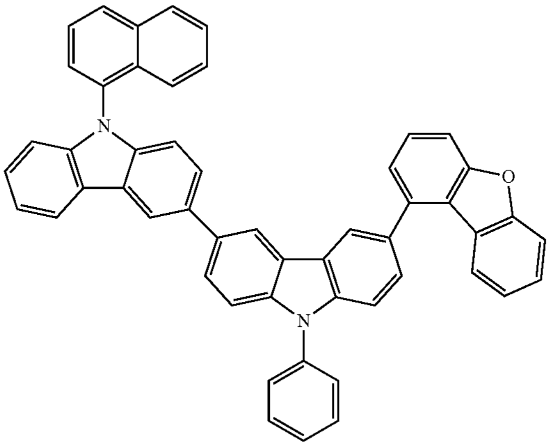
-continued
H1-129
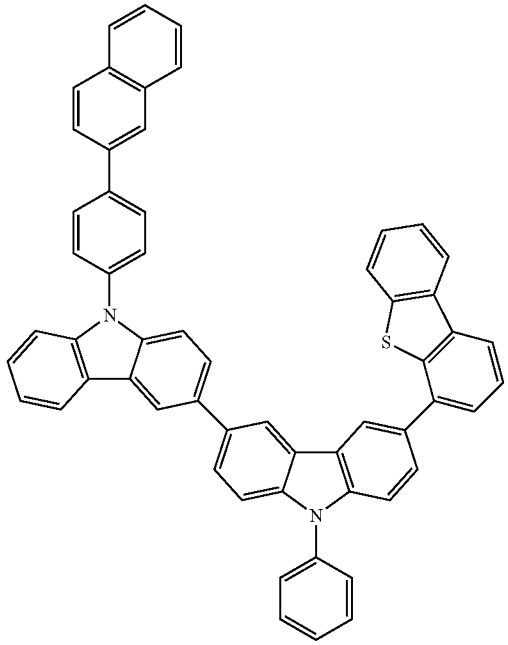
H1-130
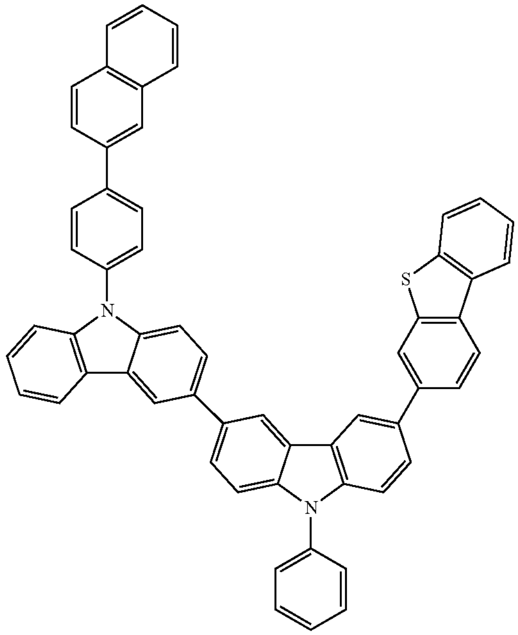

-continued
H1-131
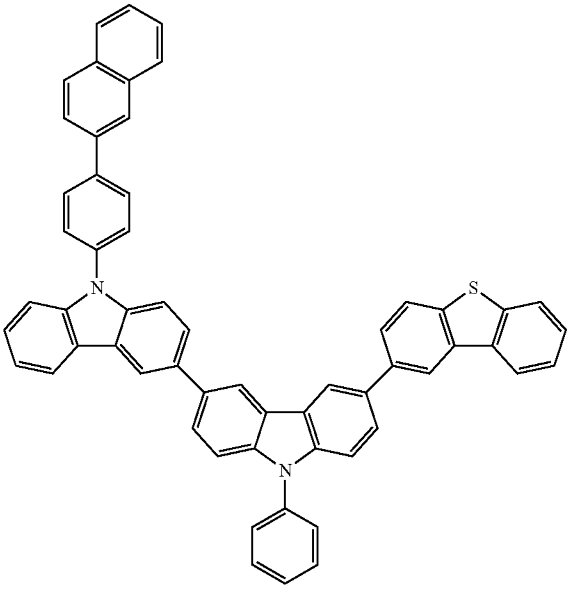
H1-132
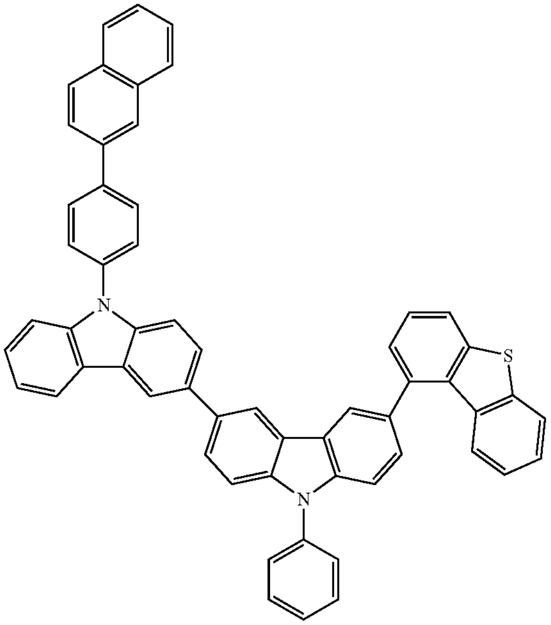
-continued
H1-133
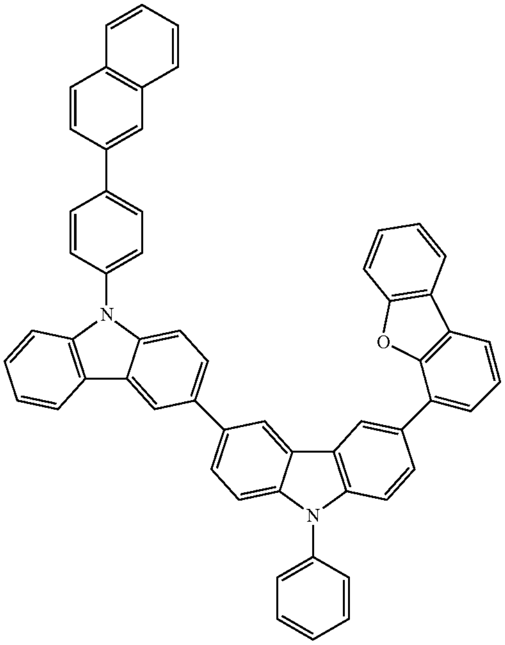
H1-134
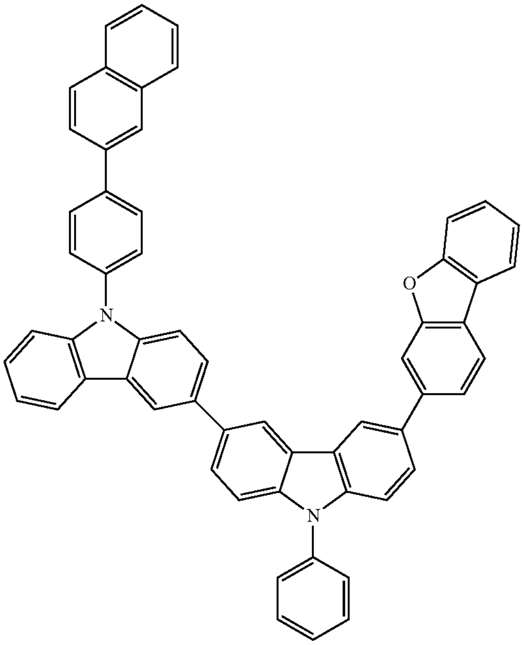

-continued
H1-135
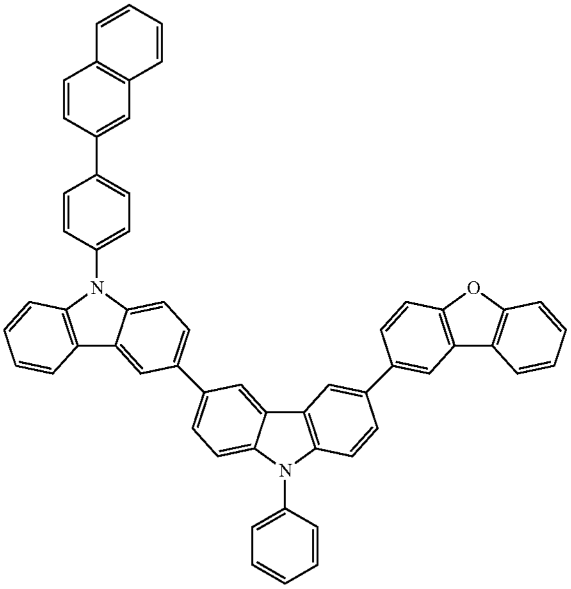
H1-136
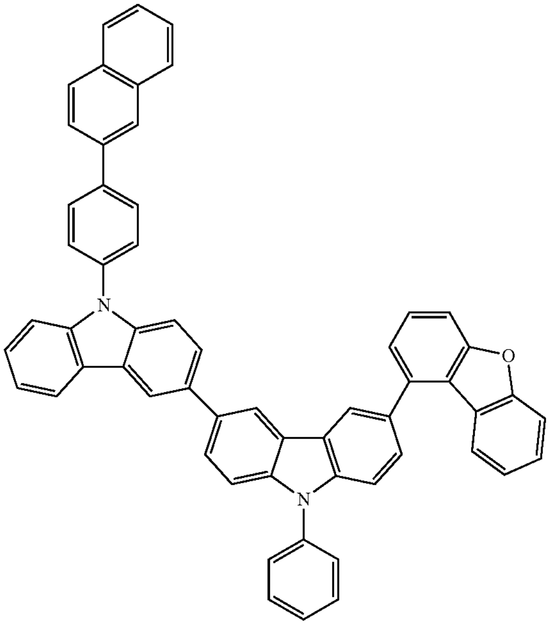
-continued
H1-137
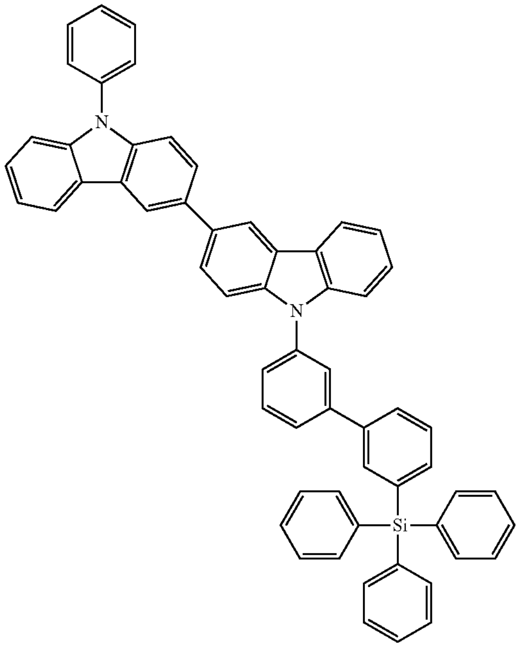
H1-138
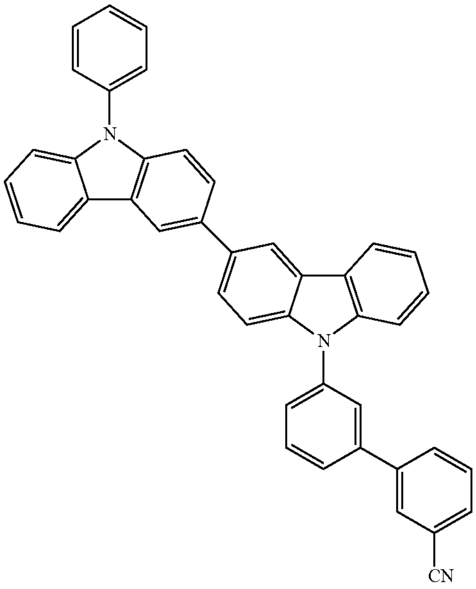

-continued
H1-139
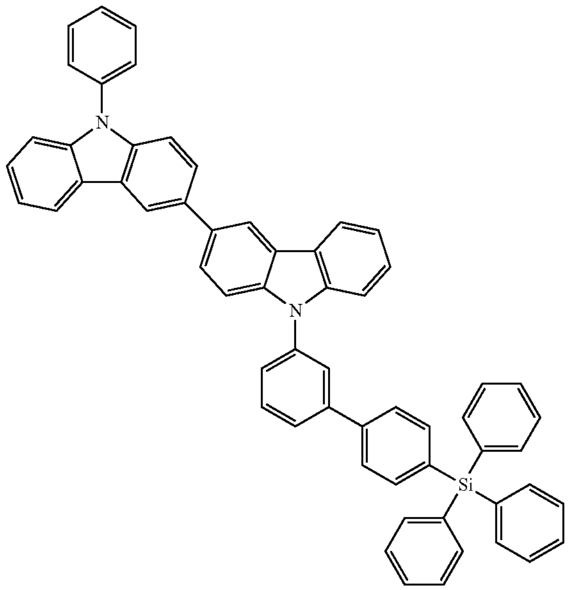
H1-140
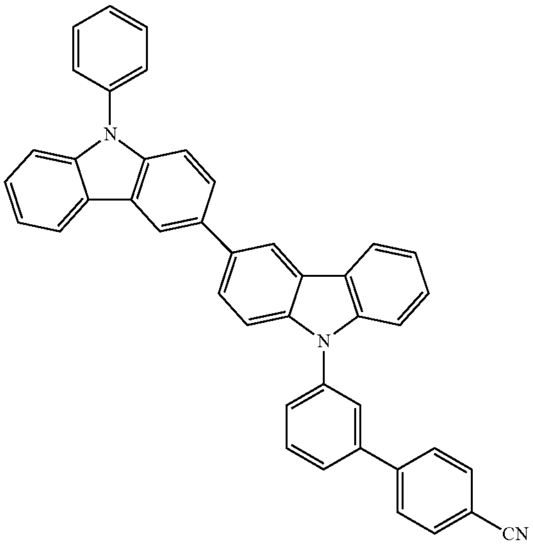
-continued
H1-141
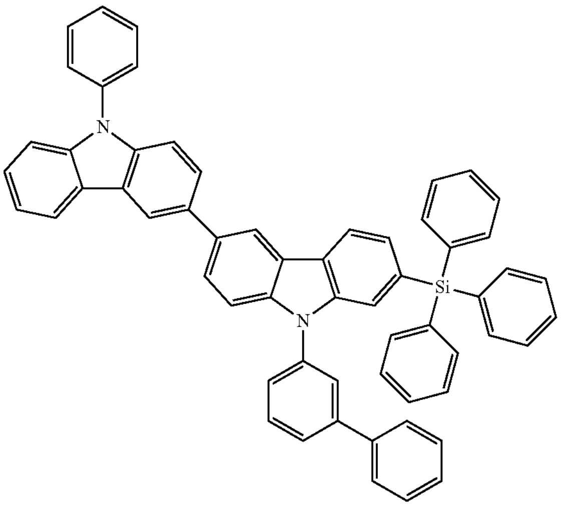
H1-142
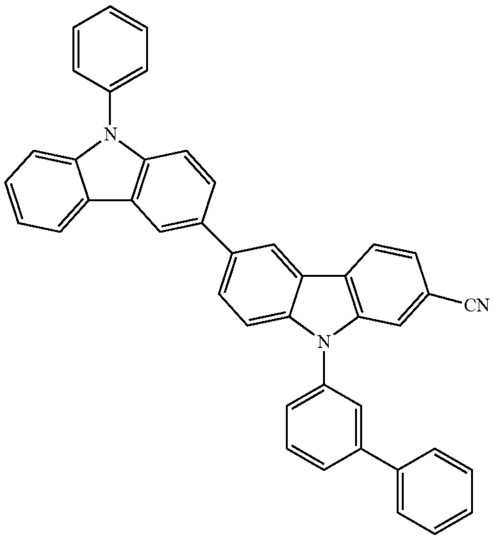
H1-143
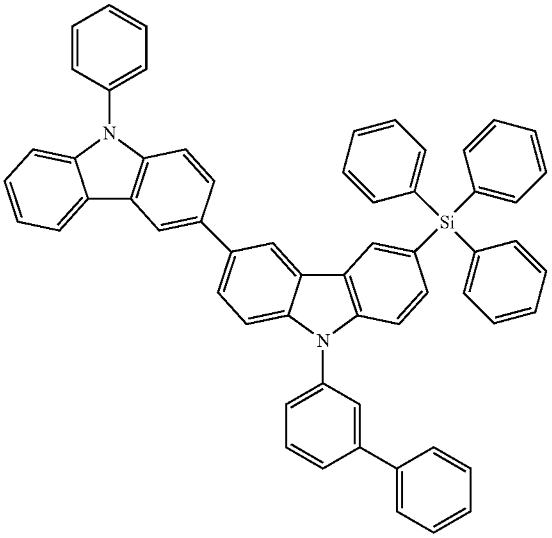

-continued
H1-144
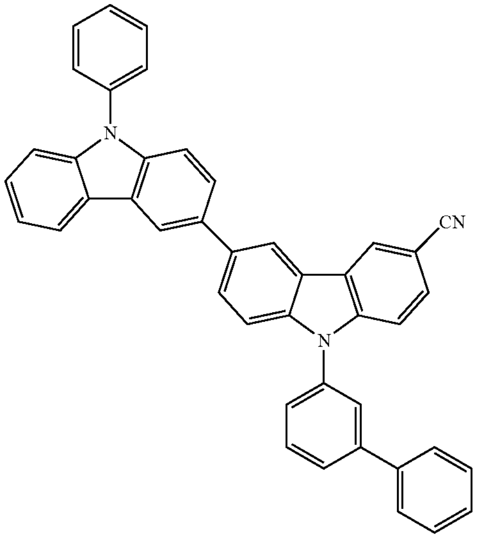
H1-145
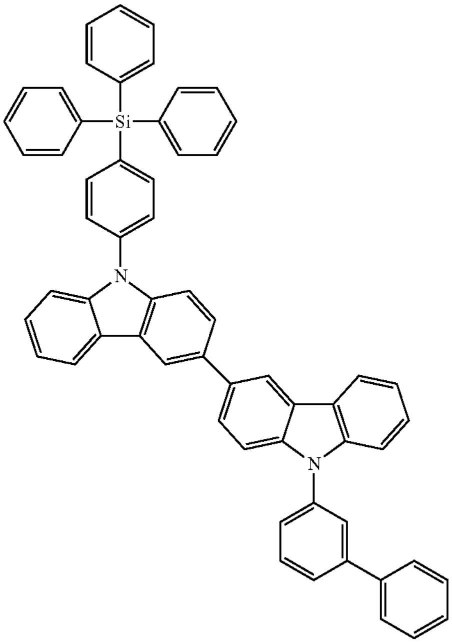
-continued
H1-146
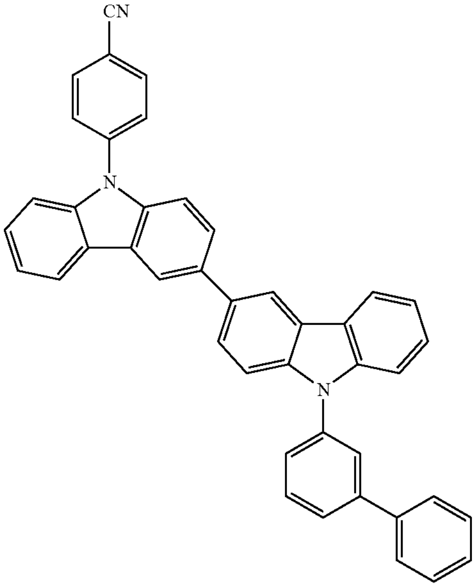
H1-147
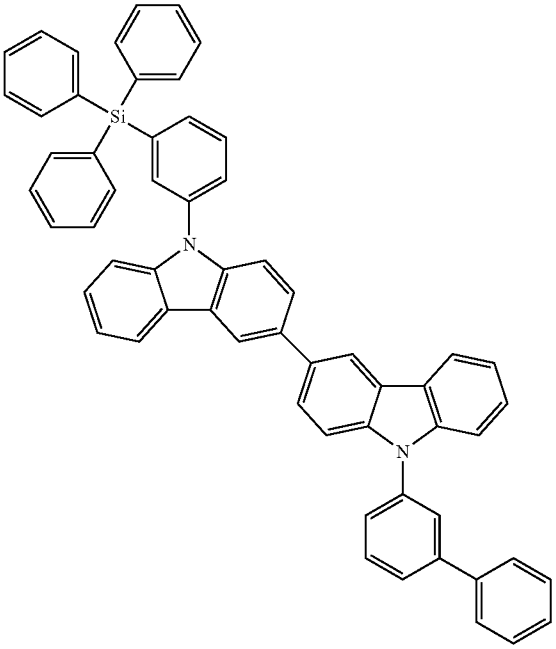

-continued
H1-148
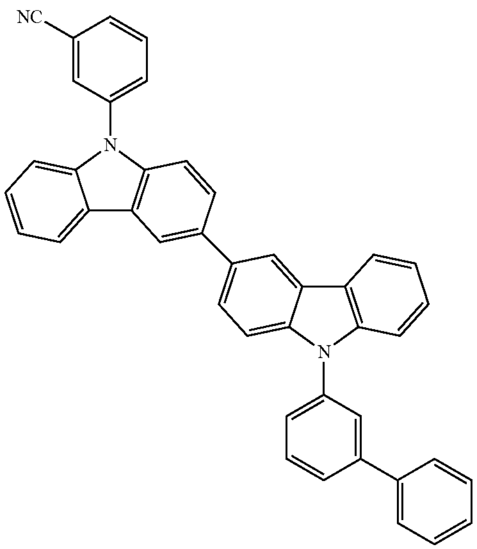
H1-149
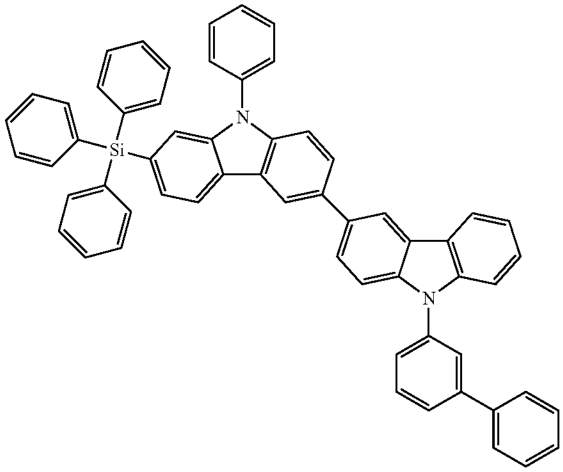
H1-150
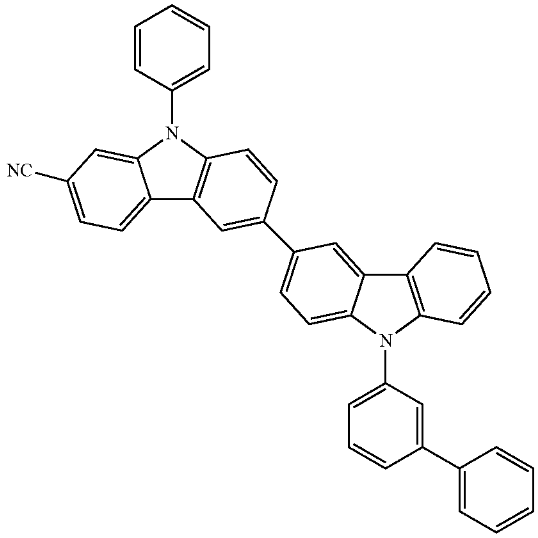
-continued
H1-151
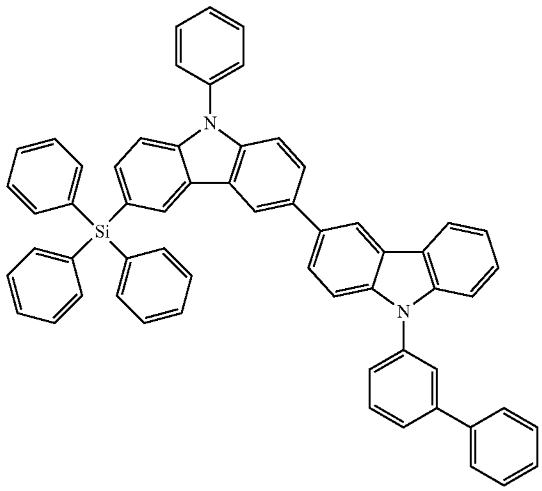
H1-152
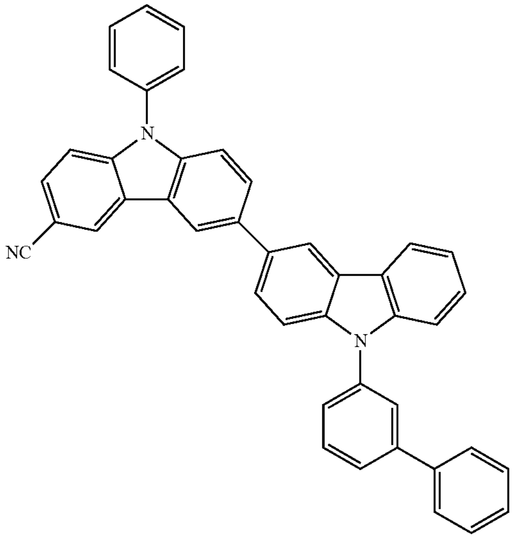
H1-153
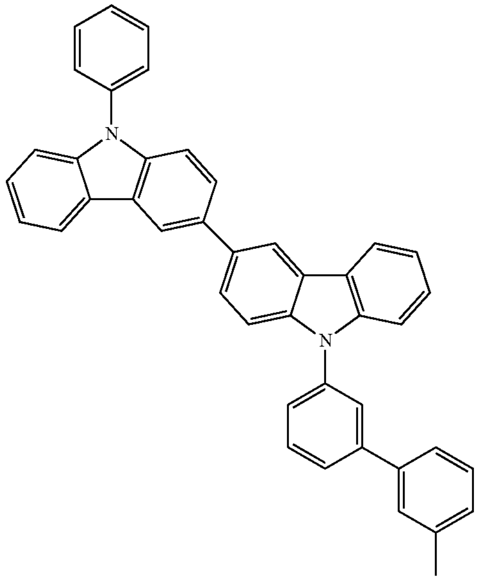

-continued
H1-154
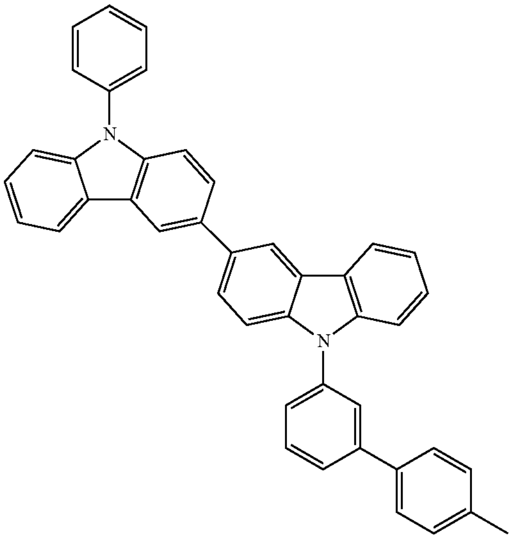
H1-155
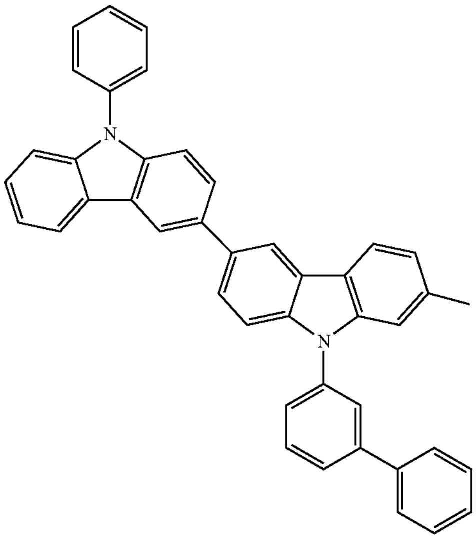
H1-156
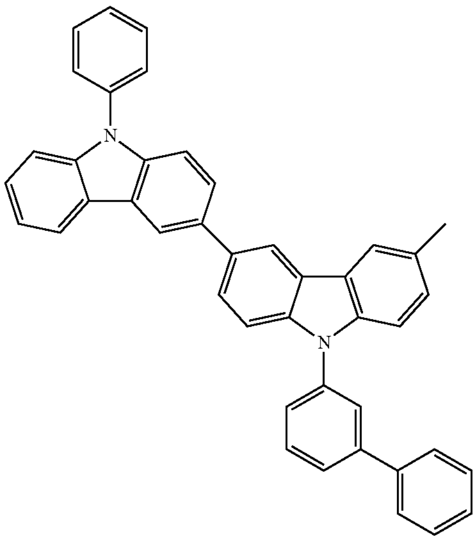
-continued
H1-157
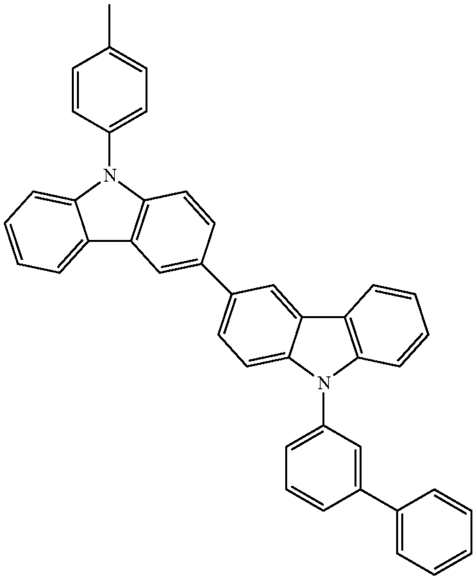
H1-158
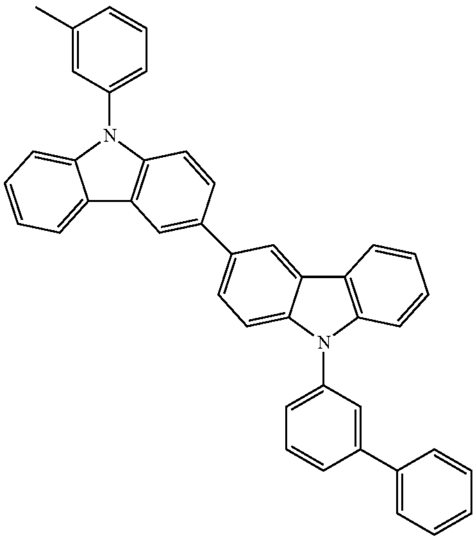

-continued
H1-159
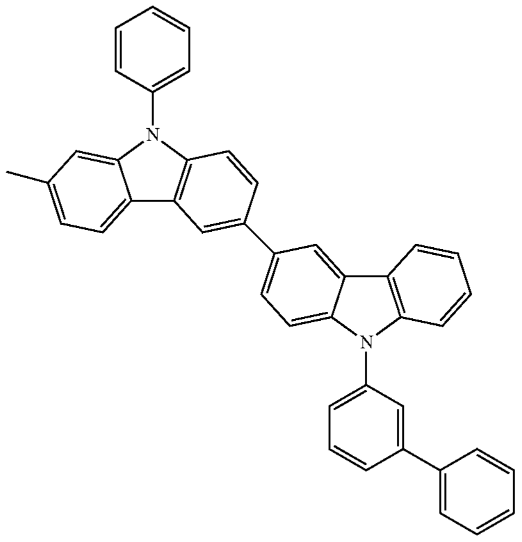
H1-160
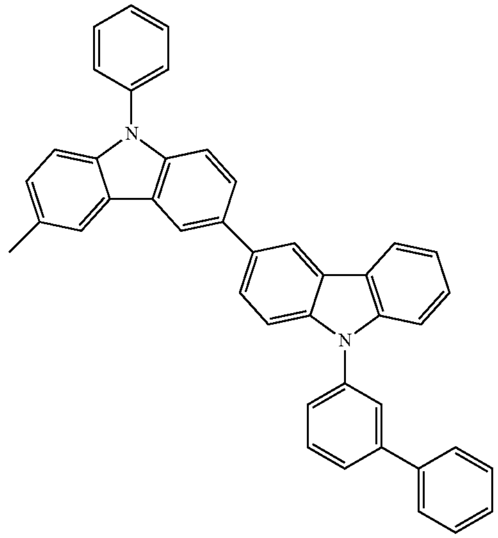
H1-161
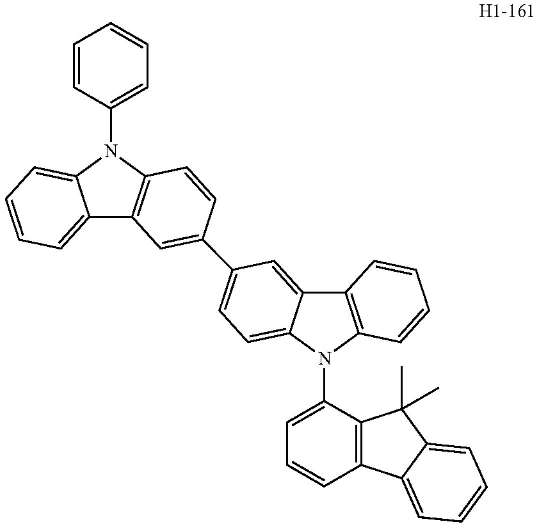
-continued
H1-162
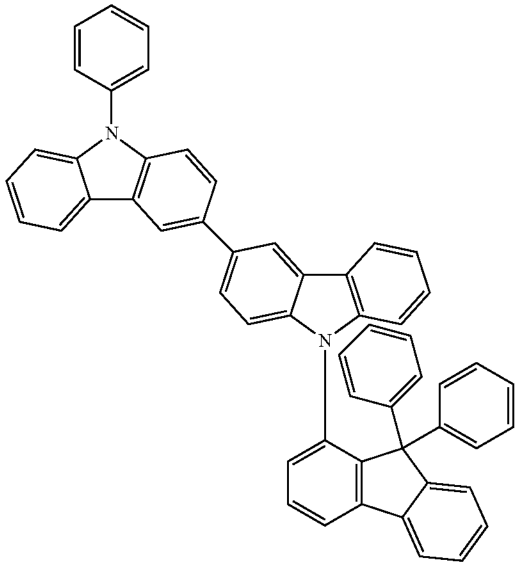
H1-163
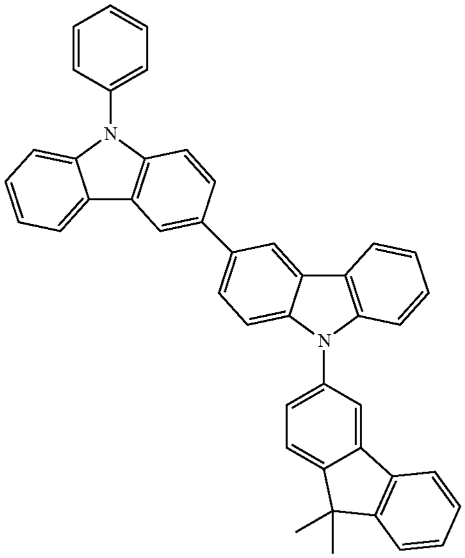

-continued
H1-164
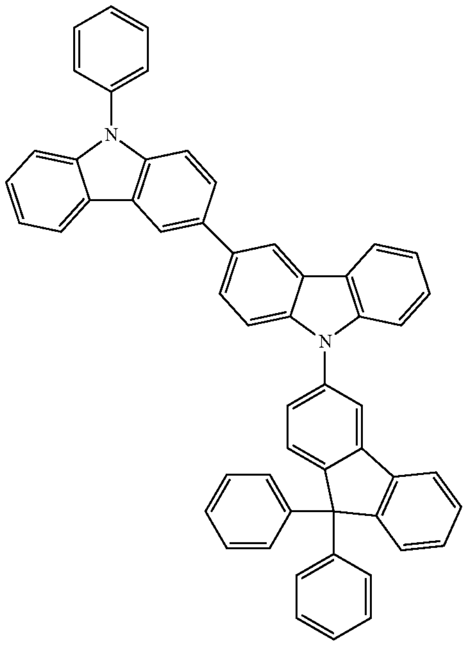
H1-165
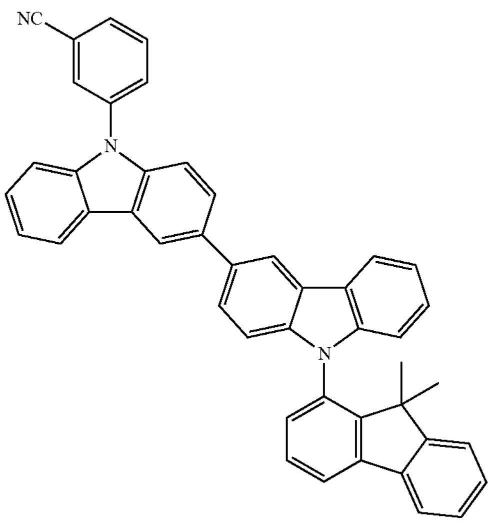
-continued
H1-166
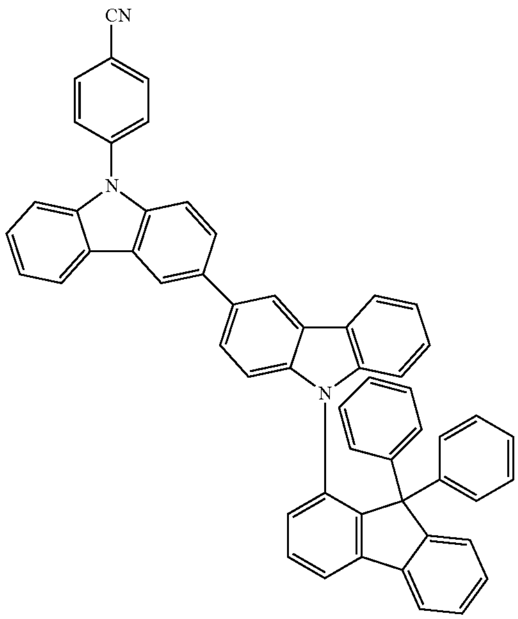
H1-167
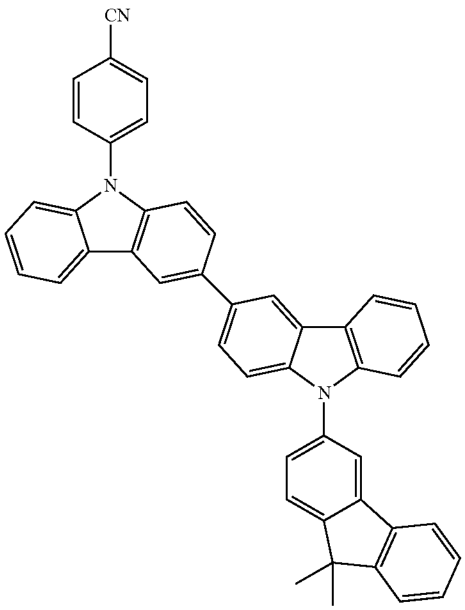

-continued
H1-168
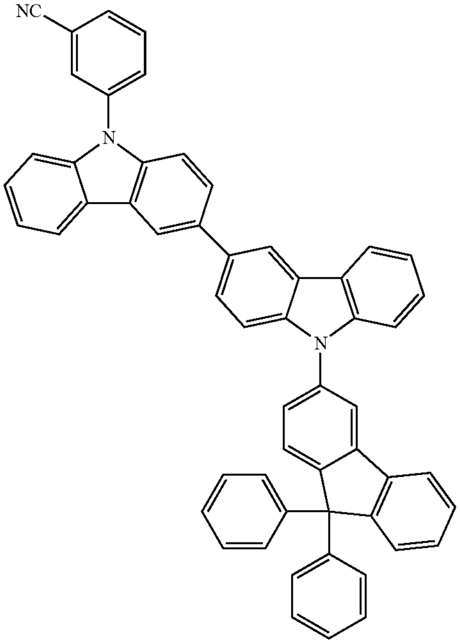
H1-169
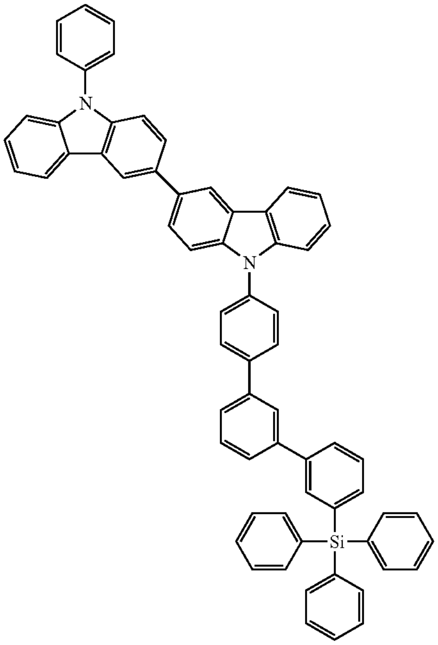
-continued
H1-170
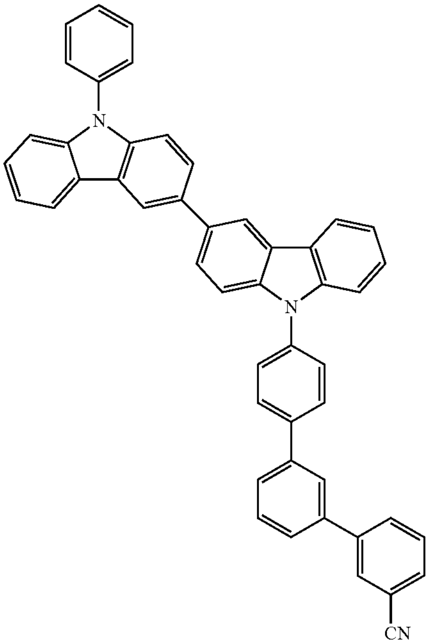
H1-171
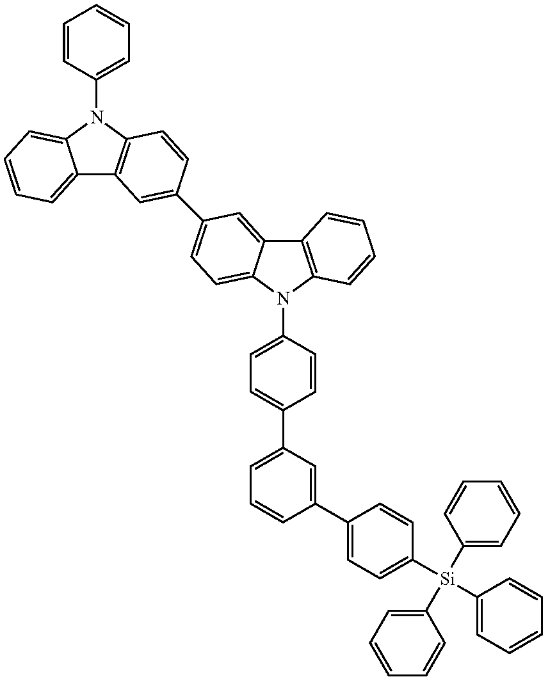

-continued
H1-172
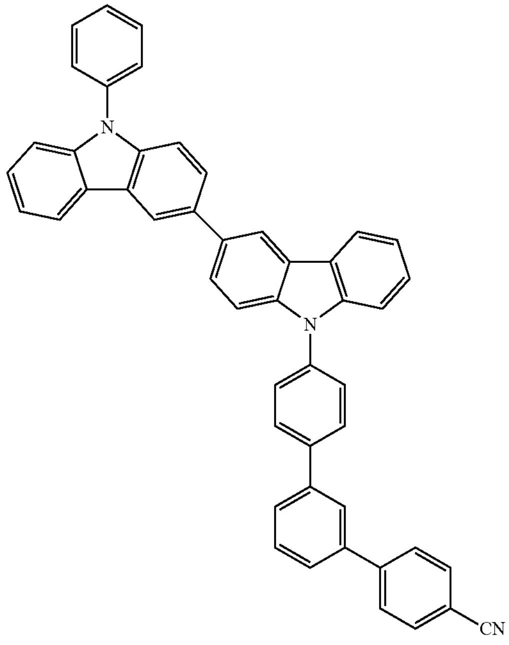
H1-173
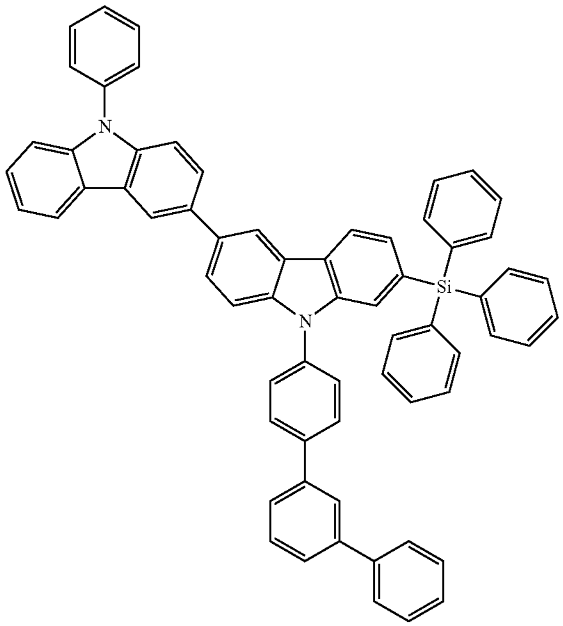
-continued
H1-174
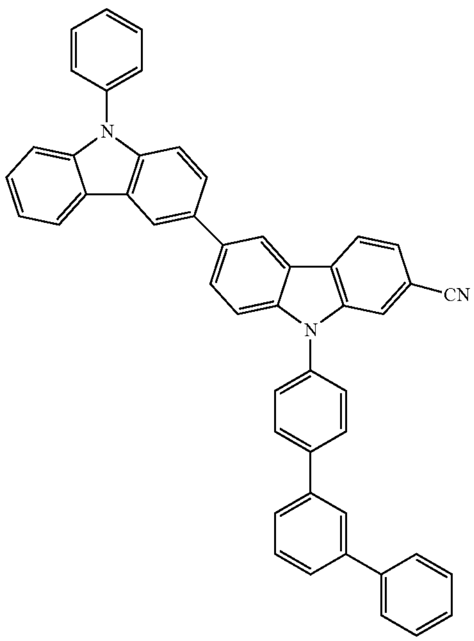
H1-175
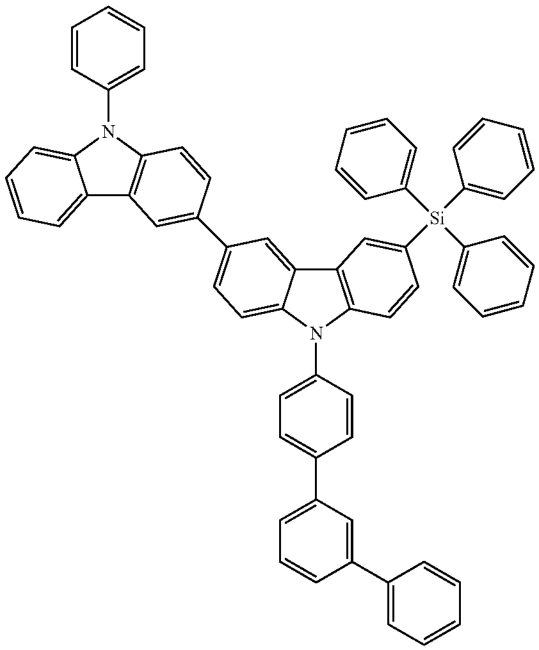

-continued
H1-176
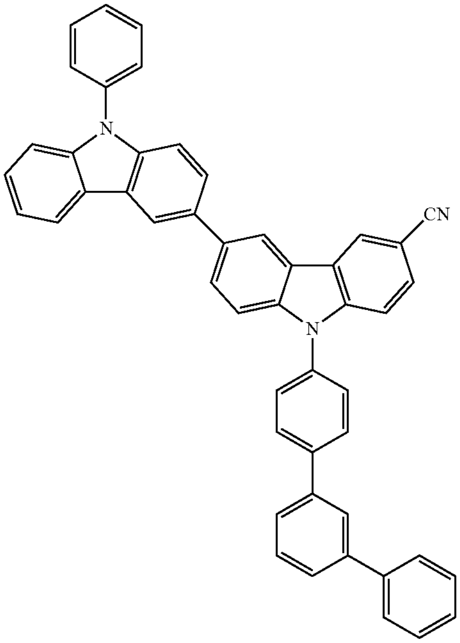
-continued
H1-178
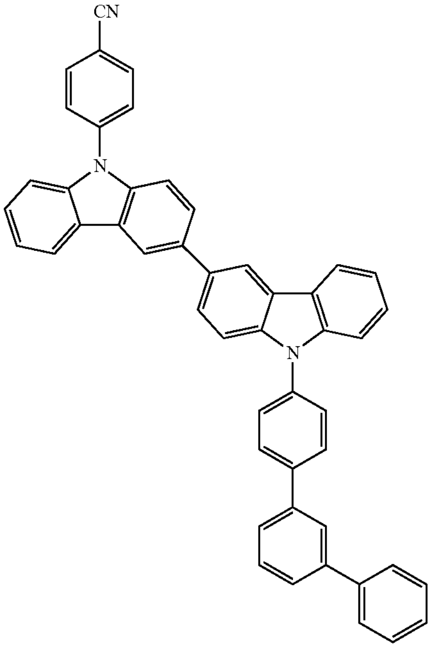
H1-177
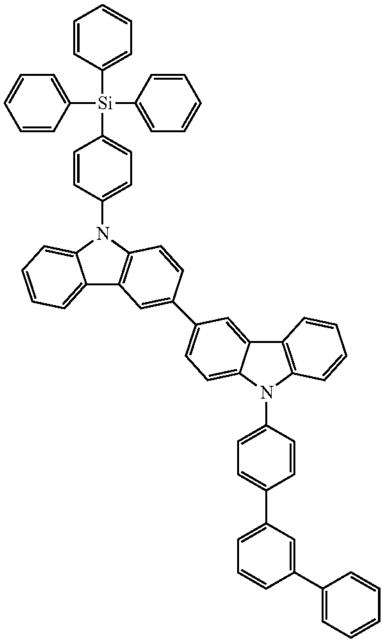
H1-179
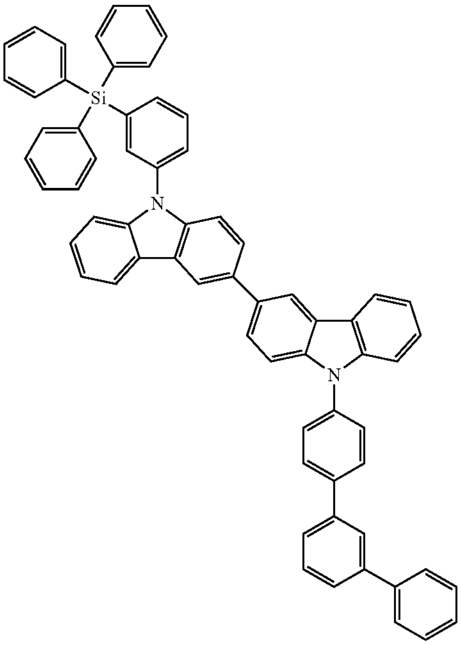

-continued
H1-180
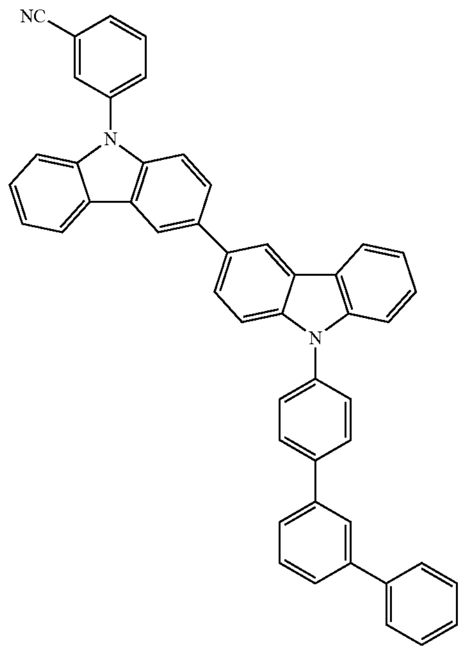
H1-181
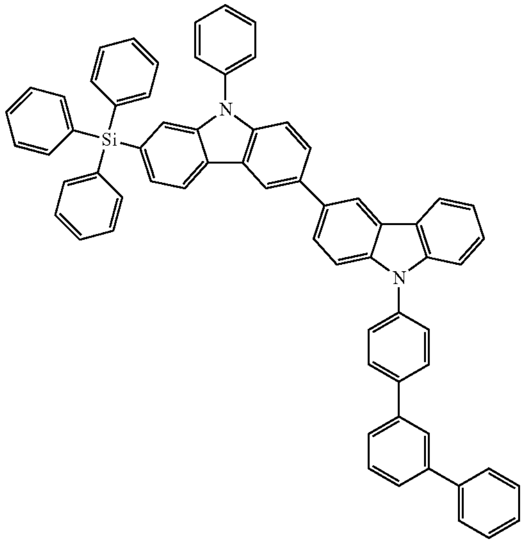
-continued
H1-182
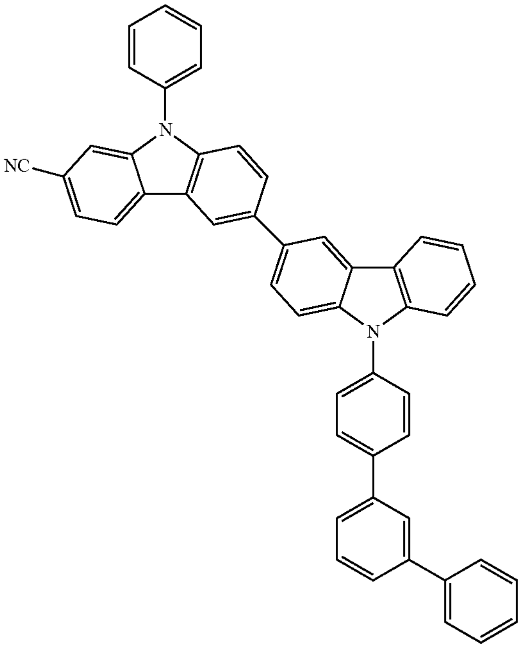
H1-183
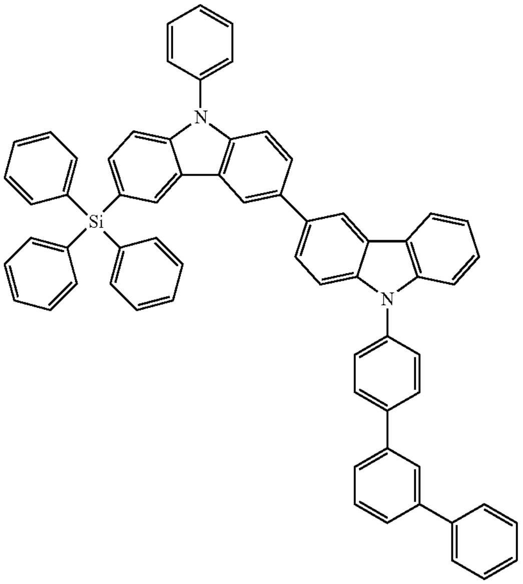

-continued
H1-184
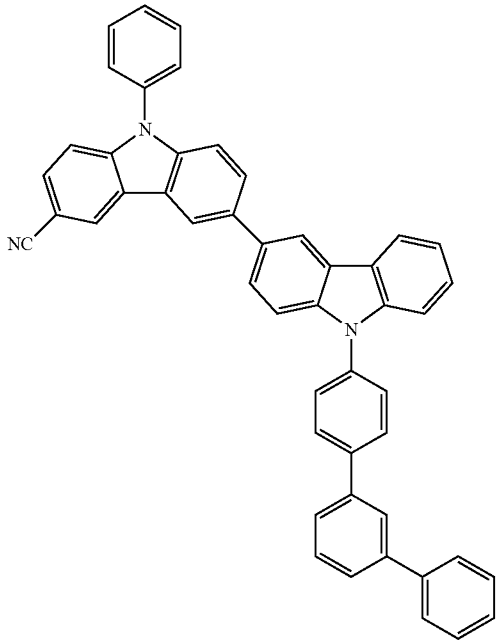
H1-185
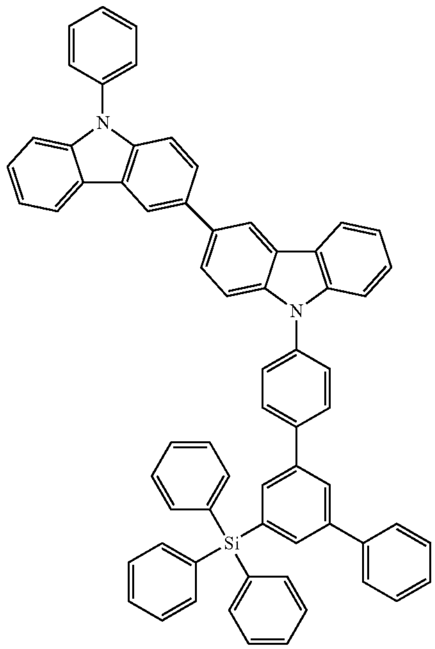
-continued
H1-186
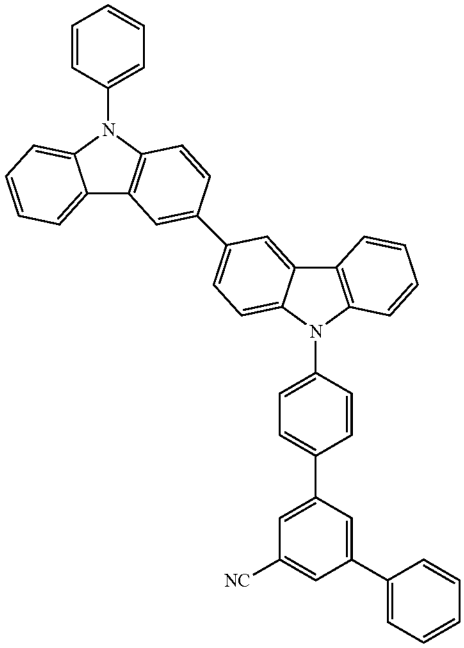
H1-187
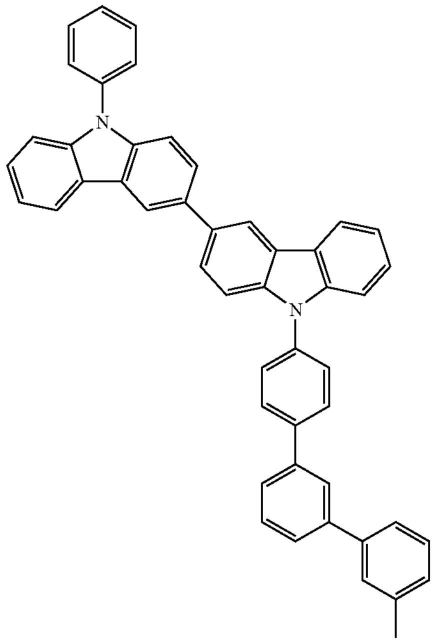

-continued
H1-188
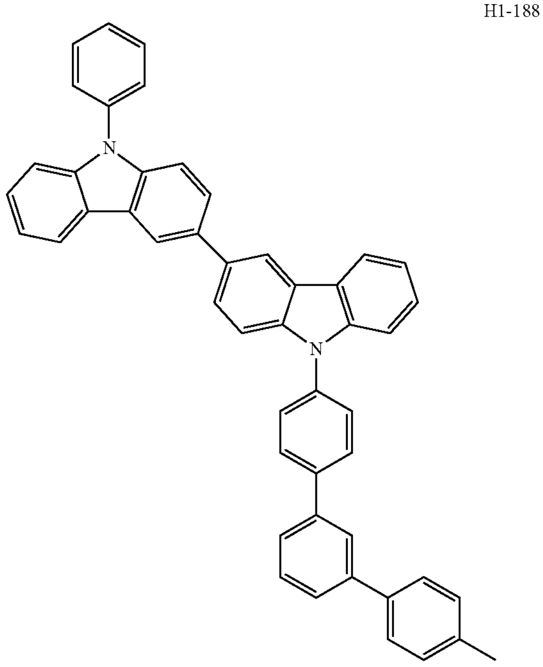
H1-189
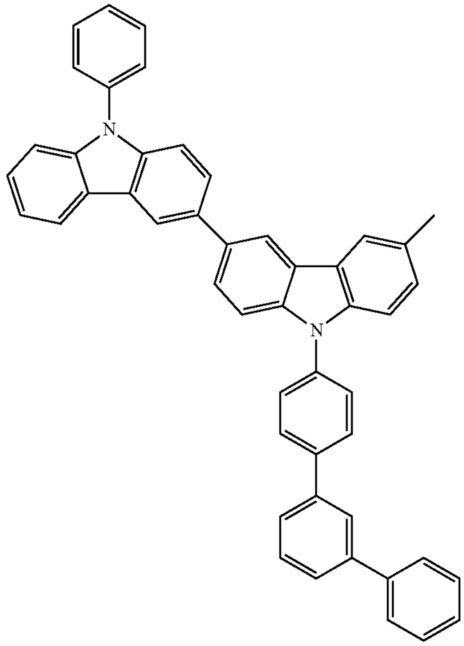
-continued
H1-190
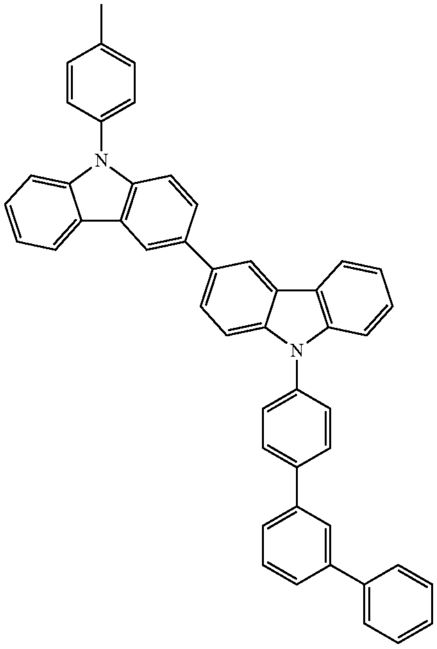
H1-191
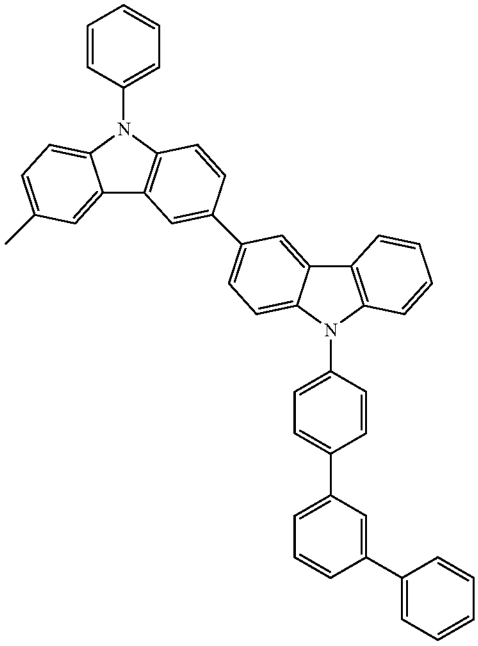

-continued
H1-192
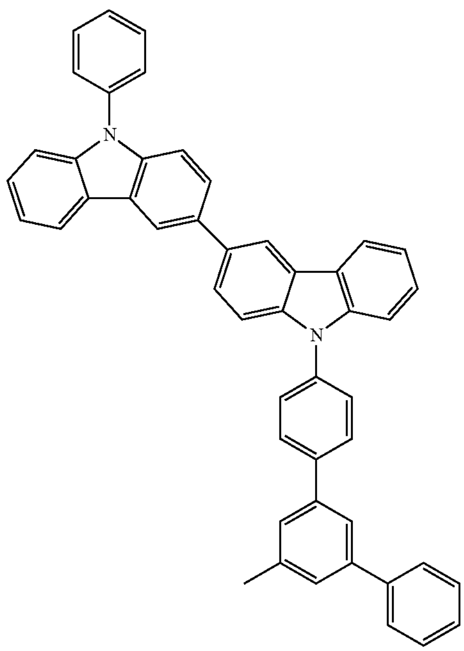
H1-193
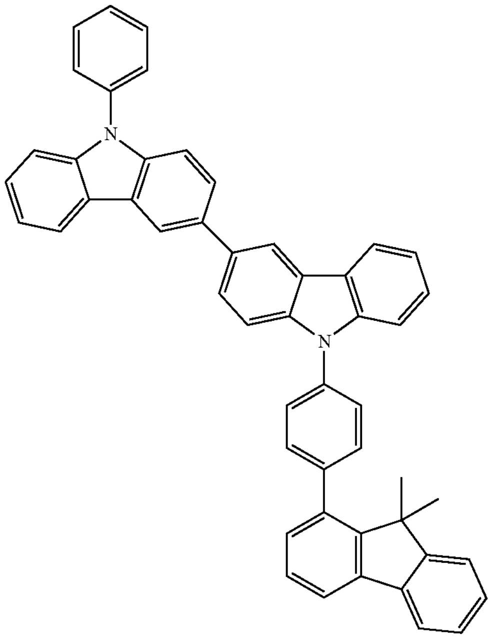
-continued
H1-194
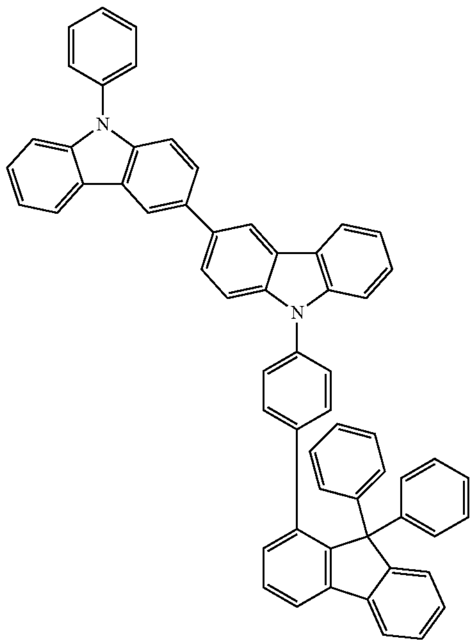
H1-195
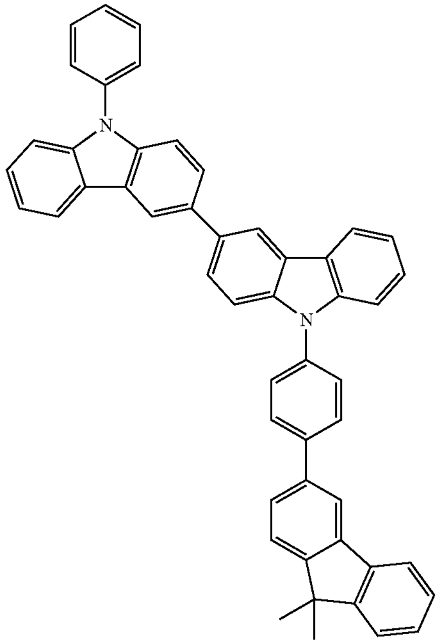

-continued
H1-196
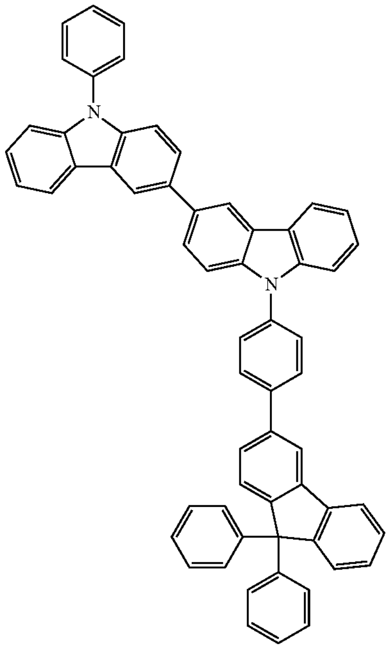
H1-197
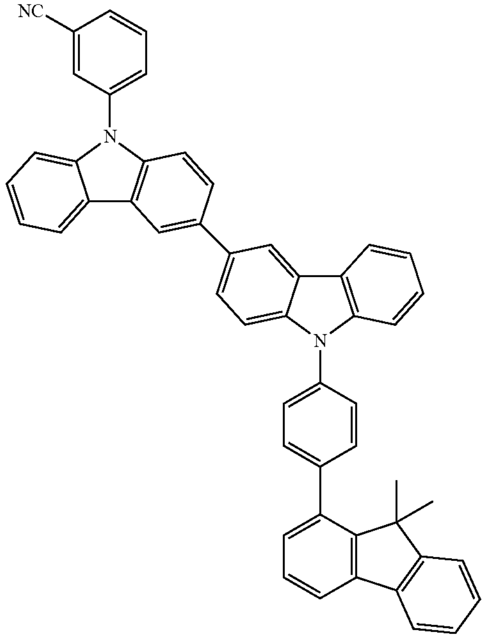
-continued
H1-198
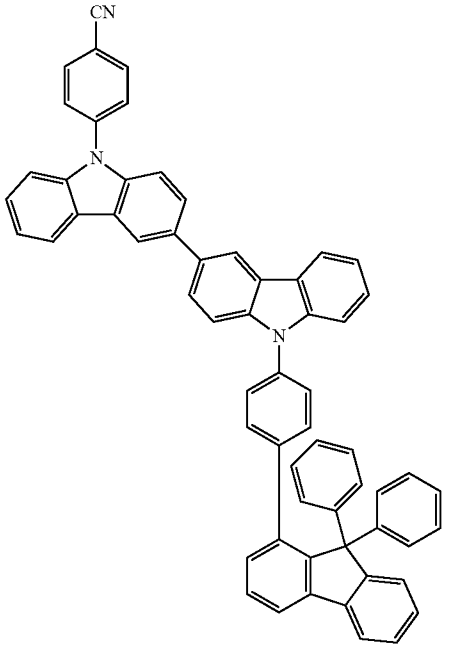
H1-199
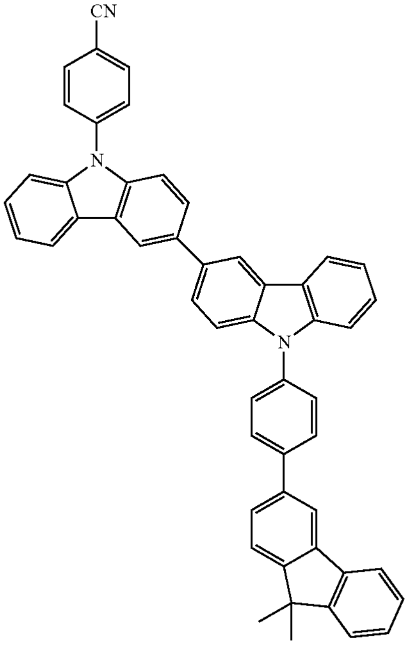

-continued
H1-200
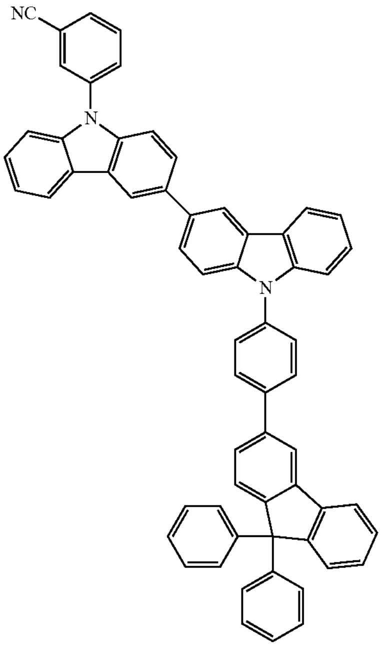
H1-201
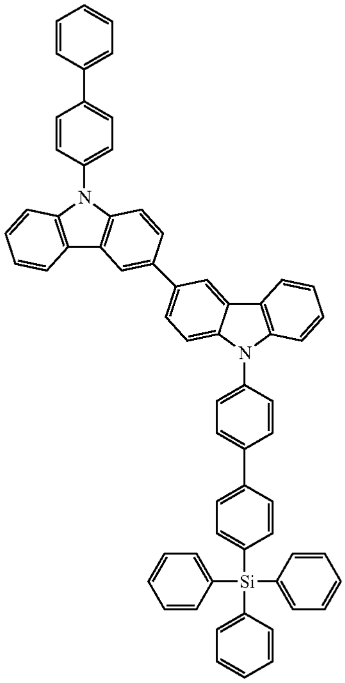
-continued
H1-202
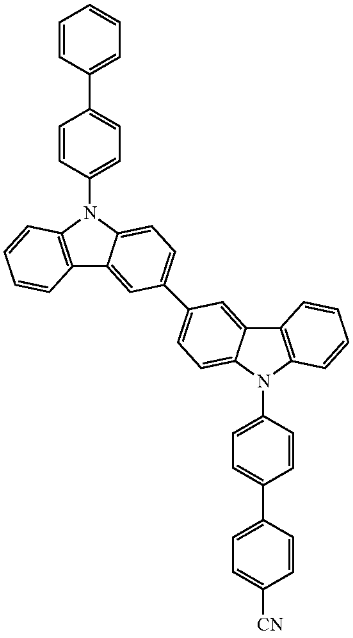
H1-203
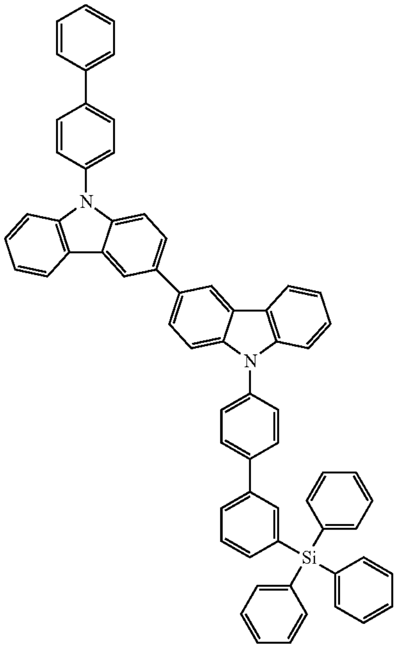

-continued
H1-204
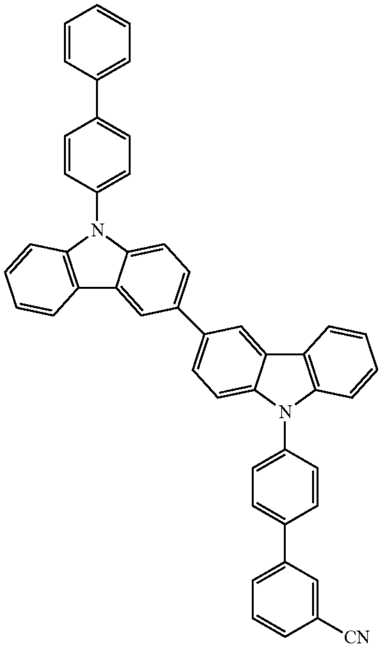
H1-205
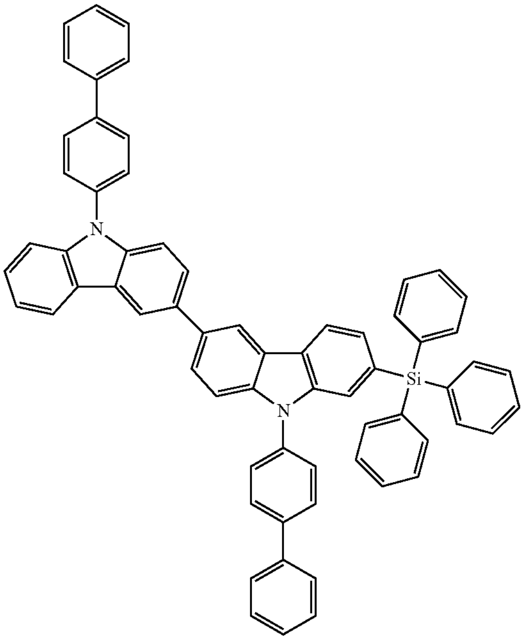
-continued
H1-206
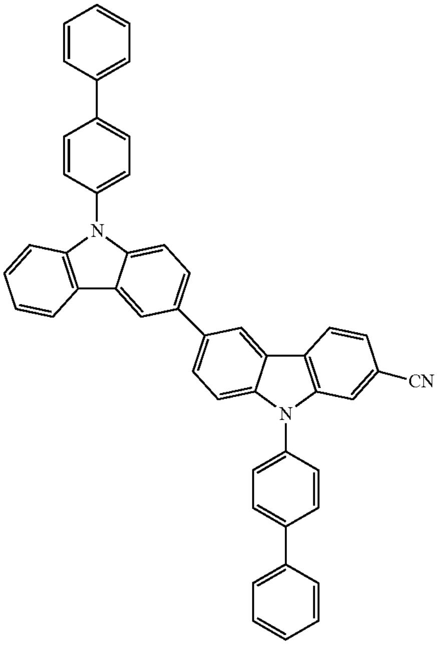
H1-207
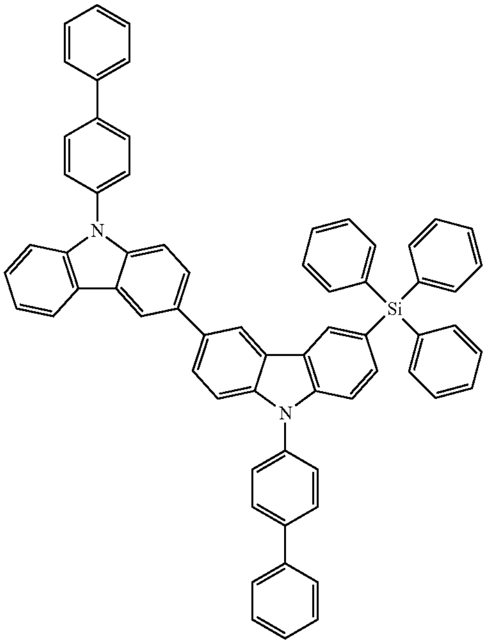

-continued
H1-208
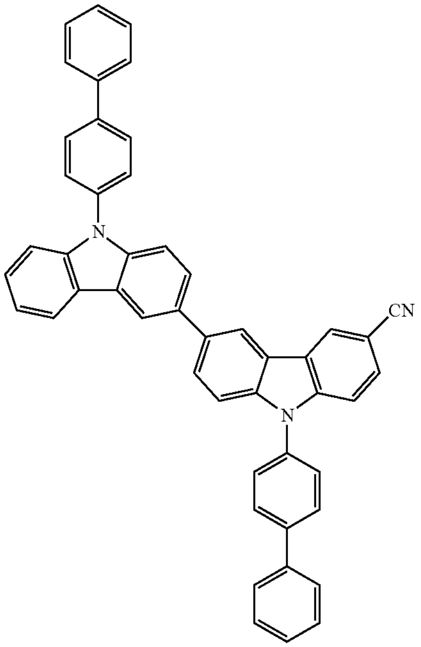
H1-209
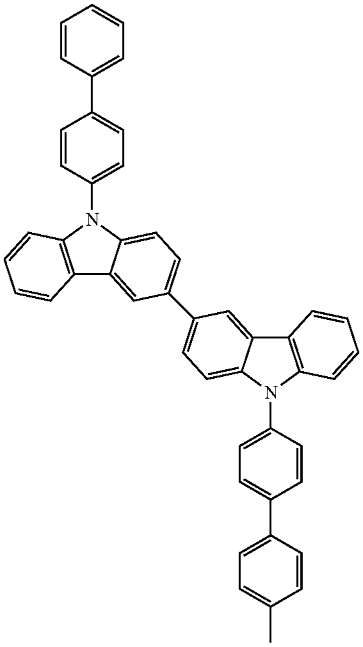
-continued
H1-210
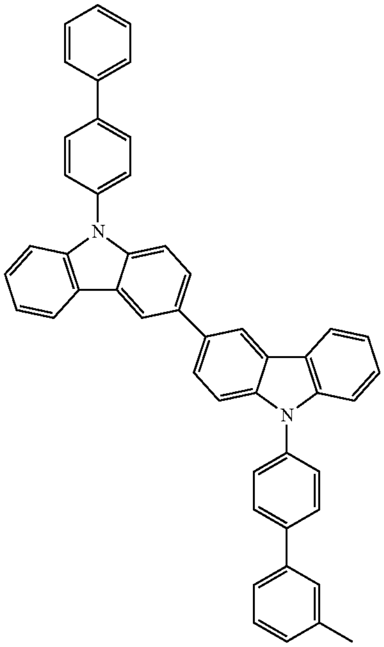
H1-211
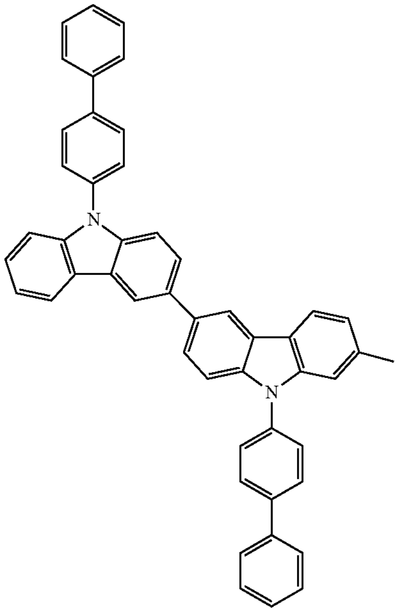

-continued
H1-212
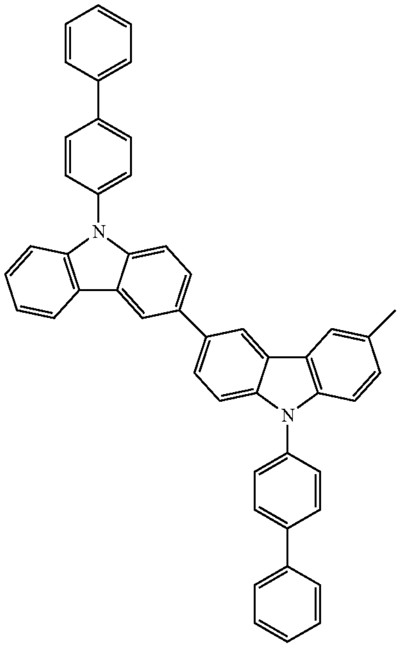
H1-213
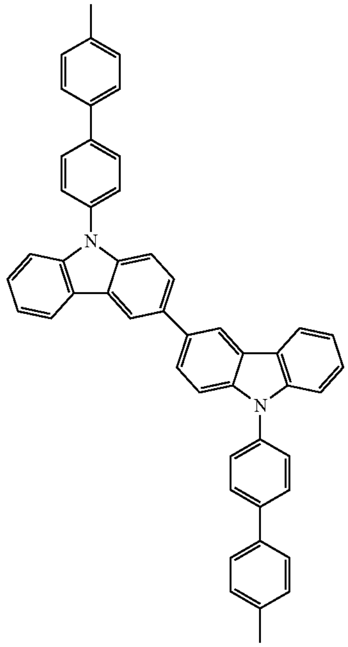
-continued
H1-214
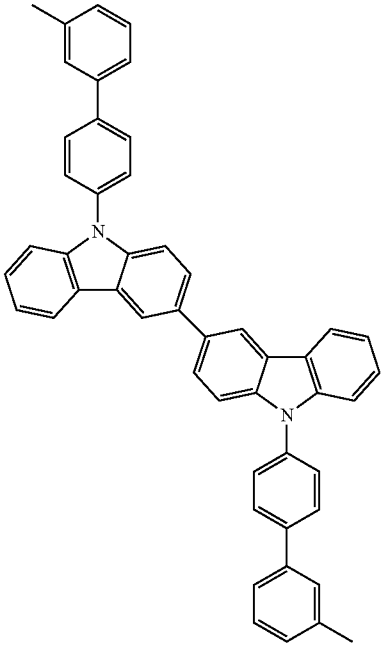
H1-215
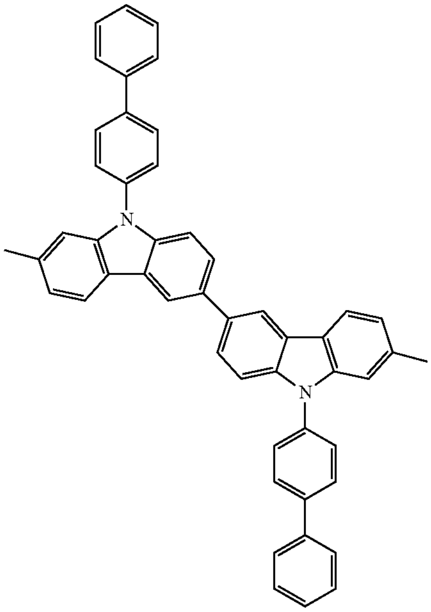

-continued
H1-216
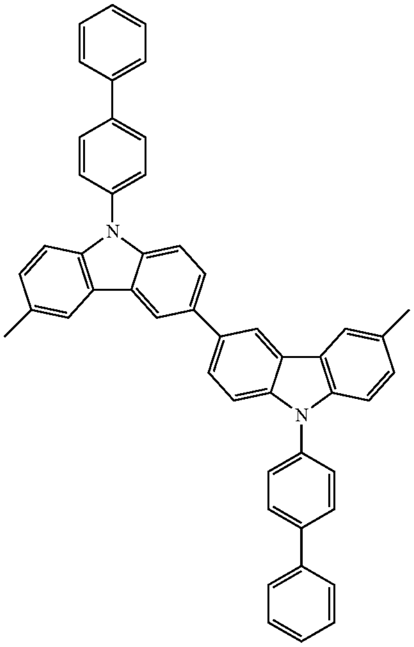
H1-217
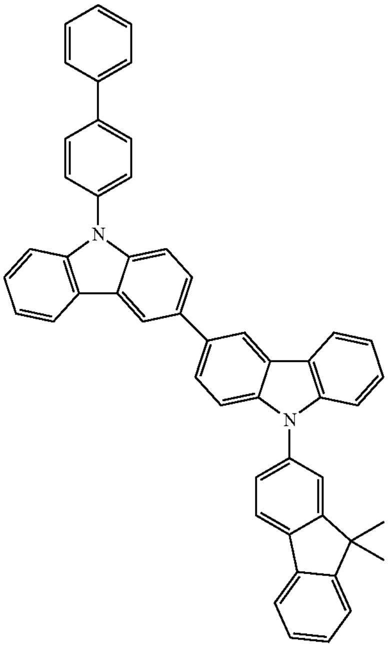
-continued
H1-218
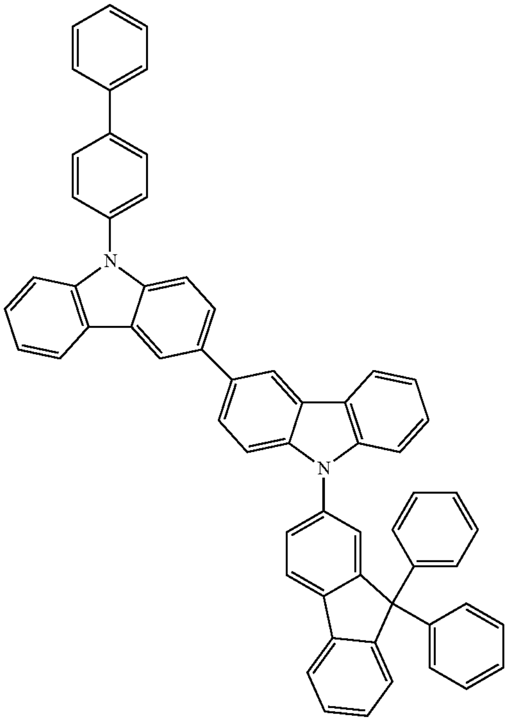
H1-219
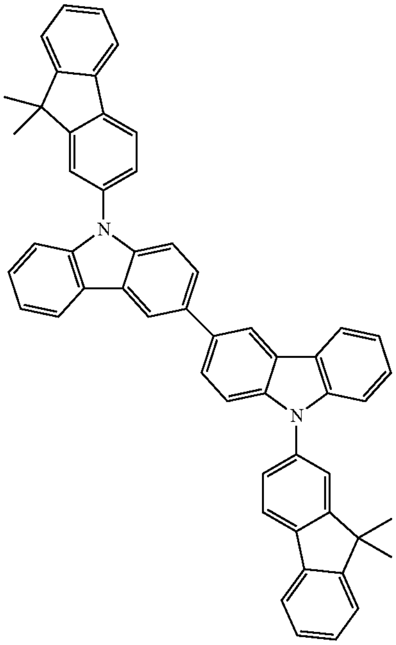

-continued
H1-220
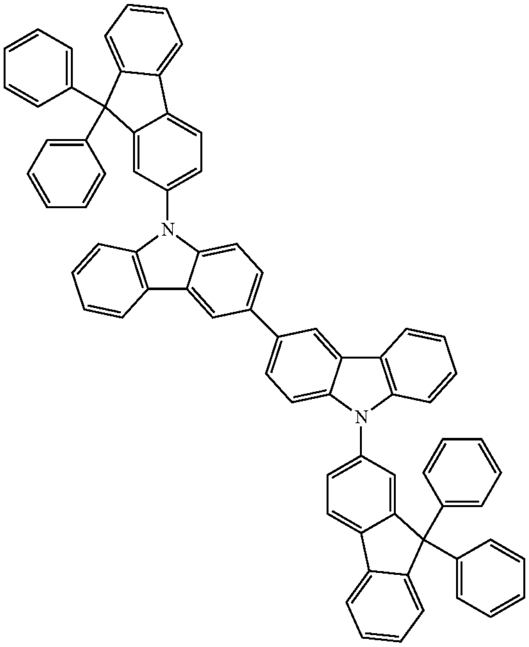
H1-221
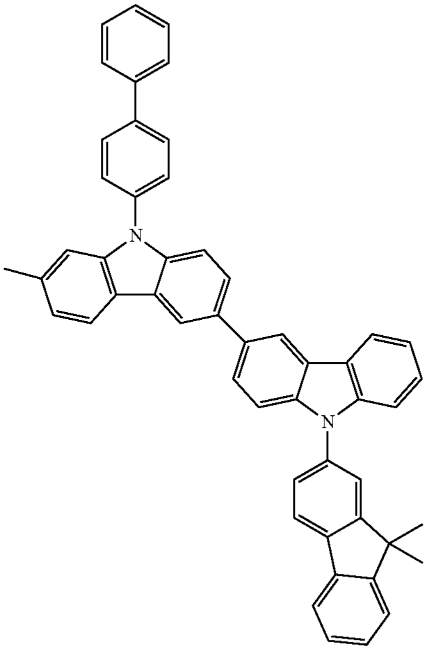
-continued
H1-222
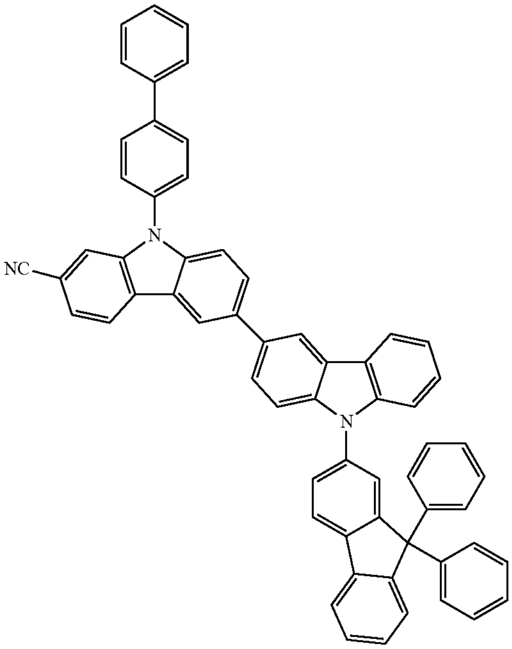
H1-223
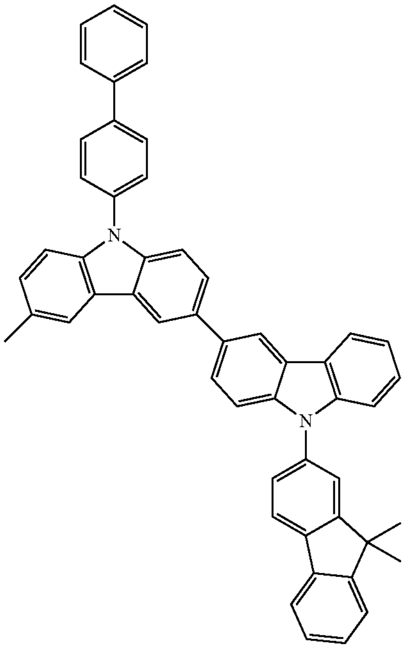

-continued
H1-224
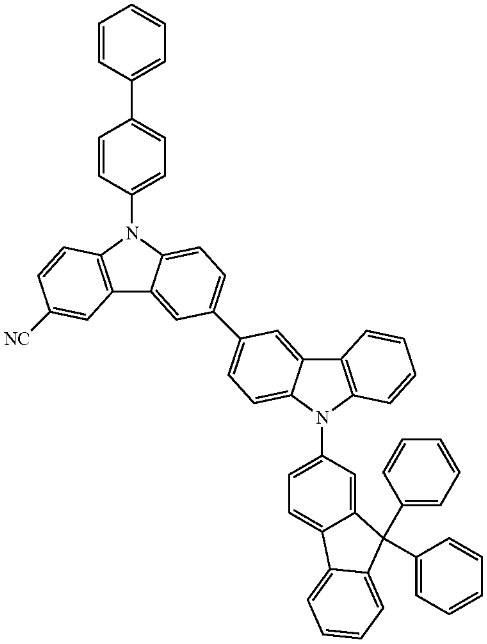
H1-225
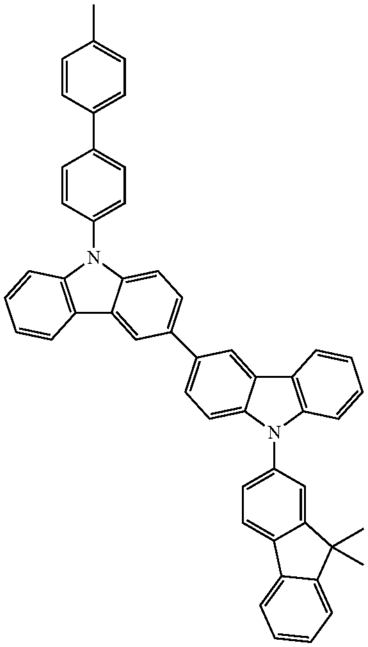
-continued
H1-226
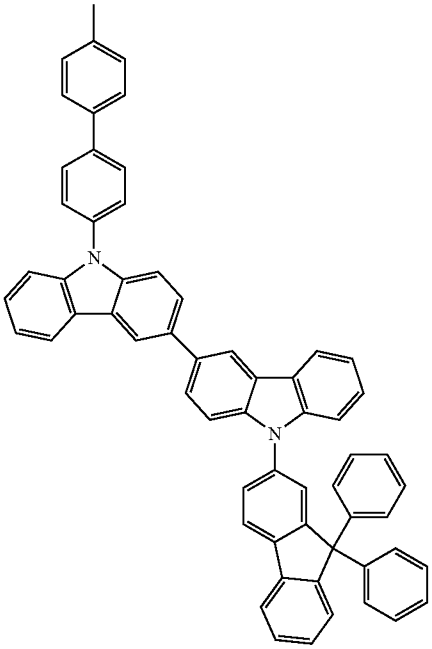
H1-227
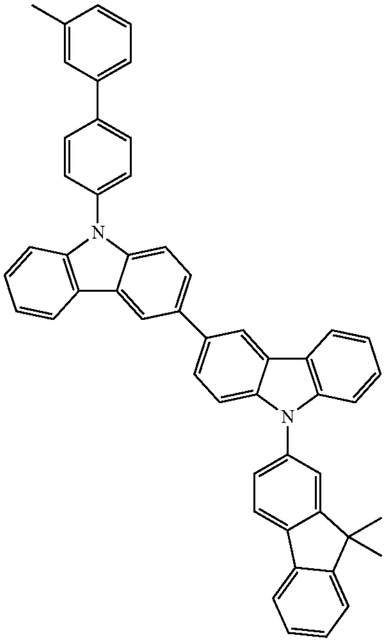

-continued
H1-228
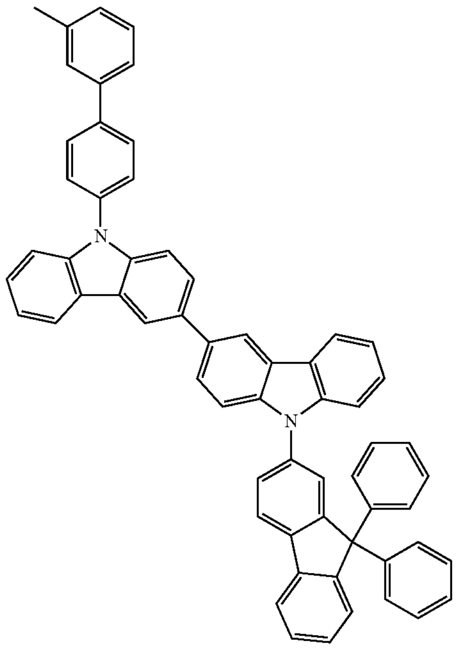
H1-229
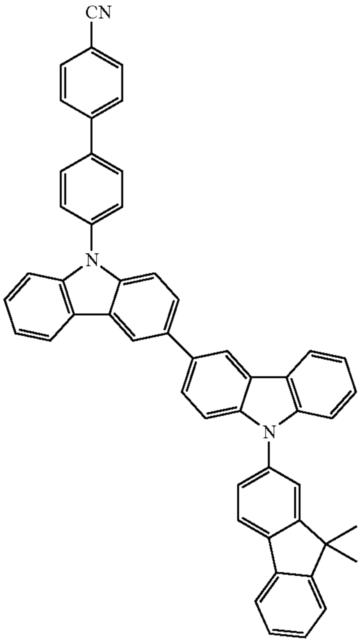
-continued
H1-230
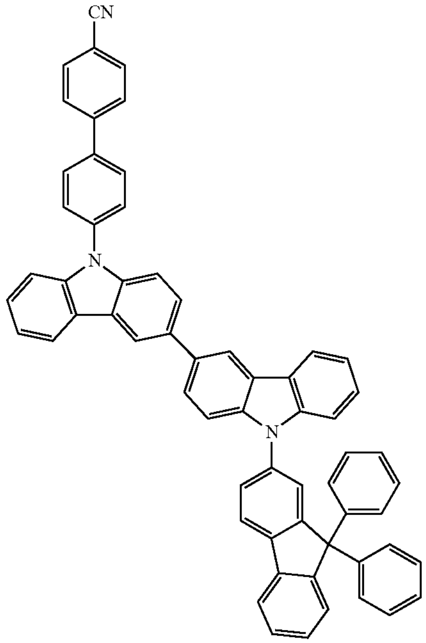
H1-231
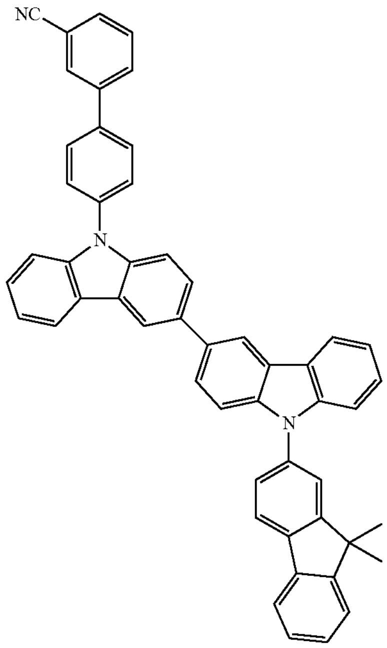

-continued
H1-232
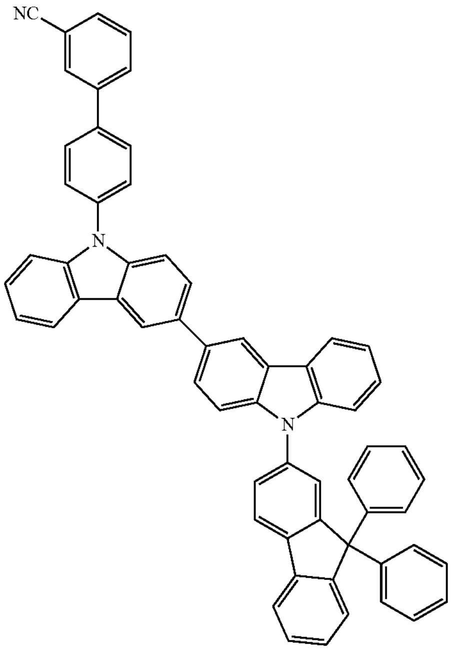
H1-233
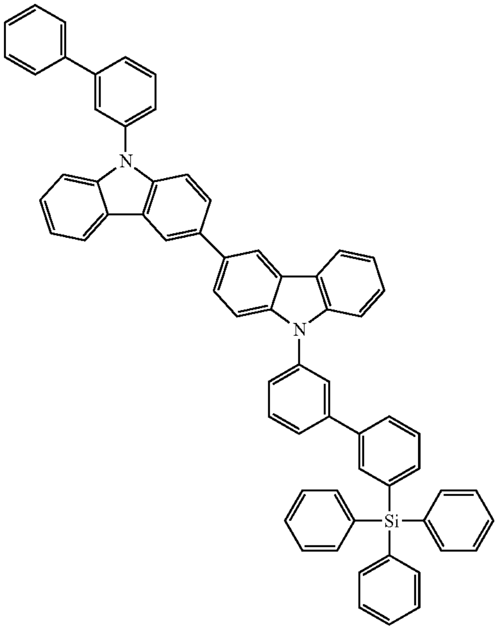
-continued
H1-234
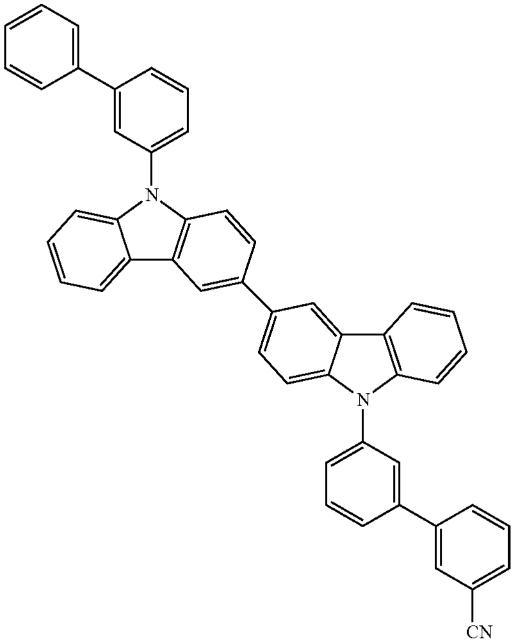
H1-235
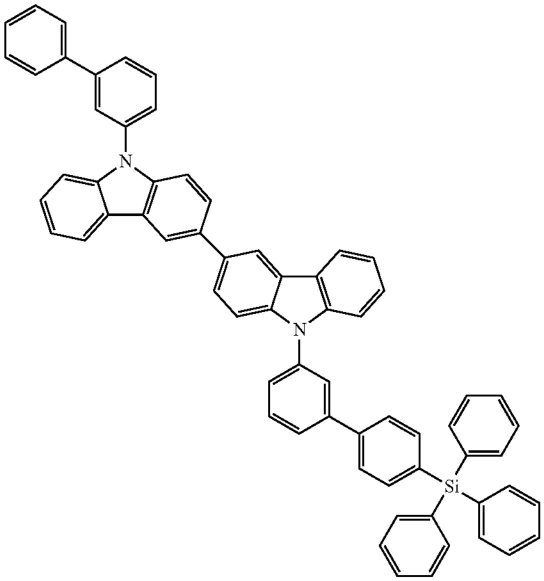

-continued
H1-236
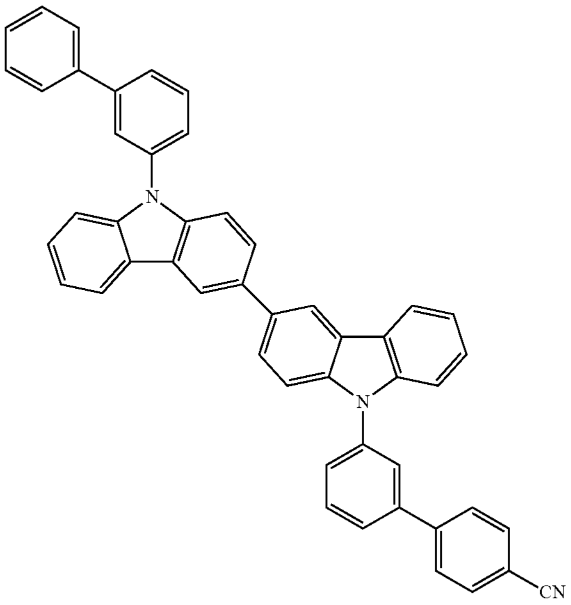
H1-237
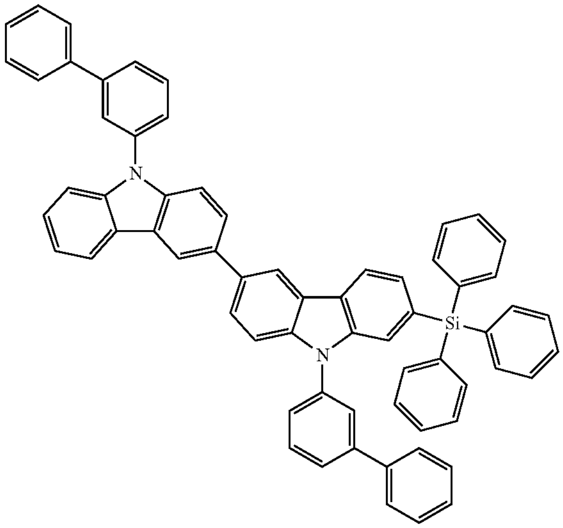
-continued
H1-238
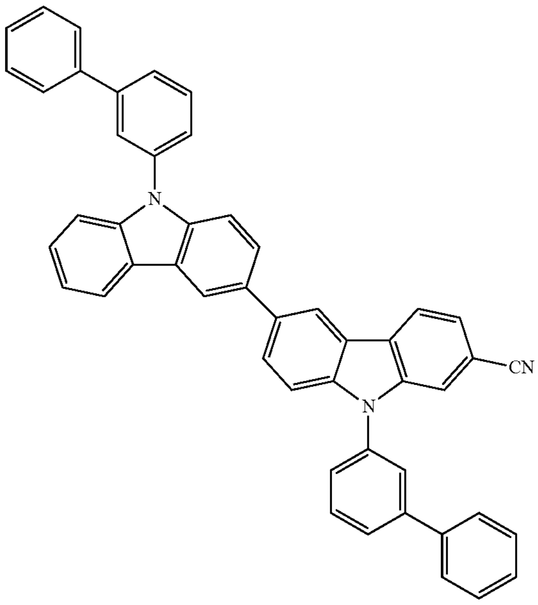
H1-239
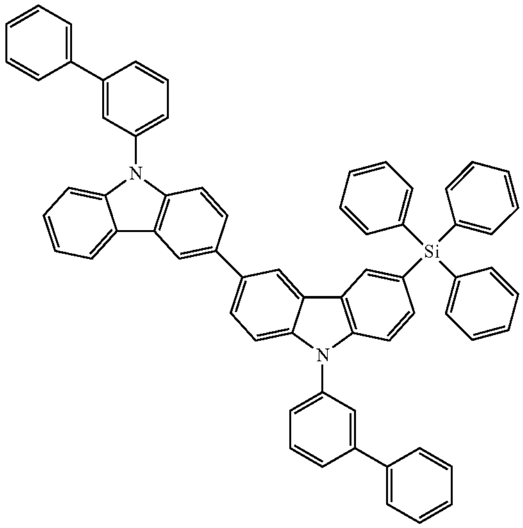

-continued
H1-240
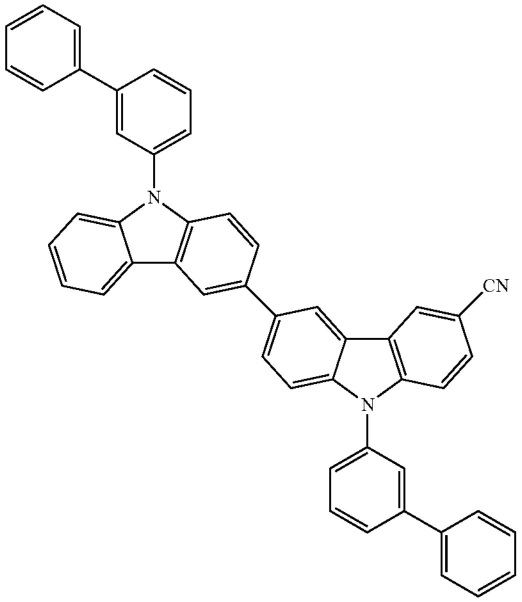
H1-241
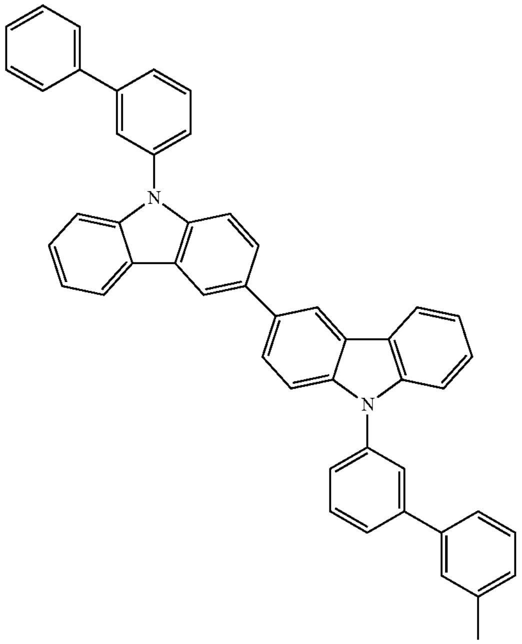
-continued
H1-242
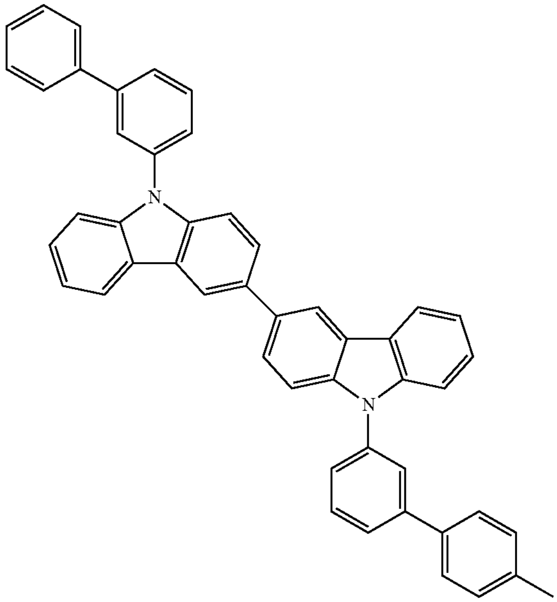
H1-243
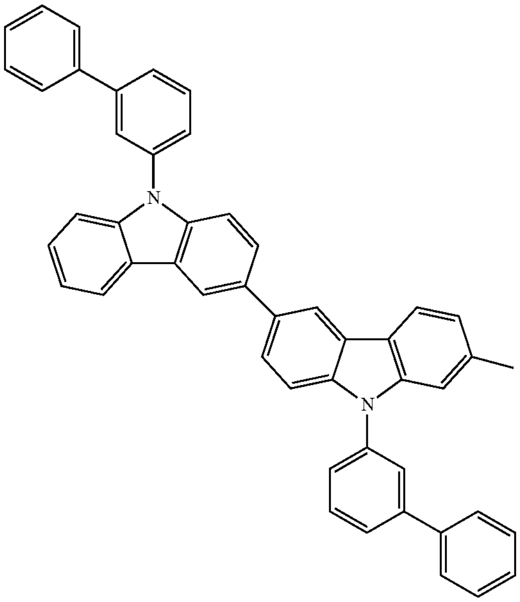

-continued
H1-244
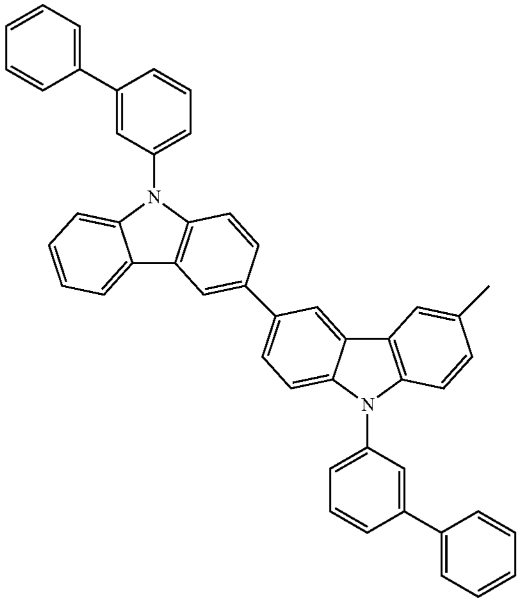
H1-245
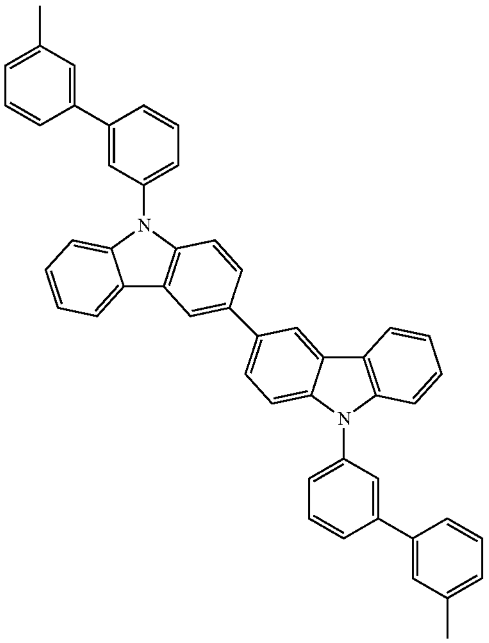
-continued
H1-246
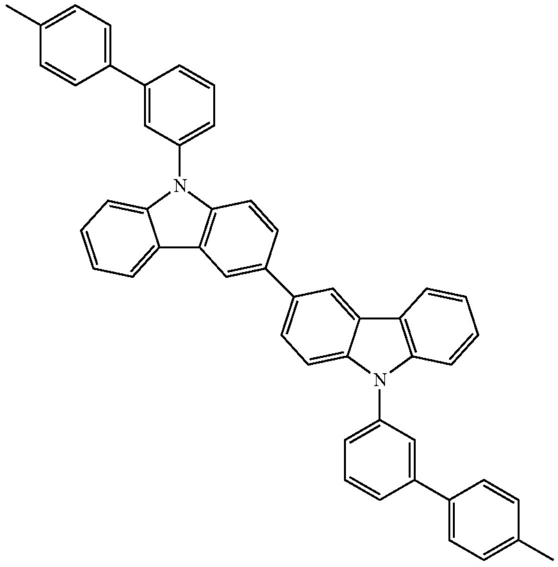
H1-247
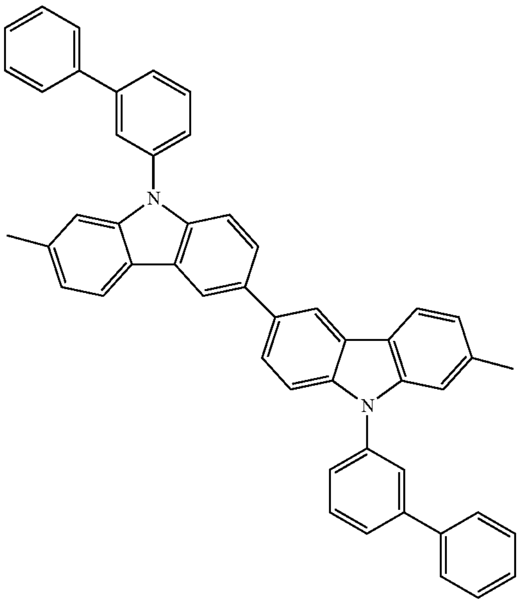

-continued
H1-248
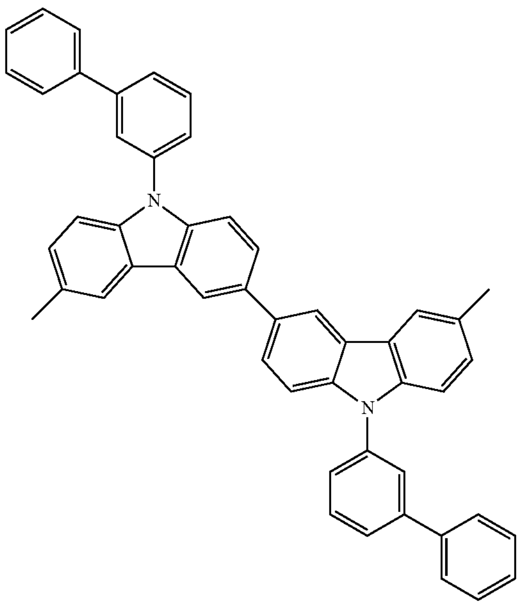
H1-249
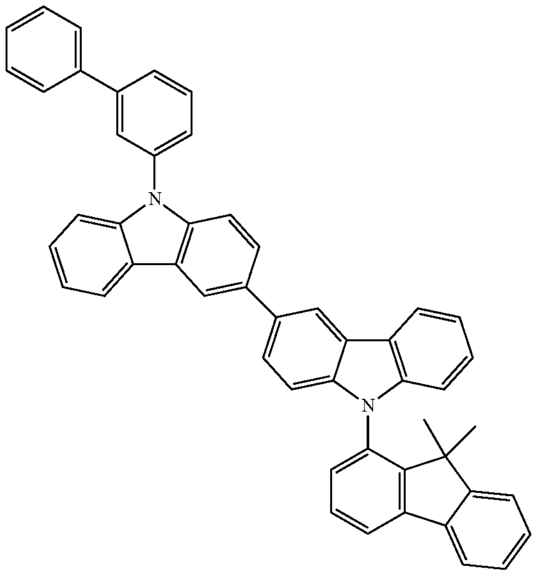
-continued
H1-250
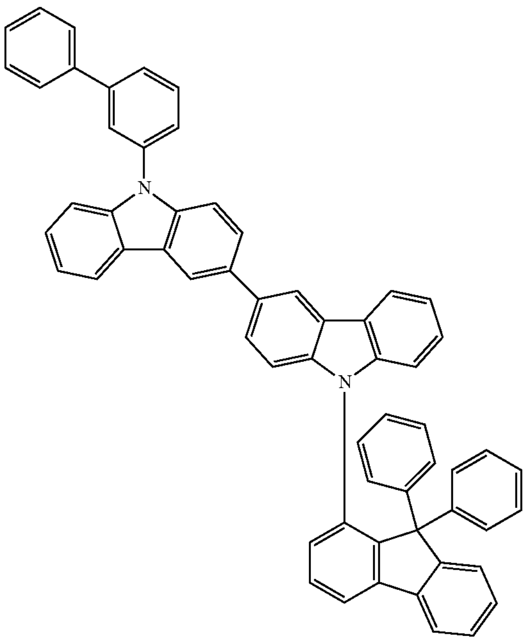
H1-251
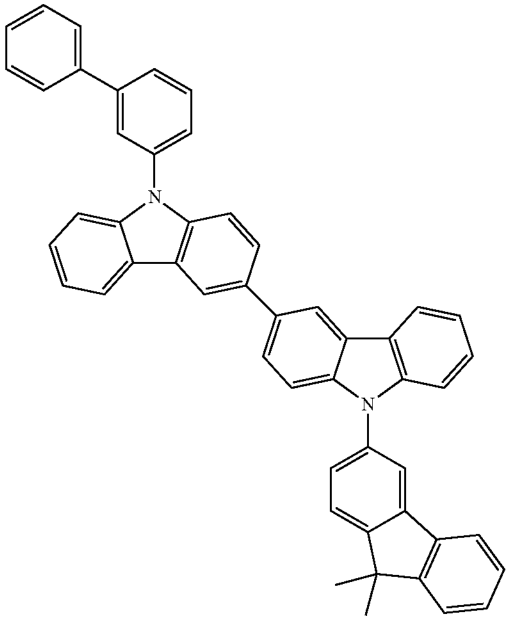

-continued
H1-252
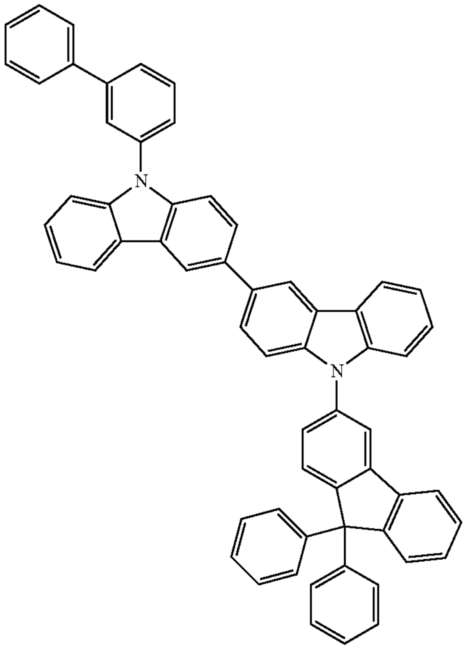
H1-253
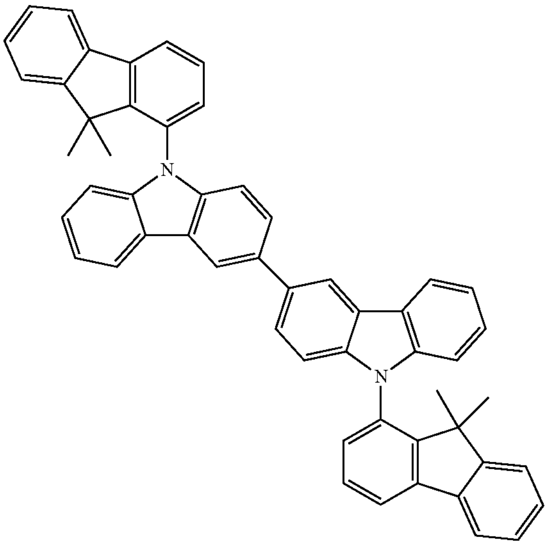
-continued
H1-254
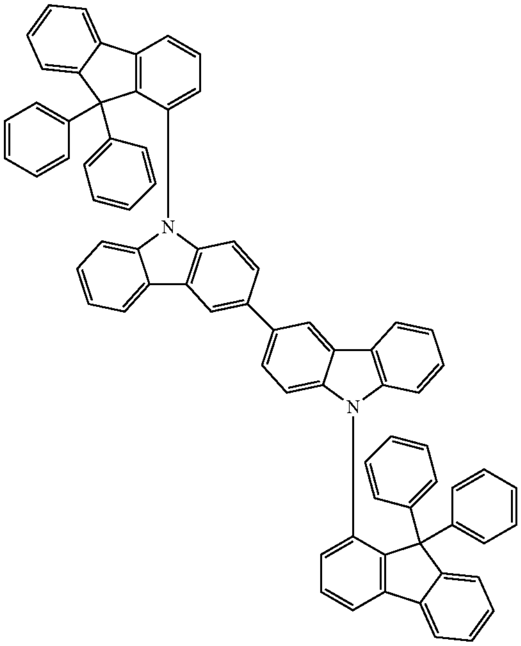
H1-255
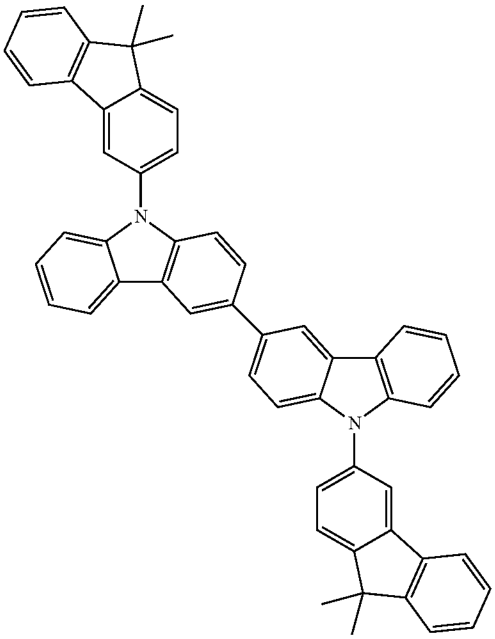

-continued
H1-256
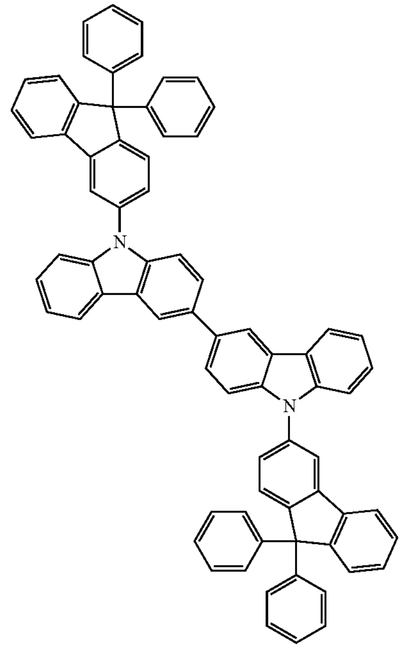
H1-257
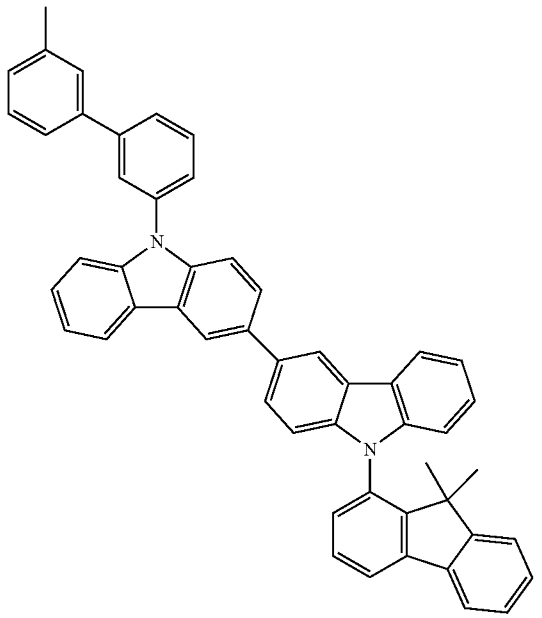
-continued
H1-258
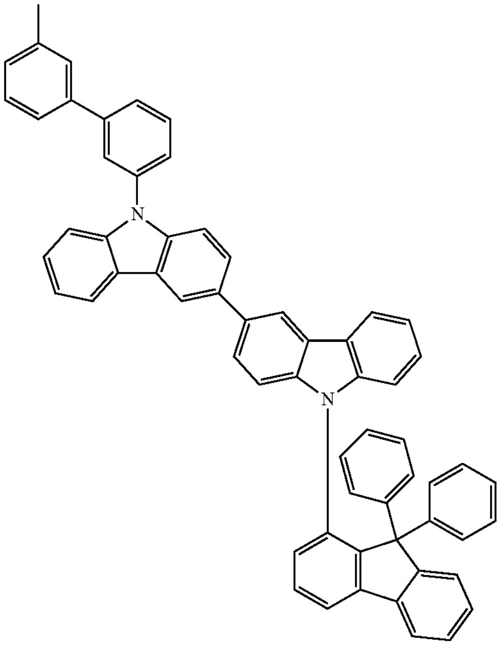
H1-259
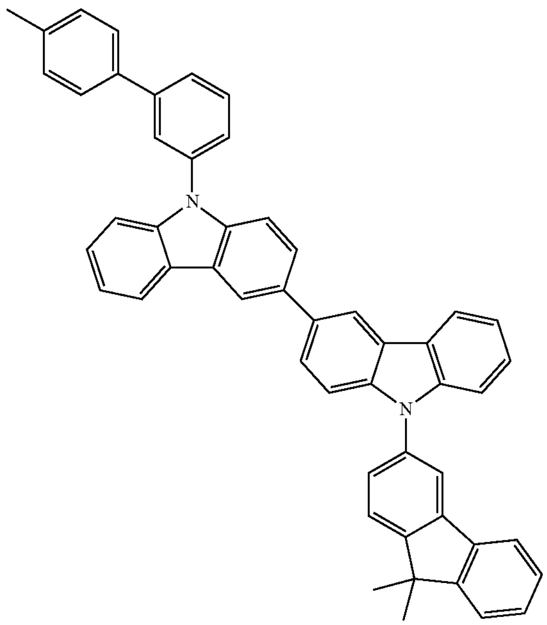

-continued
H1-260
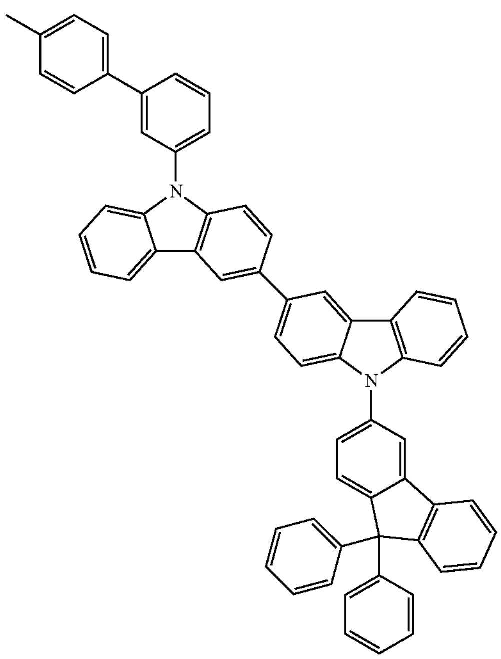
H1-261
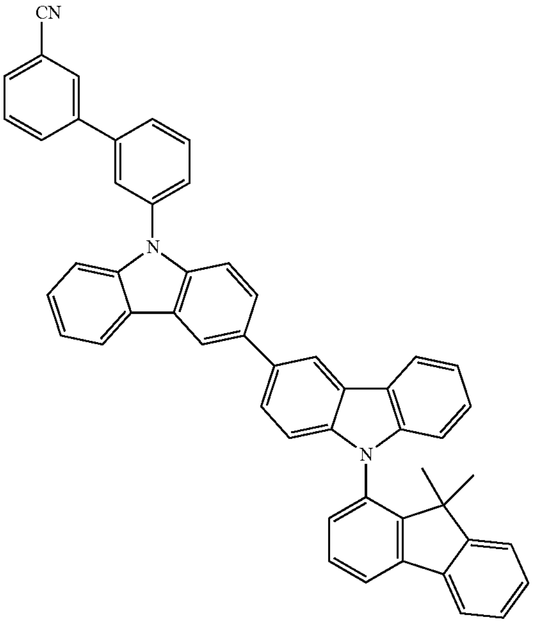
-continued
H1-262
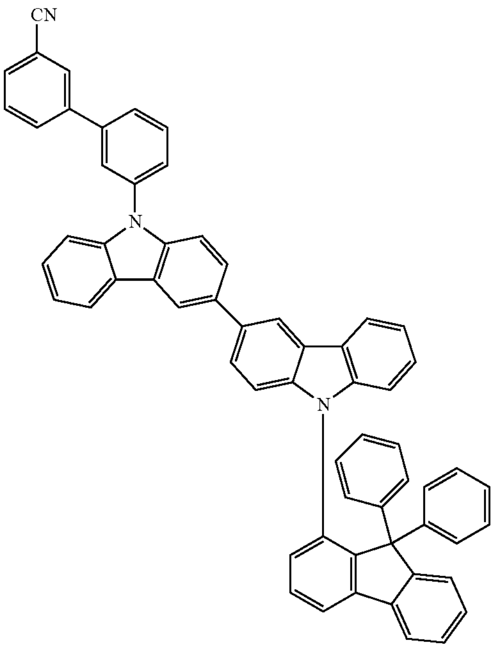
H1-263
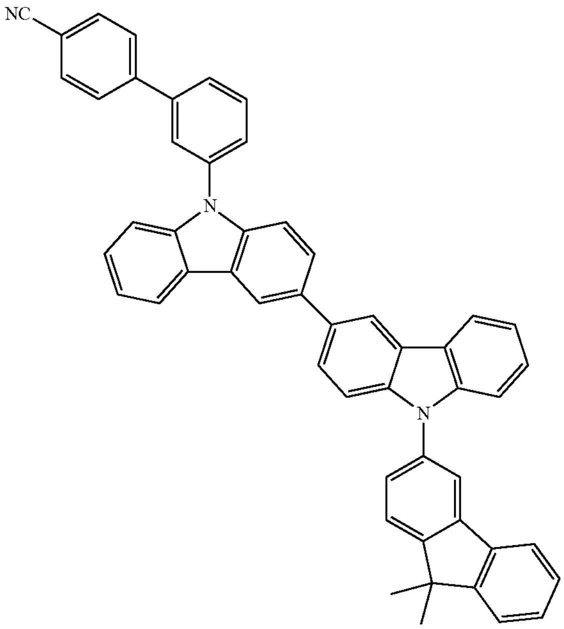

-continued
H1-264
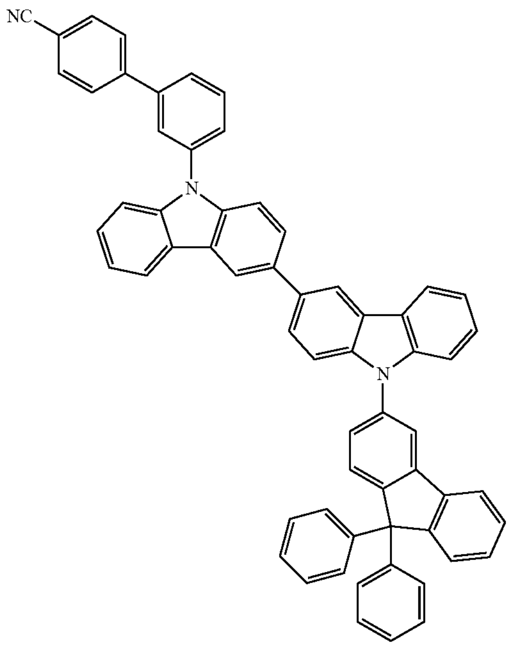
H1-265
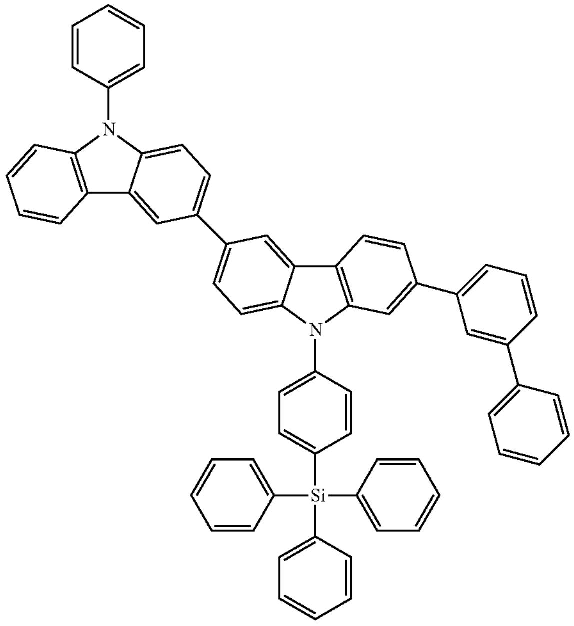
-continued
H1-266
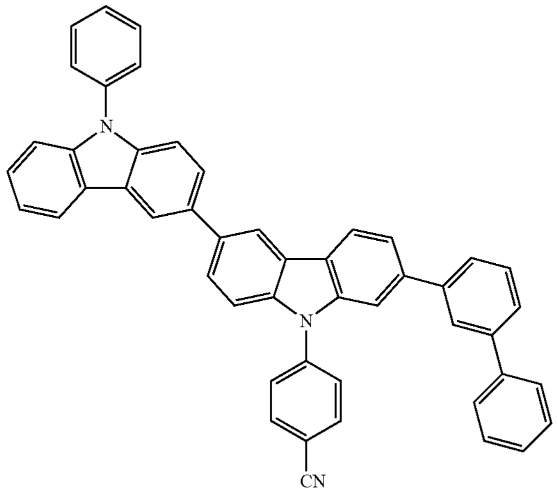
H1-267
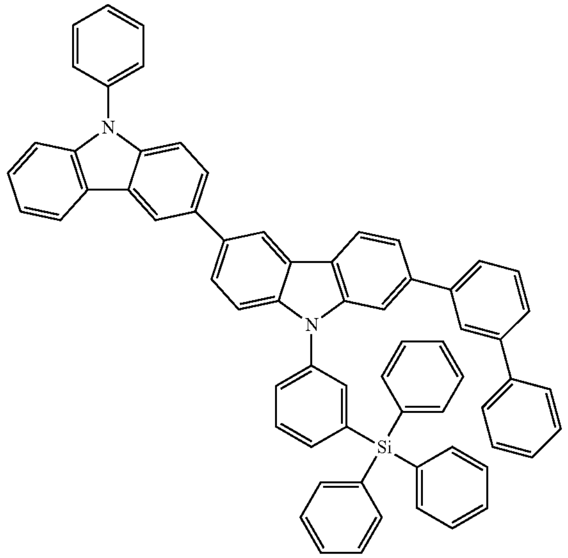
H1-268
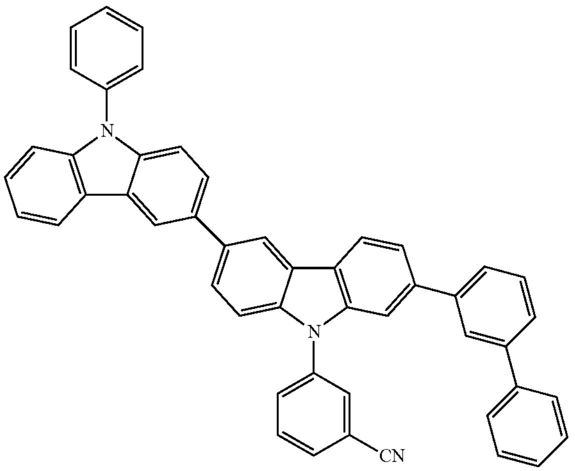

-continued
H1-269
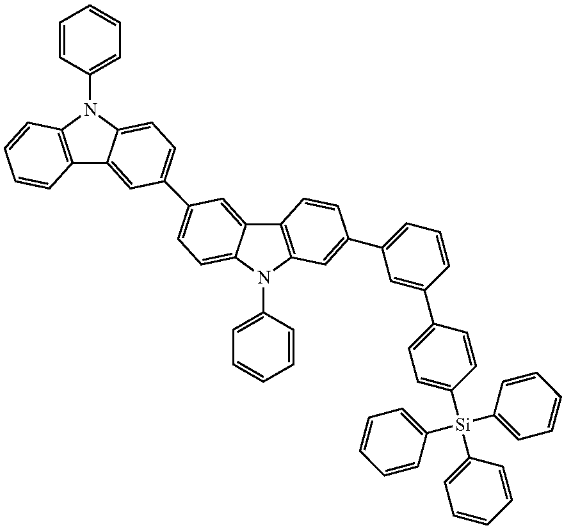
H1-270
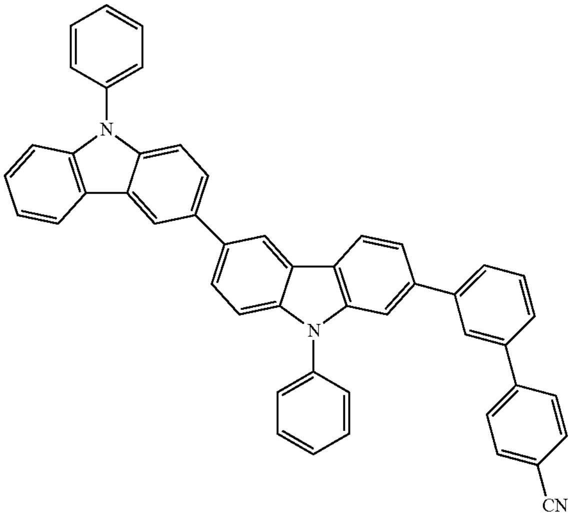
CN
H1-271
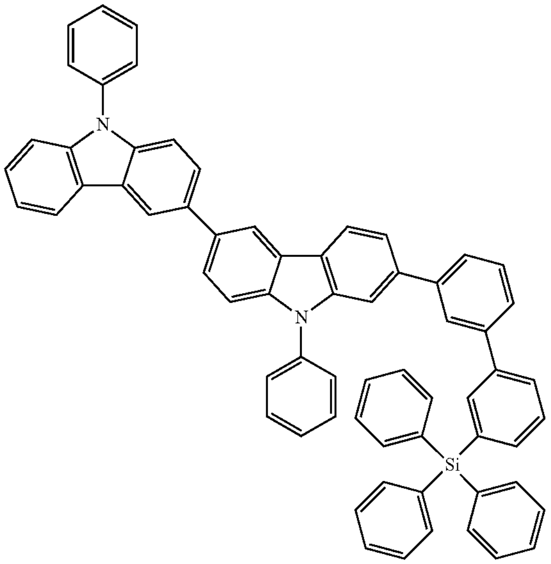
-continued
H1-272
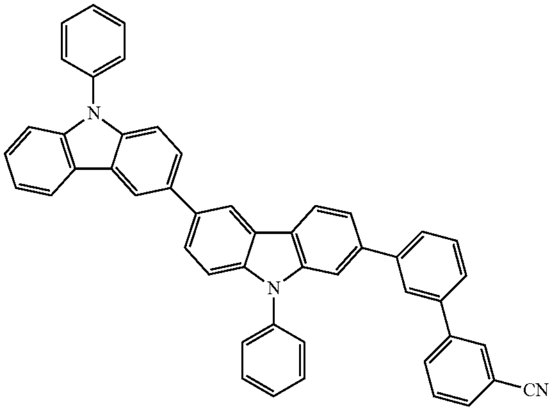
H1-273
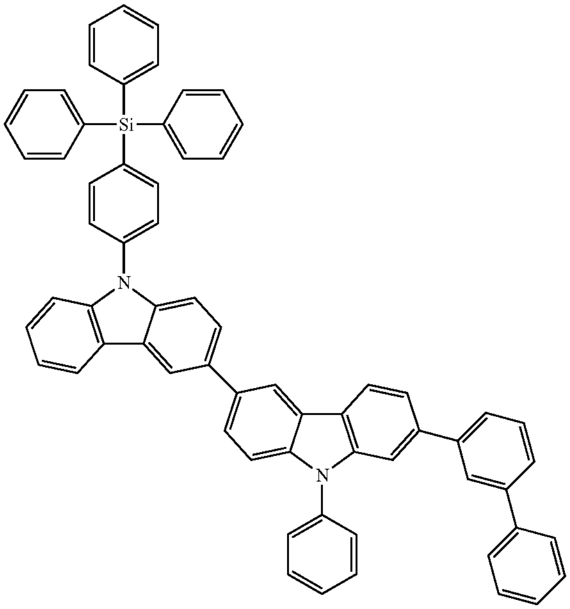
H1-274
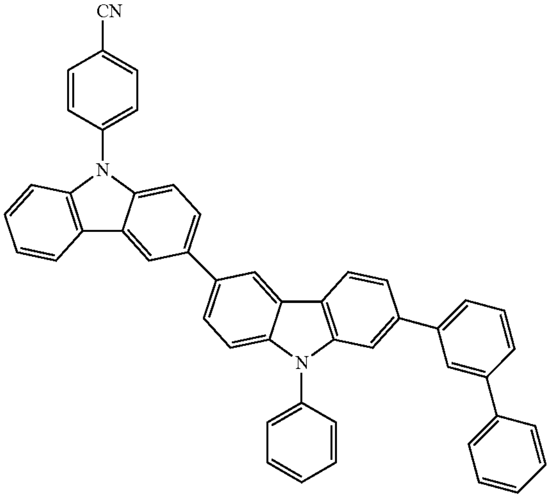

-continued
H1-275
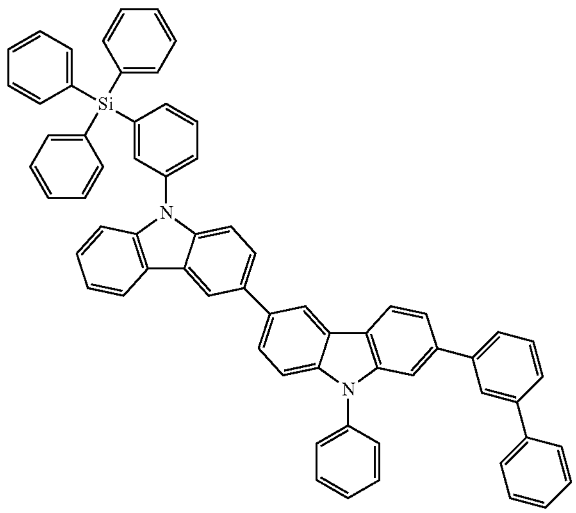
H1-276
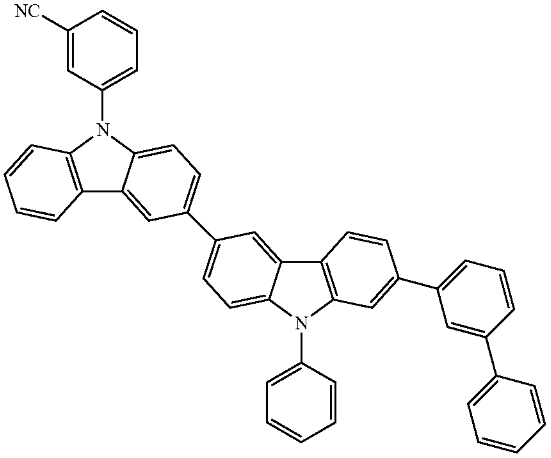
H1-277
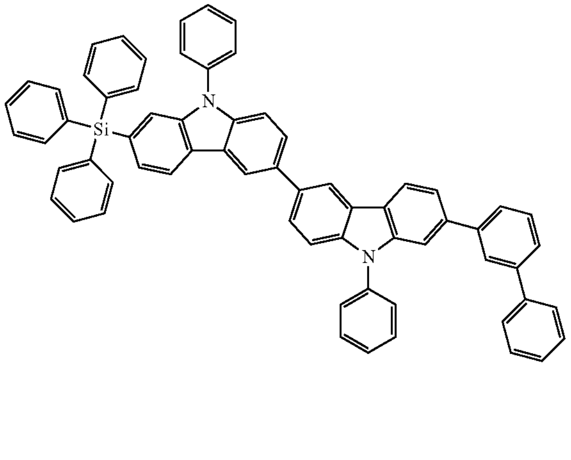
-continued
H1-278
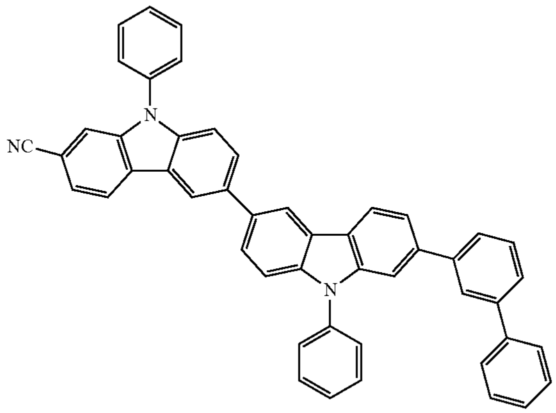
H1-279
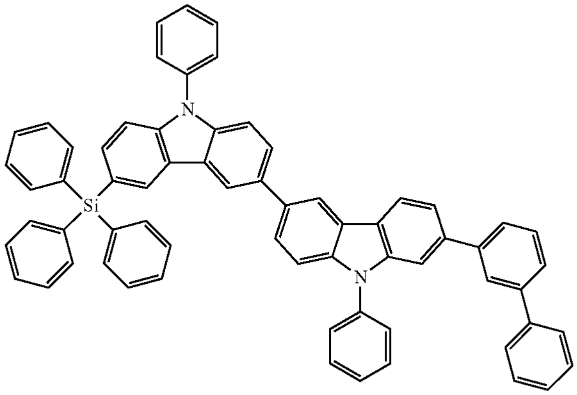
H1-280
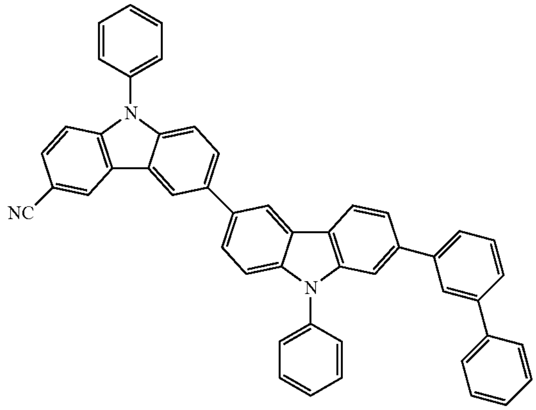

-continued
H1-281
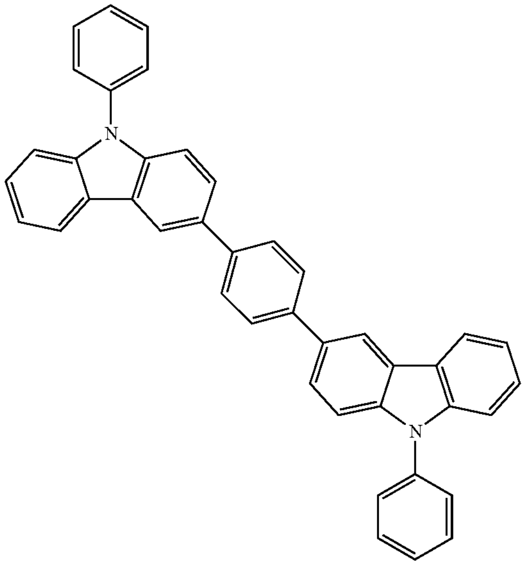
H1-282
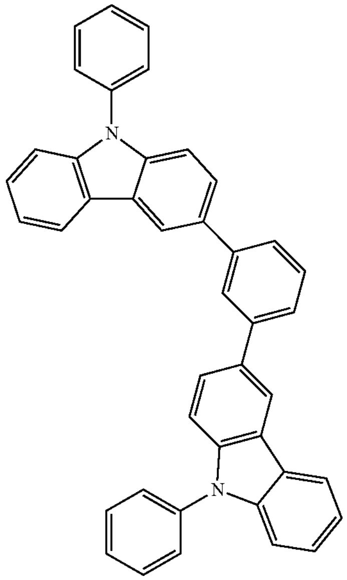
H1-283
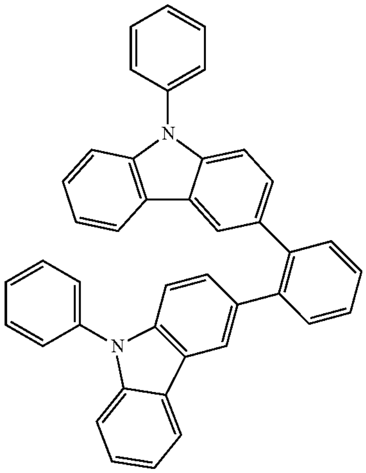
-continued
H1-284
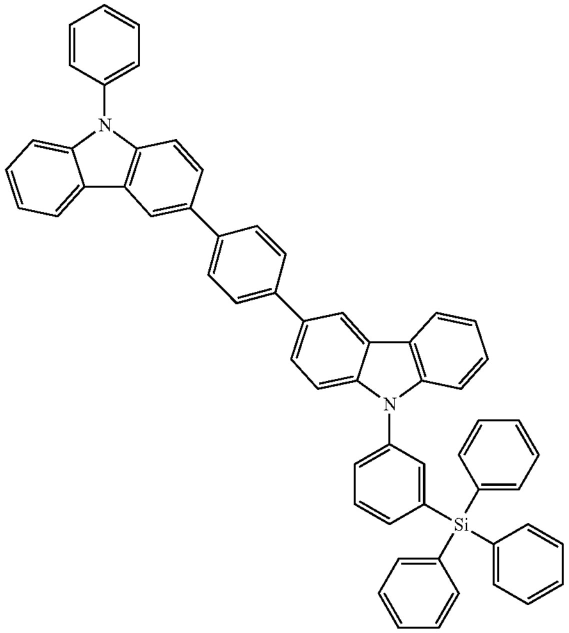
H1-285
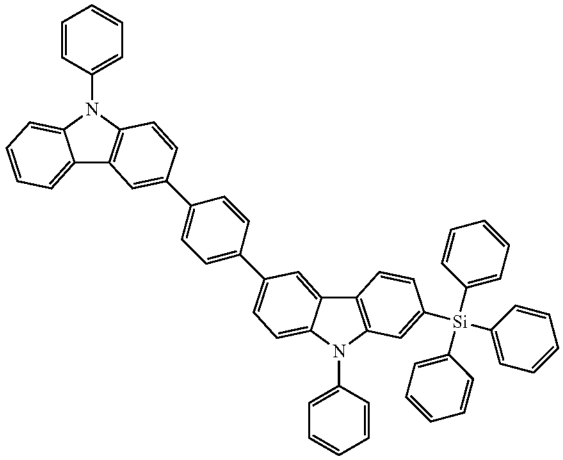

-continued
H1-286
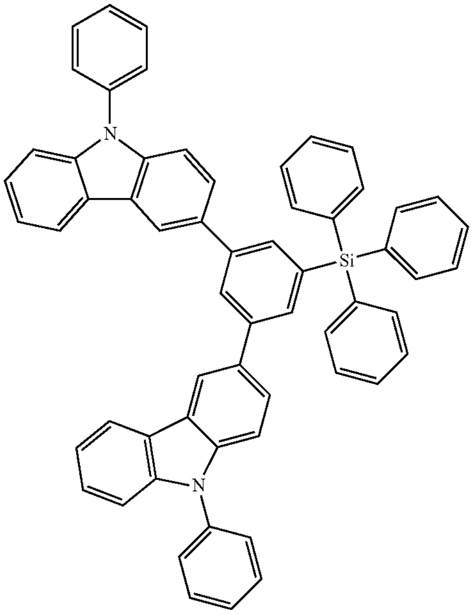
H1-287
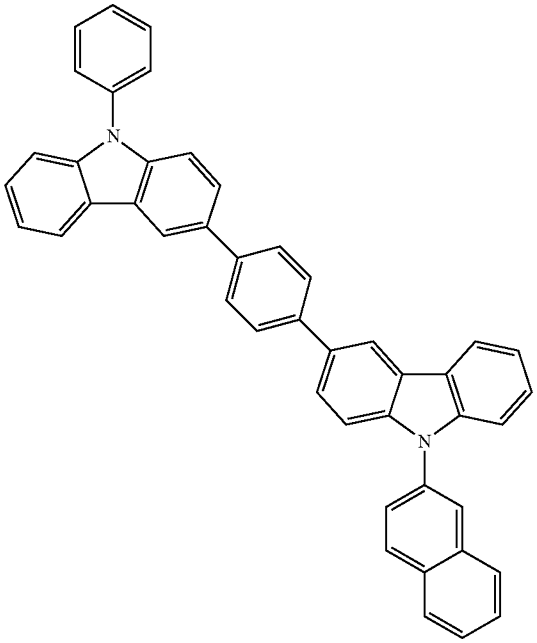
-continued
H1-288
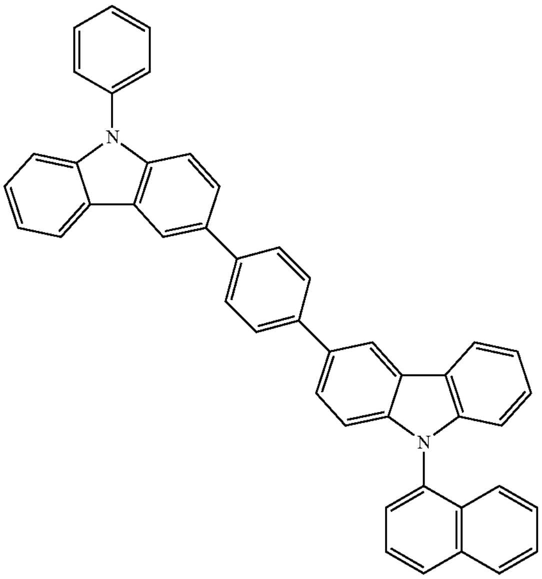
H1-289
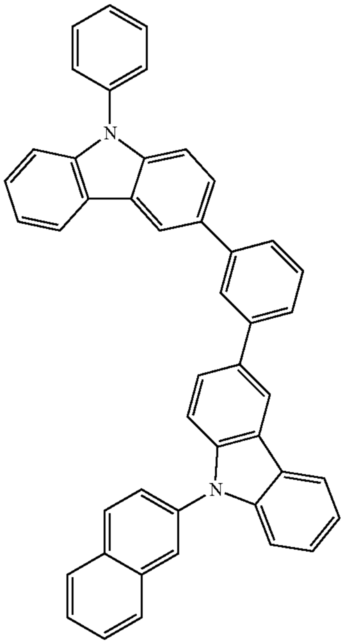

-continued
H1-290
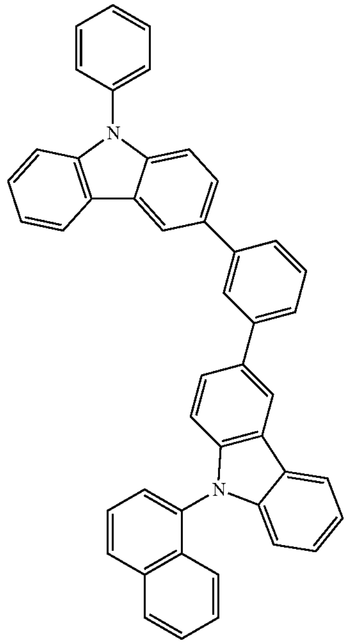
H1-291
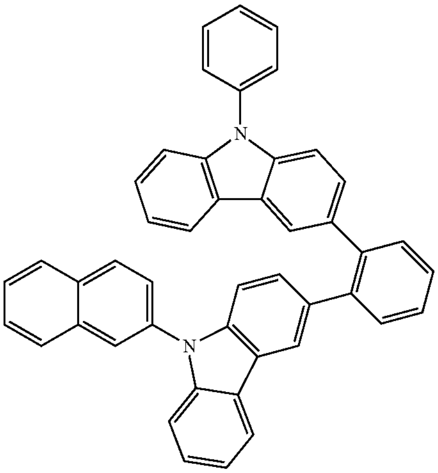
H1-292
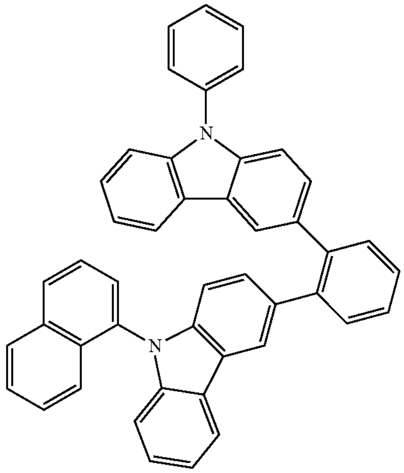
-continued
H1-293
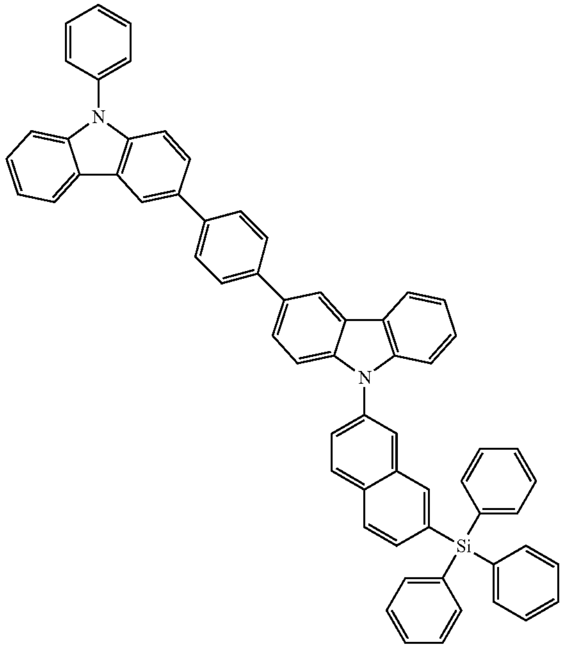
H1-294
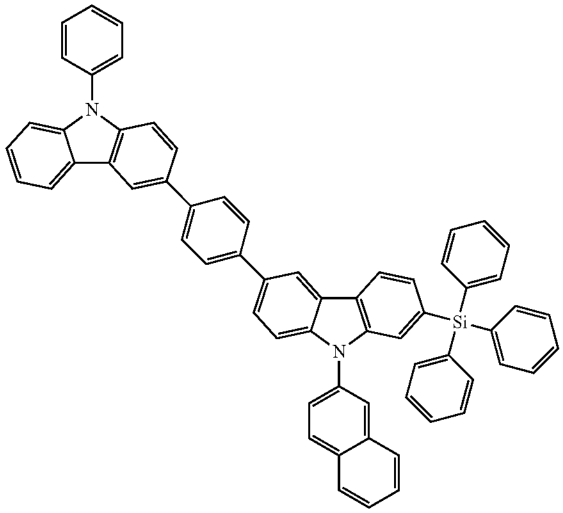

-continued
H1-295
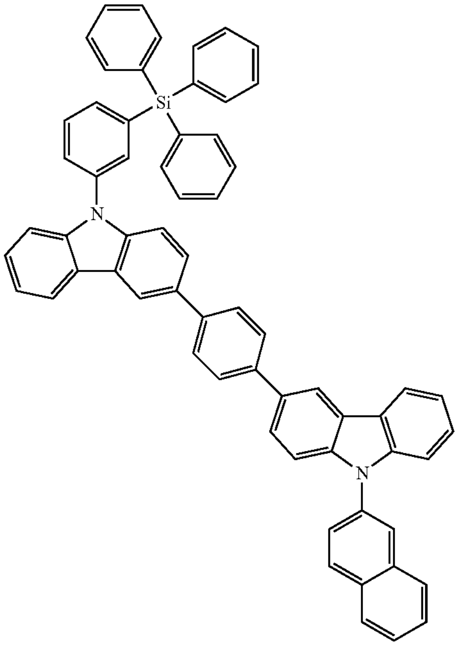
H1-296
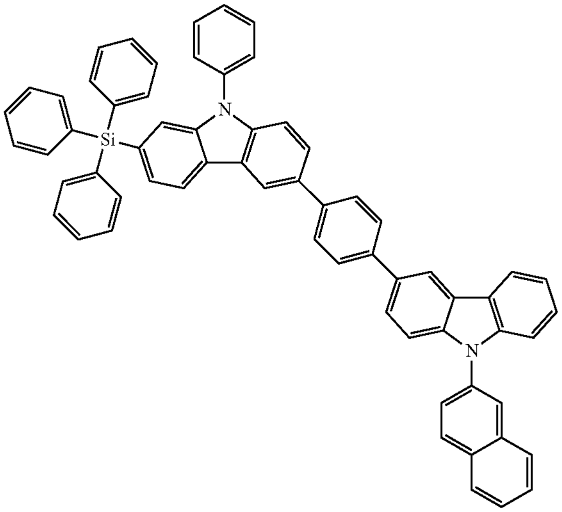
-continued
H1-297
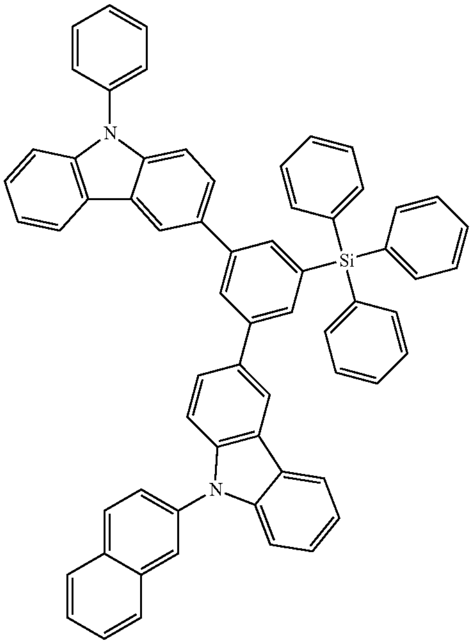
H1-298
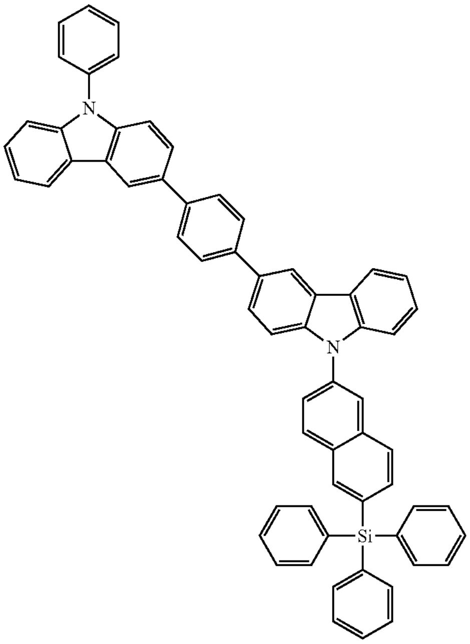

-continued
H1-299
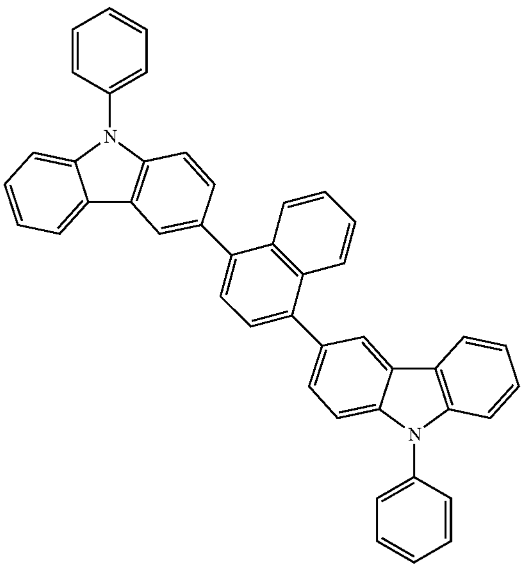
H1-300
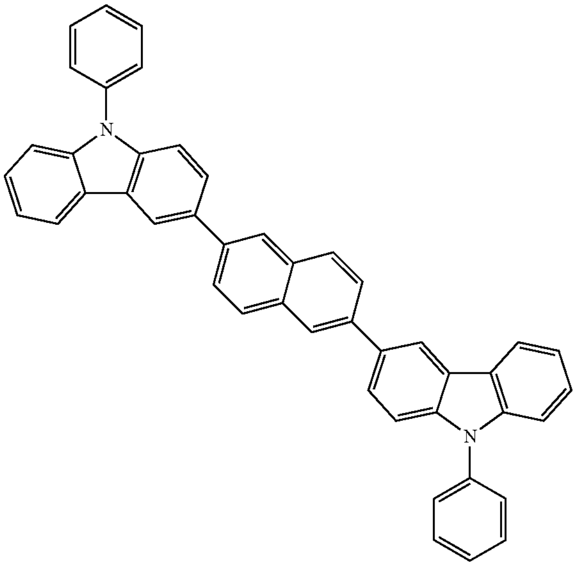
-continued
H1-301
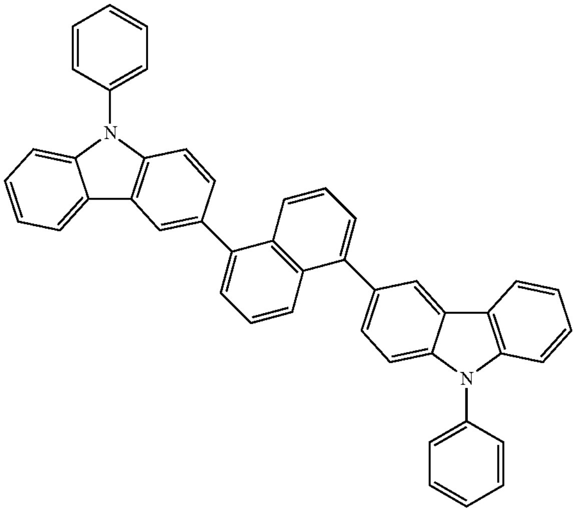
H1-302
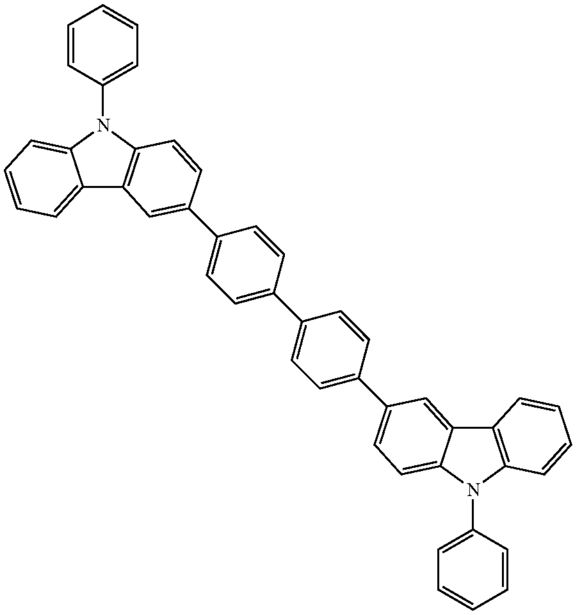
H1-303
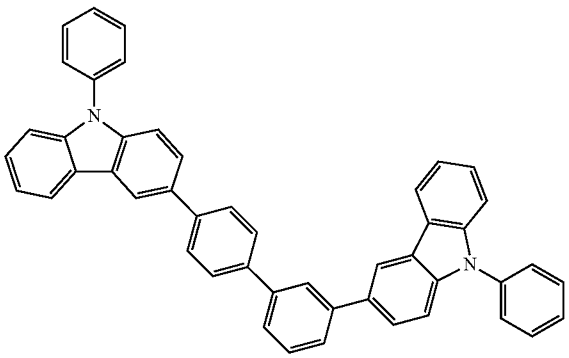

-continued
H1-304
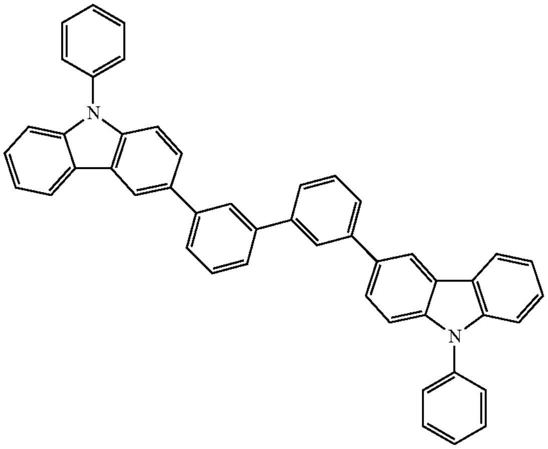
H1-305
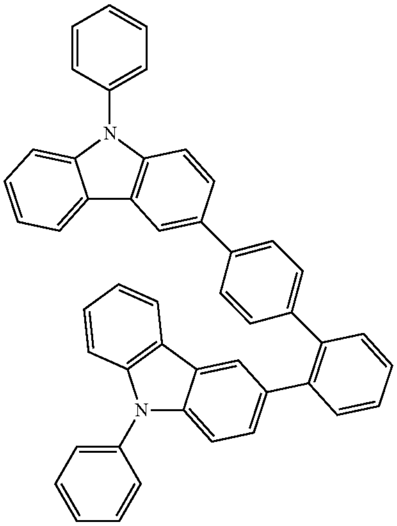
H1-306
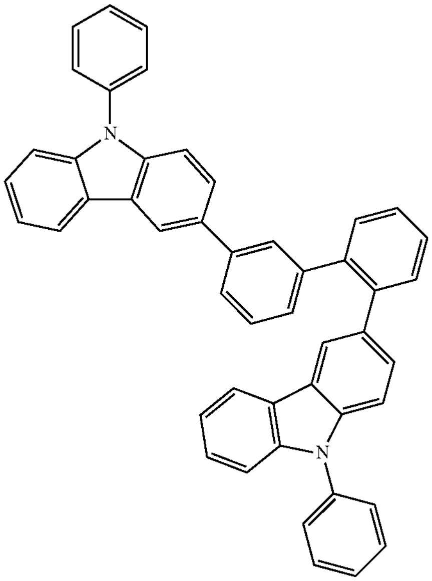
-continued
H1-307
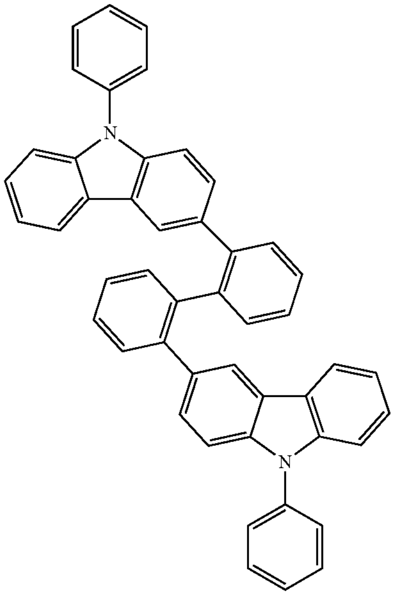
H1-308
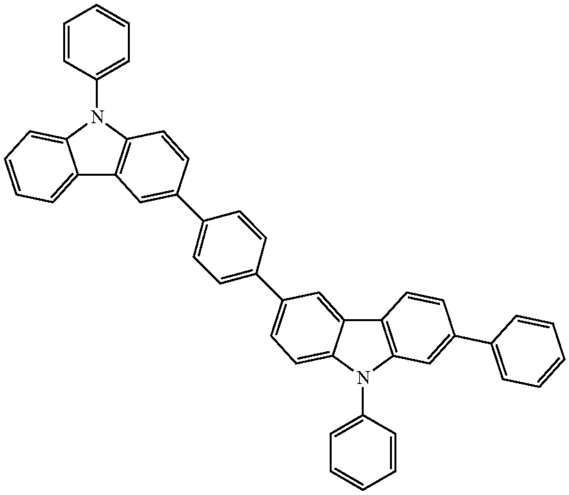

-continued
H1-309
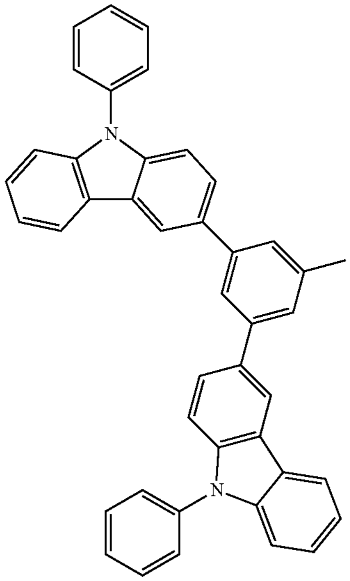
H1-310
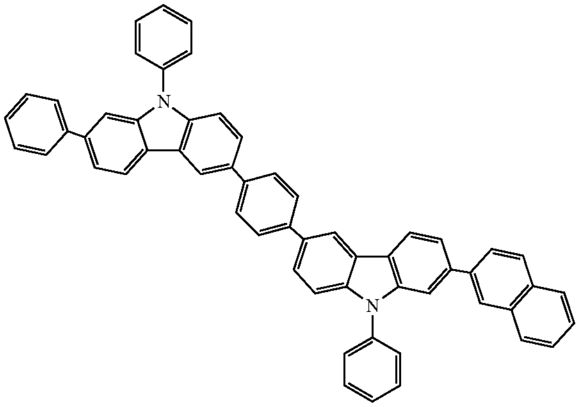
H1-311
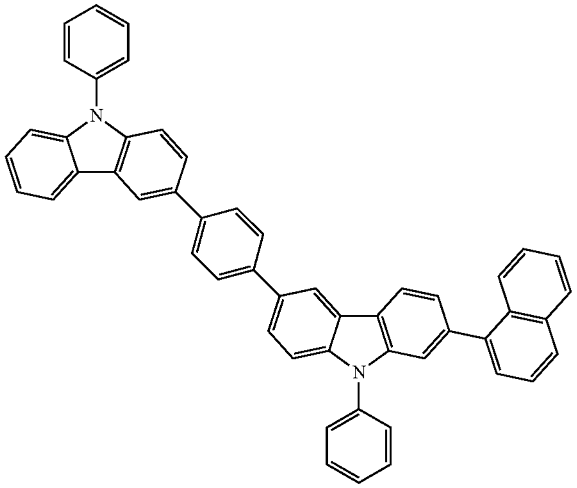
-continued
H1-312
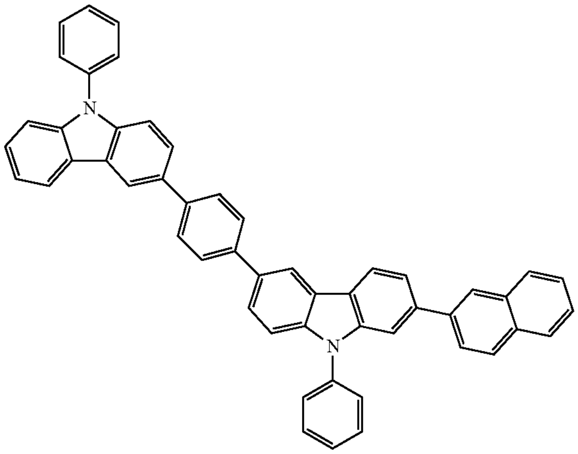
H1-313
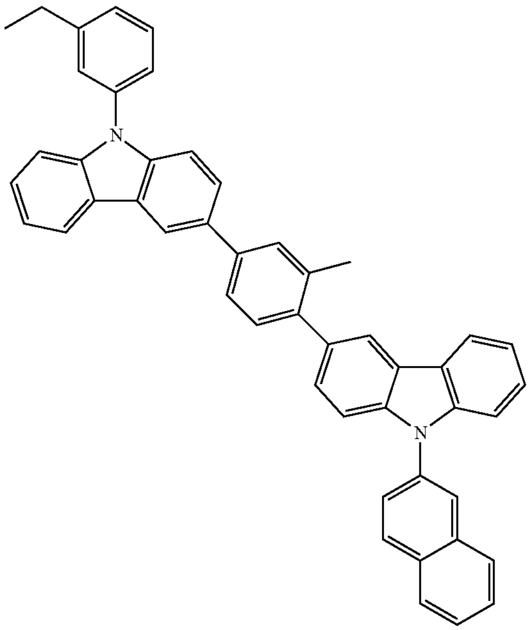

-continued
H1-314
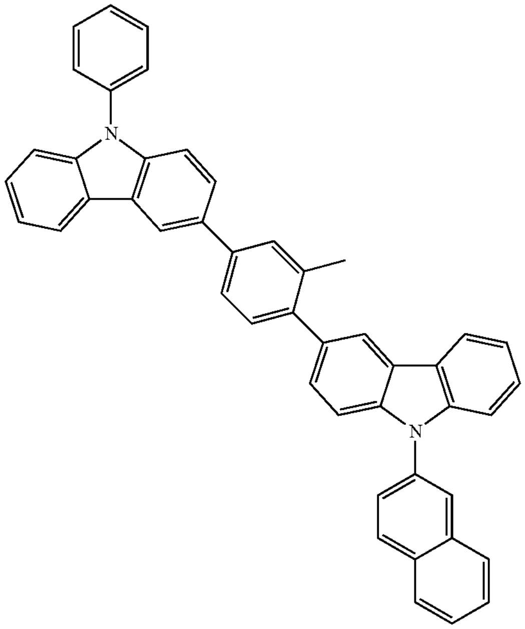
H1-315
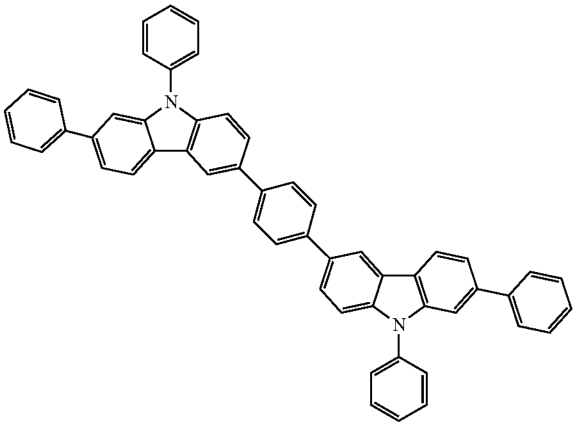
-continued
H1-316
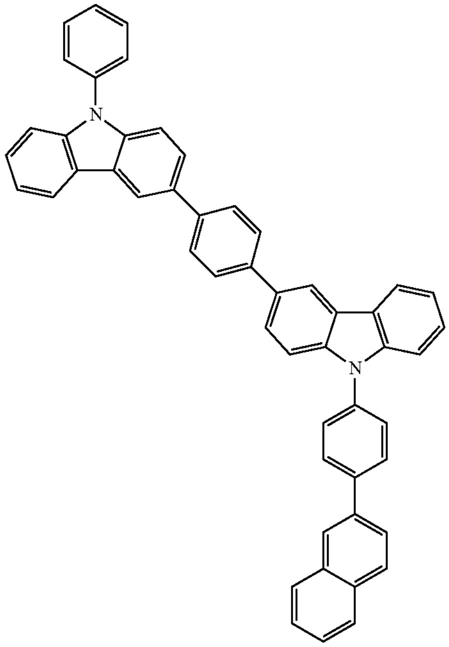
H1-317
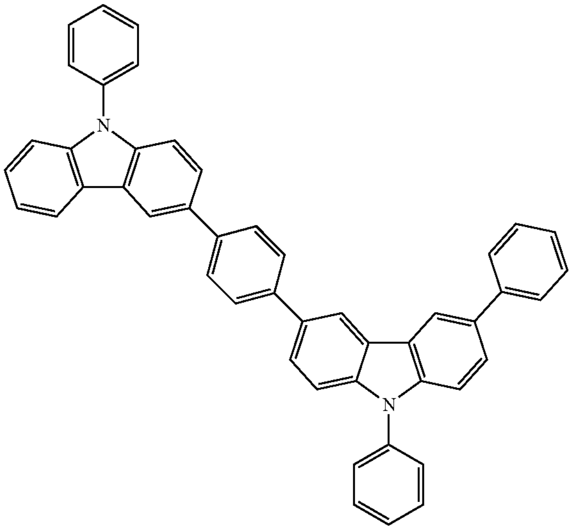

-continued
H1-318
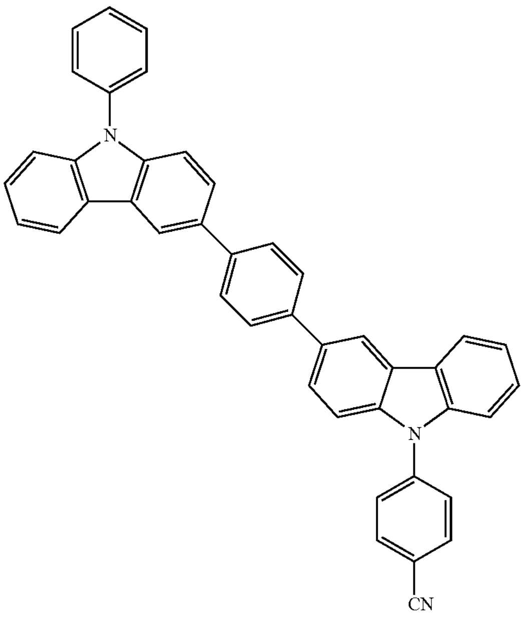
H1-319
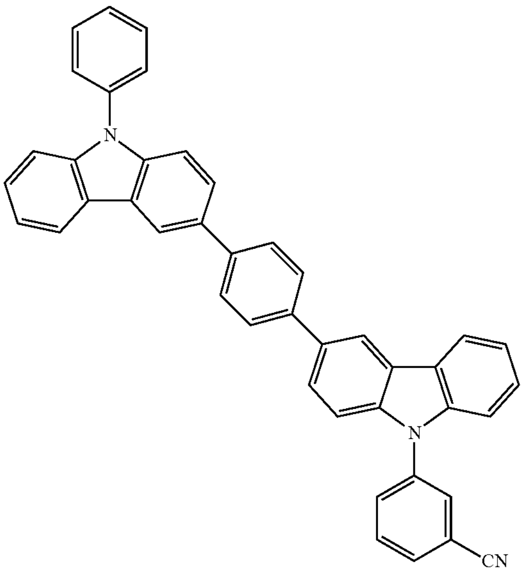
-continued
H1-320
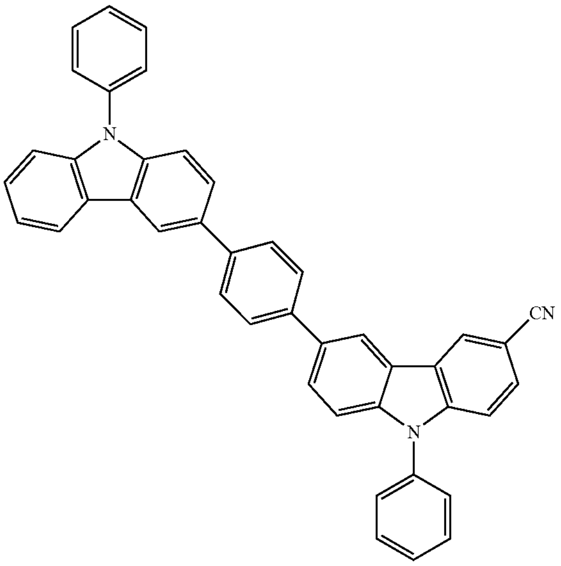
H1-321
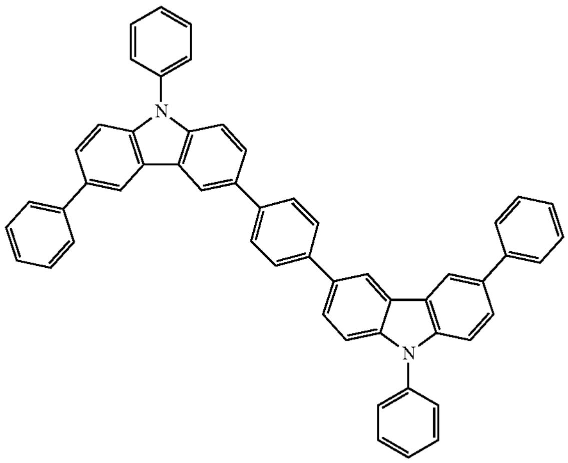
H1-322
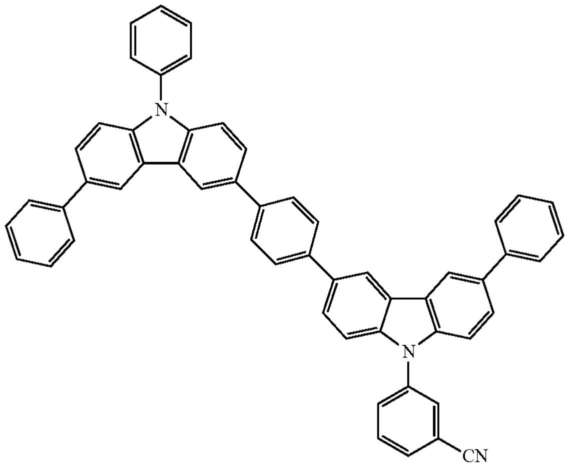

-continued
H1-323
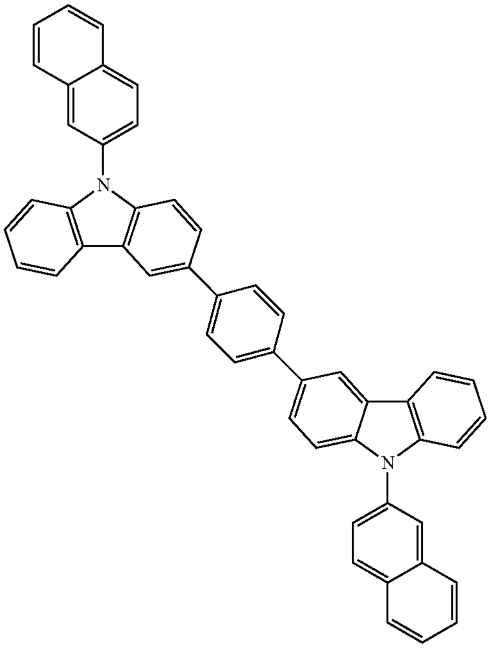
H1-324
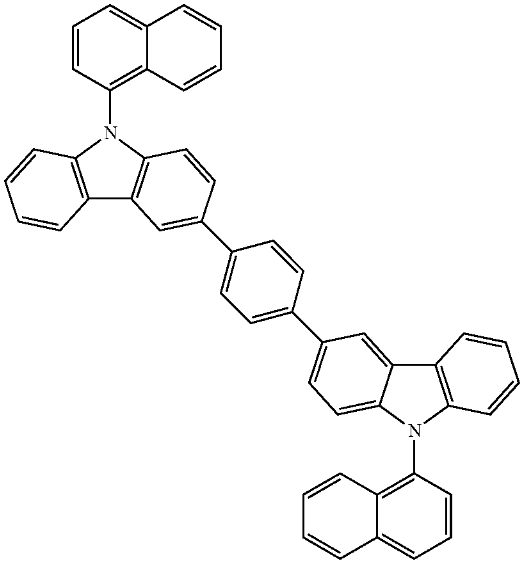
-continued
H1-325
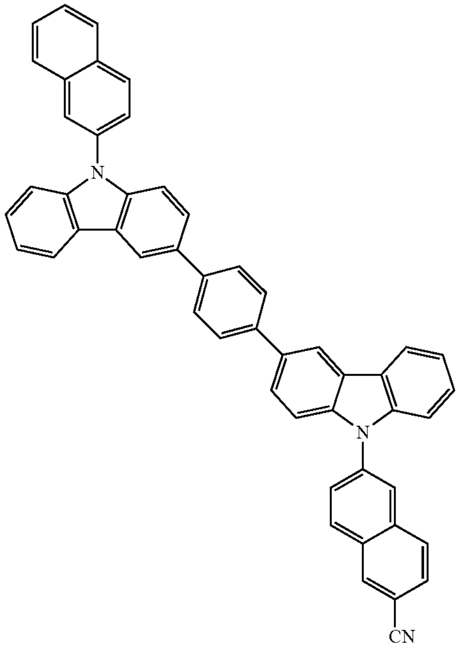
H1-326
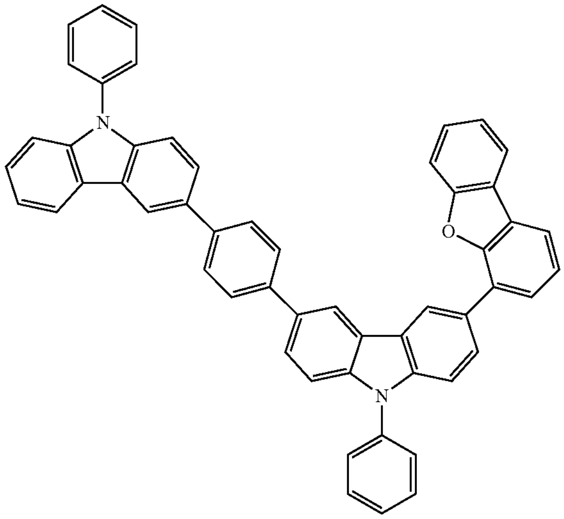

-continued
H1-327
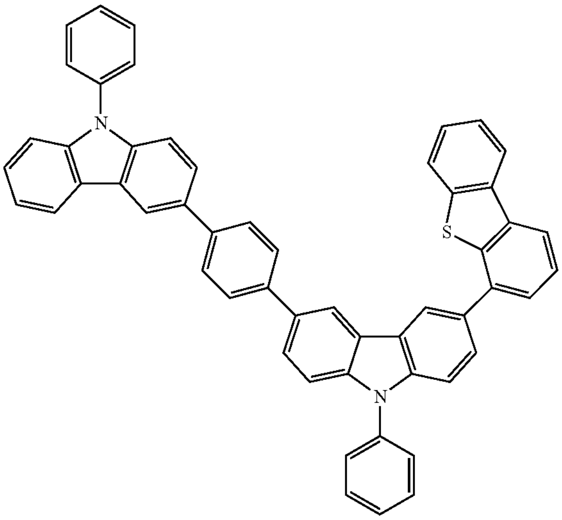
H1-328
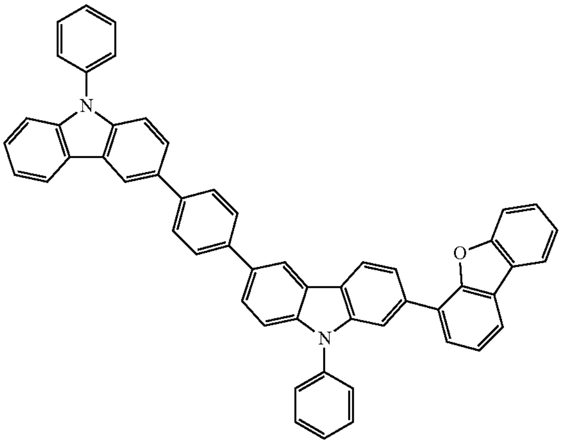
H1-329
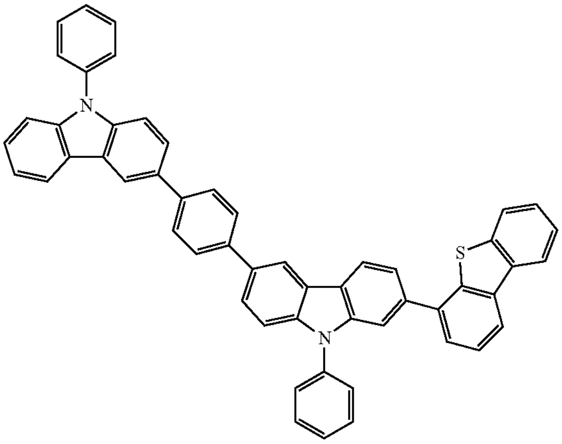
-continued
H1-330
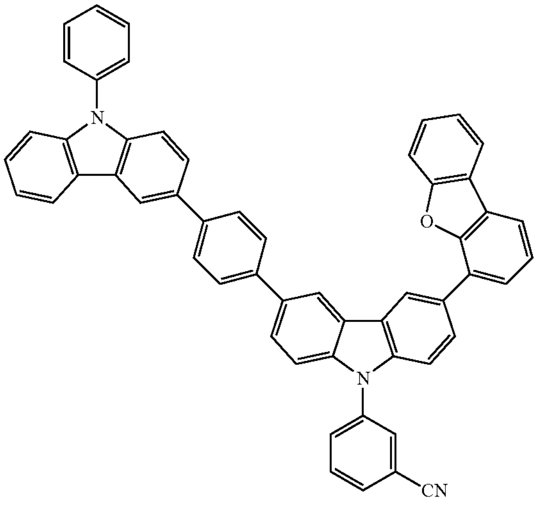
H1-331
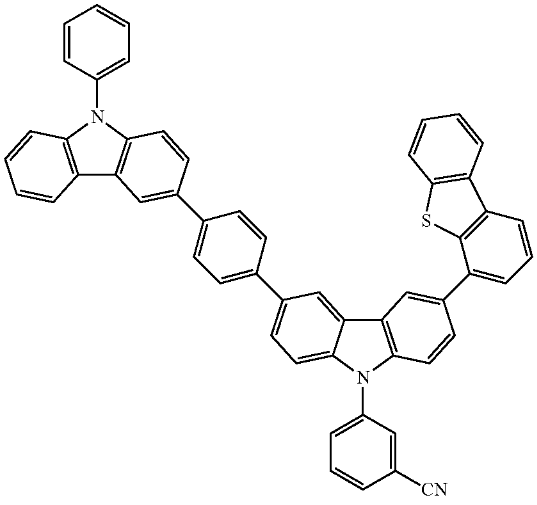
H1-332
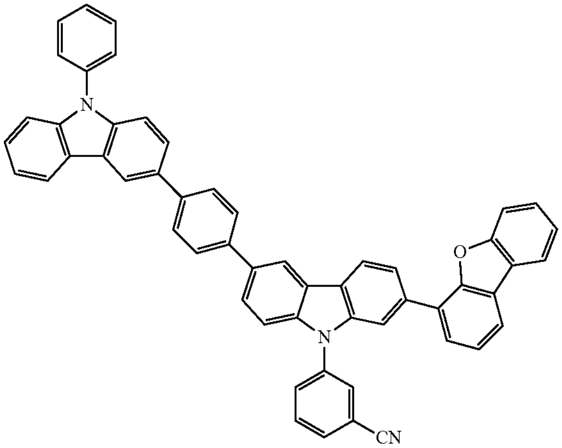

-continued
H1-333
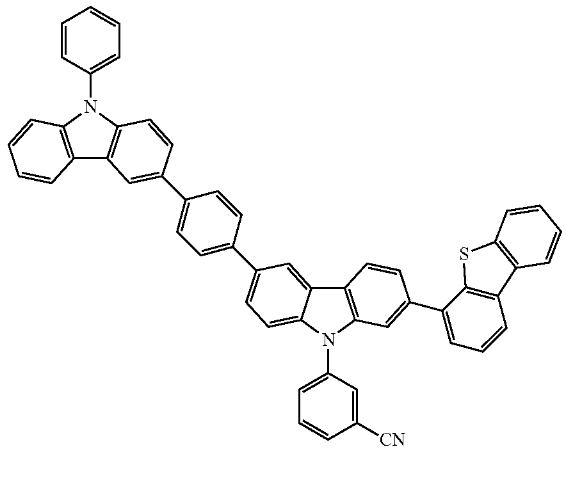
H1-334
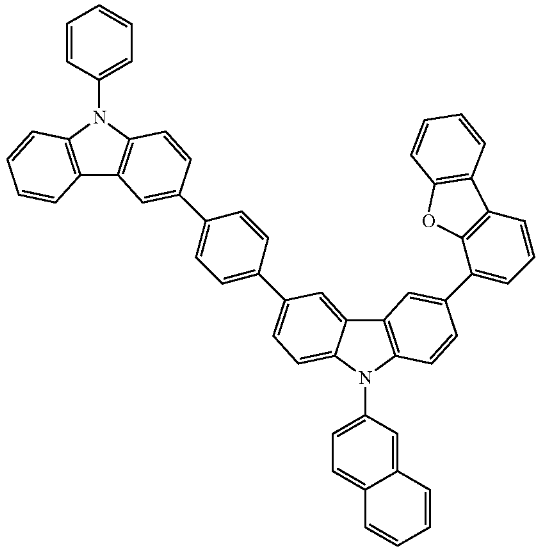
H1-335
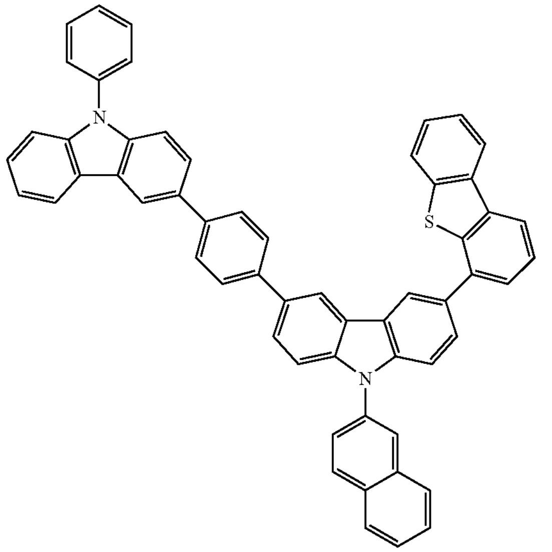
-continued
H1-336
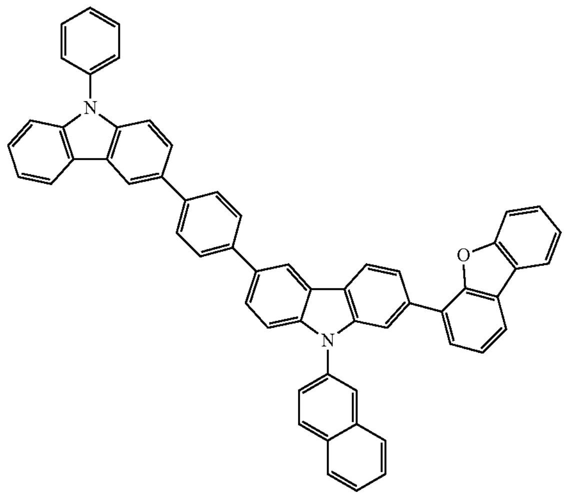
H1-337
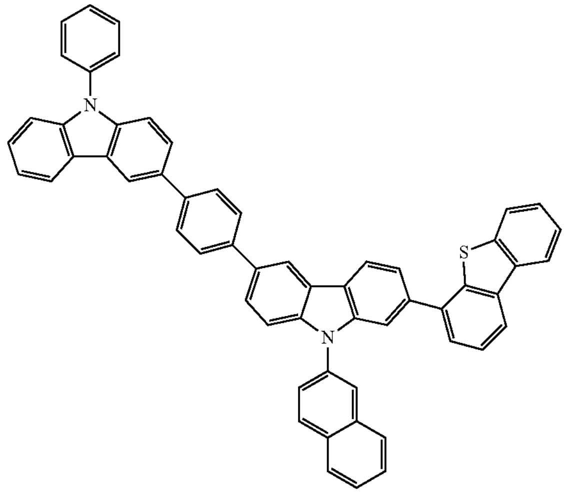
H1-338
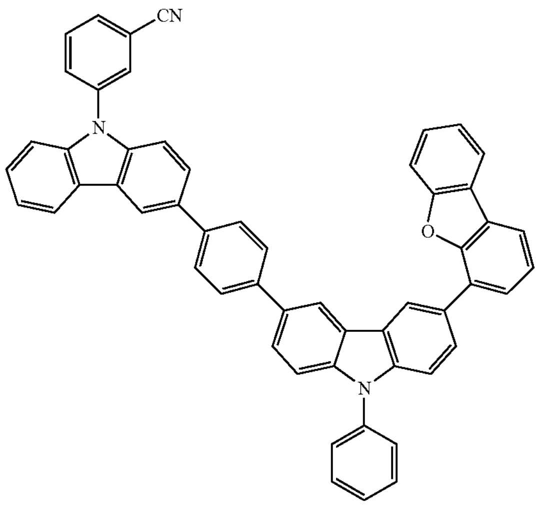

-continued
H1-339
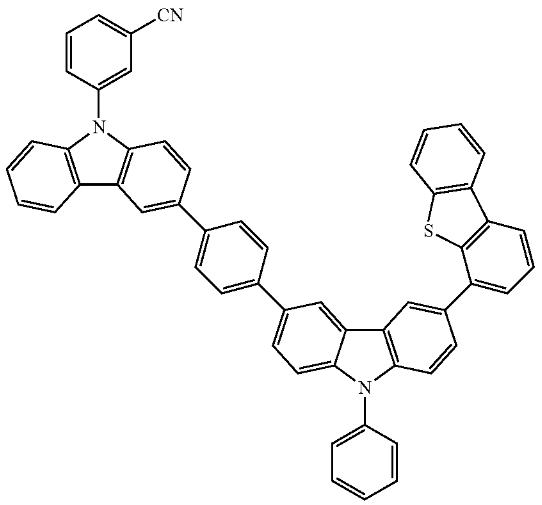
H1-340
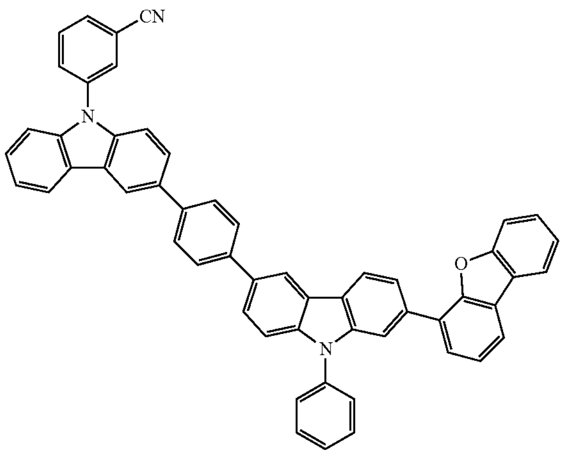
H1-341
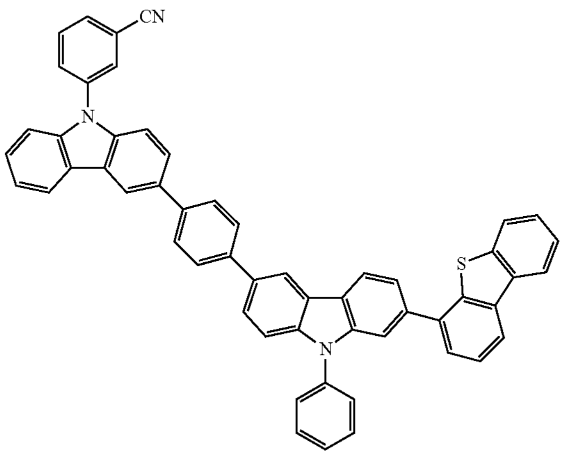
-continued
H1-342
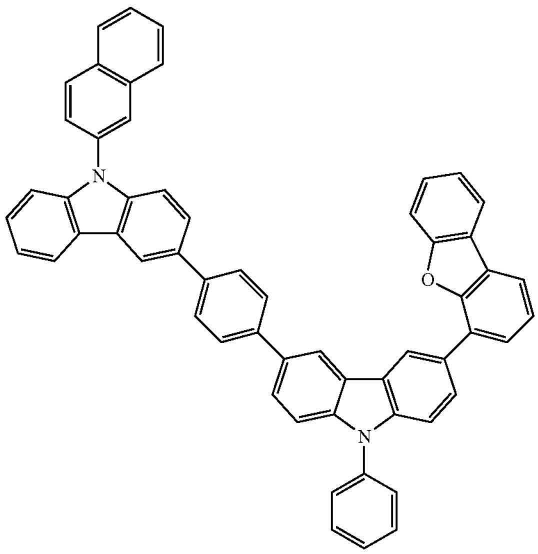
H1-343
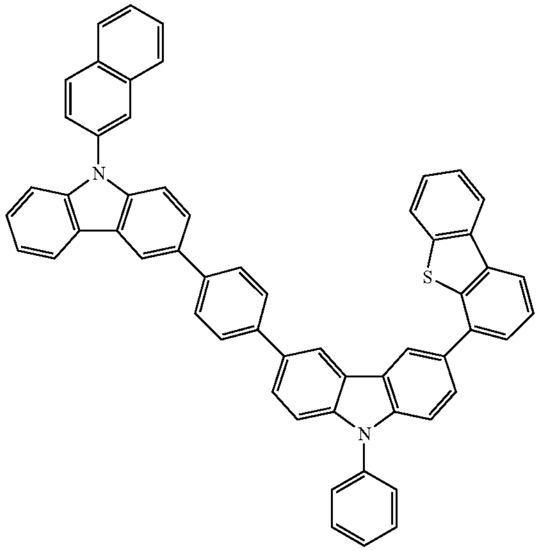
H1-344
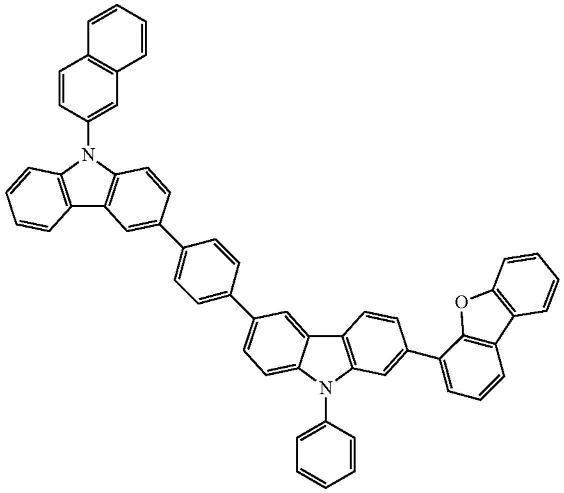

-continued
H1-345
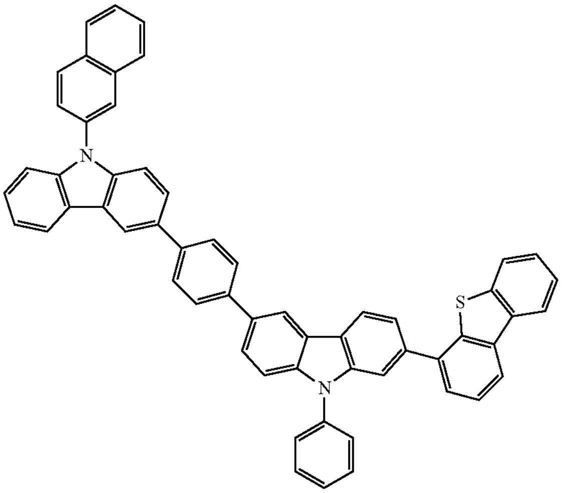
H1-347
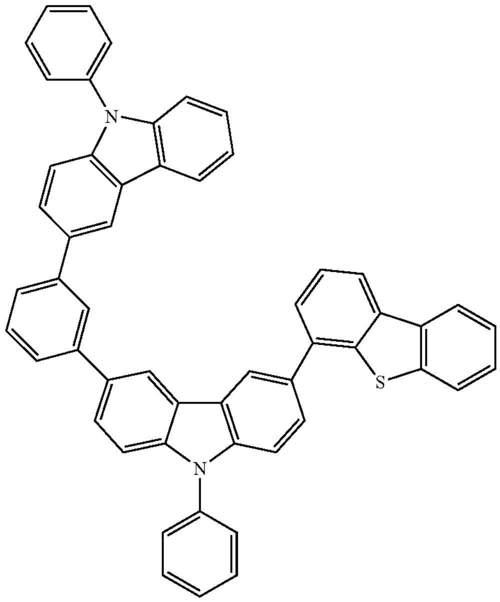
H1-346
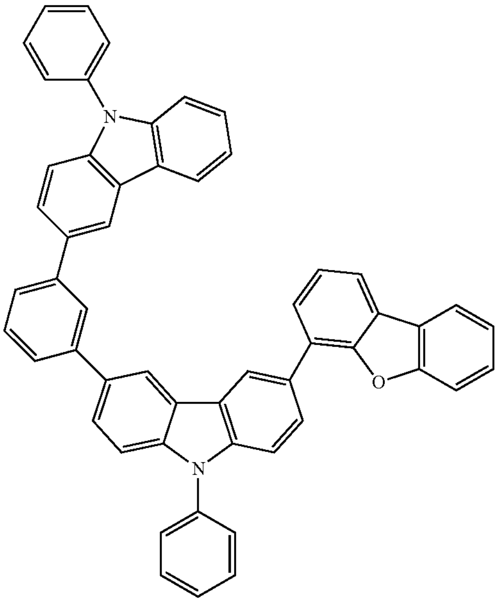
H1-348
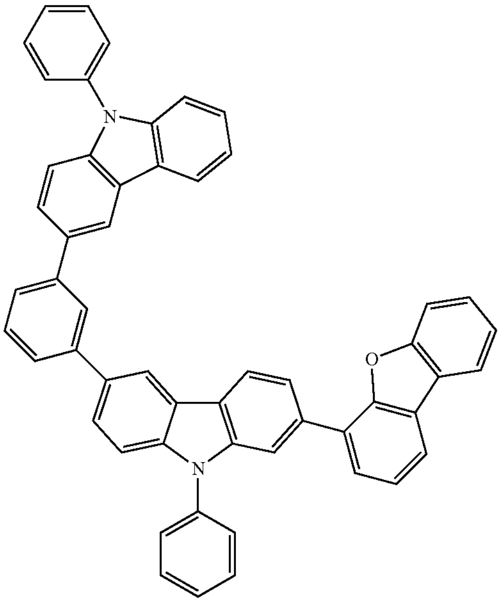

-continued
H1-349
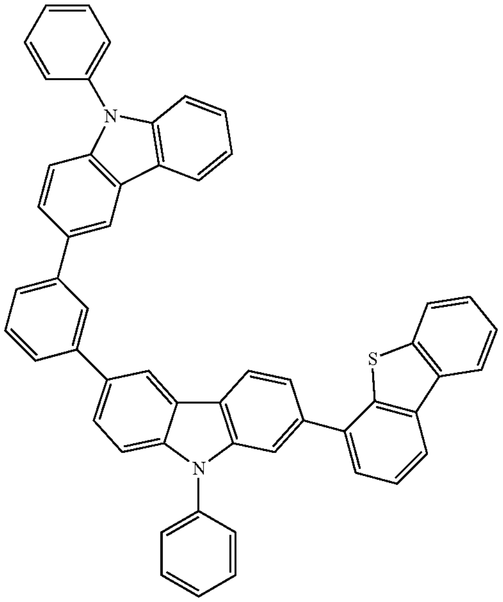
H1-350
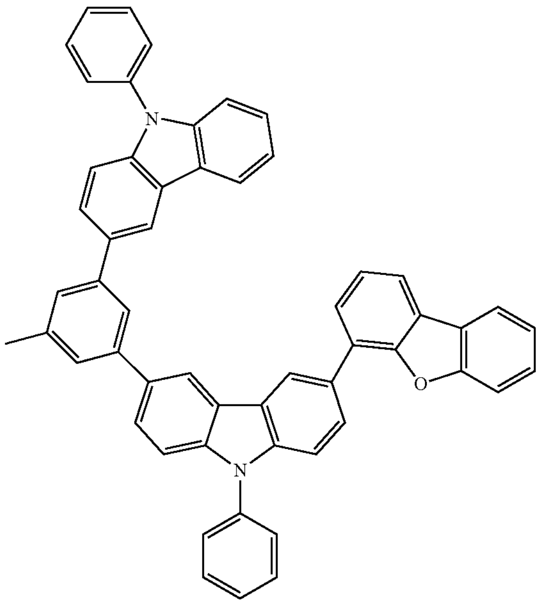
-continued
H1-351
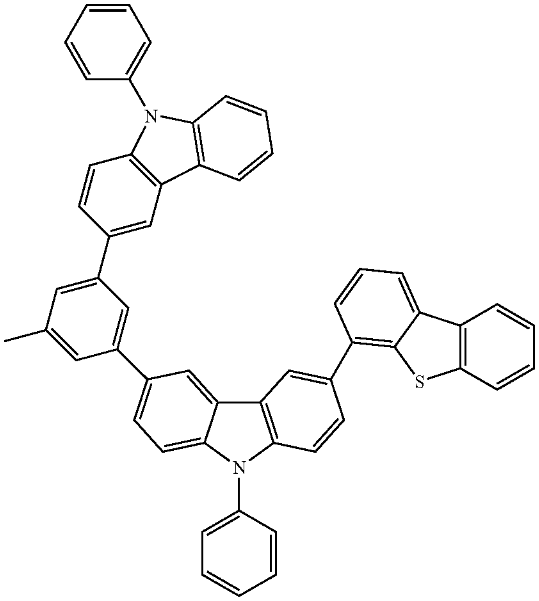
H1-352
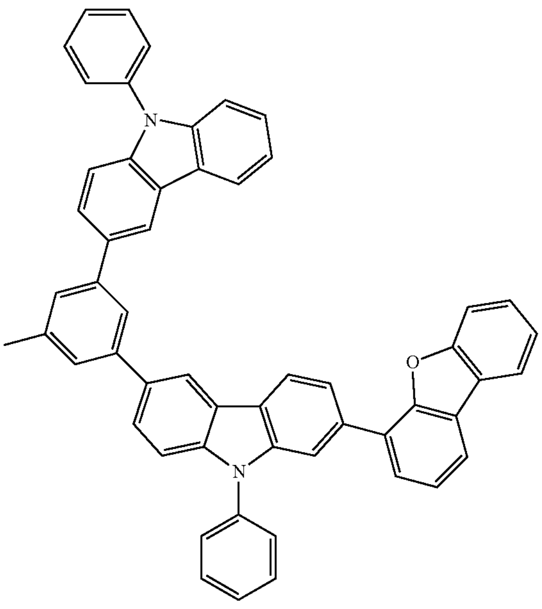

-continued
H1-353
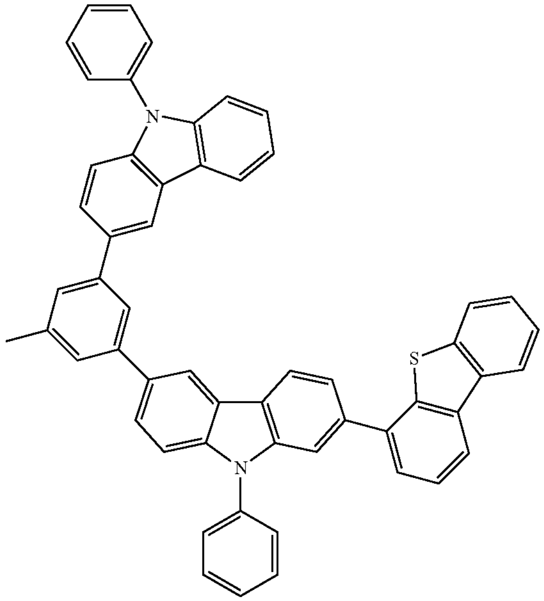
H1-354
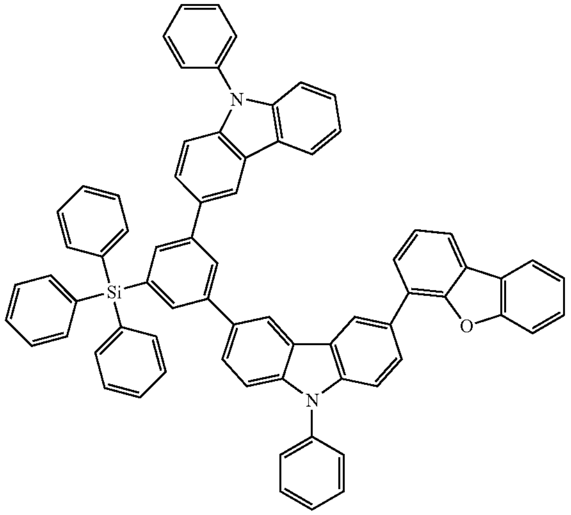
-continued
H1-355
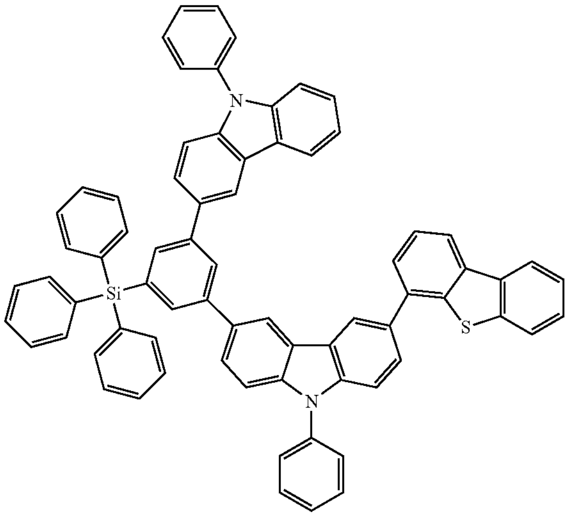
H1-356
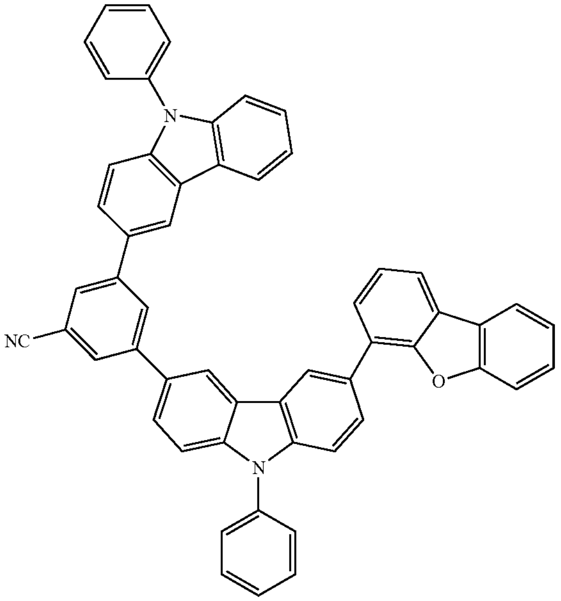

-continued
H1-357
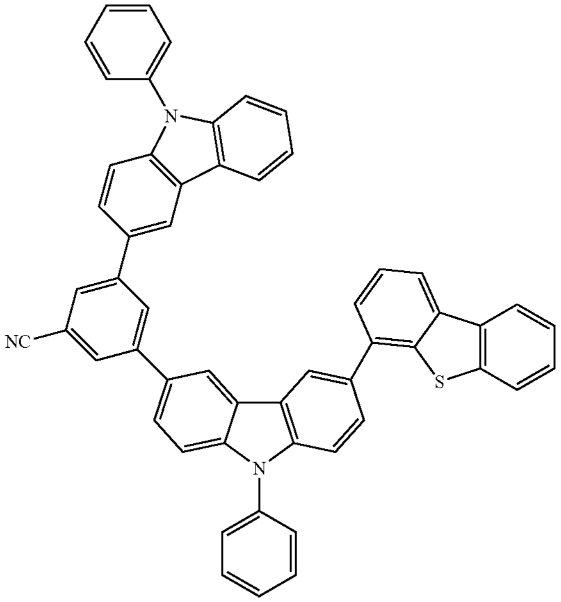
H1-358
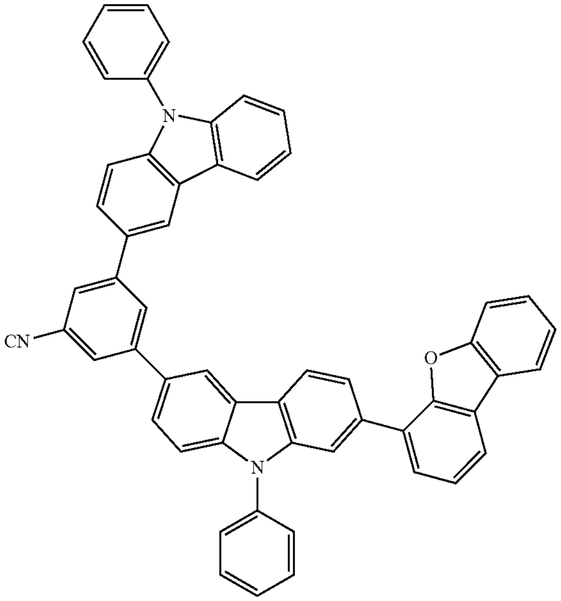
-continued
H1-359
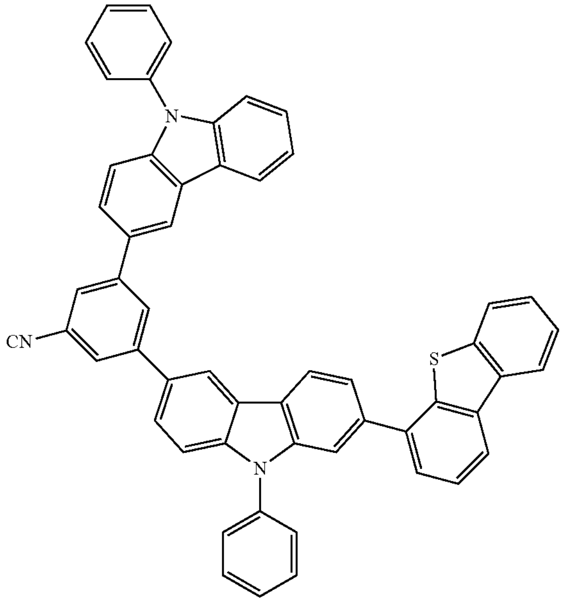
H1-360
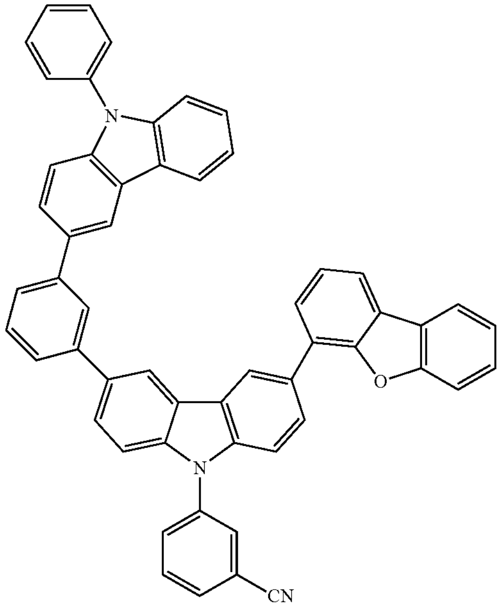

-continued
H1-361
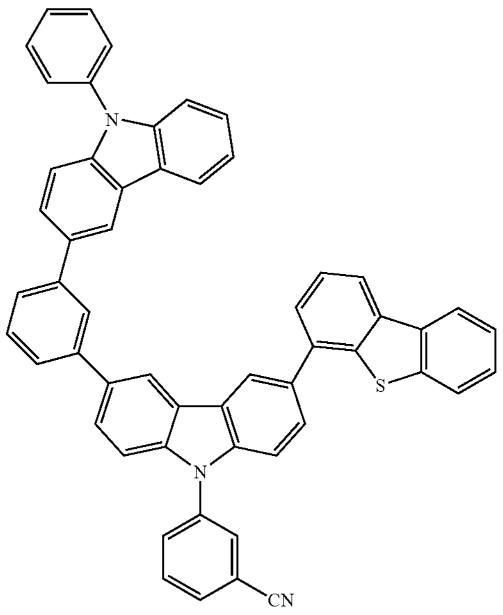
H1-362
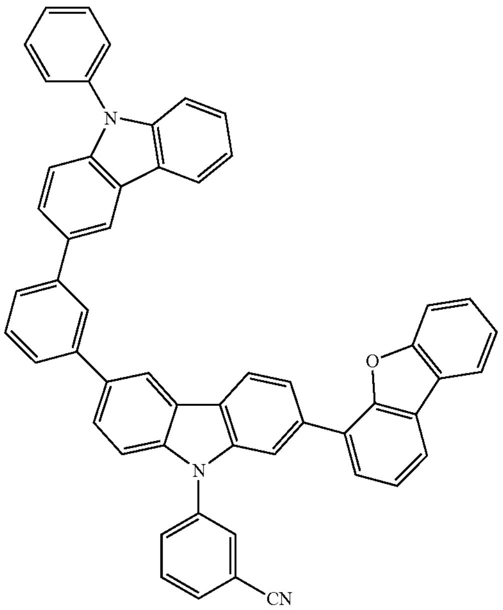
-continued
H1-363
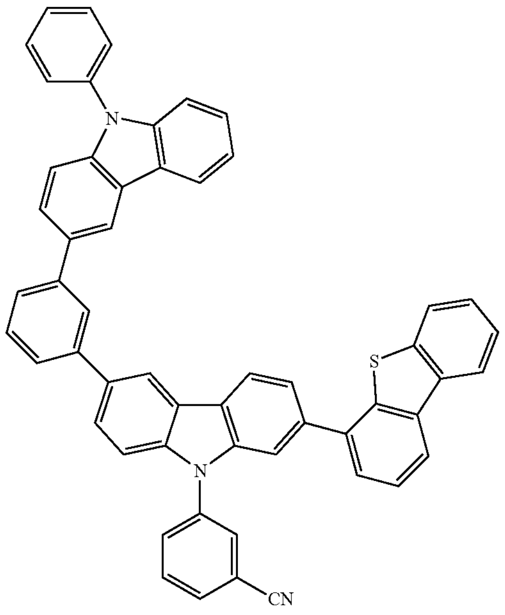
H1-364
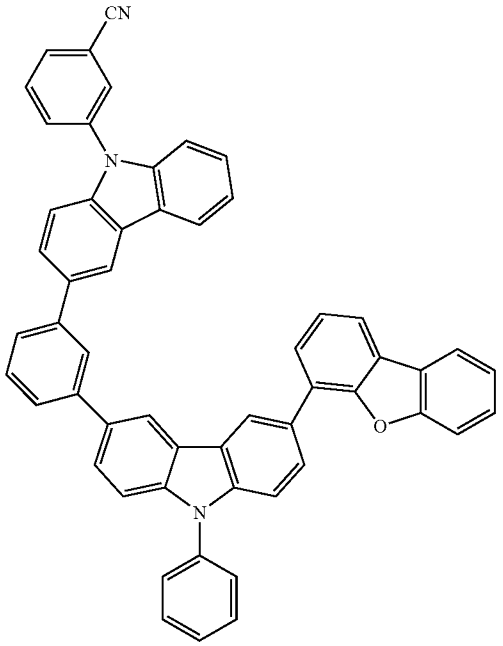

-continued
H1-365
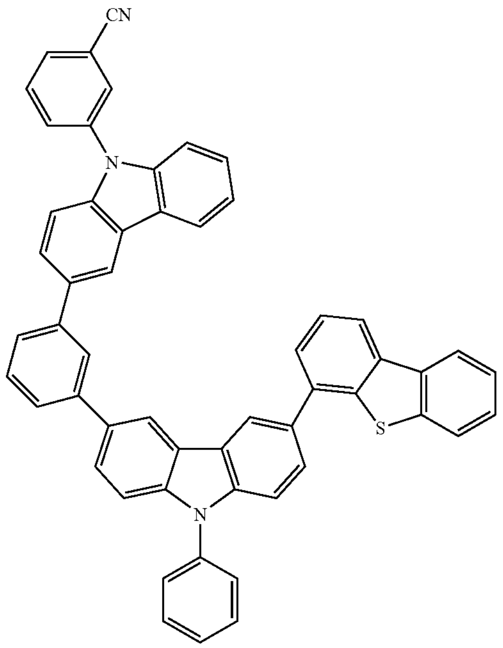
H1-366
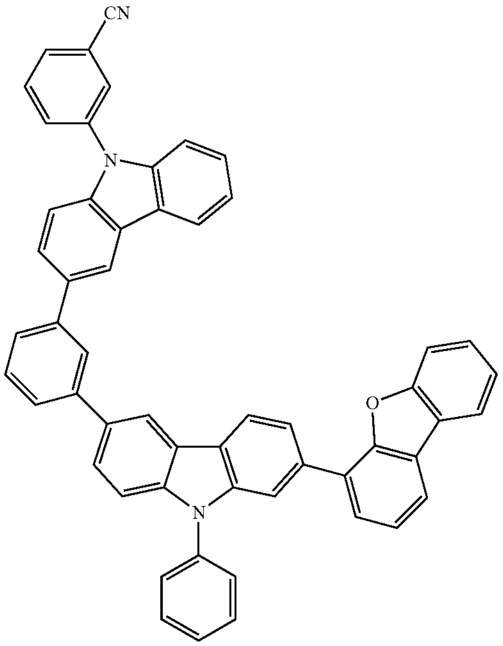
-continued
H1-367
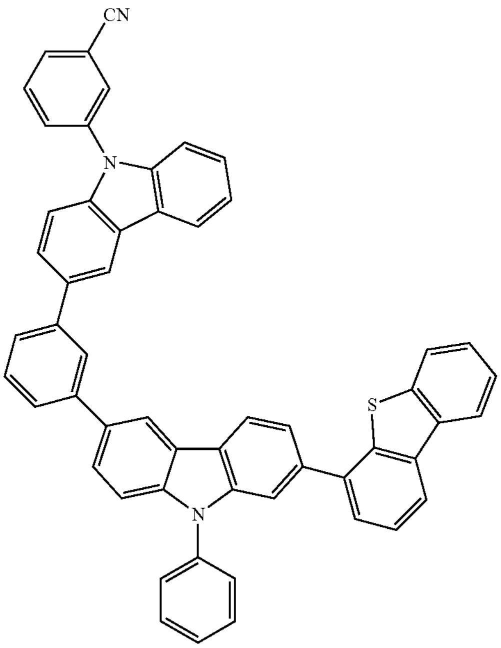
H1-368
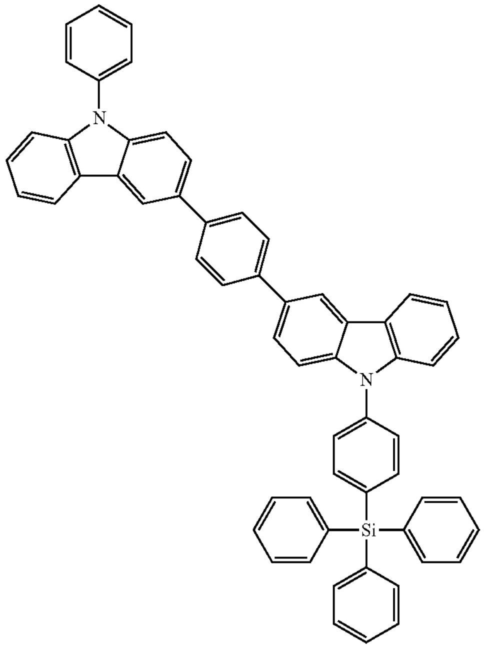

-continued
H1-369
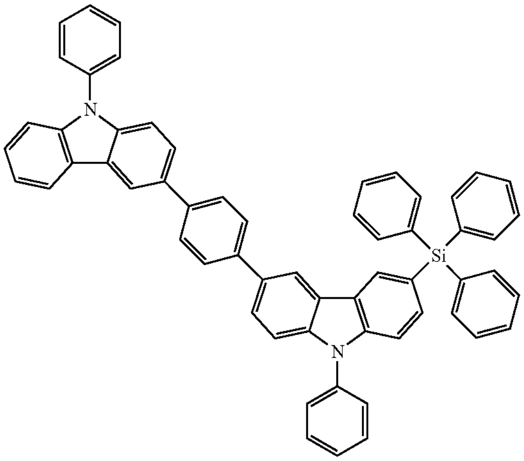
H1-370
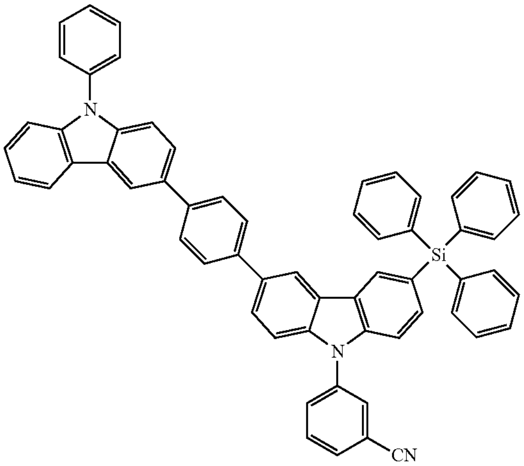
H1-371
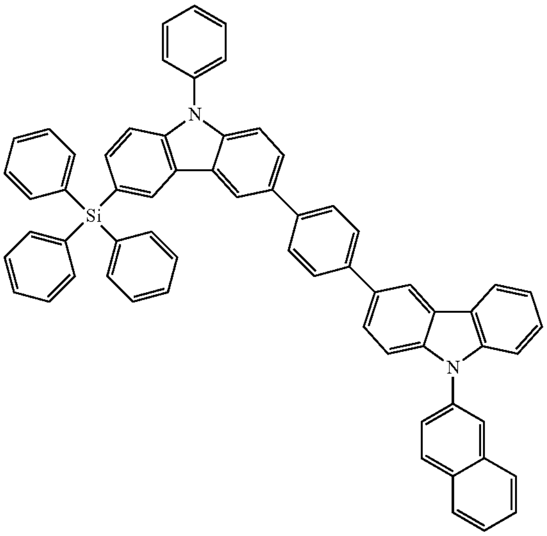
-continued
H1-372
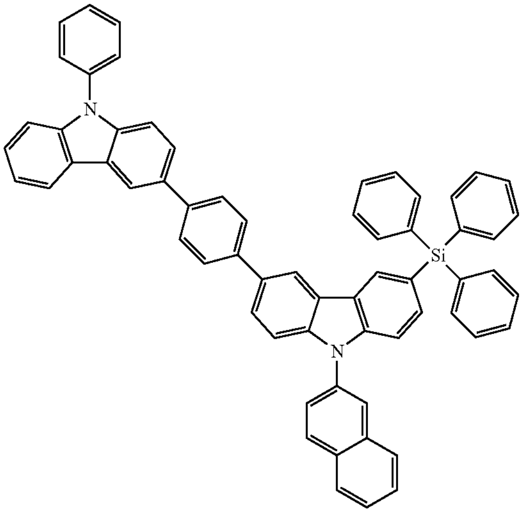
H1-373
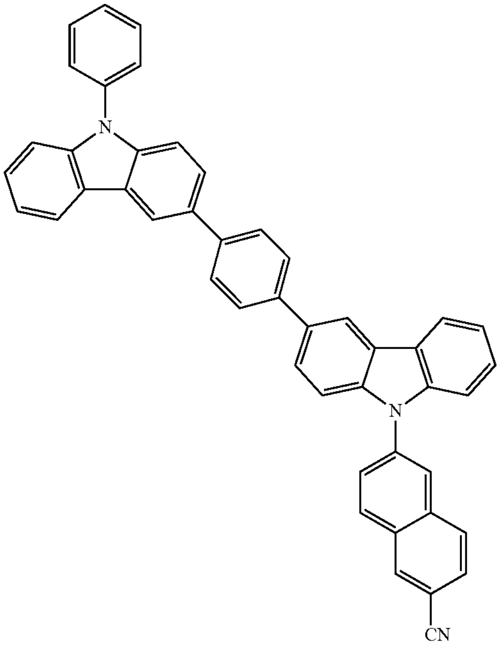

-continued
H1-374
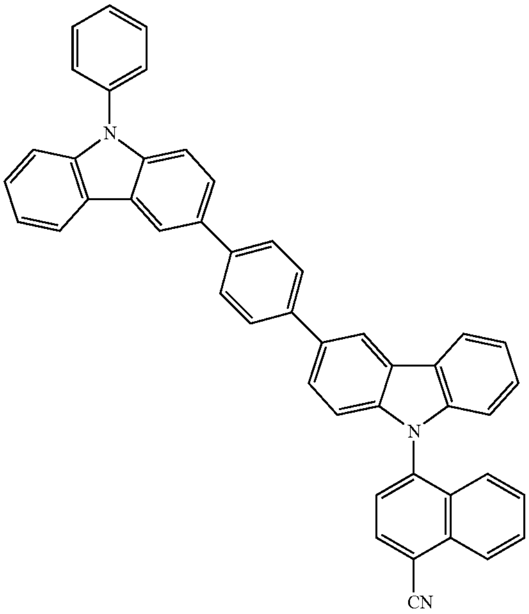
H1-375
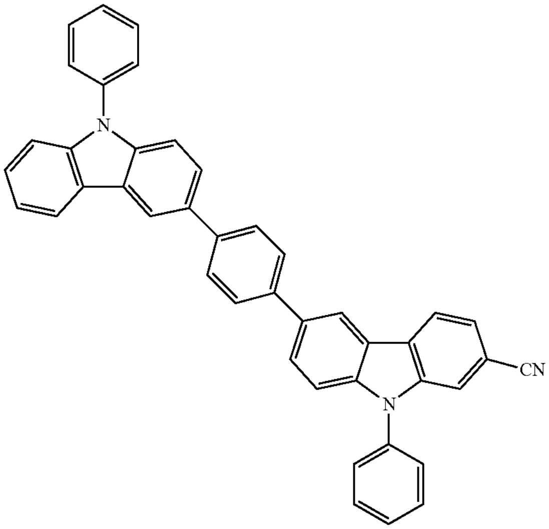
-continued
H1-376
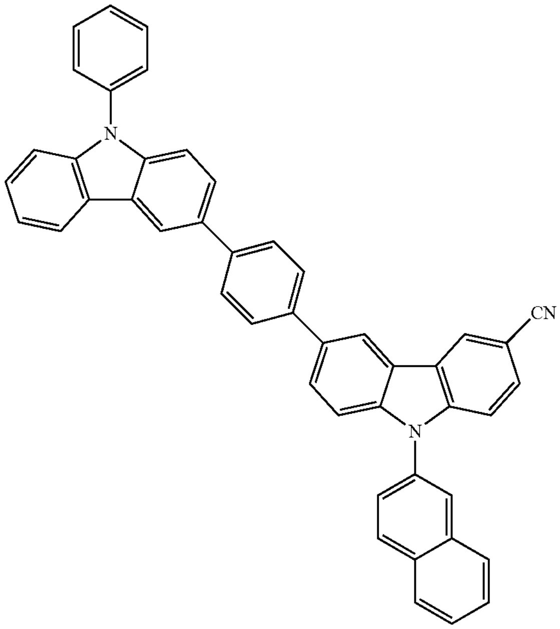
H1-377
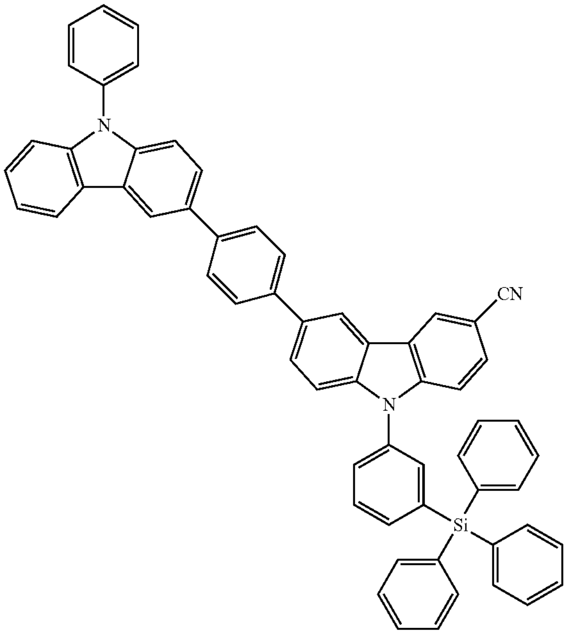
H1-378
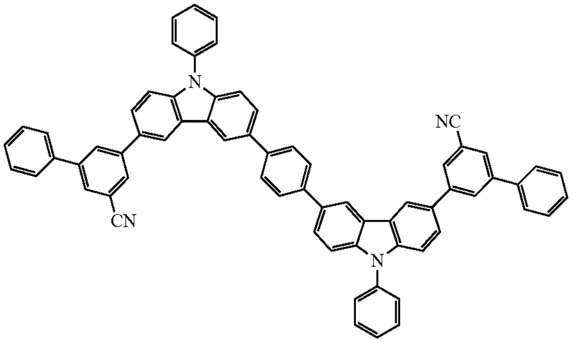

-continued
H1-379
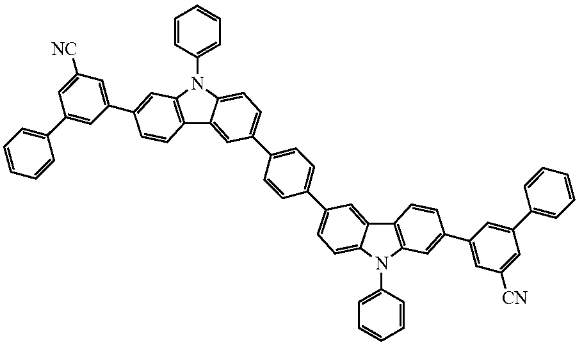
H1-380
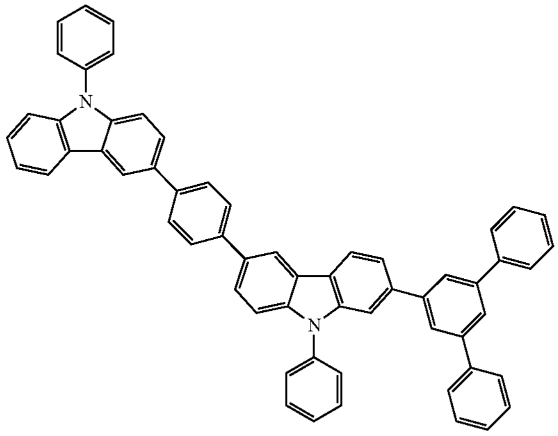
H1-381
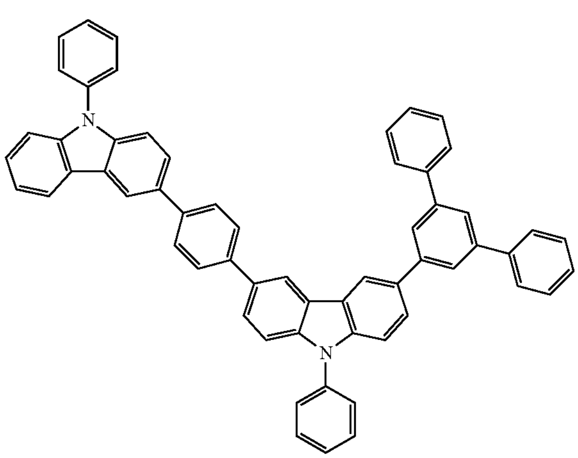
-continued
H1-382
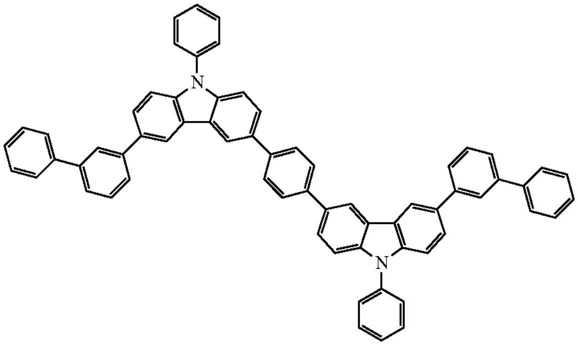
H1-383
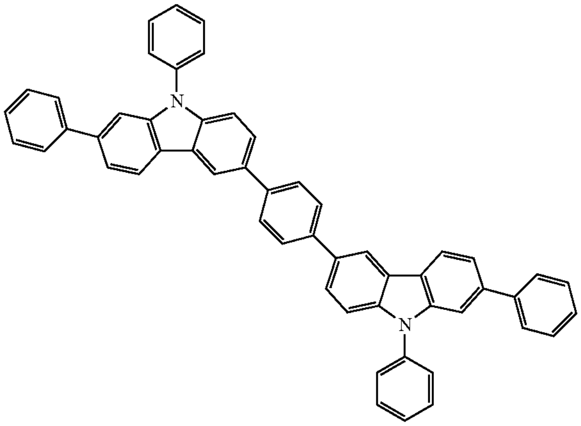
H1-384
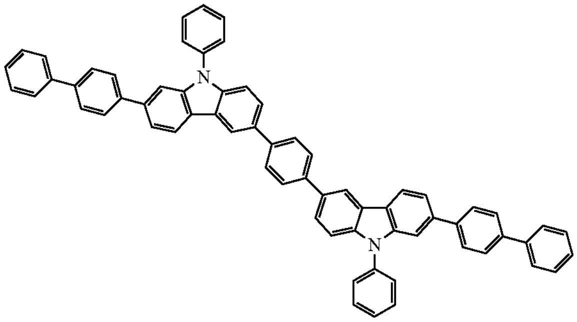
H1-385
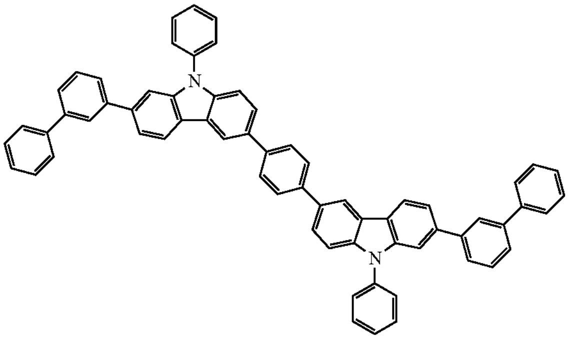

-continued
H1-386
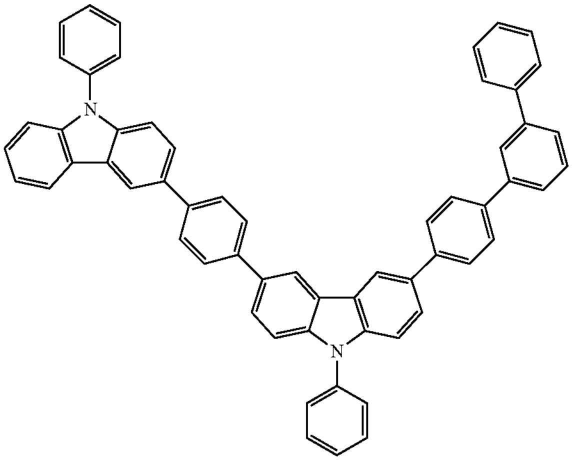
H1-387
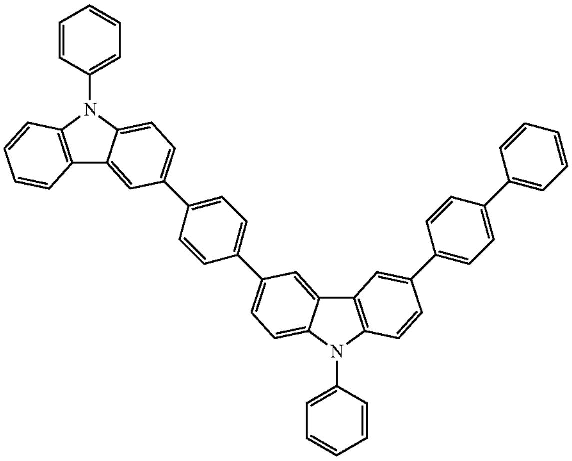
H1-388
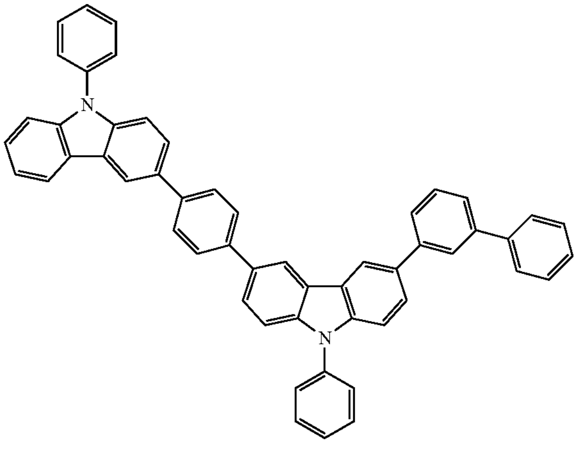
-continued
H1-389
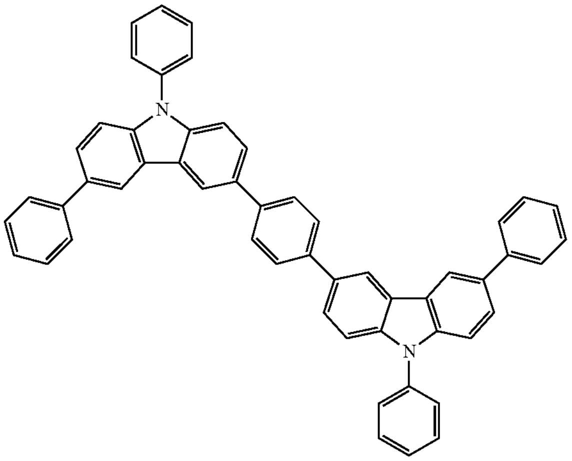
H1-390
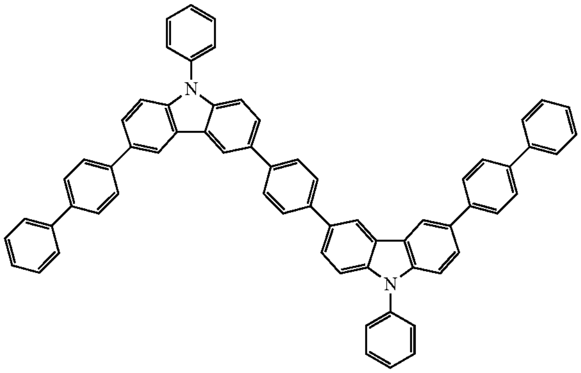
H1-391
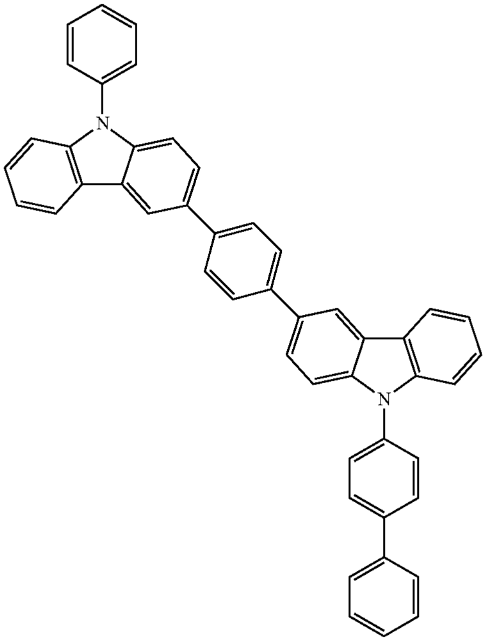

-continued
H1-392
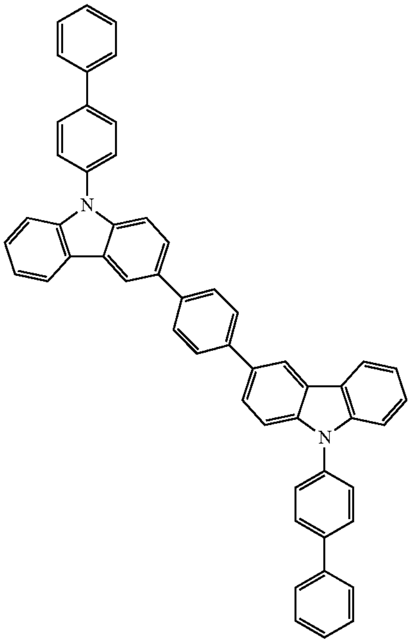
H1-393
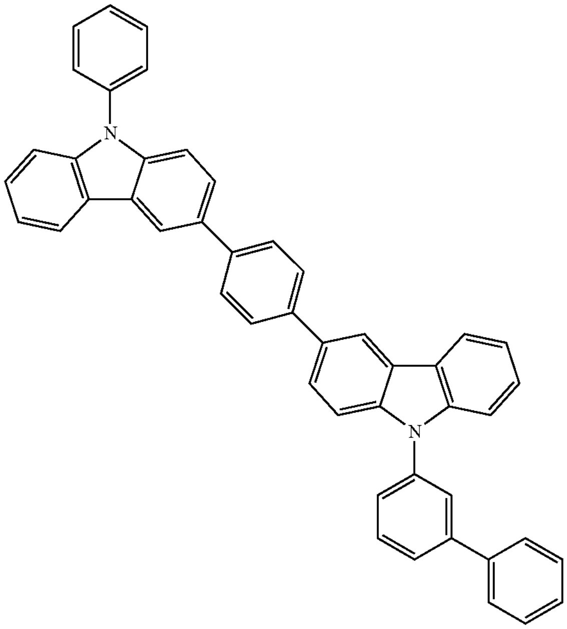
-continued
H1-394
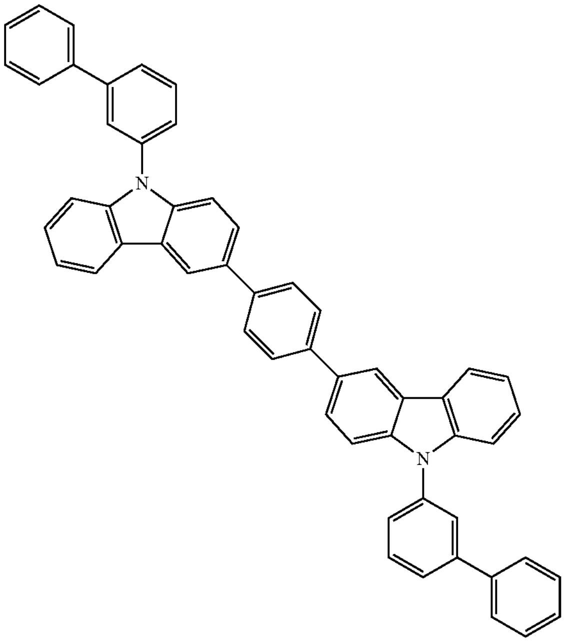
H1-395
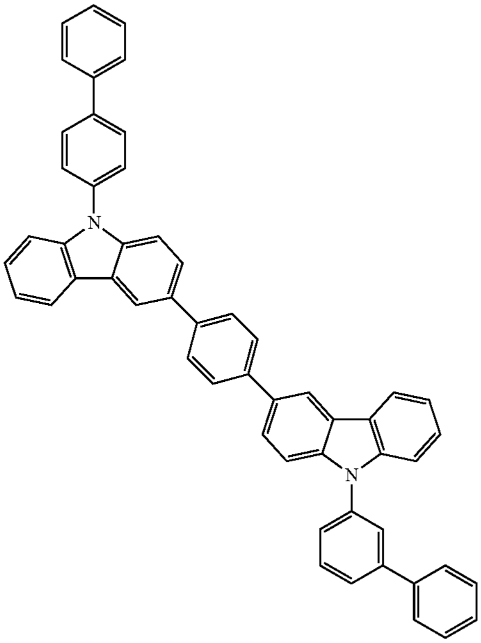

-continued
H1-396
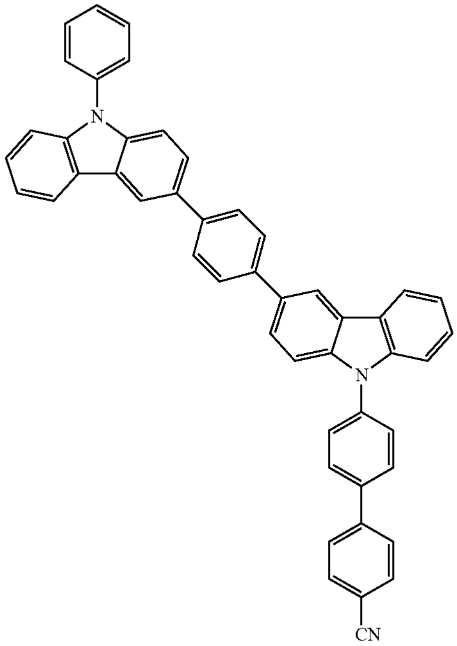
H1-397
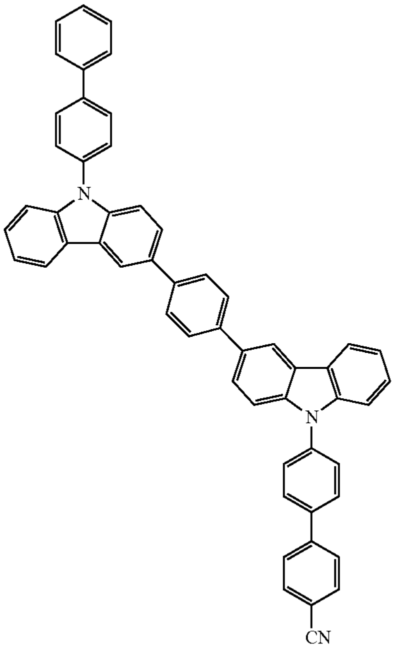
-continued
H1-398
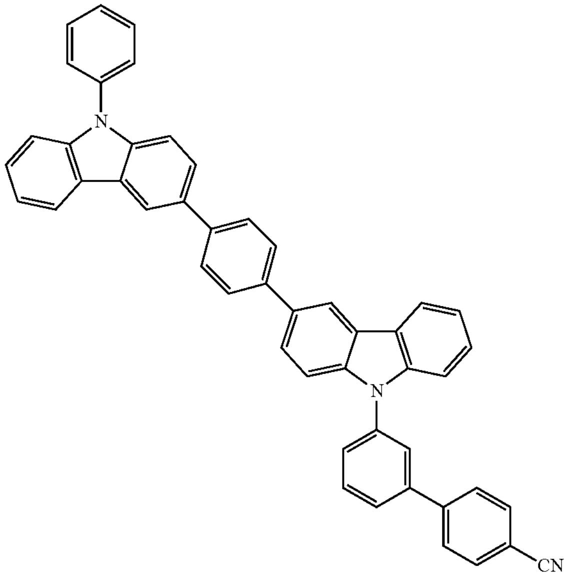
H1-399
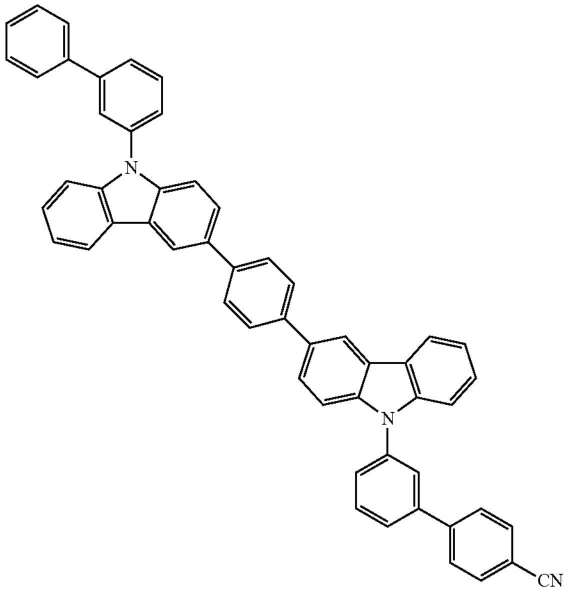

-continued
H1-400
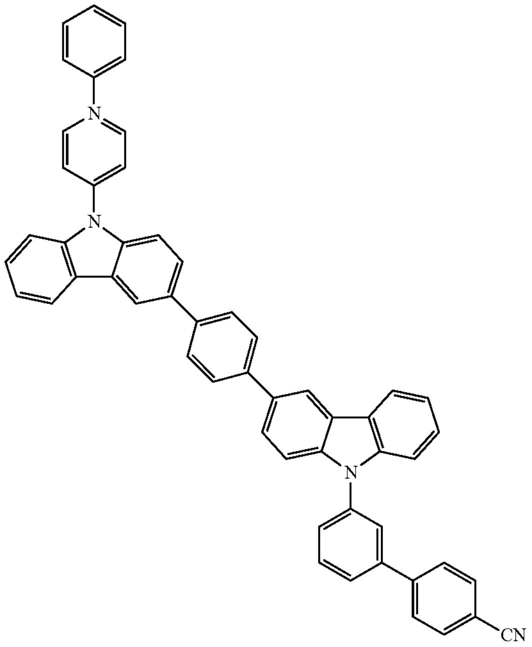
H1-401
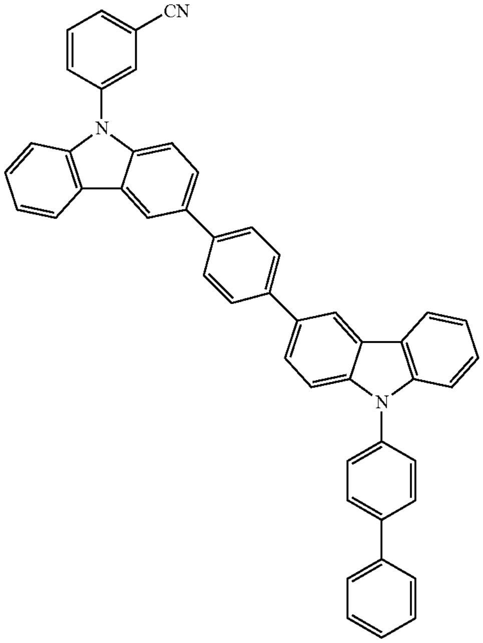
-continued
H1-402
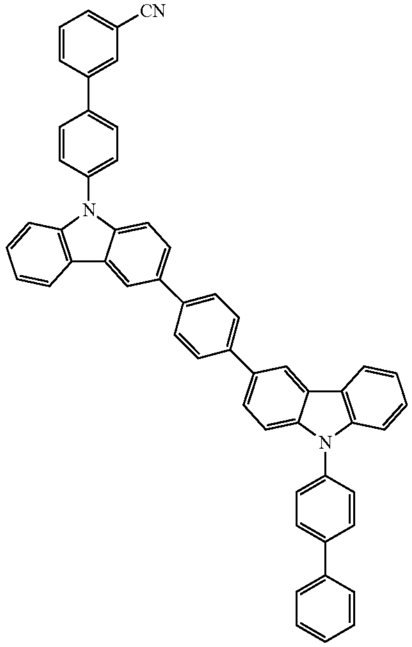
H1-403
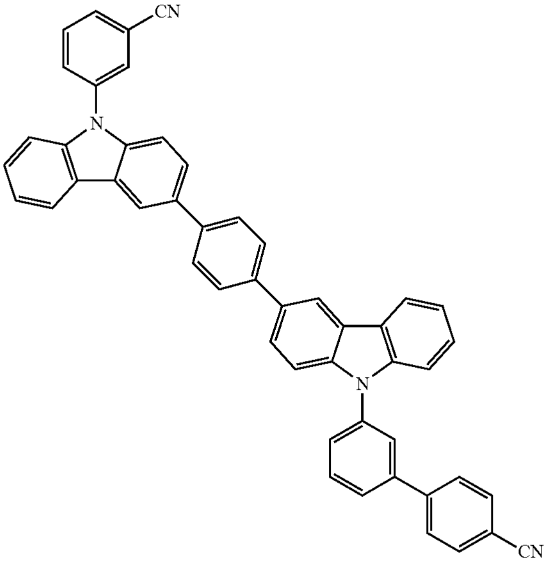

-continued
H1-404
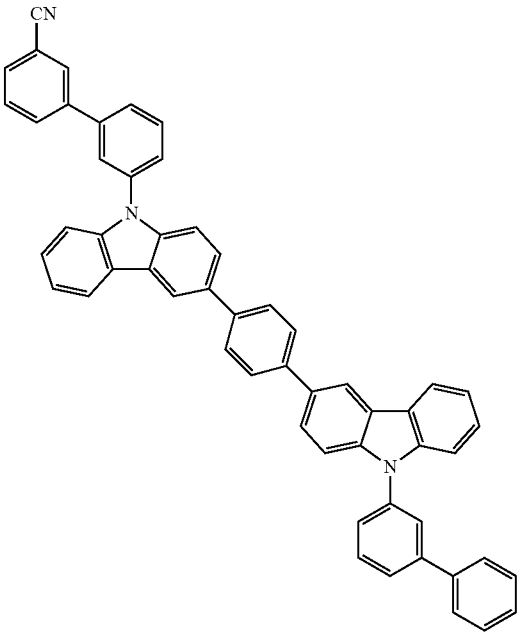
H1-405
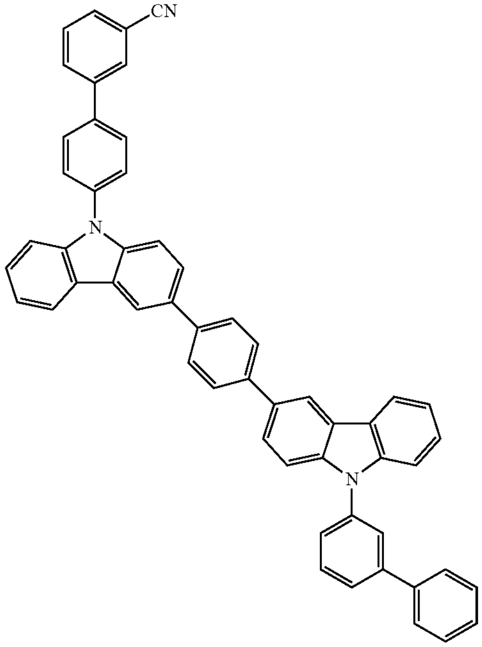
-continued
H1-406
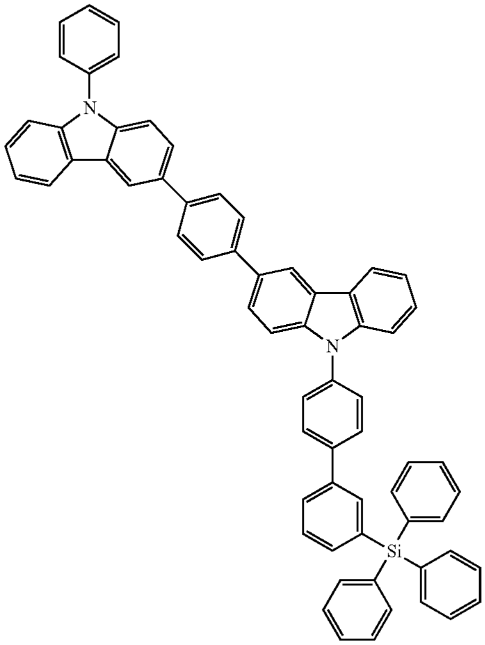
H1-407
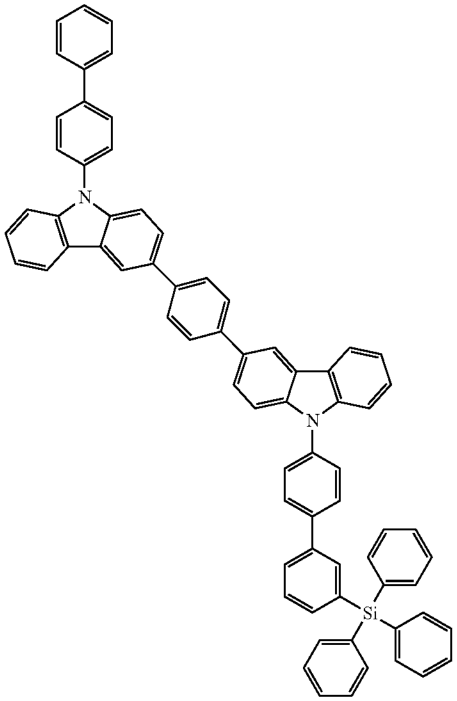

-continued
H1-408
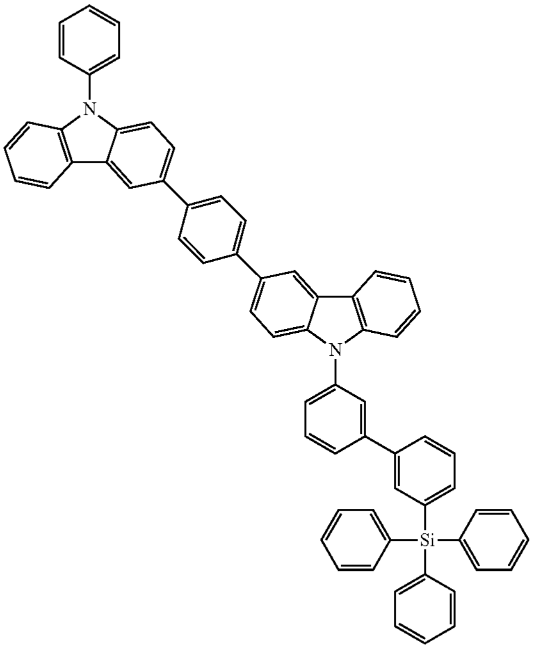
H1-409
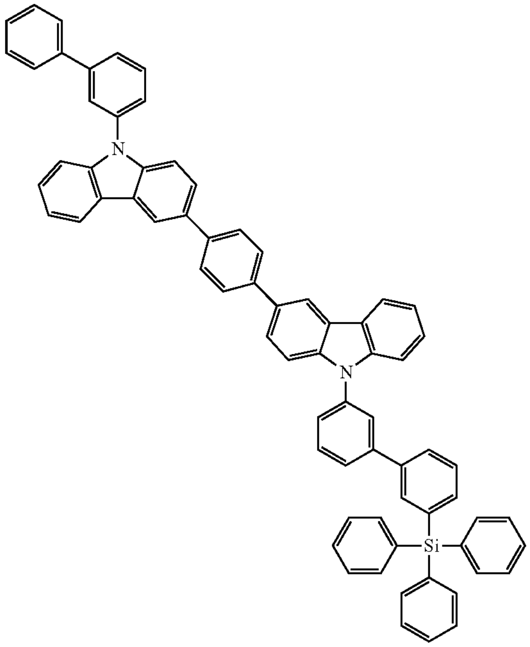
-continued
H1-410
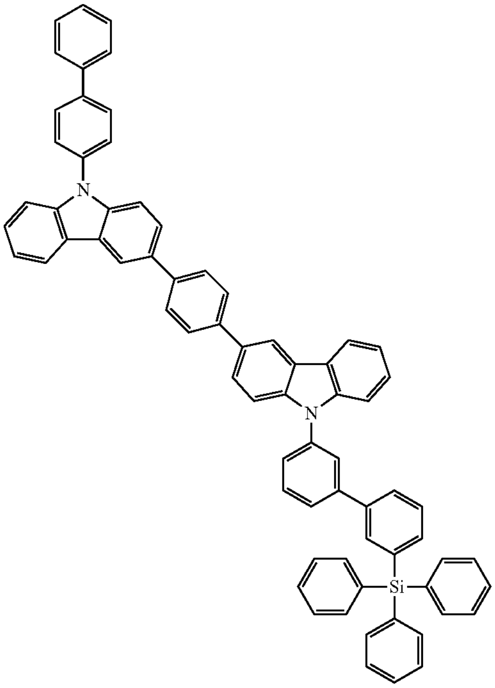
H1-411
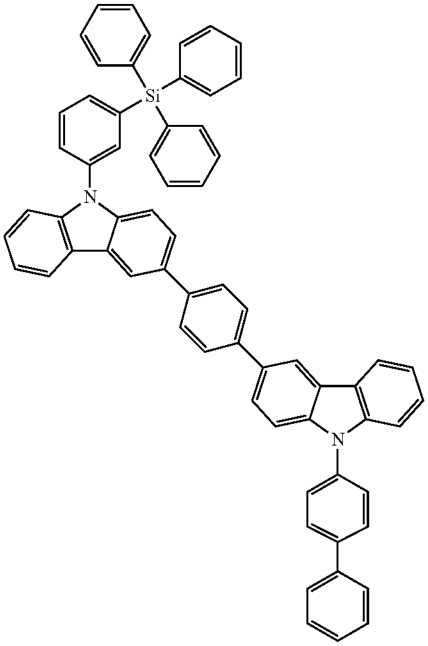

-continued
H1-412
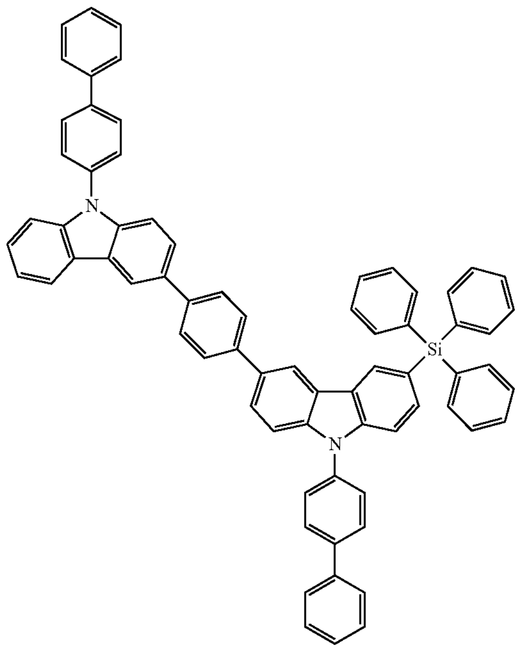
-continued
H1-414
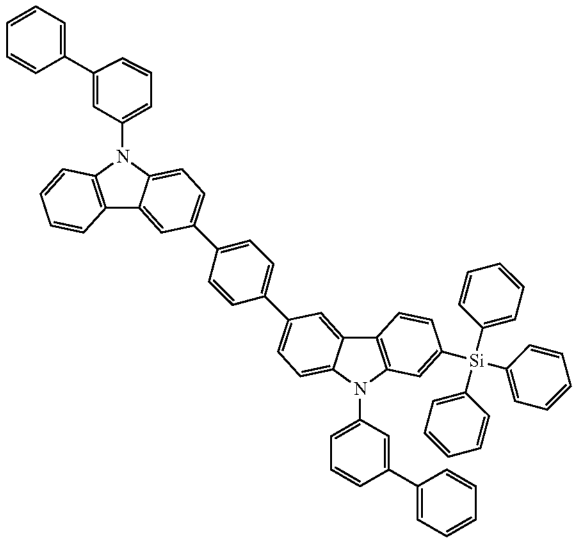
H1-413
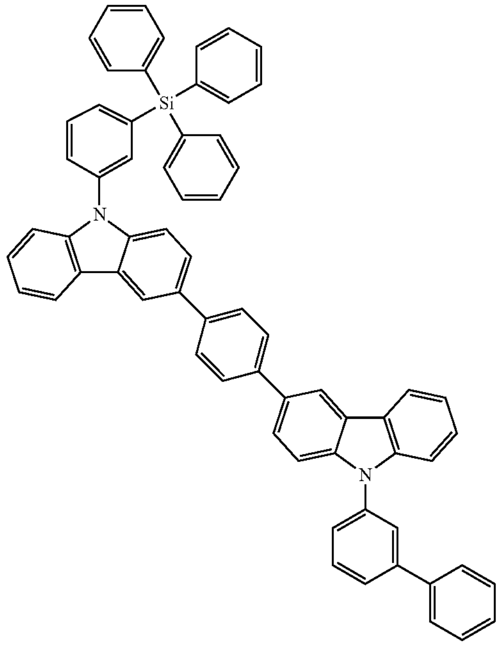
H1-415
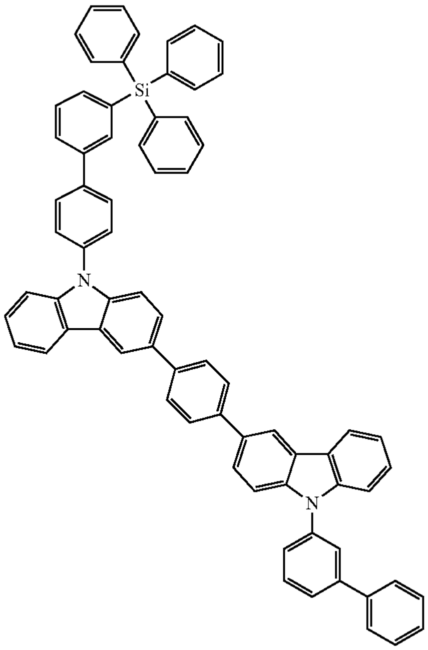

-continued
H1-416
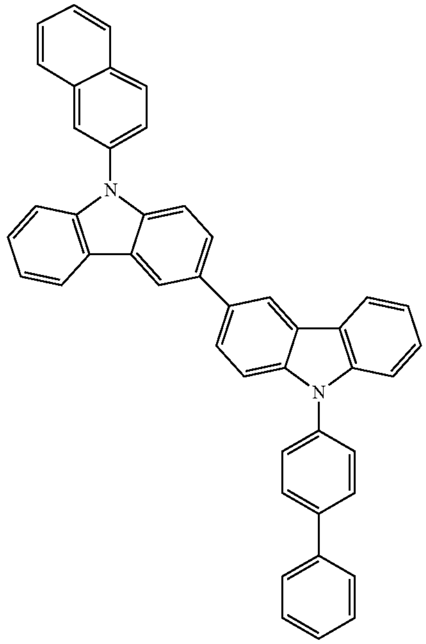
H1-418
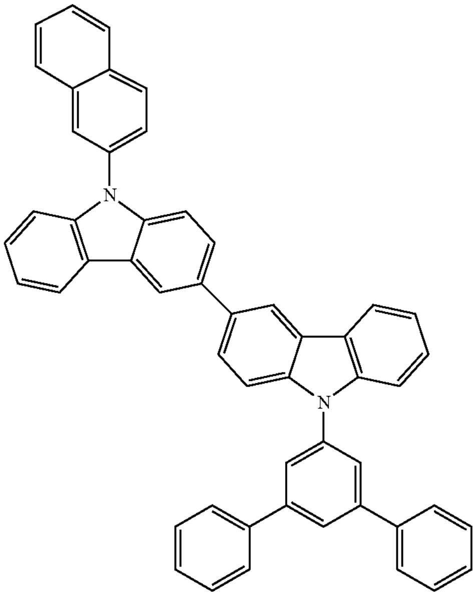
H1-417
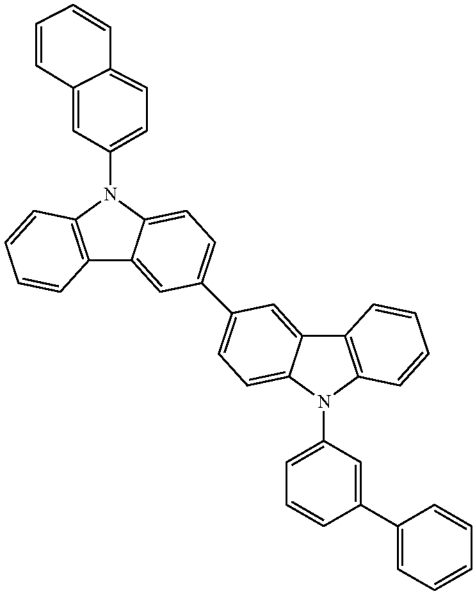
H1-419
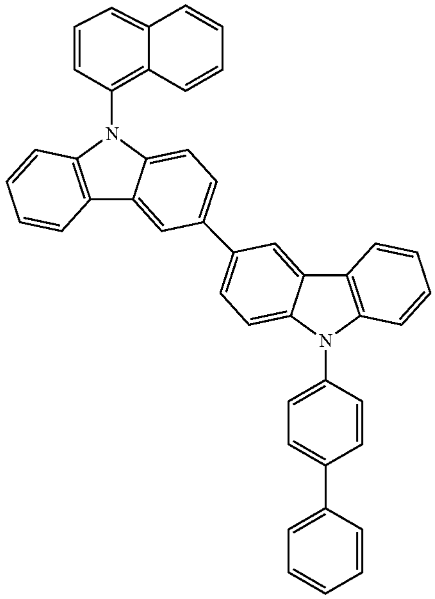

-continued
H1-420
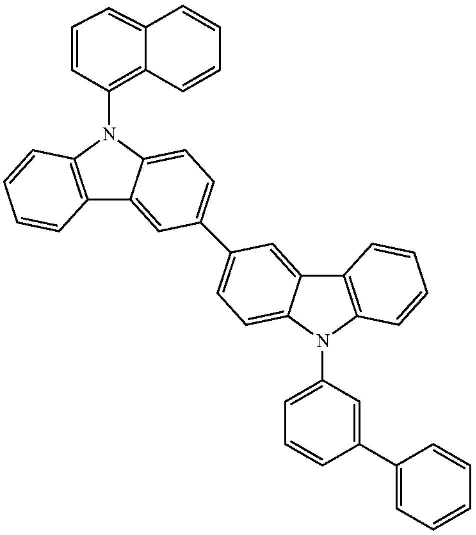
H1-421
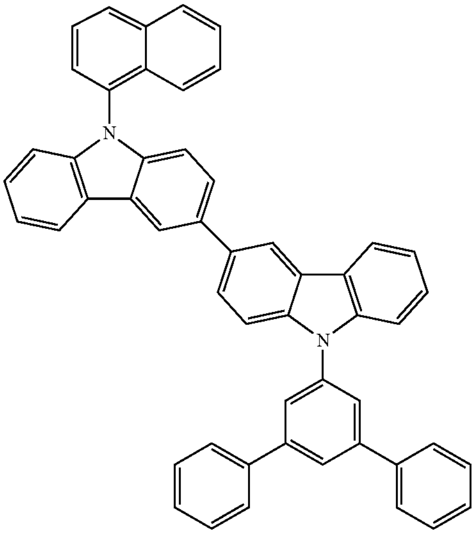
-continued
H1-422
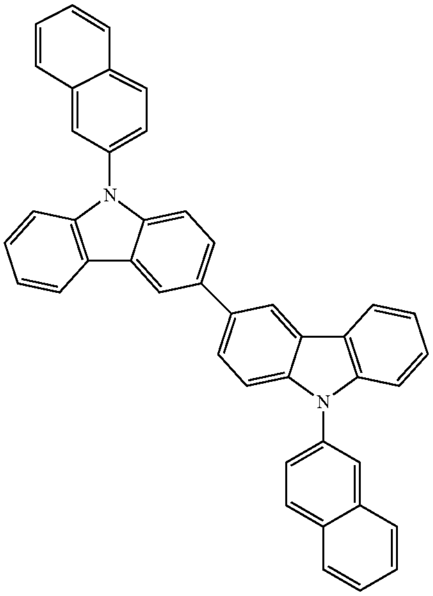
H1-423
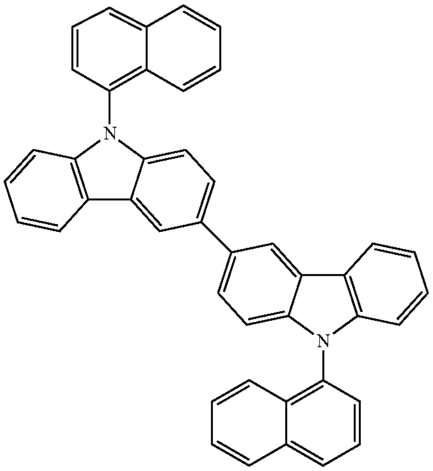
The second host compound represented by formula 2 includes the following compounds, but is not limited thereto:

-continued
A-1
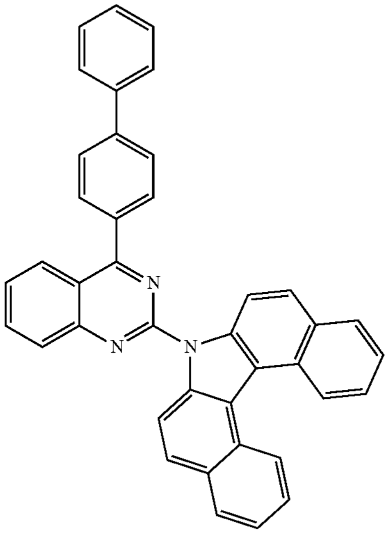
A-2
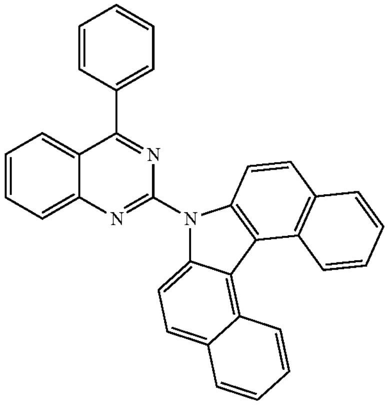
A-3
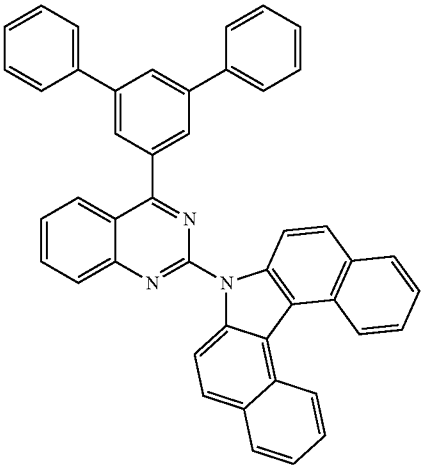
A-4
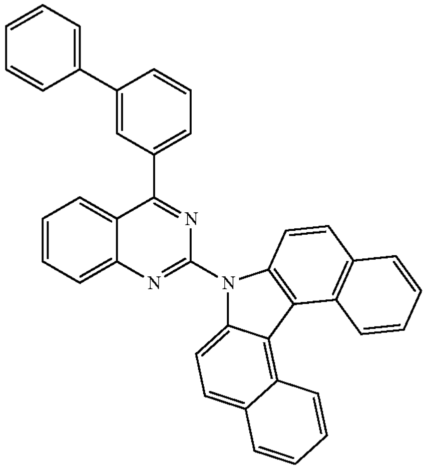
A-5
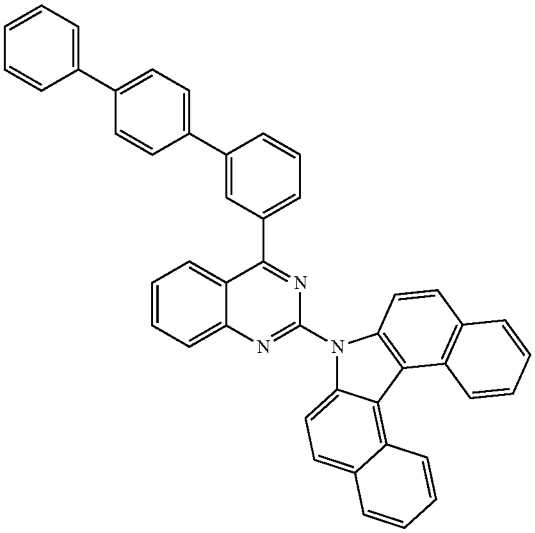
A-6
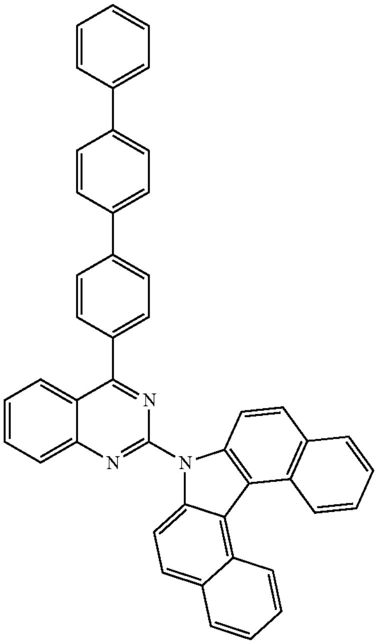

-continued
A-7
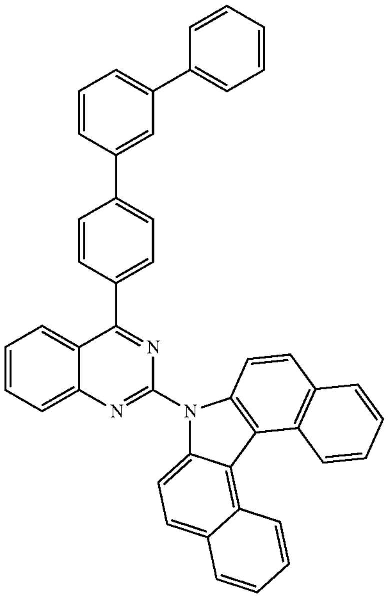
A-8
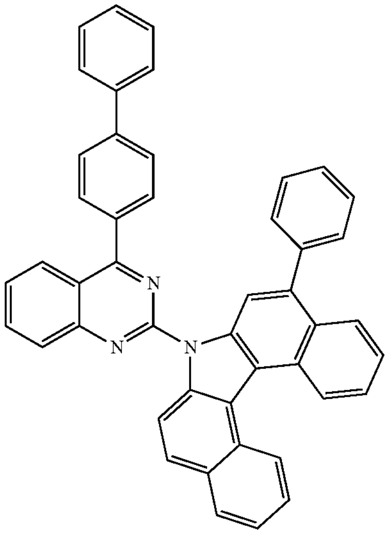
A-9
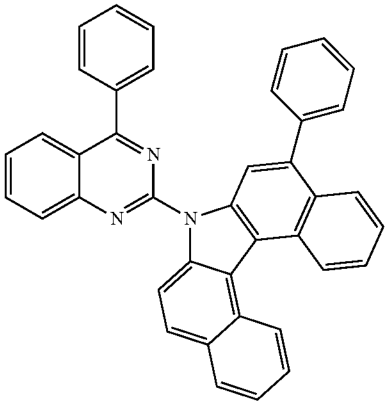
-continued
A-10
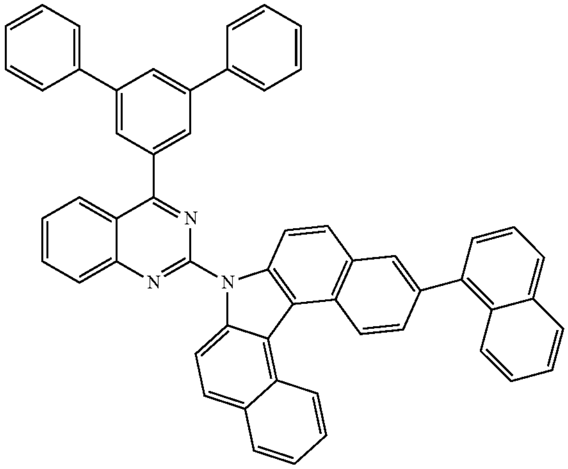
A-11
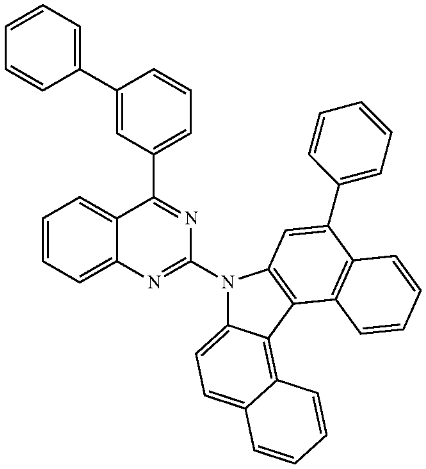
A-12
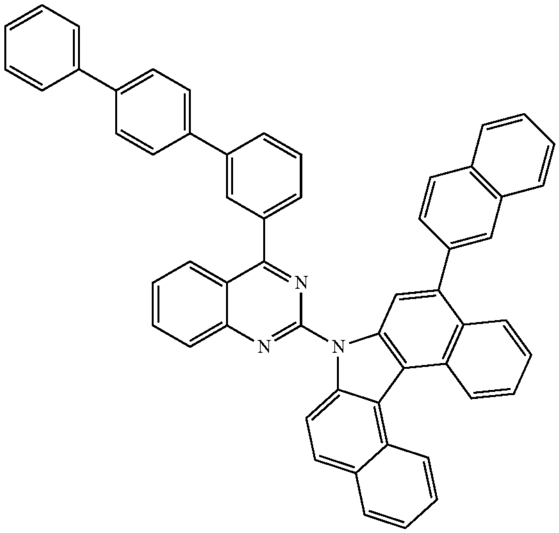

-continued
A-13
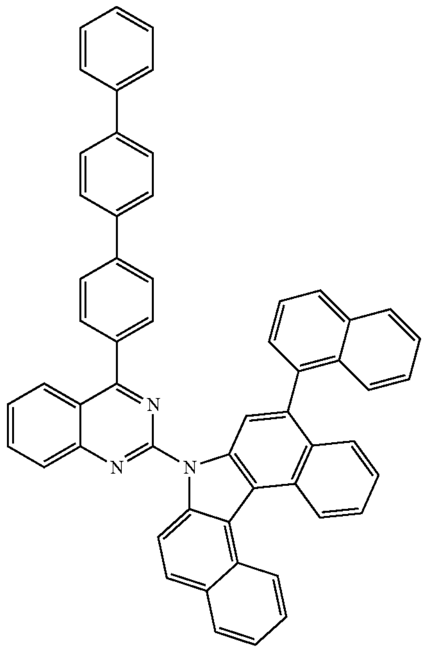
A-14
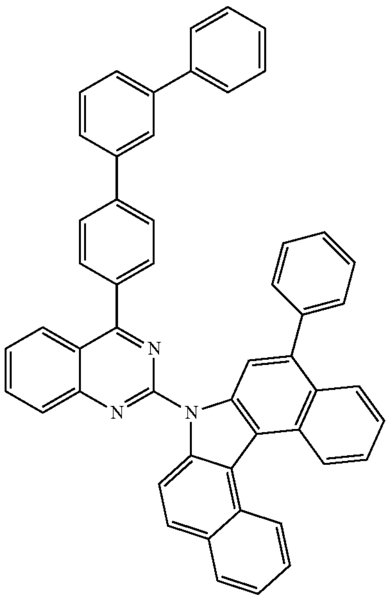
-continued
A-15
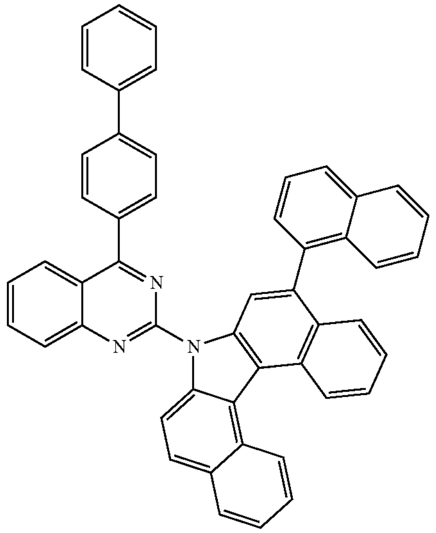
A-16
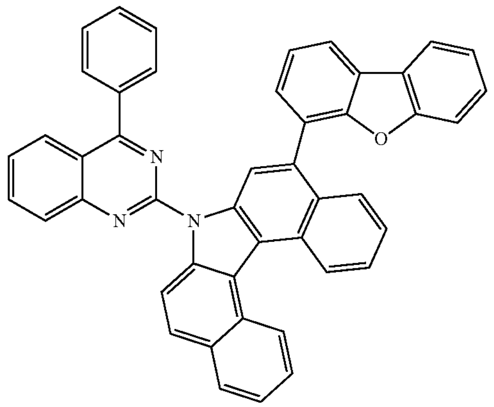
A-17
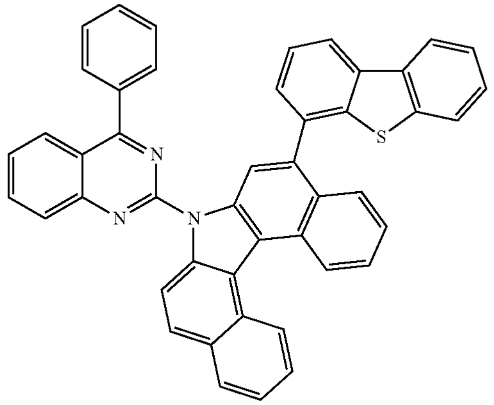

-continued
A-18
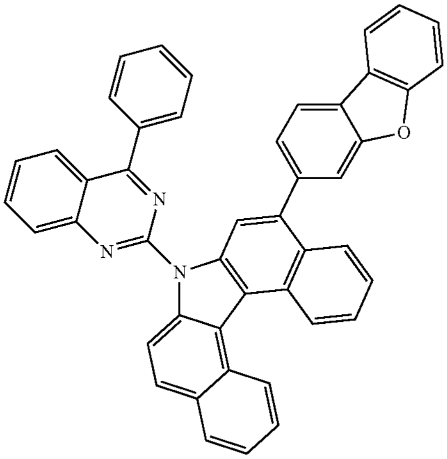
A-19
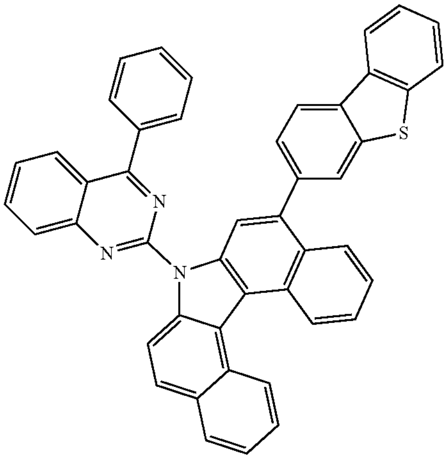
A-20
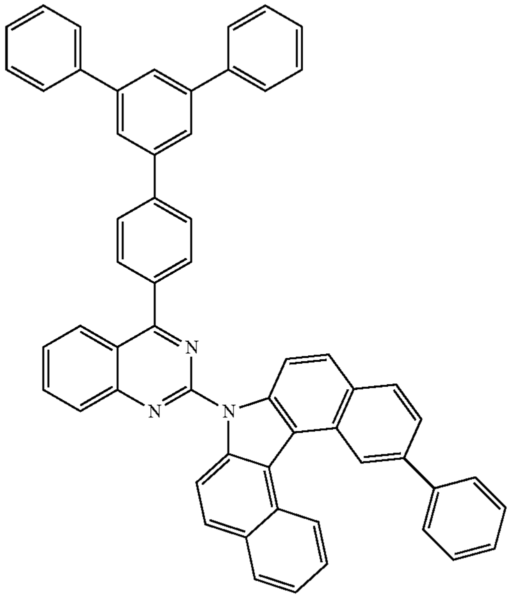
-continued
A-21
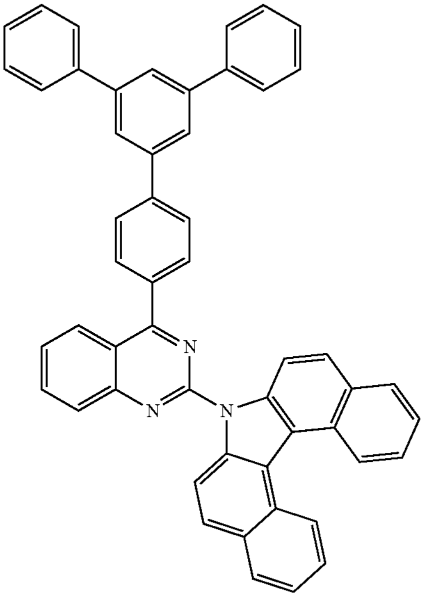
A-22
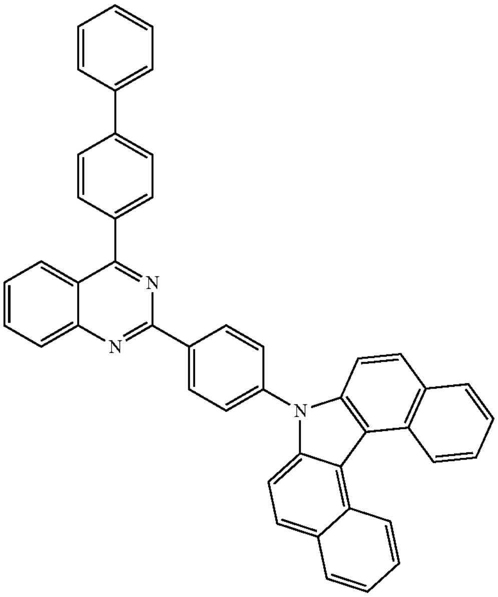

-continued
A-23
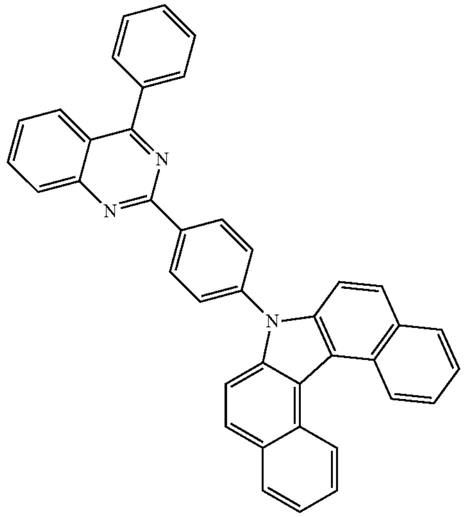
A-24
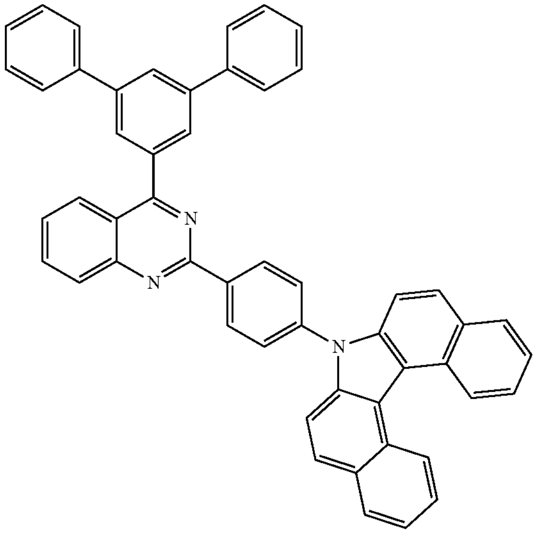
A-25
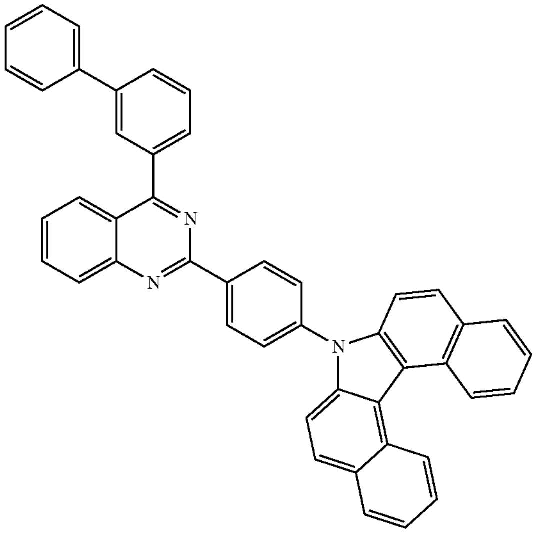
-continued
A-26
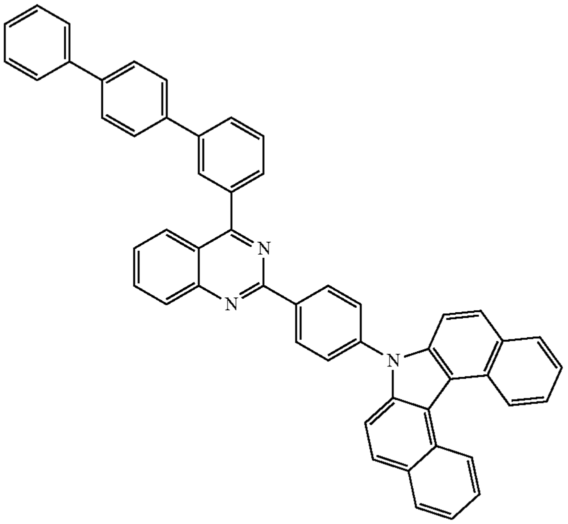
A-27
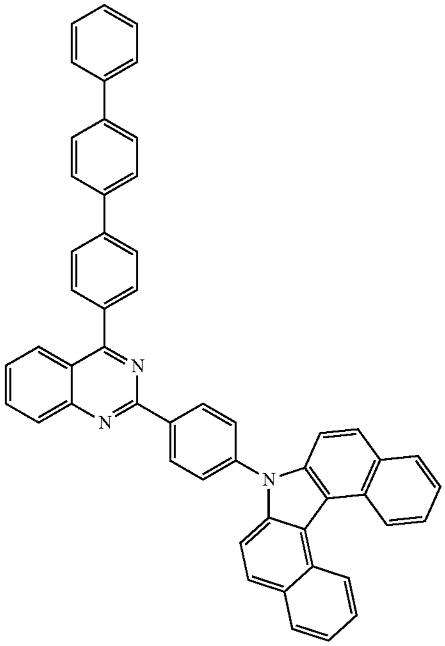

-continued
A-28
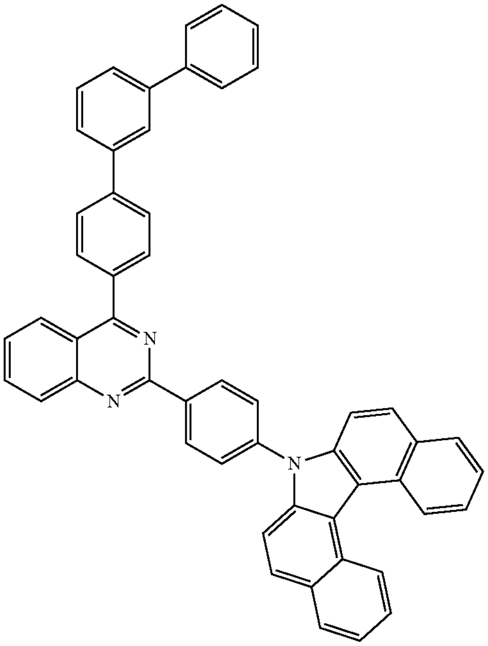
A-29
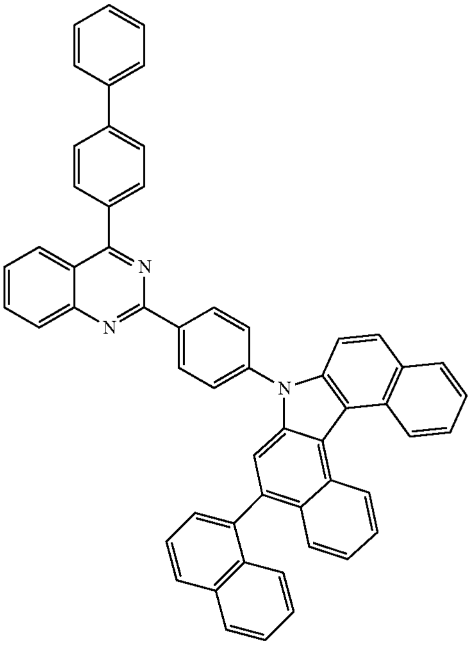
-continued
A-30
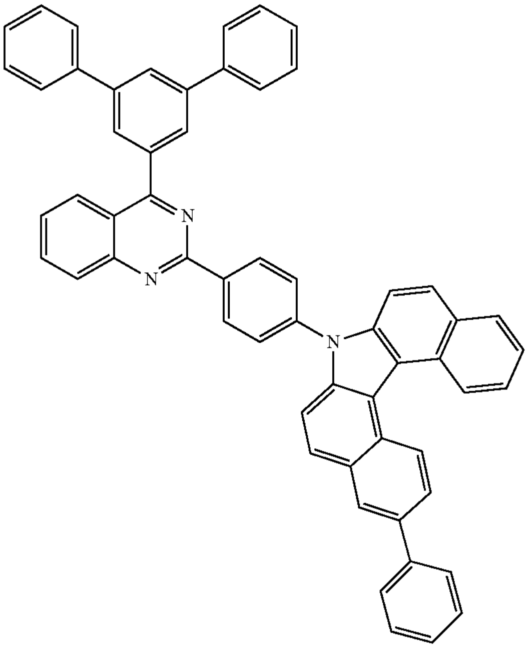
A-31
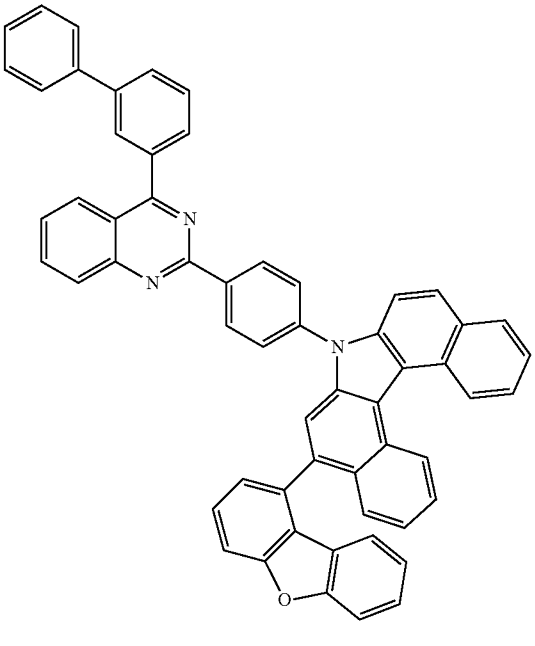

A-32
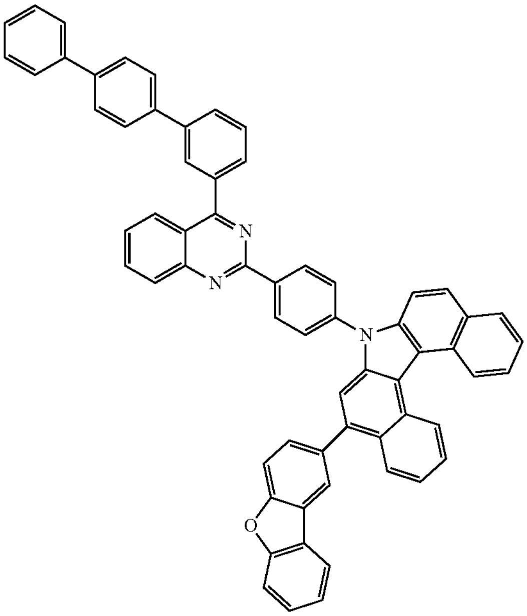
A-33
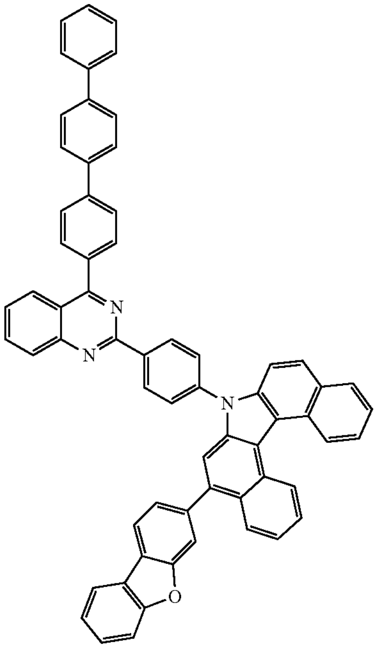
A-34
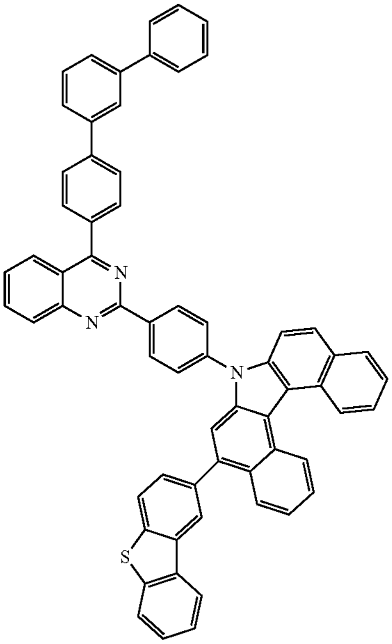
A-35
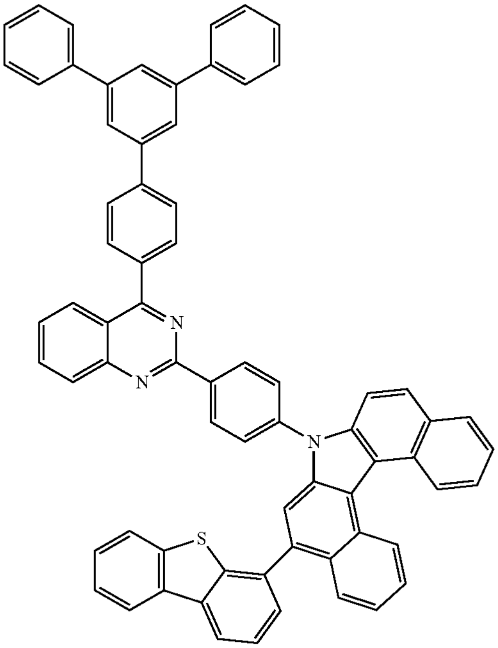

-continued
A-36
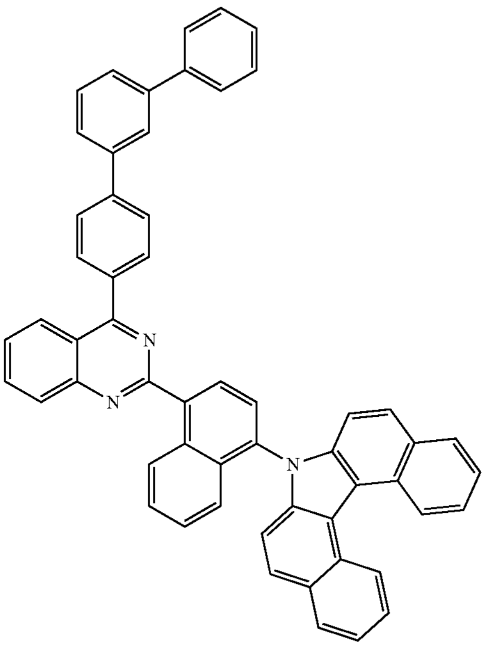
A-37
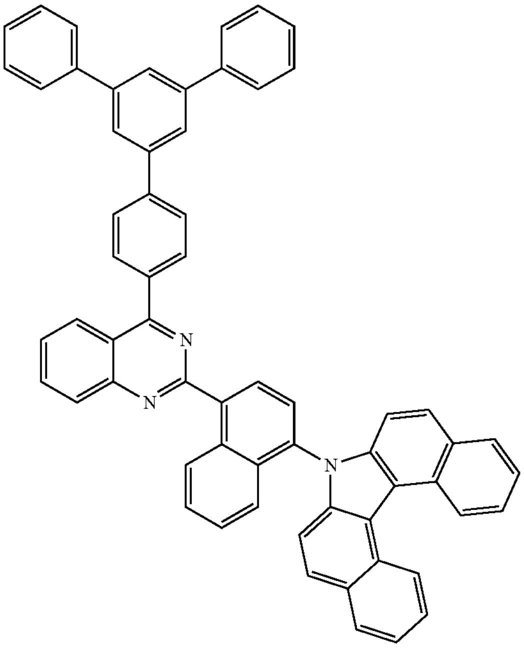
-continued
A-38
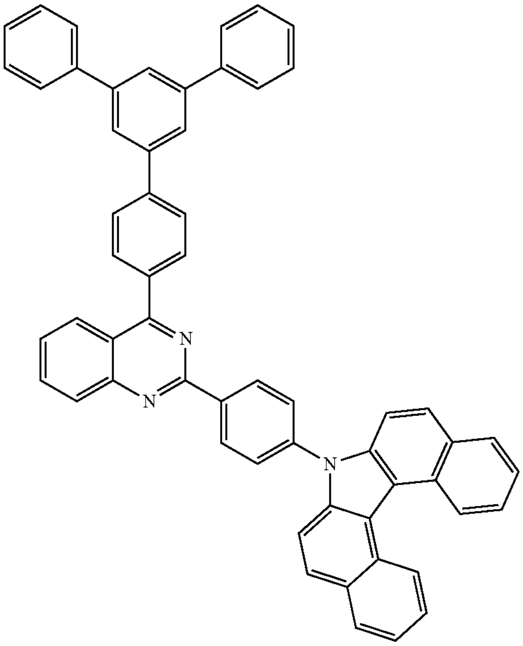
A-39
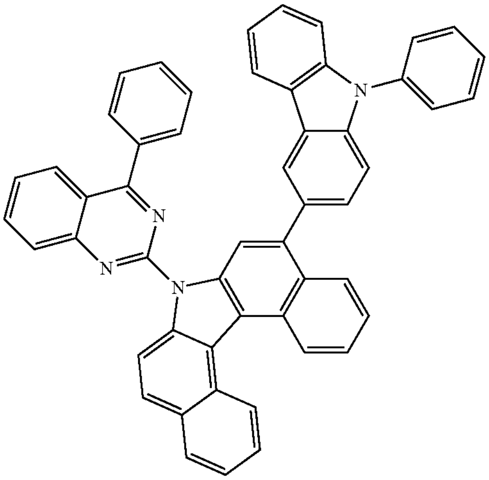
A-40
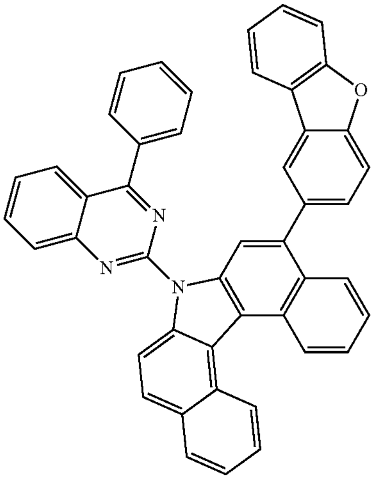

-continued
A-41
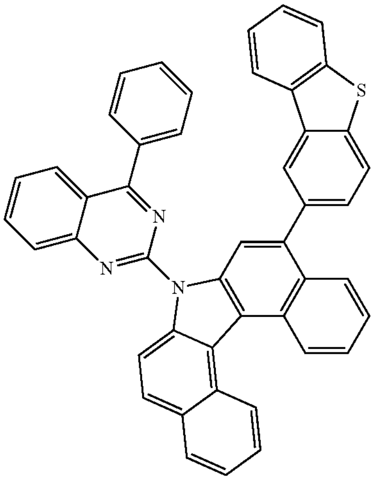
A-42
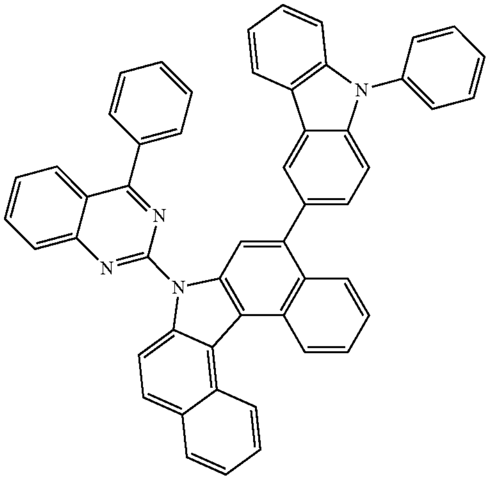
A-43
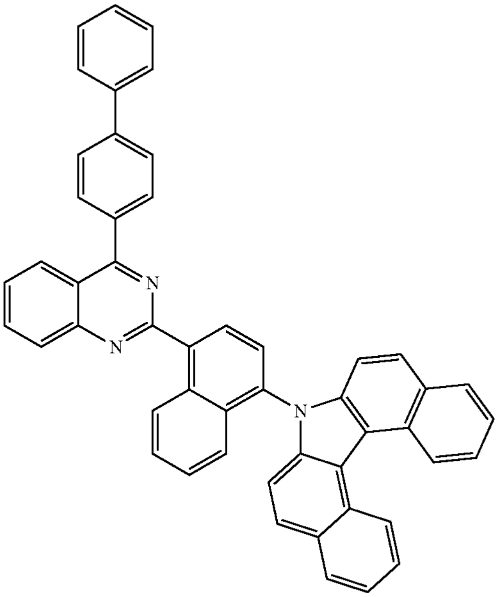
-continued
A-44
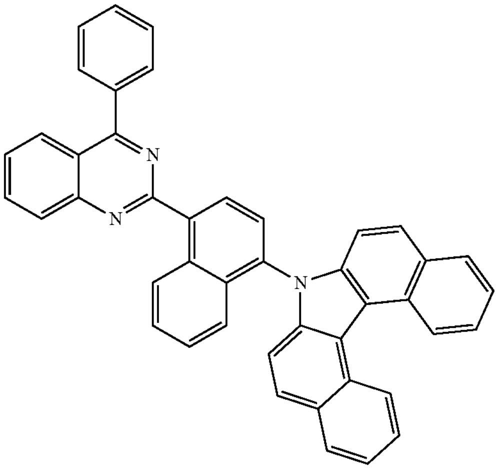
A-45
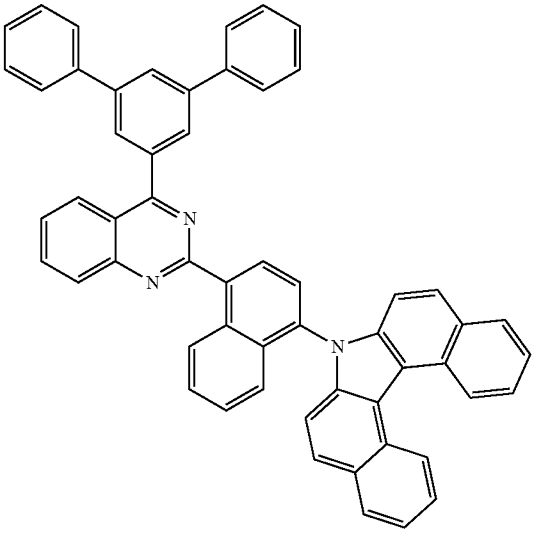
A-46
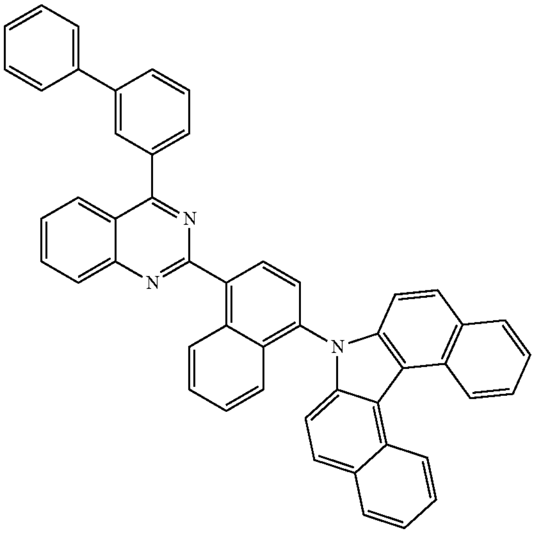

-continued
A-47
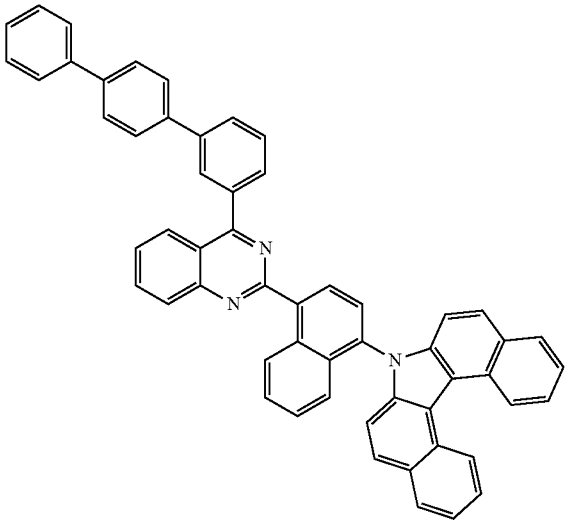
A-48
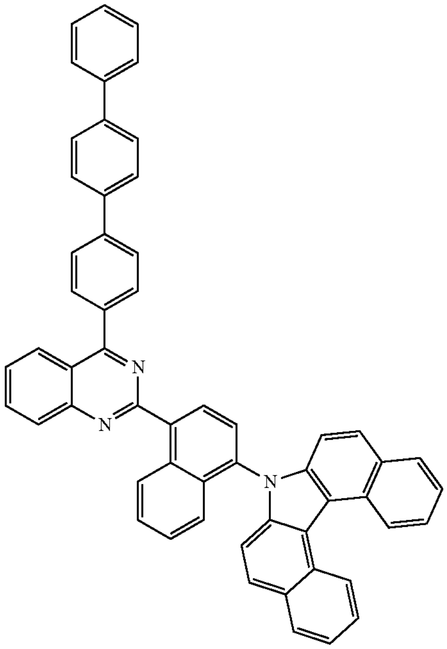
-continued
A-49
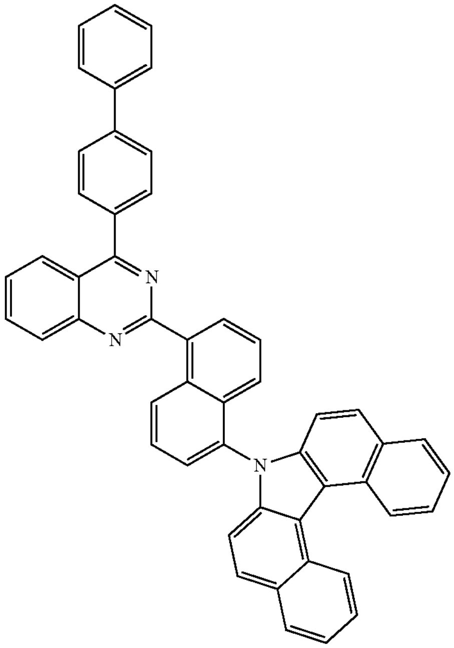
A-50
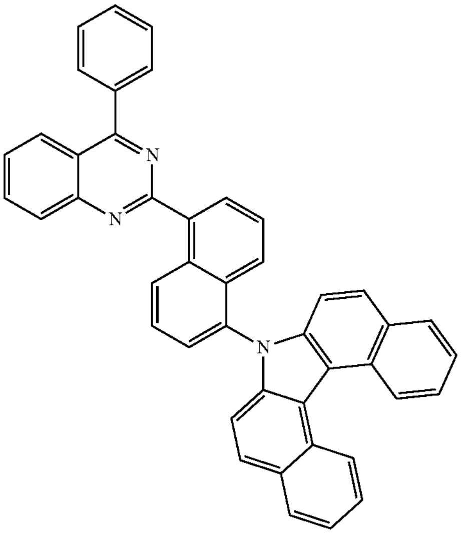

-continued
A-51
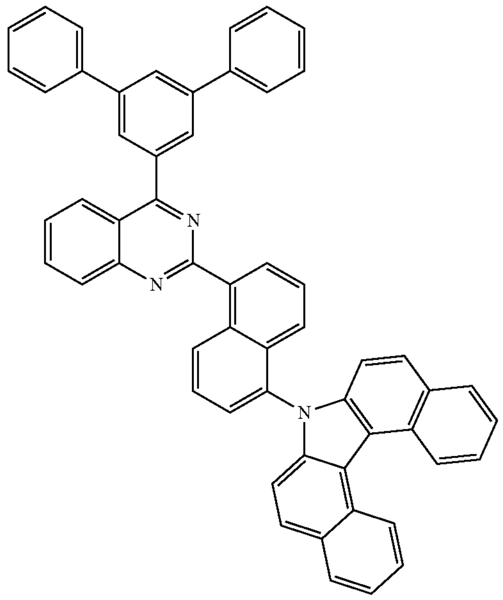
A-52
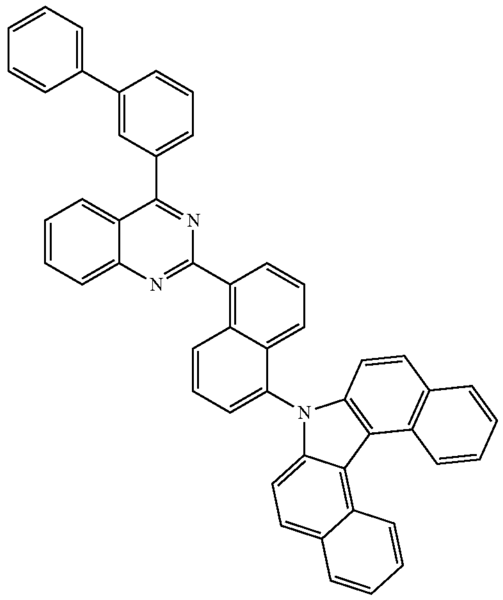
-continued
A-53
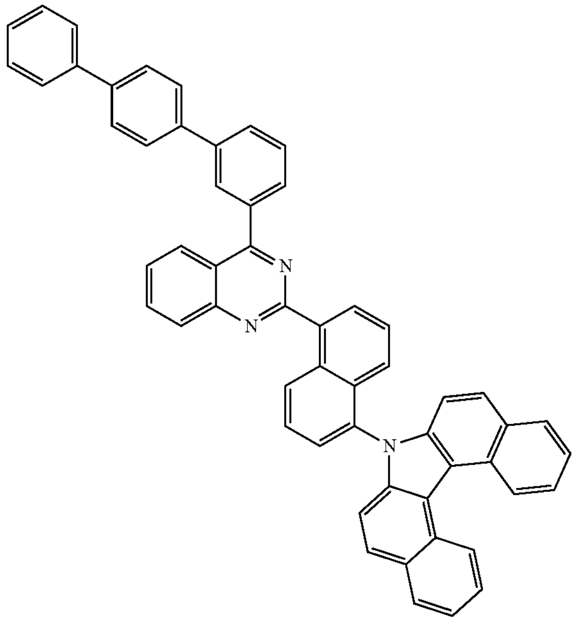
A-54
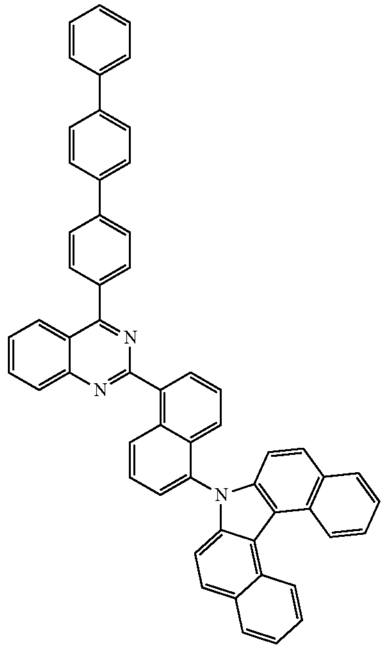

A-55
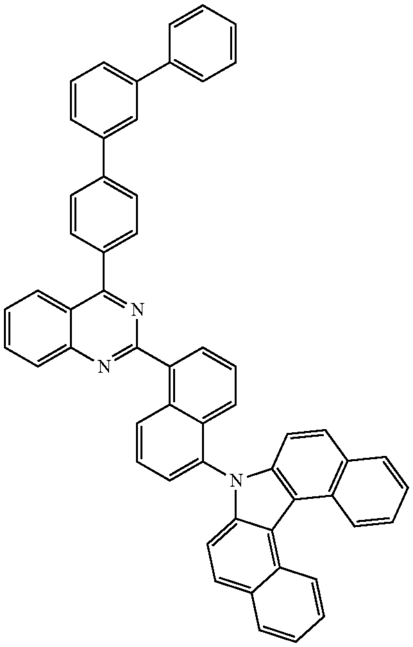
A-56
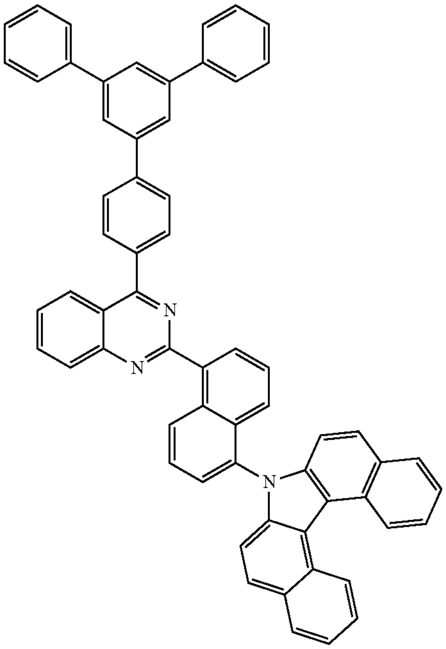
A-57
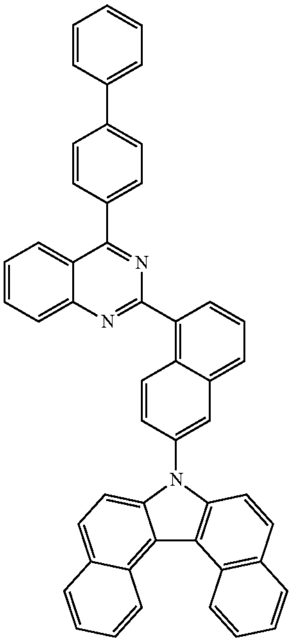
A-58
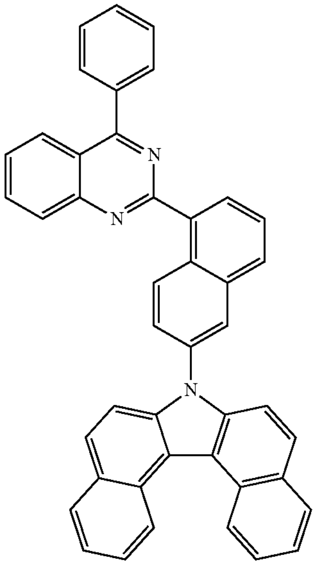

-continued
A-59
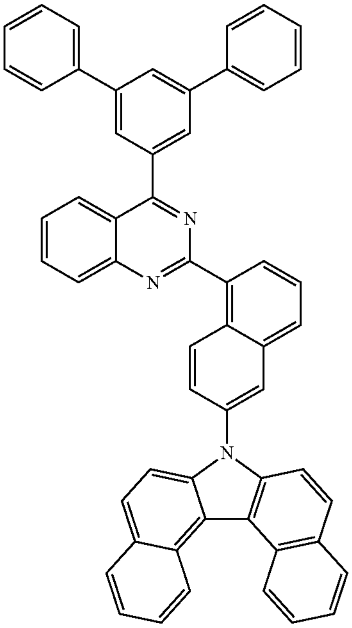
A-60
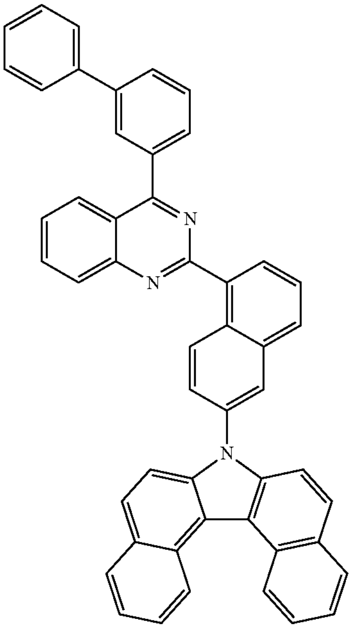
-continued
A-61
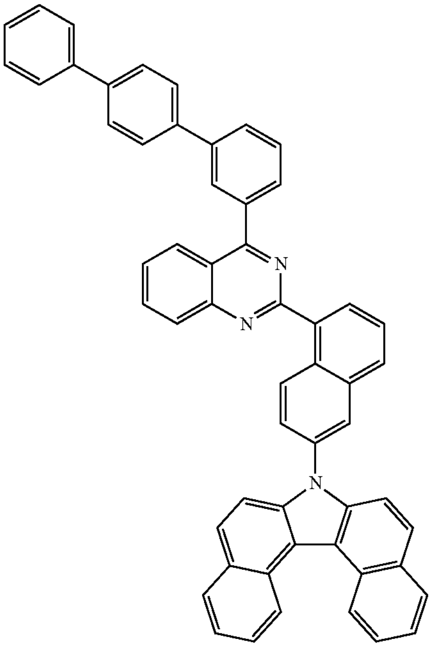
A-62
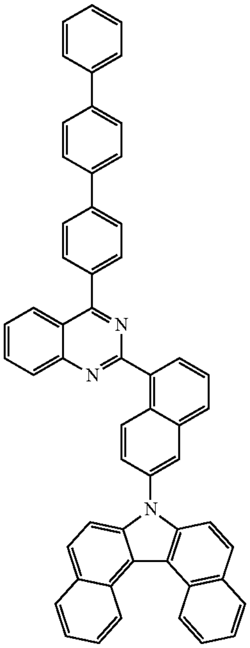

-continued
A-63
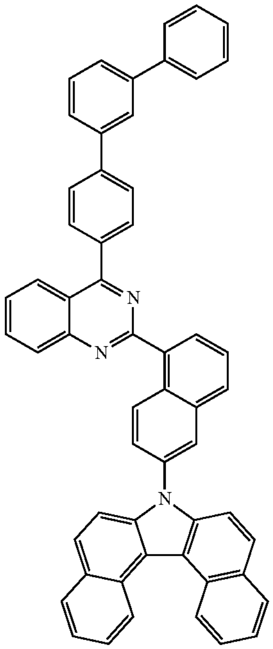
A-64
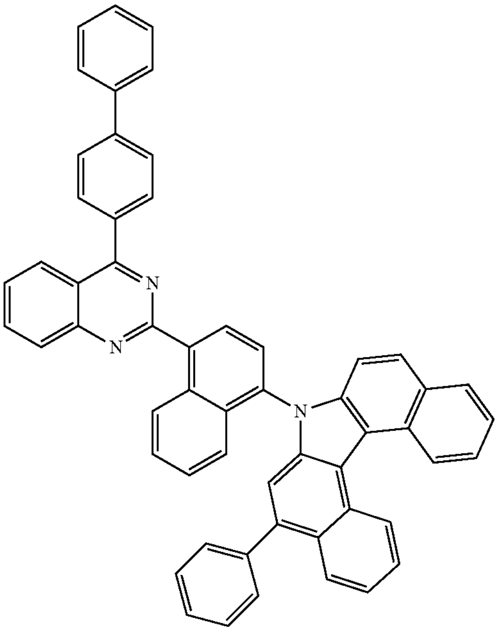
-continued
A-65
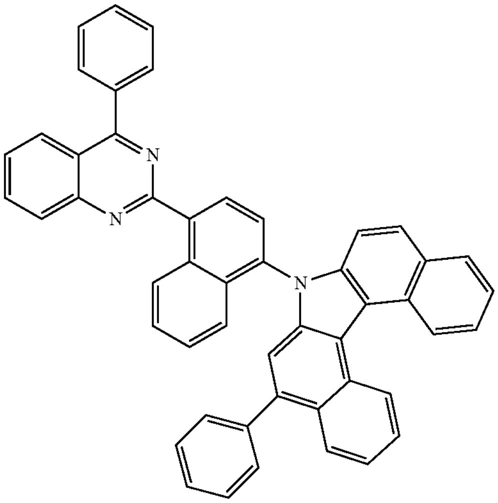
A-66
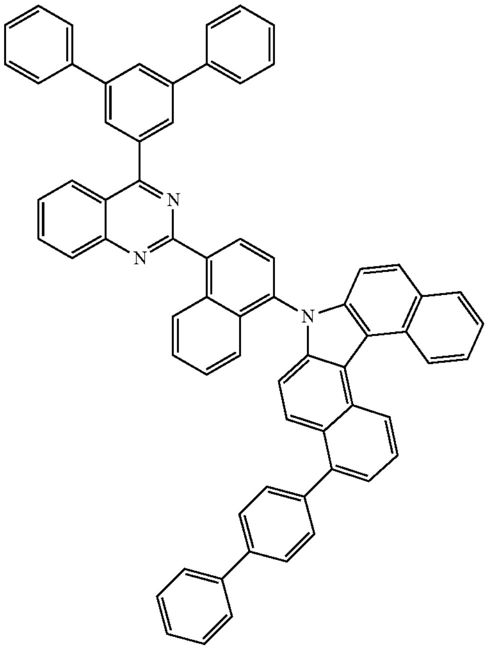

-continued
A-67
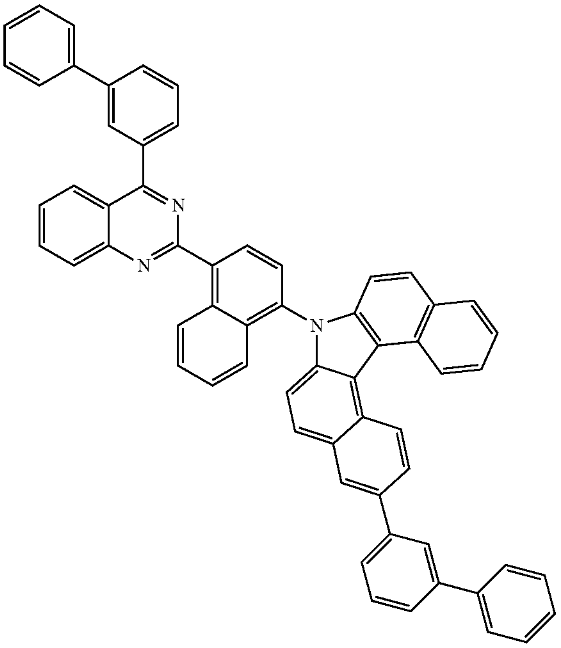
A-68
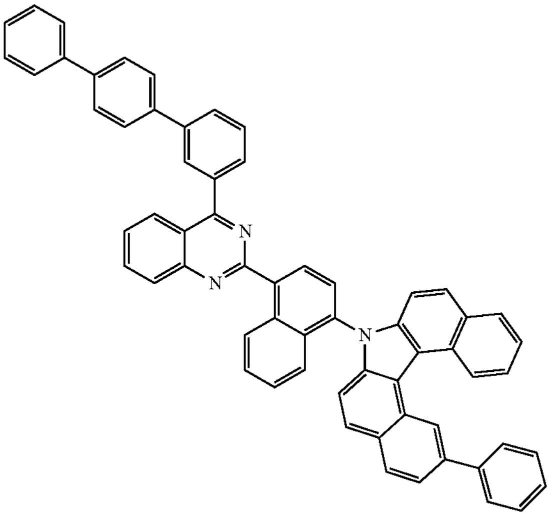
-continued
A-69
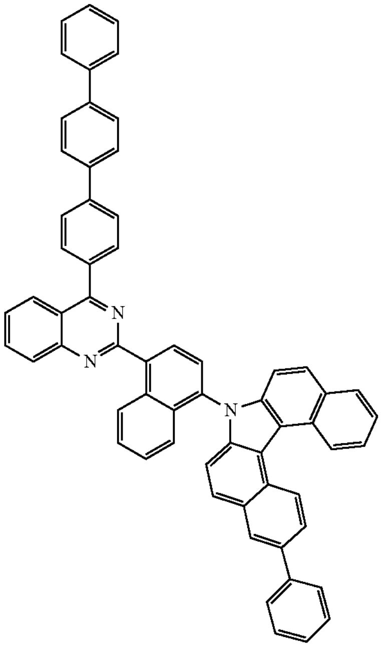
A-70
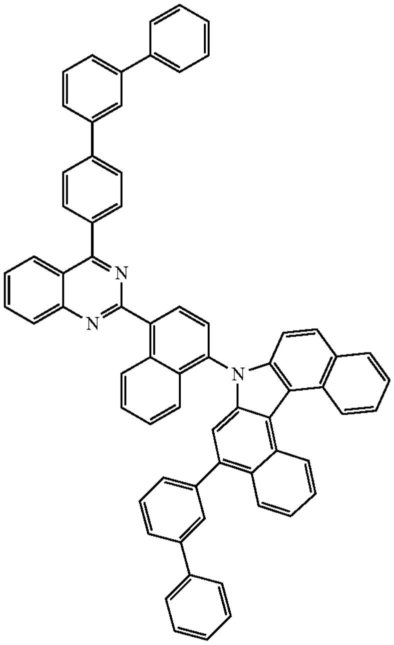

-continued
A-71
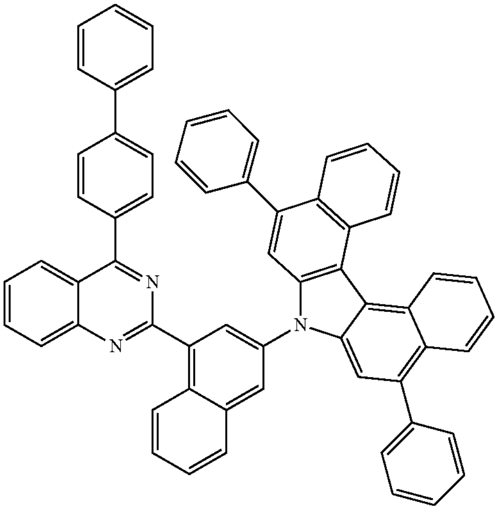
A-72
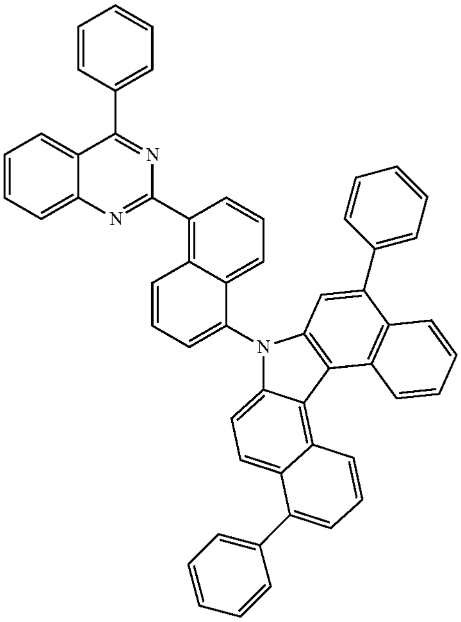
-continued
A-73
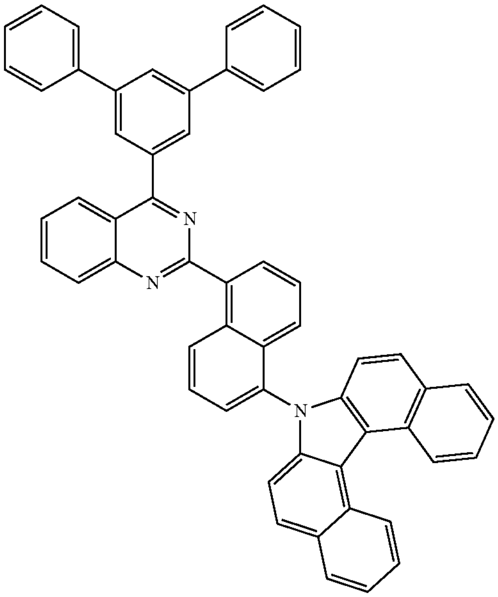
A-74
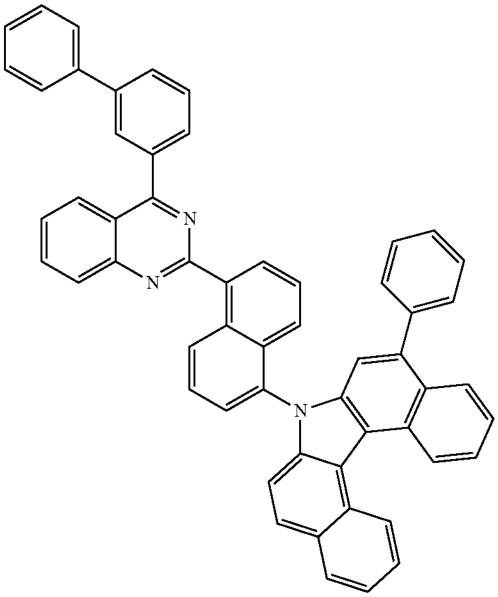

-continued
A-75
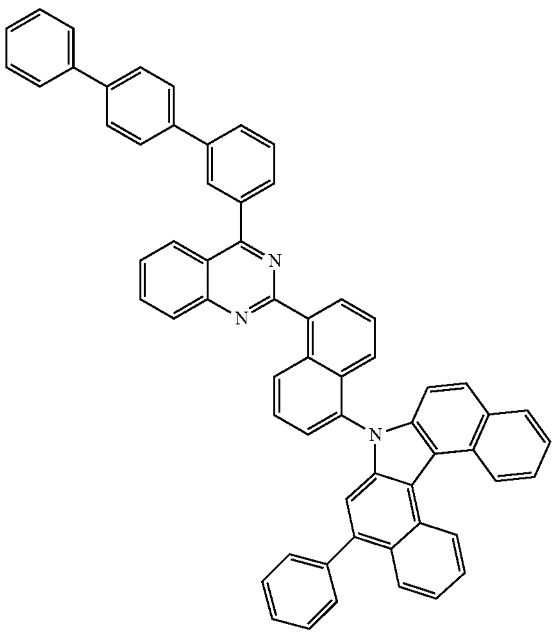
A-76
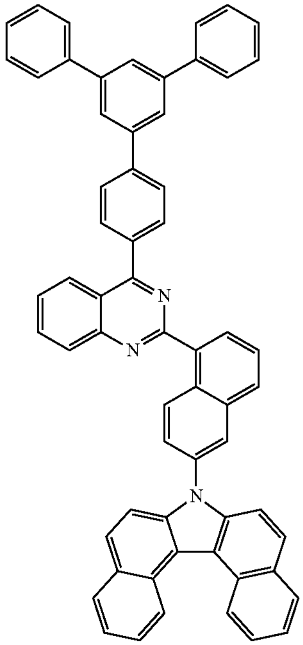
-continued
A-77
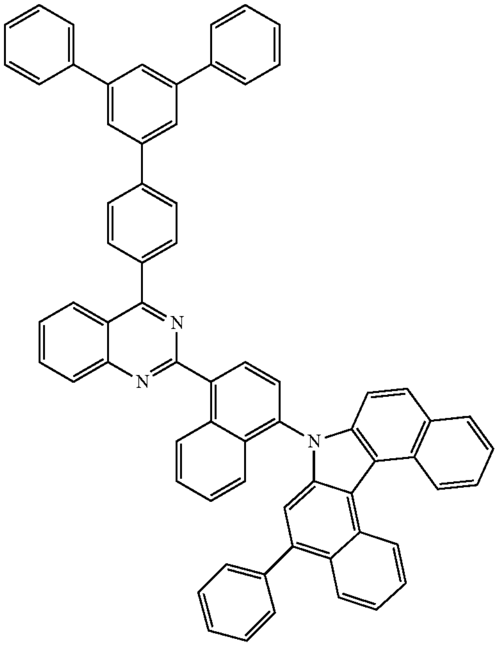
A-78
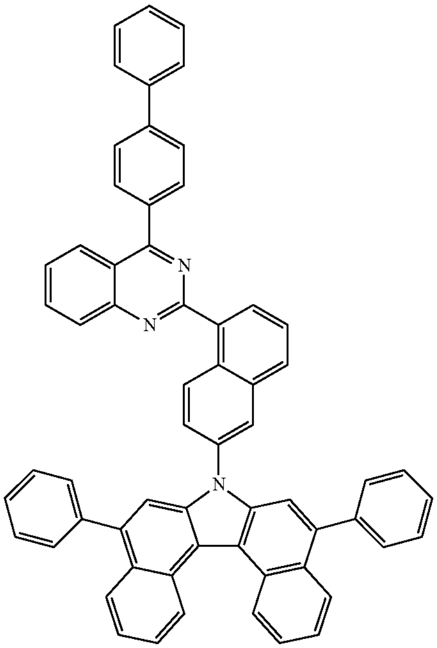

-continued
A-79
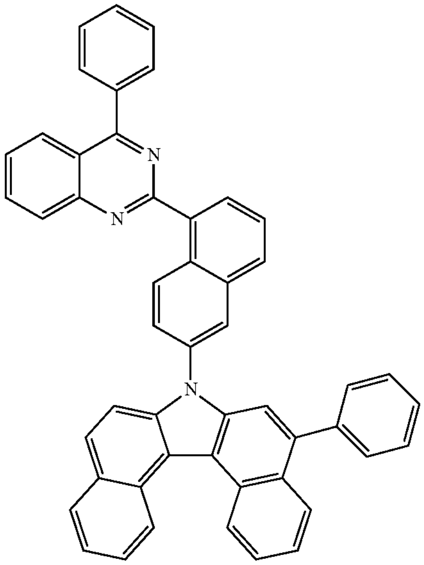
A-80
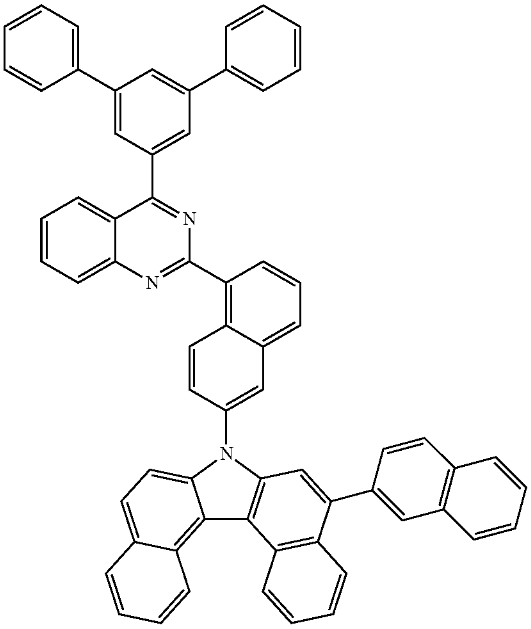
-continued
A-81
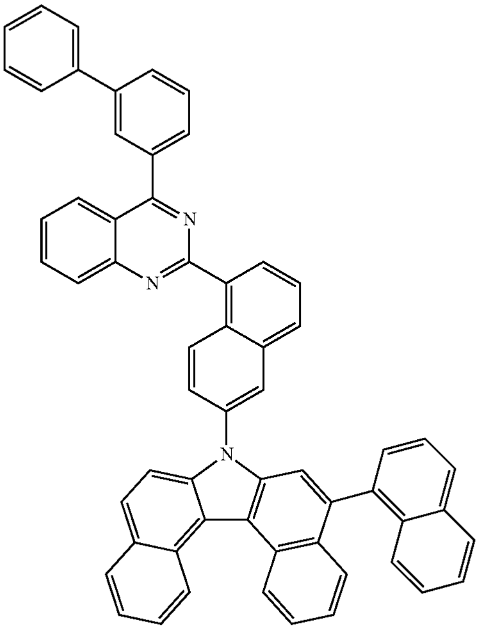
A-82
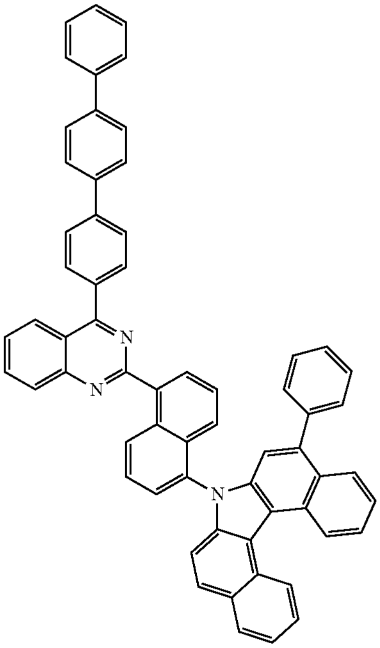

-continued
A-83
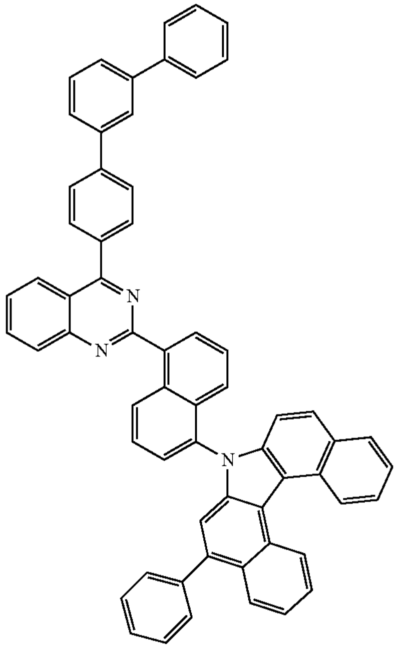
A-84
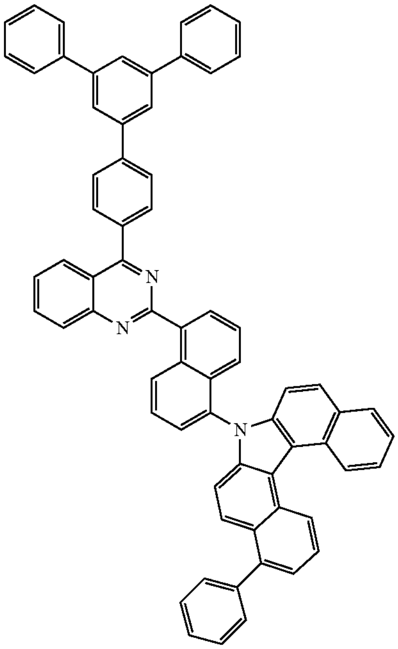
-continued
A-85
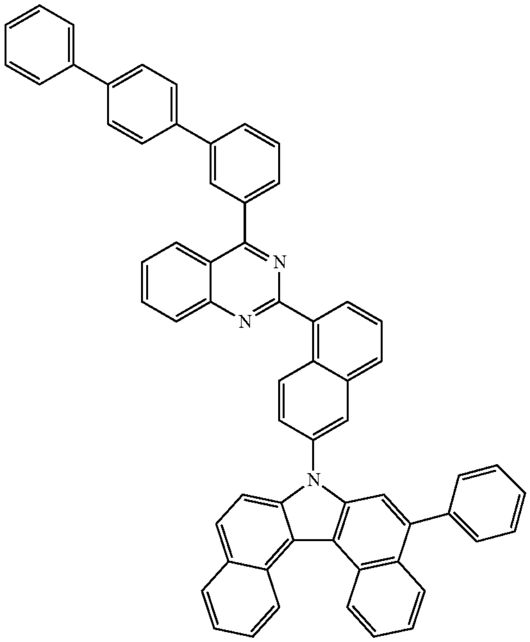
A-86
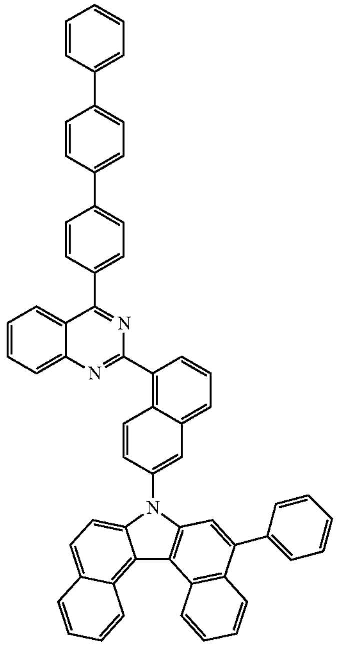

-continued
A-87
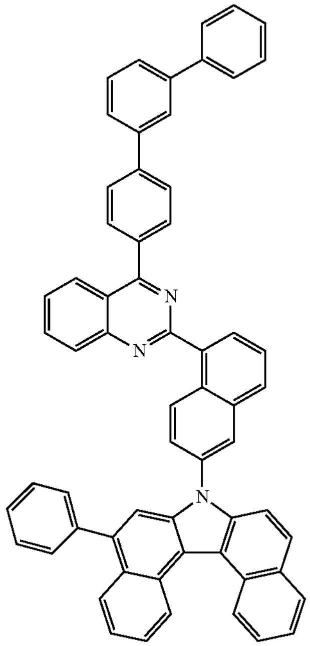
A-88
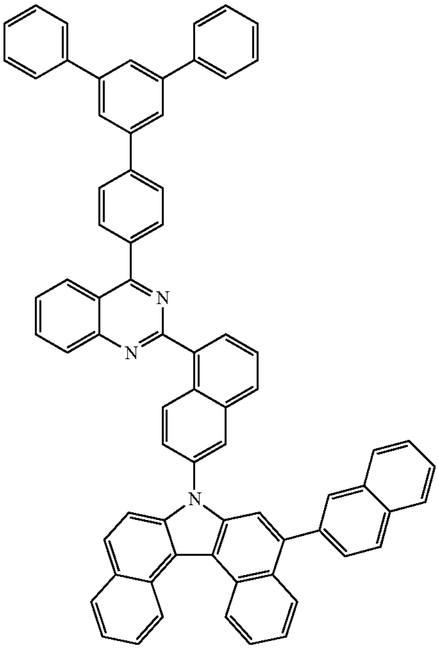
-continued
A-89
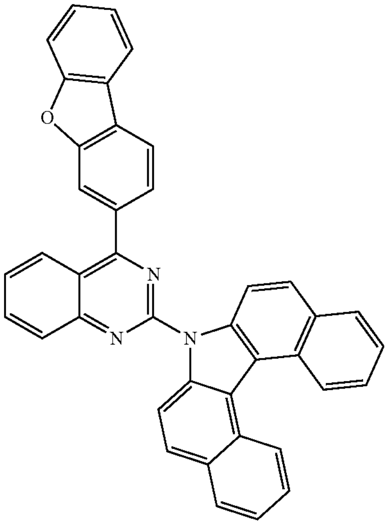
A-90
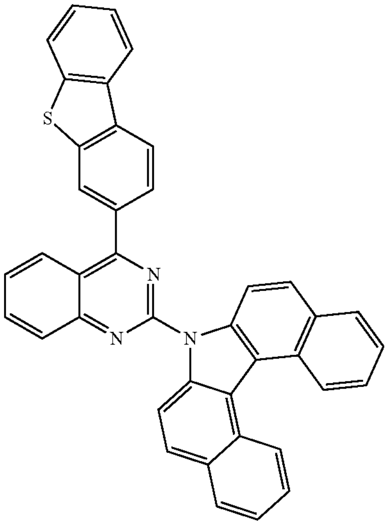
A-91
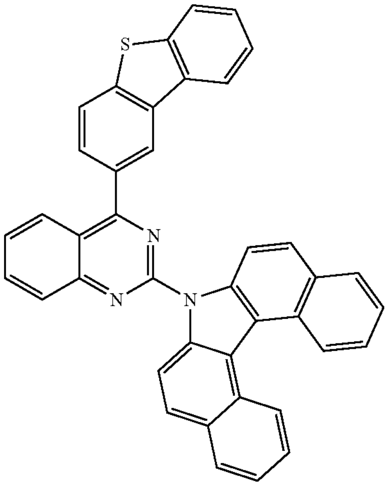

-continued
A-92
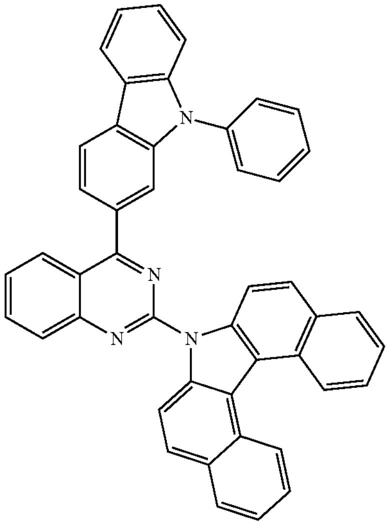
A-93
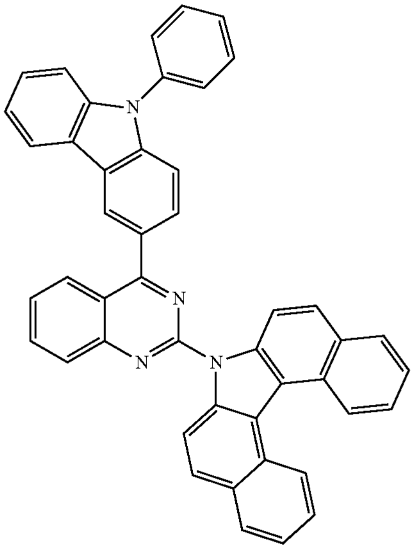
A-94
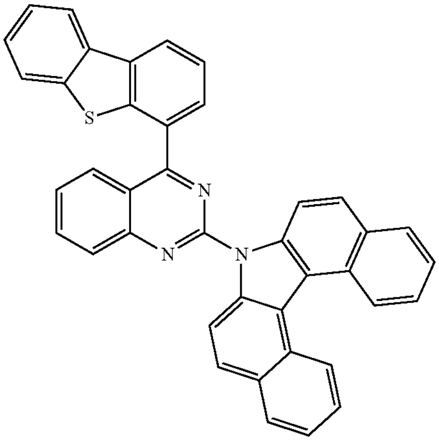
-continued
A-95
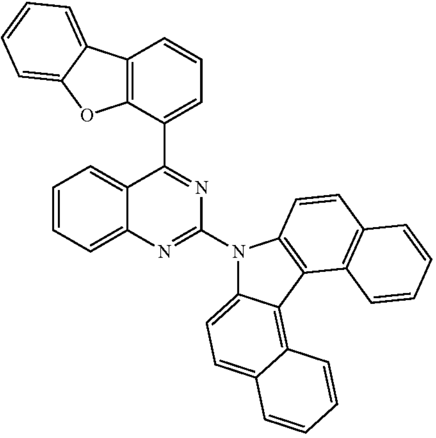
A-96
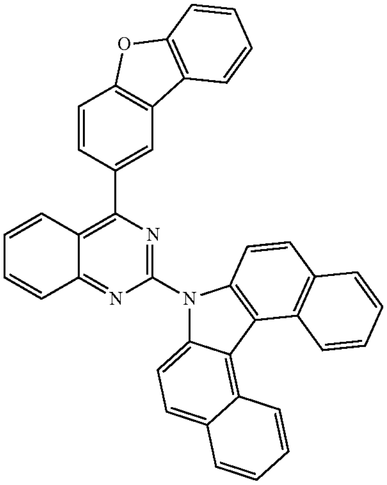
A-97
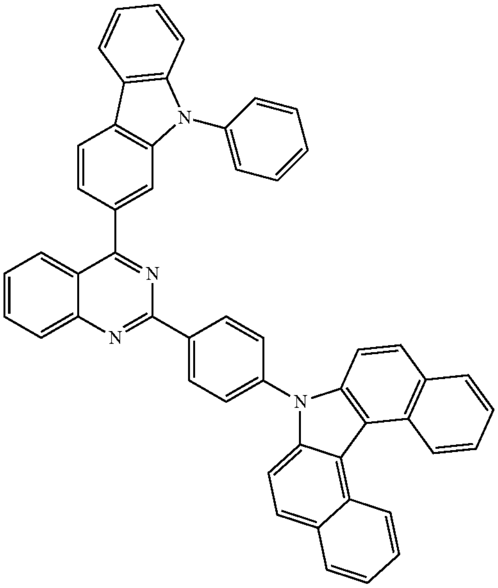

-continued
A-98
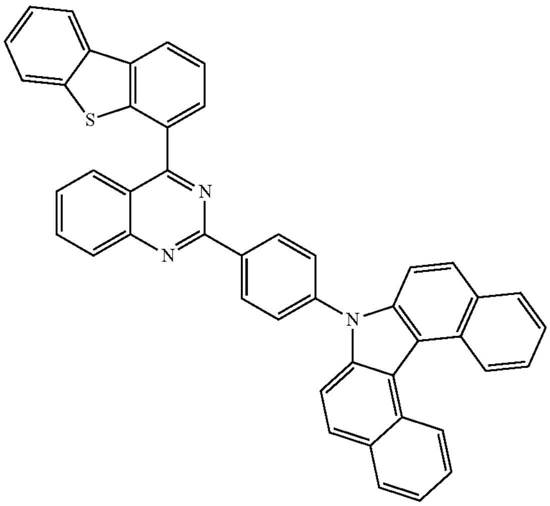
A-99
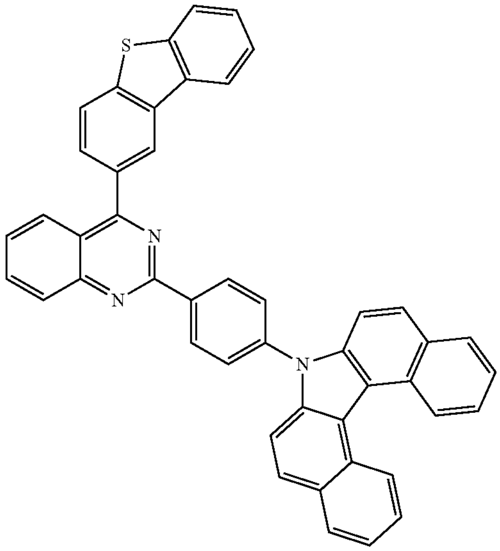
A-100
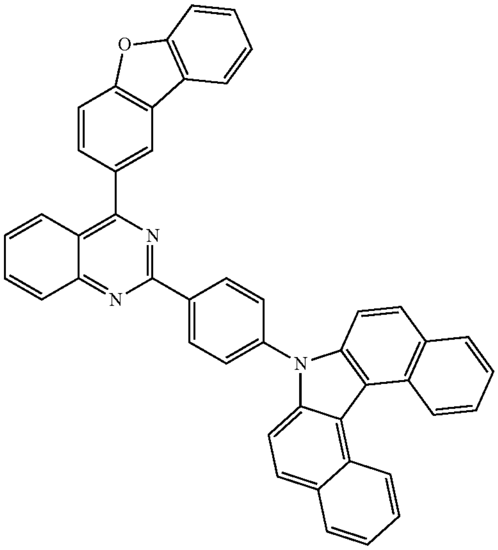
-continued
A-101
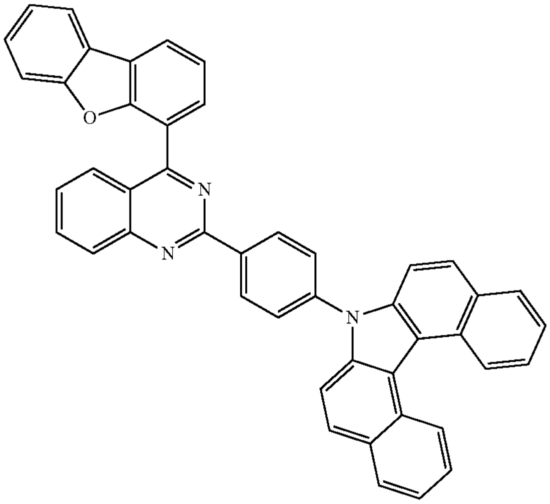
A-102
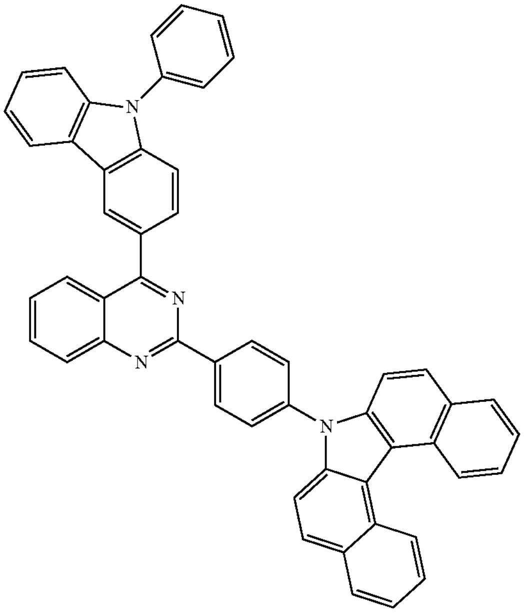

-continued
A-103
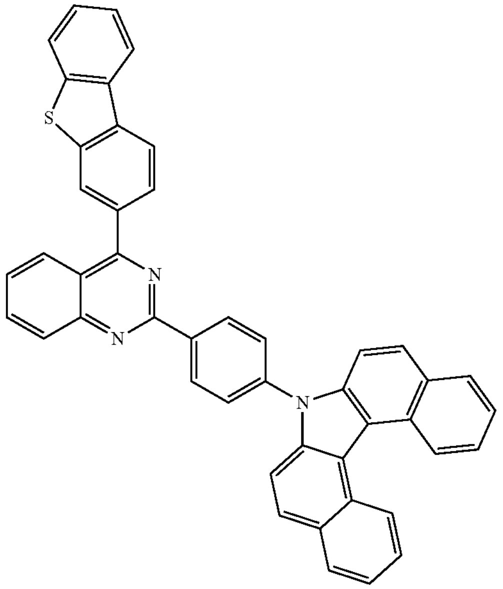
A-104
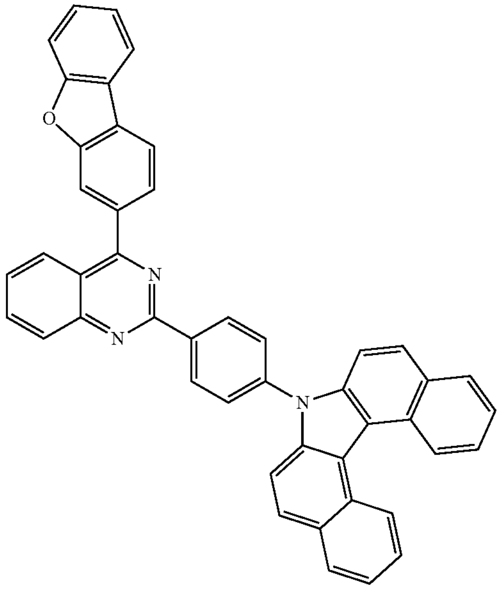
-continued
A-105
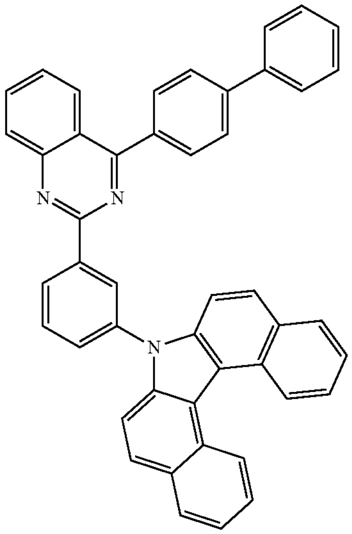
A-106
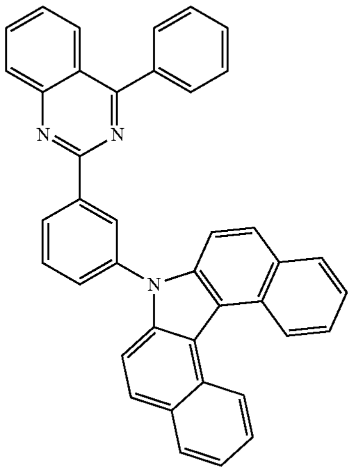
A-107
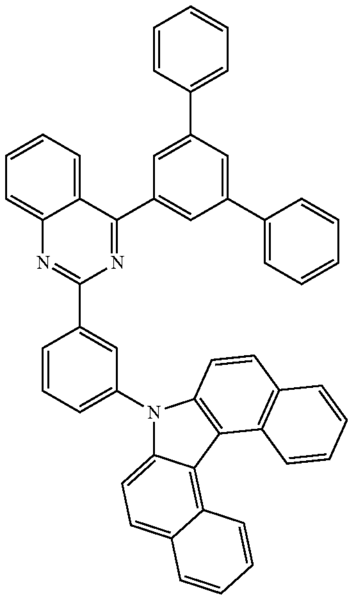

-continued
A-108
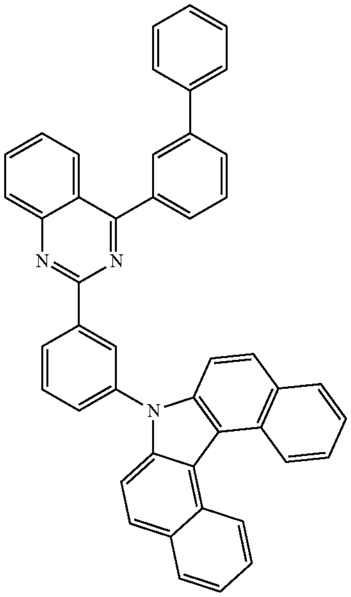
A-109
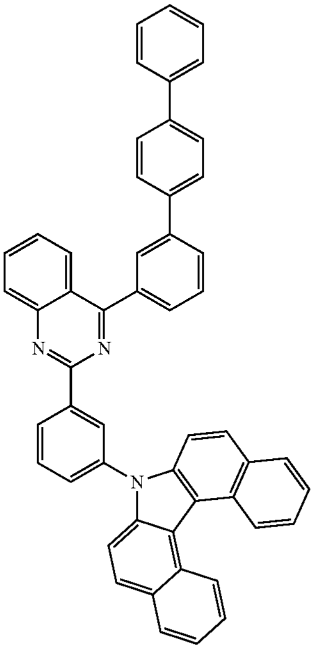
-continued
A-110
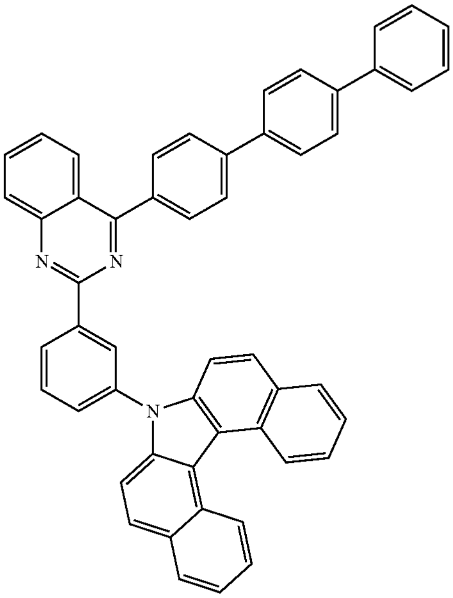
A-111
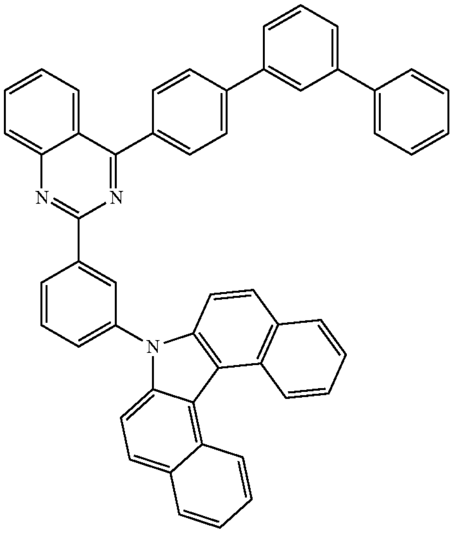
A-112
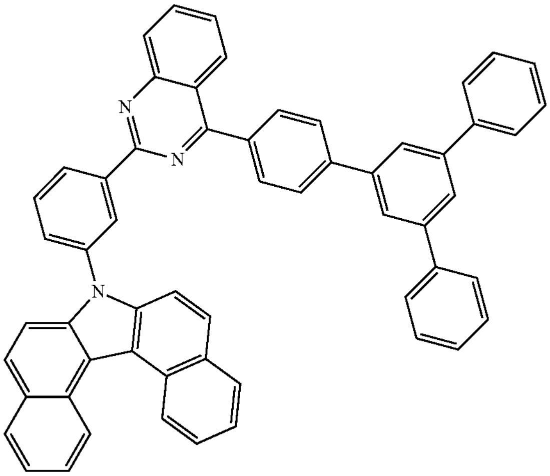

-continued
A-113
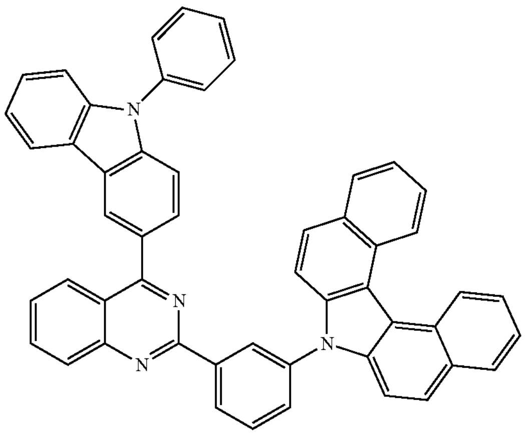
A-114
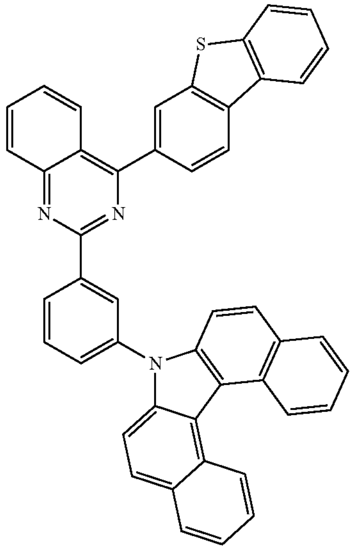
A-115
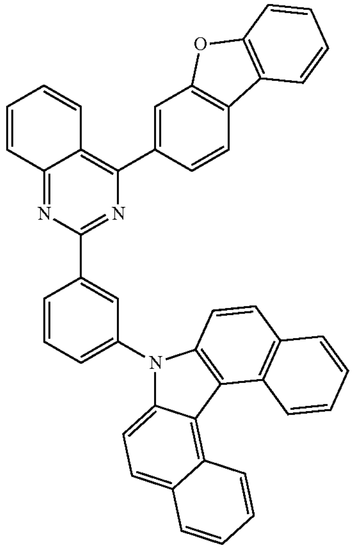
-continued
A-116
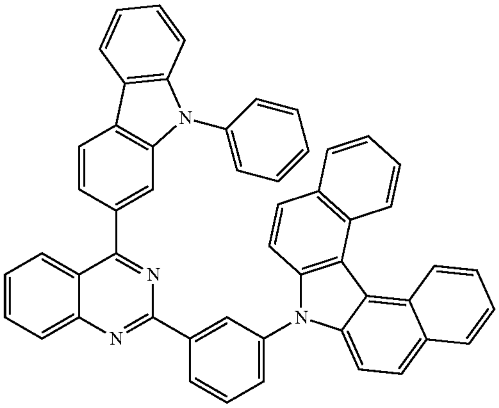
A-117
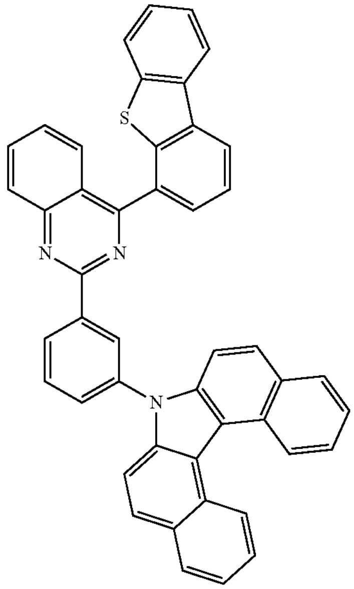
A-118
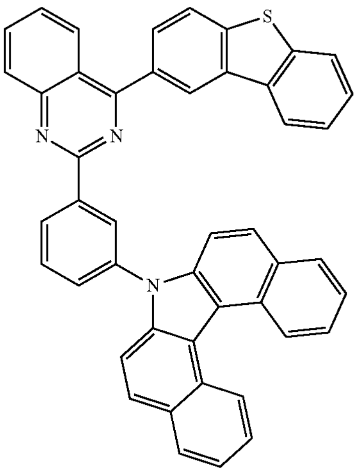

-continued
A-119
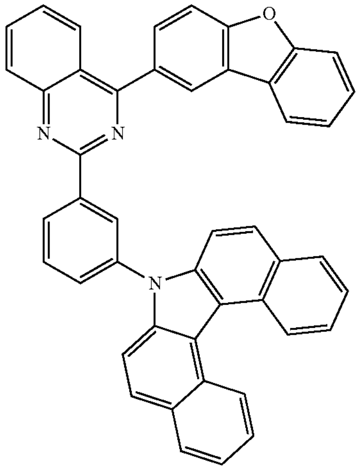
A-120
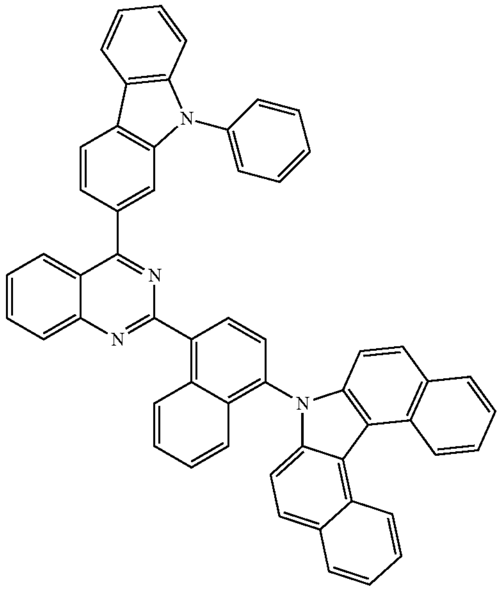
A-121
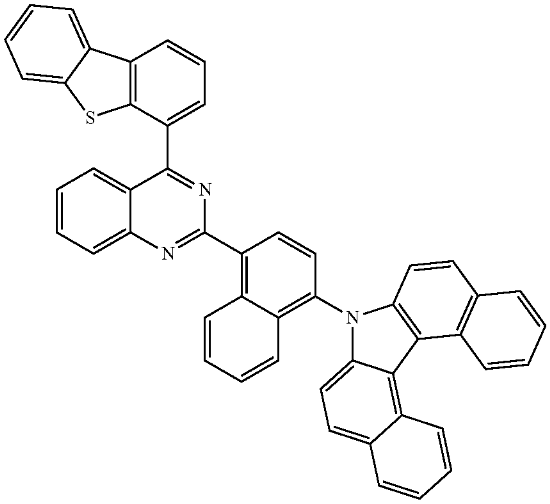
-continued
A-122
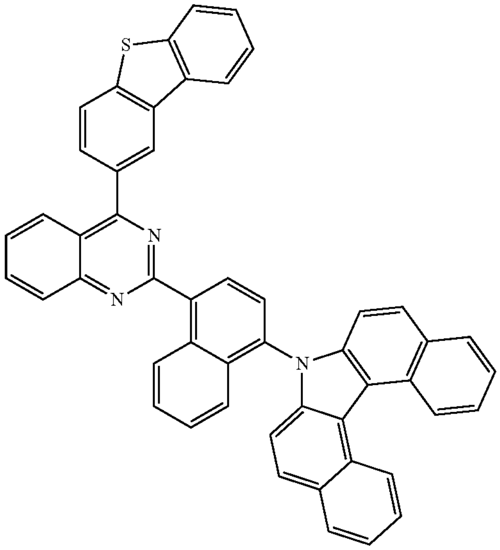
A-123
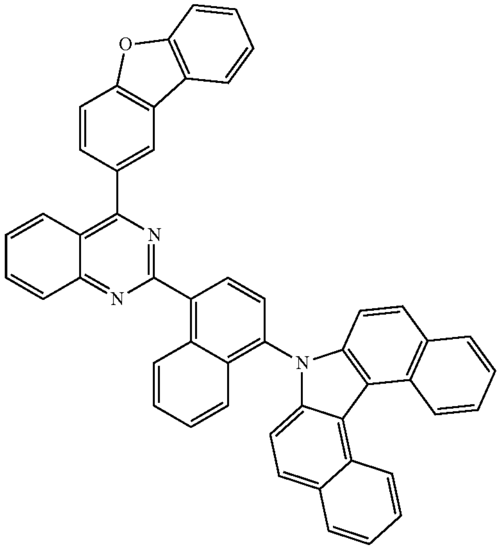
A-124
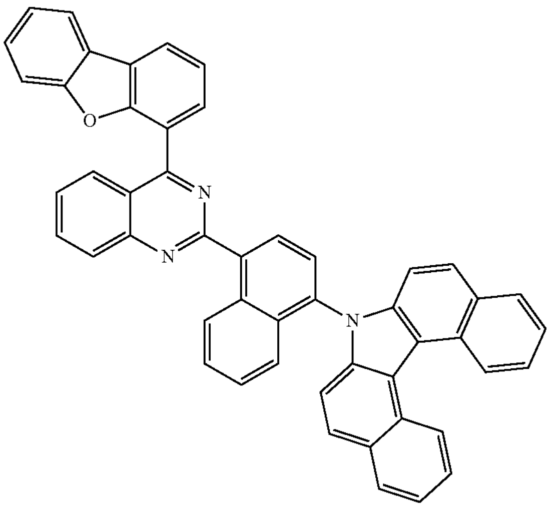

-continued
A-125
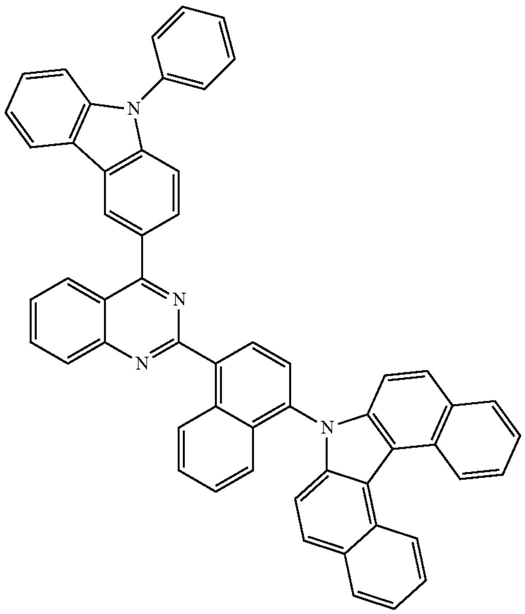
A-126
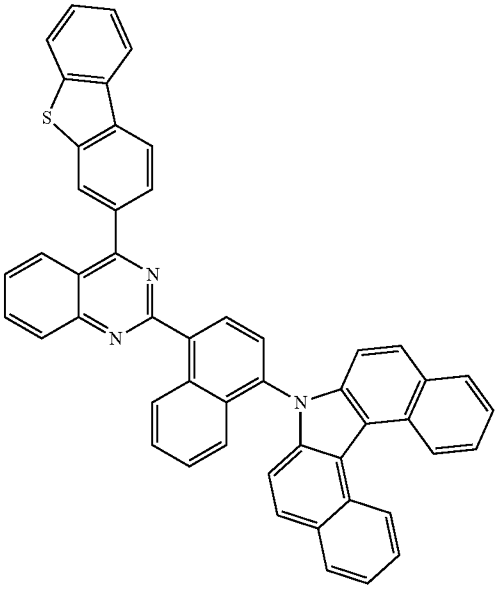
-continued
A-127
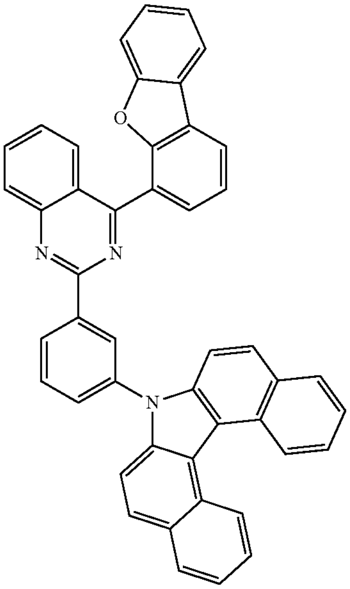
A-128
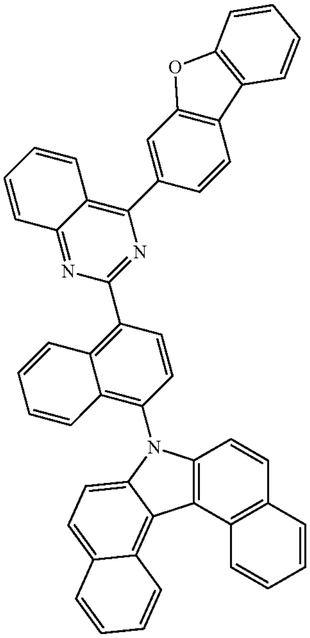
A-129
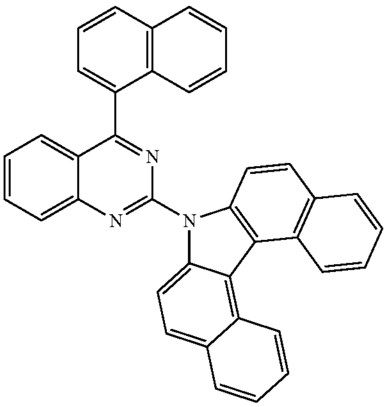

-continued
A-130
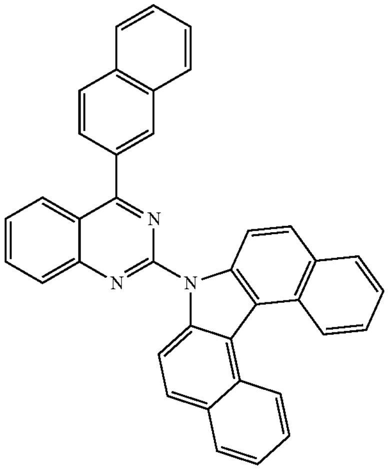
A-131
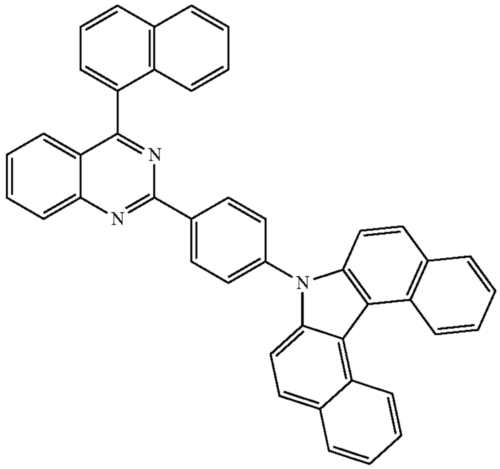
A-132
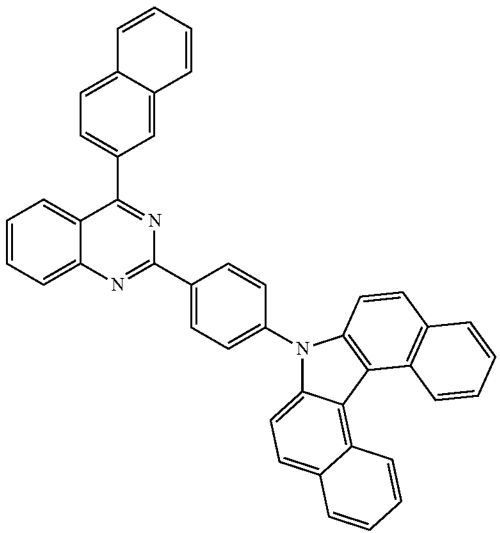
-continued
A-133
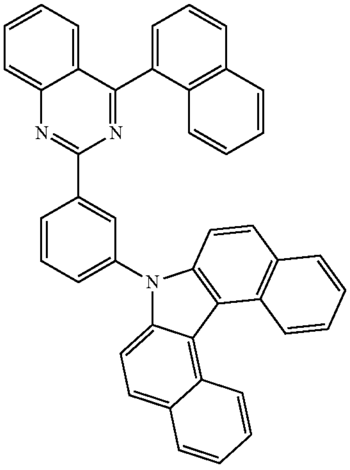
A-134
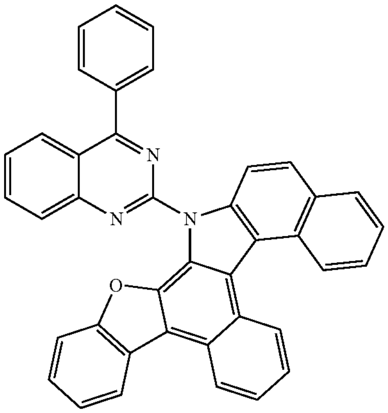
A-135
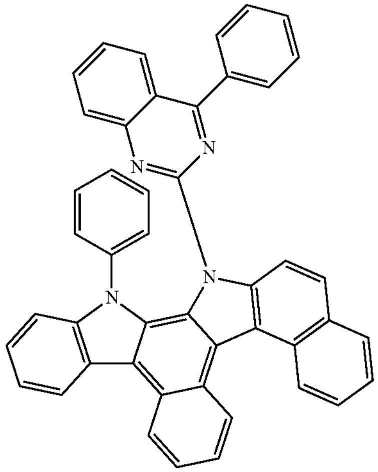

-continued
A-136
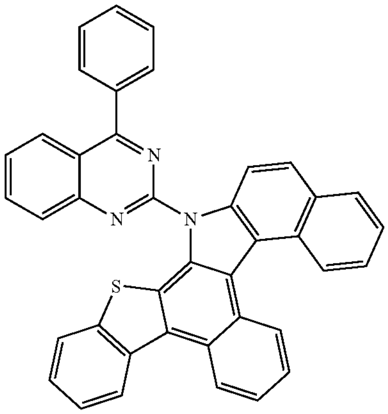
A-137
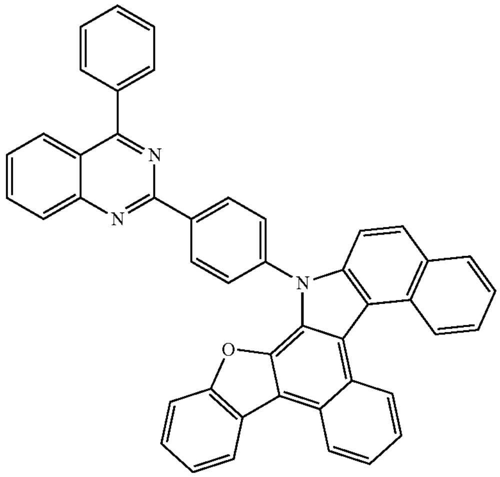
A-138
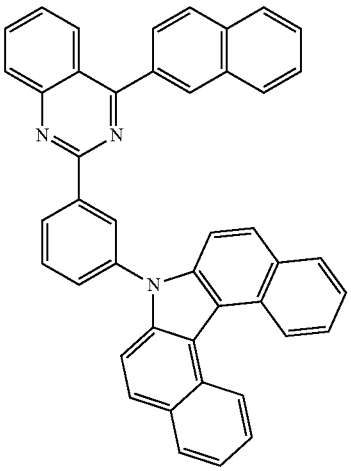
-continued
A-139
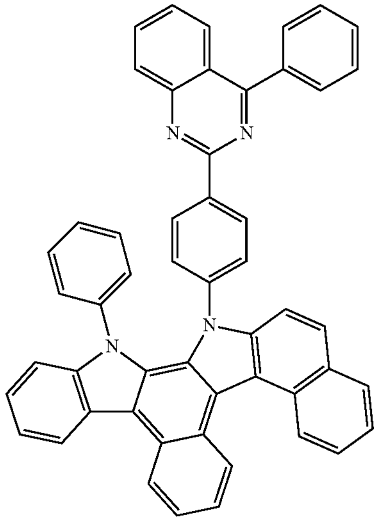
A-140
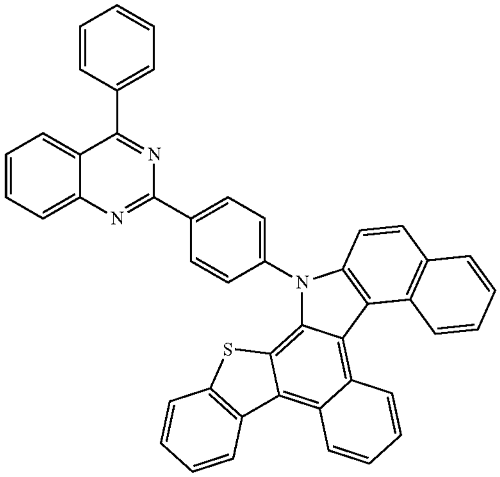
A-141
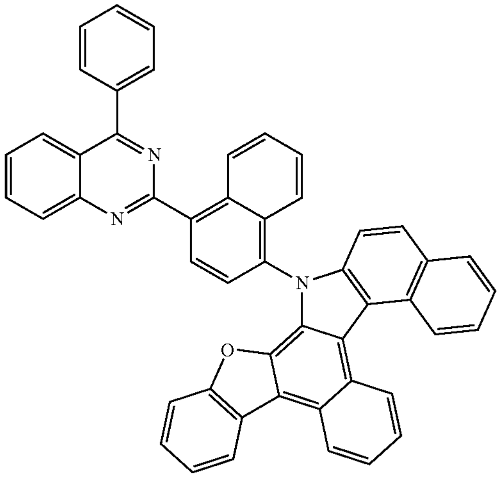

-continued
A-142
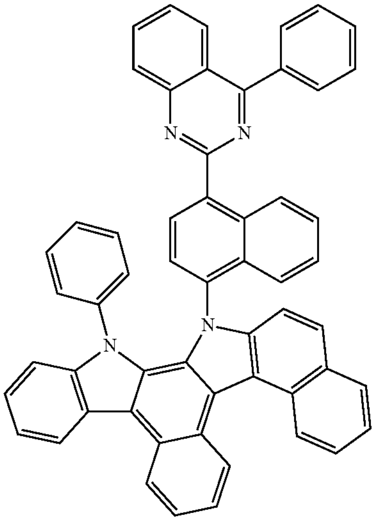
A-143
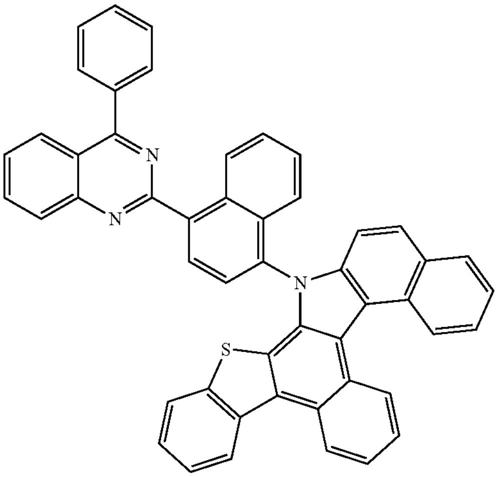
A-144
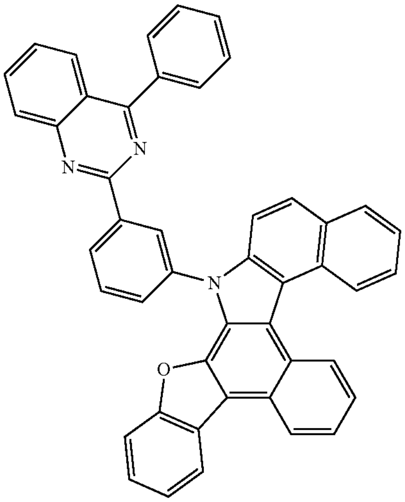
-continued
A-145
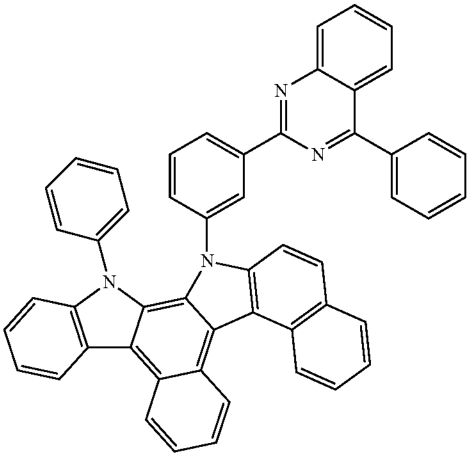
A-146
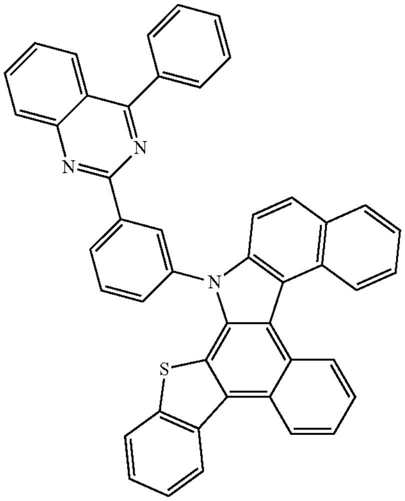
A-147
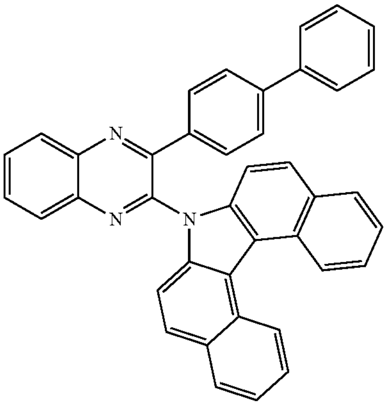

-continued
A-148
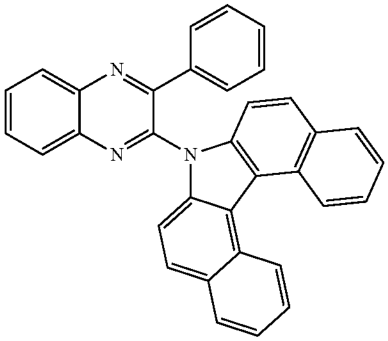
A-149
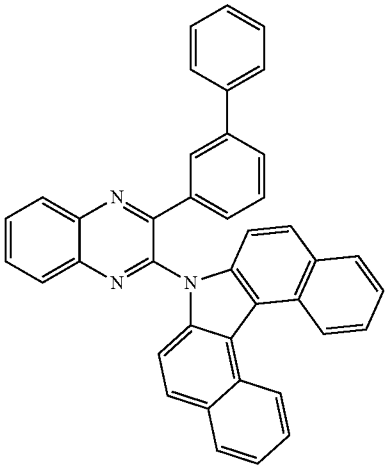
A-150
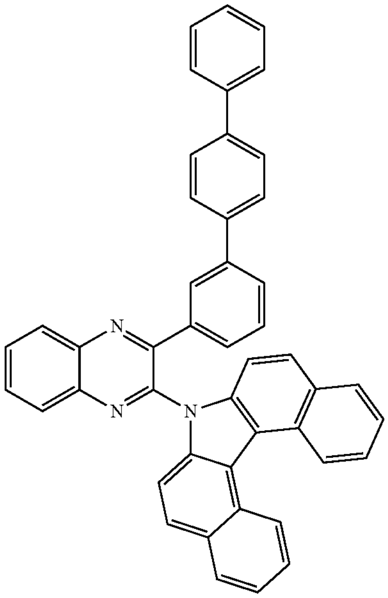
-continued
A-151
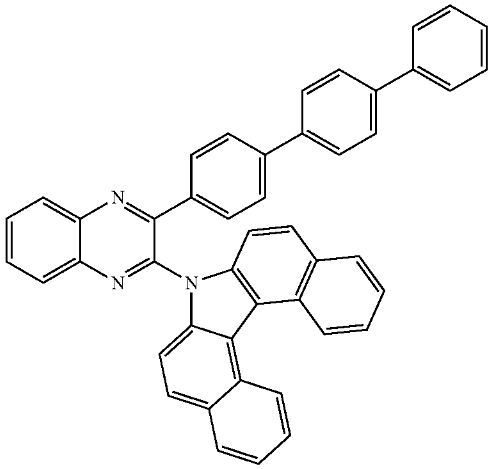
A-152
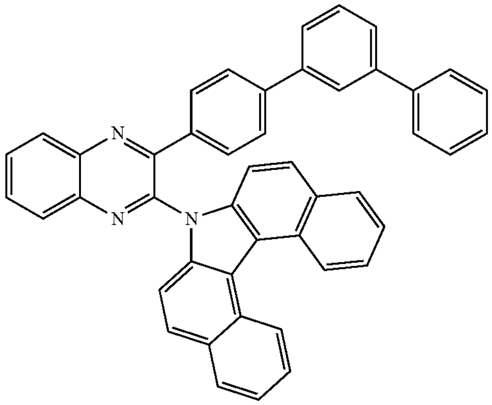
A-153
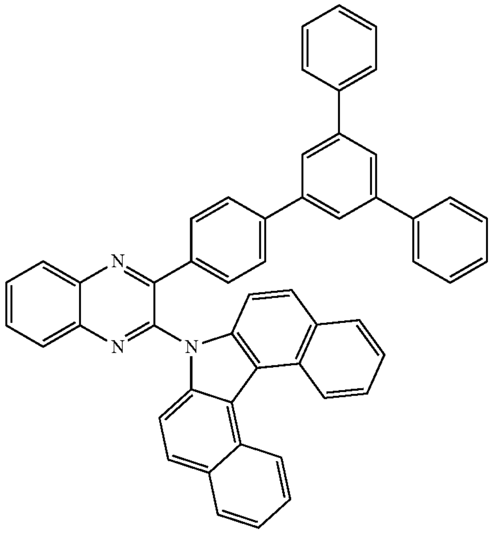

-continued
A-154
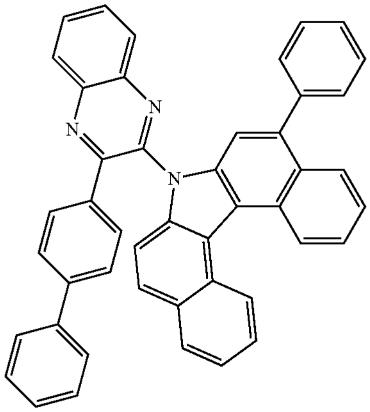
A-155
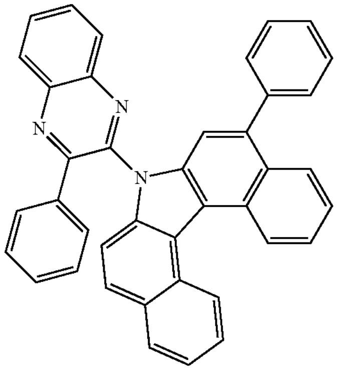
A-156
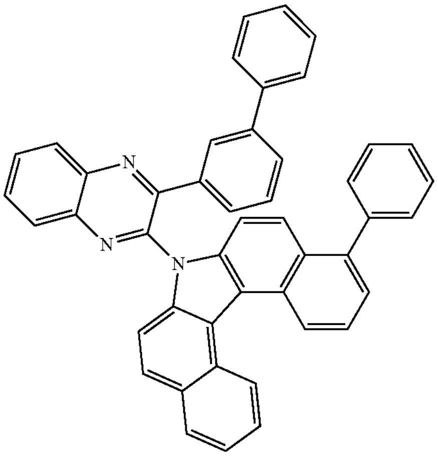
A-157
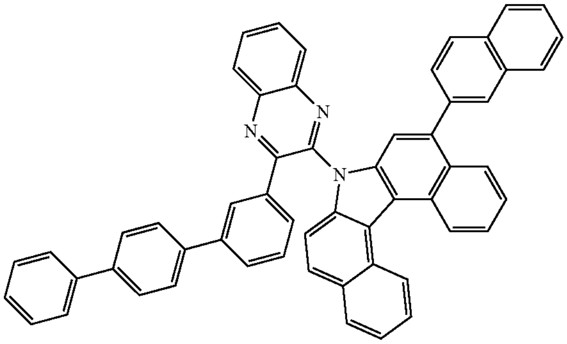
-continued
A-158
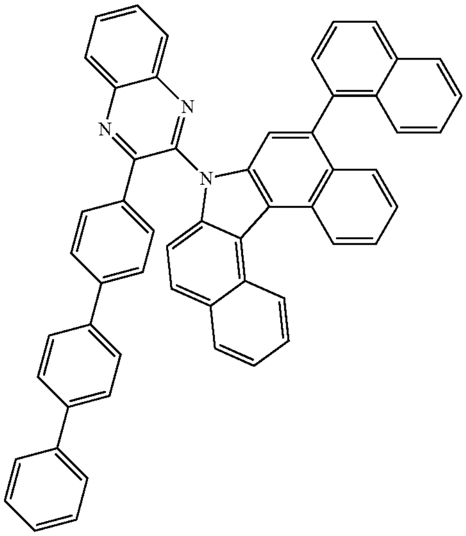
A-159
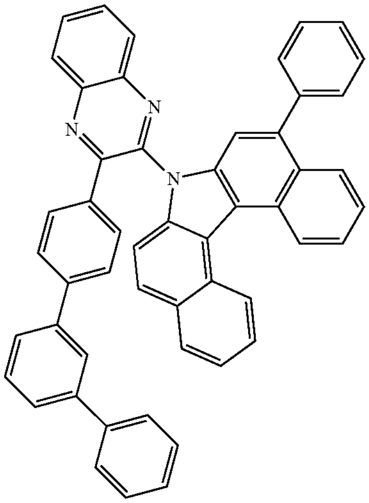
A-160
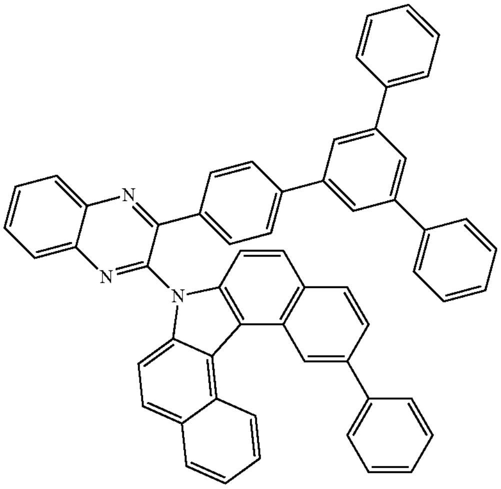

-continued
A-161
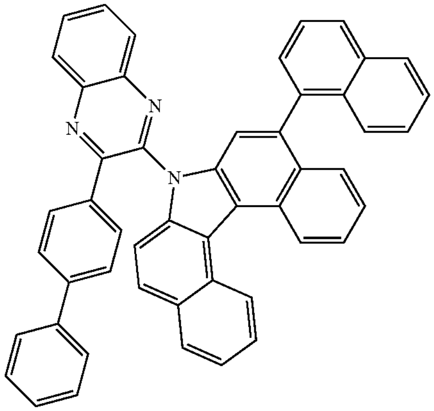
A-162
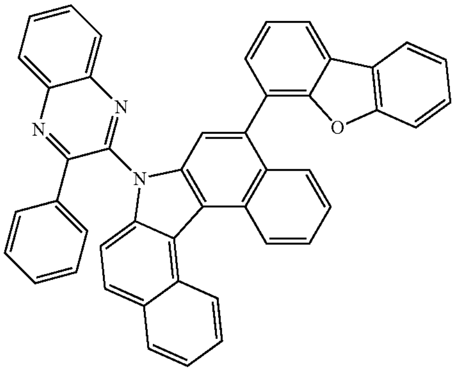
A-163
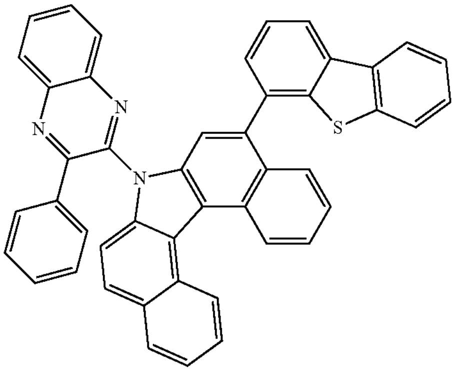
-continued
A-164
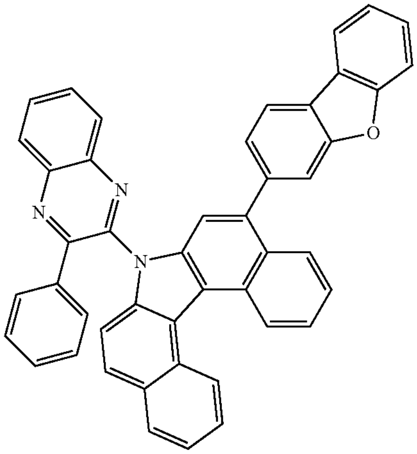
A-165
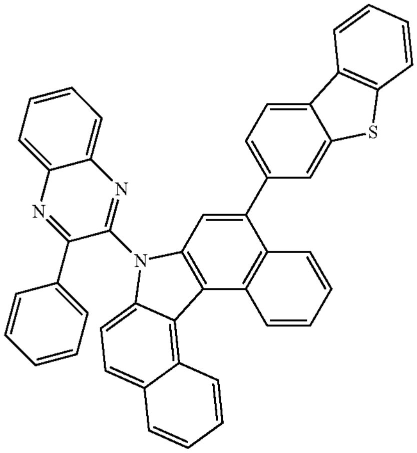
A-166
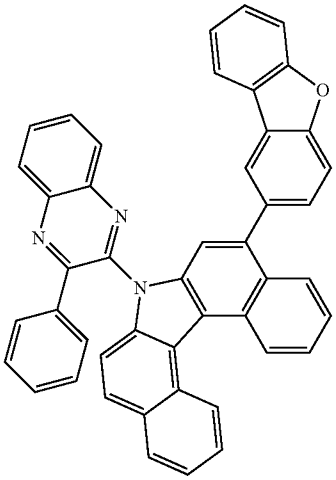

-continued
A-167
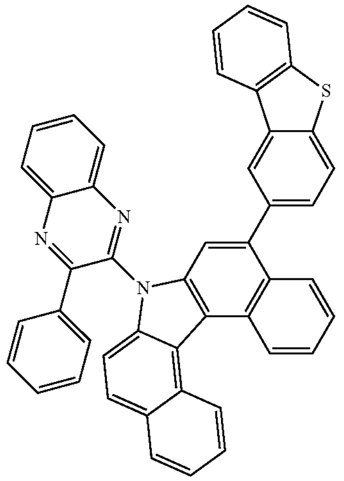
A-168
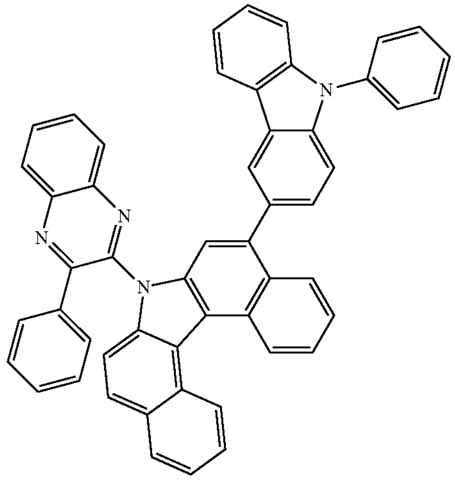
A-169
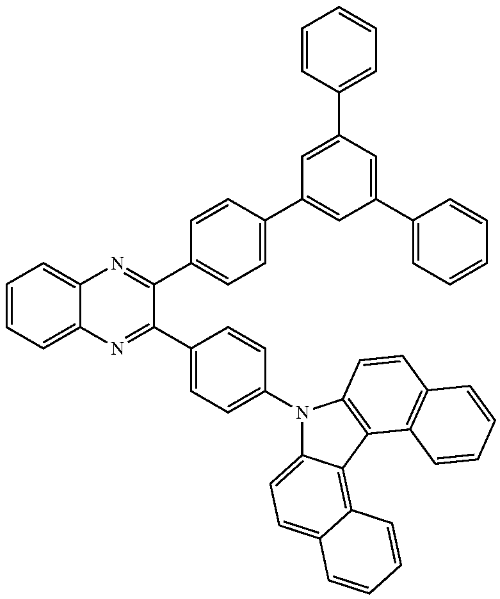
-continued
A-170
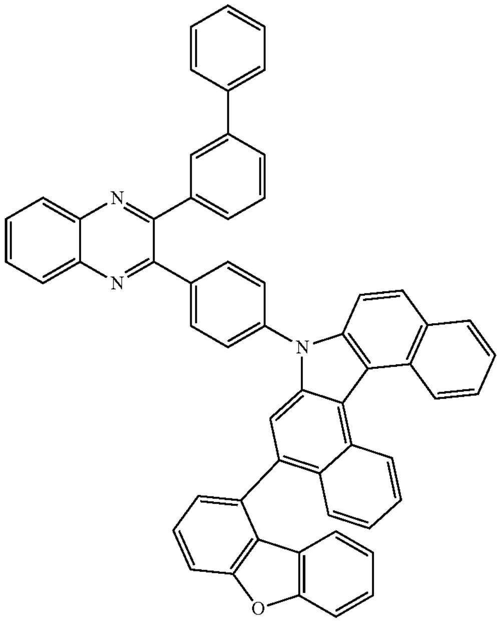
A-171
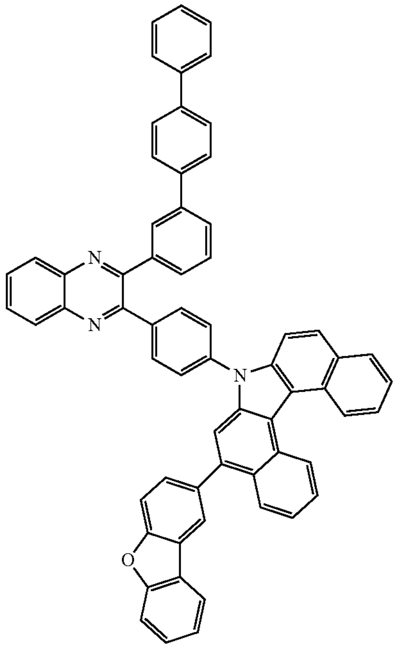

-continued
A-172
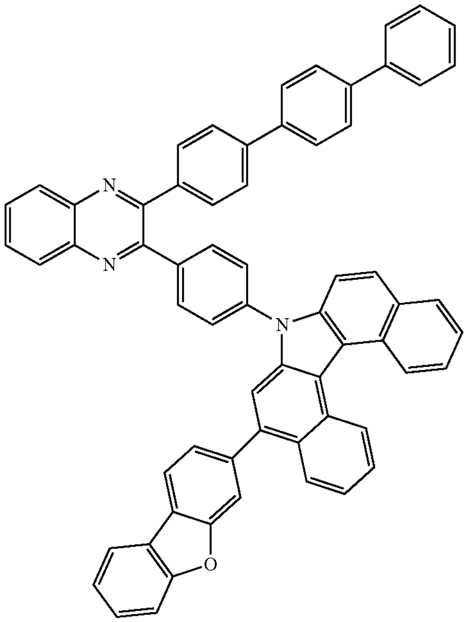
A-173
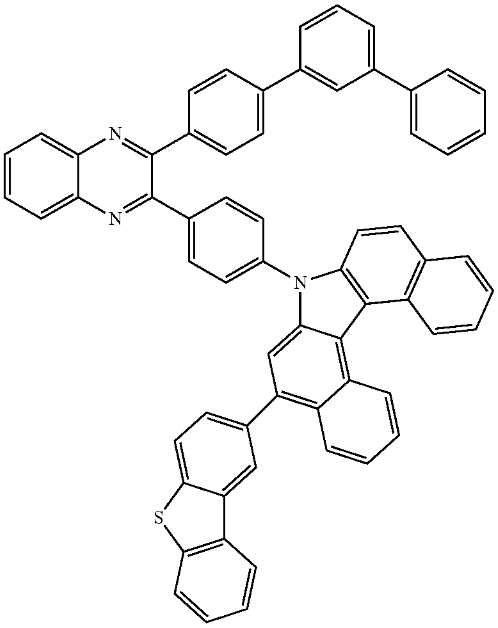
-continued
A-174
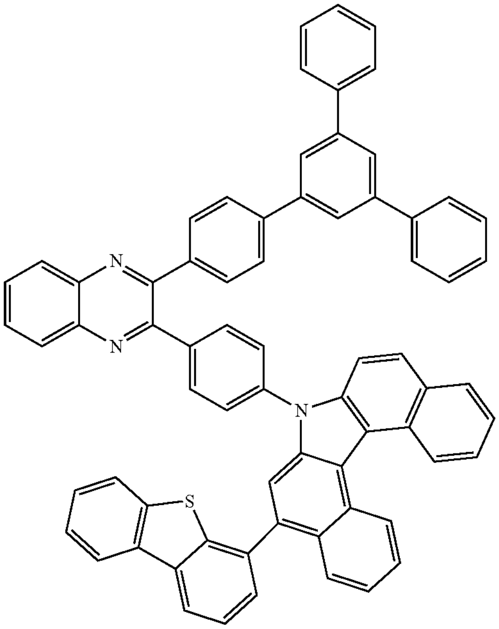
A-175
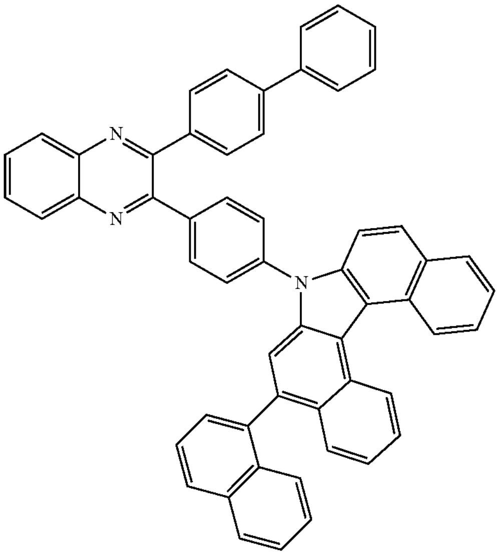

-continued
A-176
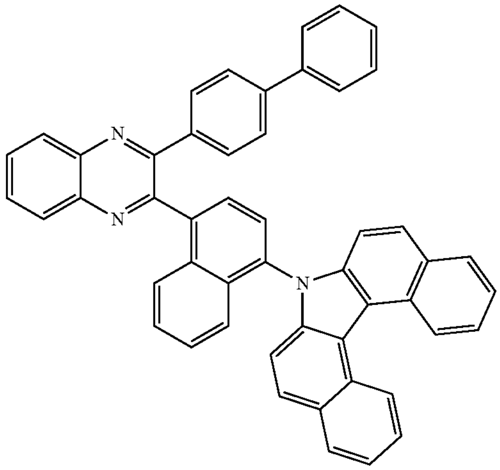
A-177
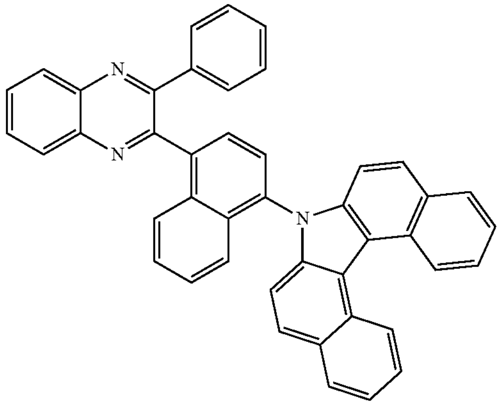
A-178
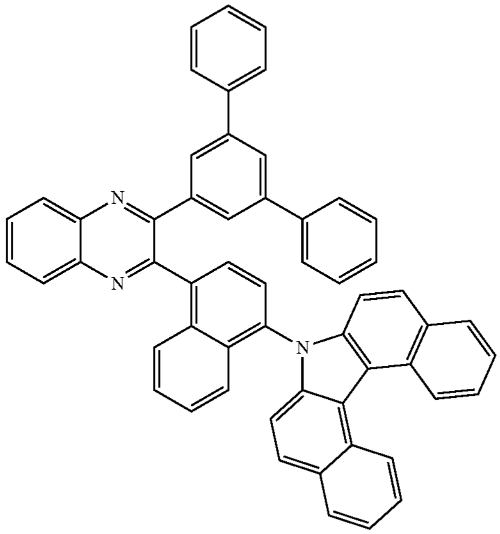
-continued
A-179
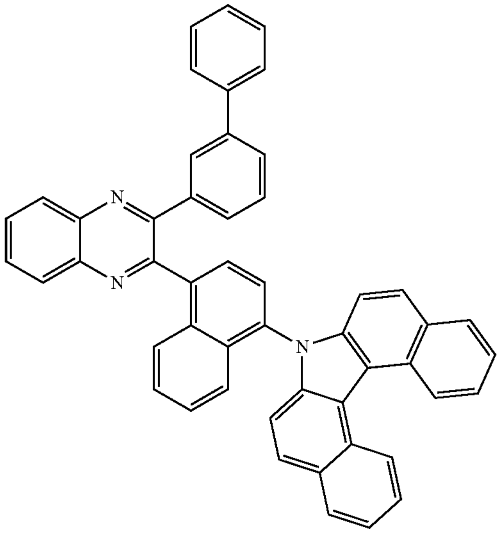
A-180
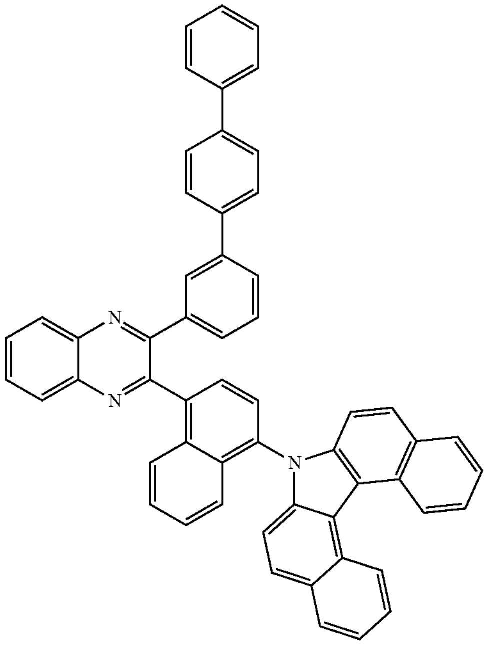

-continued
A-181
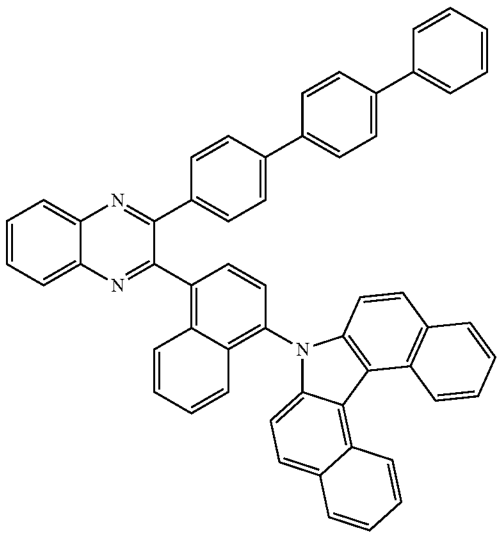
A-182
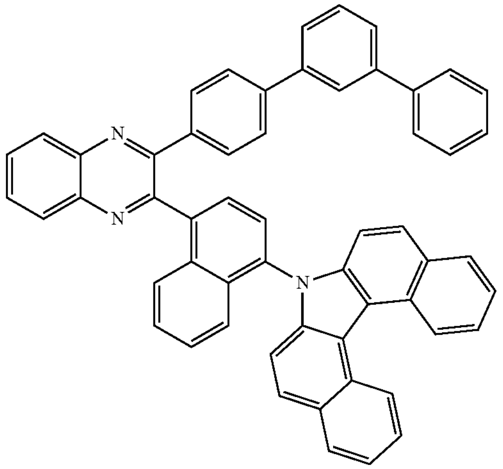
A-183
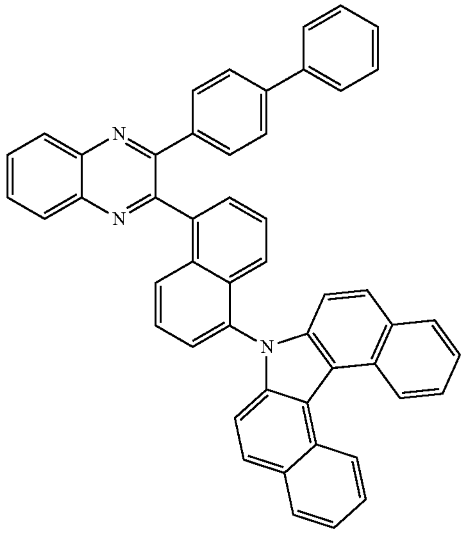
-continued
A-184
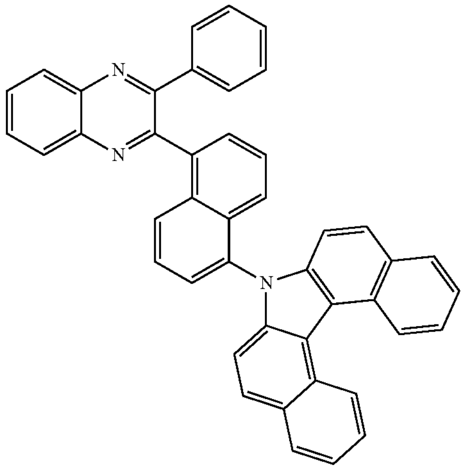
A-185
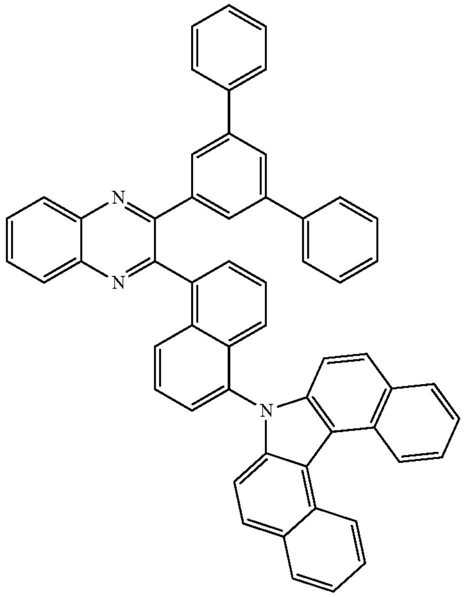

-continued
A-186
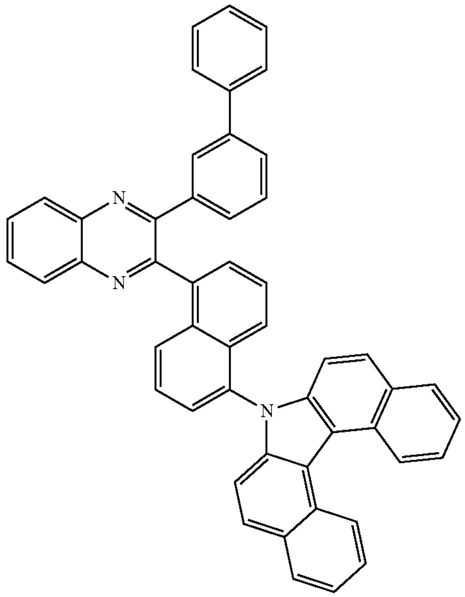
A-187
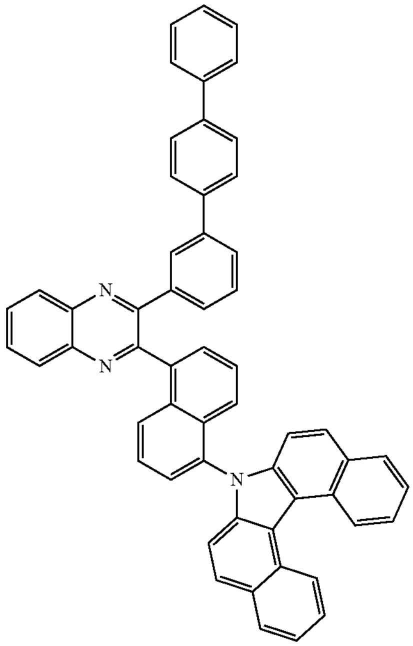
-continued
A-188
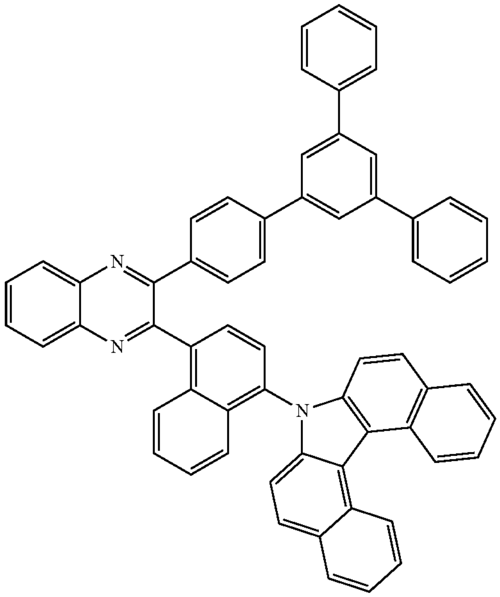
A-189
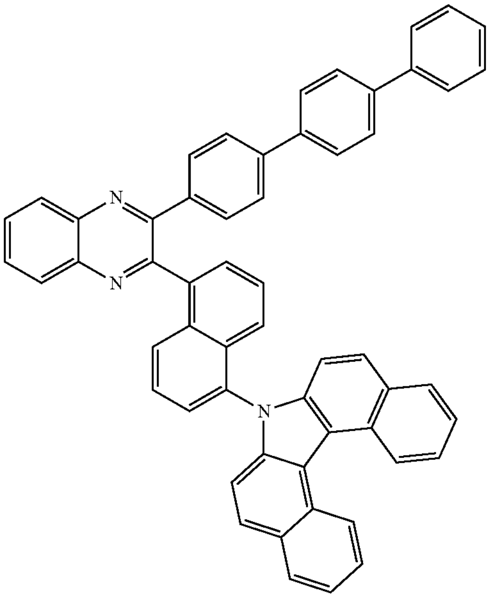

-continued
A-190
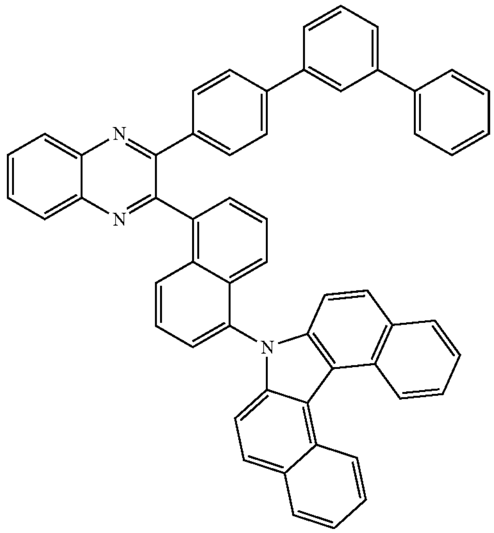
A-191
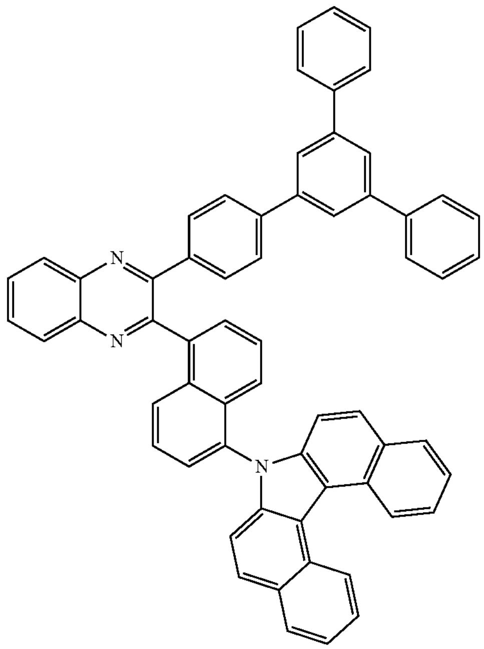
-continued
A-192
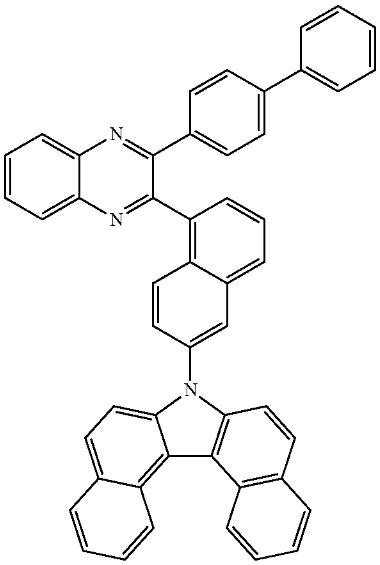
A-193
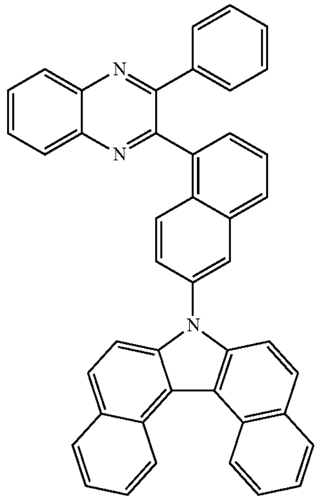

A-194
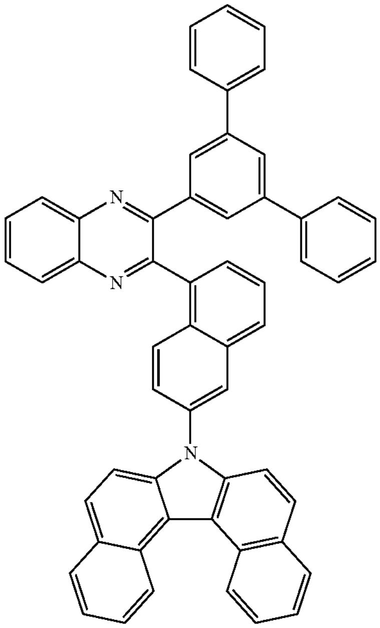
A-195
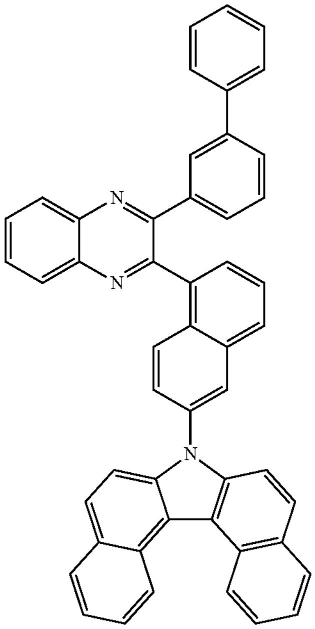
A-196
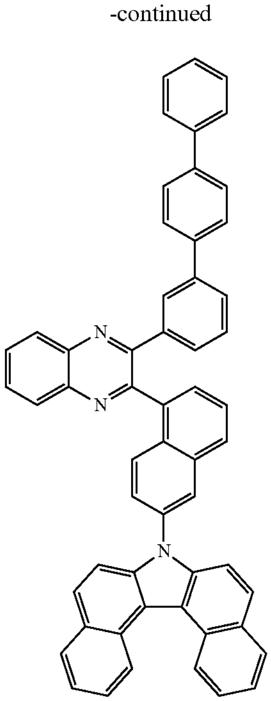
A-197
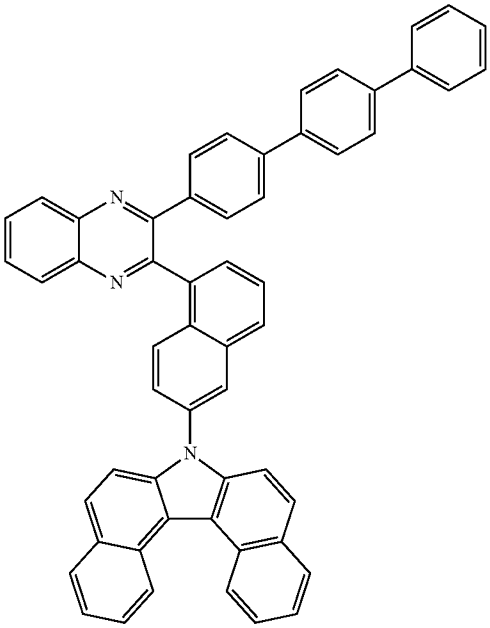

-continued
A-198
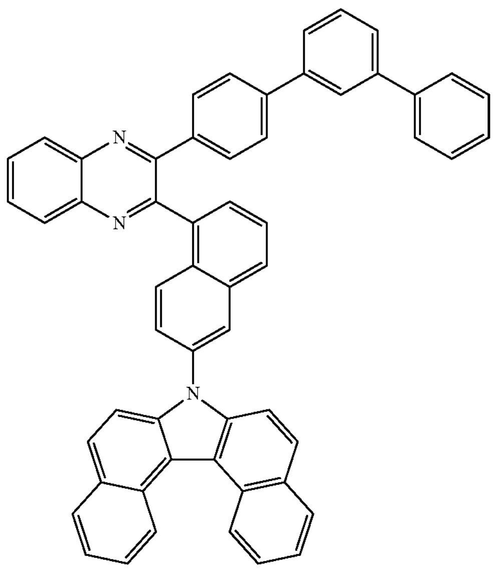
A-199
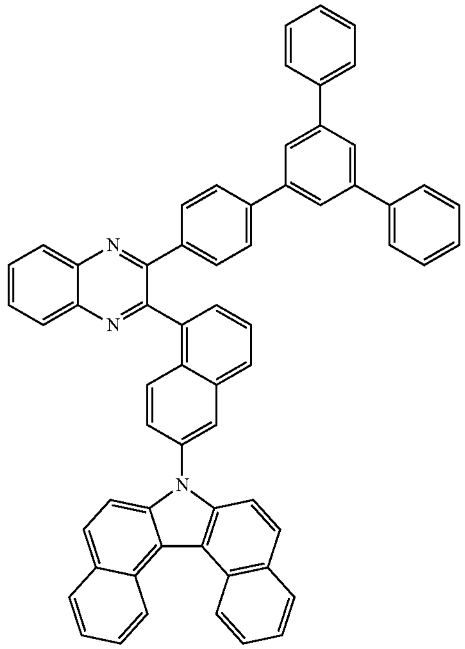
-continued
A-200
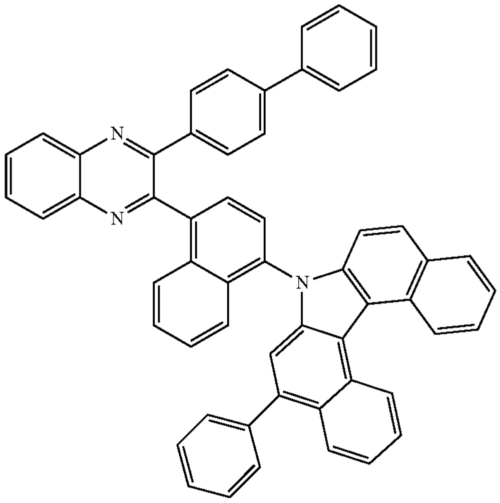
A-201
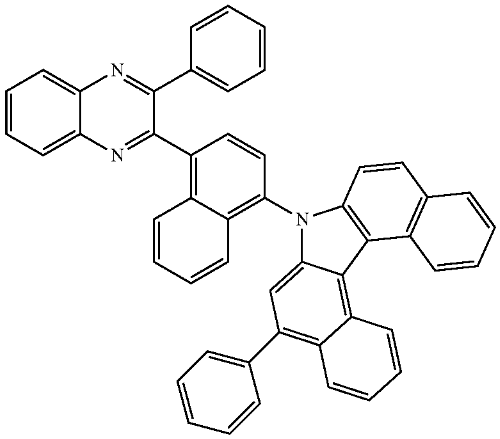
A-202
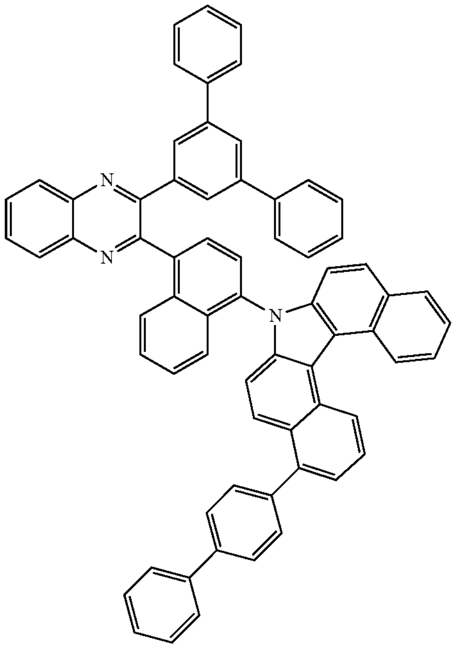

-continued
A-203
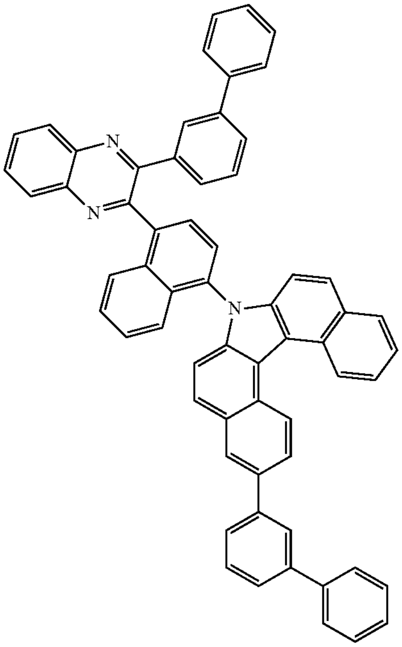
A-204
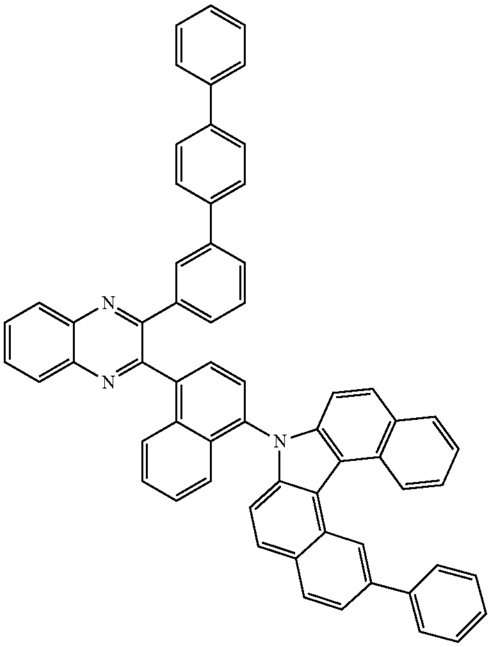
-continued
A-205
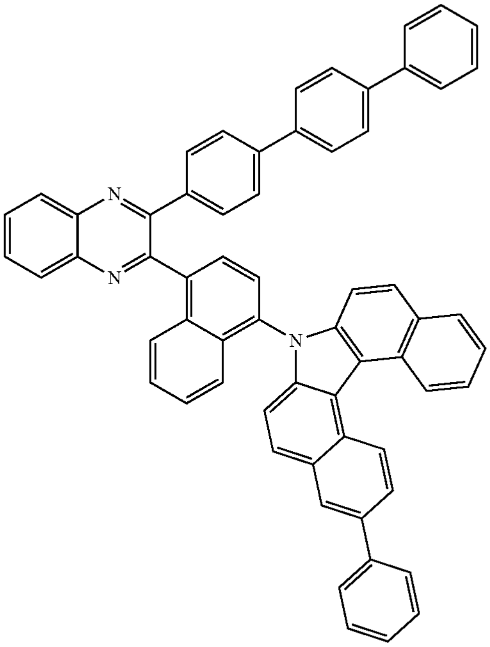
A-206
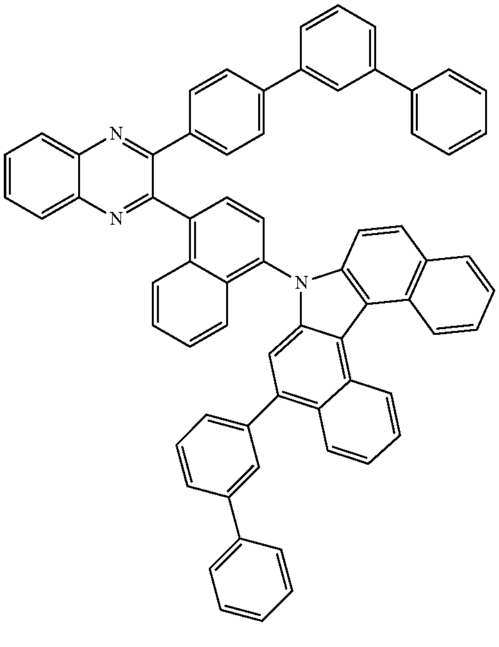

-continued
A-207
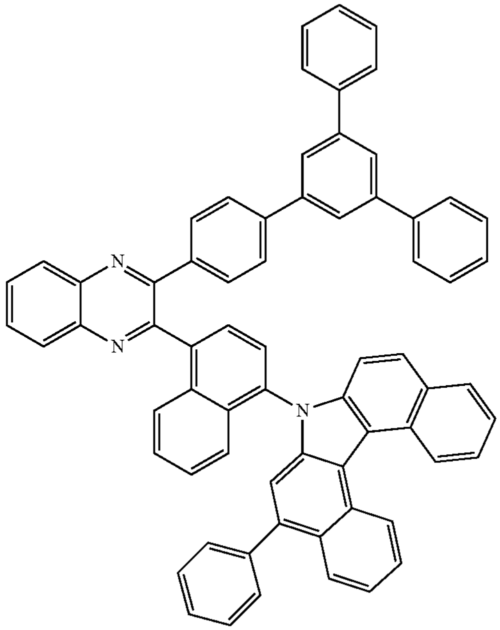
A-208
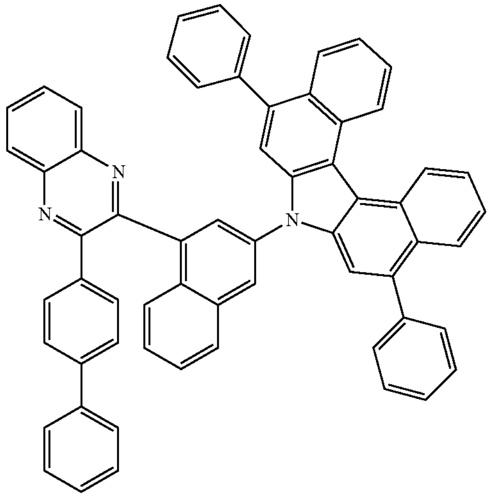
-continued
A-209
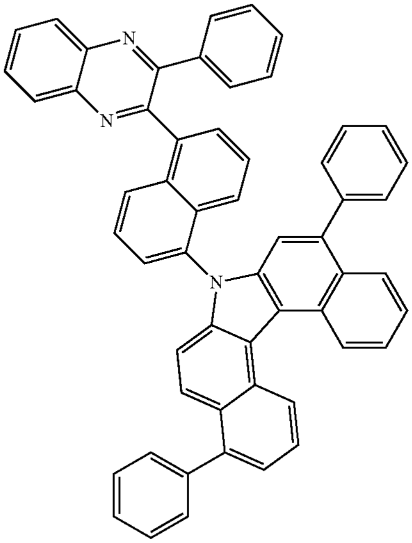
A-210
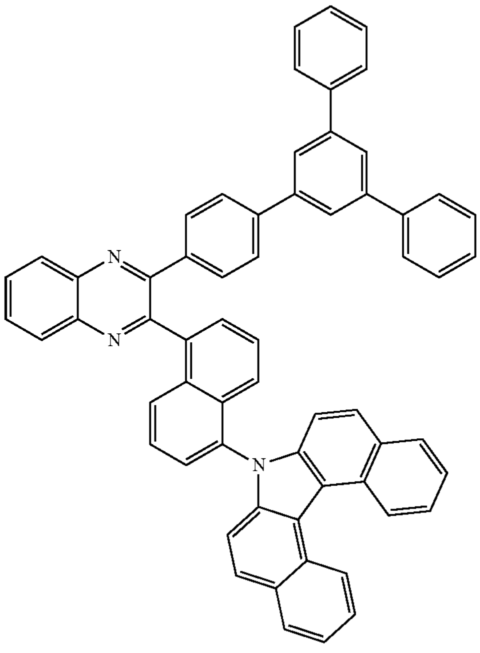

-continued
A-211
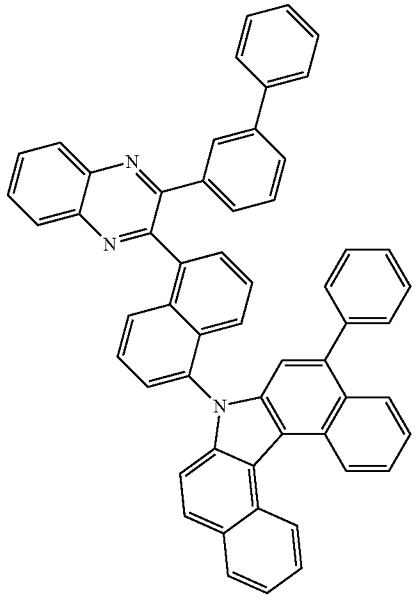
A-212
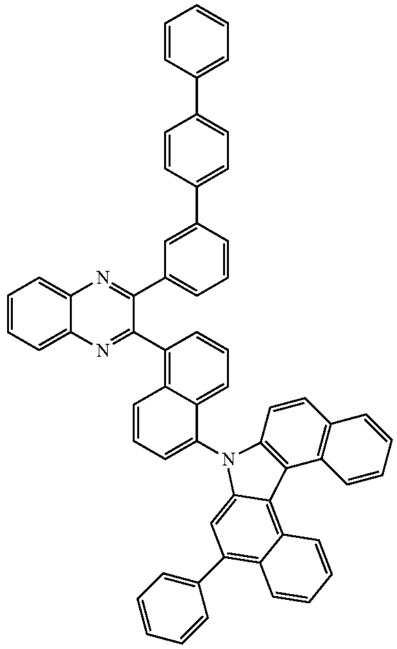
-continued
A-213
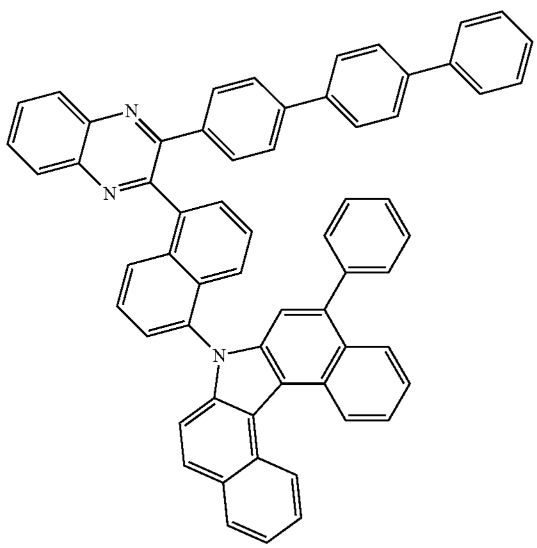
A-214
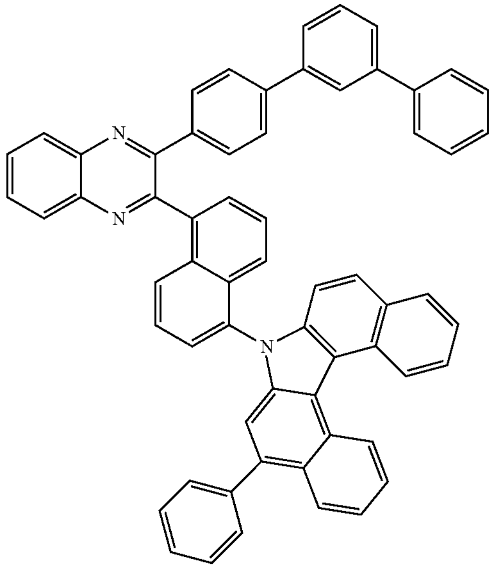

-continued
A-215
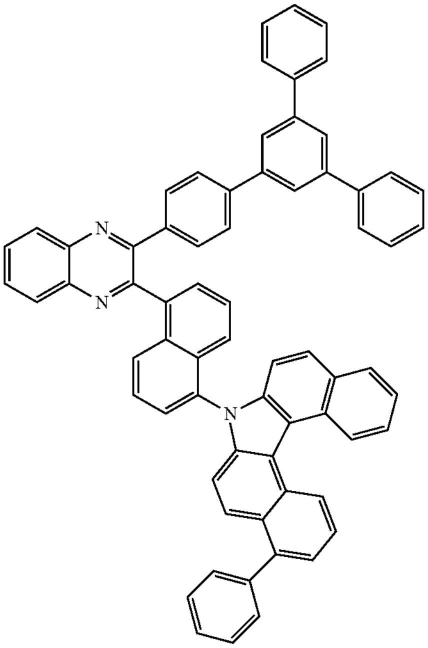
A-216
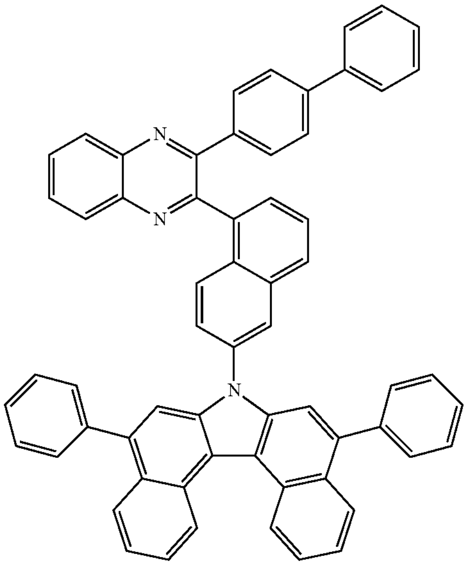
A-217
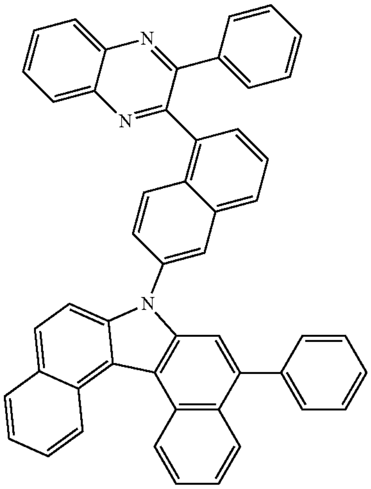
A-218
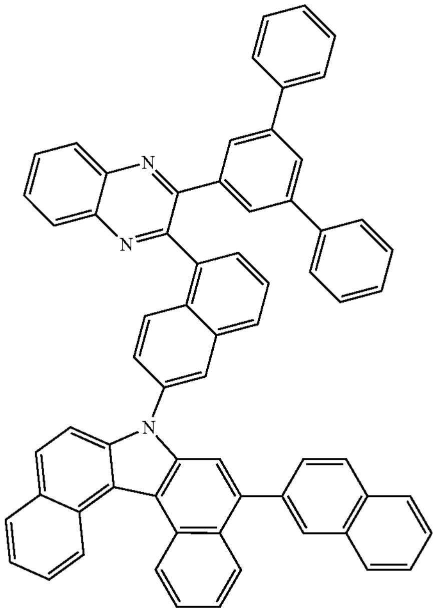

-continued
A-219
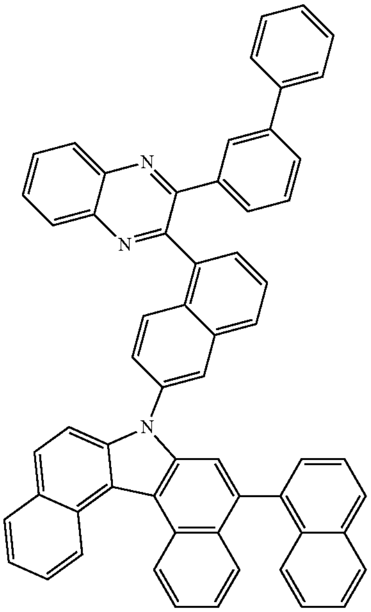
A-220
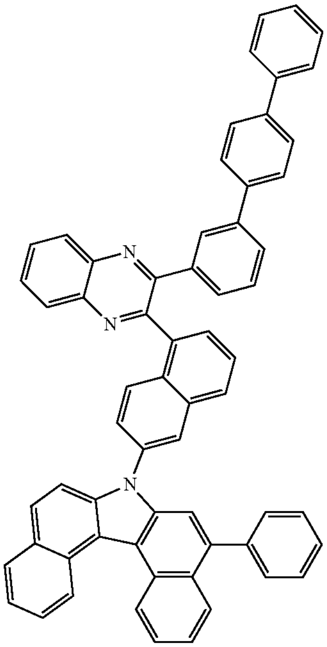
-continued
A-221
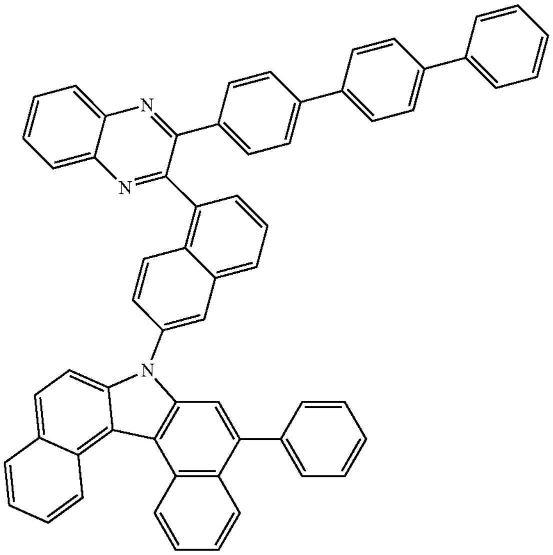
A-222
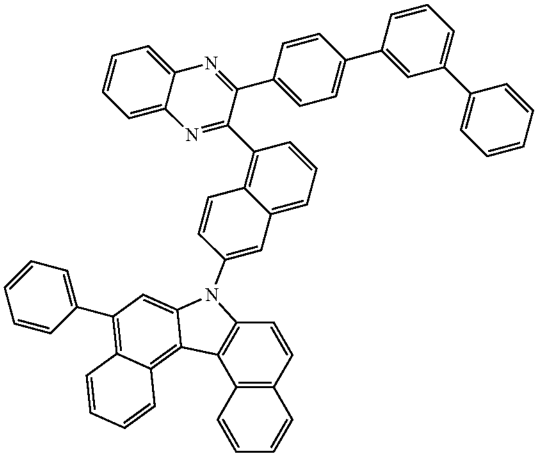
A-223
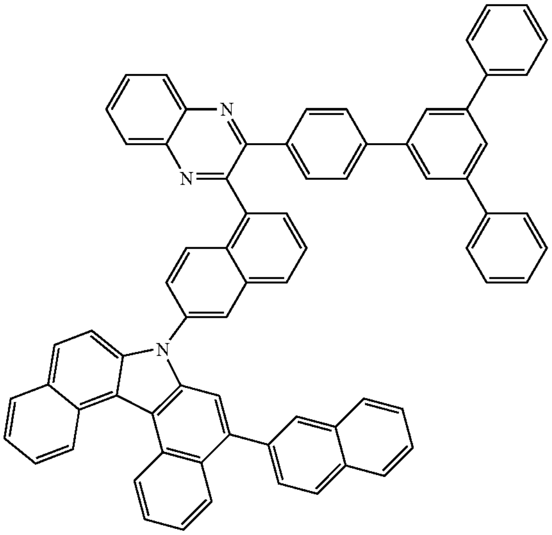

-continued
A-224
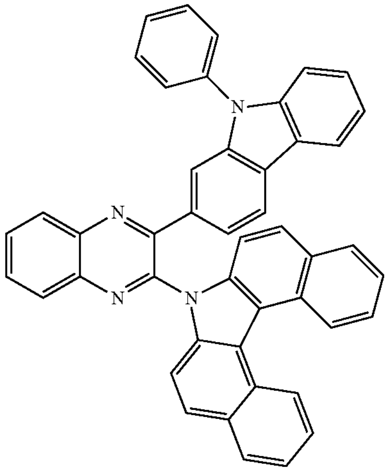
A-225
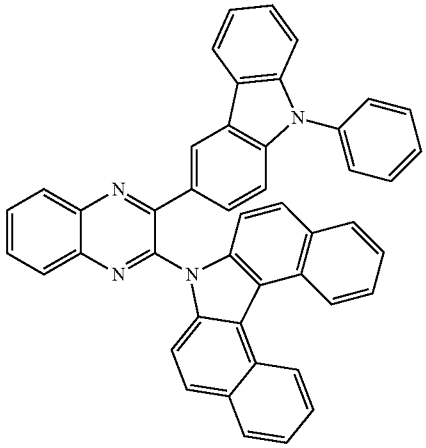
A-226
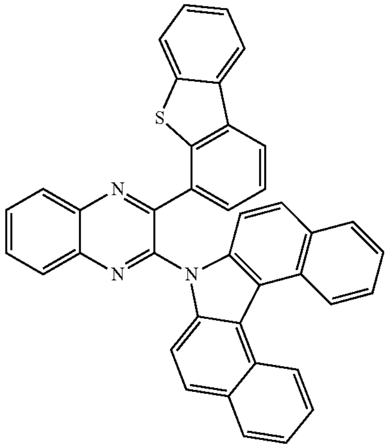
-continued
A-227
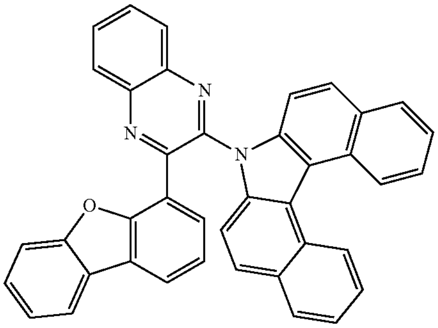
A-228
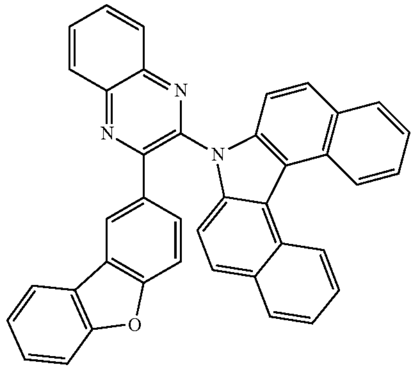
A-229
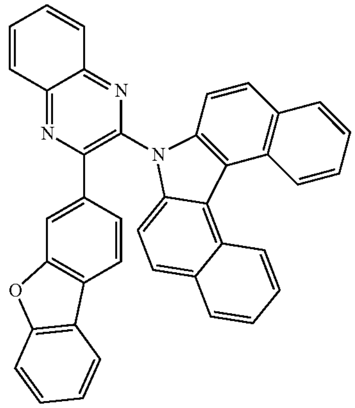
A-230
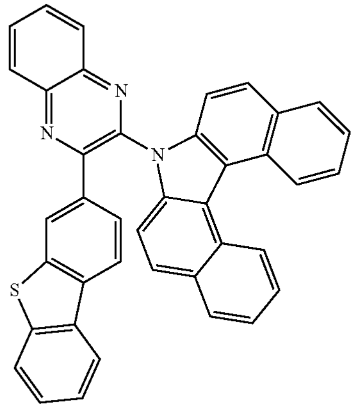

-continued
A-231
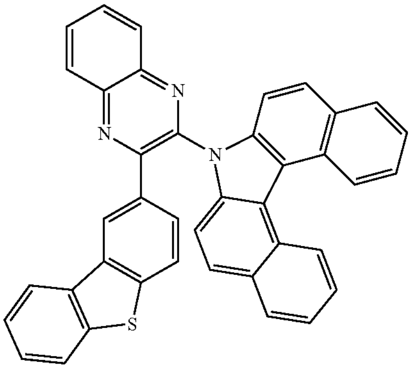
A-232
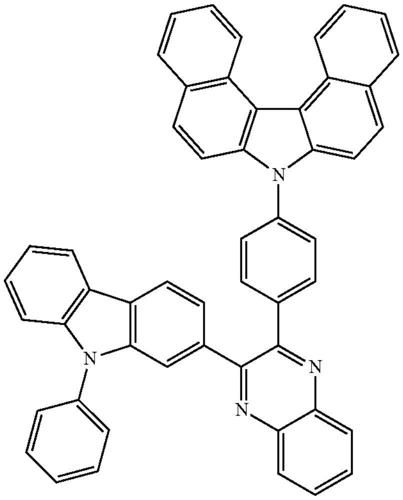
A-233
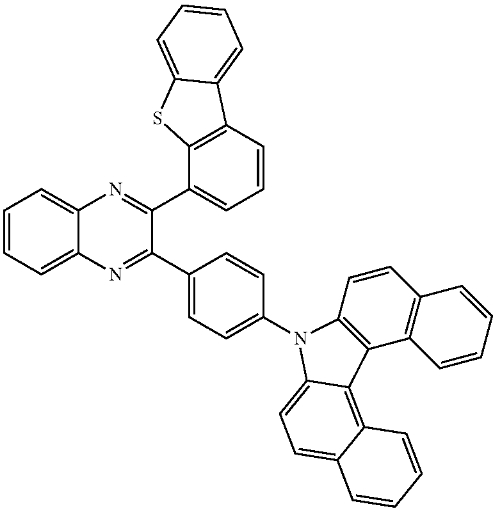
-continued
A-234
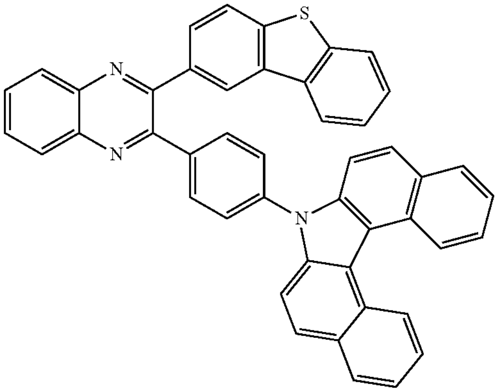
A-235
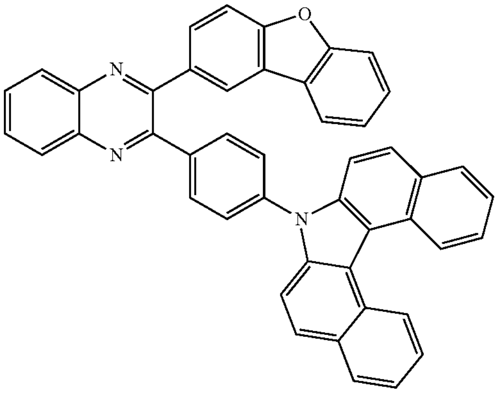
A-236
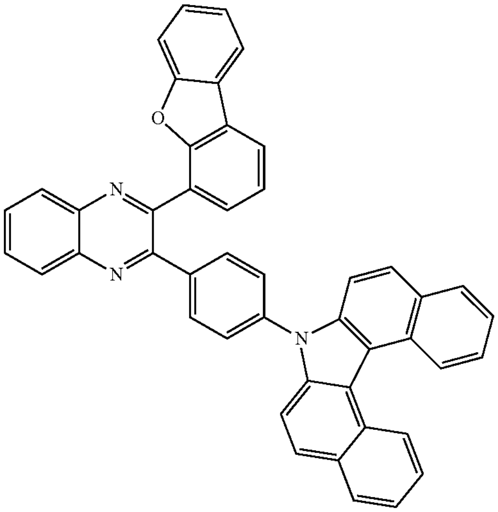

-continued
A-237
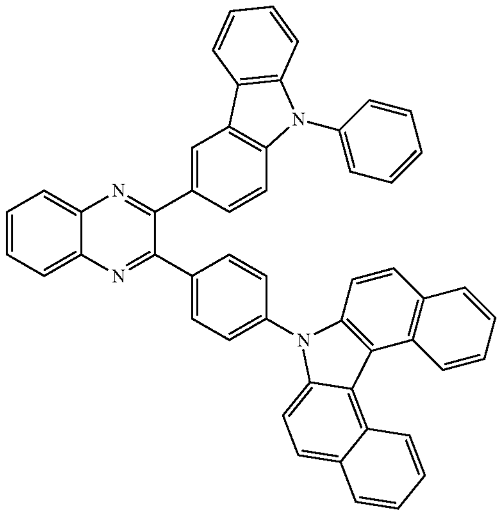
A-238
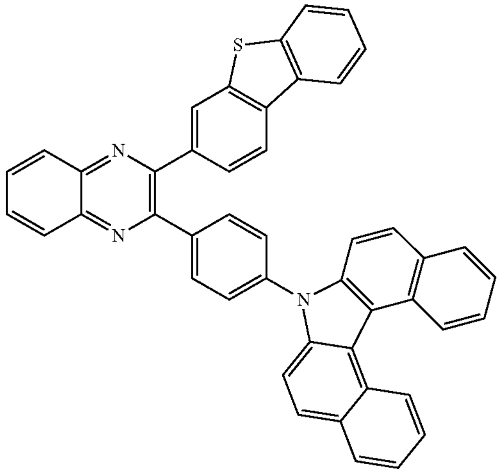
A-239
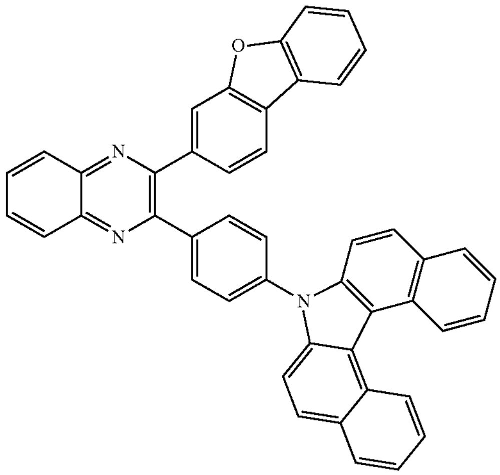
-continued
A-240
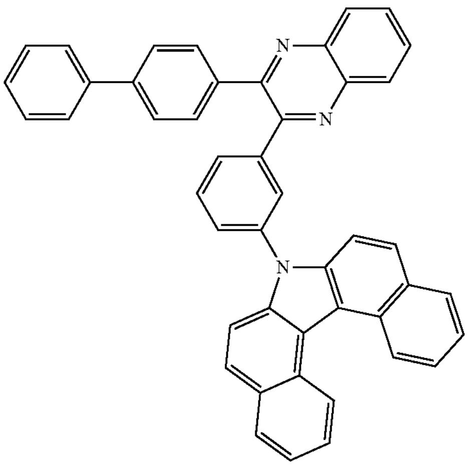
A-241
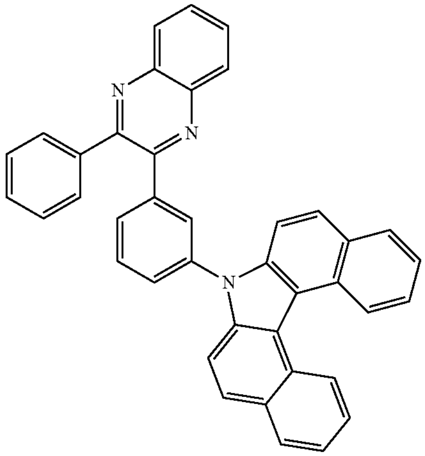
A-242
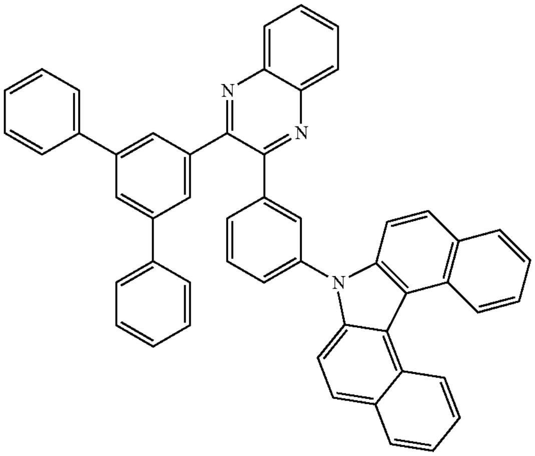

-continued
A-243
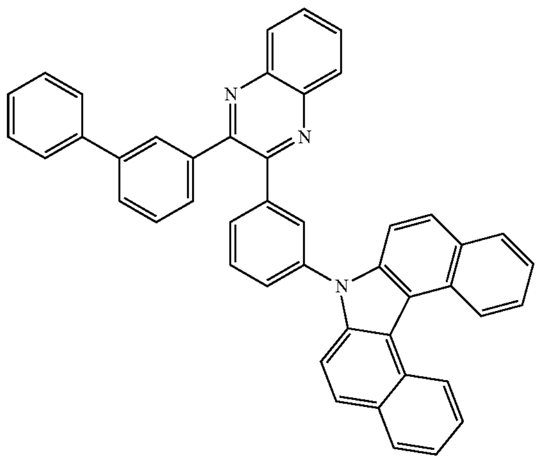
A-244
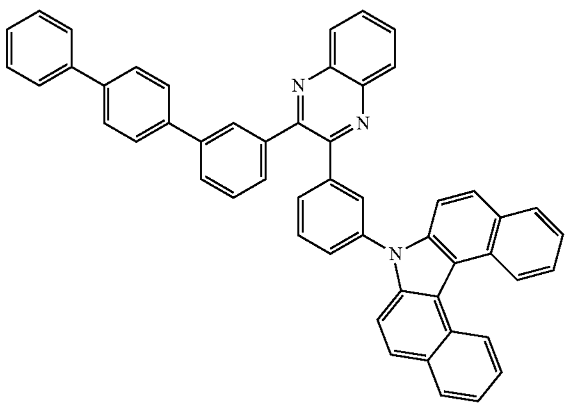
A-245
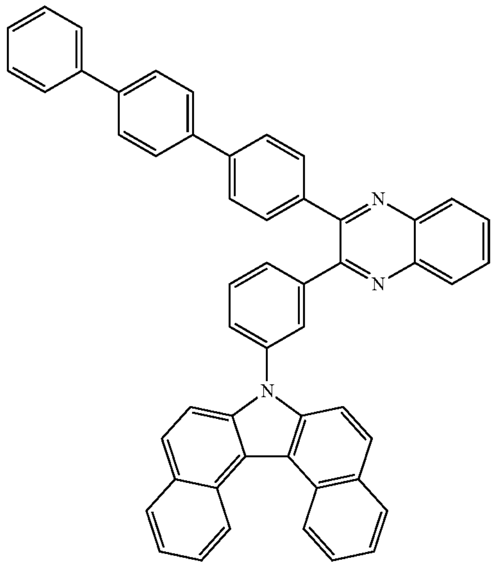
-continued
A-246
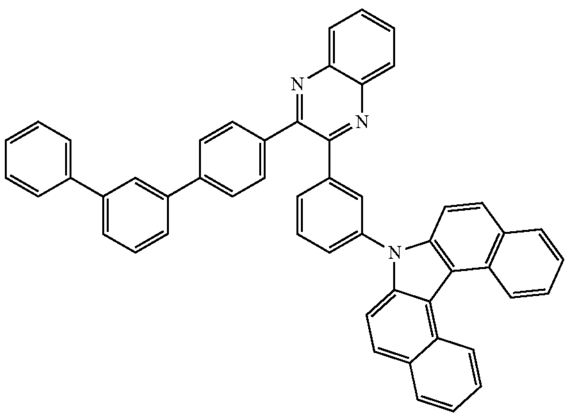
A-247
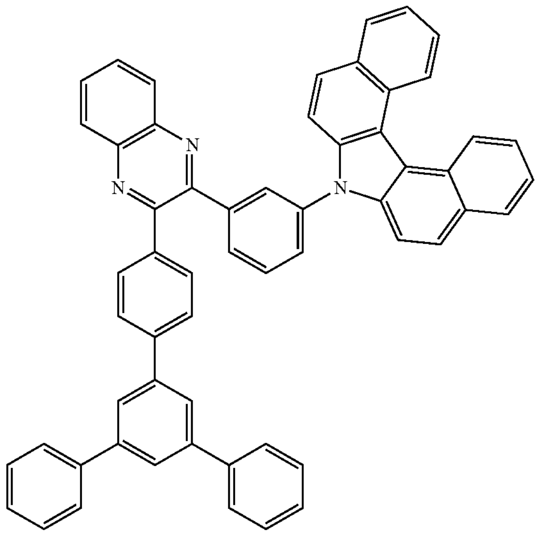
A-248
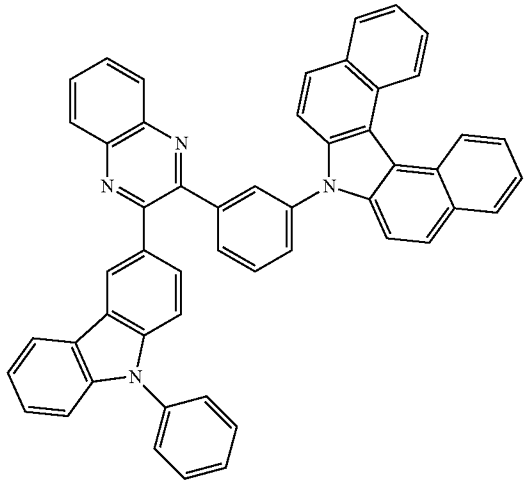

-continued
A-249
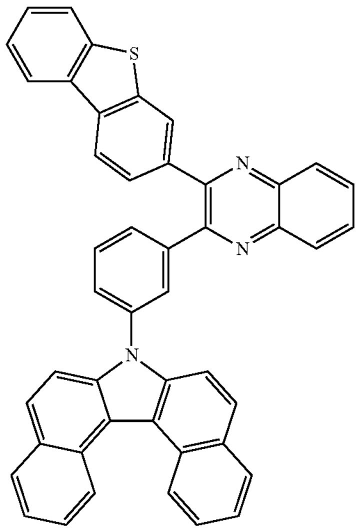
A-250
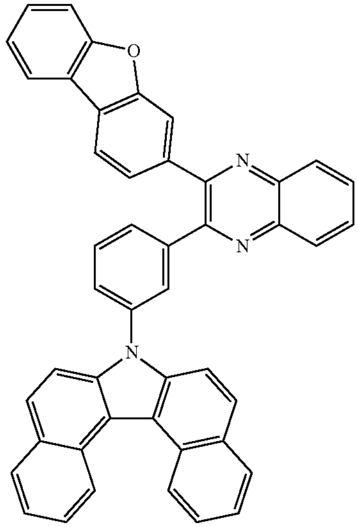
A-251
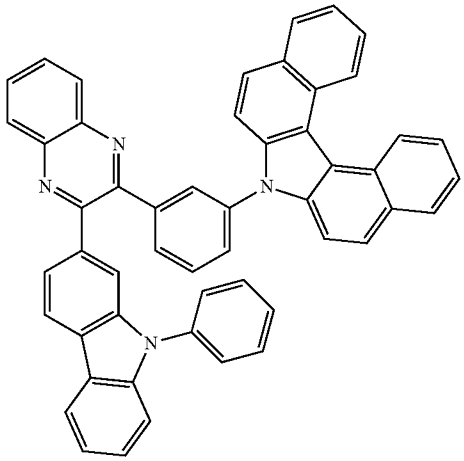
-continued
A-252
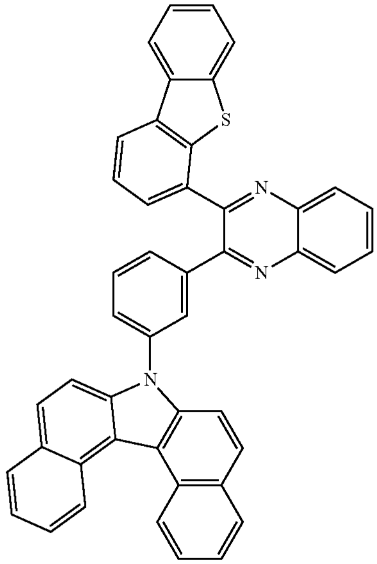
A-253
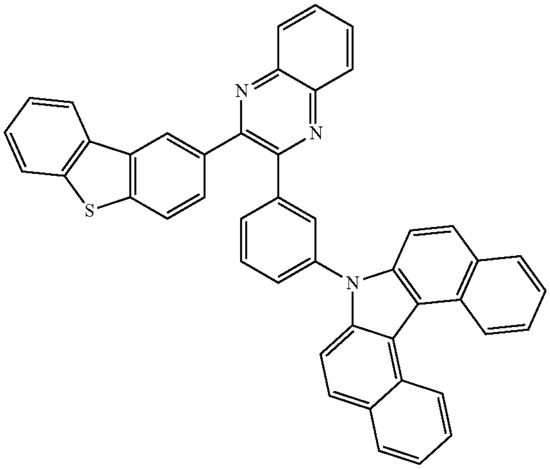
A-254
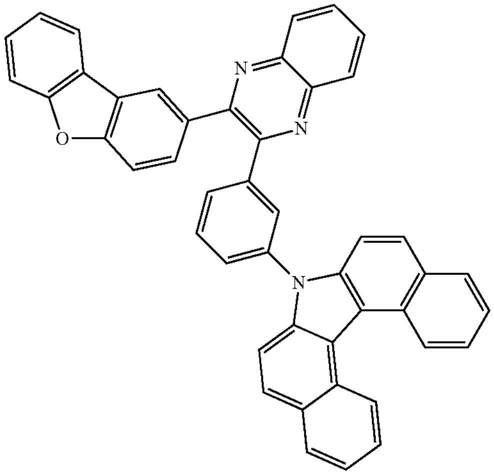

-continued
A-255
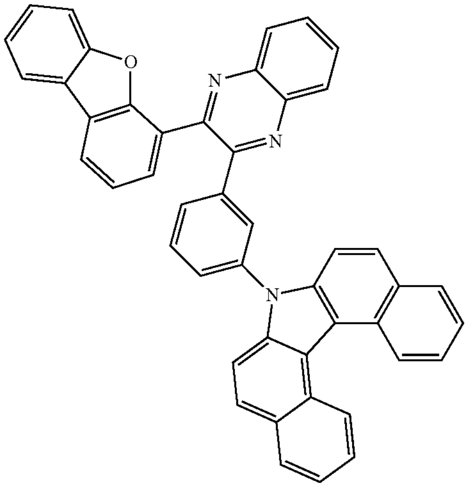
A-256
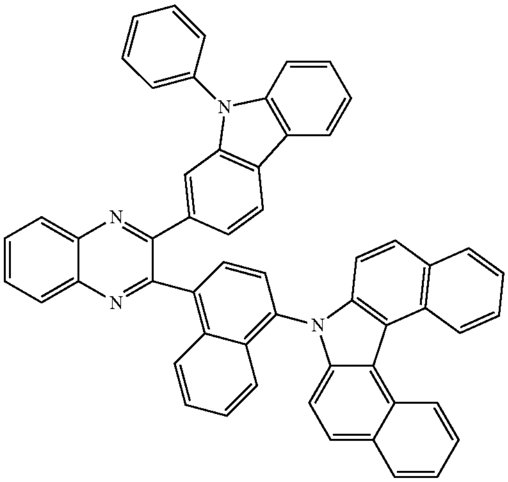
A-257
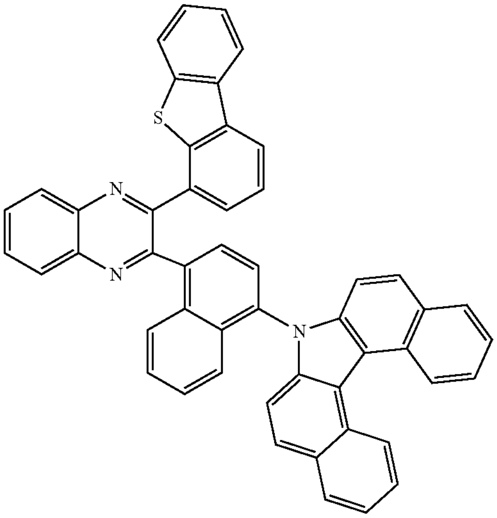
-continued
A-258
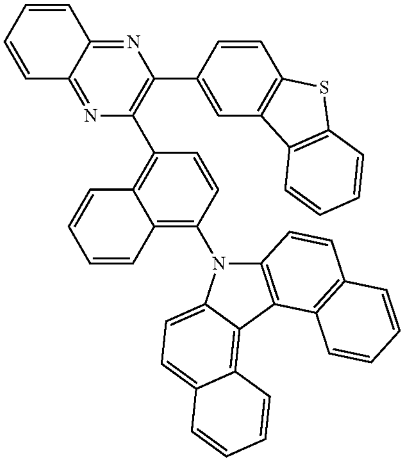
A-259
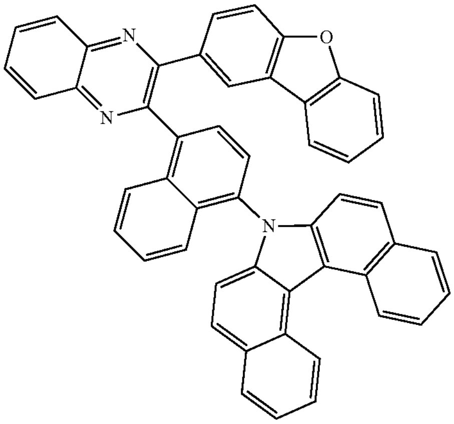
A-260
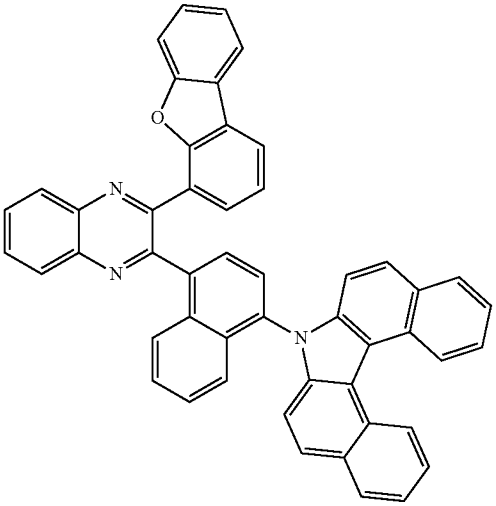

-continued
A-261
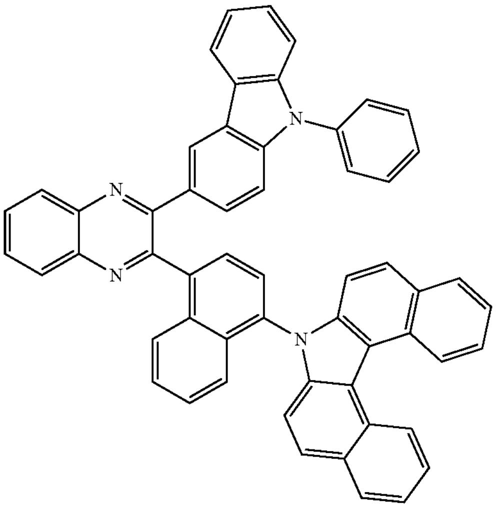
A-262
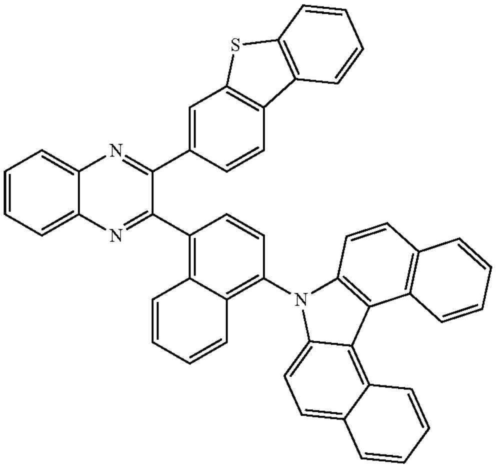
A-263
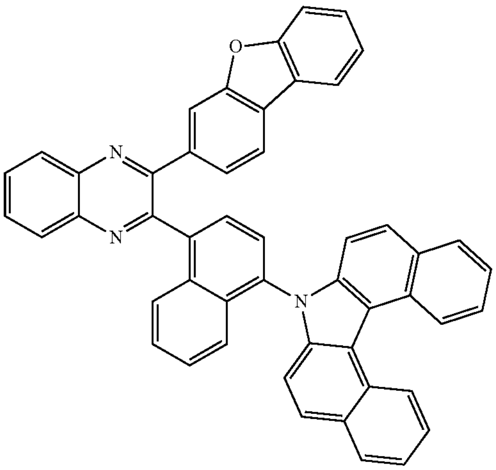
-continued
A-264
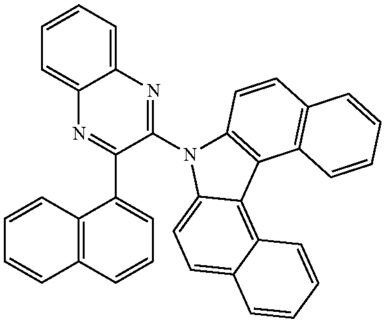
A-265
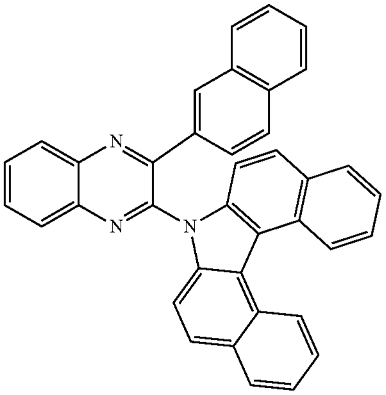
A-266
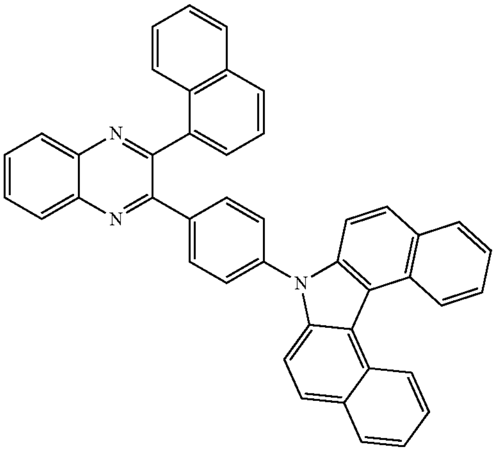
A-267
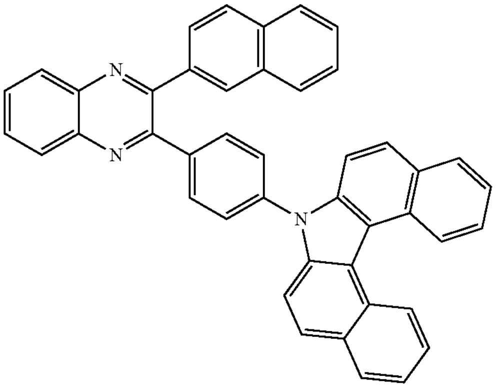

-continued
A-268
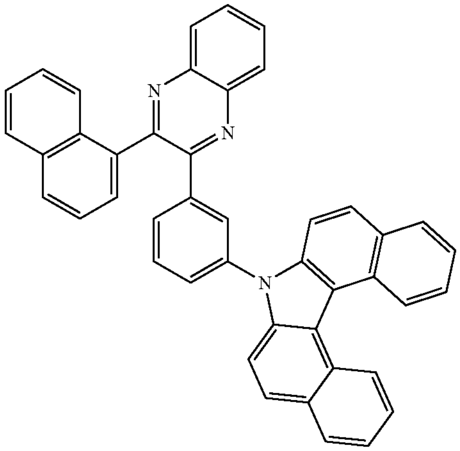
A-269
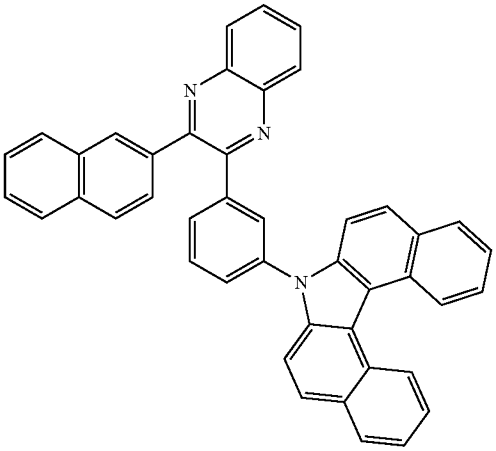
A-270
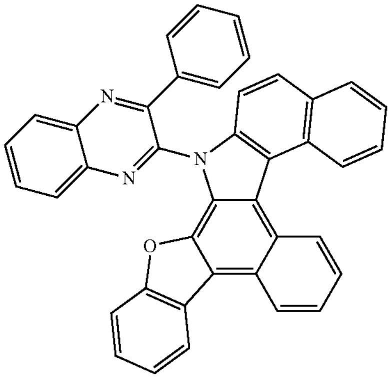
-continued
A-271
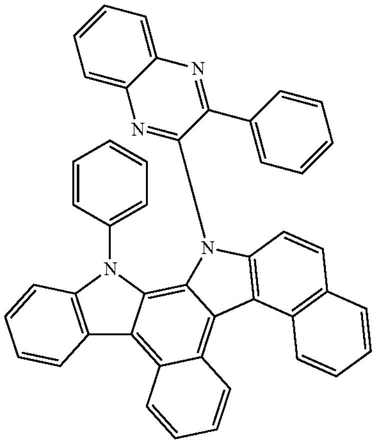
A-272
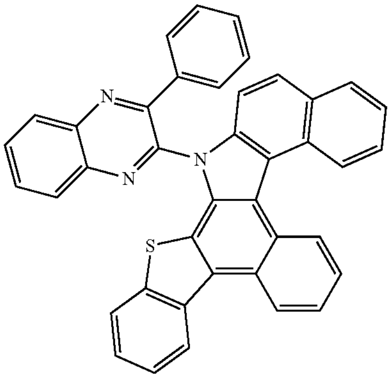
A-273
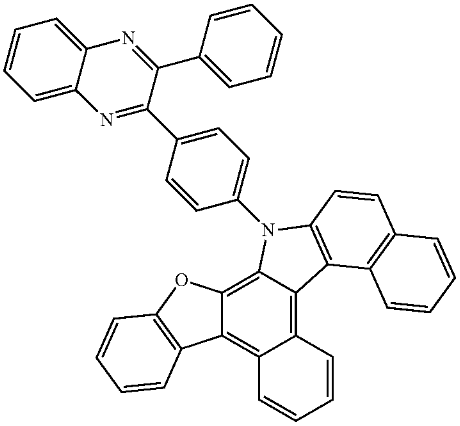

-continued
A-274
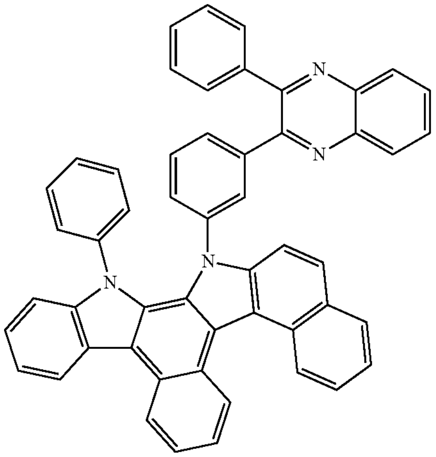
A-275
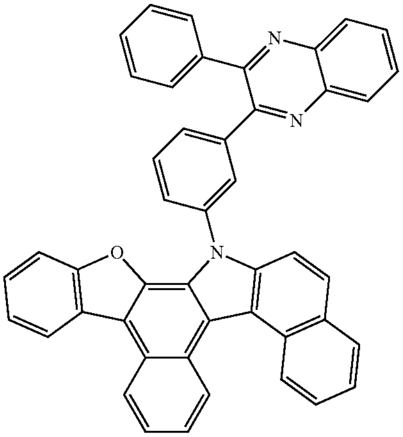
A-276
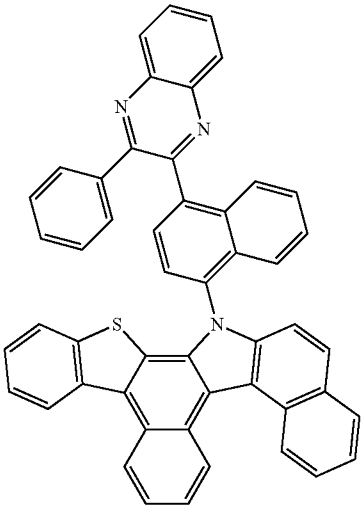
-continued
A-277
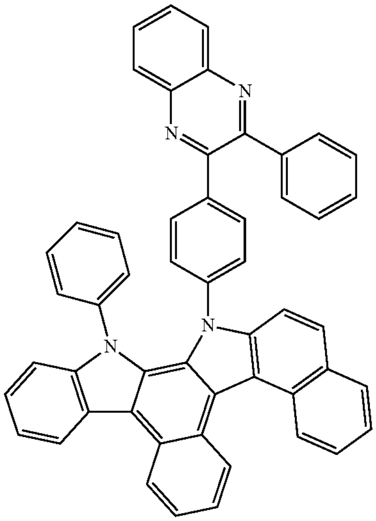
A-278
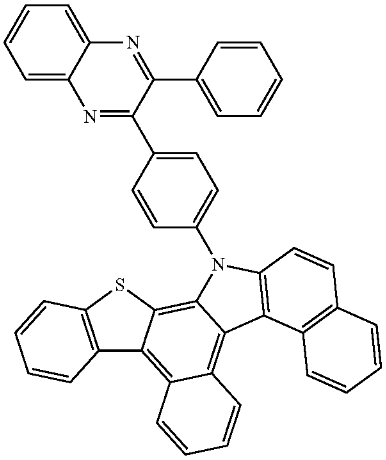
A-279
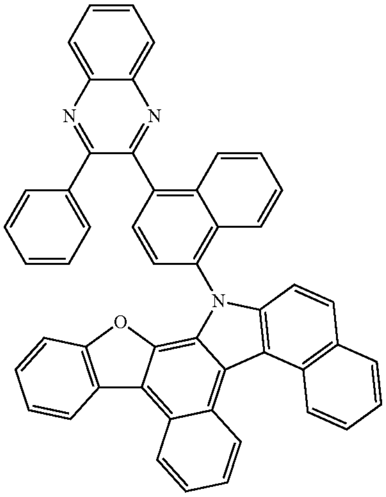

-continued
A-280
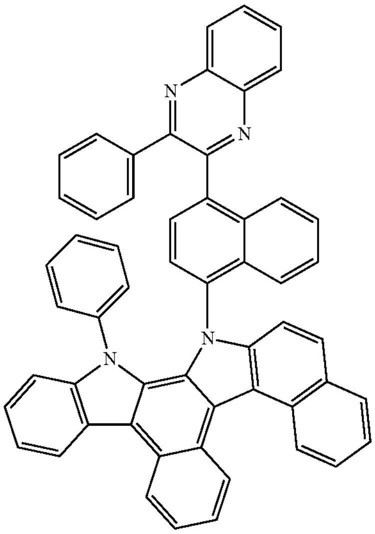
A-281
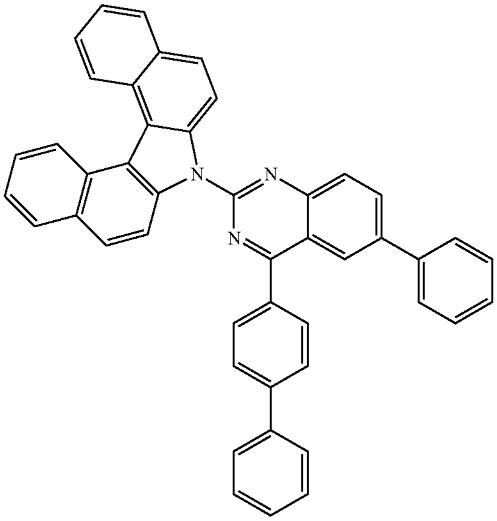
A-282
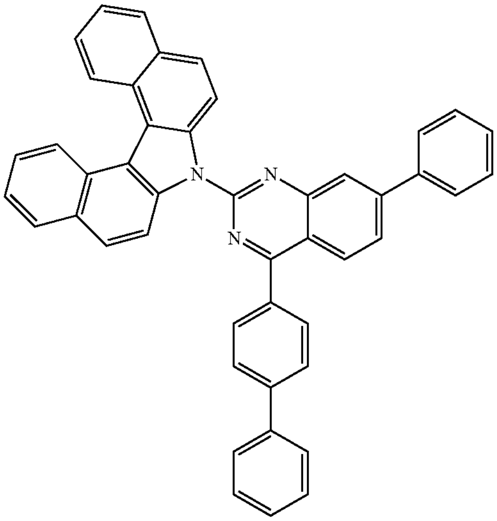
-continued
A-283
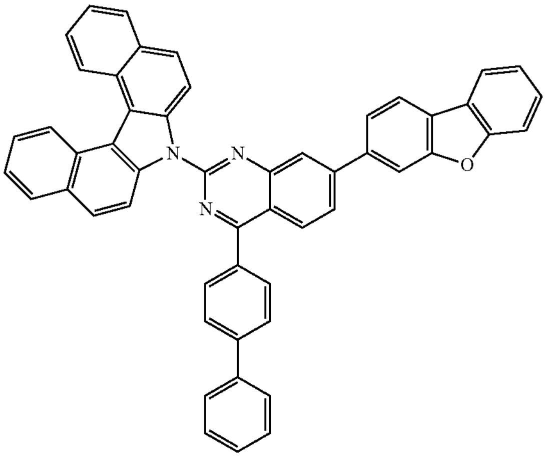
A-284
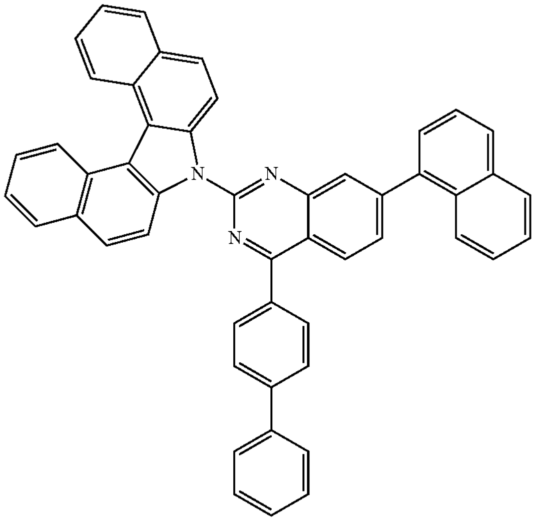
A-285
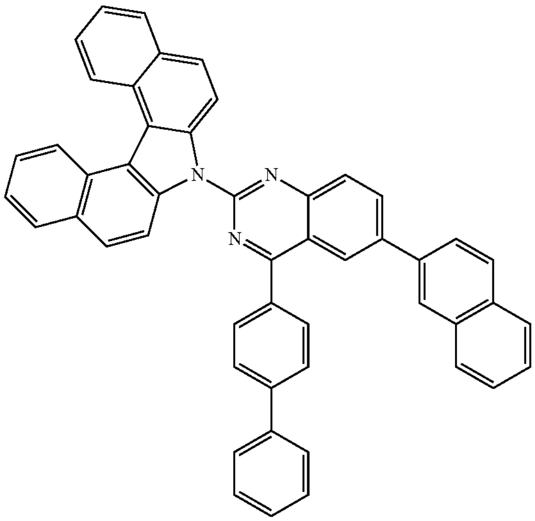

-continued

A-286

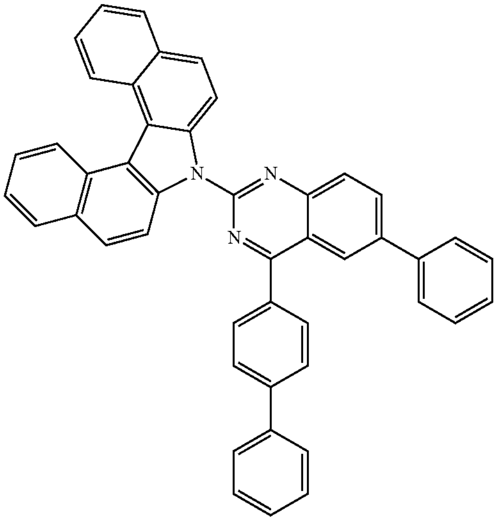

A-287

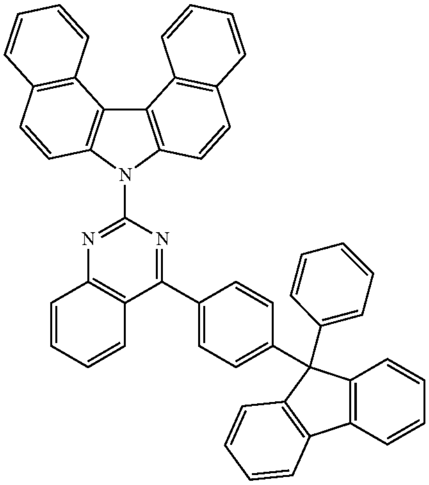

The organic electroluminescent device according to the present invention comprises an anode, a cathode, and at least one organic layer between the anode and the cathode. The organic layer comprises a light-emitting layer, and the light-emitting layer comprises a host and a phosphorescent dopant. The host material comprises plural host compounds, at least a first host compound of the plural host compounds is represented by formula 1, and a second host compound is represented by formula 2.

The light-emitting layer is a layer from which light is emitted, and can be a single layer or a multi-layer of which two or more layers are stacked. In the light-emitting layer, it is preferable that the doping concentration of the dopant compound based on the host compound is less than 20 wt %.

The organic layer comprises a light-emitting layer, and may further comprise at least one layer selected from the group consisting of a hole injection layer, a hole transport layer, an electron transport layer, an electron injection layer, an interlayer, a hole blocking layer, and an electron blocking layer.

According to the organic electroluminescent device of the present invention, the weight ratio of the first host material to the second host material is in the range of 1:99 to 99:1.

The dopant is preferably at least one phosphorescent dopant. The dopant materials applied to the organic electroluminescent device according to the present invention are not limited, but may be preferably selected from metallated complex compounds of iridium, osmium, copper, and platinum, more preferably selected from ortho-metallated complex compounds of iridium, osmium, copper and platinum, and even more preferably ortho-metallated iridium complex compounds.

The phosphorescent dopant is preferably selected from compounds represented by the following formulas 101 to 103.

(101)

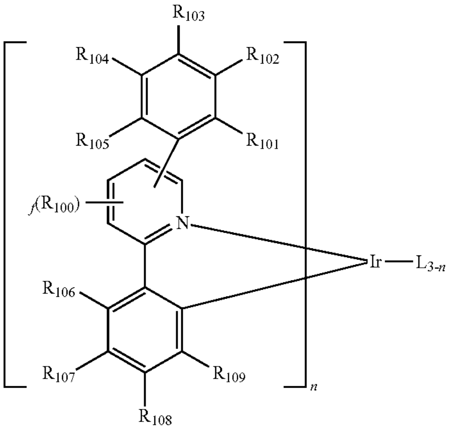

(102)

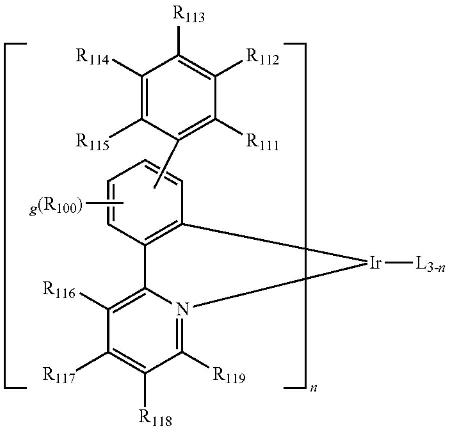

(103)

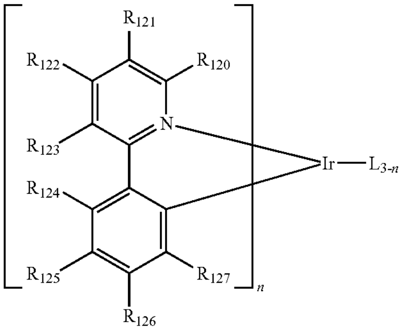

wherein L is selected from the following structures:

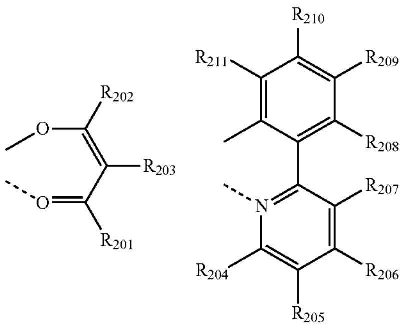

$R_{100}$ represents hydrogen, a substituted or unsubstituted (C1-C30)alkyl, or a substituted or unsubstituted (C3-C30) cycloalkyl;

$R_{101}$ to $R_{109}$, and $R_{111}$ to $R_{123}$ each independently represent hydrogen, deuterium, a halogen, a (C1-C30)alkyl unsubstituted or substituted with a halogen(s), a substituted or unsubstituted (C3-C30)cycloalkyl, a substituted or unsubstituted (C6-C30)aryl, a cyano, or a substituted or unsubstituted (C1-C30)alkoxy; adjacent substituents of $R_{106}$ to $R_{109}$ may be linked to each other to form a substituted or unsubstituted fused ring, e.g., fluorene unsubstituted or substituted with alkyl, dibenzothiophene unsubstituted or substituted with alkyl, or dibenzofuran unsubstituted or substituted with alkyl; and adjacent substituents of $R_{120}$ to $R_{123}$ may be linked to each other to form a substituted or unsubstituted fused ring, e.g., quinoline unsubstituted or substituted with alkyl or aryl;

$R_{124}$ to $R_{127}$ each independently represent hydrogen, deuterium, a halogen, a substituted or unsubstituted (C1-C30) alkyl, or a substituted or unsubstituted (C6-C30)aryl; and adjacent substituents of $R_{124}$ to $R_{127}$ may be linked to each other to form a substituted or unsubstituted fused ring, e.g., fluorene unsubstituted or substituted with alkyl, dibenzothiophene unsubstituted or substituted with alkyl, or dibenzofuran unsubstituted or substituted with alkyl;

$R_{201}$ to $R_{211}$ each independently represent hydrogen, deuterium, a halogen, a (C1-C30)alkyl unsubstituted or substituted with a halogen(s), a substituted or unsubstituted (C3-C30)cycloalkyl, or a substituted or unsubstituted (C6-C30) aryl; and adjacent substituents of $R_{208}$ to $R_{211}$ may be linked to each other to form a substituted or unsubstituted fused ring, e.g., fluorene unsubstituted or substituted with alkyl, dibenzothiophene unsubstituted or substituted with alkyl, or dibenzofuran unsubstituted or substituted with alkyl;

f and g each independently represent an integer of 1 to 3; where f or g is an integer of 2 or more, each of $R_{100}$ may be the same or different; and n represents an integer of 1 to 3.

Specifically, the phosphorescent dopant materials include the following:

D-1

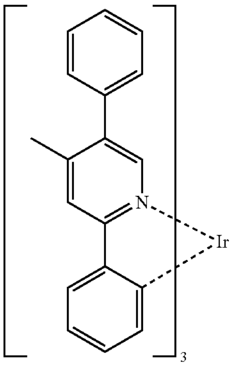

D-2

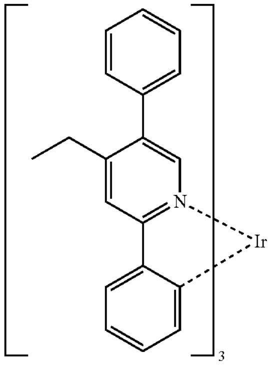

D-3

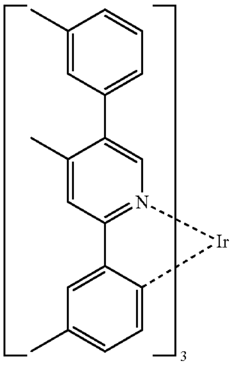

D-4

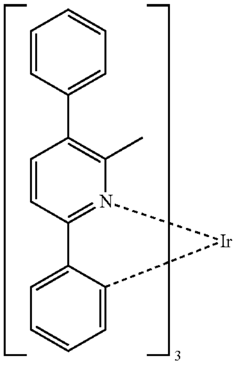

-continued
D-5
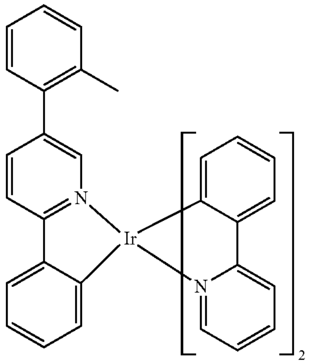
D-6
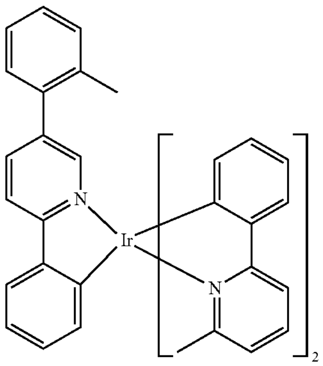
D-7
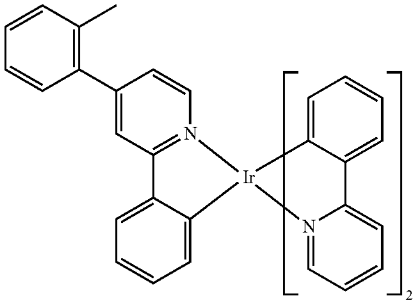
D-8
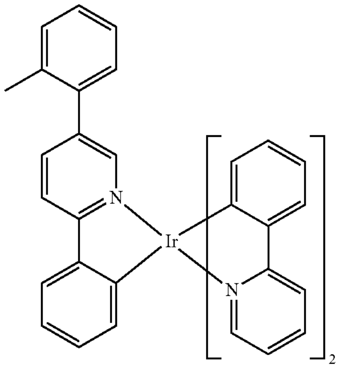
-continued
D-9
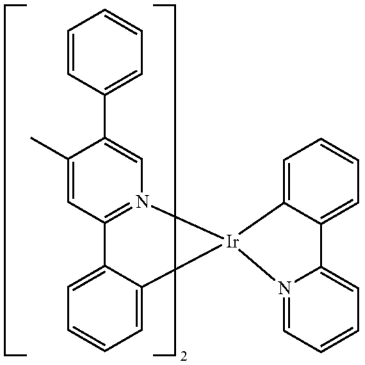
D-10
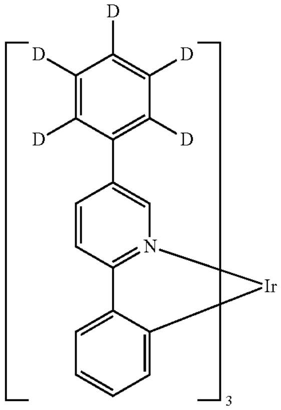
D-11
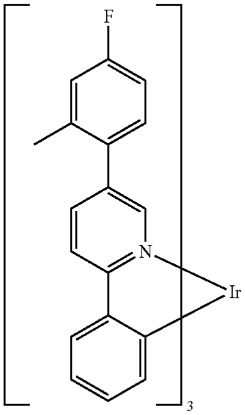
D-12
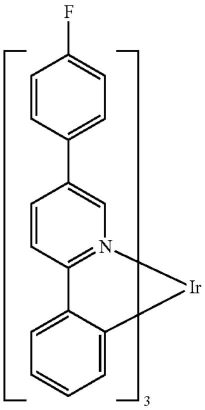

-continued
D-13
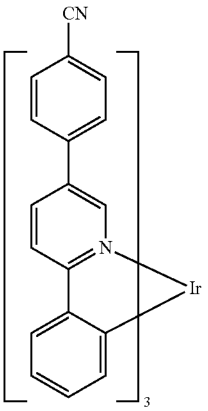
D-14
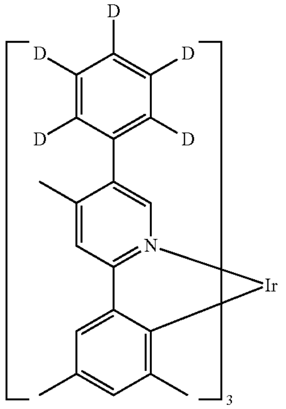
D-15
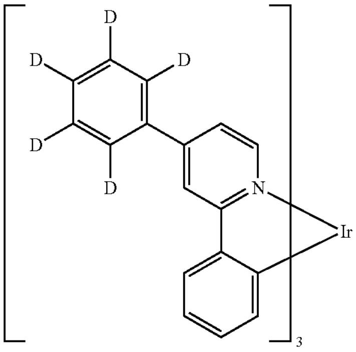
D-16
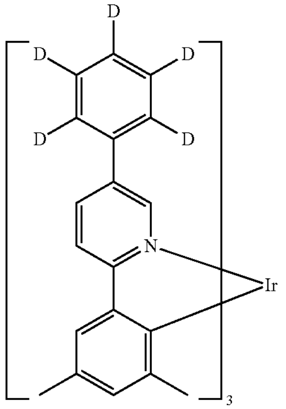
-continued
D-17
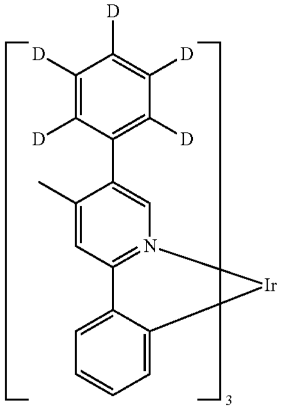
D-18
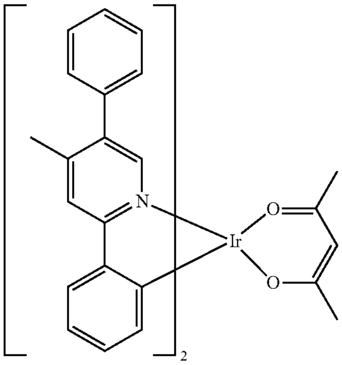
D-19
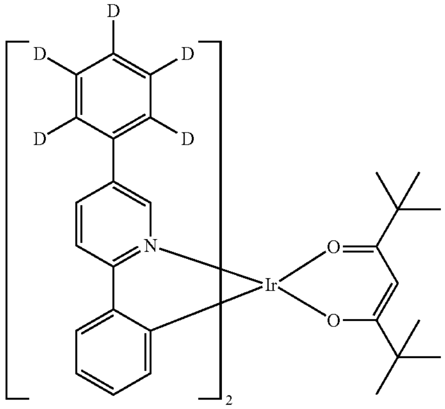
D-20
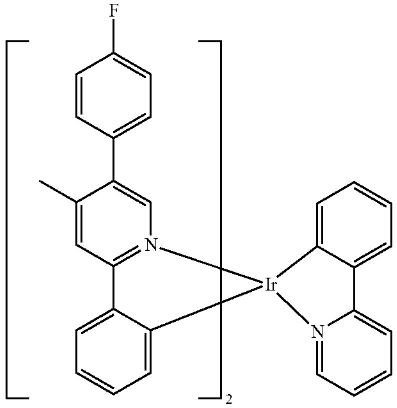

-continued
D-21
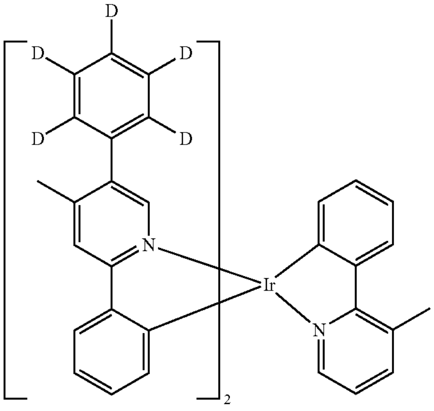
D-22
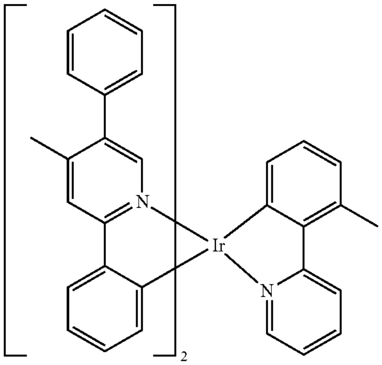
D-23
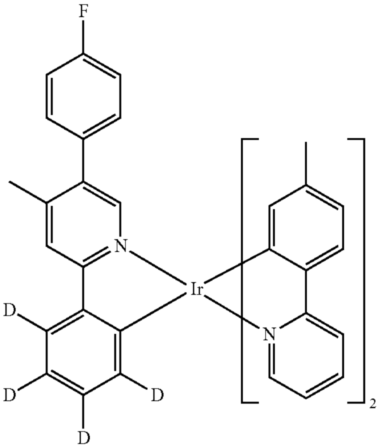
-continued
D-24
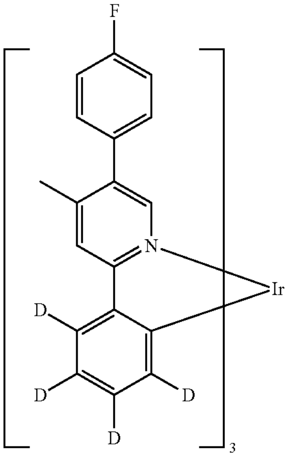
D-25
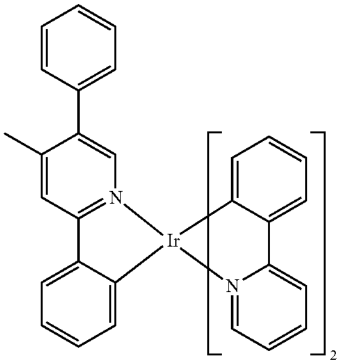
D-26
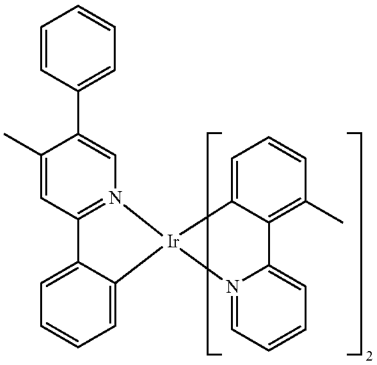
D-27
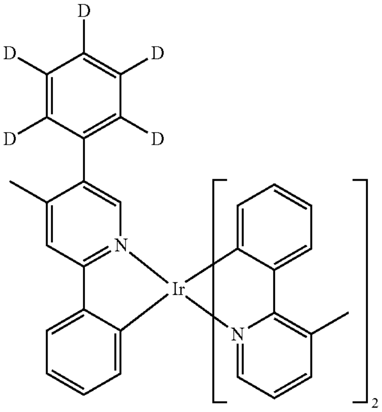

-continued
D-28
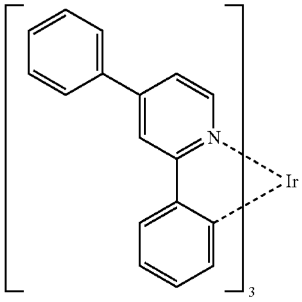
D-29
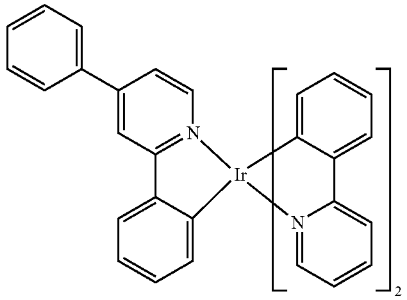
D-30
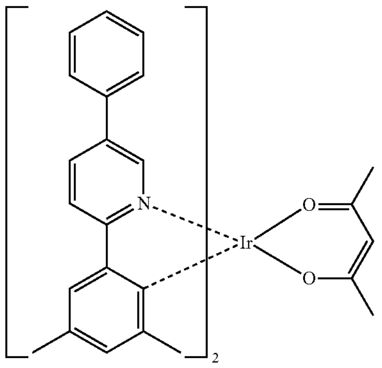
D-31
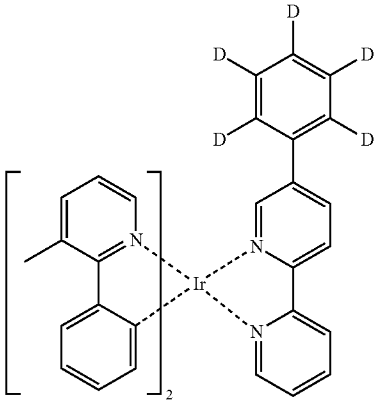
-continued
D-32
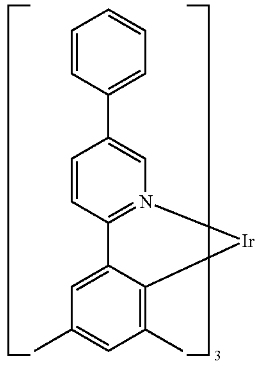
D-33
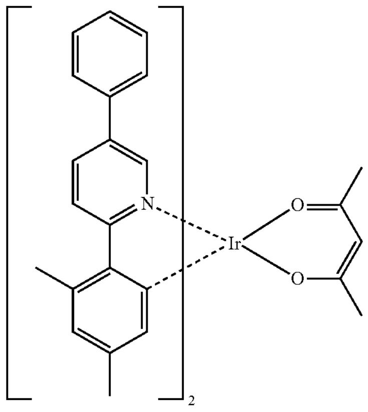
D-34
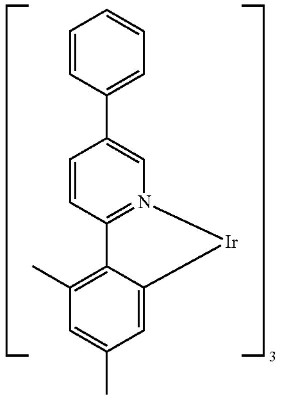
D-35
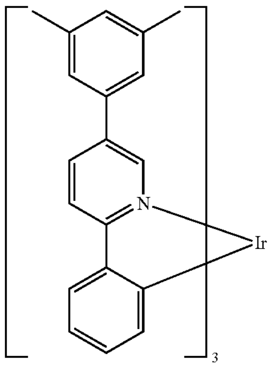

D-36
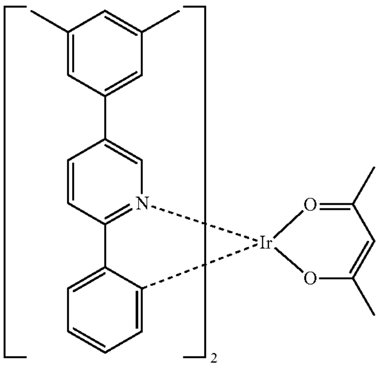
D-37
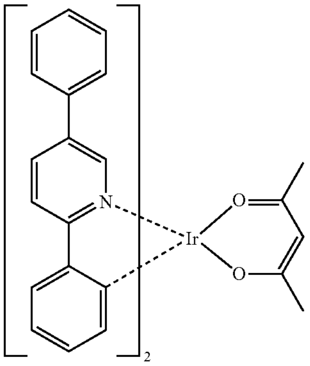
D-38
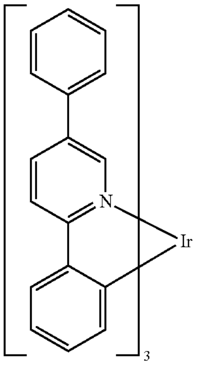
D-39
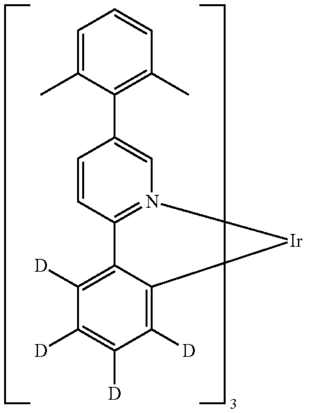
D-40
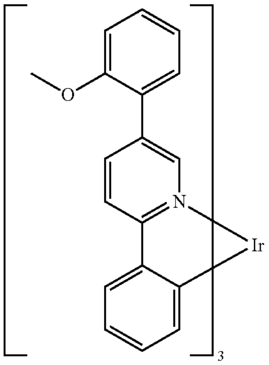
D-41
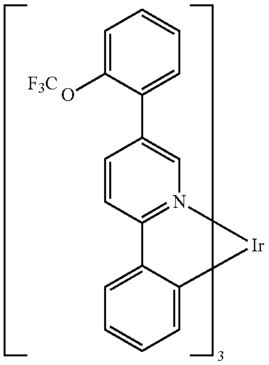
D-42
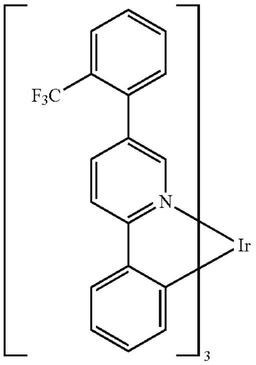
D-43
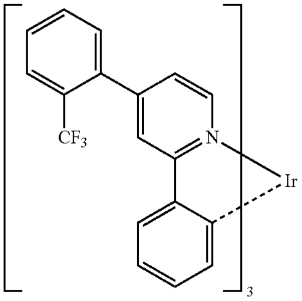

-continued
D-44
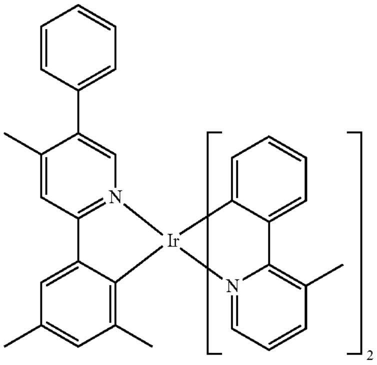
D-45
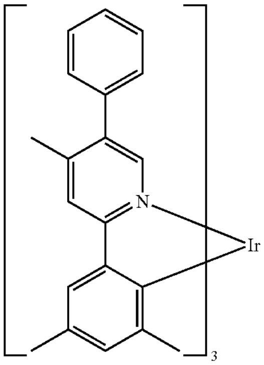
D-46
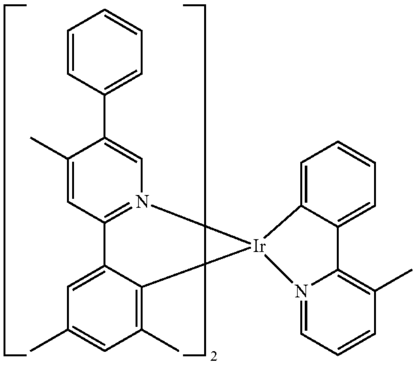
D-47
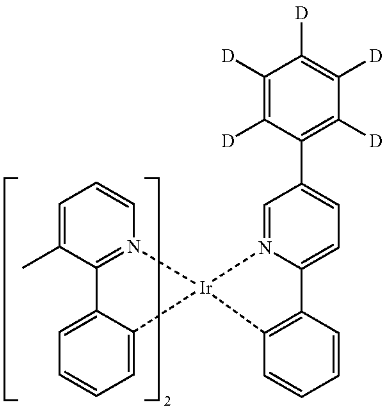
-continued
D-48
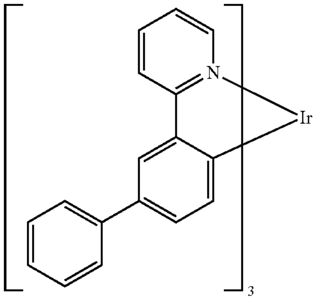
D-49
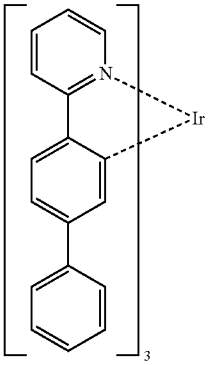
D-50
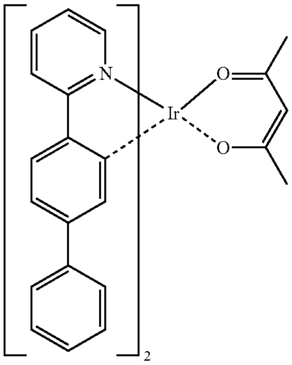
D-51
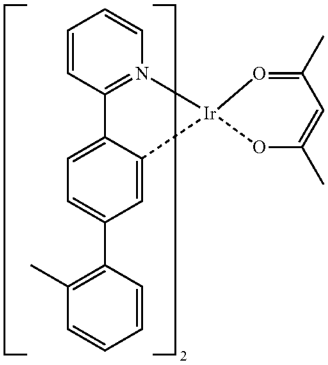

-continued
D-52
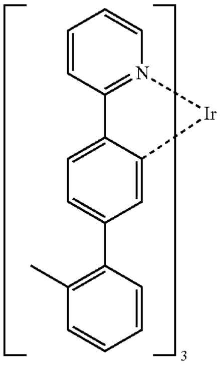
D-53
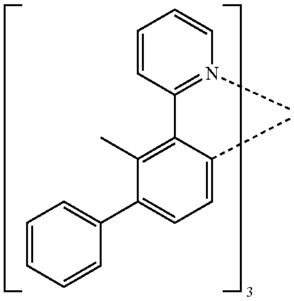
D-54
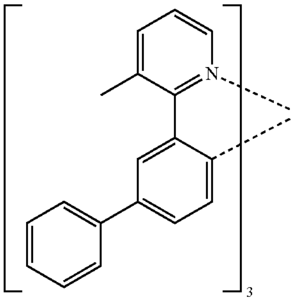
D-55
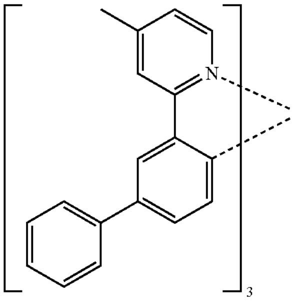
D-56
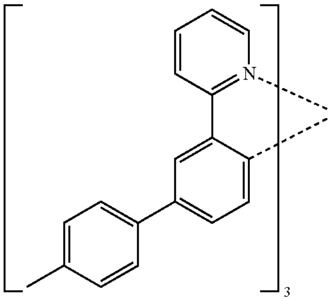
-continued
D-57
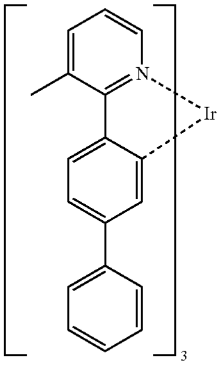
D-58
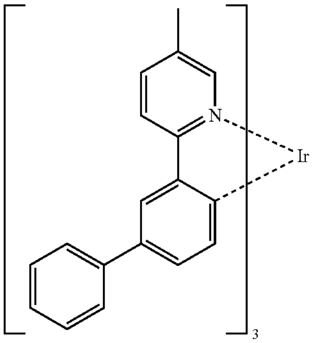
D-59
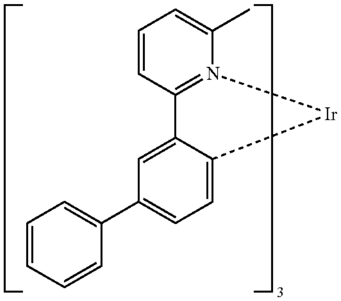
D-60
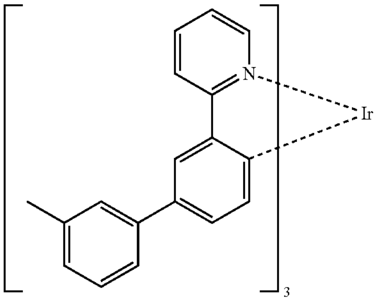

-continued
D-61
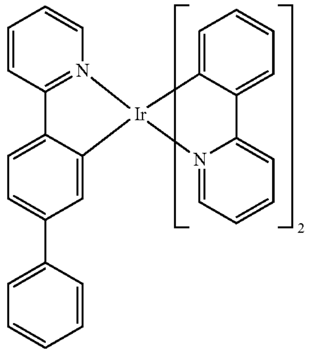
D-62
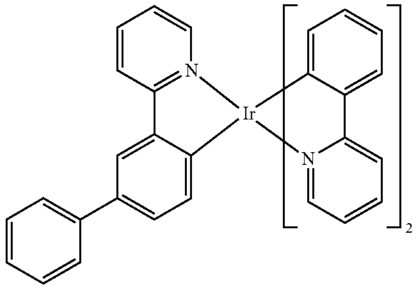
D-63
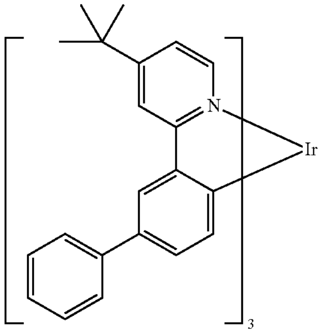
D-64
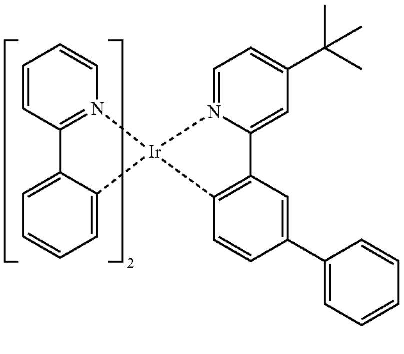
-continued
D-65
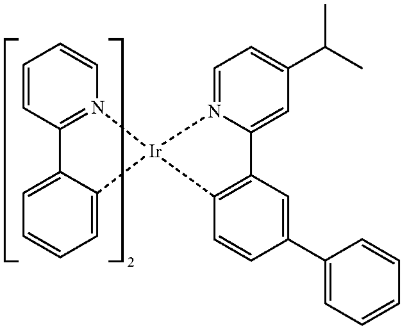
D-66
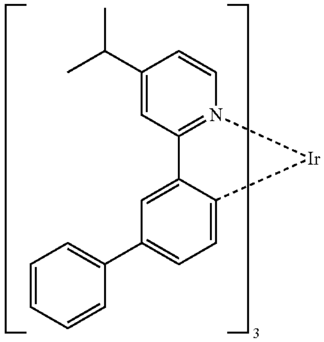
D-67
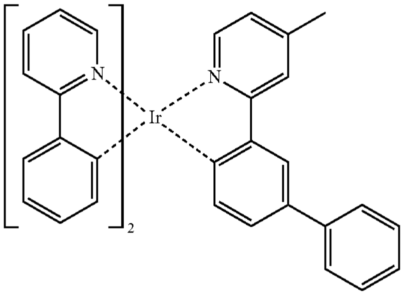
D-68
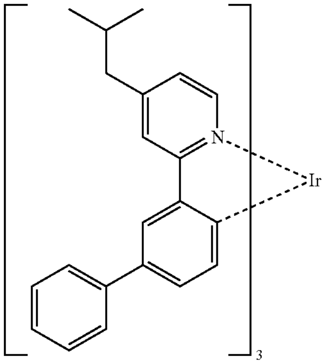

-continued
D-69
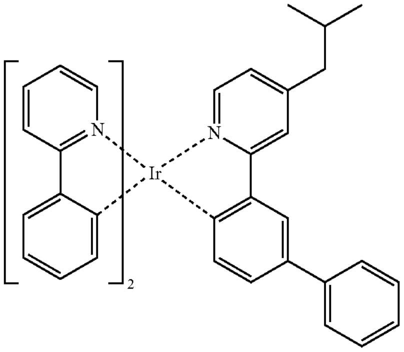
D-70
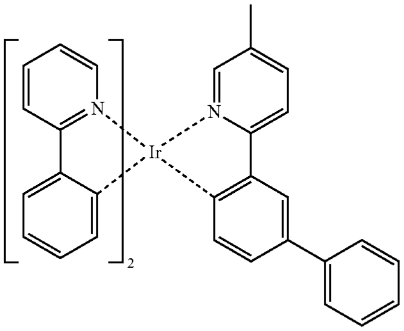
D-71
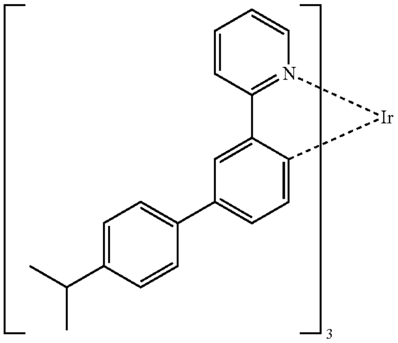
D-72
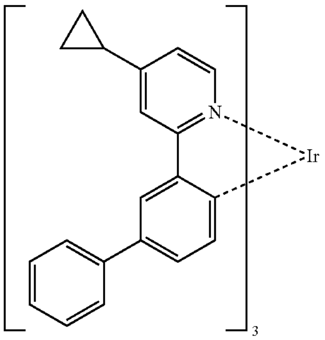
-continued
D-73
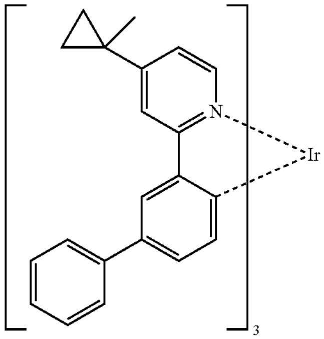
D-74
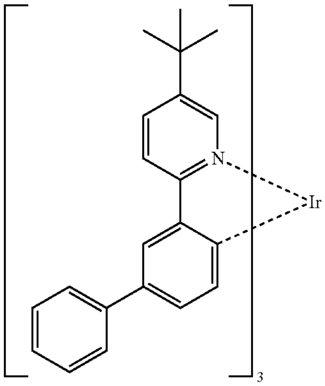
D-75
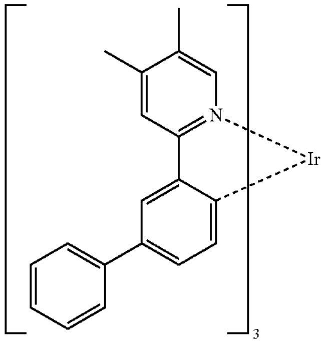
D-76
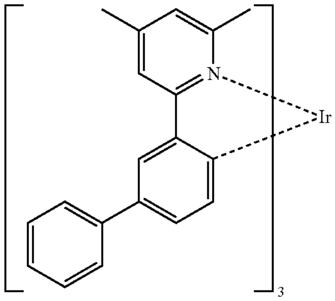

-continued
D-77
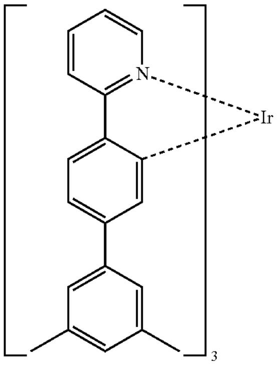
D-78
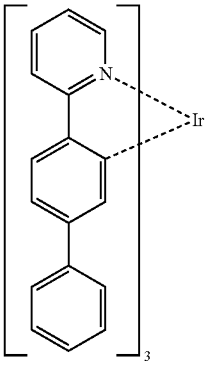
D-79
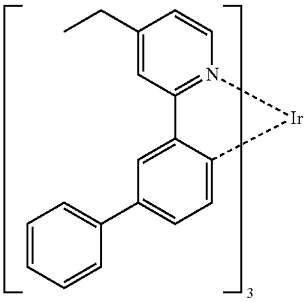
D-80
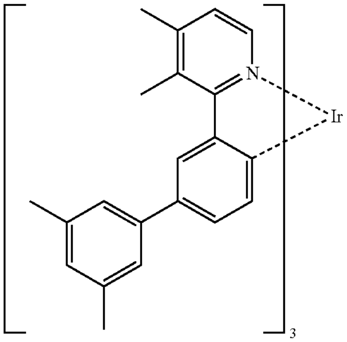
-continued
D-81
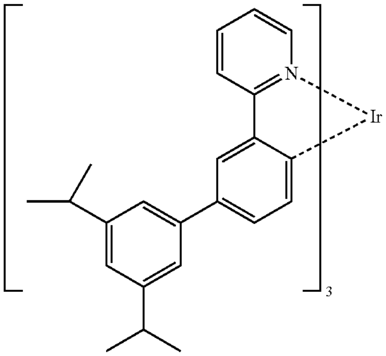
D-82
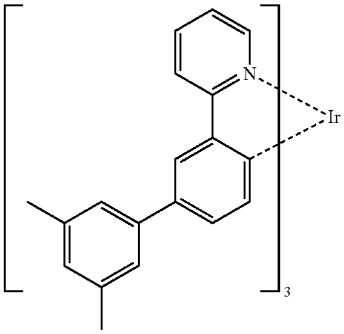
D-83
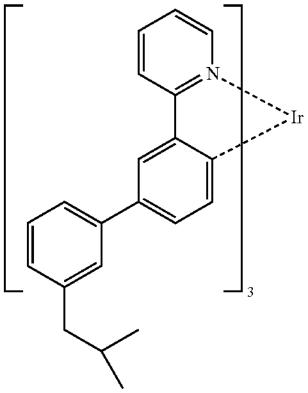
D-84
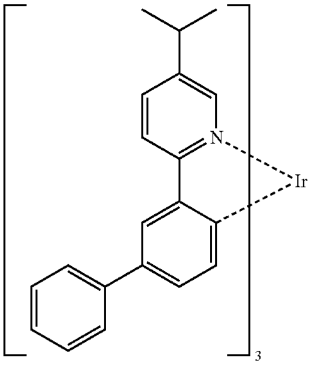

-continued
D-85
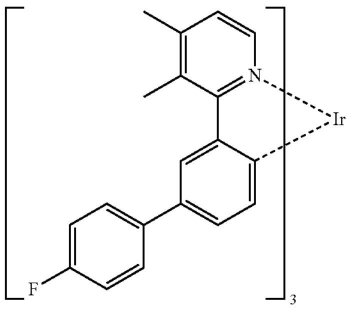
D-86
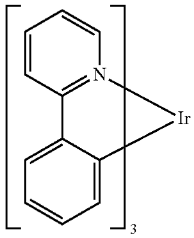
D-87
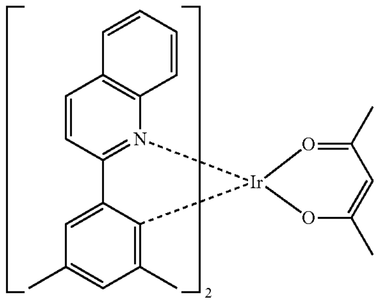
D-88
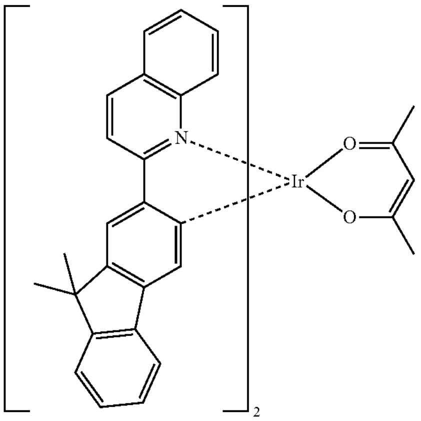
D-89
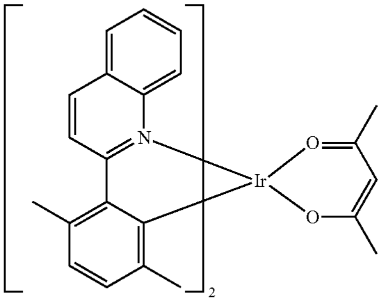
-continued
D-90
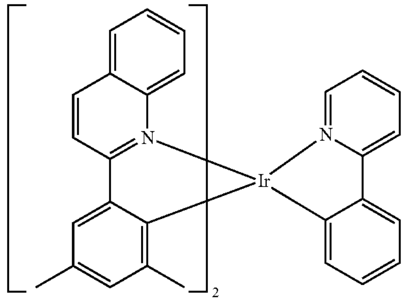
D-91
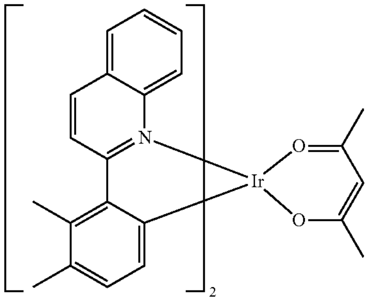
D-92
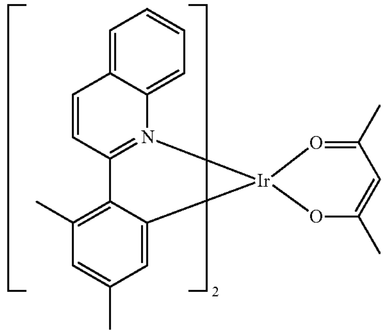
D-93
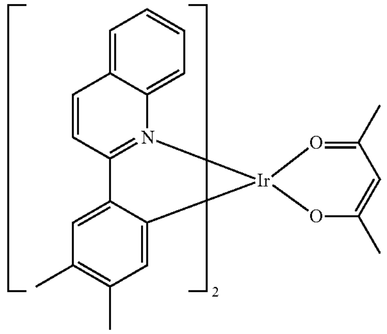

-continued
D-94
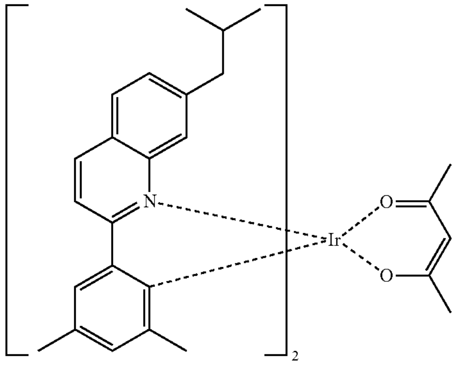
D-95
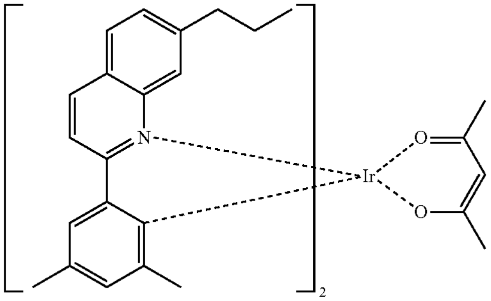
D-96
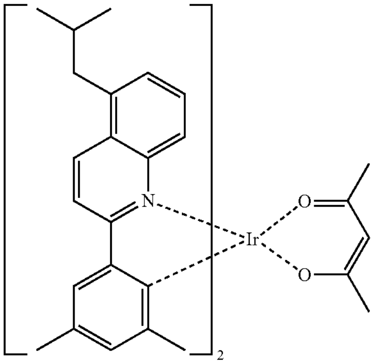
D-97
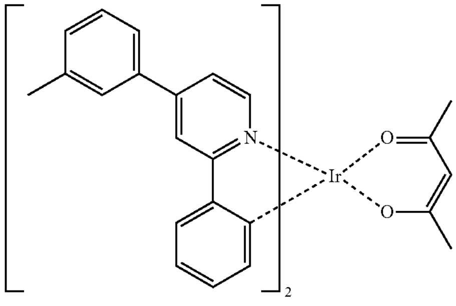
-continued
D-98
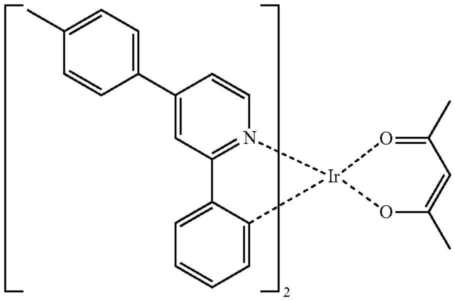
D-99
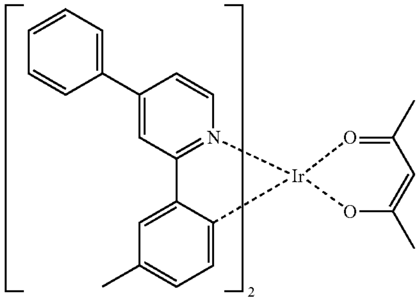
D-100
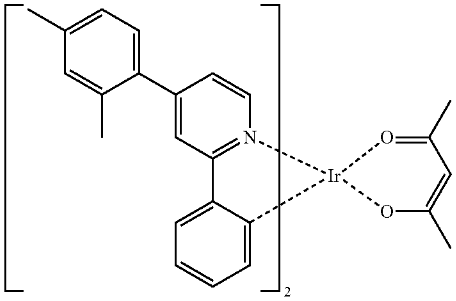
D-101
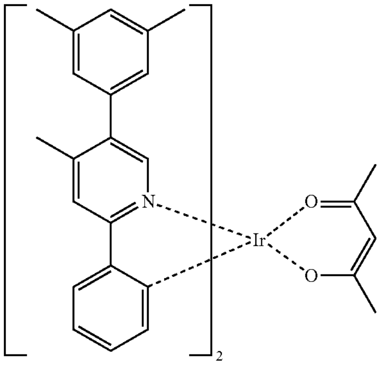

-continued
D-102
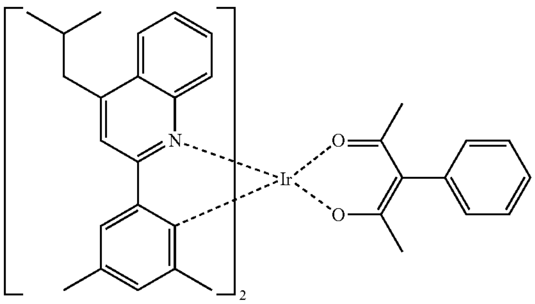
D-103
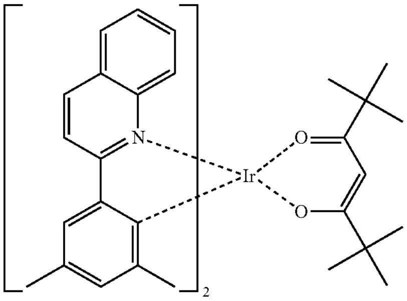
D-104
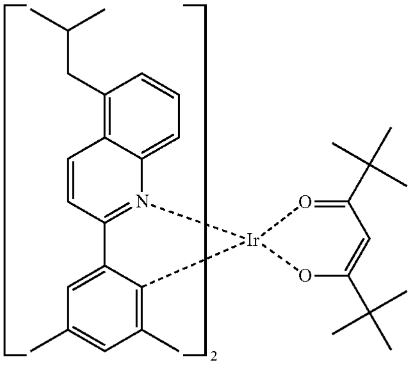
D-105
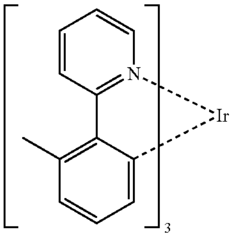
D-106
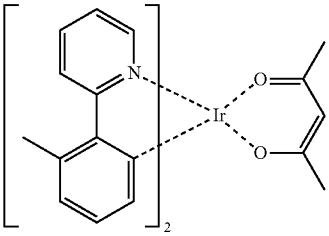
-continued
D-107
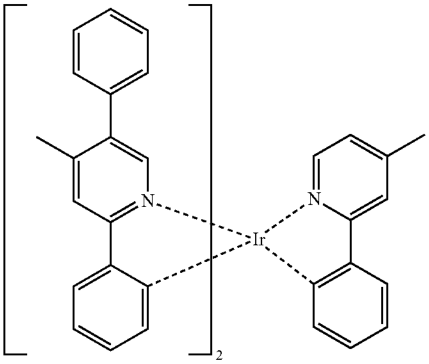
D-108
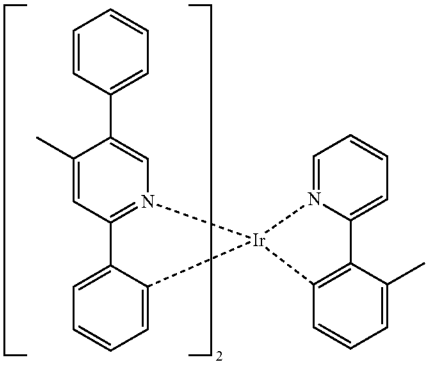
D-109
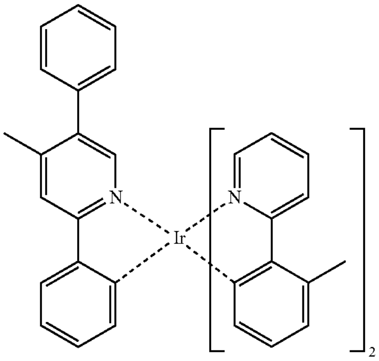
D-110
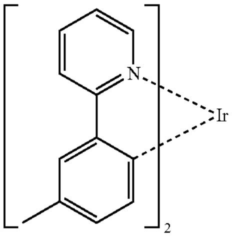
D-111
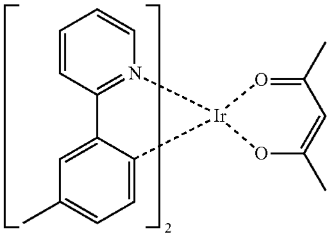

-continued
D-112
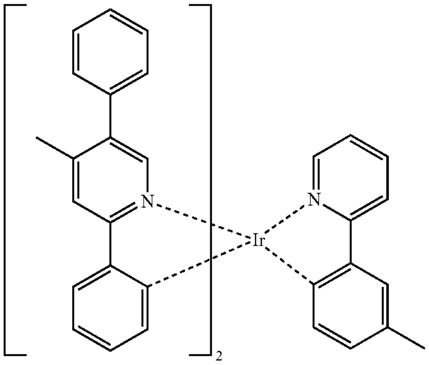
D-113
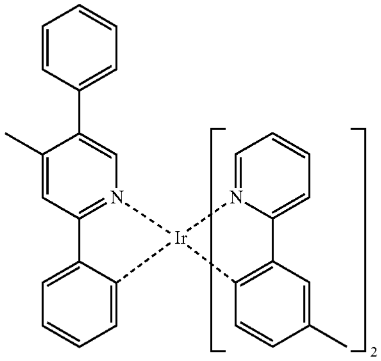
D-114
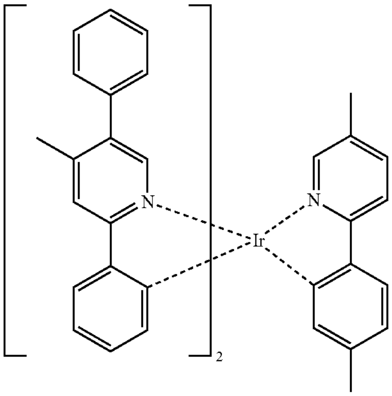
D-115
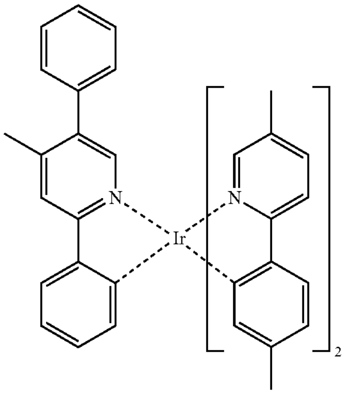
-continued
D-116
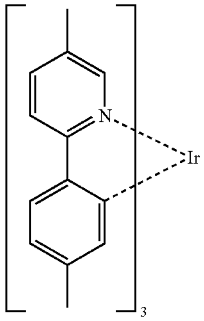
D-117
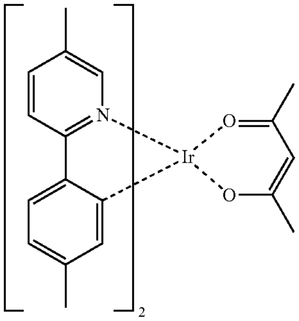
D-118
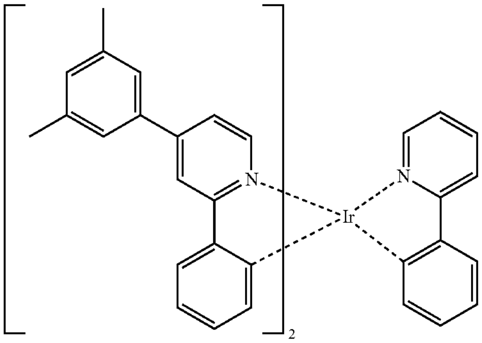
D-119
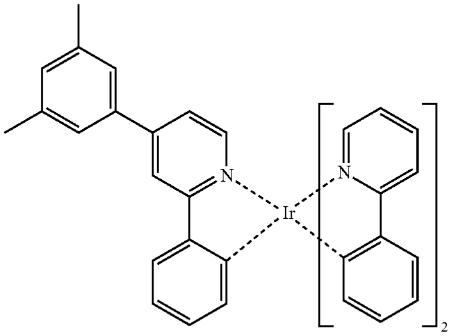

-continued
D-120
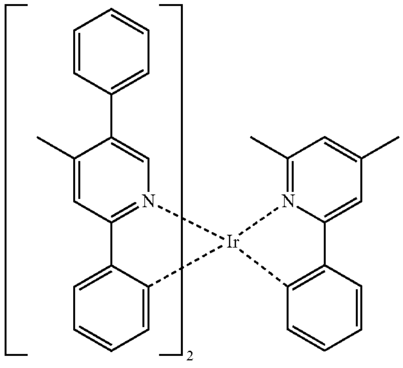
D-121
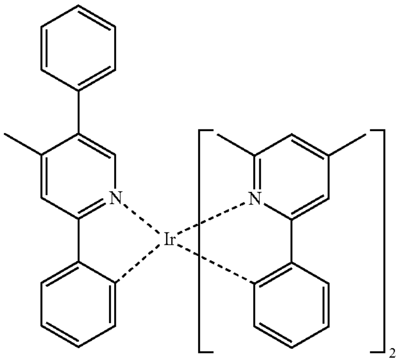
D-122
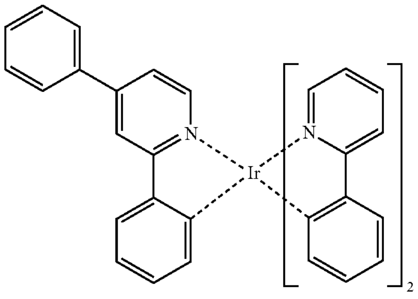
D-123
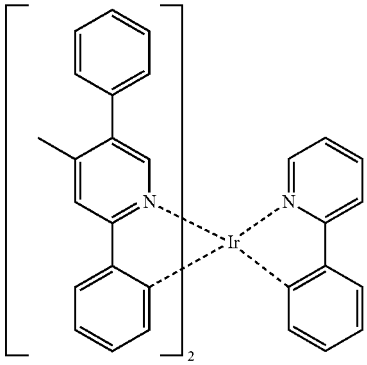
-continued
D-124
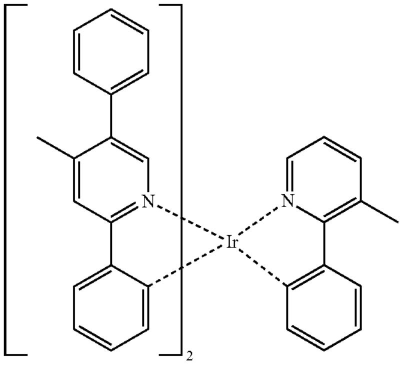
D-125
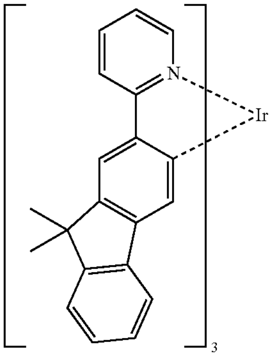
D-126
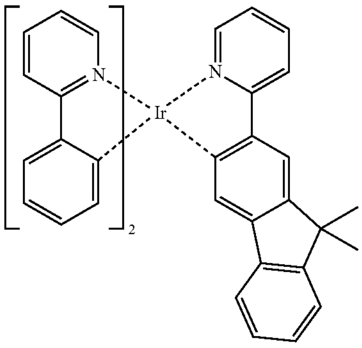
D-127
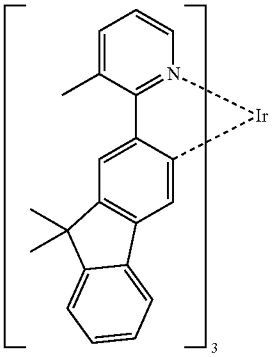

-continued
D-128
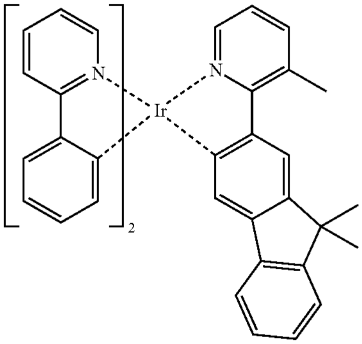
D-129
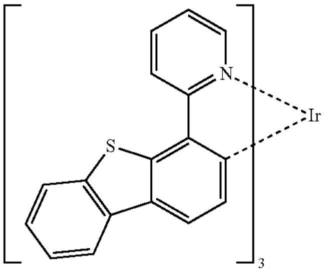
D-130
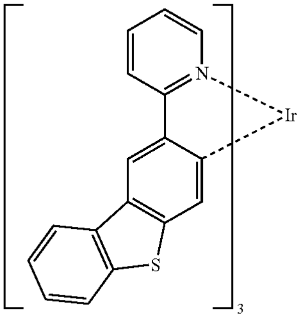
D-131
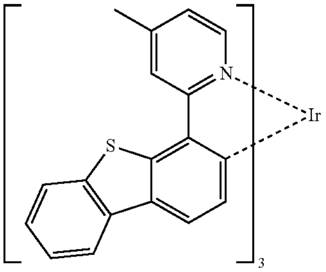
D-132
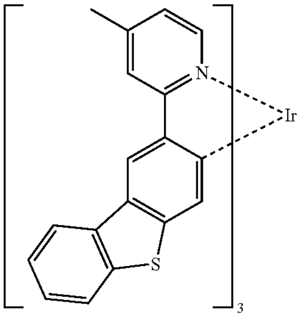
-continued
D-133
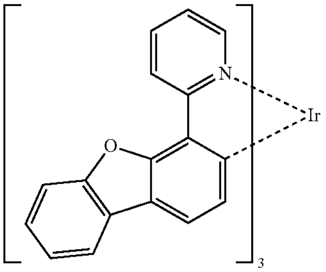
D-134
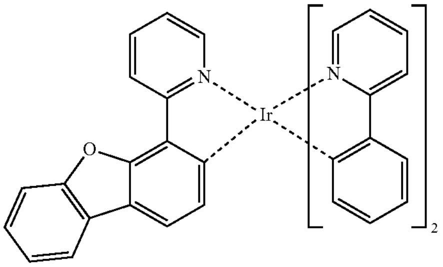
D-135
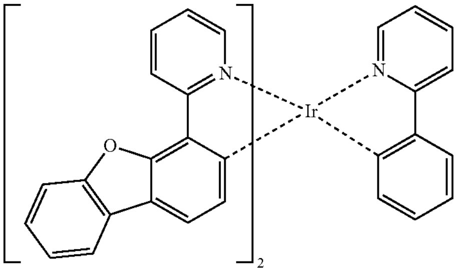
D-136
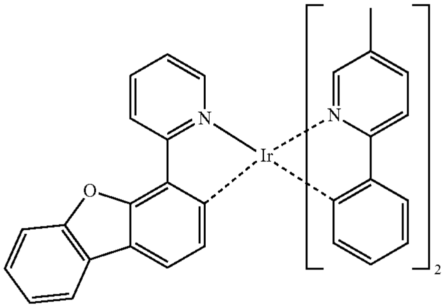
D-137
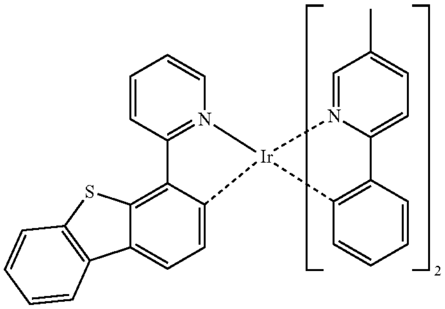

-continued
D-138
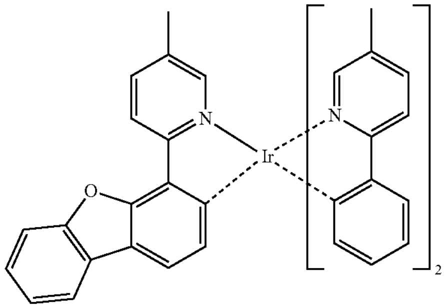
D-139
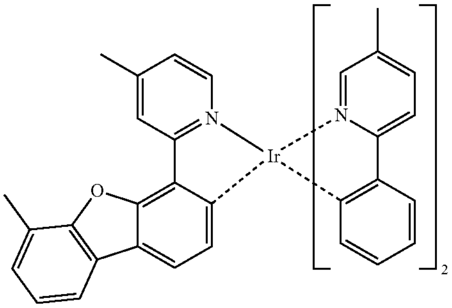
D-140
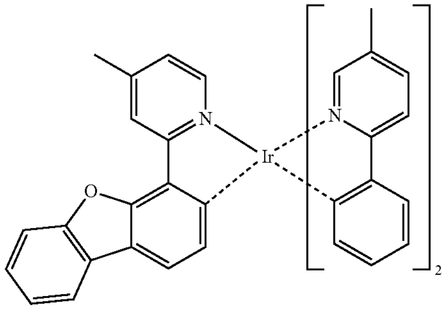
D-141
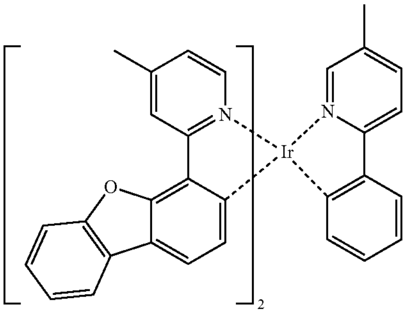
D-142
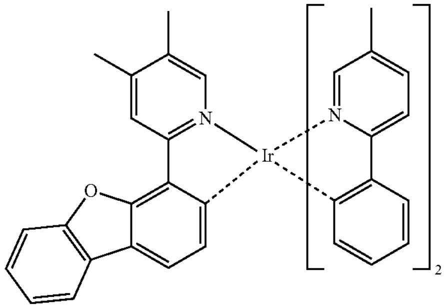
-continued
D-143
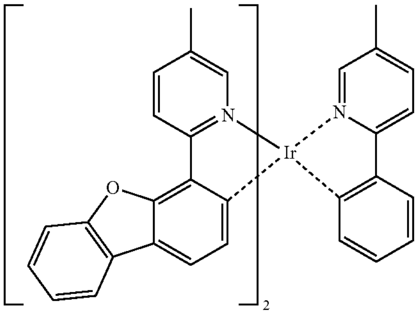
D-144
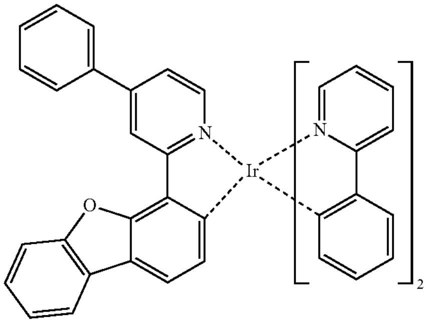
D-145
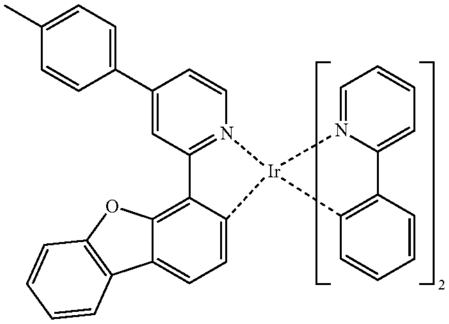
D-146
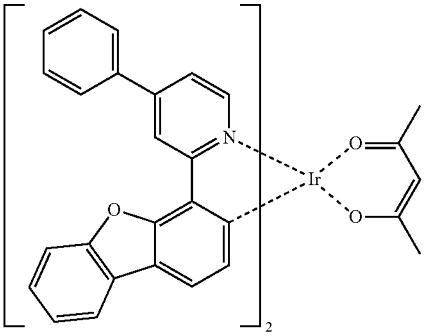

-continued
D-147
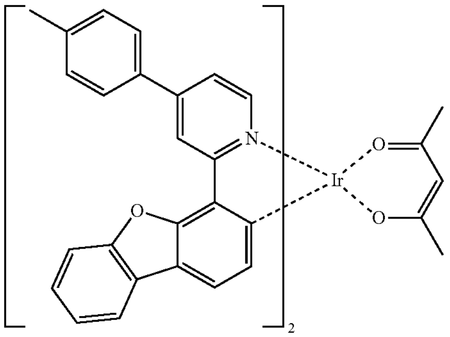
D-148
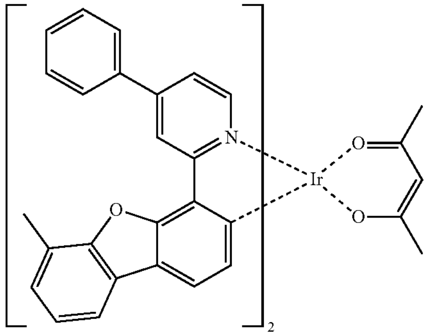
D-149
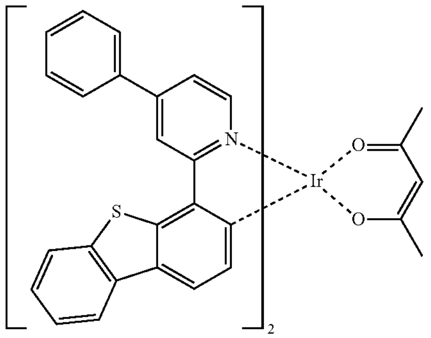
D-150
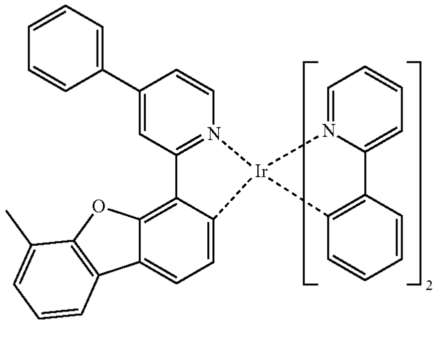
-continued
D-151
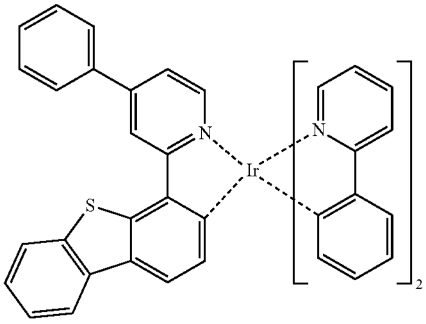
D-152
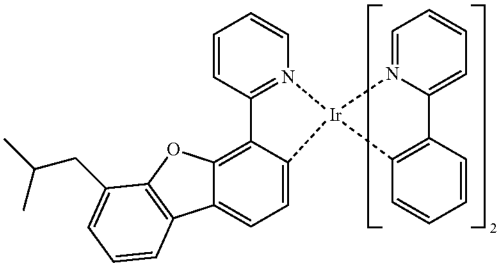
D-153
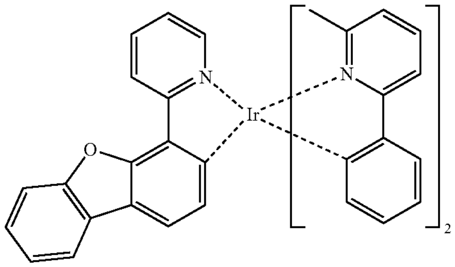
D-154
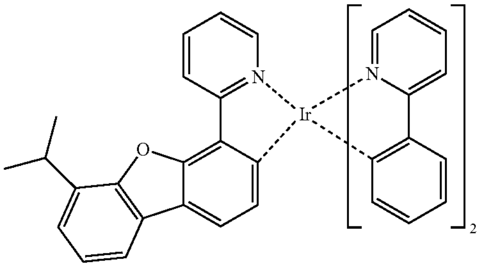
D-155
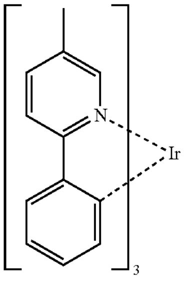

-continued
D-156
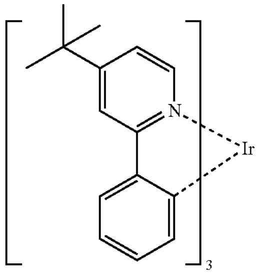
D-157
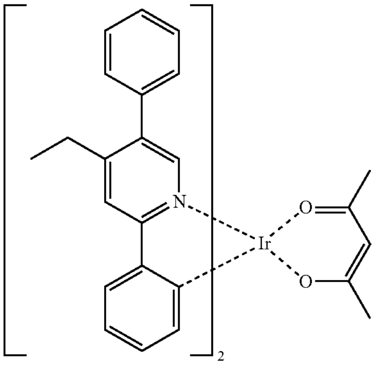
D-158
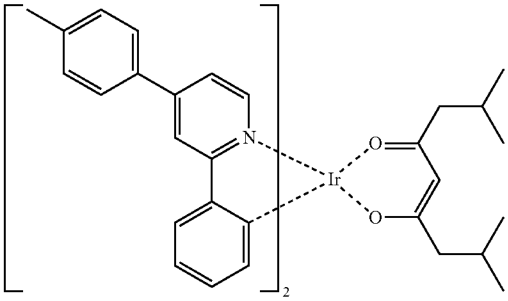
D-159
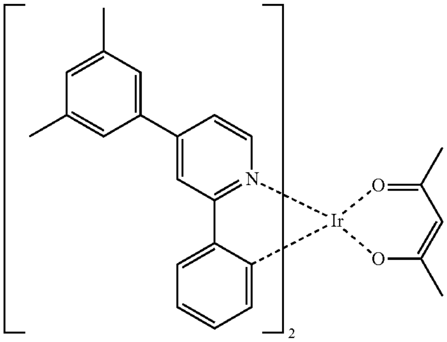
D-160
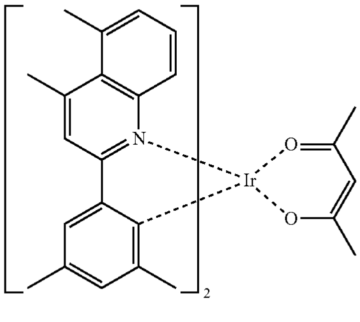
-continued
D-161
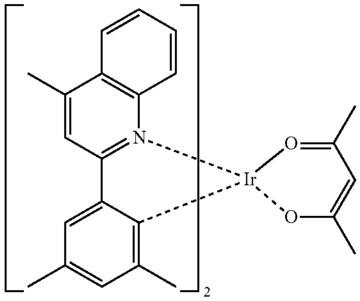
D-162
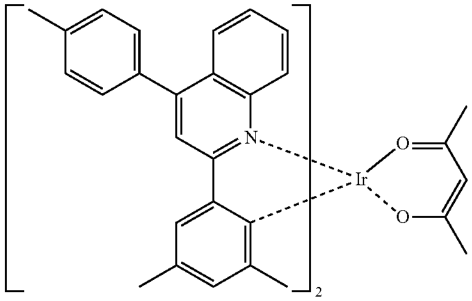
D-163
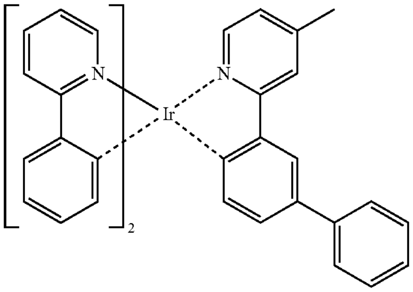
D-164
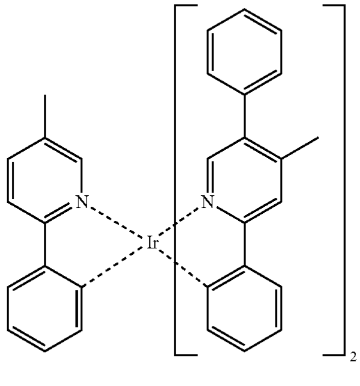

-continued
D-165
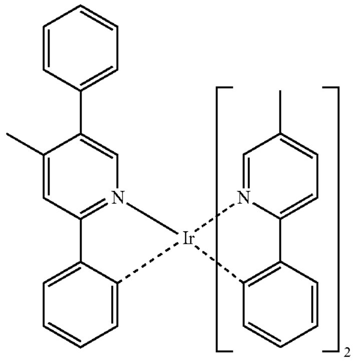
D-166
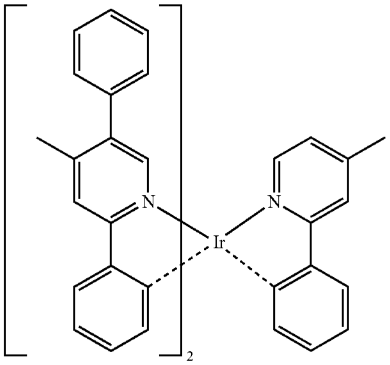
D-167
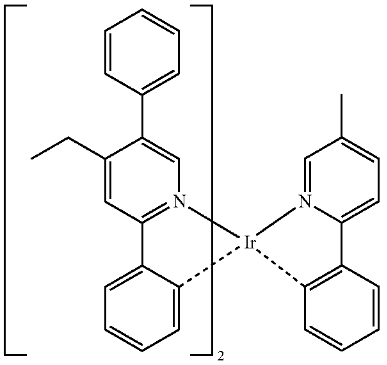
D-168
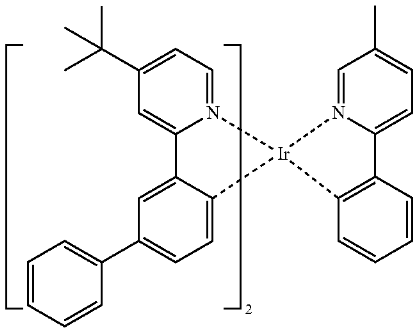
-continued
D-169
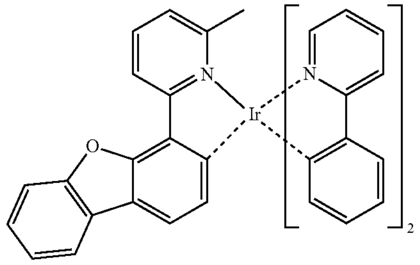
D-170
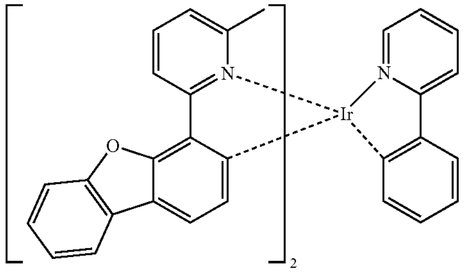
D-171
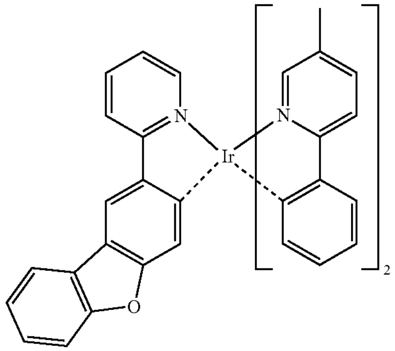
D-172
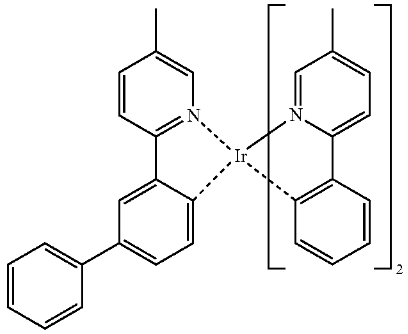
D-173
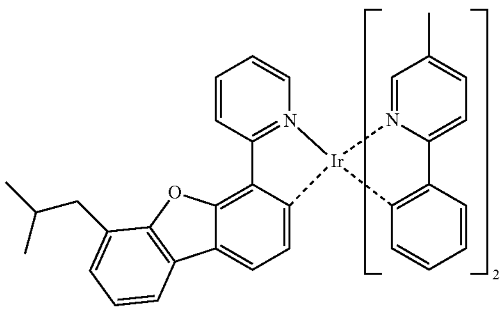

-continued
D-174
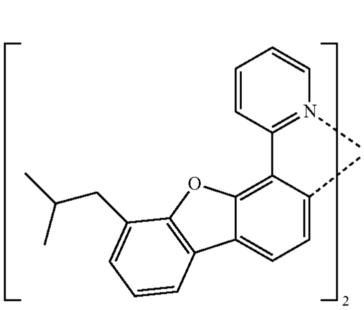
D-175
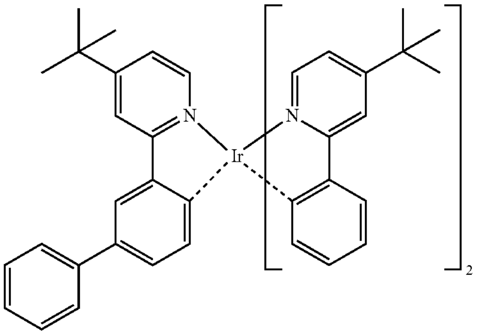
D-176
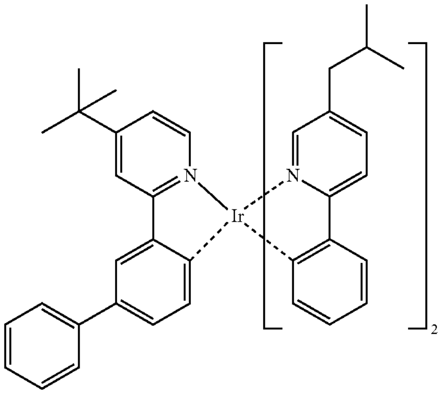
D-177
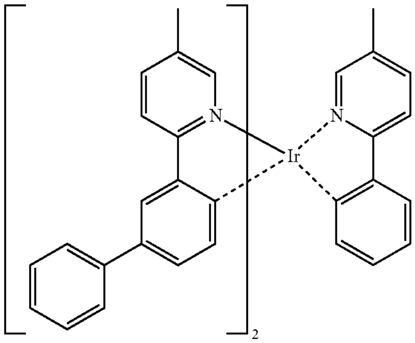
-continued
D-178
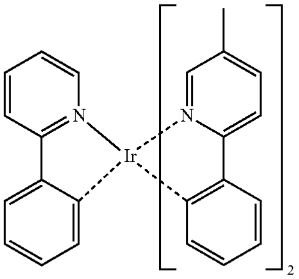
D-179
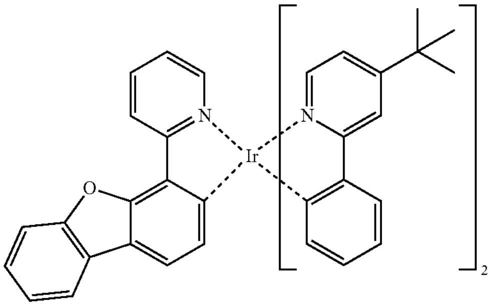
D-180
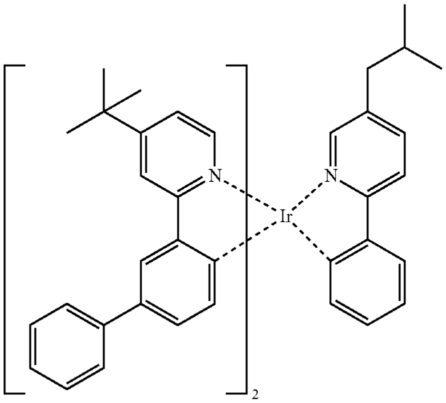
D-181
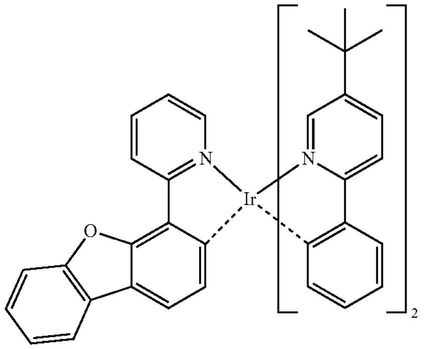

-continued
D-182
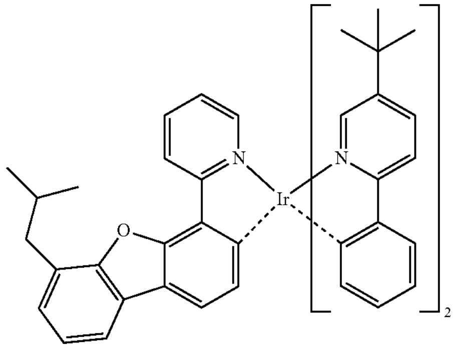
D-183
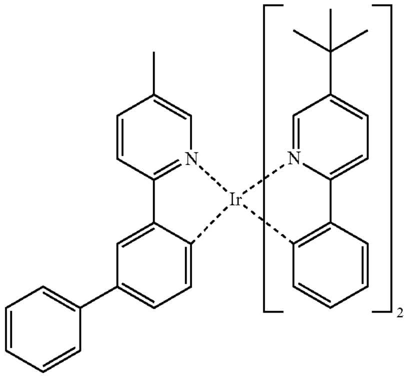
D-184
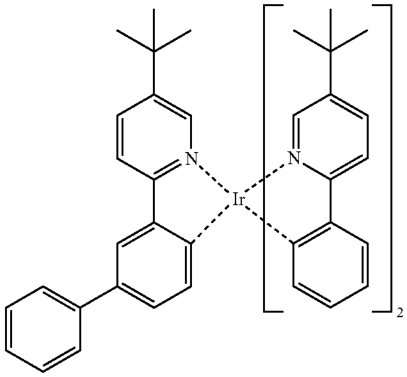
D-185
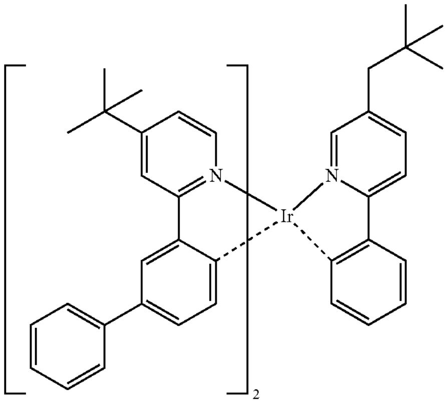
-continued
D-186
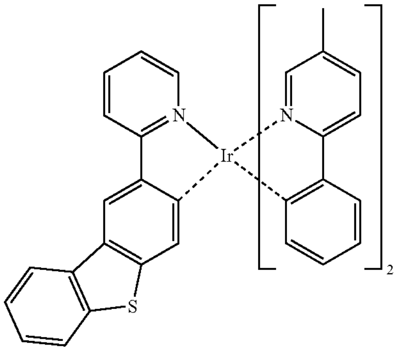
D-187
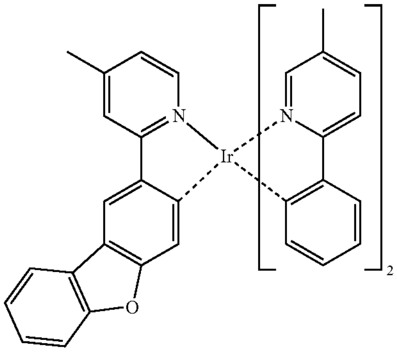
D-188
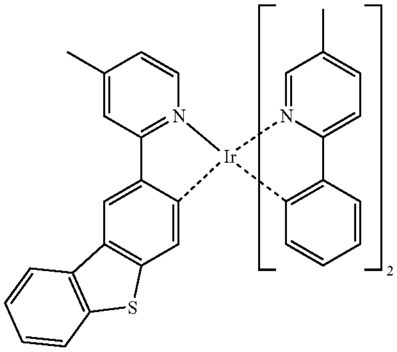
D-189
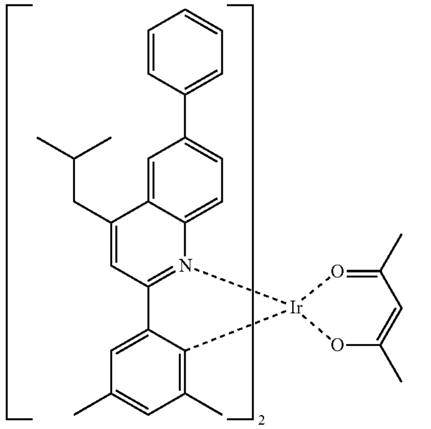

D-190
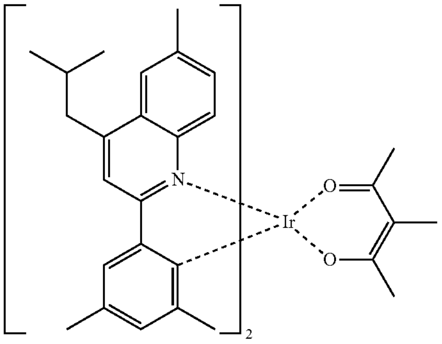
D-191
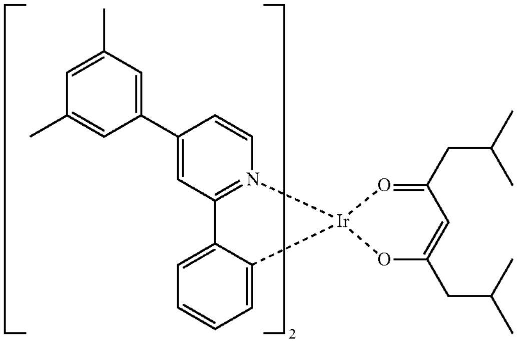
D-192
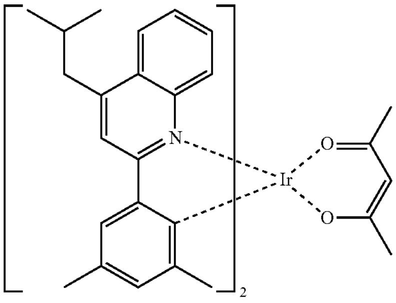
D-193
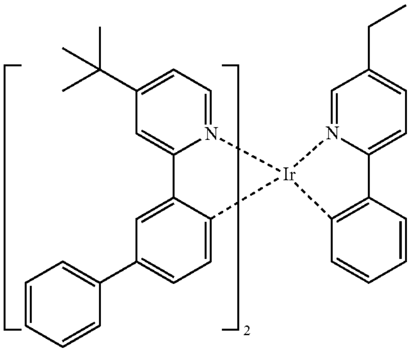
D-194
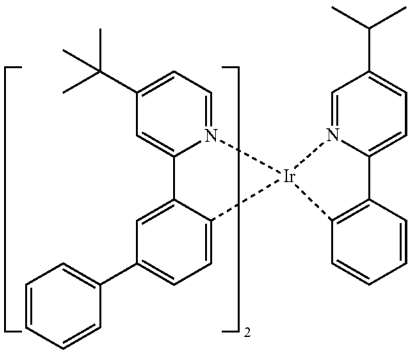
D-195
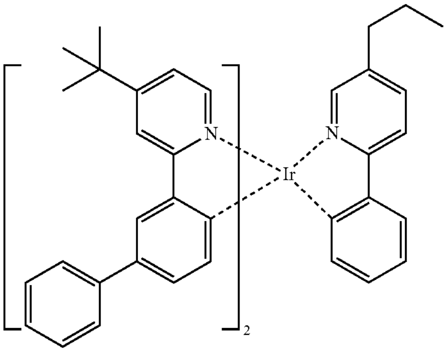
D-196
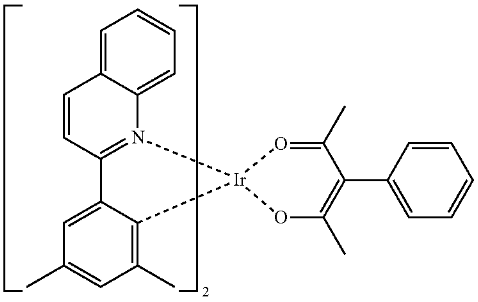
D-197
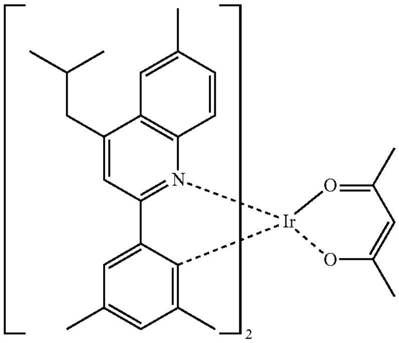

-continued

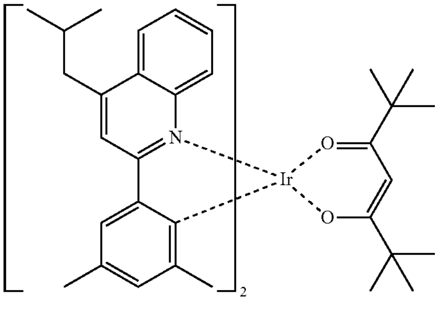

D-198

The organic electroluminescent device according to the present invention may further comprise at least one compound selected from the group consisting of arylamine-based compounds and styrylarylamine-based compounds in the organic layer.

In addition, in the organic electroluminescent device according to the present invention, the organic layer may further comprise at least one metal selected from the group consisting of metals of Group 1, metals of Group 2, transition metals of the 4$^{th}$ period, transition metals of the 5$^{th}$ period, lanthanides and organic metals of d-transition elements of the Periodic Table, or at least one complex compound comprising said metal.

According to the present invention, at least one layer (hereinafter, "a surface layer") is preferably placed on an inner surface(s) of one or both electrodes; selected from a chalcogenide layer, a metal halide layer and a metal oxide layer. Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, said chalcogenide includes $SiO_x(1 \leq X \leq 2)$, $AlO_x(1 \leq X \leq 1.5)$, SiON, SiAlON, etc.; said metal halide includes LiF, $MgF_2$, $CaF_2$, a rare earth metal fluoride, etc.; and said metal oxide includes $Cs_2O$, $Li_2O$, MgO, SrO, BaO, CaO, etc.

Between the anode and the light-emitting layer, a layer selected from a hole injection layer, a hole transport layer, or an electron blocking layer, or formed by a combination thereof can be used. Multi-layers can be used for the hole injection layer in order to lower the hole injection barrier (or hole injection voltage) from the anode to the hole transport layer or the electron blocking layer. Two compounds can be simultaneously used in each layer. The hole transport layer and the electron blocking layer can also be formed of multi-layers.

Between the light-emitting layer and the cathode, a layer selected from an electron buffer layer, a hole blocking layer, an electron transport layer, or an electron injection layer, or formed by a combination thereof can be used. Multi-layers can be used for the electron buffer layer in order to control the injection of the electrons and enhance the interfacial characteristics between the light-emitting layer and the electron injection layer. Two compounds can be simultaneously used in each layer. The hole blocking layer and the electron transport layer can also be formed of multi-layers, and each layer can comprise two or more compounds.

In the organic electroluminescent device according to the present invention, a mixed region of an electron transport compound and a reductive dopant, or a mixed region of a hole transport compound and an oxidative dopant is preferably placed on at least one surface of a pair of electrodes. In this case, the electron transport compound is reduced to an anion, and thus it becomes easier to inject and transport electrons from the mixed region to an electroluminescent medium. Further, the hole transport compound is oxidized to a cation, and thus it becomes easier to inject and transport holes from the mixed region to the electroluminescent medium. Preferably, the oxidative dopant includes various Lewis acids and acceptor compounds; and the reductive dopant includes alkali metals, alkali metal compounds, alkaline earth metals, rare-earth metals, and mixtures thereof. A reductive dopant layer may be employed as a charge-generating layer to prepare an electroluminescent device having two or more electroluminescent layers and emitting white light.

In order to form each layer of the organic electroluminescent device of the present invention, dry film-forming methods such as vacuum evaporation, sputtering, plasma and ion plating methods, or wet film-forming methods such as ink jet printing, nozzle printing, slot coating, spin coating, dip coating, and flow coating methods can be used. The first and second host compounds of the present invention may be co-evaporated or mixture-evaporated.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

Herein, a co-evaporation indicates a process for two or more materials to be deposited as a mixture, by introducing each of the two or more materials into respective crucible cells, and applying an electric current to the cells for each of the materials to be evaporated. Herein, a mixture-evaporation indicates a process for two or more materials to be deposited as a mixture, by mixing the two or more materials in one crucible cell before the deposition, and applying an electric current to the cell for the mixture to be evaporated.

By using the organic electroluminescent device of the present invention, a display system or a lighting system can be produced.

Hereinafter, the luminescent properties of the device comprising the host compound of the present invention will be explained in detail with reference to the following examples.

Device Examples 1-1 to 1-11: Preparation of an OLED Device by Co-Evaporating the First Host Compound and the Second Host Compound of the Present Invention An OLED device was produced using the organic electroluminescent compound according to the present invention. A transparent electrode indium tin oxide (ITO) thin film (10 Ω/sq) on a glass substrate for an organic light-emitting diode (OLED) device (Geomatec) was subjected to an ultrasonic washing with acetone, ethanol, and distilled water, sequentially, and then was stored in isopropanol. The ITO substrate was then mounted on a substrate holder of a vacuum vapor depositing apparatus. HI-1 was introduced into a cell of said vacuum vapor depositing apparatus, and then the pressure in the chamber of said apparatus was controlled to $10^{-6}$ torr. Thereafter, an electric current was applied to the cell to evaporate the above introduced material, thereby forming a first hole injection layer having a thickness of 80 nm on the ITO substrate. Next, HI-2 was introduced into another cell of said vacuum vapor depositing apparatus, and was evaporated by applying an electric current to the cell, thereby forming a second hole injection layer having a thickness of 5 nm on the first hole injection layer. HT-1 was then introduced into another cell of said vacuum vapor depositing apparatus, and was evaporated by applying an electric current to the cell, thereby forming a first hole transport layer having a thickness of 10 nm on the second hole injection layer. HT-2 or HT-3 was then introduced into another cell of said vacuum vapor depositing apparatus, and was evaporated by applying an electric current to the cell, thereby forming a second hole transport layer having a thickness of 60 nm on the first hole transport layer. As a host material, a first host compound and a second host compound listed in Table 1 were introduced into two cells of the vacuum vapor depositing apparatus, respectively. Compound D-96 was introduced into another cell. The two host materials were evaporated at 1:1 rate, while the dopant was evaporated at a different rate from the host materials, so that the dopant was deposited in a doping amount of 3 wt % based on the total amount of the host and dopant to form a light-emitting layer having a thickness of 40 nm on the second hole transport layer. ET-1 and EI-1 were then introduced into two cells of the vacuum vapor depositing apparatus, respectively, and evaporated at 1:1 rate to form an electron transport layer having a thickness of 30 nm on the light-emitting layer. After depositing EI-1 as an electron injection layer having a thickness of 2 nm on the electron transport layer, an Al cathode having a thickness of 80 nm was deposited by another vacuum vapor deposition apparatus. Thus, an OLED device was produced.

HI-1

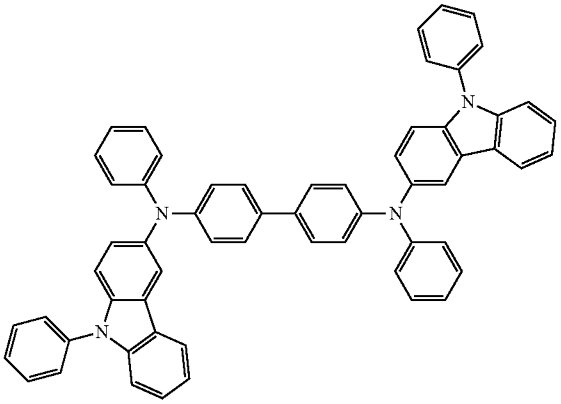

-continued

HI-2

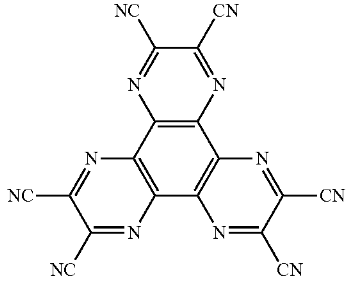

HT-1

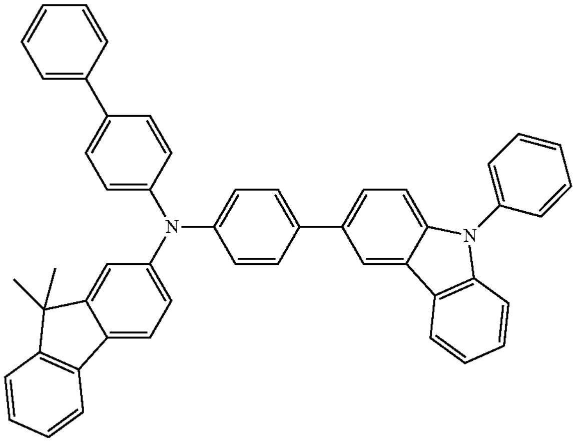

HT-2

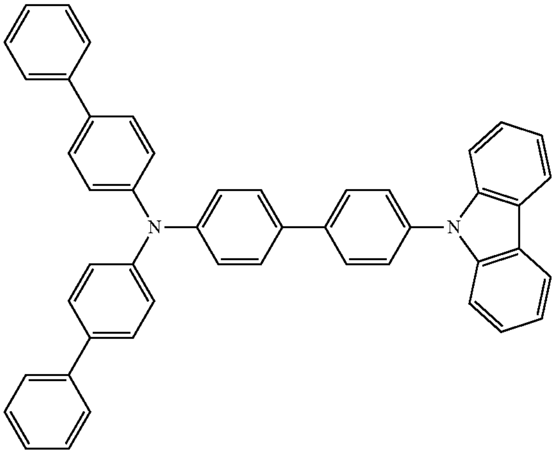

-continued

HT-3

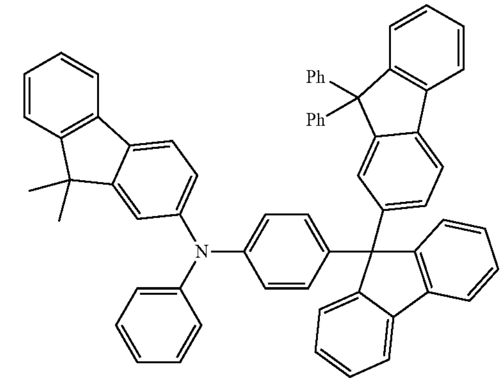

ET-1

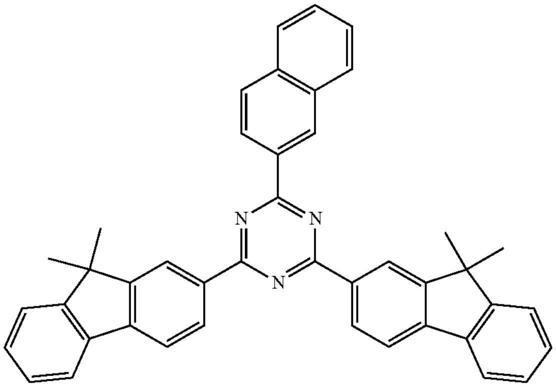

-continued

EI-1

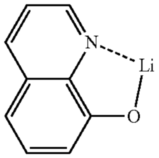

Comparative Examples 1-1 to 1-5: Preparation of an OLED Device Using Only the Second Host Compound as a Host An OLED device was produced in the same manner as in Device Examples 1-1 to 1-11, except for using only the second host compound listed in Table 1 as a host of the light-emitting layer.

Comparative Examples 2-1 and 2-2: Preparation of an OLED Device Using Only the First Host Compound as a Host An OLED device was produced in the same manner as in Device Examples 1-1 to 1-11, except for using only the first host compound listed in Table 1 as a host of the light-emitting layer.

Table 1 below shows the evaluation results of the organic electroluminescent devices produced as in Device Examples 1-1 to 1-11, Comparative Examples 1-1 to 1-5, and Comparative Examples 2-1 and 2-2.

TABLE 1

| | Host | Second Hole Transport Layer | Voltage [V] | Efficiency [cd/A] | Color | Lifespan T97 [hr] |
|---|---|---|---|---|---|---|
| Device Ex. 1-1 | H1-287:A-224 (1:1) | HT-2 | 4.2 | 27.5 | Red | 100 |
| Device Ex. 1-2 | H1-35:A-224 (1:1) | HT-2 | 4.2 | 28.1 | Red | 100 |
| Device Ex. 1-3 | H1-28:A-224 (1:1) | HT-2 | 4.2 | 27.3 | Red | 140 |
| Device Ex. 1-4 | H1-15:A-224 (1:1) | HT-2 | 4.2 | 28.3 | Red | 90 |
| Device Ex. 1-5 | H1-12:A-224 (1:1) | HT-2 | 3.9 | 27.9 | Red | 100 |
| Device Ex. 1-6 | H1-287:A-92 (1:1) | HT-2 | 4.3 | 27.8 | Red | 190 |
| Device Ex. 1-7 | H1-28:A-92 (1:1) | HT-2 | 4.2 | 27.6 | Red | 200 |
| Device Ex. 1-8 | H1-35:A-92 (1:1) | HT-2 | 4.2 | 27.5 | Red | 160 |
| Device Ex. 1-9 | H1-12:A-23 (1:1) | HT-3 | 3.9 | 29.1 | Red | 70 |
| Device Ex. 1-10 | H1-12:A-94 (1:1) | HT-3 | 4.4 | 27.7 | Red | 240 |
| Device Ex. 1-11 | H1-12:A-287 (1:1) | HT-3 | 4.7 | 25.0 | Red | 120 |
| Comp. Ex. 1-1 | A-224 | HT-2 | 4.2 | 27.9 | Red | 26 |
| Comp. Ex. 1-2 | A-92 | HT-2 | 4.0 | 27.1 | Red | 70 |
| Comp. Ex. 1-3 | A-23 | HT-2 | 3.7 | 28.2 | Red | 5 |
| Comp. Ex. 1-4 | A-94 | HT-2 | 5.6 | 26.1 | Red | 52 |
| Comp. Ex. 1-5 | A-287 | HT-2 | 5.1 | 26.4 | Red | 20 |
| Comp. Ex. 2-1 | H1-28 | HT-2 | 8.5 | 2.4 | Red | X |
| Comp. Ex. 2-2 | H1-12 | HT-2 | 8.6 | 2.4 | Red | X |

* X in "Lifespan" means the efficiency of the device is too low to measure the lifespan.

Compared to conventional devices using a single host, the organic electroluminescent device of the present invention provides long lifespan while maintaining high luminous efficiency by using plural host compounds.

The invention claimed is:

1. An organic electroluminescent device comprising at least one light-emitting layer between an anode and a cathode, wherein the light-emitting layer comprises a host and a phosphorescent dopant, the host comprises plural host compounds, at least a first host compound of the plural host compounds is represented by the following formula 1, and a second host compound is represented by the following formula 2, (1)

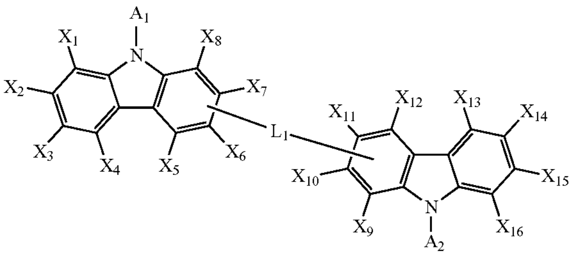

wherein $A_1$ and $A_2$ each independently represent a substituted or unsubstituted (C6-C30)aryl, wherein the substituents on the substituted (C6-30)aryl group of $A_1$ and $A_2$ are—deuterium, a halogen, a unsubstituted (C1-C30) alkyl group, unsubstituted (C6-30)aryl group, 3- to 30-membered heteroaryl containing at least one hetero atom selected from O and S, a tri(C6-C30)arylsilyl, a tri(C1-C30)alkylsilyl, a di(C1-C30)alkyl(C6-C30)arylsilyl, a (C1-C30)alkyldi(C6-C30)arylsilyl, an amino, a mono- or di(C1-C30)alkylamino, a mono- or di(C6-C30)arylamino, a (C1-C30)alkyl(C6-C30)arylamino, a (C6-C30)aryl(C1-C30)alkyl, or a (C1-C30)alkyl(C6-C30)aryl;

$L_1$ represents a single bond, or a substituted or unsubstituted (C6-C30)arylene;

$X_1$ to $X_{16}$ each independently represent hydrogen, deuterium, a halogen, a cyano, a substituted or unsubstituted (C1-C30)alkyl, a substituted or unsubstituted (C2-C30) alkenyl, a substituted or unsubstituted (C2-C30)alkynyl, a substituted or unsubstituted (C3-C30)cycloalkyl, a substituted or unsubstituted (C6-C60)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi (C6-C30)arylsilyl, or a substituted or unsubstituted mono- or di-(C6-C30)arylamino; or are linked to an adjacent substituent(s) to form a substituted or unsubstituted, mono- or polycyclic, (C3-C30) alicyclic or aromatic ring, whose carbon atom(s) may be replaced with at least one hetero atom selected from nitrogen, oxygen, and sulfur;

(2)

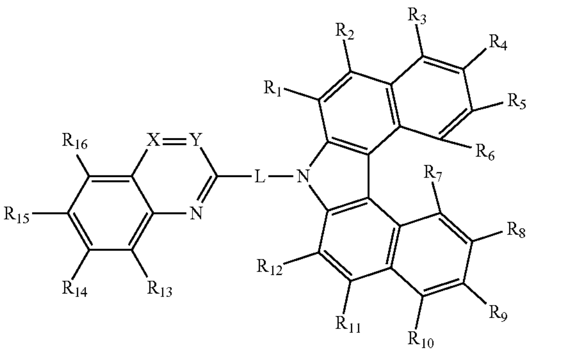

wherein

L represents a single bond, or a substituted or unsubstituted (C6-C30)arylene;

X and Y each independently represent N or $CR_{17}$;

$R_1$ to $R_{17}$ each independently represent hydrogen, deuterium, a substituted or unsubstituted (C3-C30)cycloalkyl, a substituted or unsubstituted (C6-C30)aryl, a substituted or unsubstituted 3- to 30-membered heteroaryl, a substituted or unsubstituted mono- or di-(C6-C30)arylamino, a substituted or unsubstituted (C1-C30)alkyl(C6-C30)arylamino, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, or a substituted or unsubstituted (C1-C30)alkyldi(C6-C30) arylsilyl; or are linked to an adjacent substituent(s) to form a substituted or unsubstituted, mono- or polycyclic, (C3-C30) alicyclic or aromatic ring, whose carbon atom(s) may be replaced with at least one hetero atom selected from nitrogen, oxygen, and sulfur; and the heteroaryl contains at least one hetero atom selected from B, N, O, S, Si, and P.

2. The organic electroluminescent device according to claim 1, wherein formula 1 is represented by one of the following formulas 3 to 6:

(3)

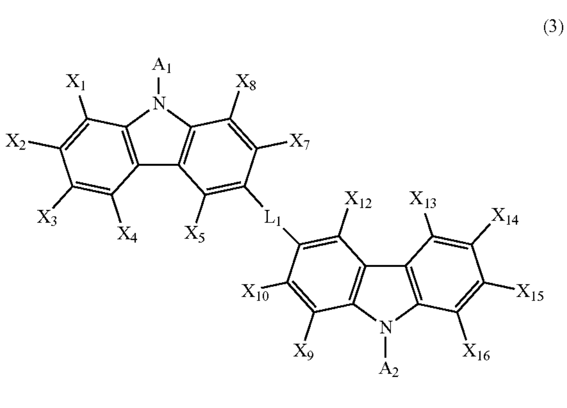

-continued
(4)
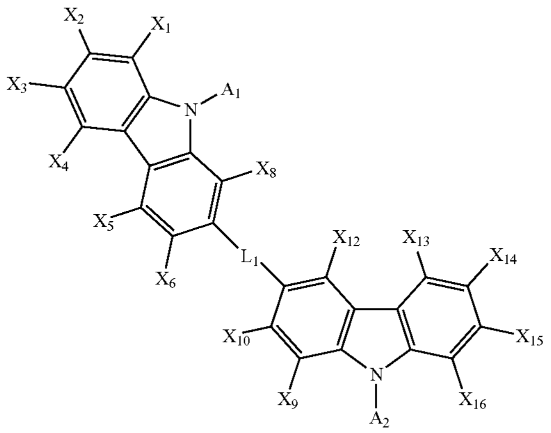
(5)
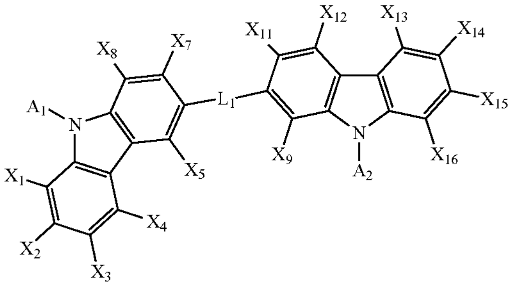
(6)
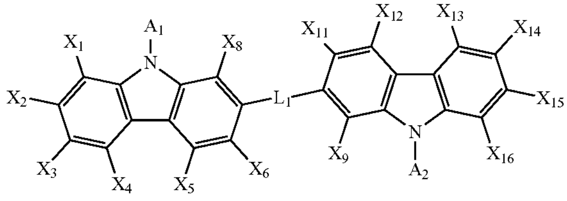
wherein
$A_1$, $A_2$, $L_1$, and $X_1$ to $X_{16}$ are as defined in claim 1.
3. The organic electroluminescent device according to claim 1, wherein in formula 1,
$L_1$ is represented by one of the following formulas 7 to 19:
(7)
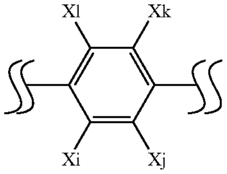
(8)
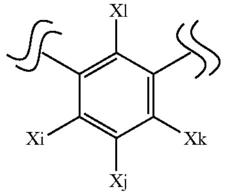
-continued
(9)
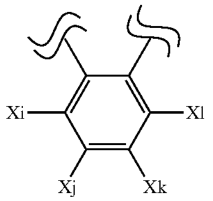
(10)
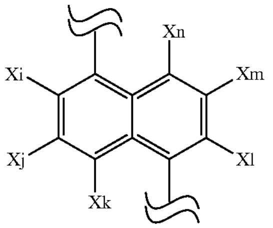
(11)
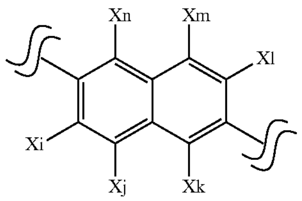
(12)
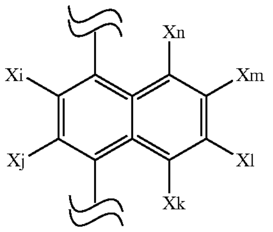
(13)
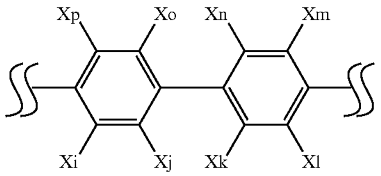
(14)
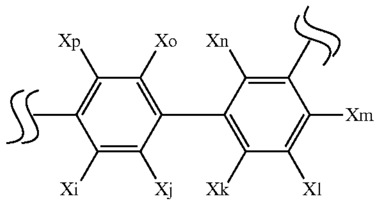
(15)
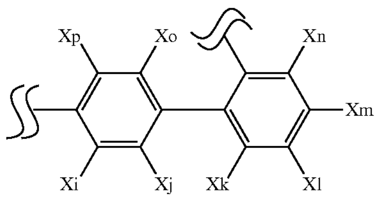

-continued (16)

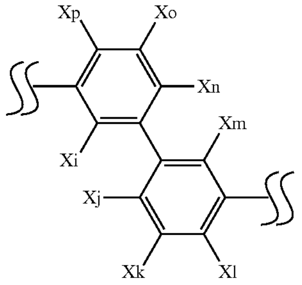

(17)

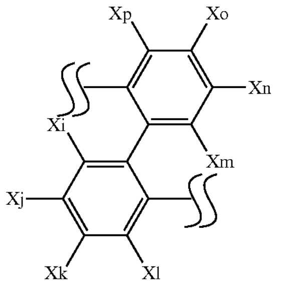

(18)

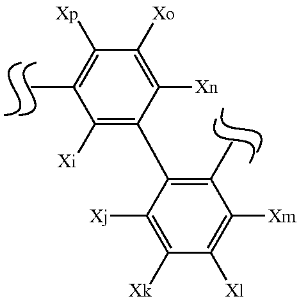

(19)

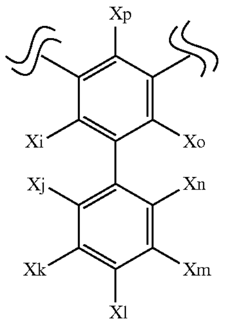

wherein

Xi to Xp each independently represent hydrogen, deuterium, a halogen, a cyano, a substituted or unsubstituted (C1-C30)alkyl, a substituted or unsubstituted (C2-C30) alkenyl, a substituted or unsubstituted (C2-C30)alkynyl, a substituted or unsubstituted (C3-C30)cycloalkyl, a substituted or unsubstituted (C6-C60)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted mono- or di-(C6-C30)arylamino; or are linked to an adjacent substituent(s) to form a substituted or unsubstituted, mono- or polycyclic, (C3-C30) alicyclic or aromatic ring, whose carbon atom(s) may be replaced with at least one hetero atom selected from nitrogen, oxygen, and sulfur.

4. The organic electroluminescent device according to claim 1, wherein formula 2 is represented by formula 20 or 21:

(20)

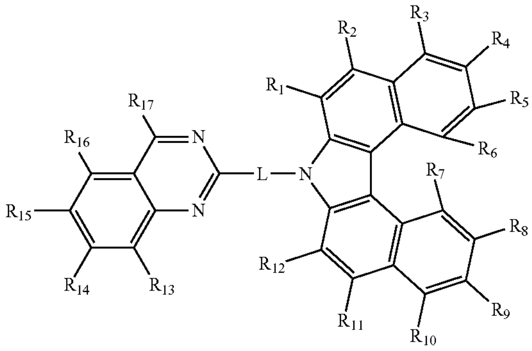

(21)

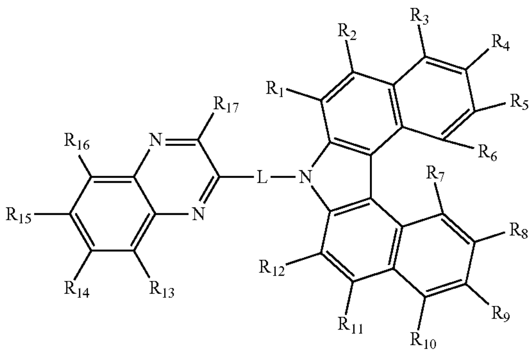

wherein

L and $R_1$ to $R_{17}$ are as defined in claim 1.

5. The organic electroluminescent device according to claim 1, wherein the substituents of the substituted alkyl, the substituted alkenyl, the substituted alkynyl, the substituted cycloalkyl, the substituted aryl(ene), the substituted heteroaryl, the substituted trialkylsilyl, the substituted triarylsilyl, the substituted dialkylarylsilyl, the substituted alkyldiarylsilyl, the substituted mono- or di-arylamino, the substituted alkylarylamino, and the substituted mono- or polycyclic, alicyclic or aromatic ring in $L_1$, $X_1$ to $X_{16}$, L, and $R_1$ to $R_{17}$ each independently are at least one selected from the group consisting of deuterium; a halogen; a carboxyl; a nitro; a hydroxyl; a (C1-C30)alkyl; a halo(C1-C30)alkyl; a (C2-C30) alkenyl; a (C2-C30) alkynyl; a (C1-C30)alkoxy; a (C1-C30)alkylthio; a (C3-C30)cycloalkyl; a (C3-C30)cycloalkenyl; a 3- to 7-membered heterocycloalkyl; a (C6-C30)aryloxy; a (C6-C30)arylthio; a 3- to 30-membered heteroaryl unsubstituted or substituted with a (C6-C30)aryl; a (C6-C30)aryl unsubstituted or substituted with a cyano, a 3- to 30-membered heteroaryl, or a tri(C6-C30)arylsilyl; a tri(C1-C30)alkylsilyl; a tri(C6-C30)arylsilyl; a di(C1-C30) alkyl(C6-C30)arylsilyl; a (C1-C30)alkyldi(C6-C30)arylsilyl; an amino; a mono- or di-(C1-C30)alkylamino; a mono- or di-(C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl (C6-C30)aryl.
6. The organic electroluminescent device according to claim 1, wherein the compound represented by formula 1 is selected from the group consisting of:
H1-1
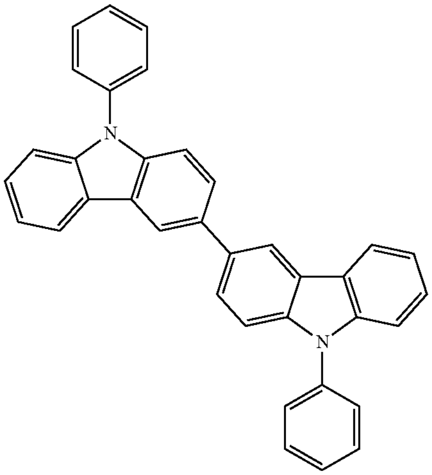
H1-2
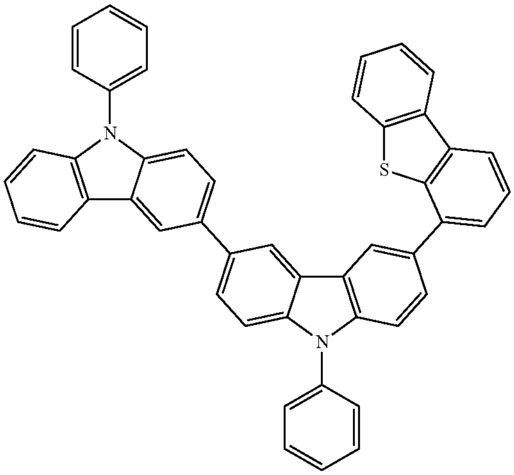
H1-3
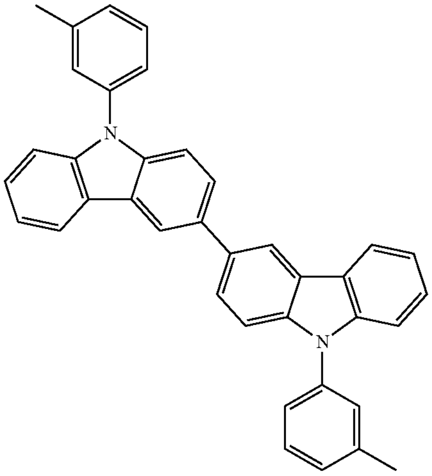
H1-4
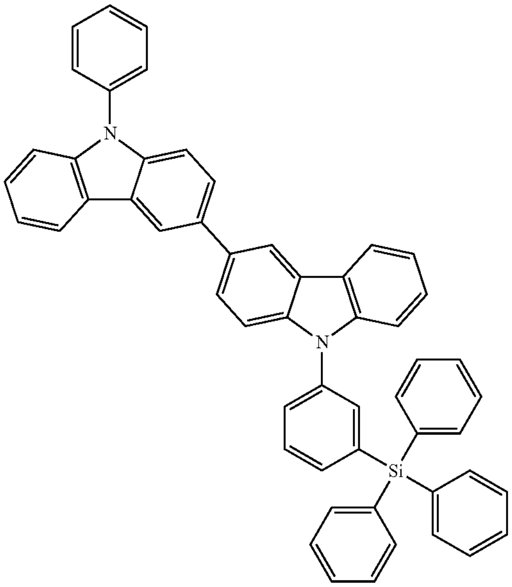
H1-5
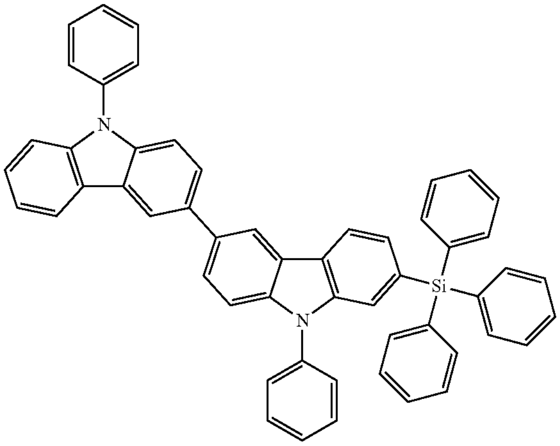
H1-6
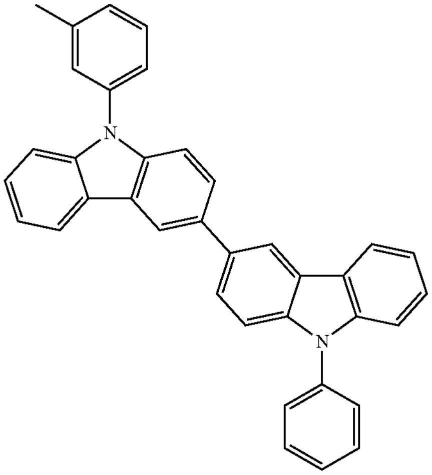

-continued
H1-7
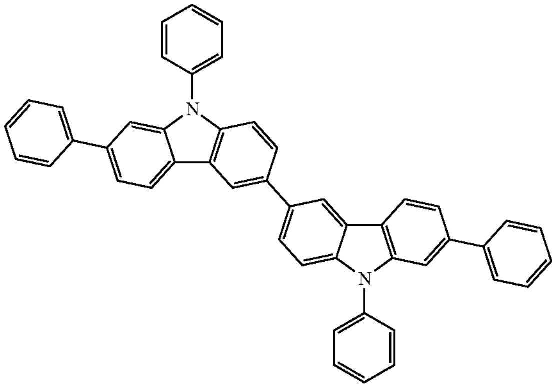
H1-8
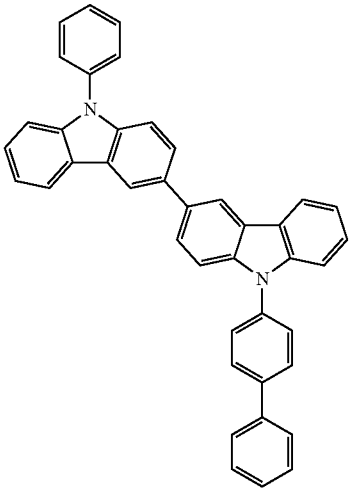
H1-9
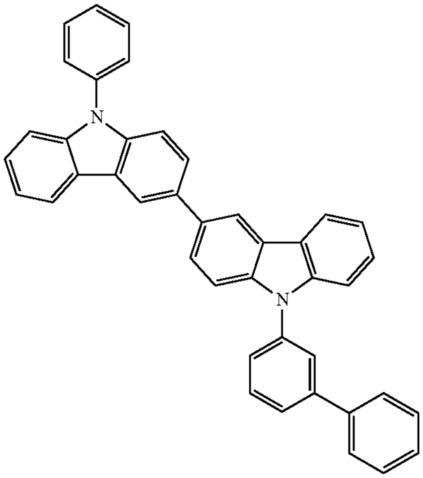
H1-10
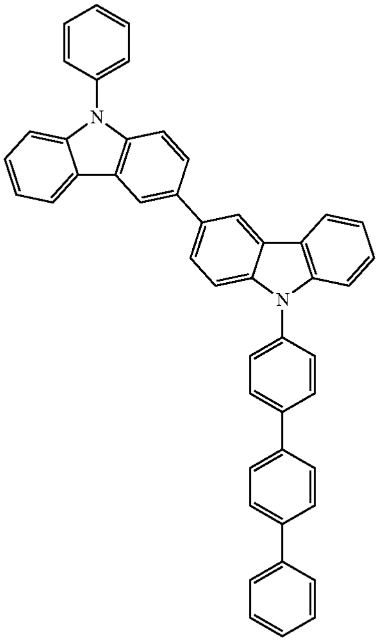

-continued
H1-11
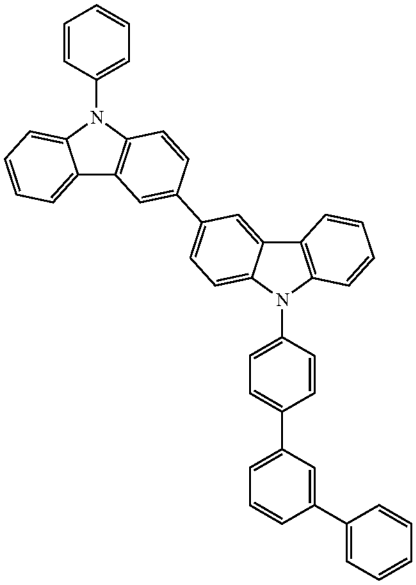
H1-12
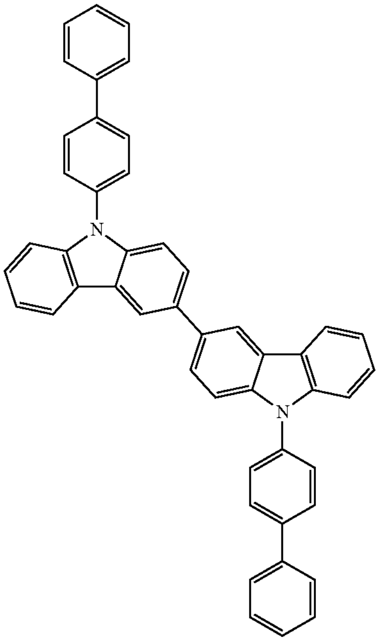
H1-13
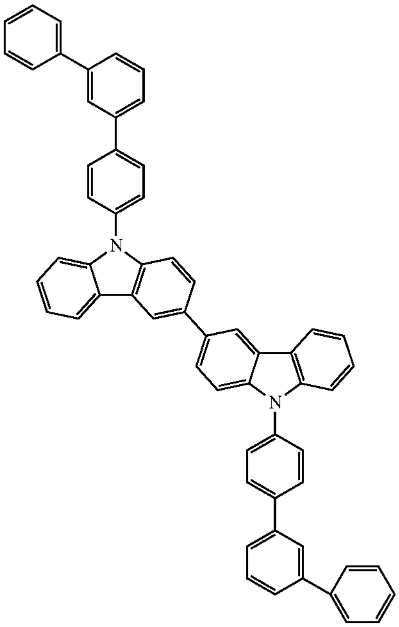
H1-14
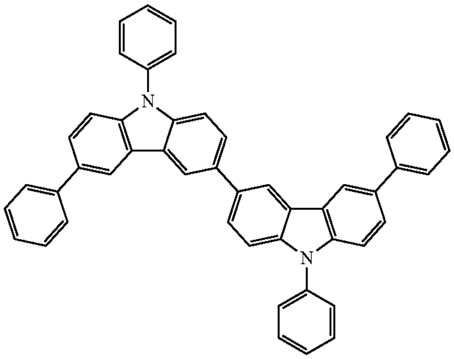

-continued
H1-15
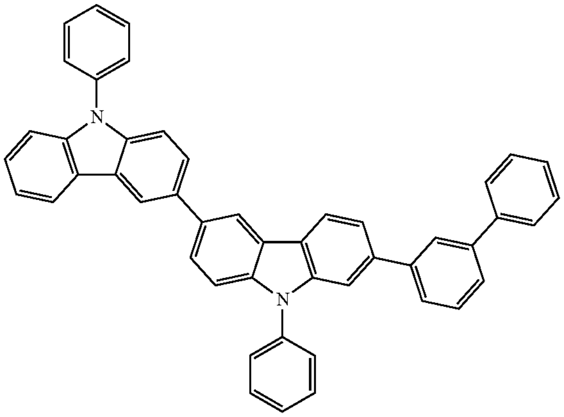
H1-16
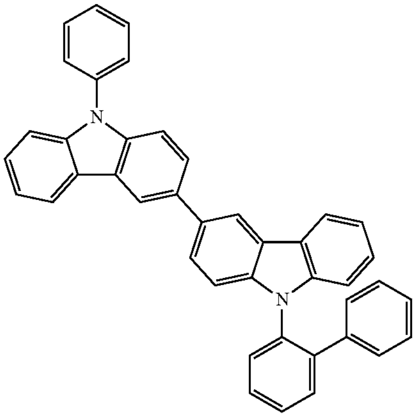
H1-17
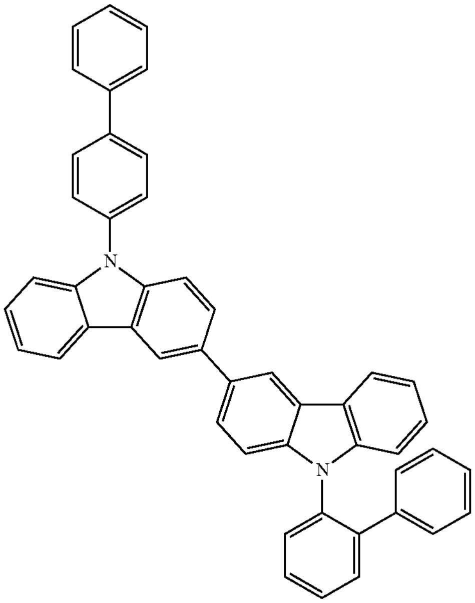
H1-18
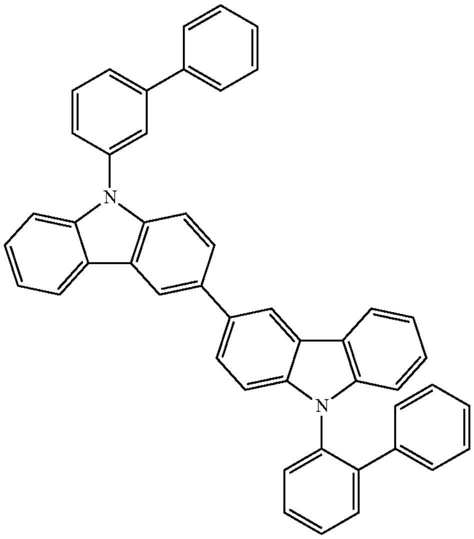
H1-19
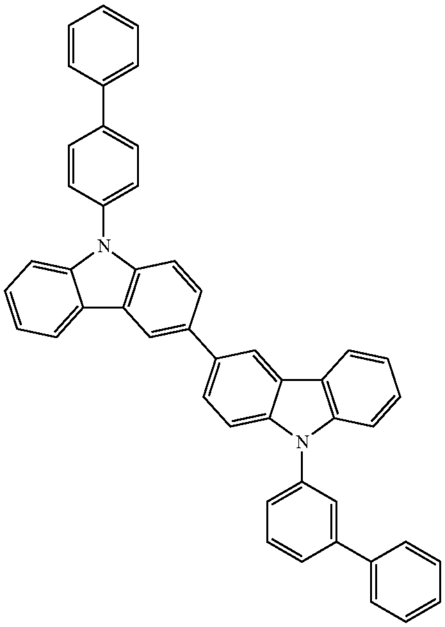
H1-20
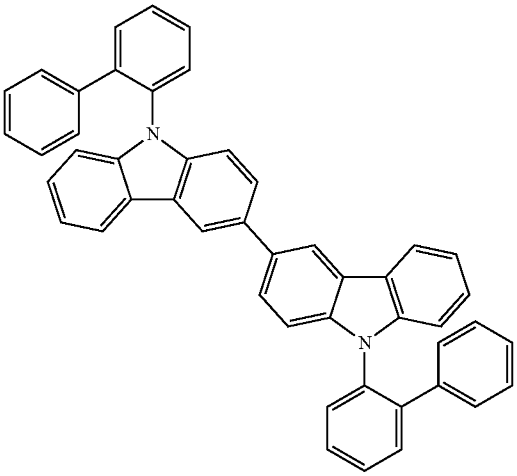

-continued
H1-21
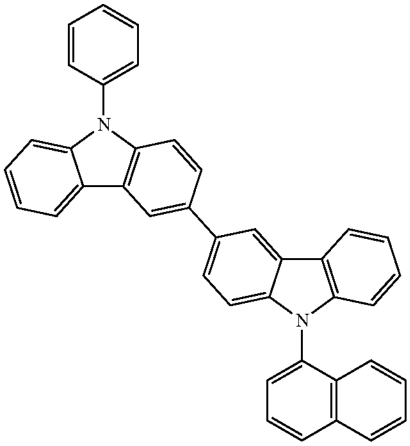
H1-22
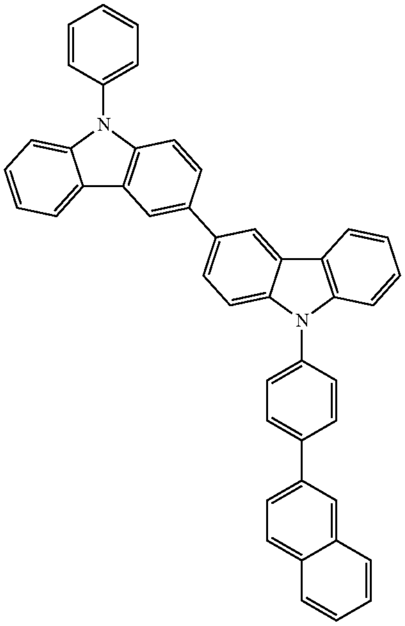
H1-23
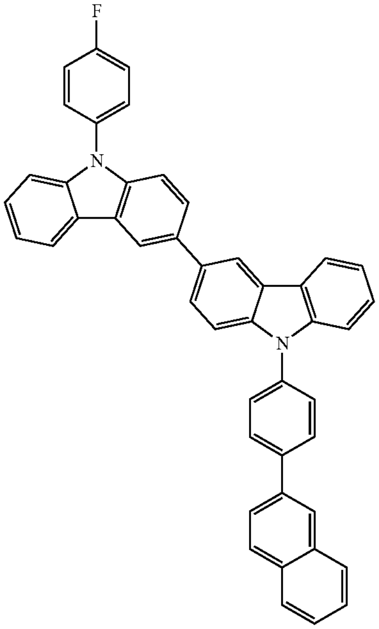
H1-24
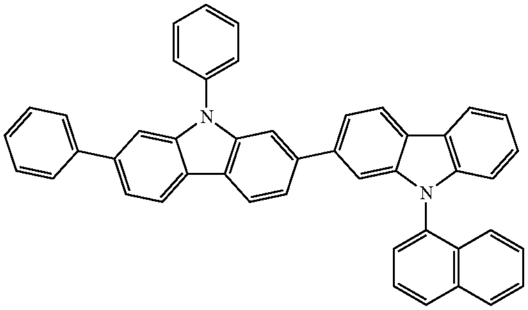

-continued
H1-25
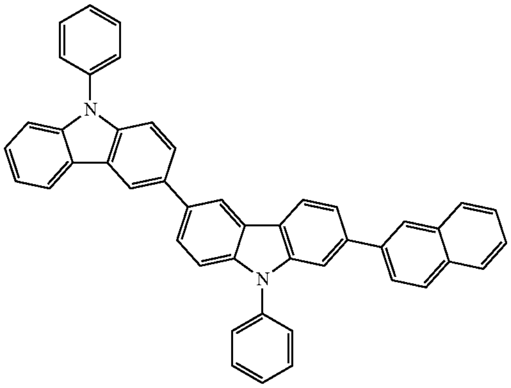
H1-26
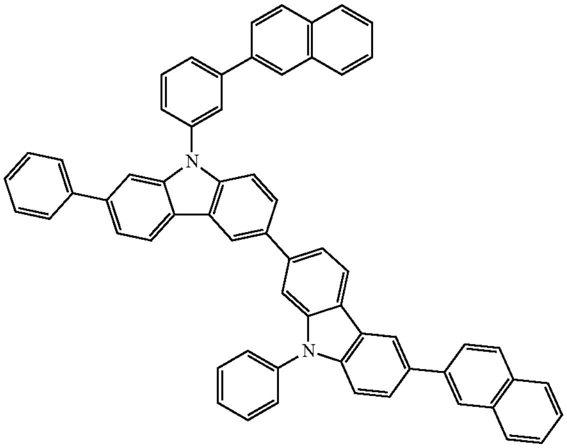
H1-27
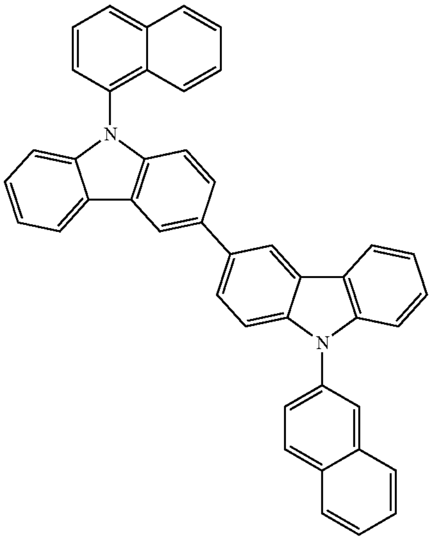
H1-28
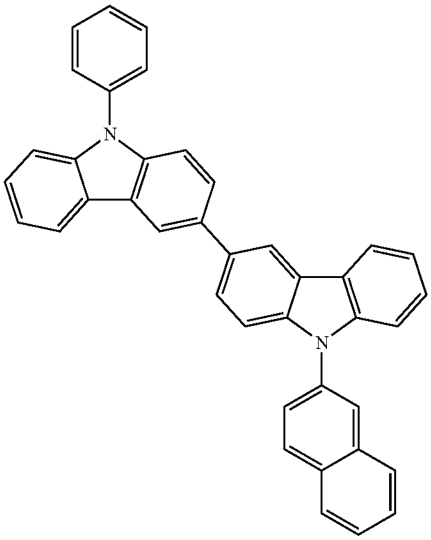
H1-29
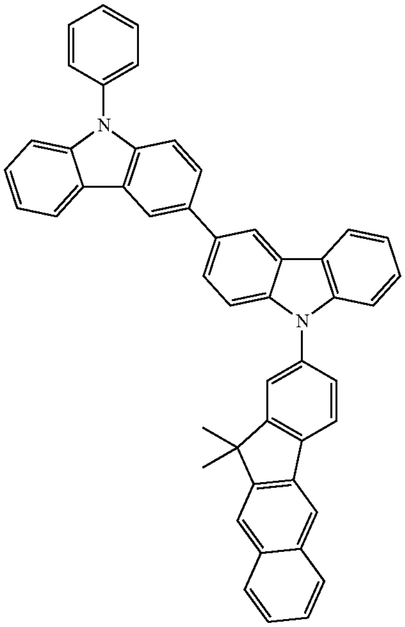
H1-30
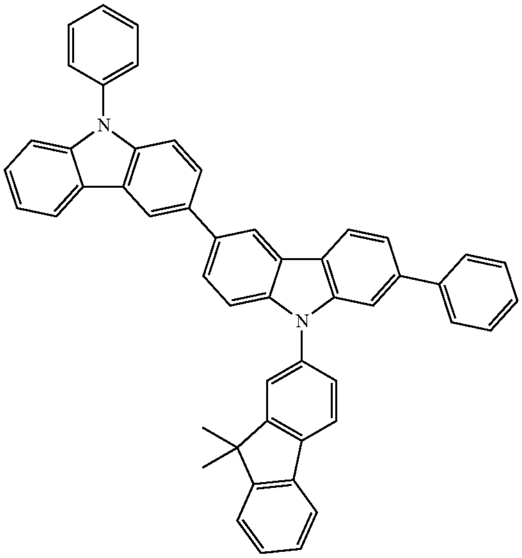

-continued
H1-31
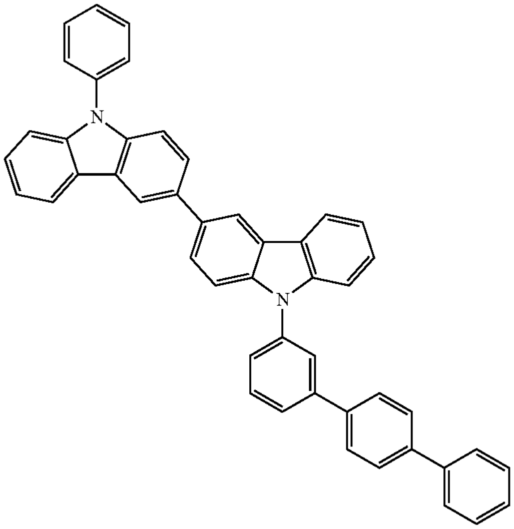
H1-32
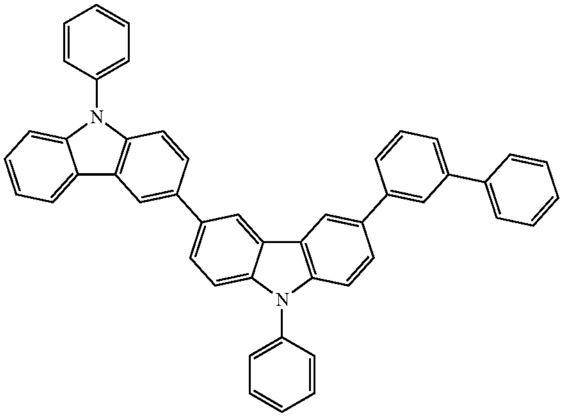
H1-33
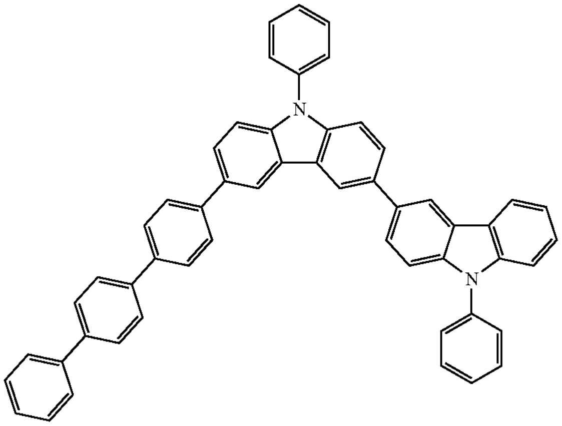
H1-34
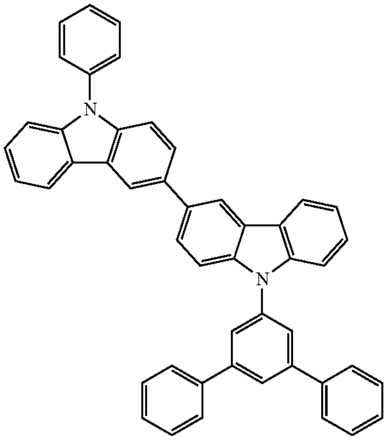
H1-35
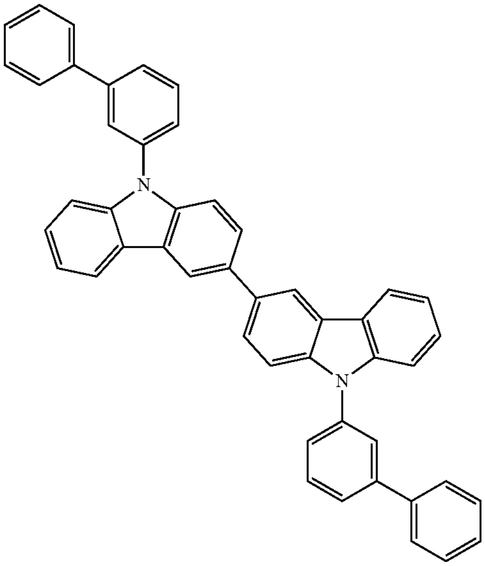
H1-36
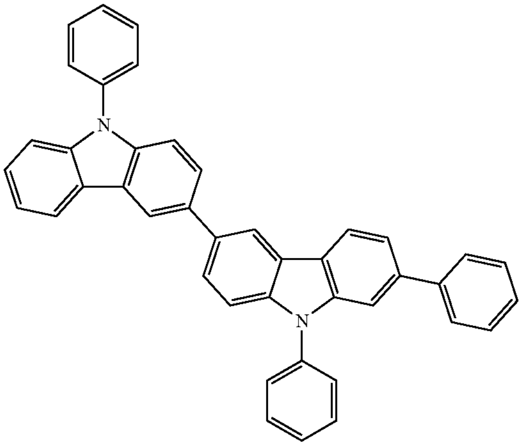

-continued
H1-37
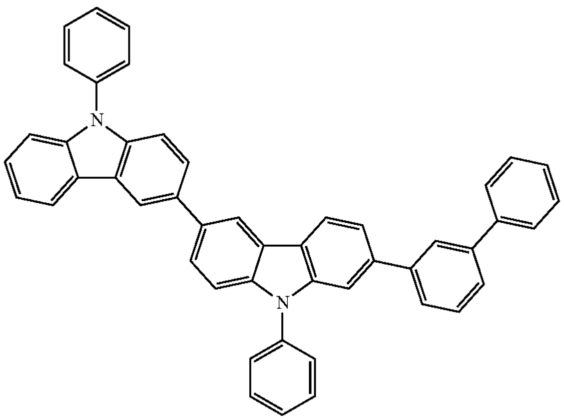
H1-38
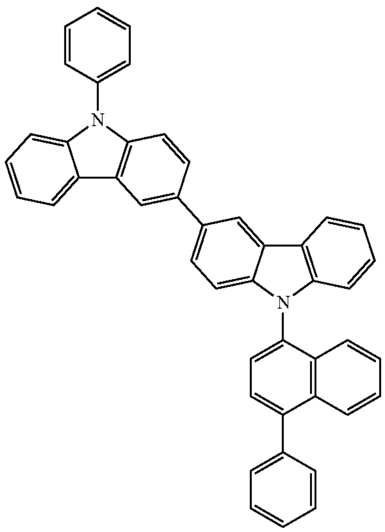
H1-39
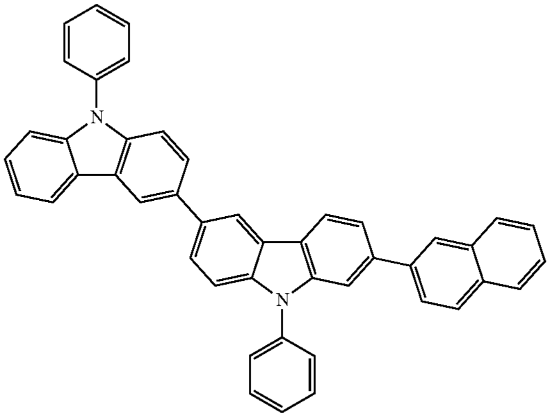
H1-40
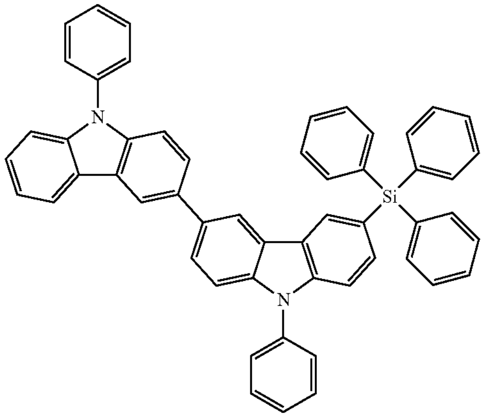
H1-41
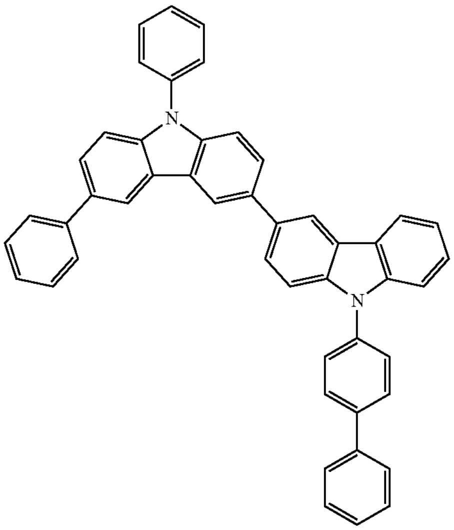
H1-42
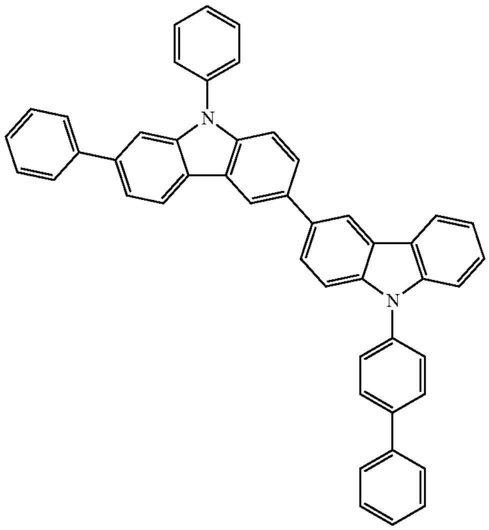

-continued
H1-43
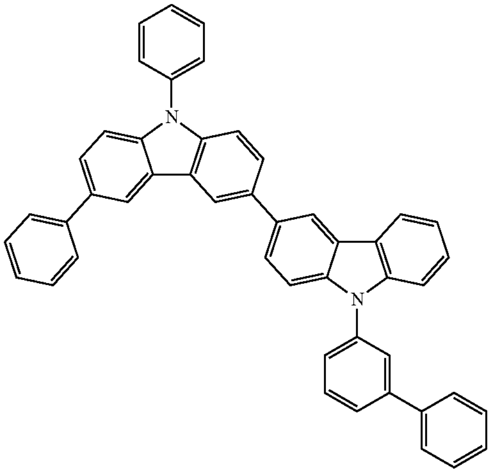
H1-44
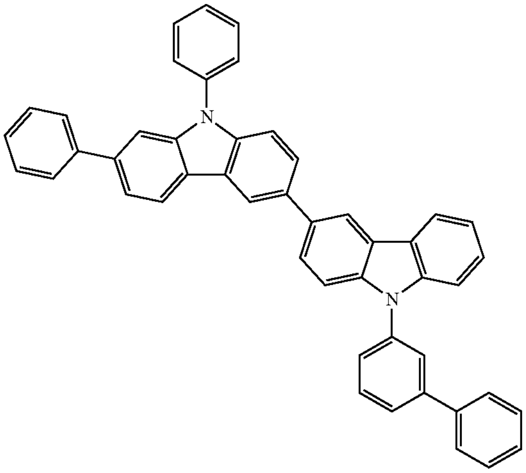
H1-45
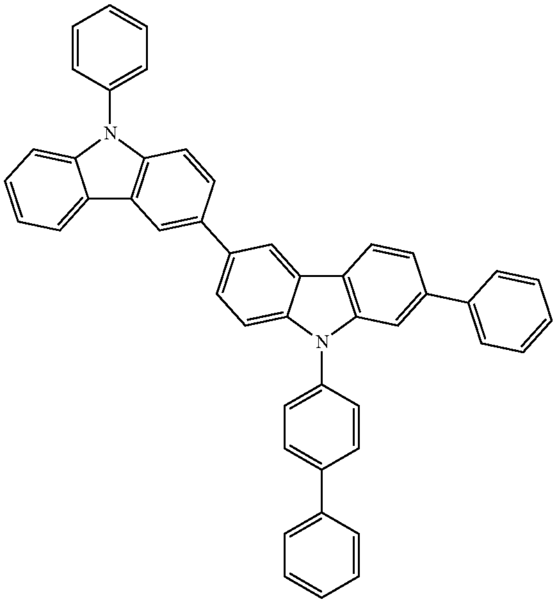
H1-46
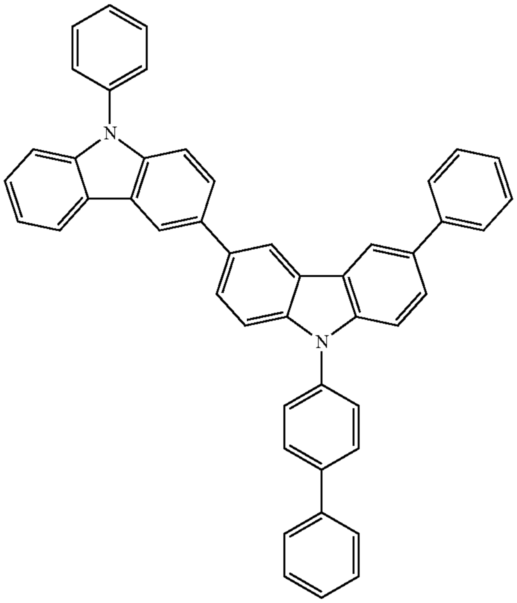
H1-47
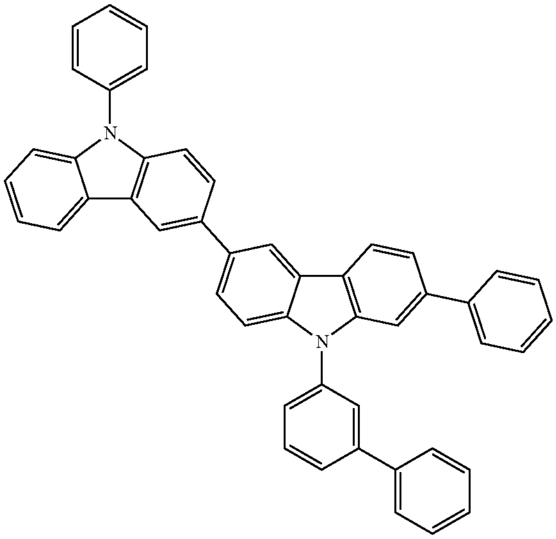
H1-48
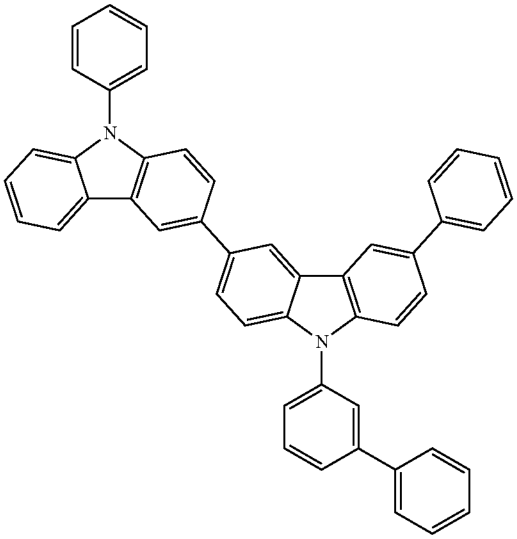

-continued
H1-49
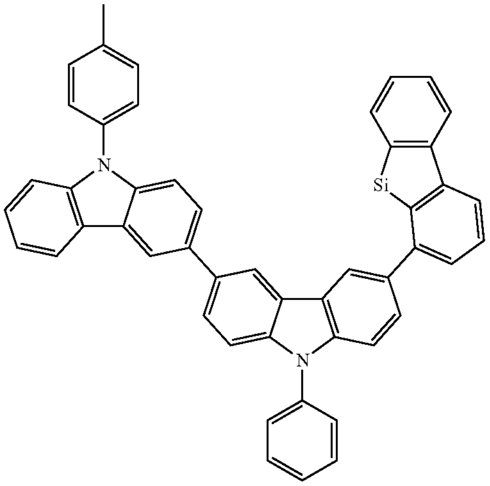
H1-50
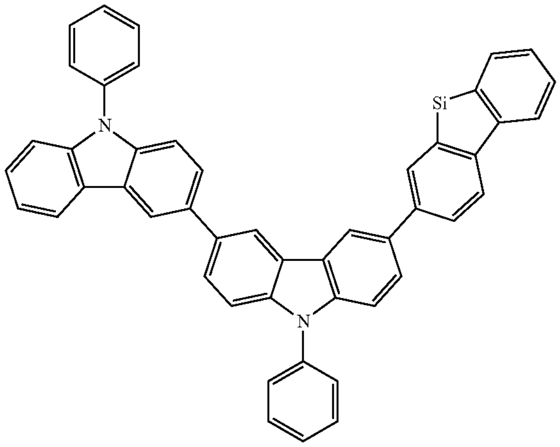
H1-51
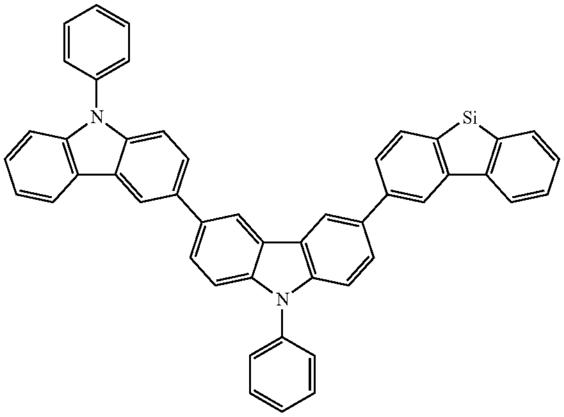
H1-52
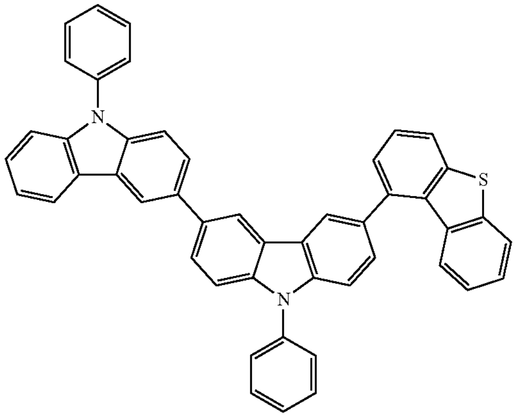
H1-53
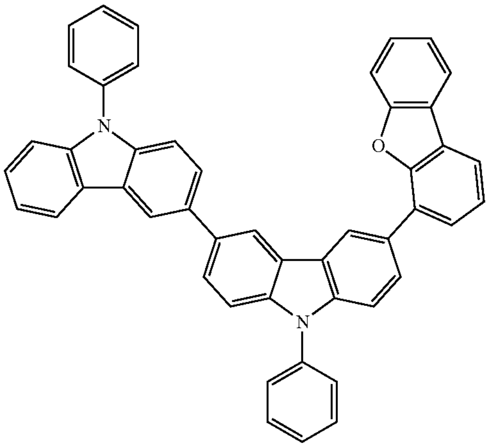
H1-54
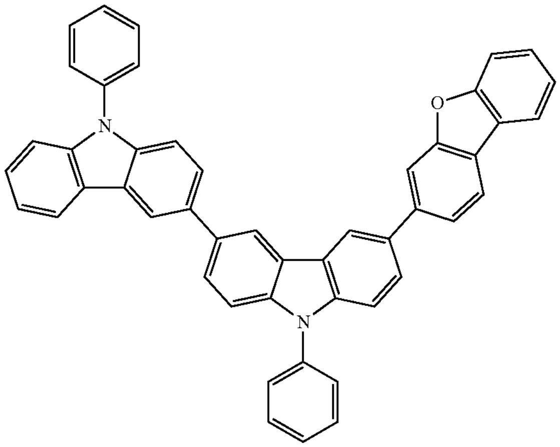

-continued
H1-55
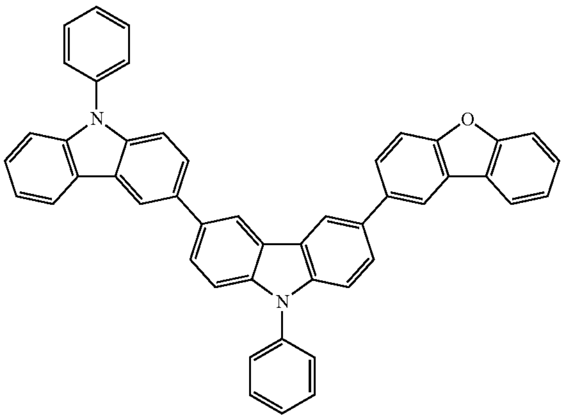
H1-56
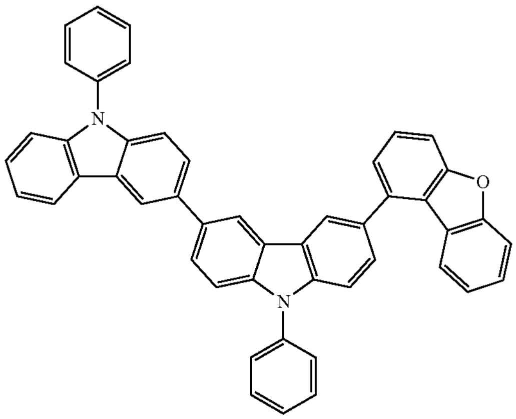
H1-57
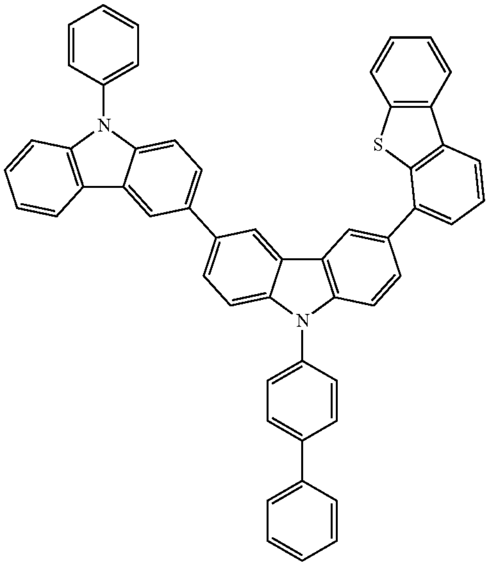
H1-58
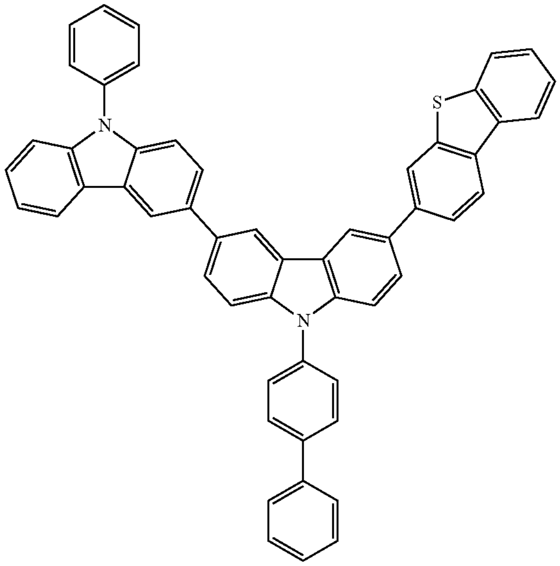
H1-59
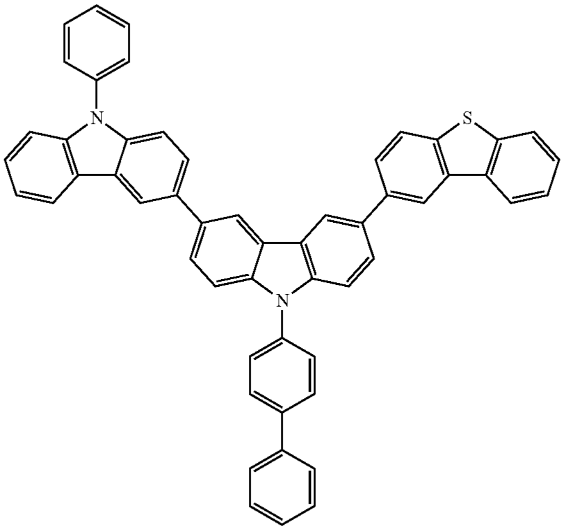
H1-60
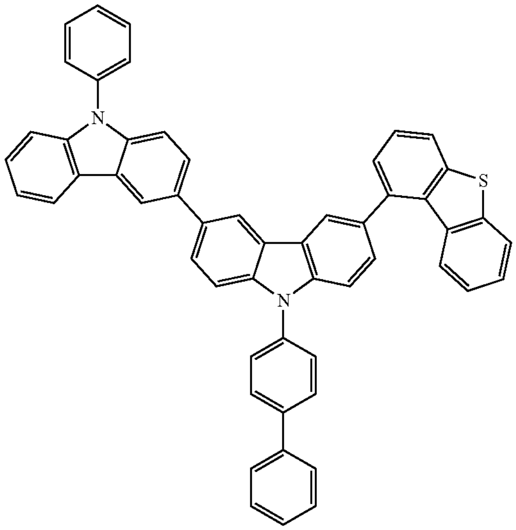

-continued
H1-61
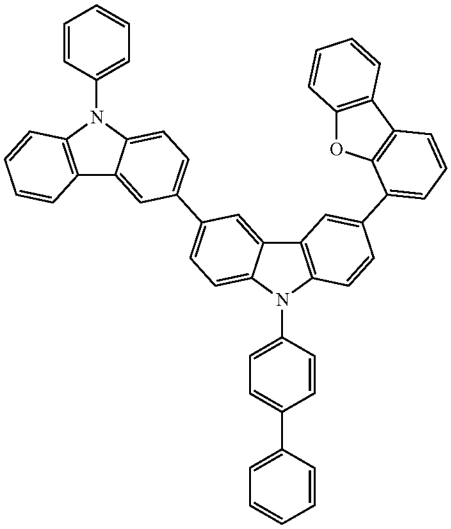
H1-62
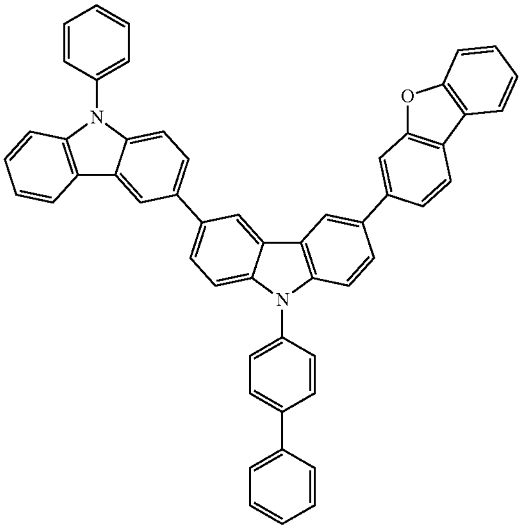
H1-63
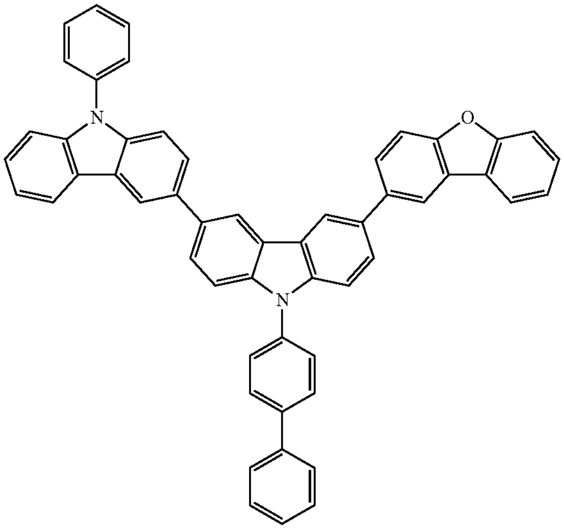
H1-64
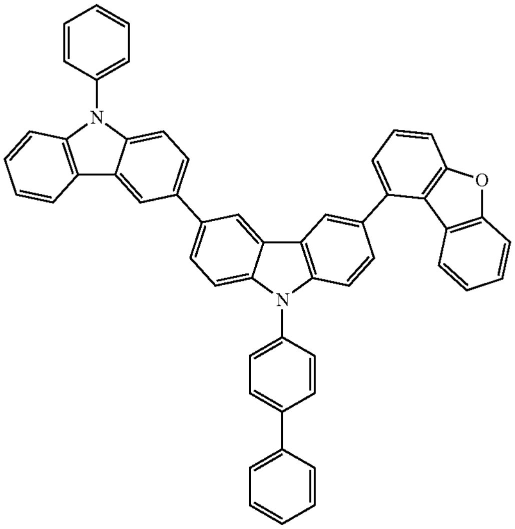
H1-65
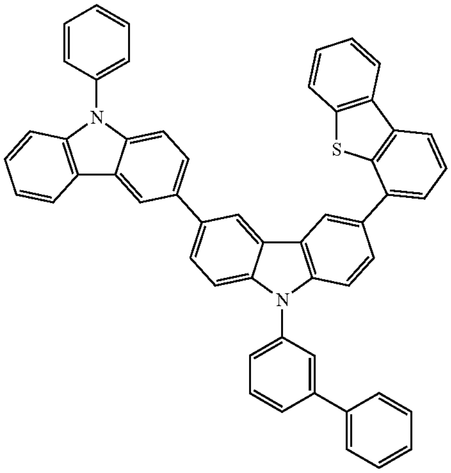
H1-66
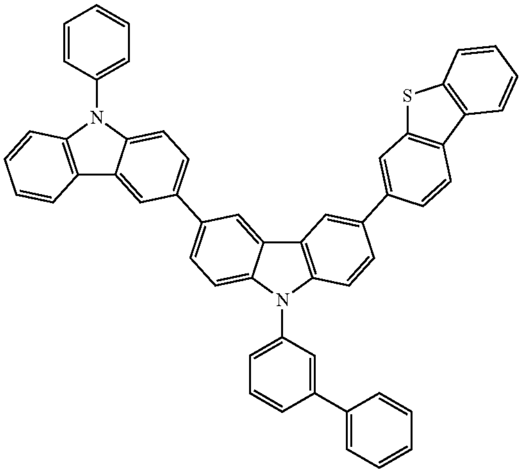

-continued
H1-67
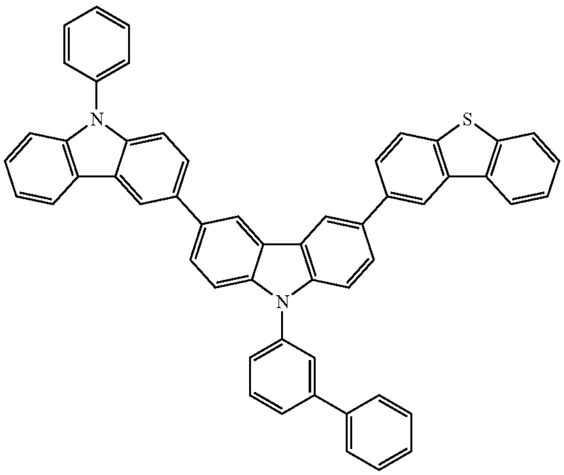
H1-68
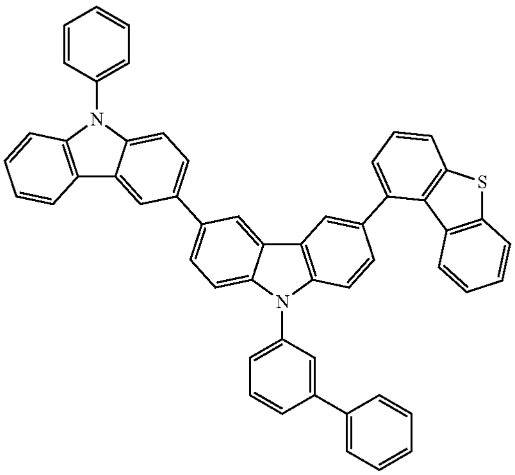
H1-69
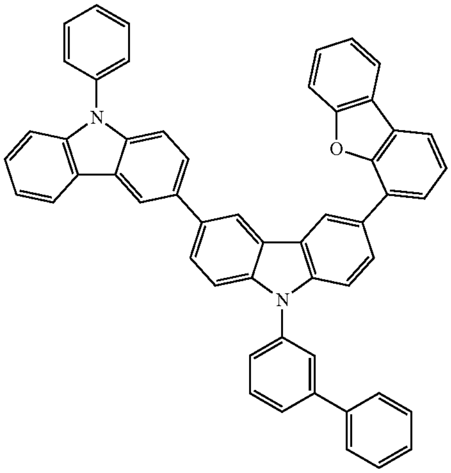
H1-70
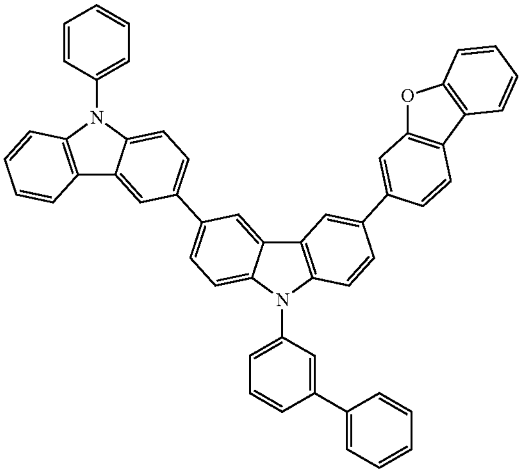
H1-71
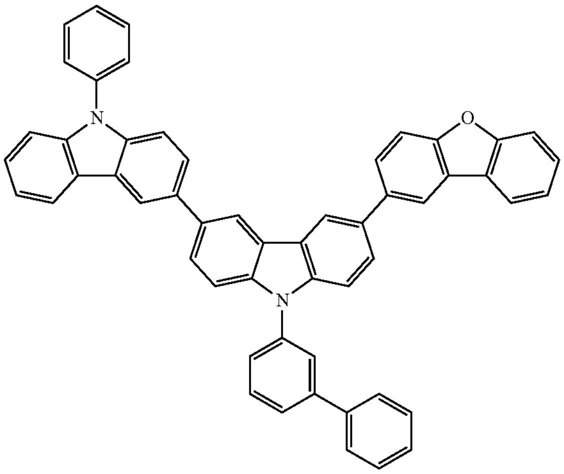
H1-72
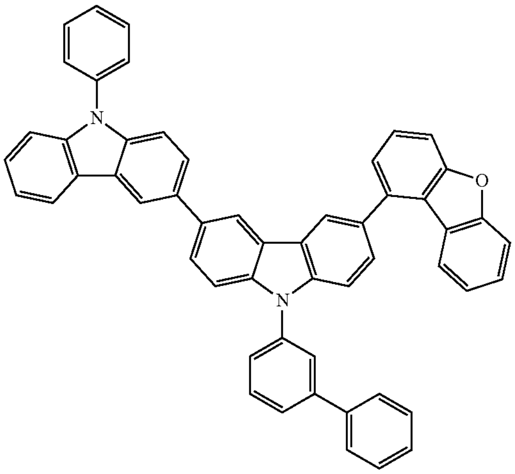

-continued
H1-73
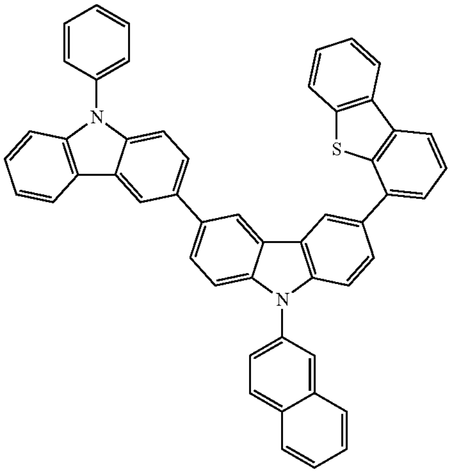
H1-74
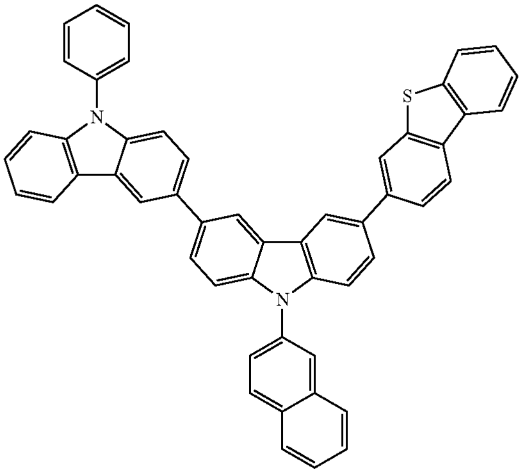
H1-75
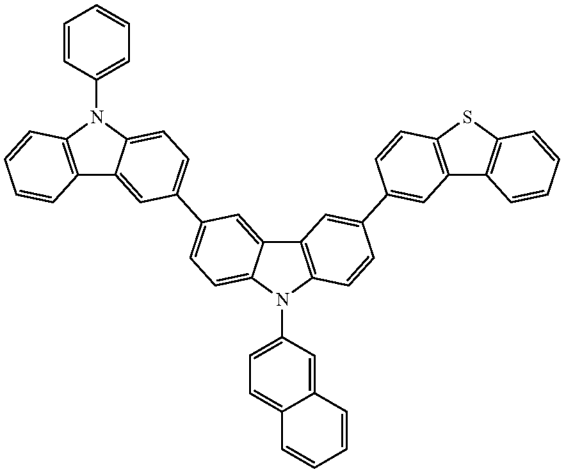
H1-76
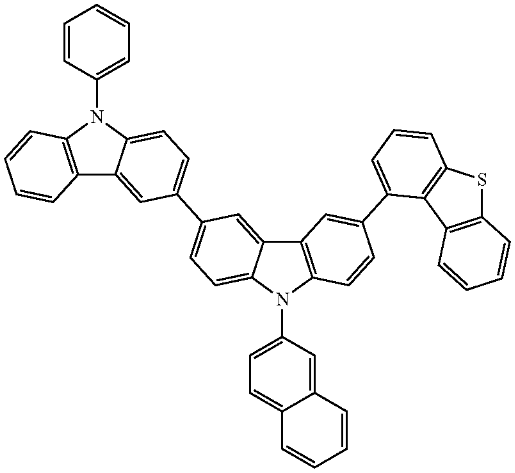
H1-77
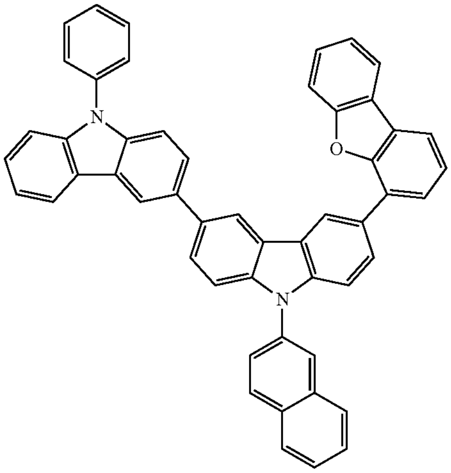
H1-78
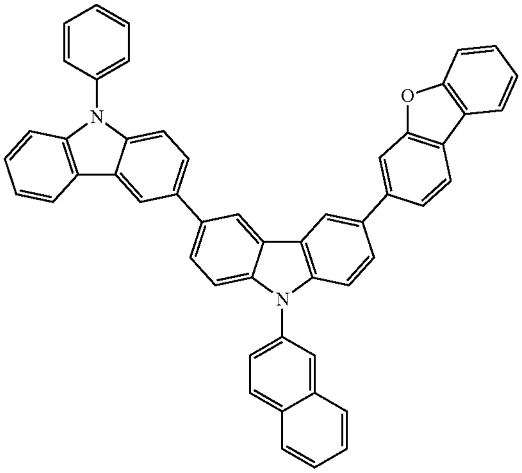

-continued
H1-79
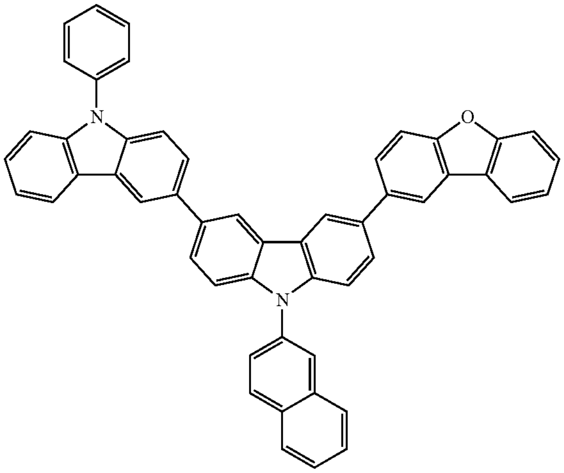
H1-80
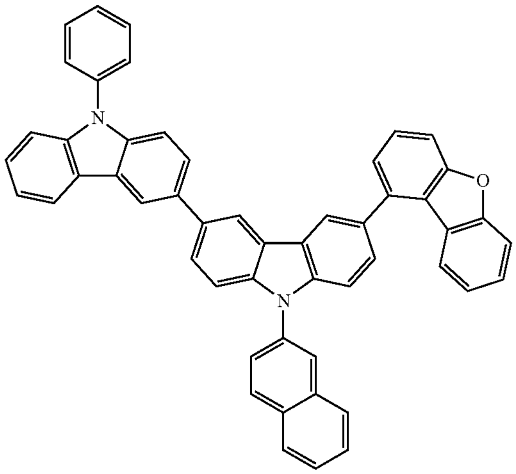
H1-81
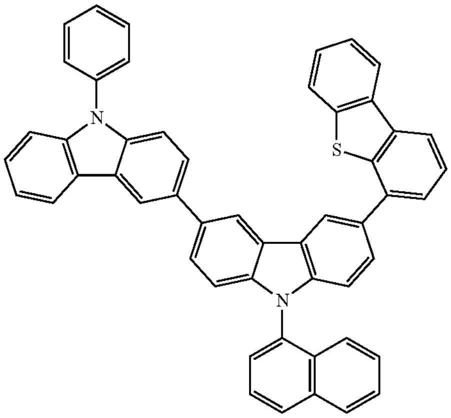
H1-82
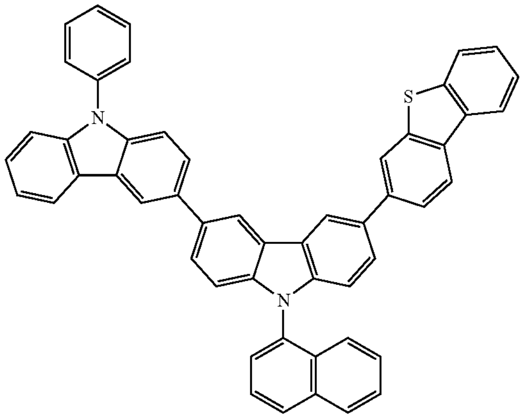
H1-83
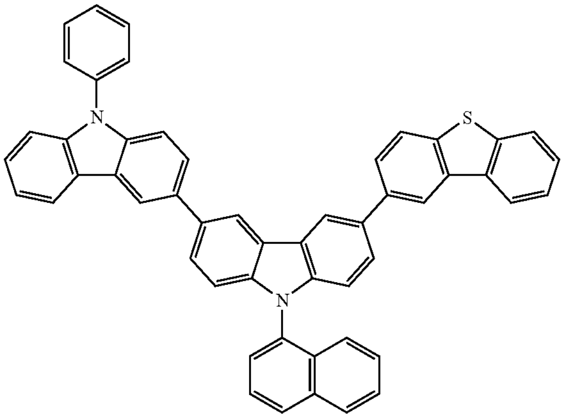
H1-84
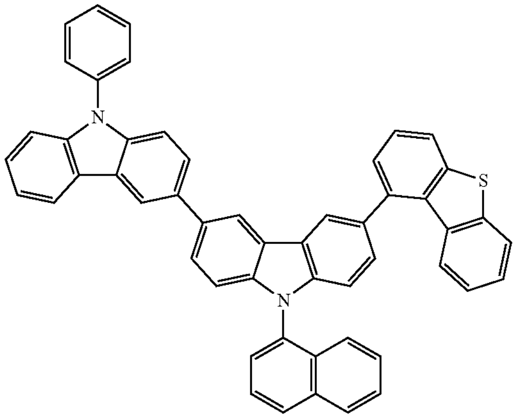

-continued
H1-85
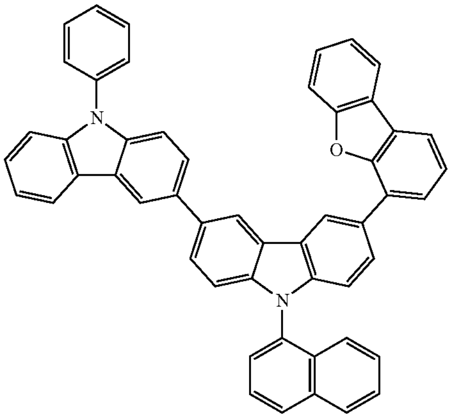
H1-86
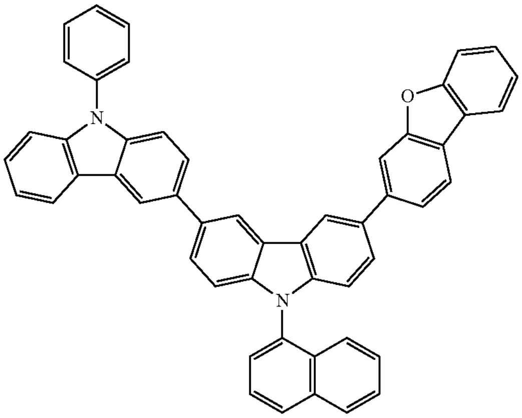
H1-87
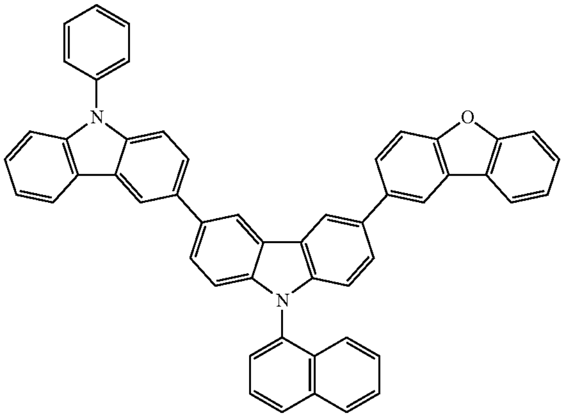
H1-88
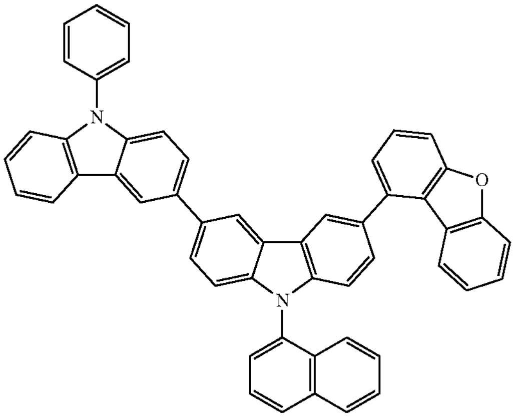
H1-89
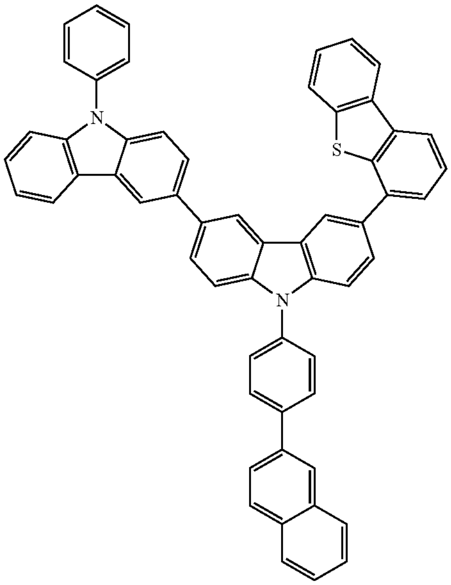
H1-90
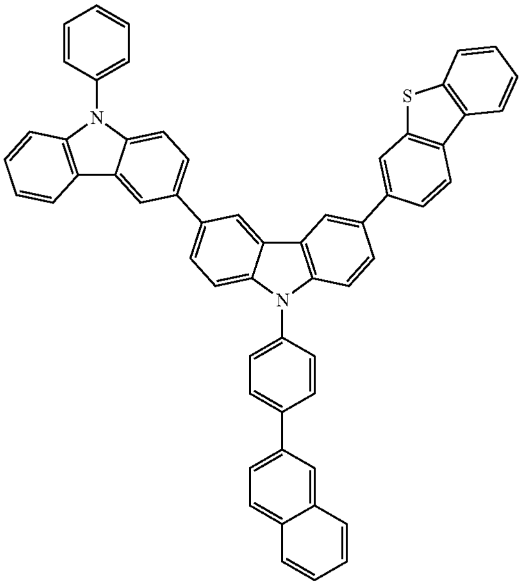

-continued
H1-91
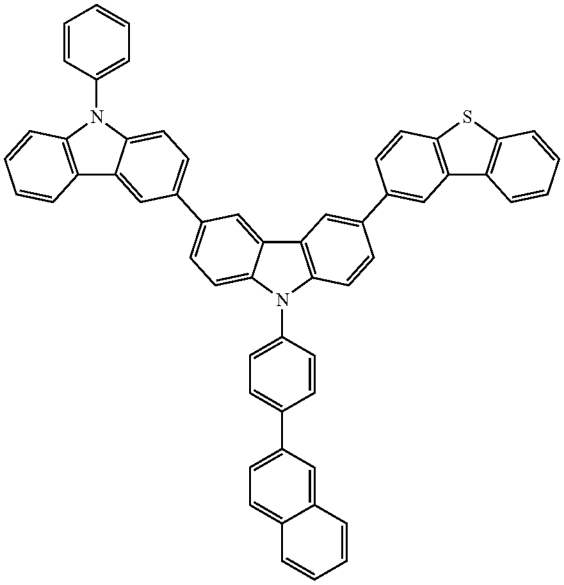
H1-92
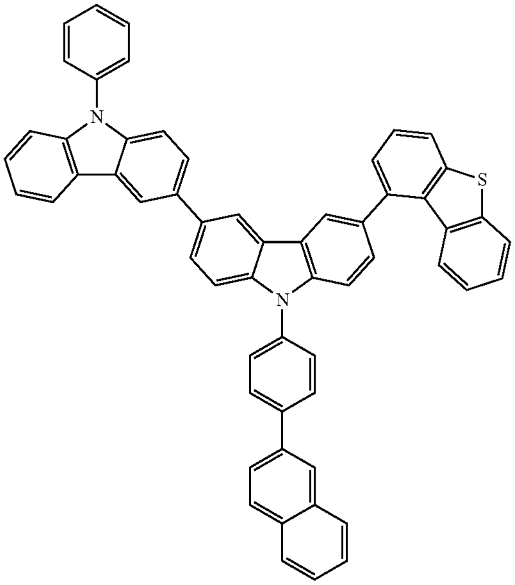
H1-93
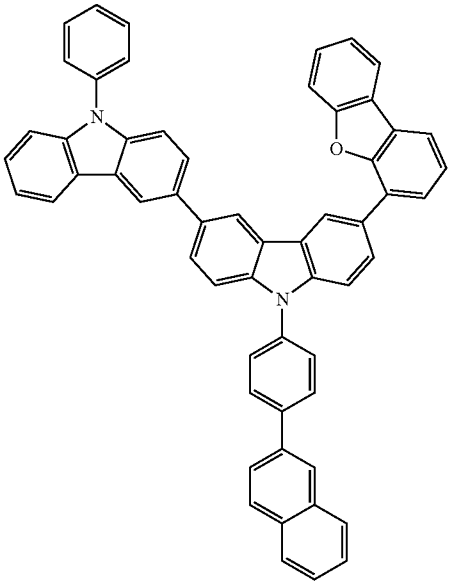
H1-94
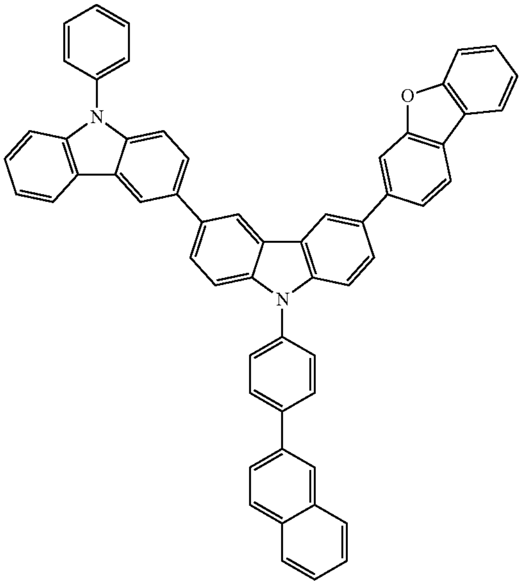

-continued
H1-95
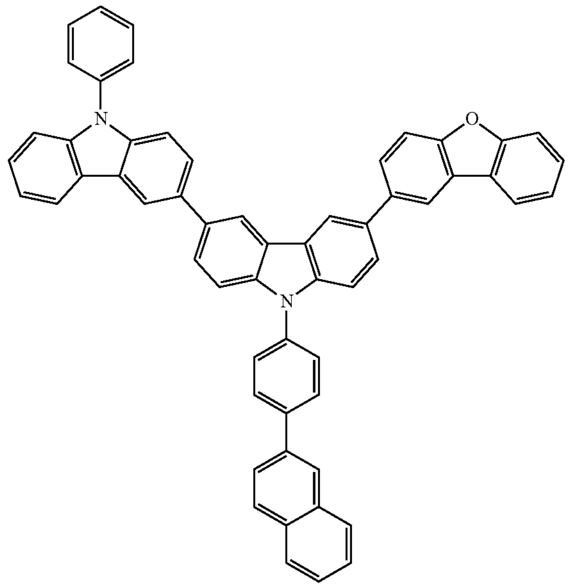
H1-96
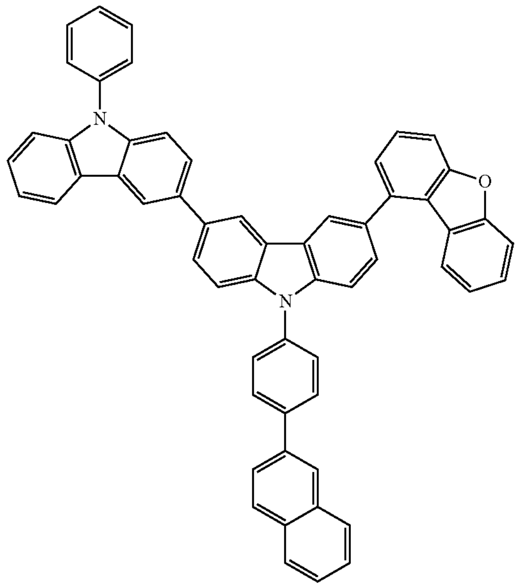
H1-97
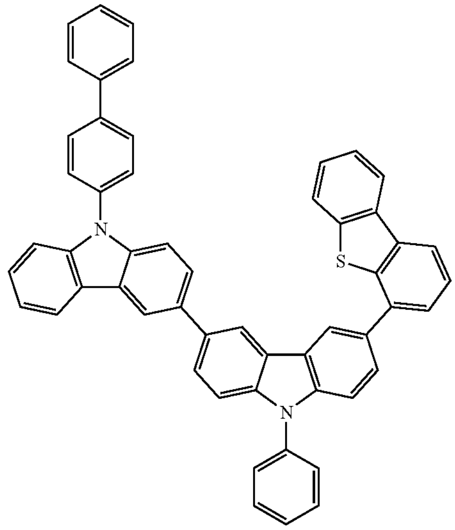
H1-98
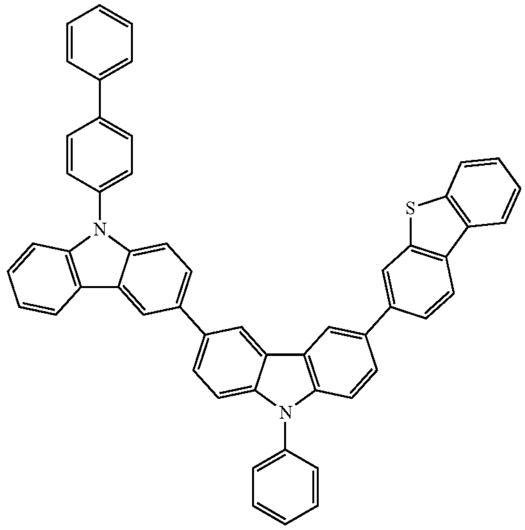

-continued
H1-99
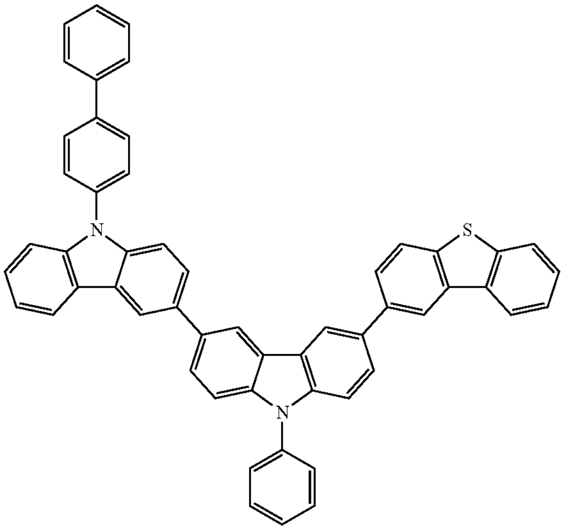
H1-100
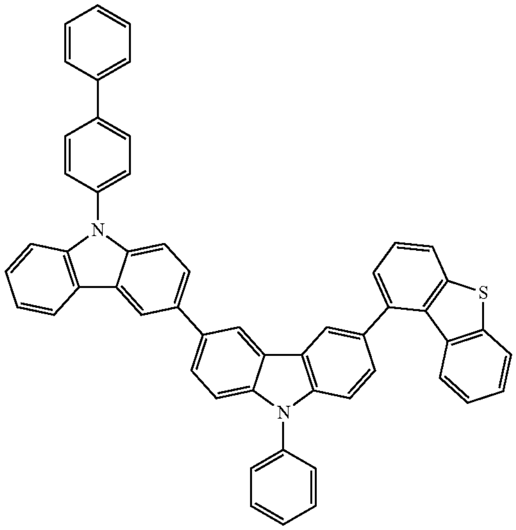
H1-101
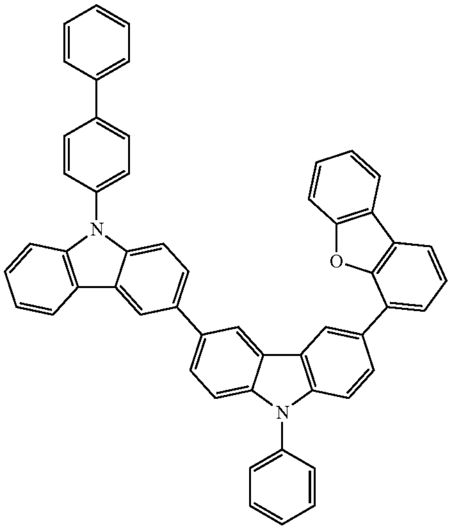
H1-102
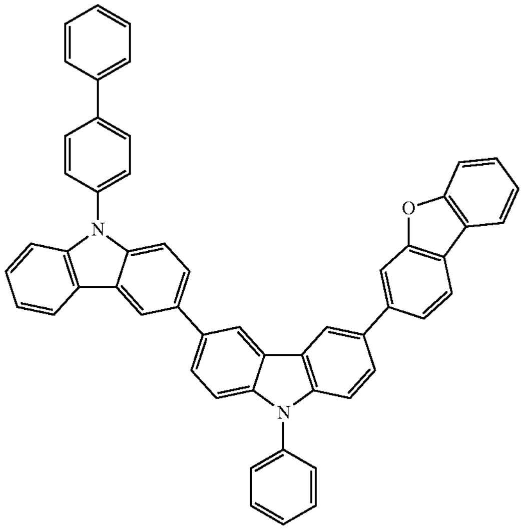
H1-103
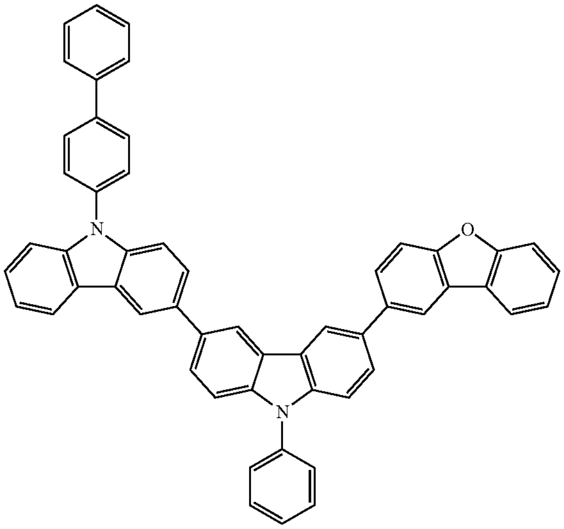
H1-104
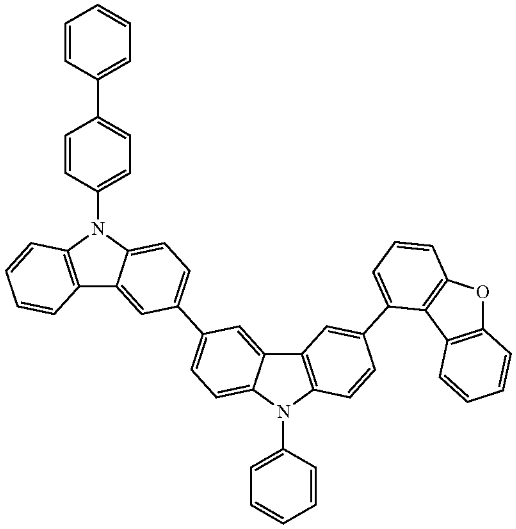

-continued
H1-105
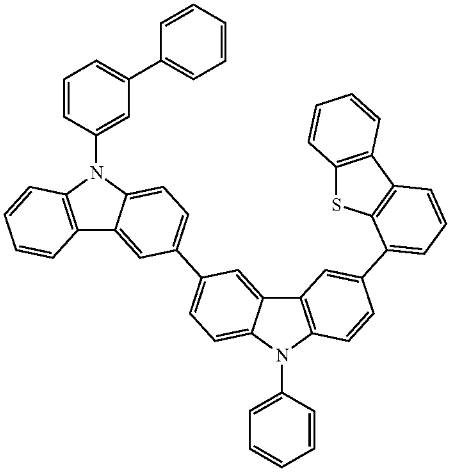
H1-106
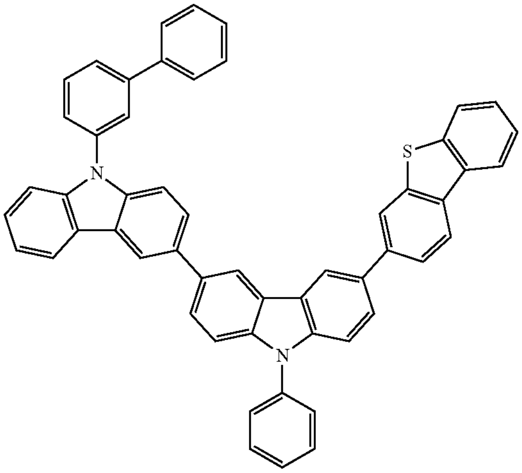
H1-107
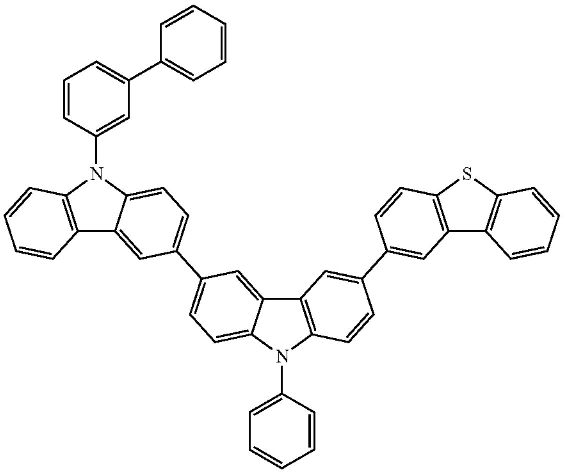
H1-108
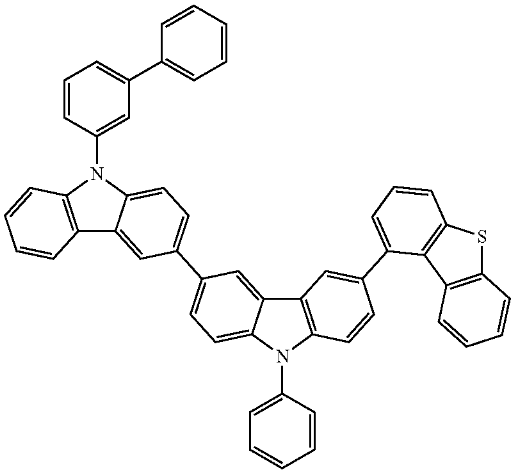
H1-109
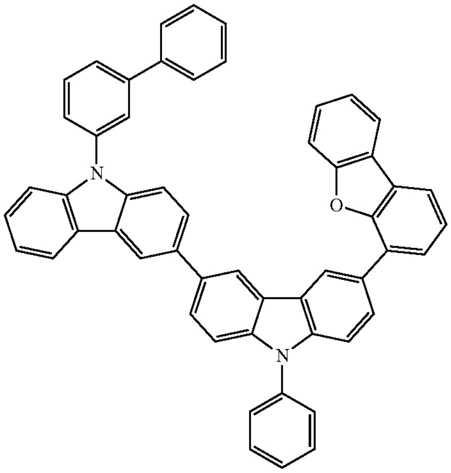
H1-110
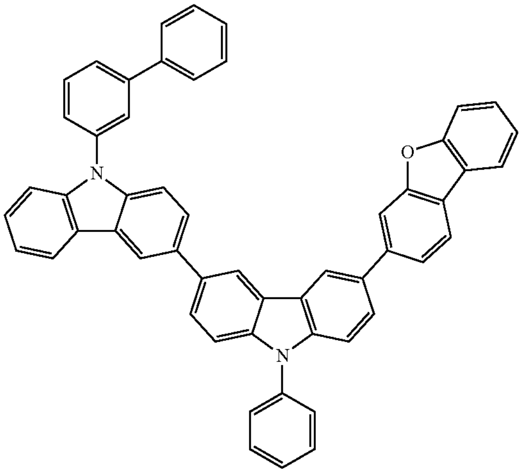

-continued
H1-111
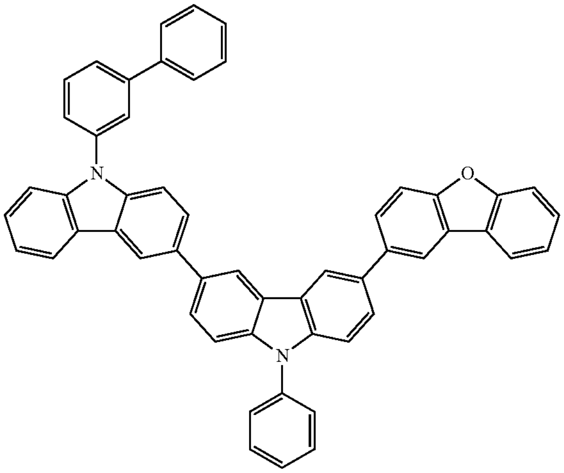
H1-112
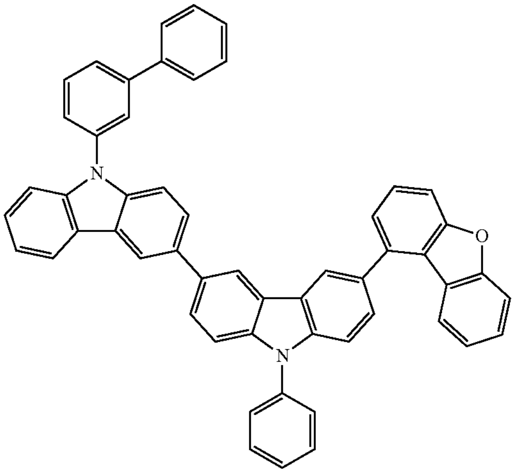
H1-113
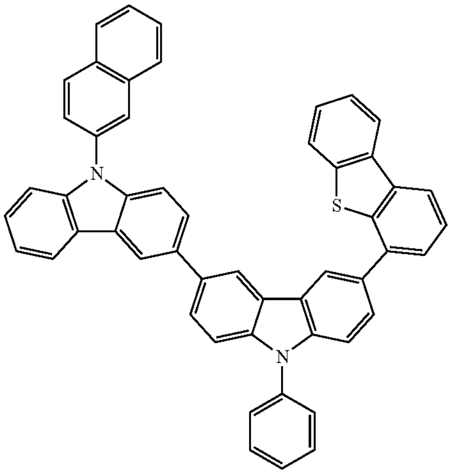
H1-114
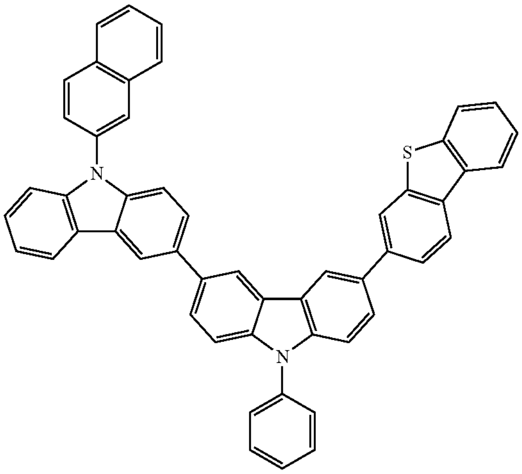
H1-115
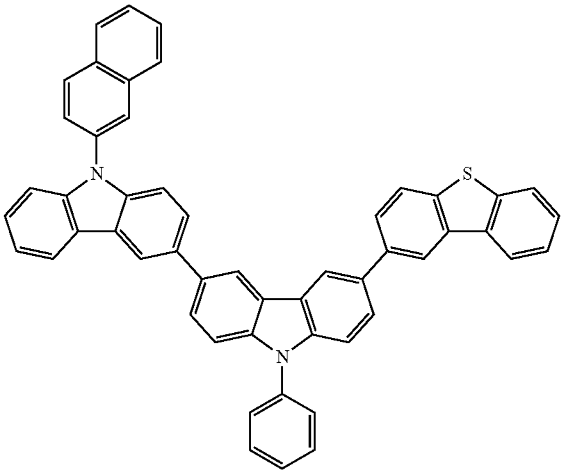
H1-116
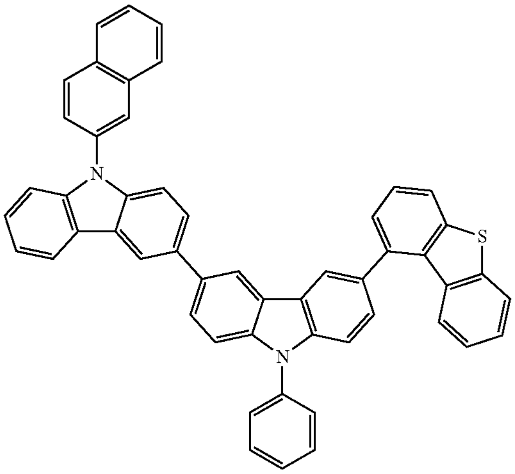

-continued
H1-117
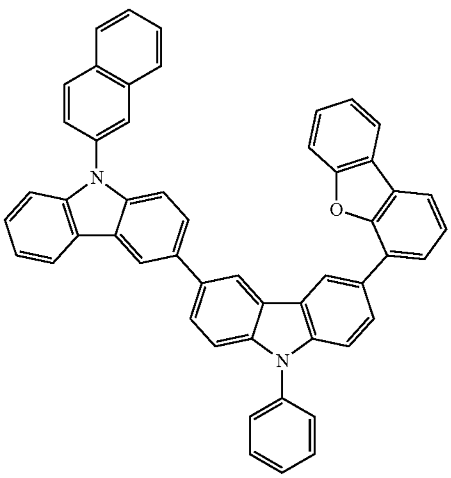
H1-118
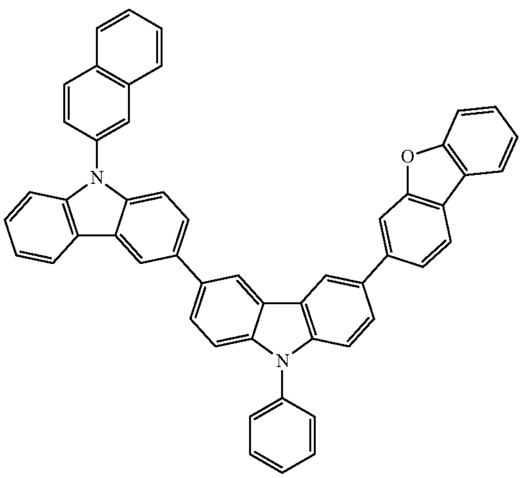
H1-119
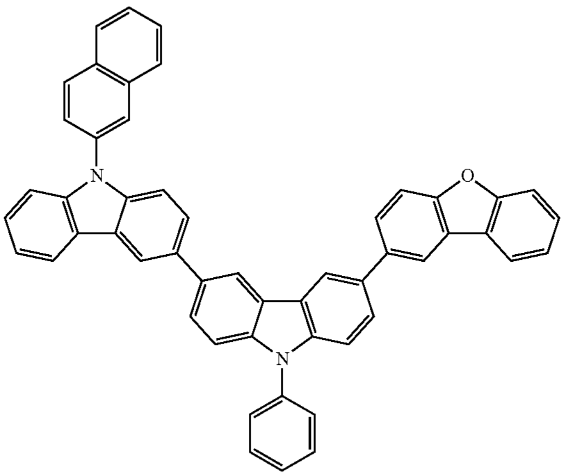
H1-120
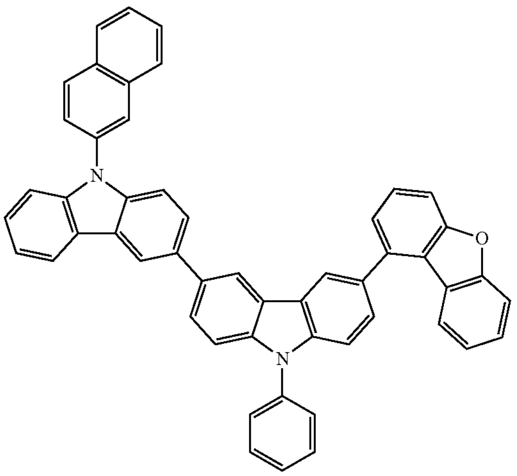
H1-121
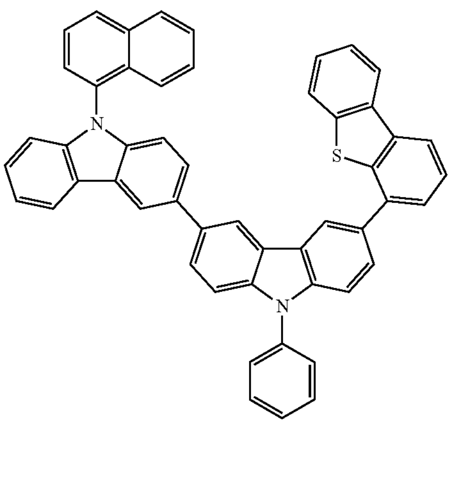
H1-122
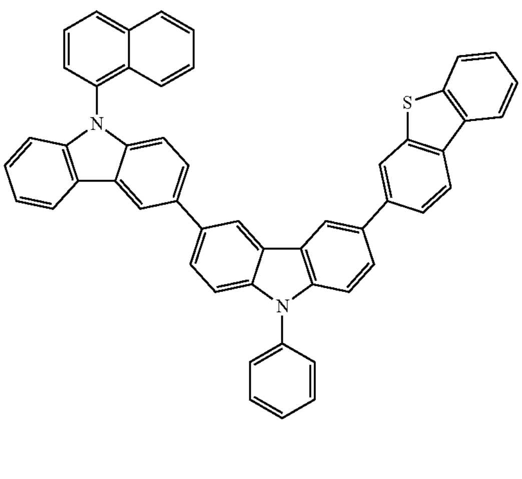

-continued
H1-123
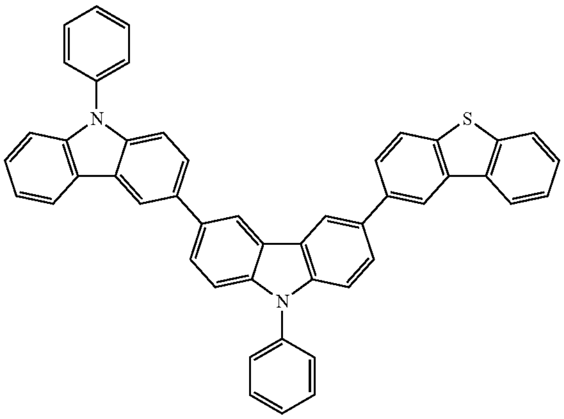
H1-124
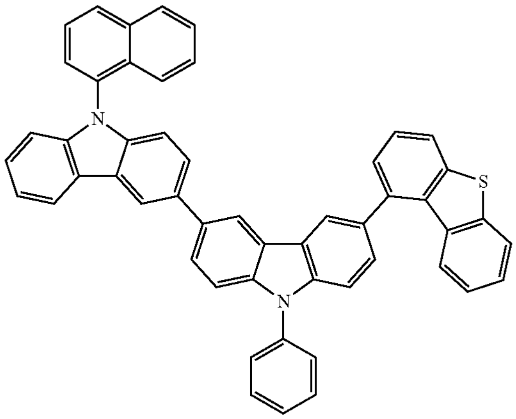
H1-125
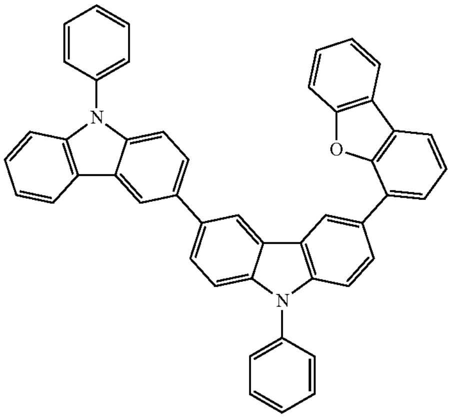
H1-126
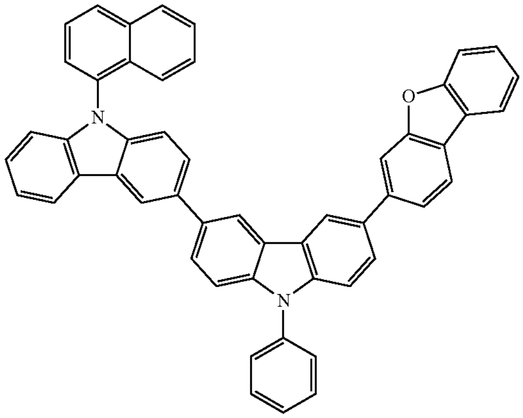
H1-127
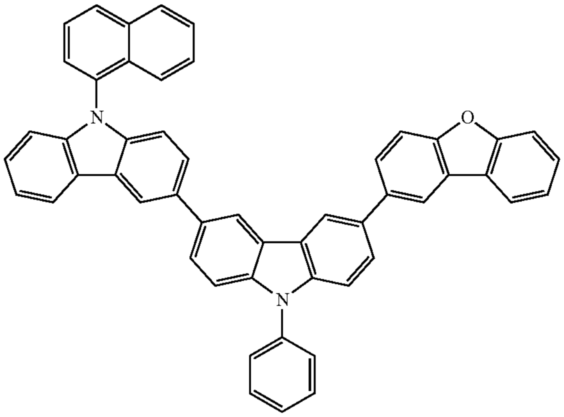
H1-128
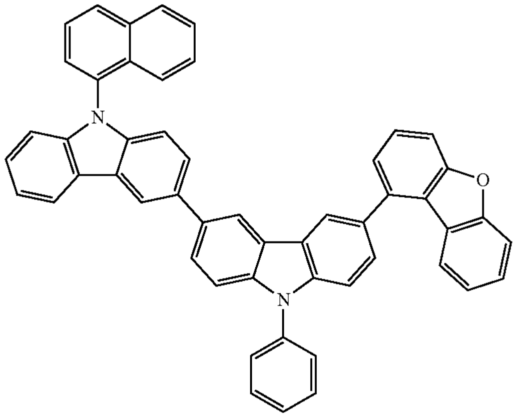

-continued
H1-129
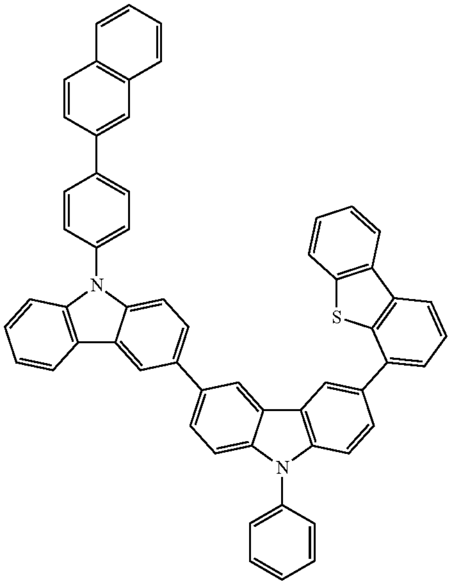
H1-130
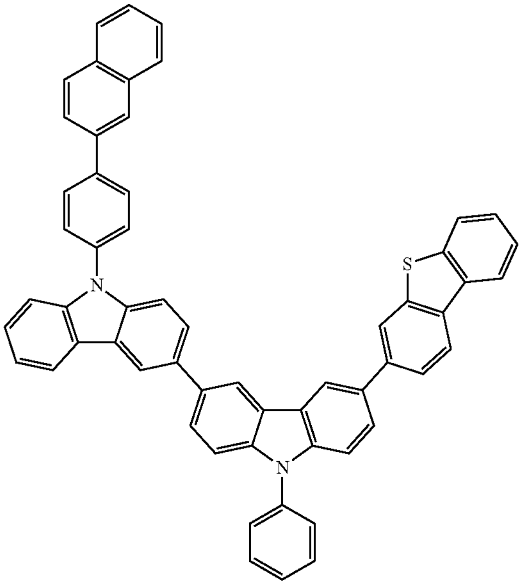
H1-131
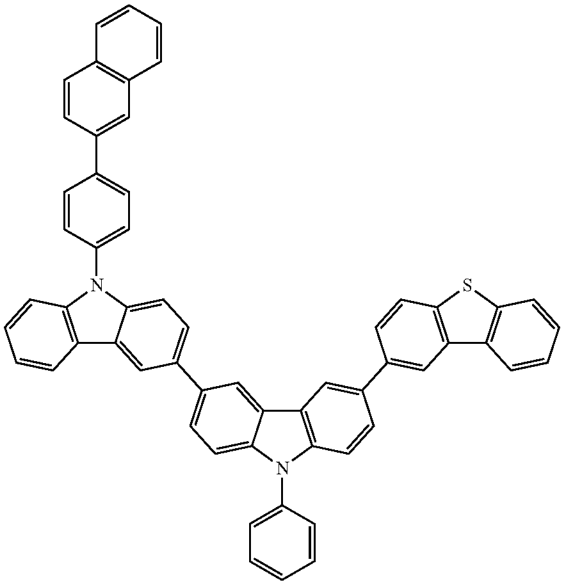
H1-132
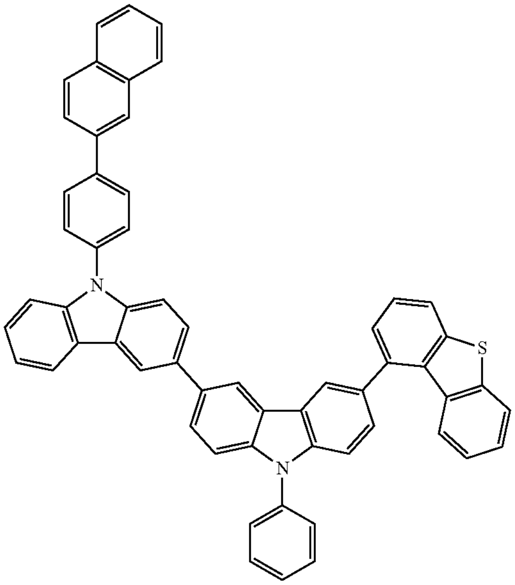

-continued
H1-133
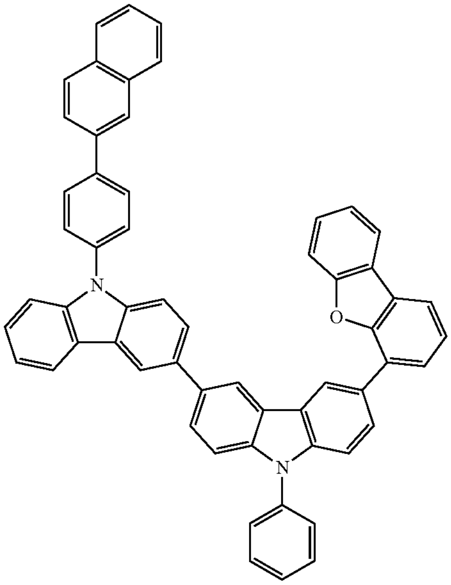
H1-134
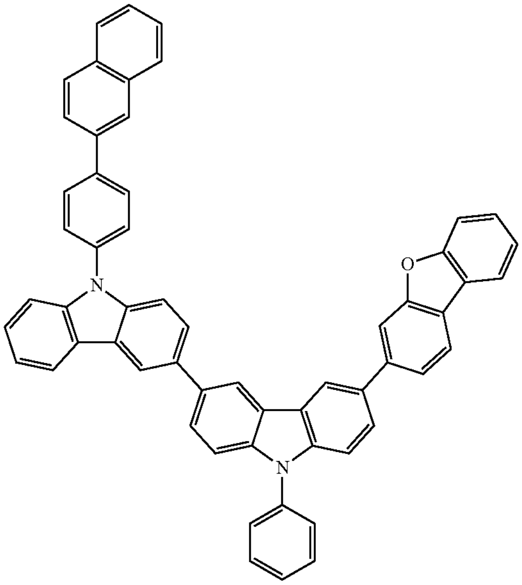
H1-135
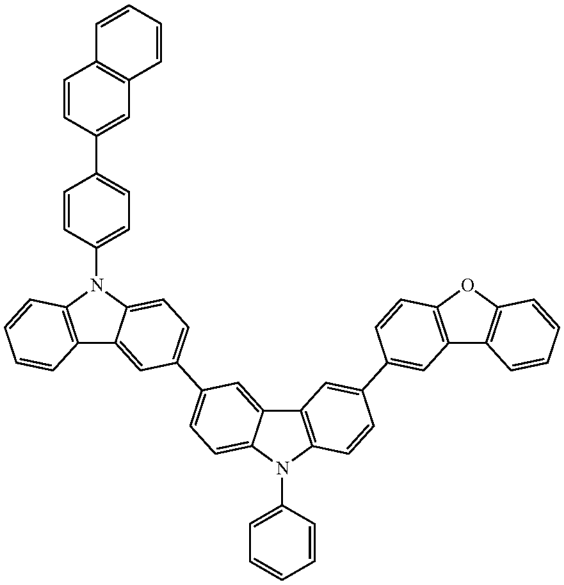
H1-136
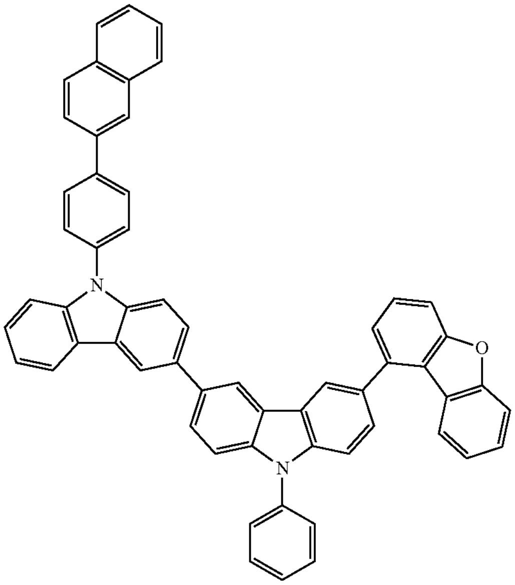

-continued
H1-137
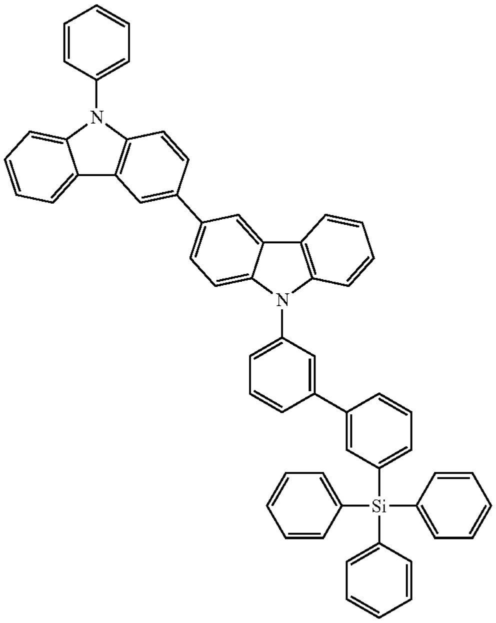
H1-138
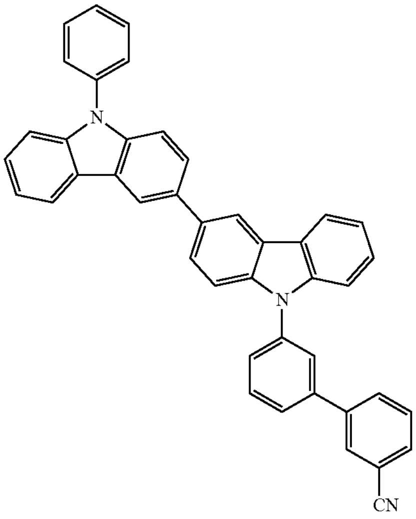
H1-139
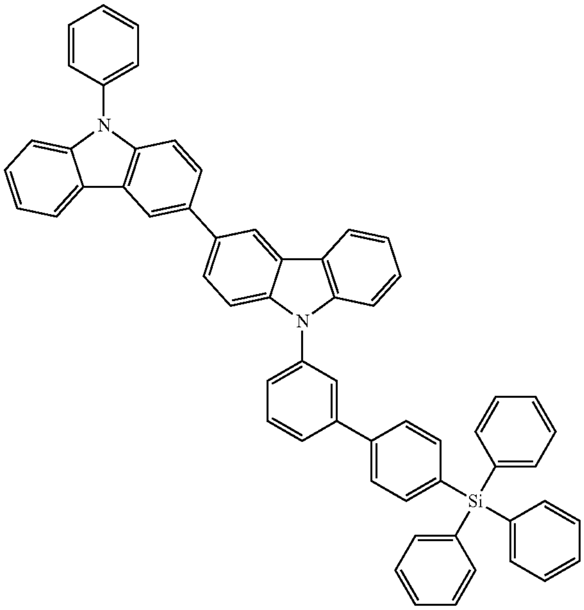

-continued
H1-141
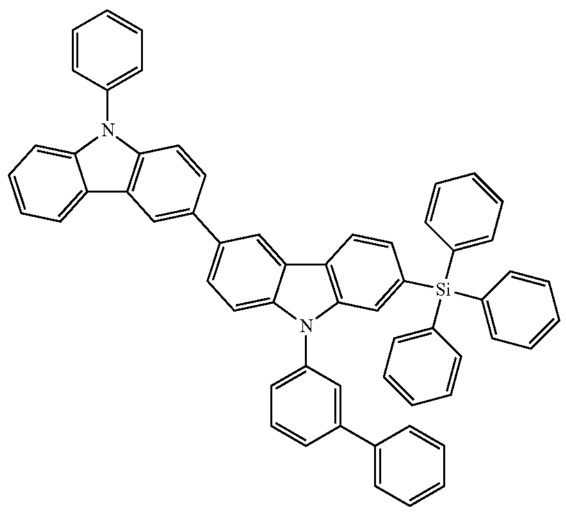
H1-142
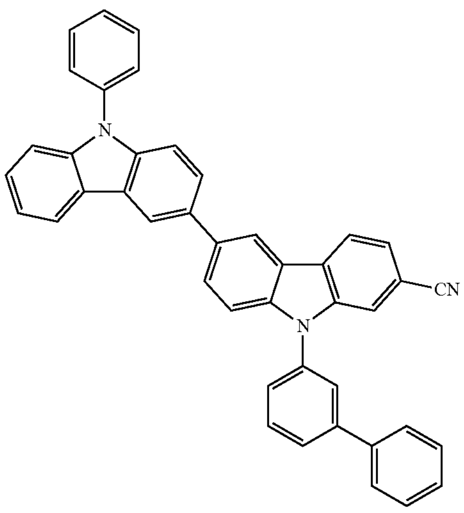
H1-143
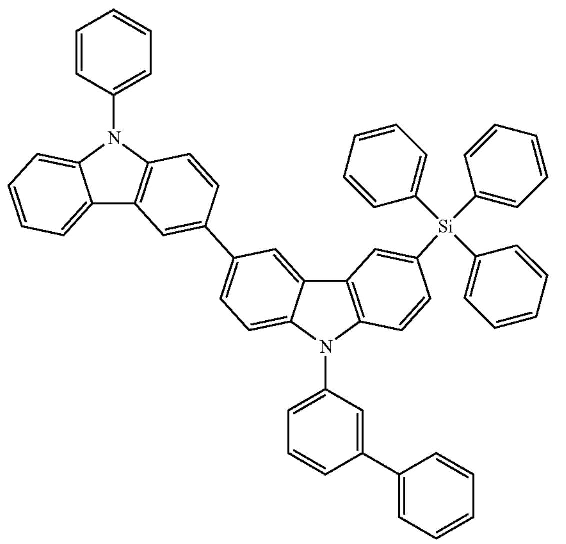
H1-144
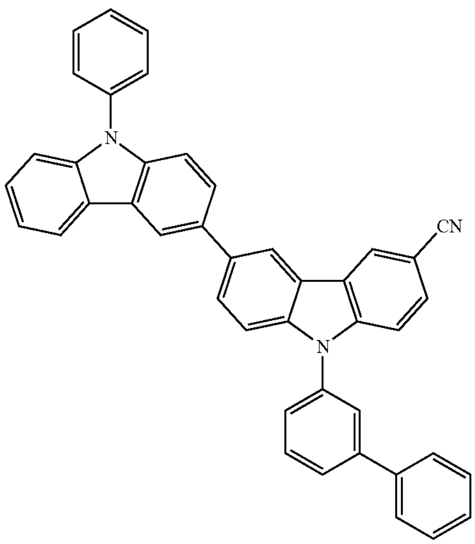

-continued
H1-145
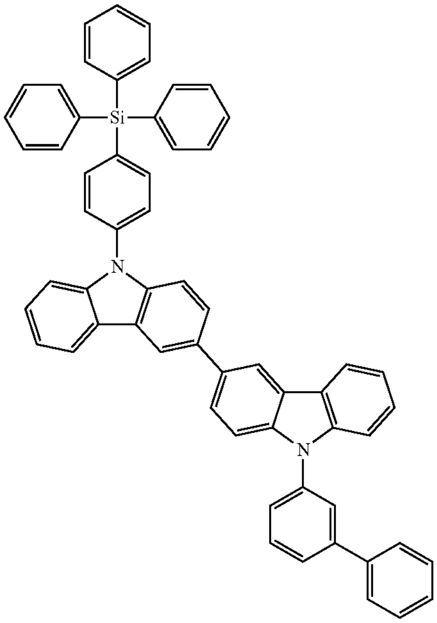
H1-147
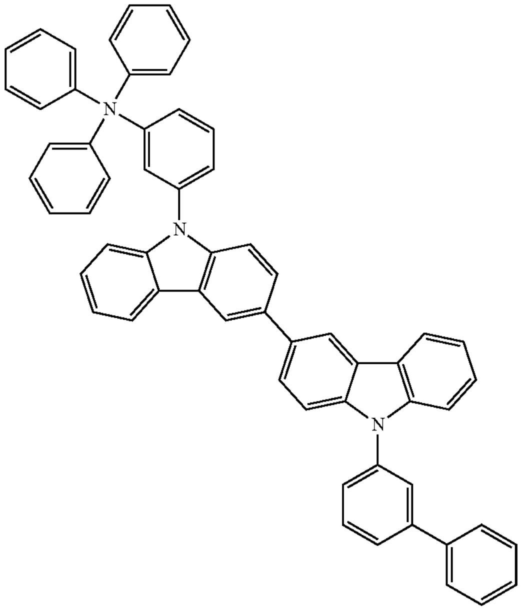
H1-149
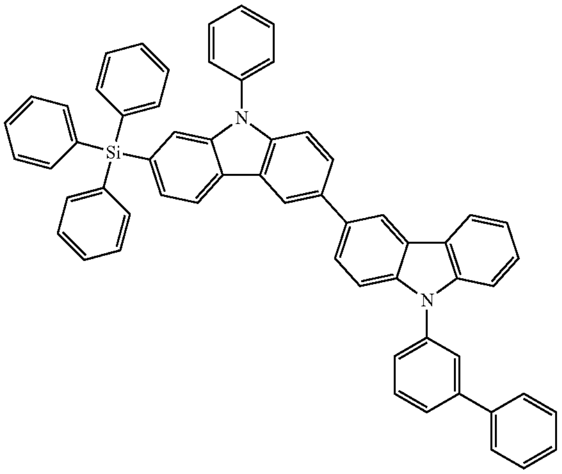
H1-150
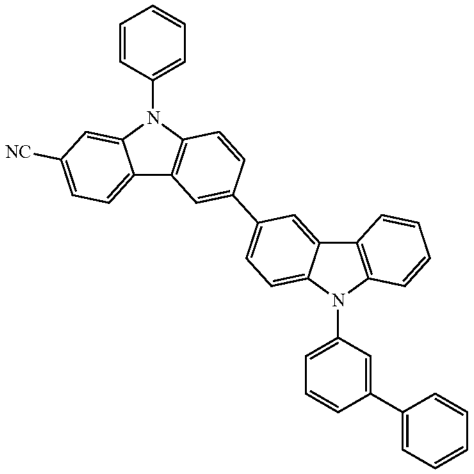
H1-151
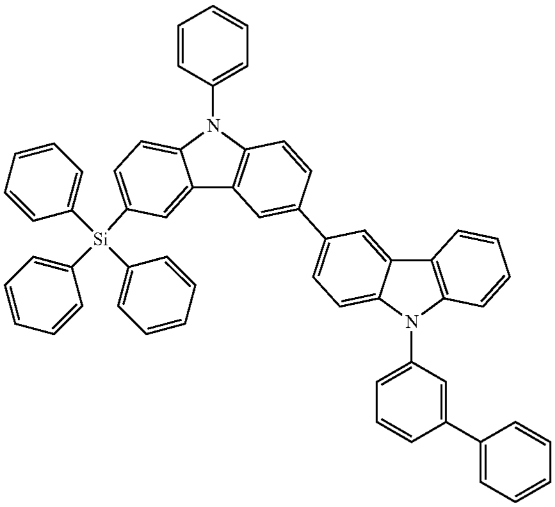
H1-152
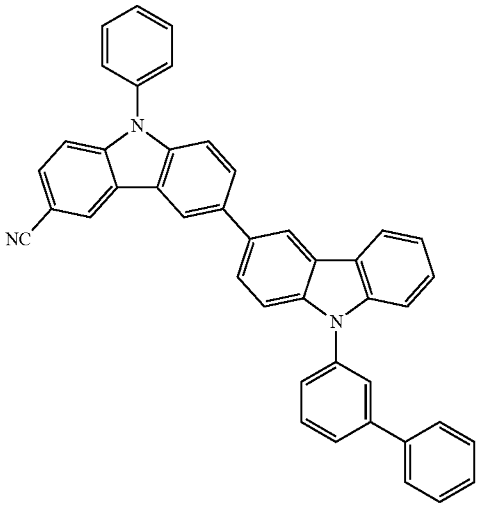

-continued
H1-153
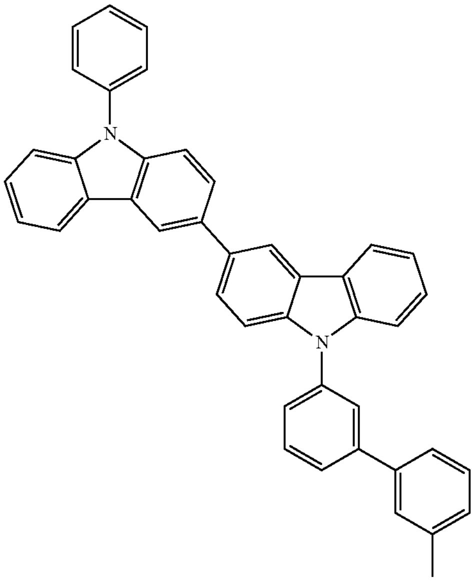
H1-154
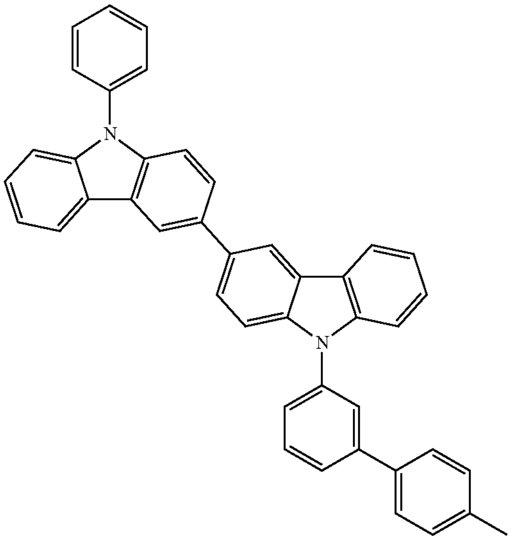
H1-155
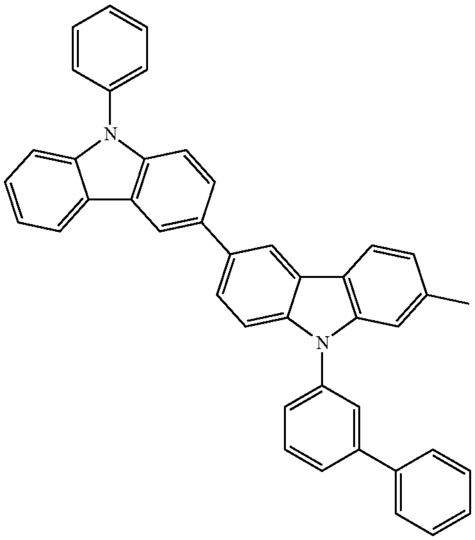
H1-156
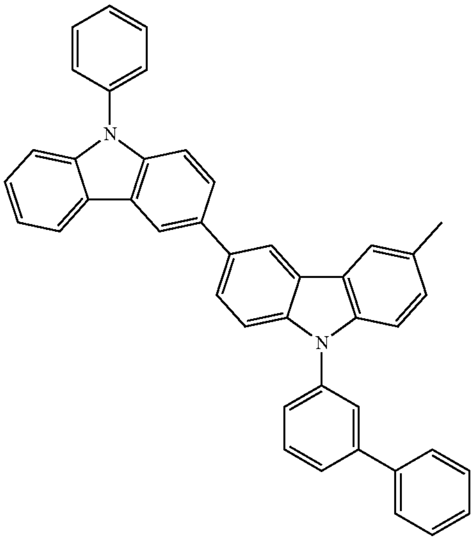

-continued
H1-157
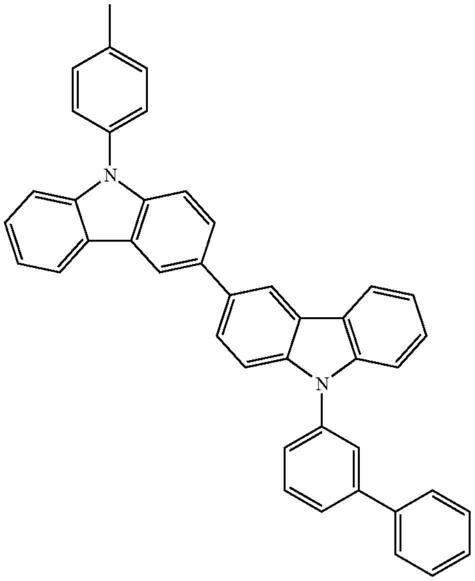
H1-158
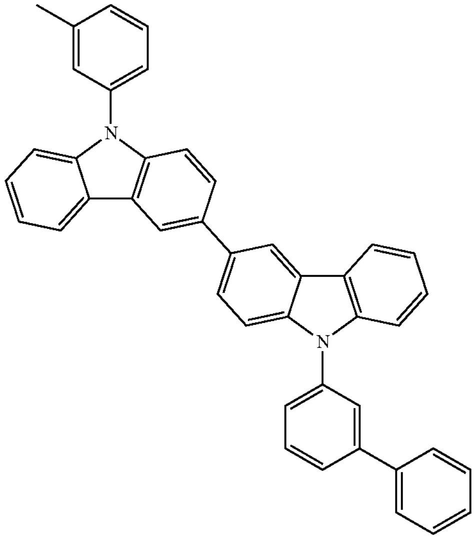
H1-159
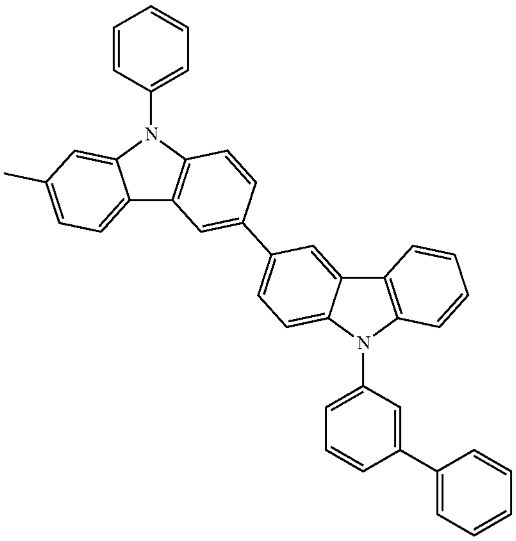
H1-160
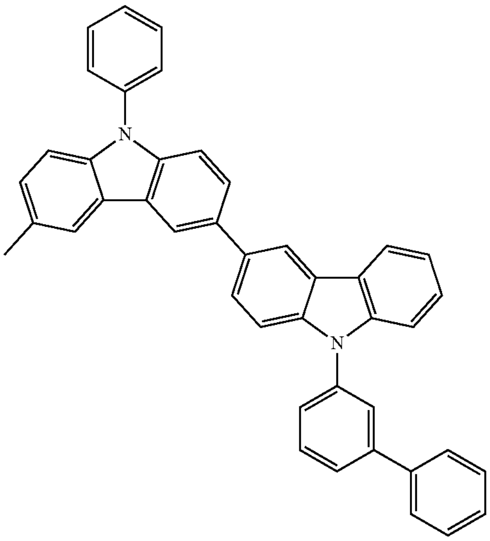

-continued
H1-161
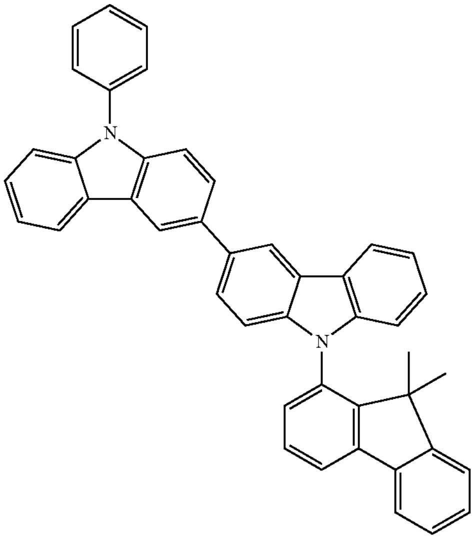
H1-162
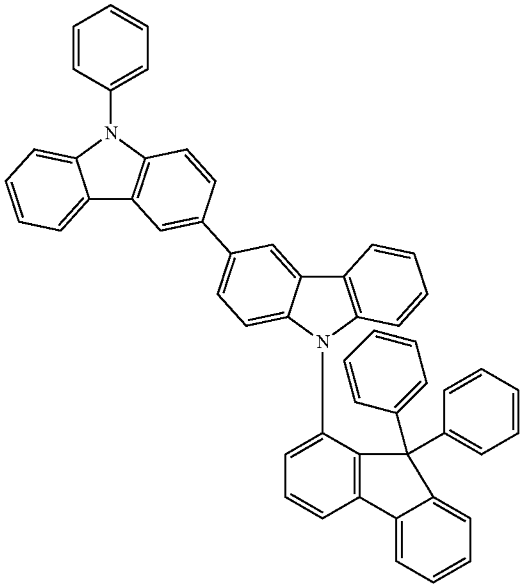
H1-163
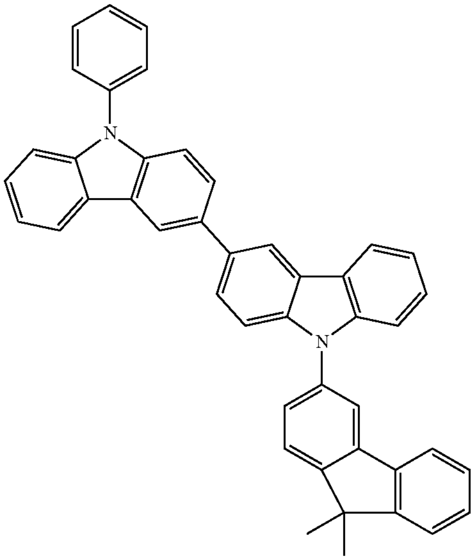
H1-164
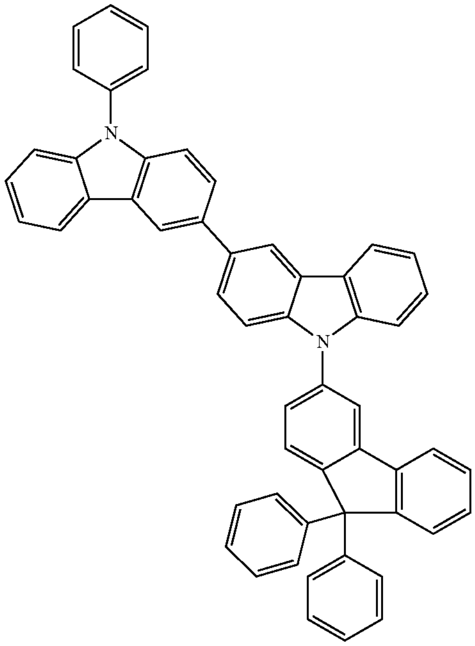

-continued
H1-169
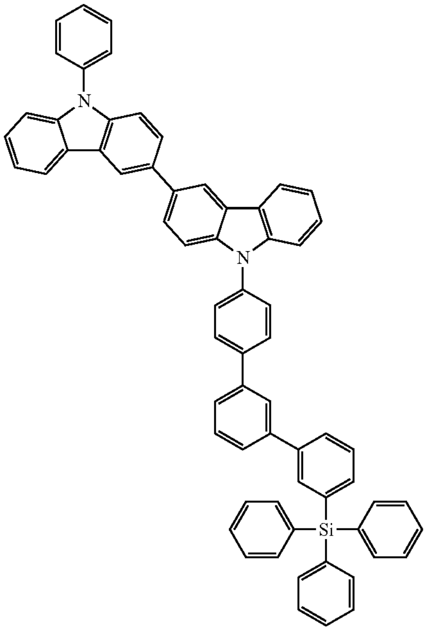
H1-171
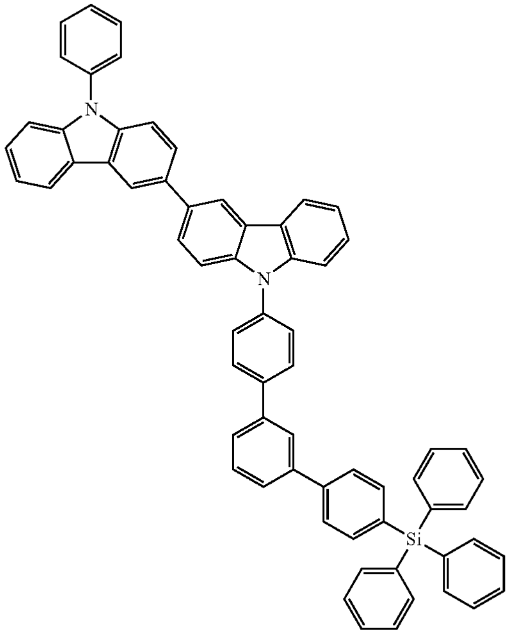
H1-173
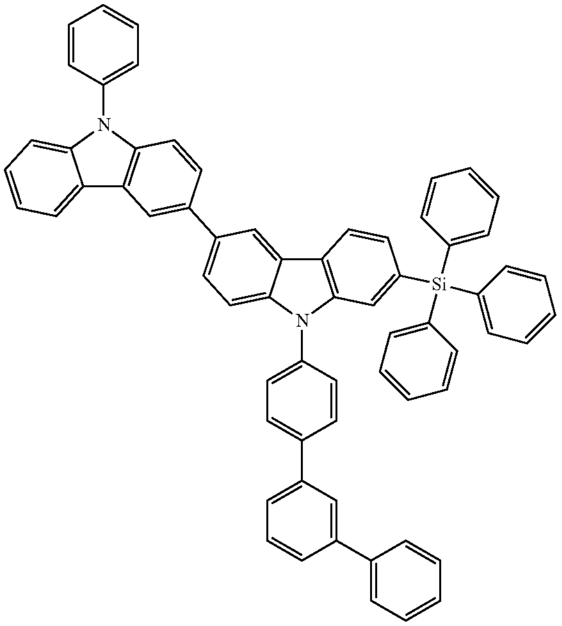
H1-174
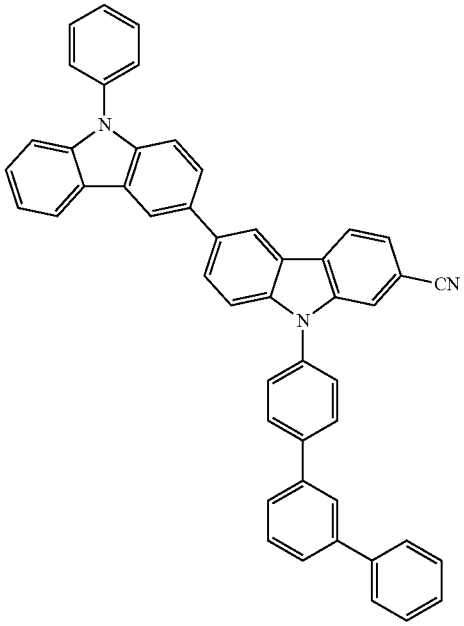

-continued
H1-175
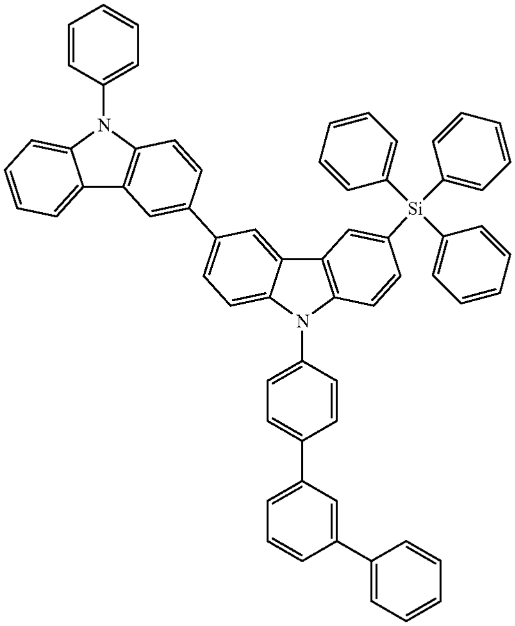
H1-176
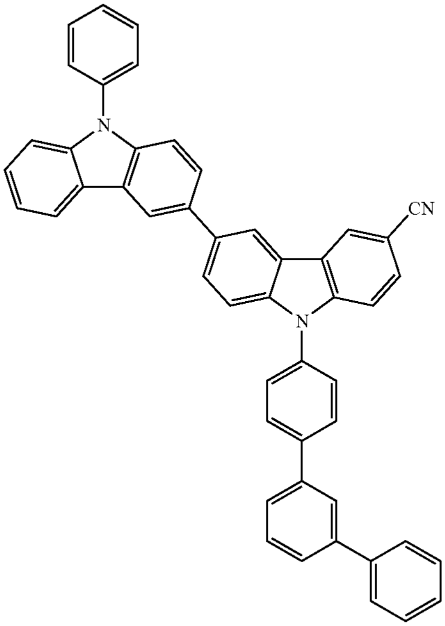
H1-177
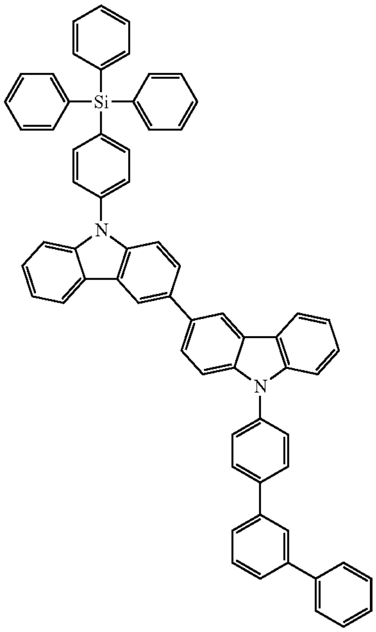
H1-179
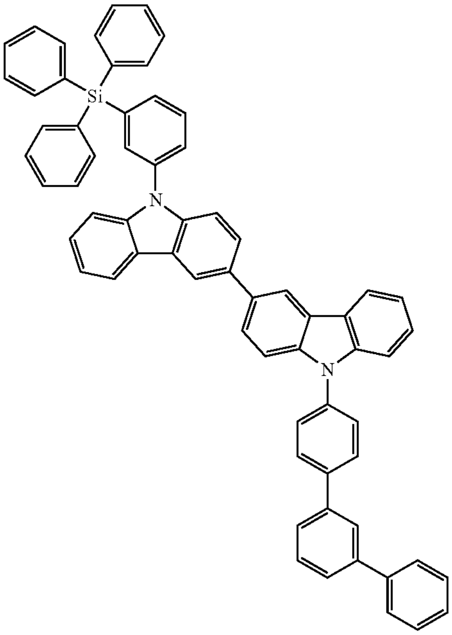

-continued
H1-181
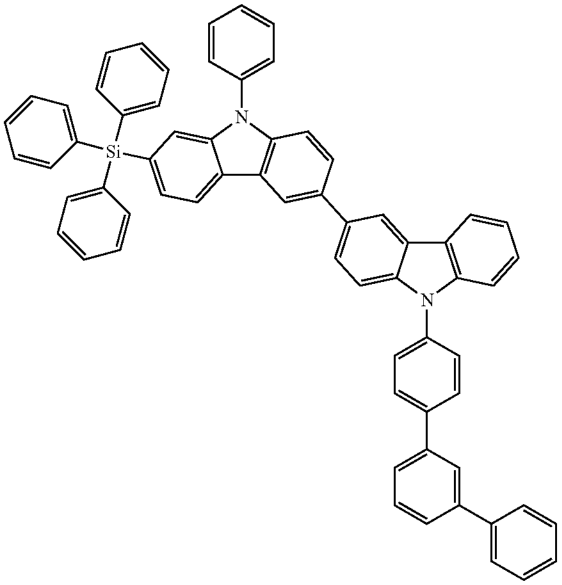
H1-182
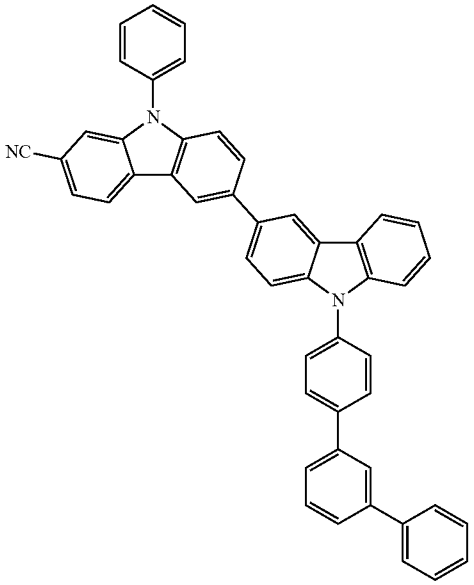
H1-183
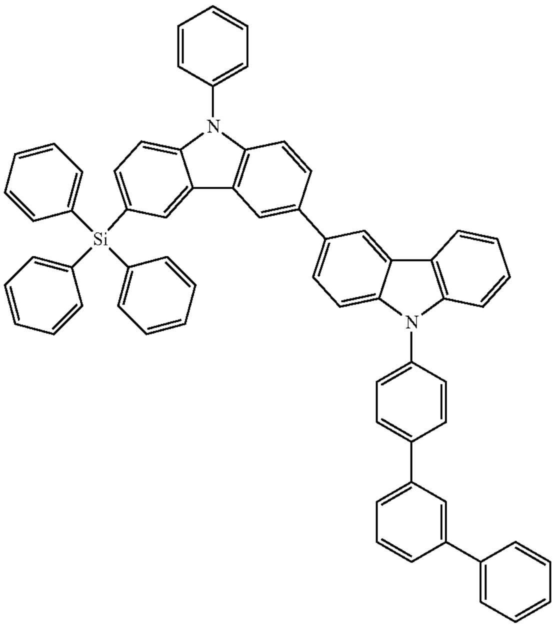
H1-184
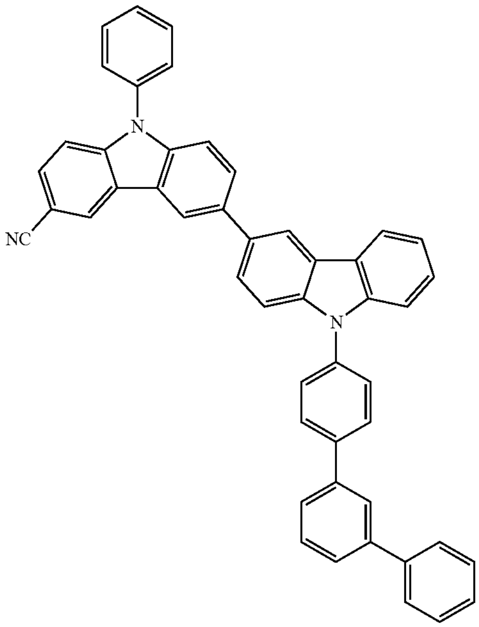

-continued
H1-185
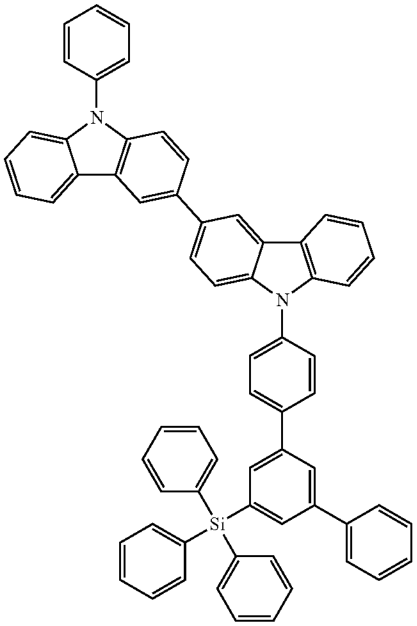
H1-187
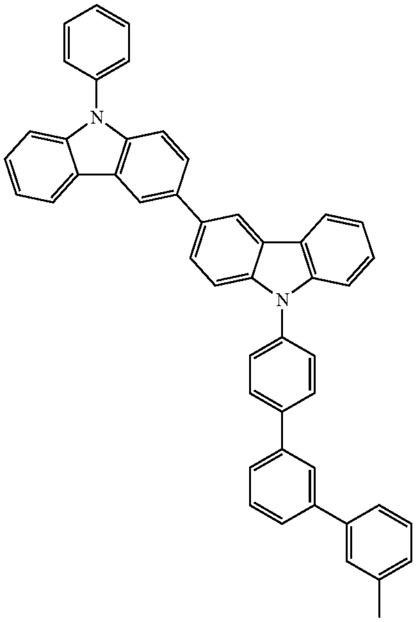
H1-188
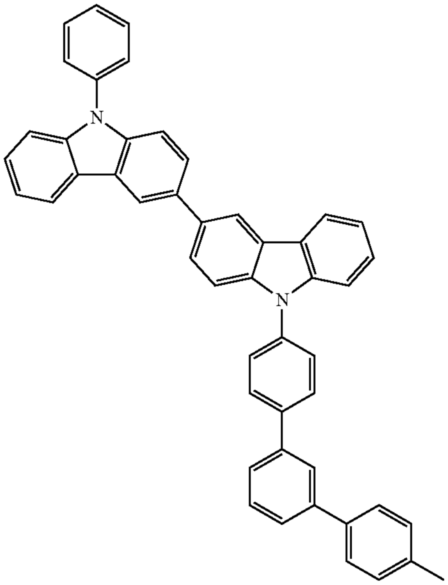

-continued
H1-189
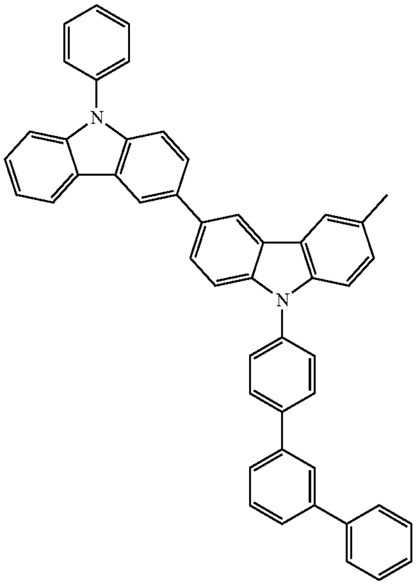
H1-190
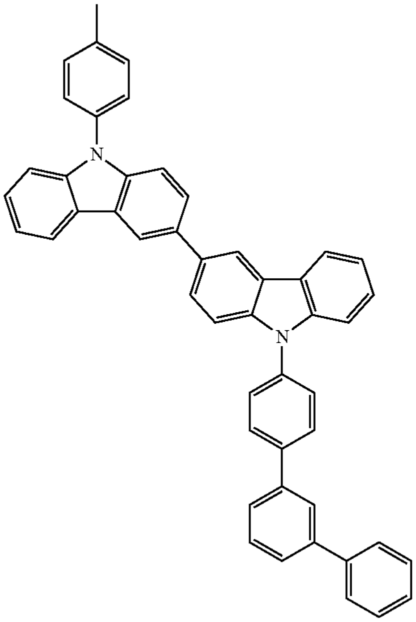
H1-191
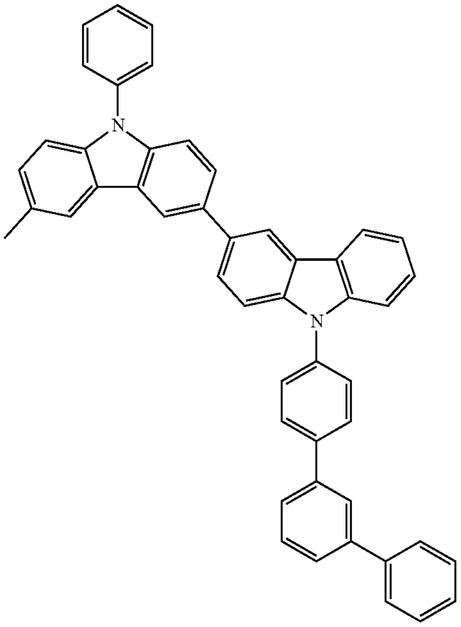
H1-192
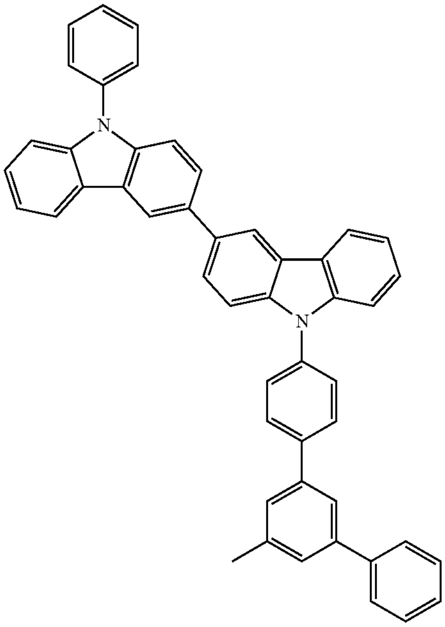

-continued
H1-193
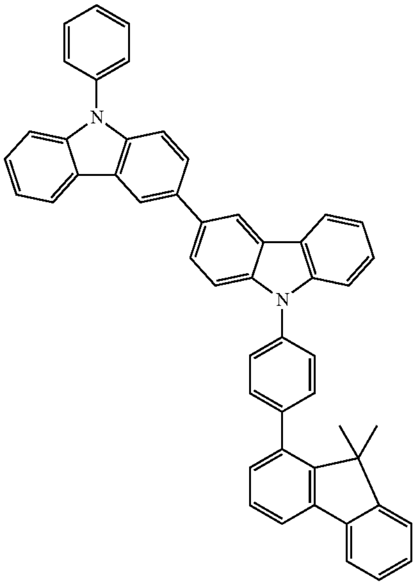
H1-194
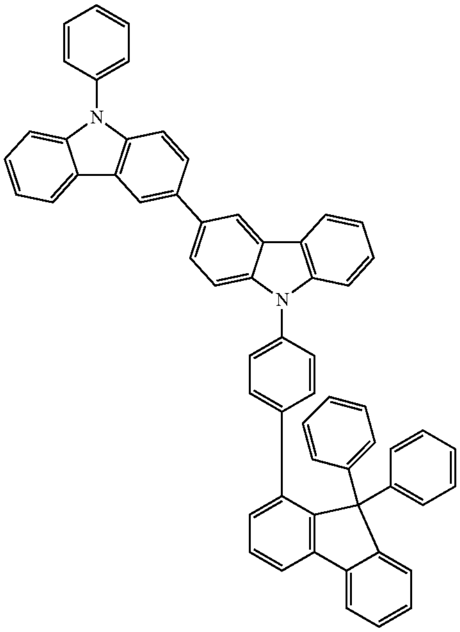
H1-195
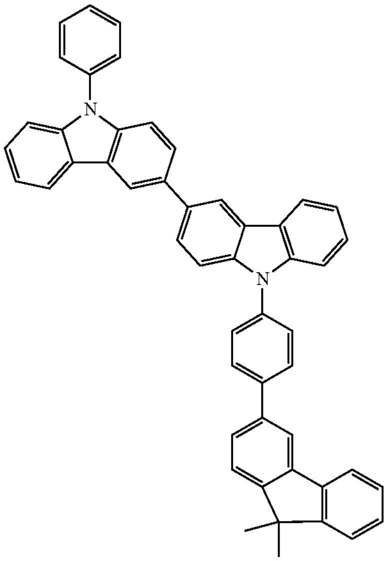
H1-196
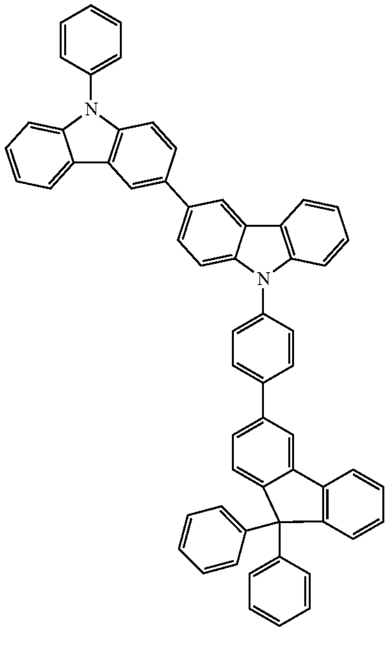

-continued
H1-201
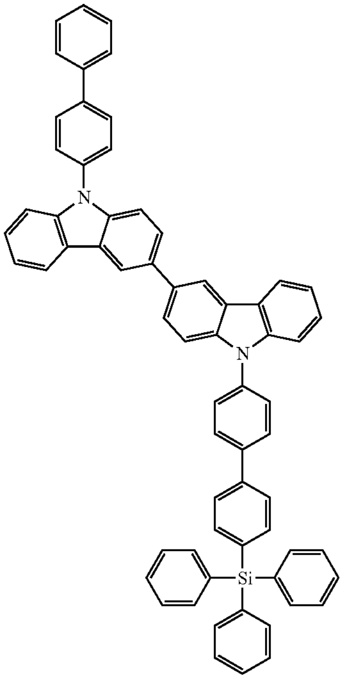
H1-203
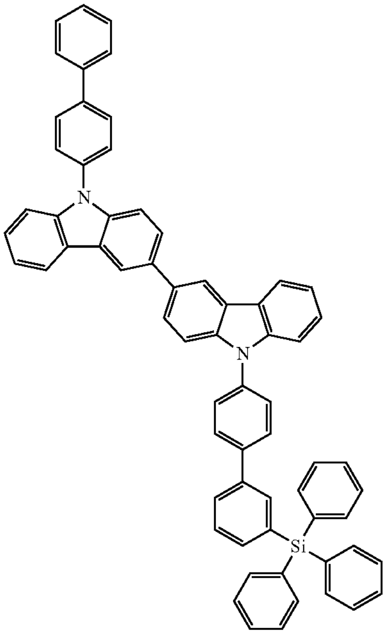
H1-205
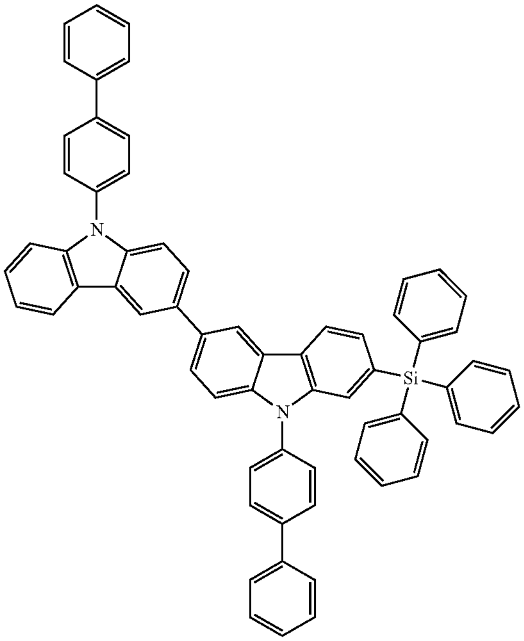
H1-206
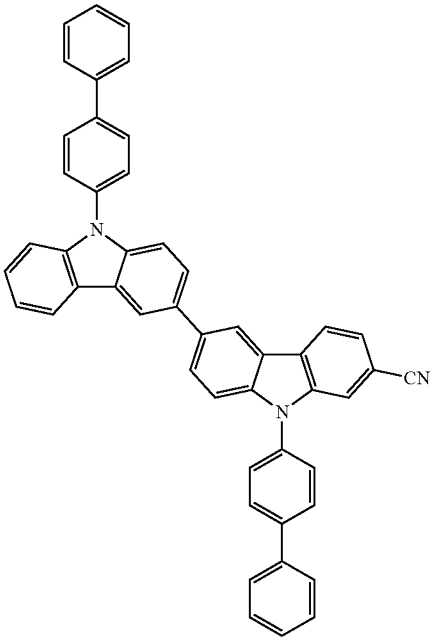

-continued
H1-207
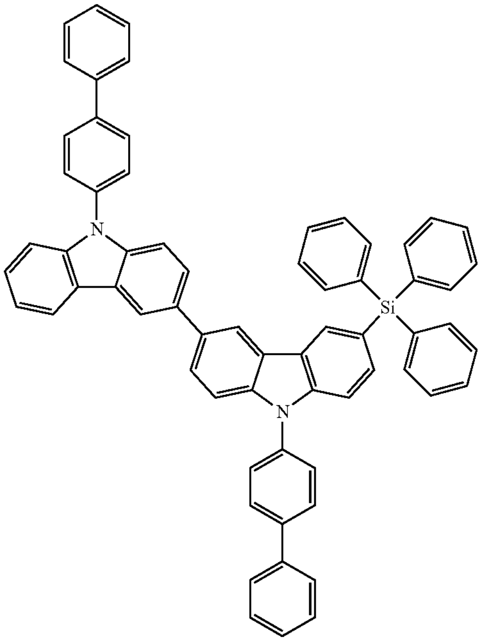
H1-208
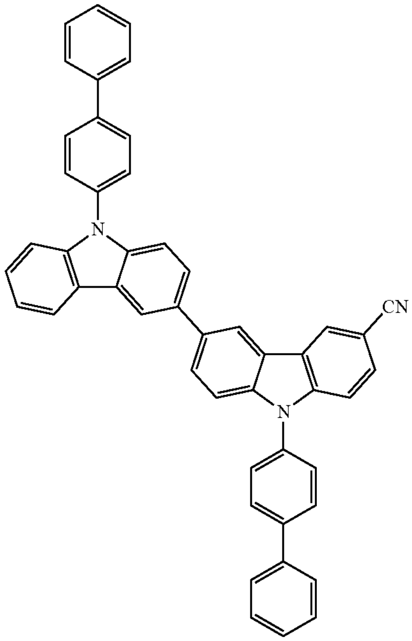
H1-209
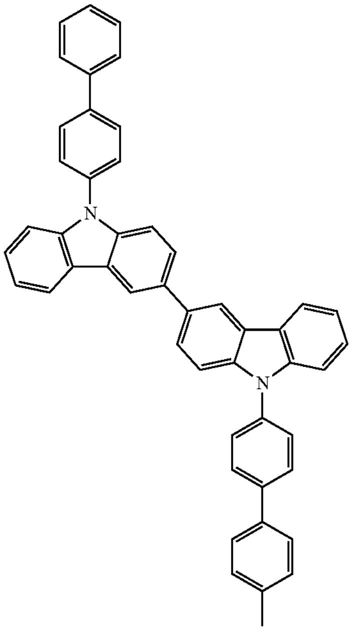
H1-210
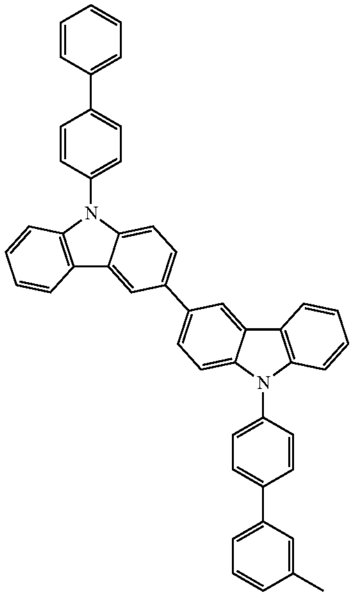

-continued
H1-211
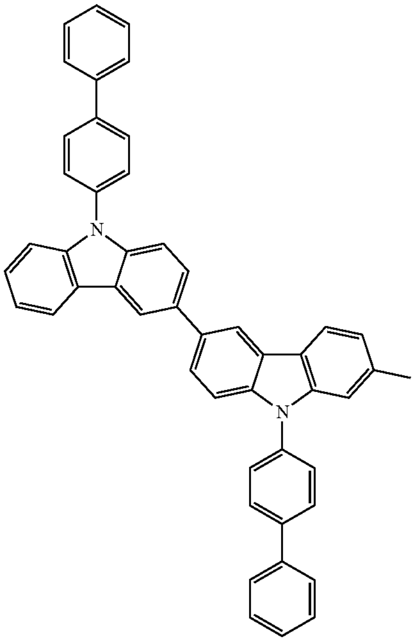
H1-212
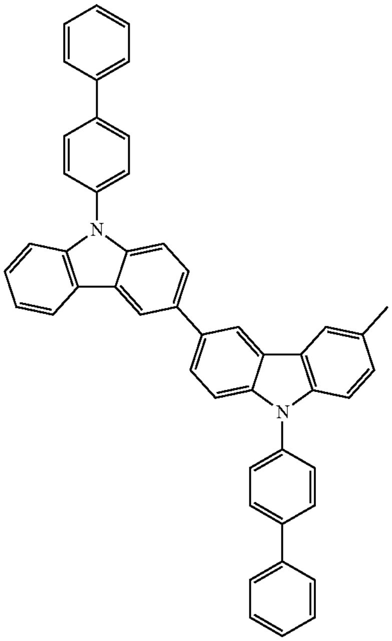
H1-213
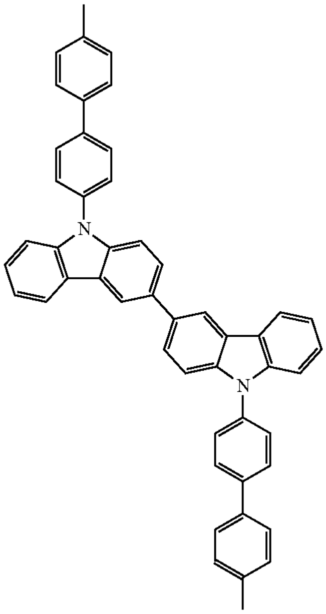
H1-214
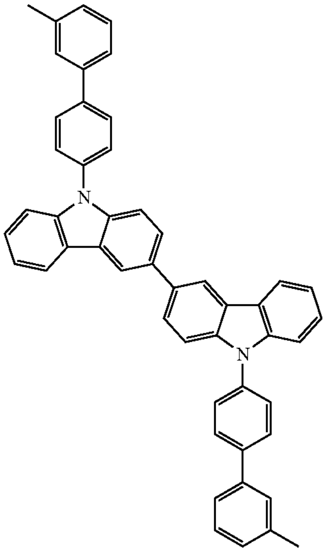

-continued
H1-215
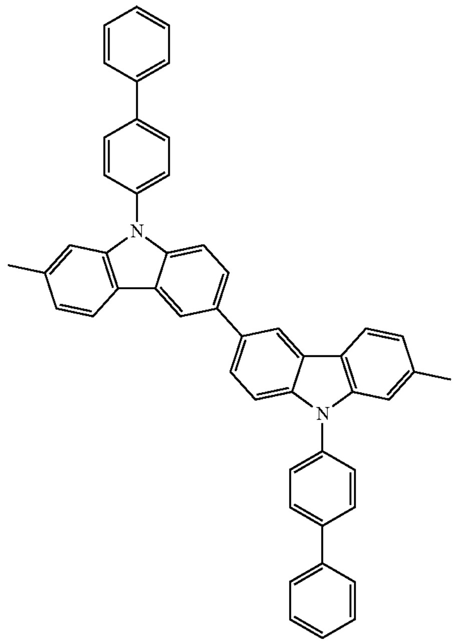
H1-216
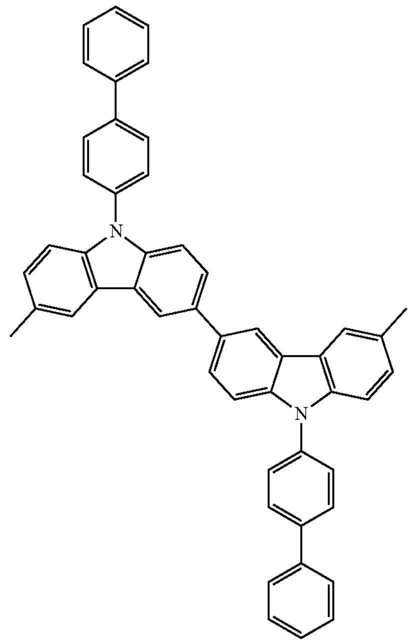
H1-217
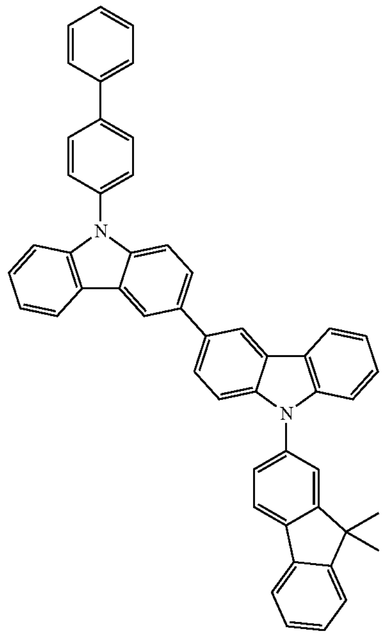
H1-218
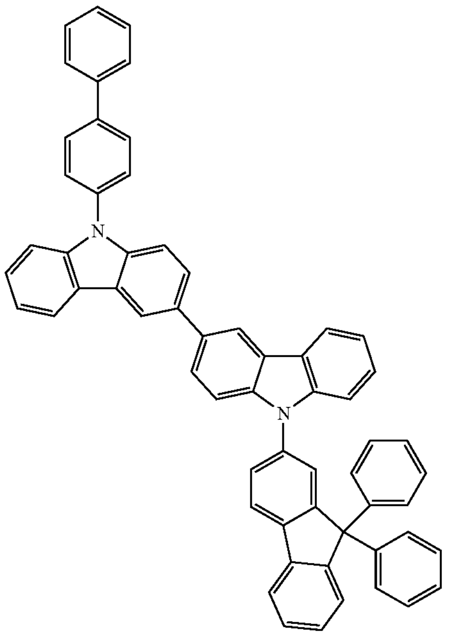

-continued
H1-219
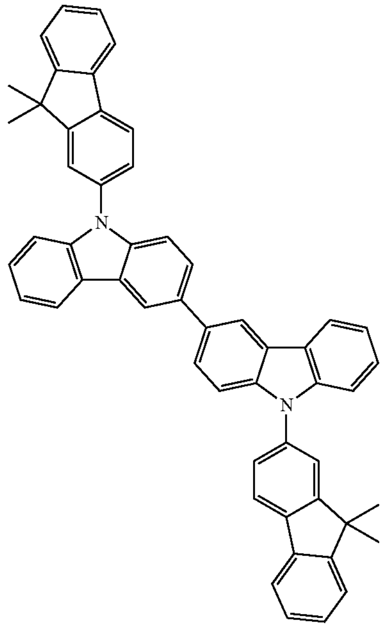
H1-220
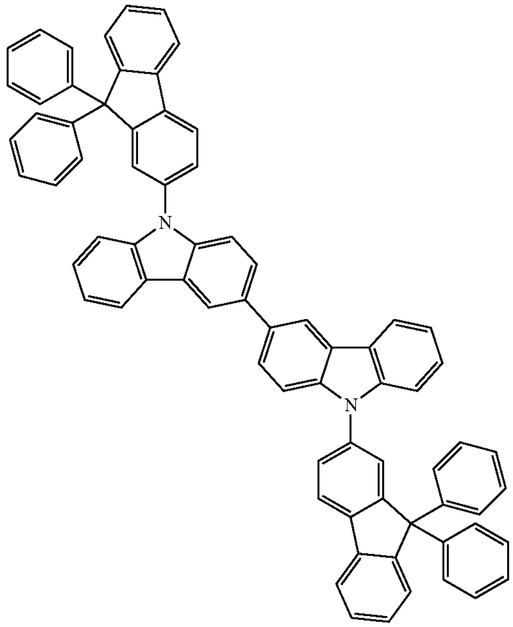
H1-221
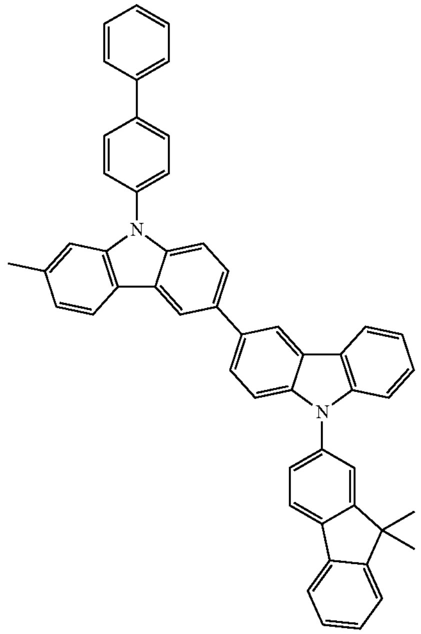
H1-222
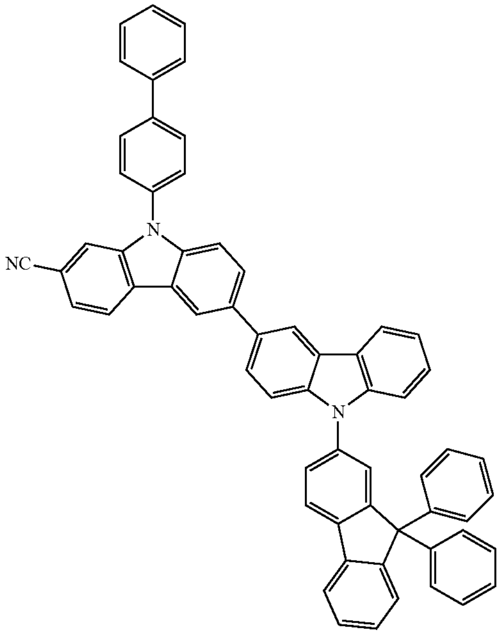

-continued
H1-223
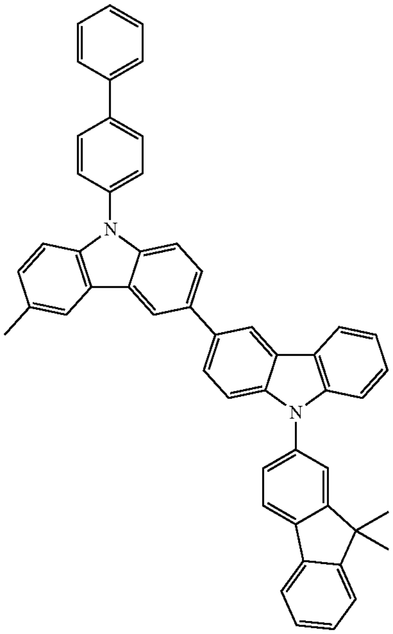
H1-224
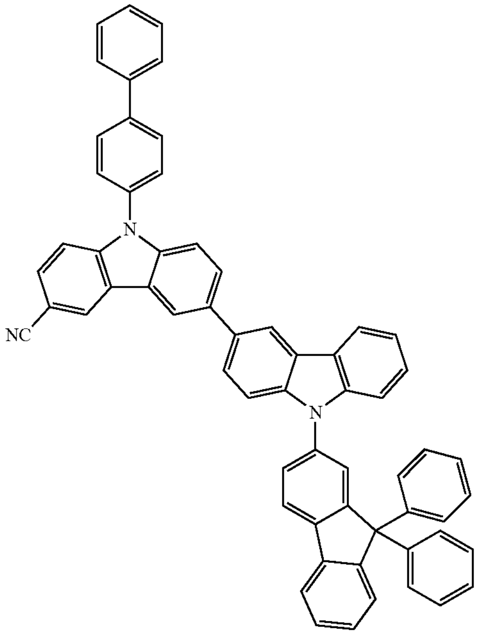
H1-225
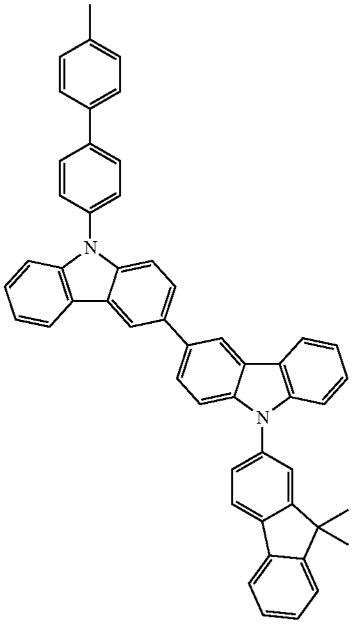
H1-226
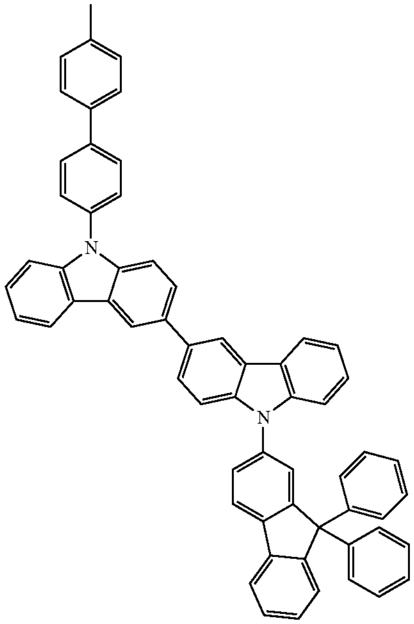

-continued
H1-227
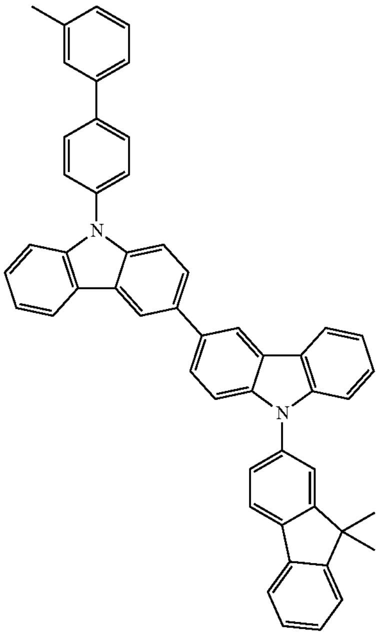
H1-228
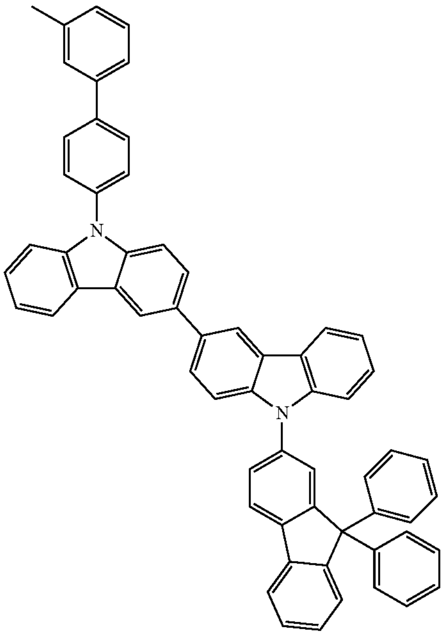
H1-233
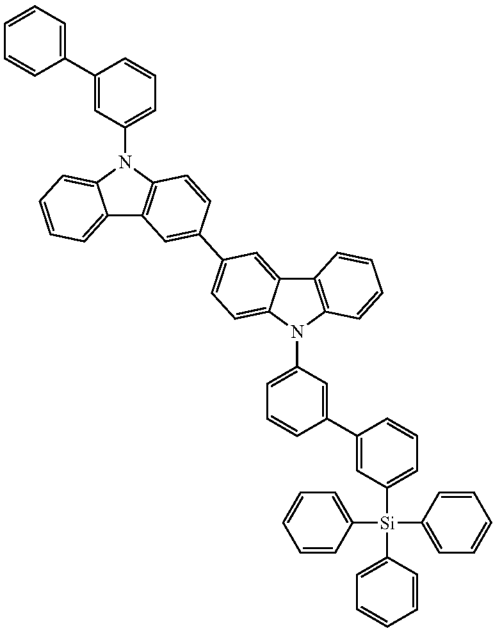
H1-235
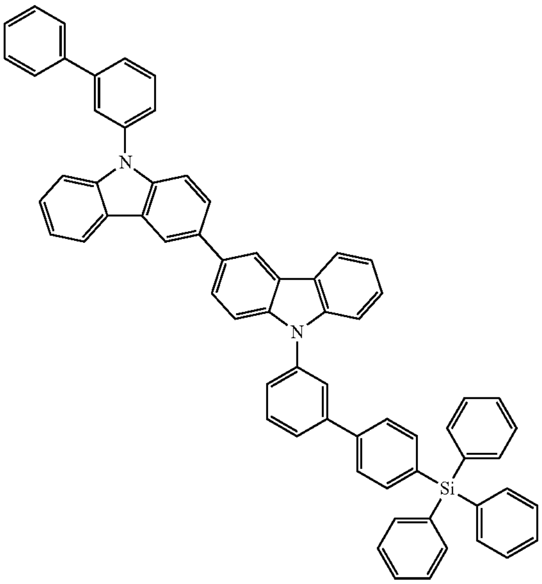

-continued
H1-237
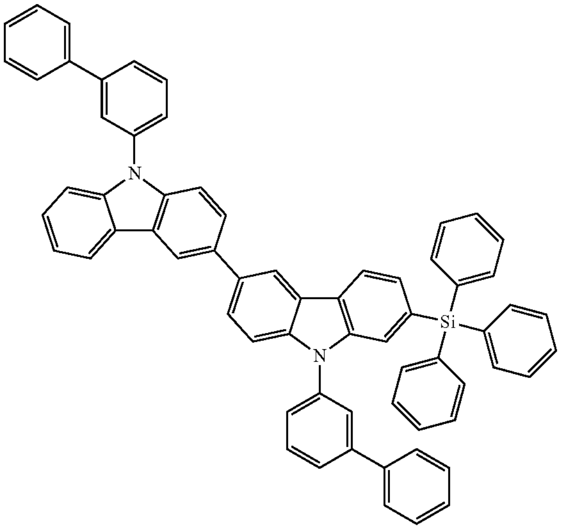
H1-238
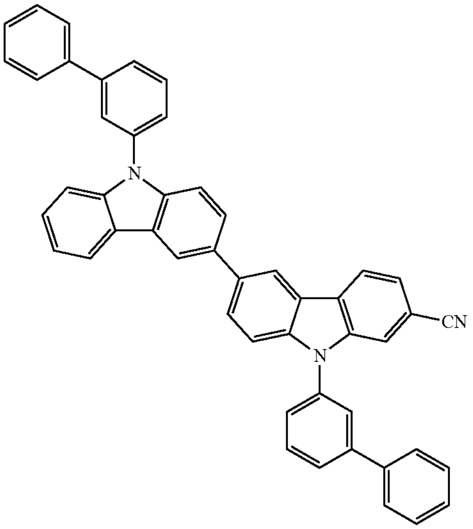
H1-239
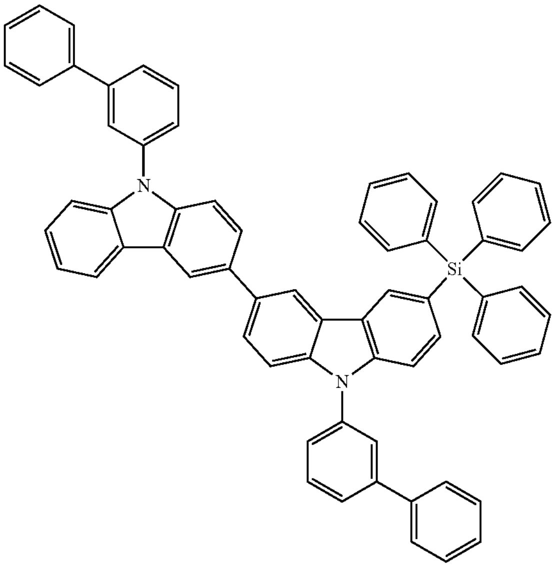
H1-240
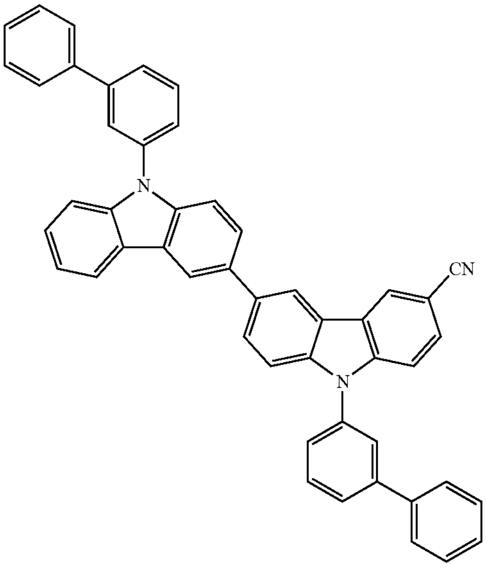

-continued
H1-241
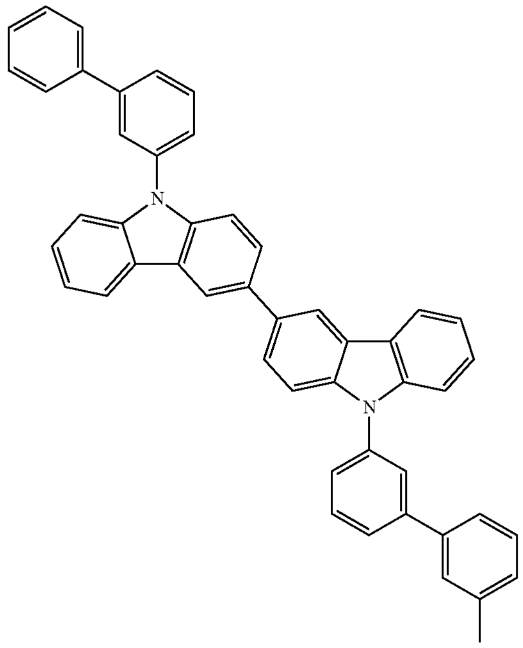
H1-242
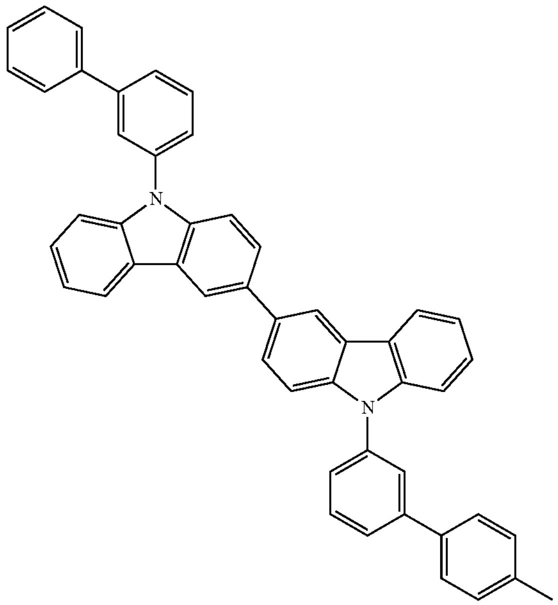
H1-234
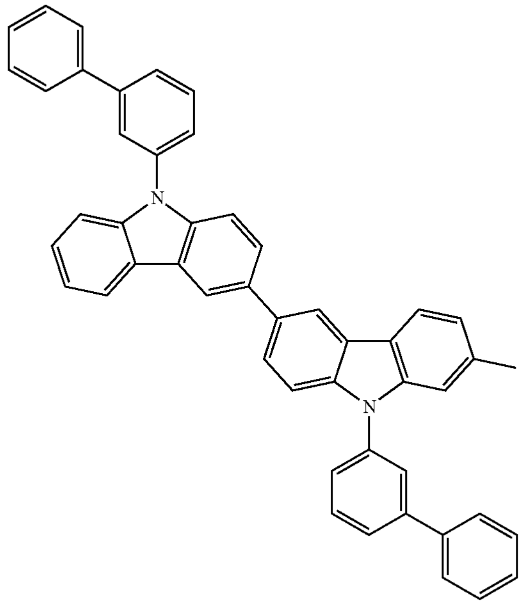
H1-244
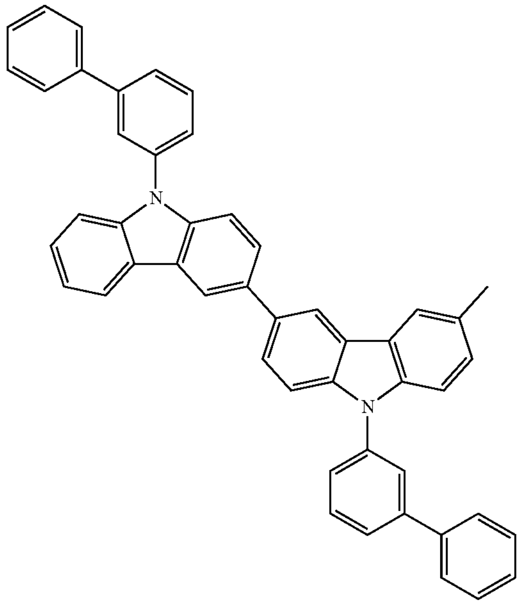

-continued
H1-245
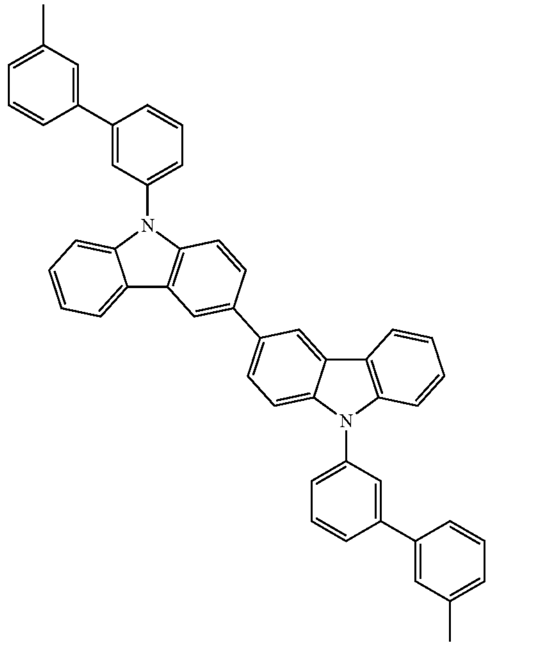
H1-246
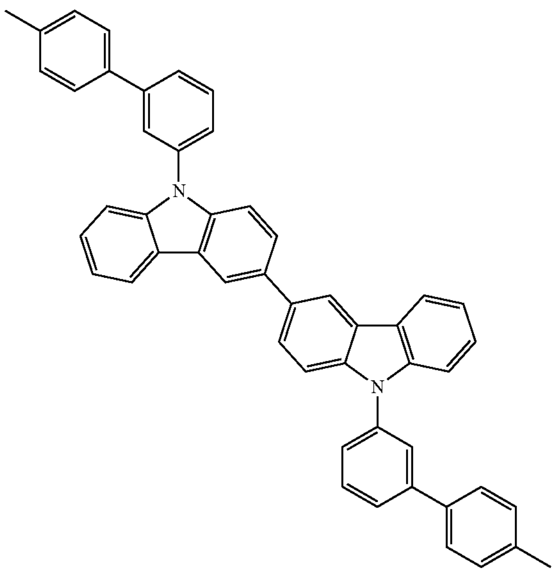
H1-247
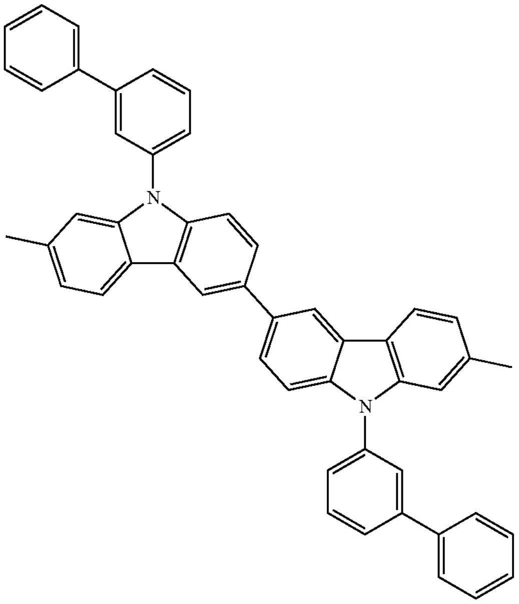
H1-248
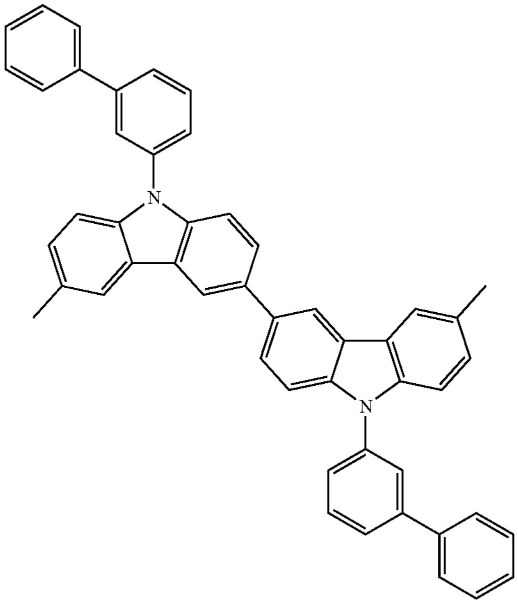

-continued
H1-249
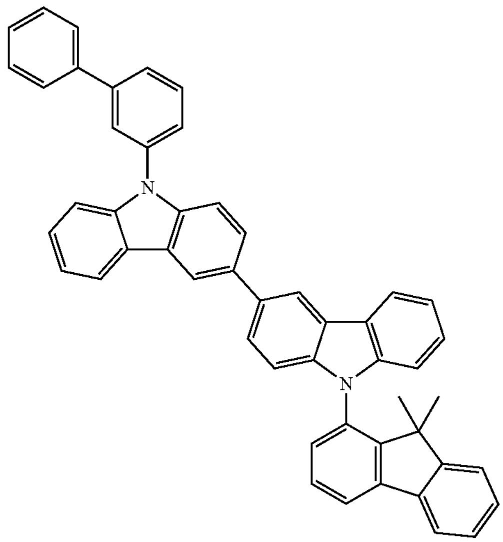
H1-250
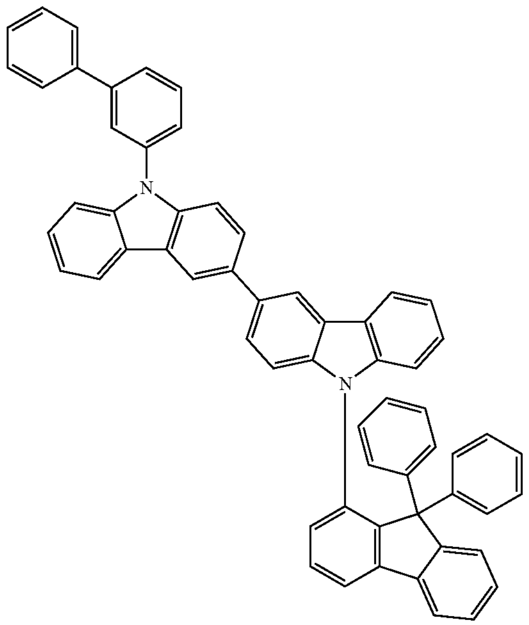
H1-251
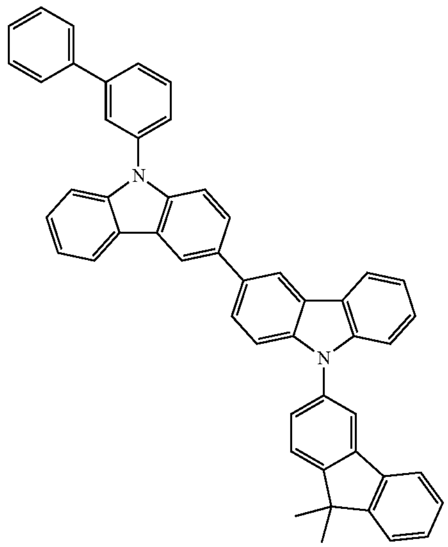
H1-252
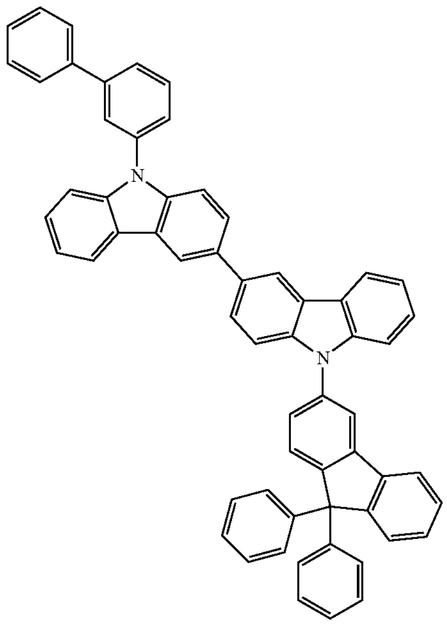

-continued
H1-253
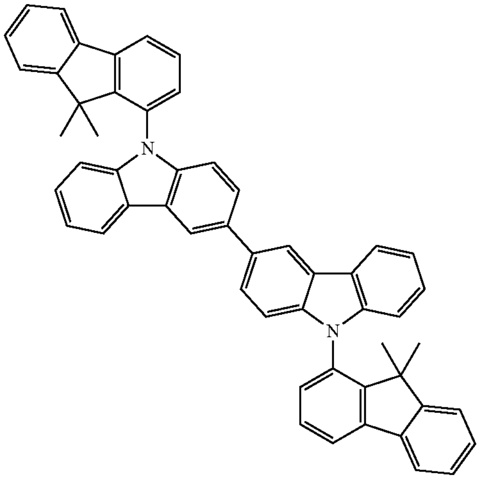
H1-254
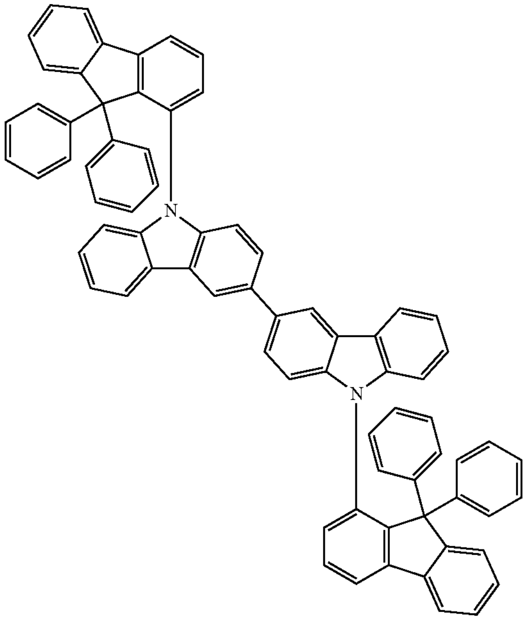
H1-255
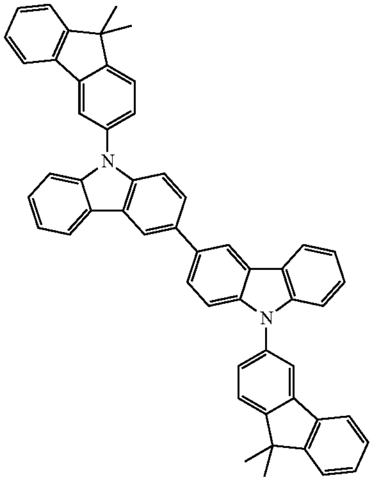
H1-256
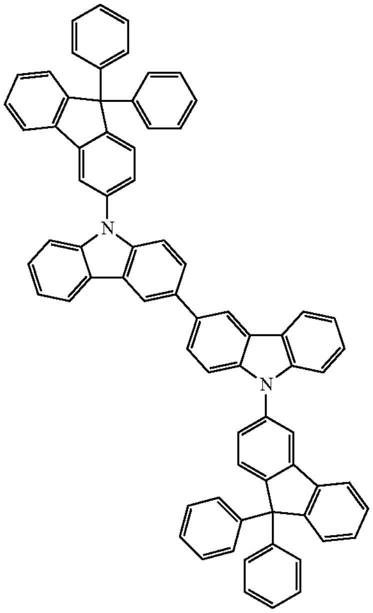

-continued
H1-257
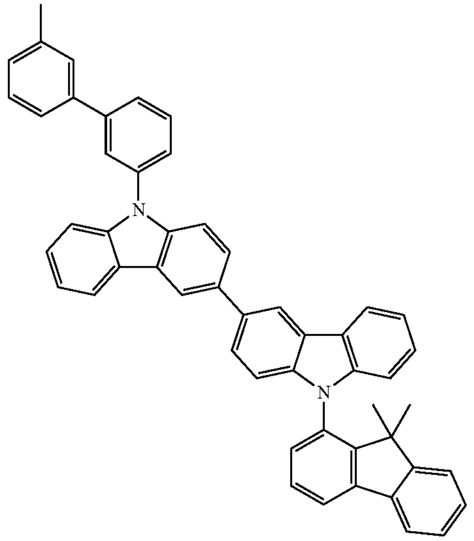
H1-258
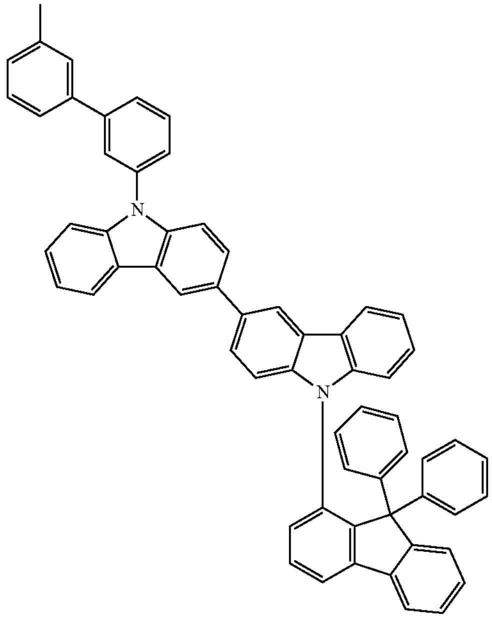
H1-259
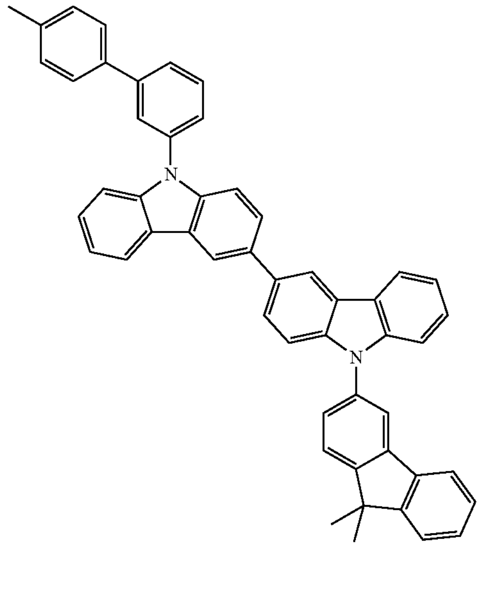
H1-260
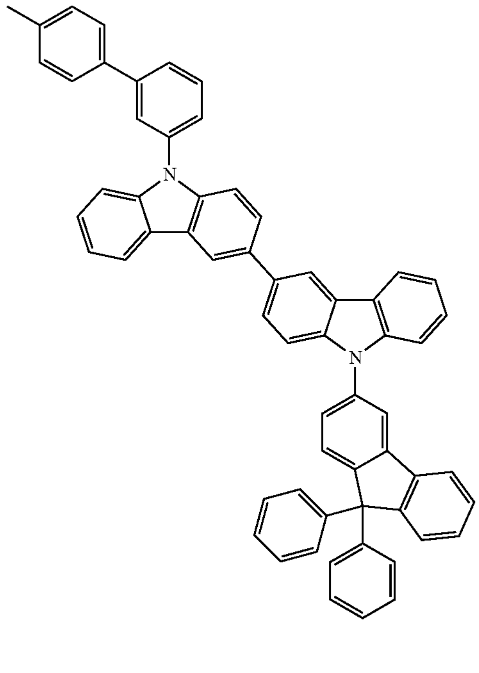

-continued
H1-265
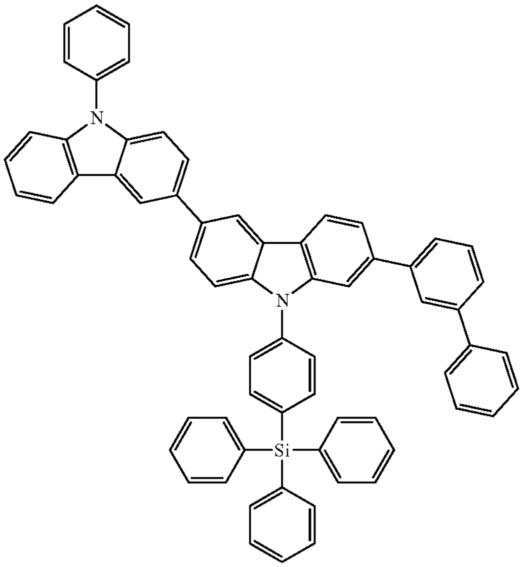
H1-267
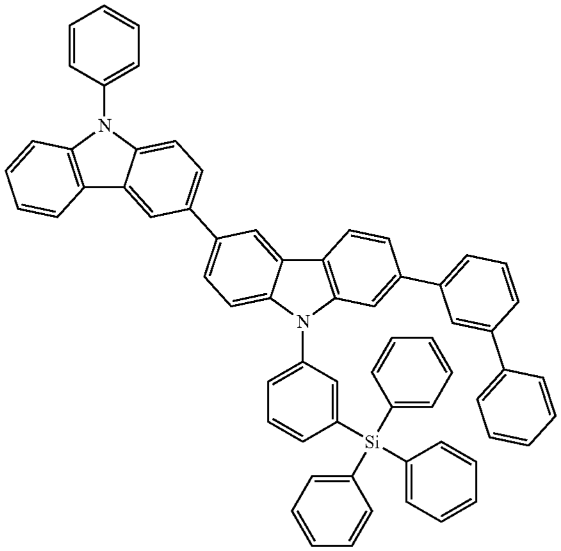
H1-269
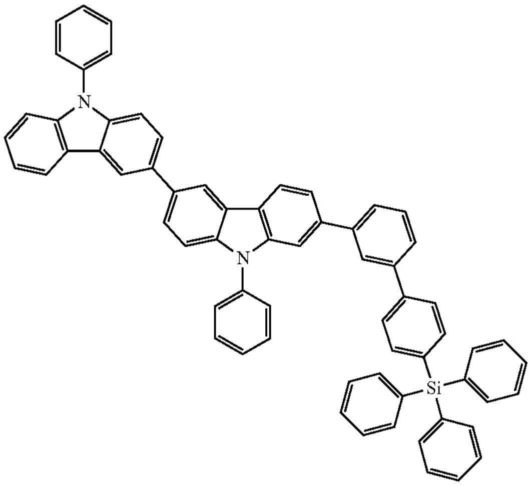
H1-270
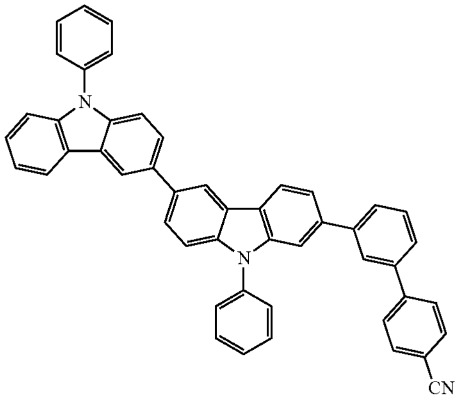
H1-271
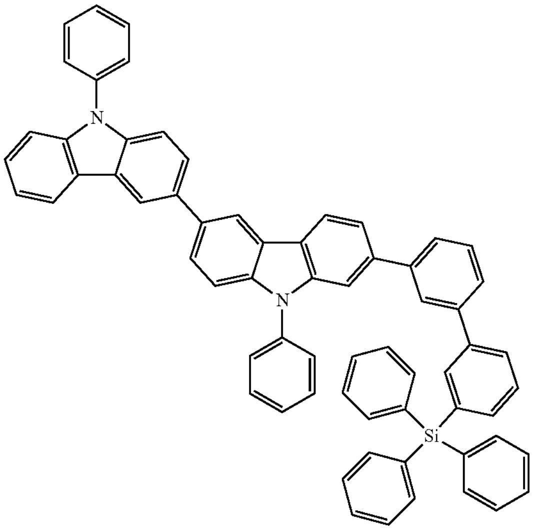
H1-272
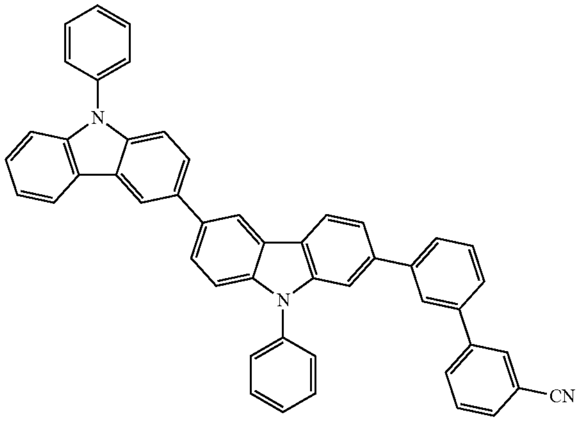

-continued
H1-273
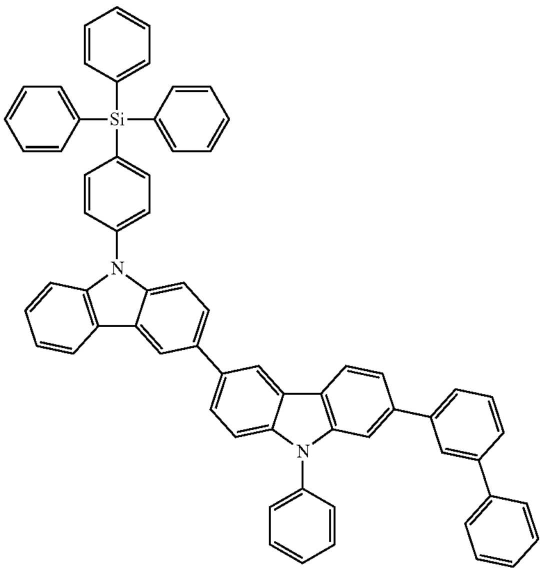
H1-275
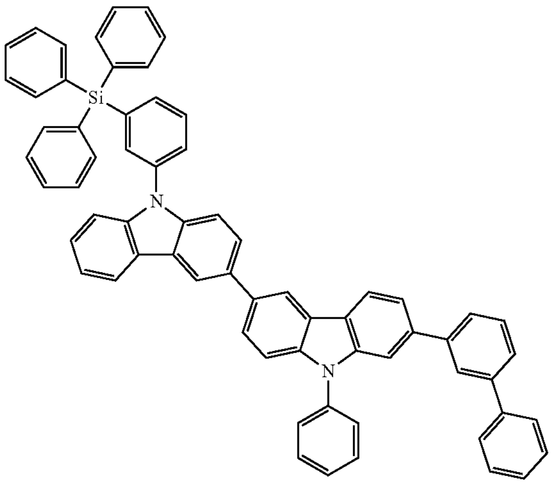
H1-277
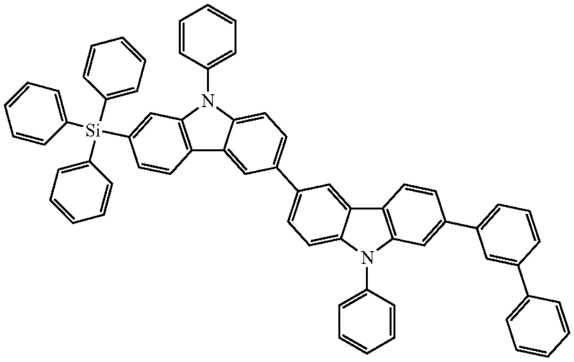
H1-278
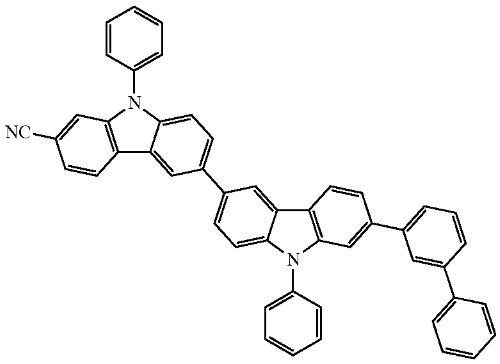
H1-279
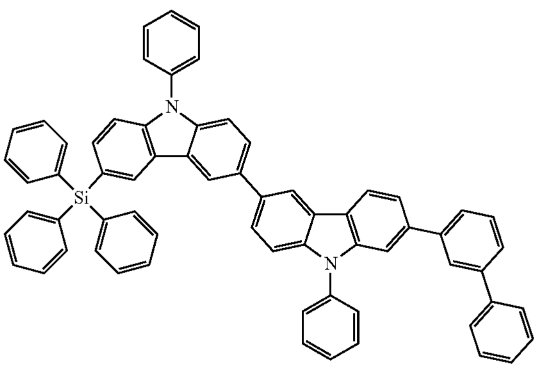
H1-280
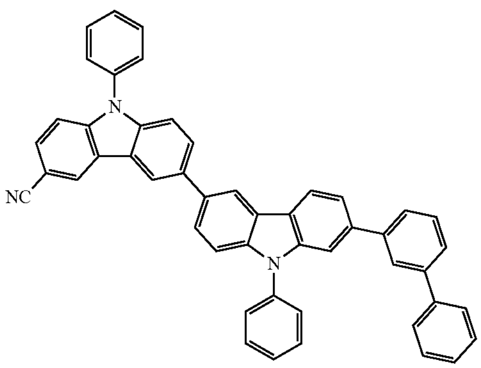

-continued
H1-281
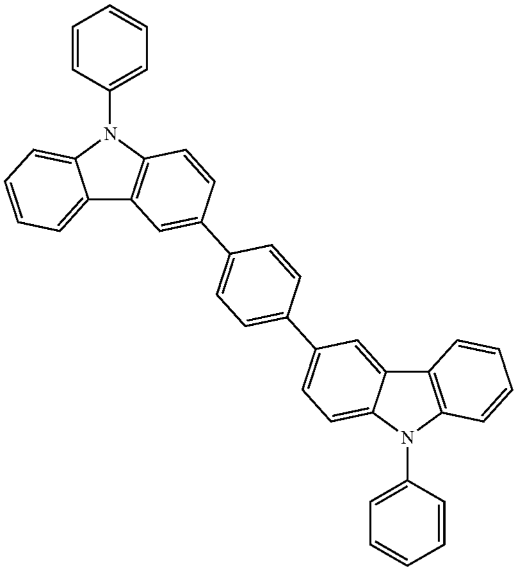
H1-282
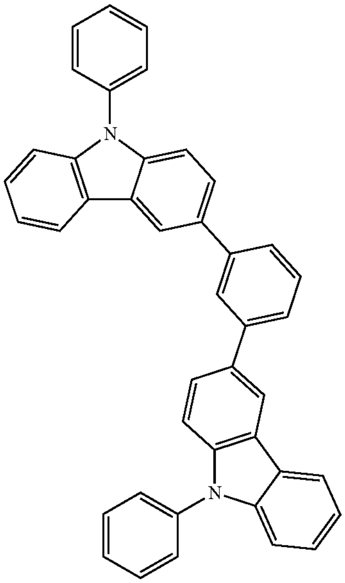
H1-283
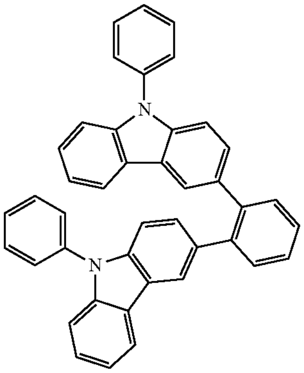
H1-284
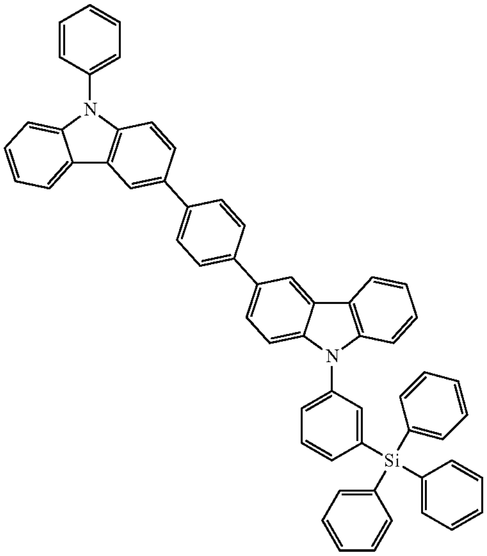
H1-285
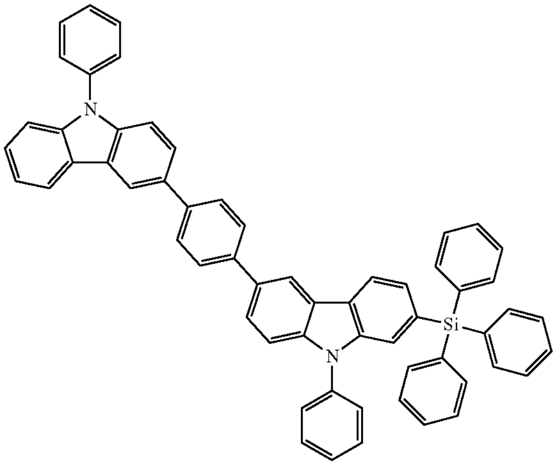
H1-286
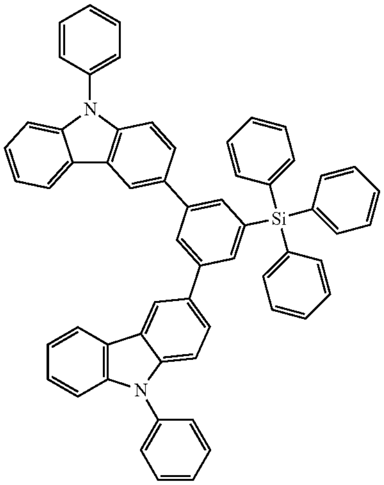

-continued
H1-287
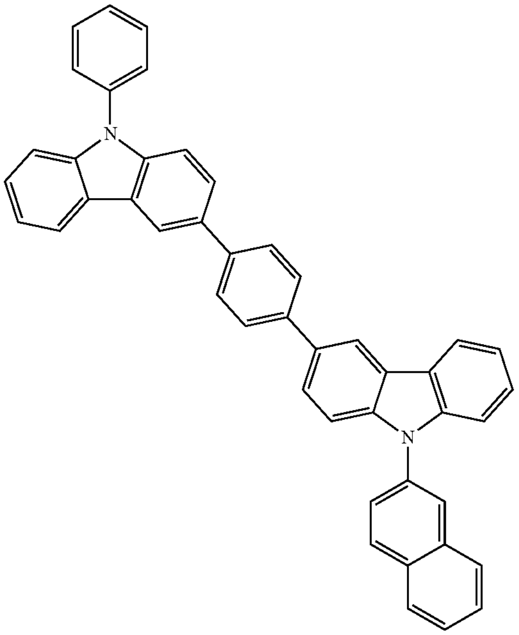
H1-288
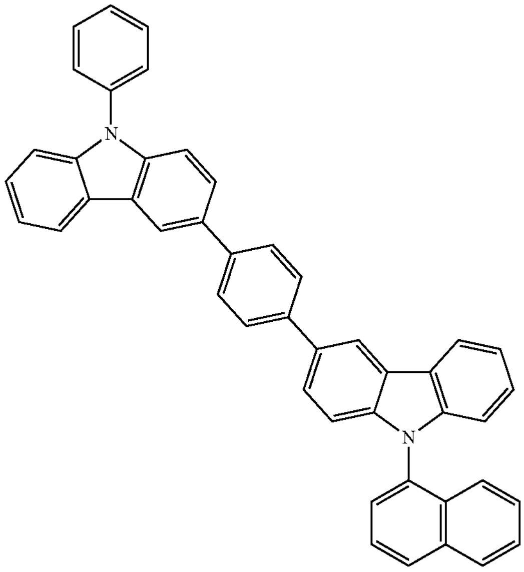
H1-289
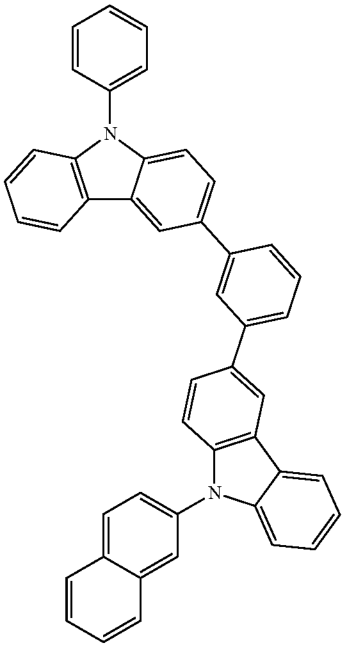
H1-290
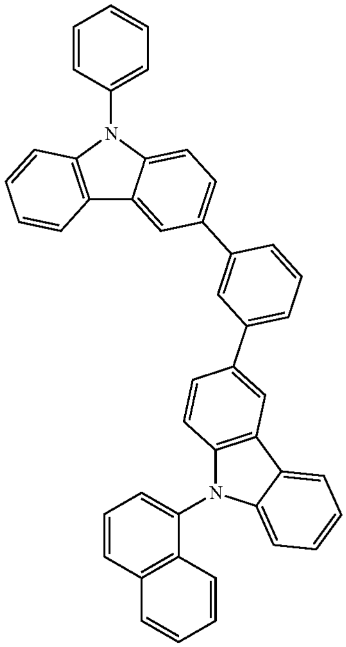

-continued
H1-291
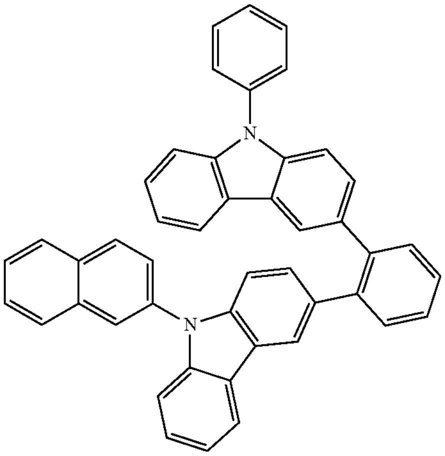
H1-292
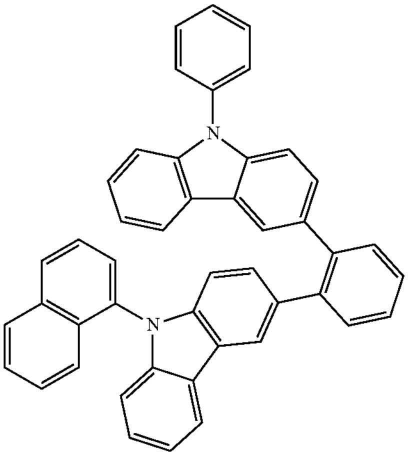
H1-293
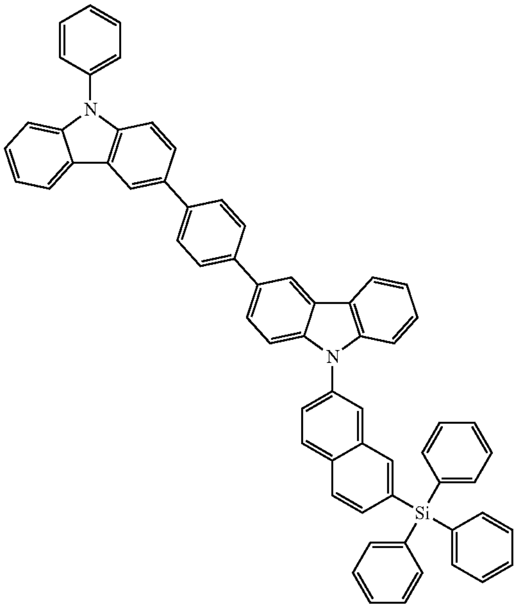
H1-294
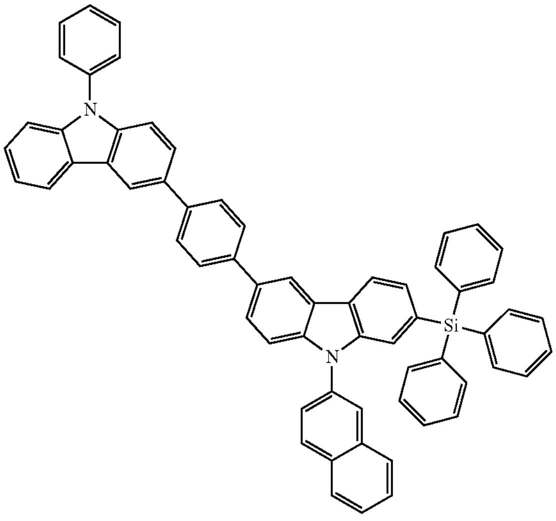

-continued
H1-295
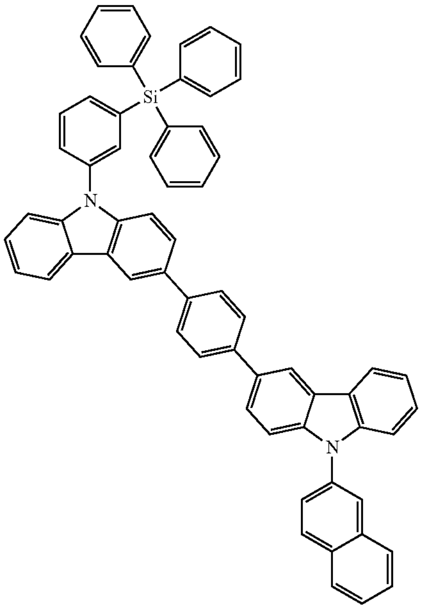
H1-296
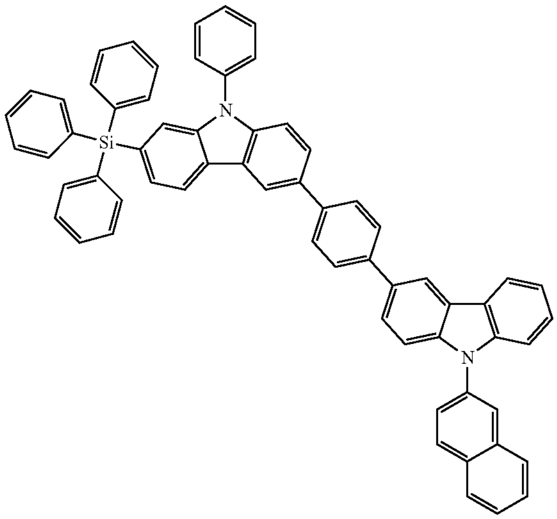
H1-297
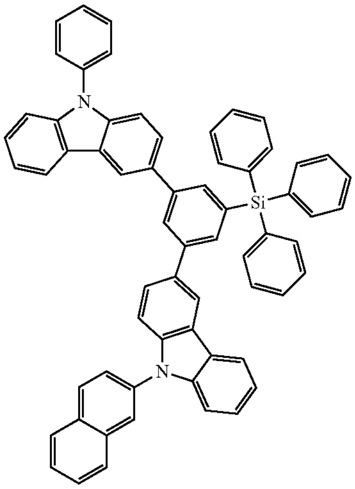
H1-298
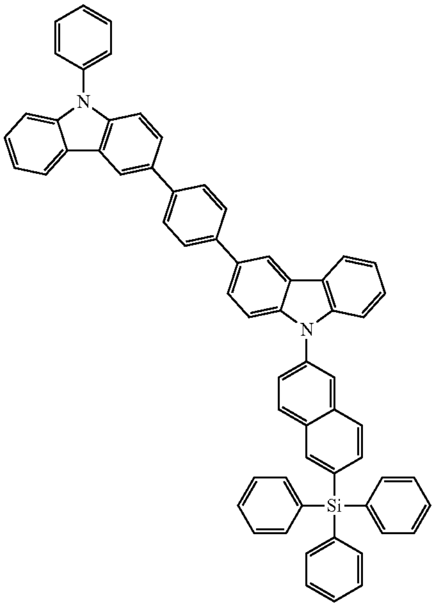

-continued
H1-299
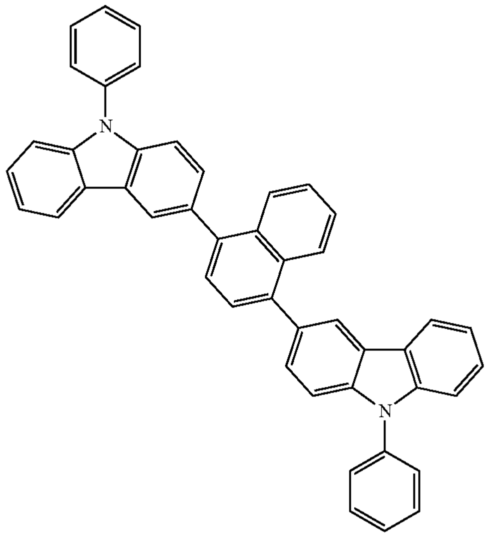
H1-300
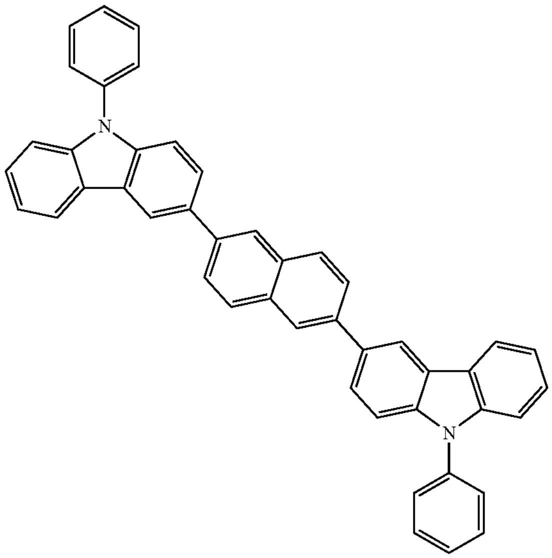
H1-301
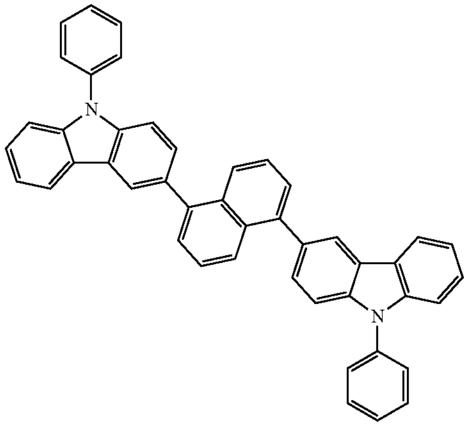
H1-302
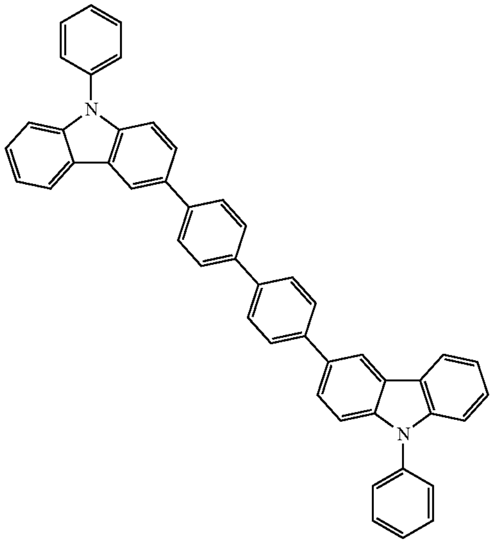
H1-303
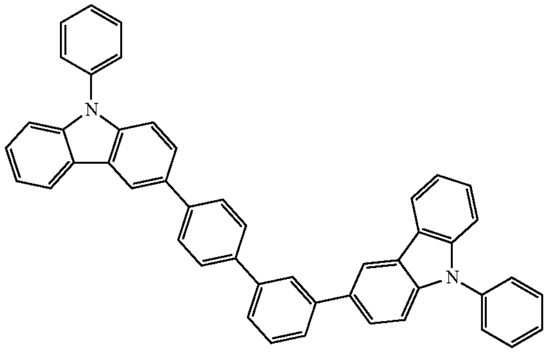
H1-304
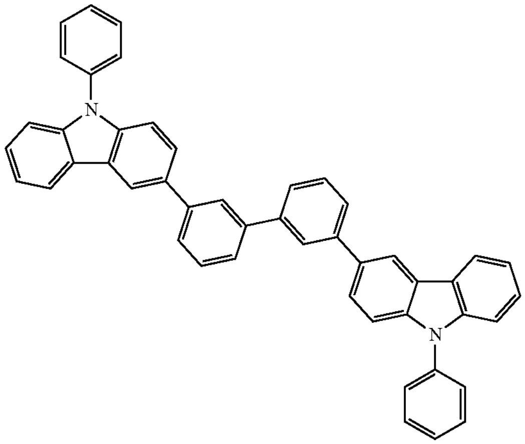

-continued
H1-305
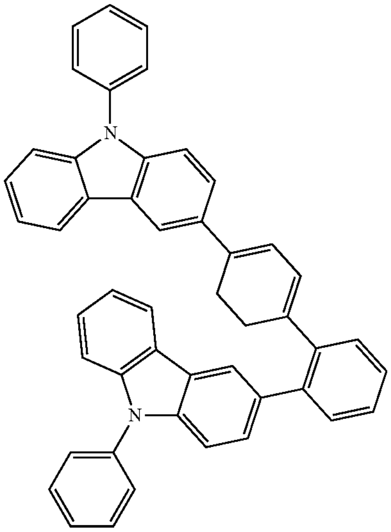
H1-306
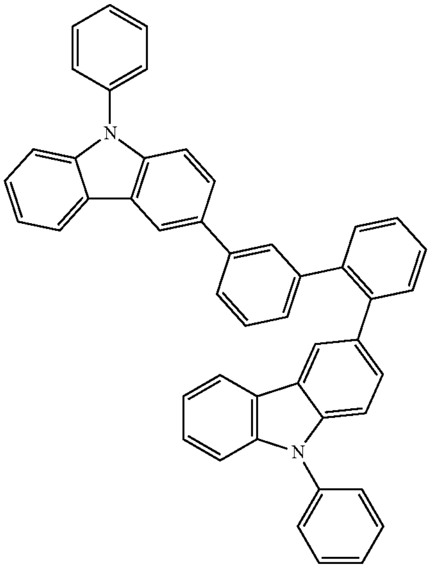
H1-307
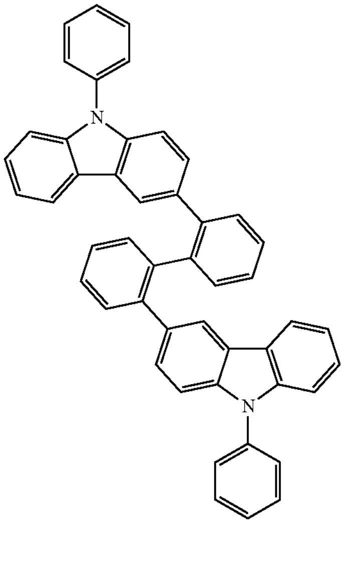
H1-308
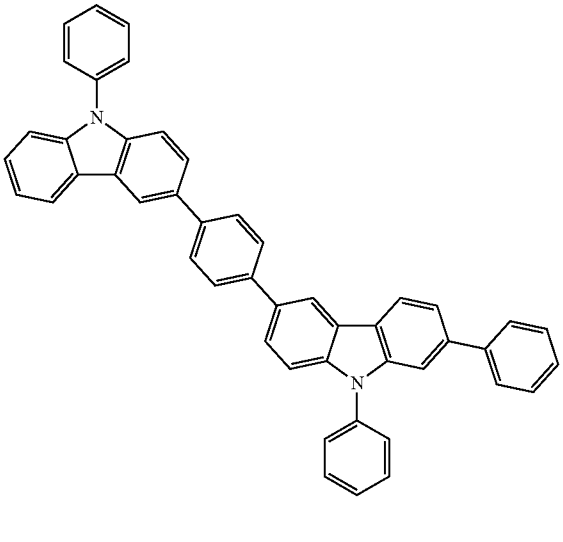

-continued
H1-309
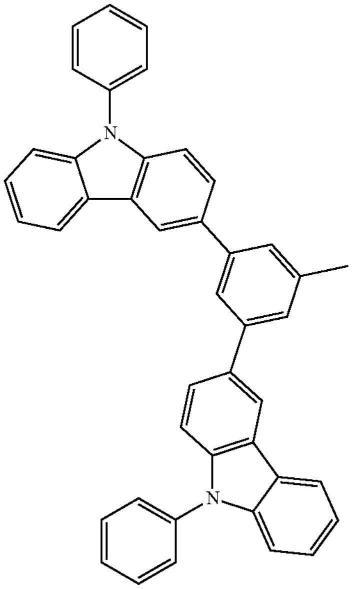
H1-310
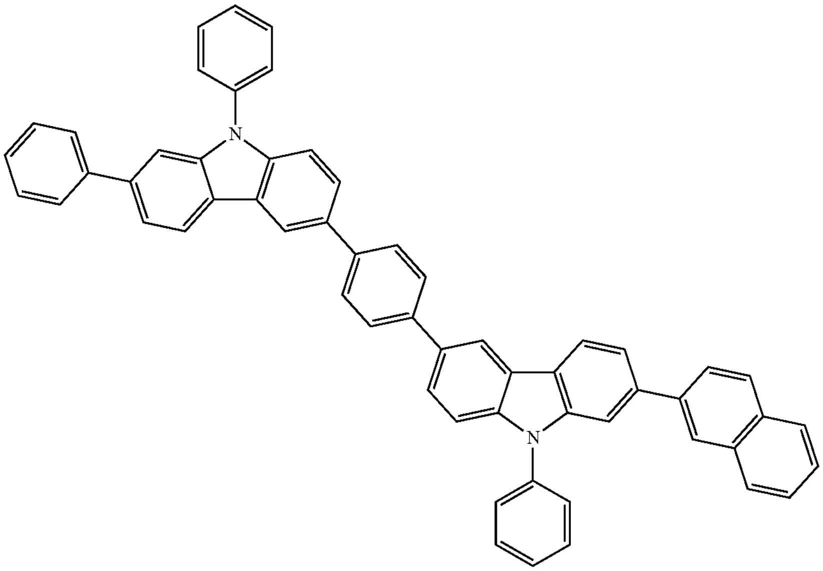
H1-311
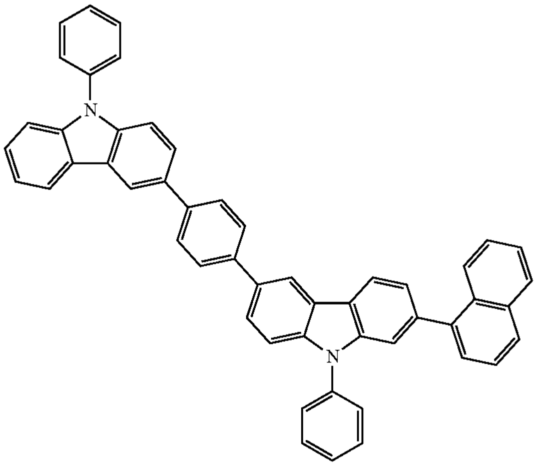
H1-312
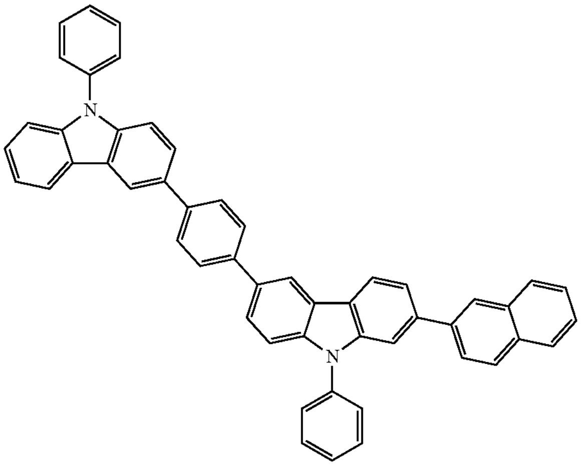

-continued
H1-313
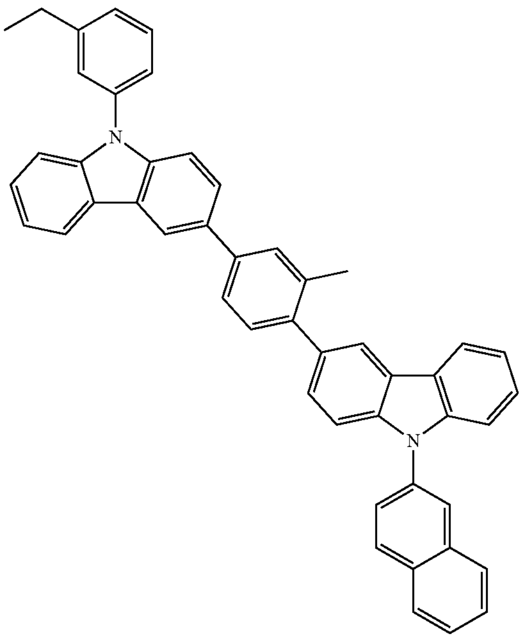
H1-314
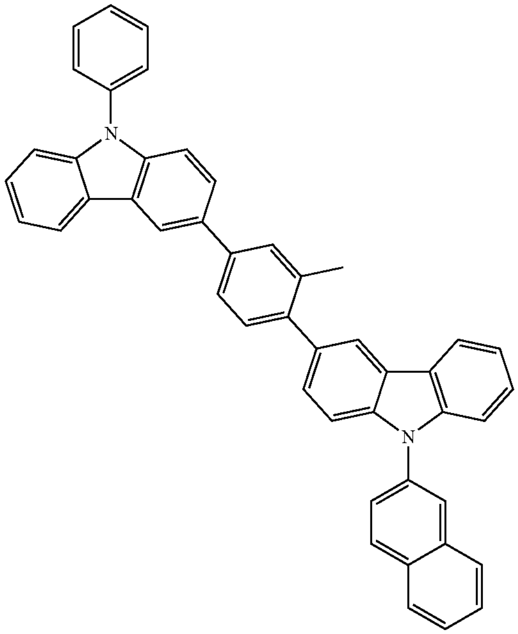
H1-315
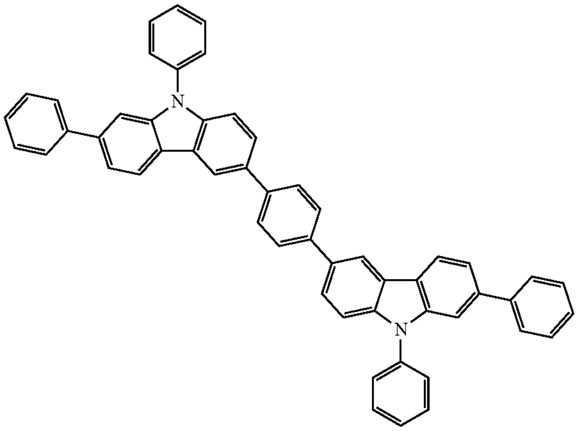
H1-316
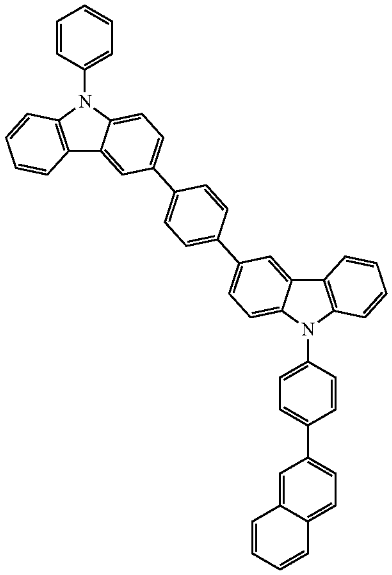

-continued
H1-317
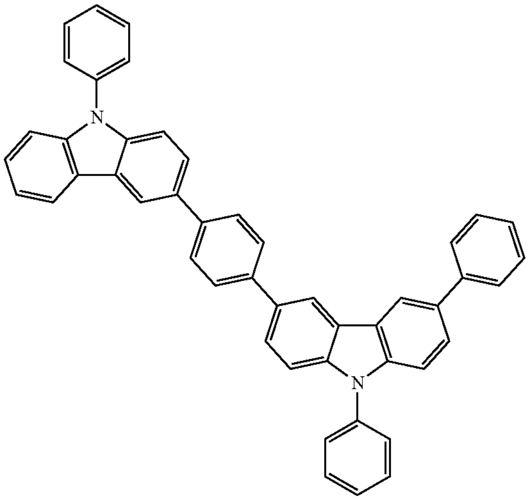
H1-321
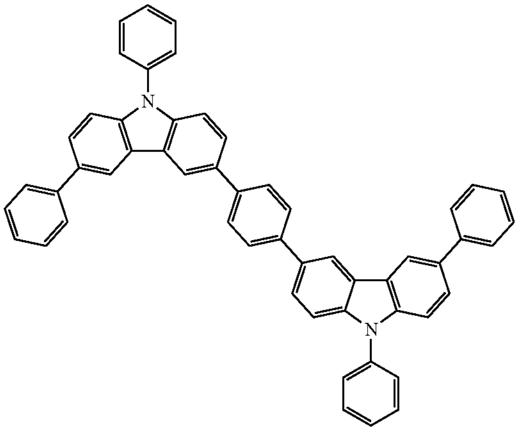
H1-323
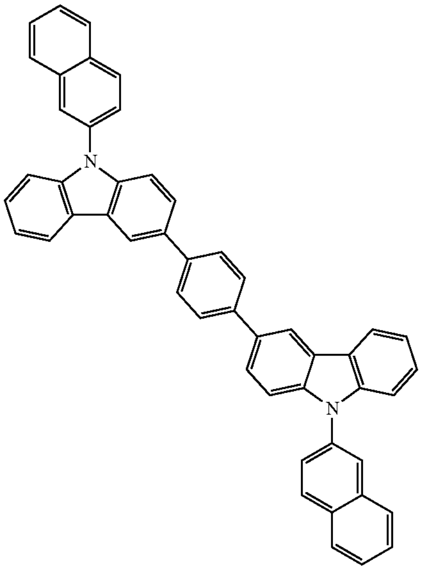
H1-324
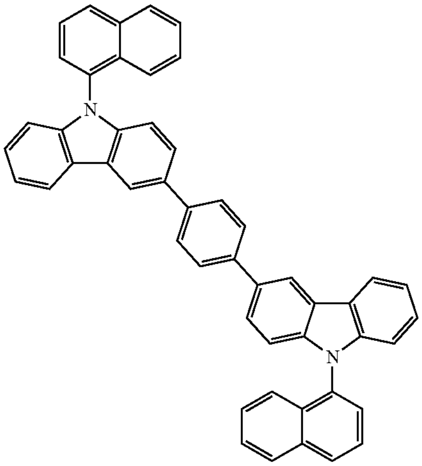

-continued
H1-325
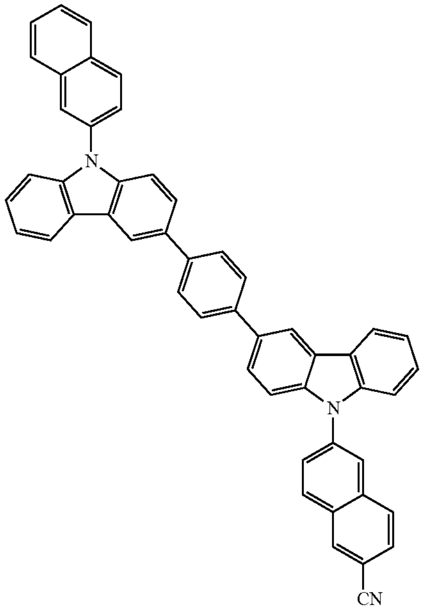
H1-327
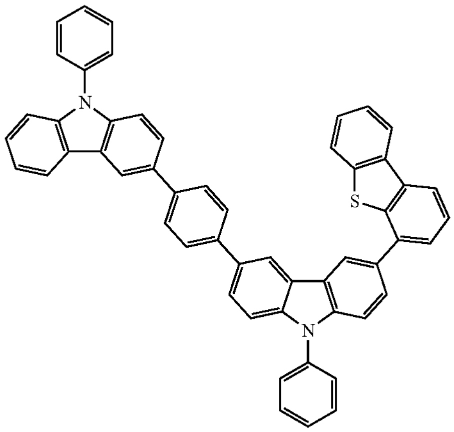
H1-328
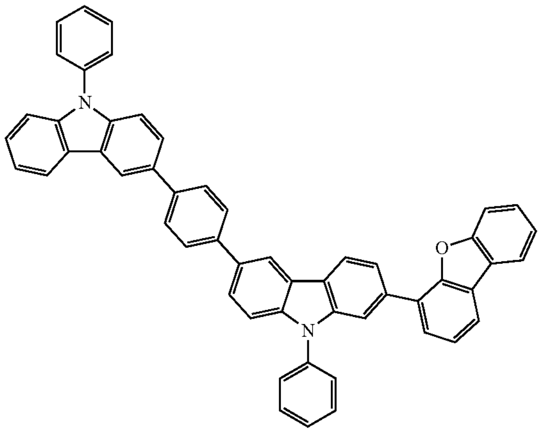
H1-329
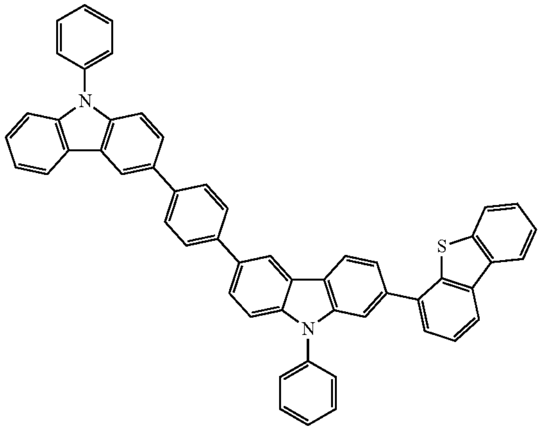
H1-334
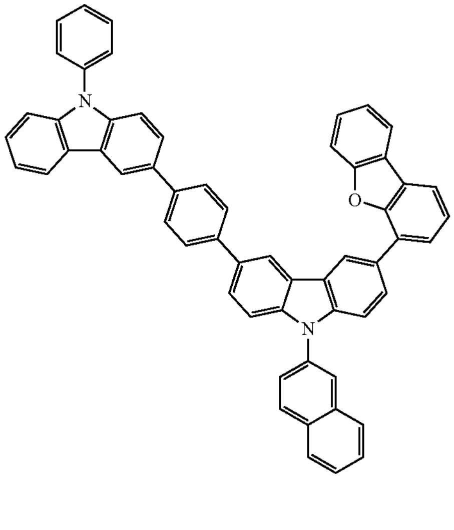

-continued
H1-335
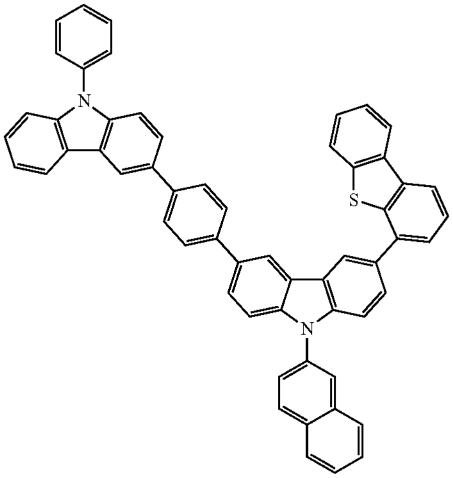
H1-336
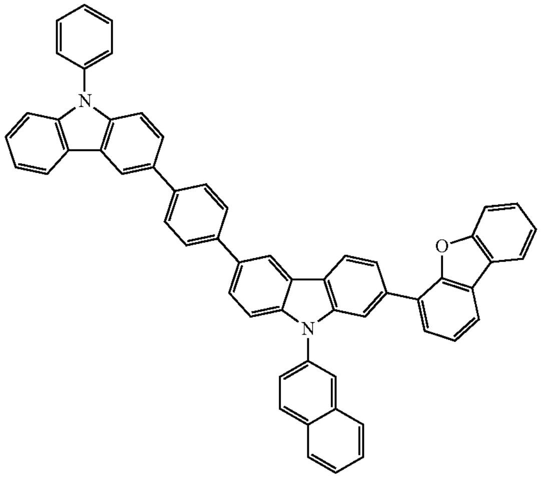
H1-337
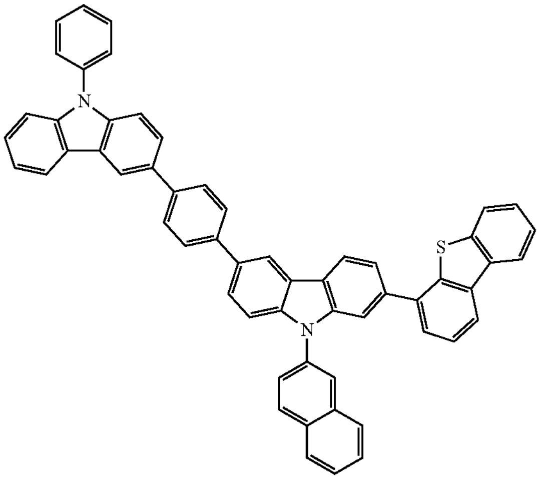
H1-342
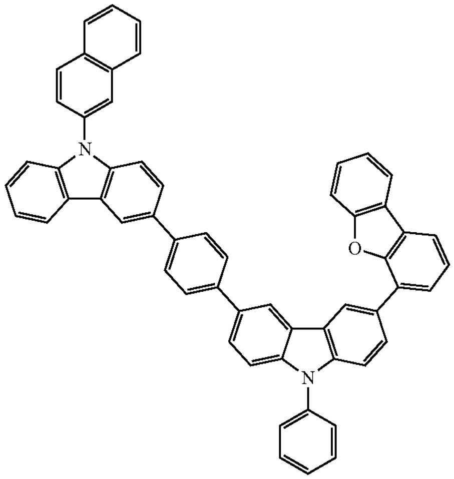
H1-343
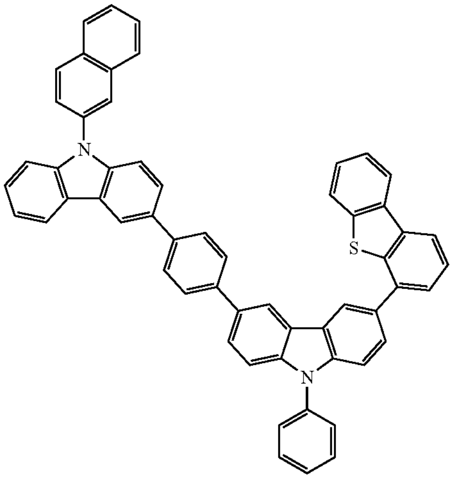
H1-344
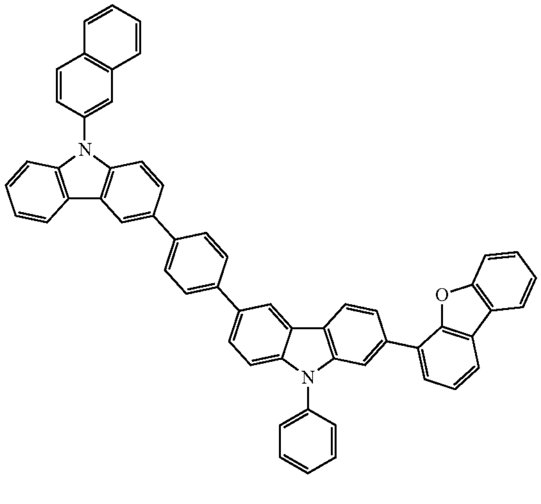

-continued
H1-345
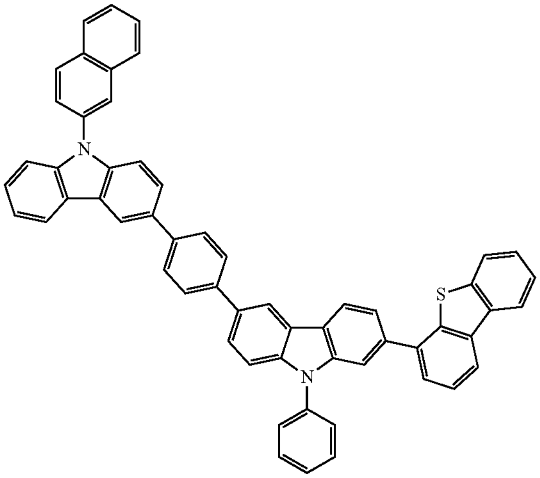
H1-346
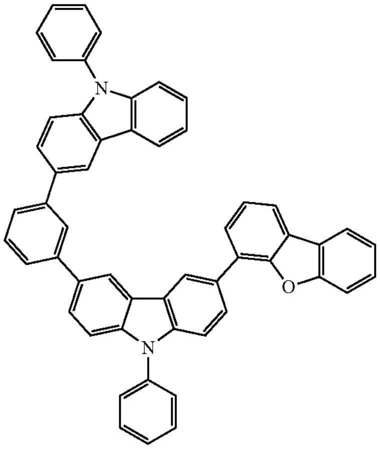
H1-347
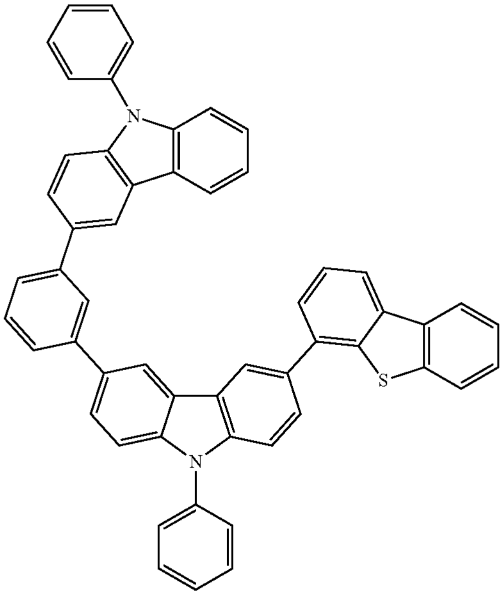
H1-348
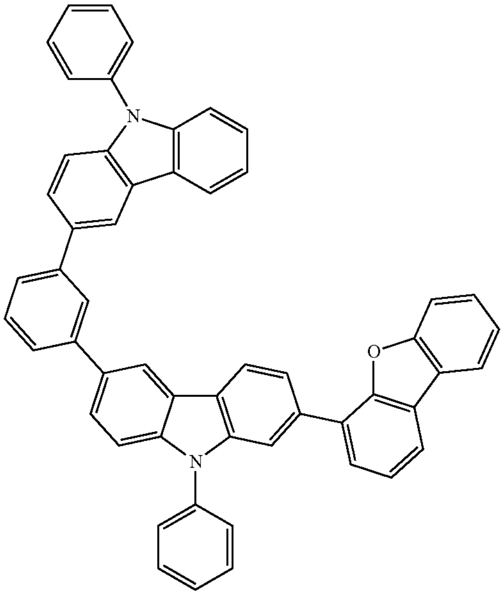

-continued
H1-349
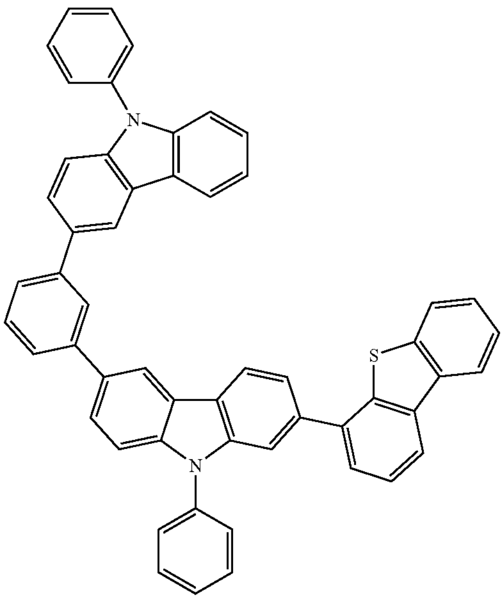
H1-350
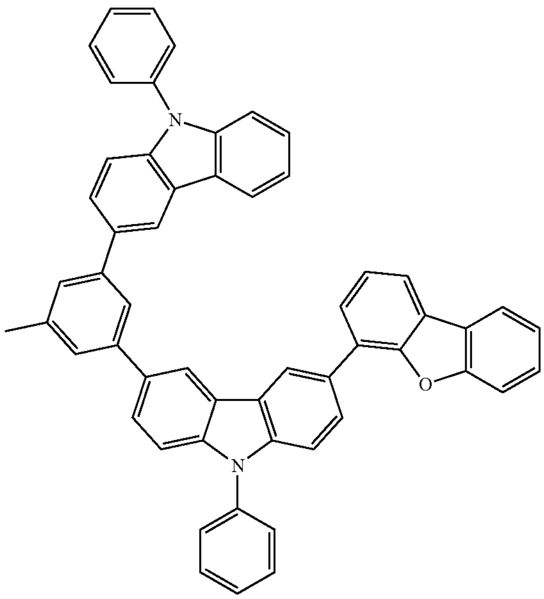
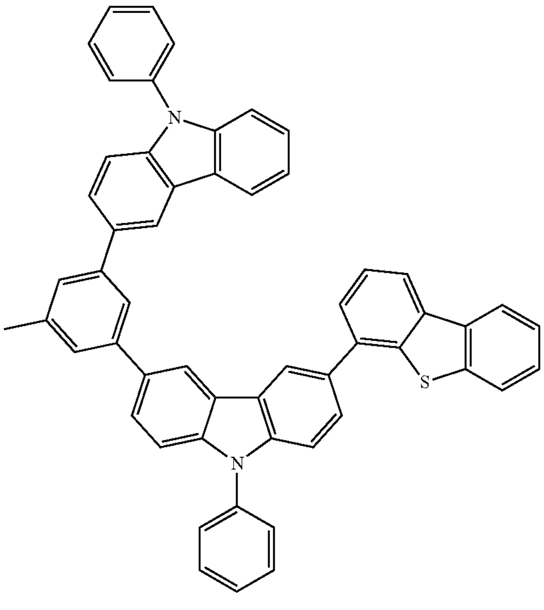
H1-352
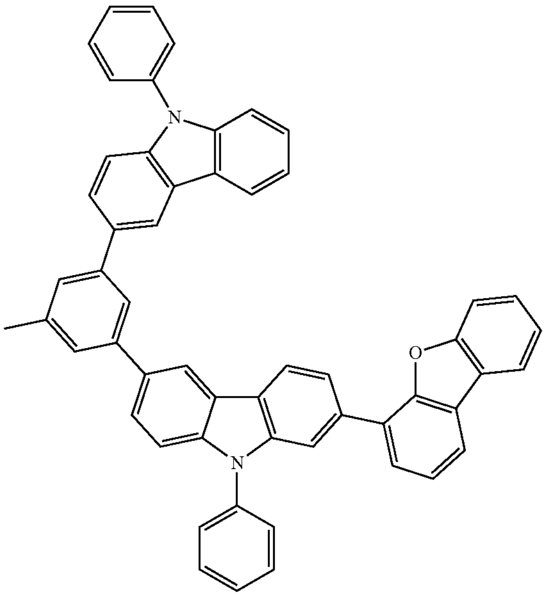

-continued
H1-353
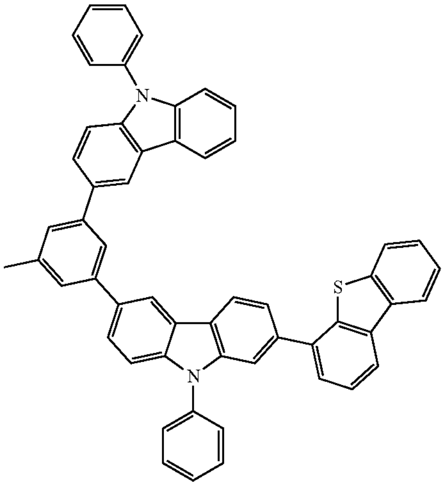
H1-354
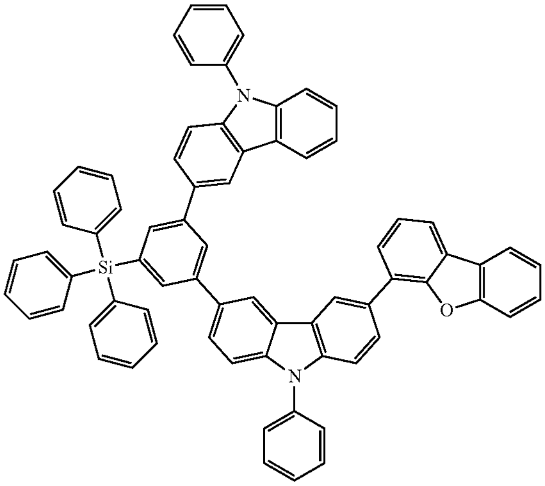
H1-355
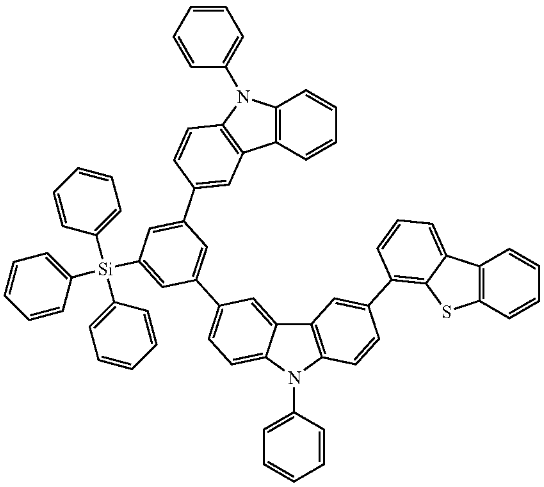
H1-356
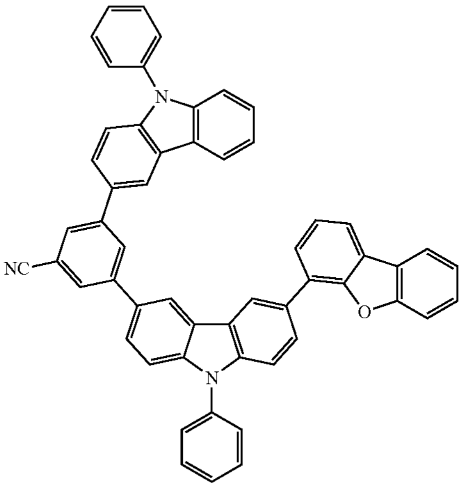
H1-357
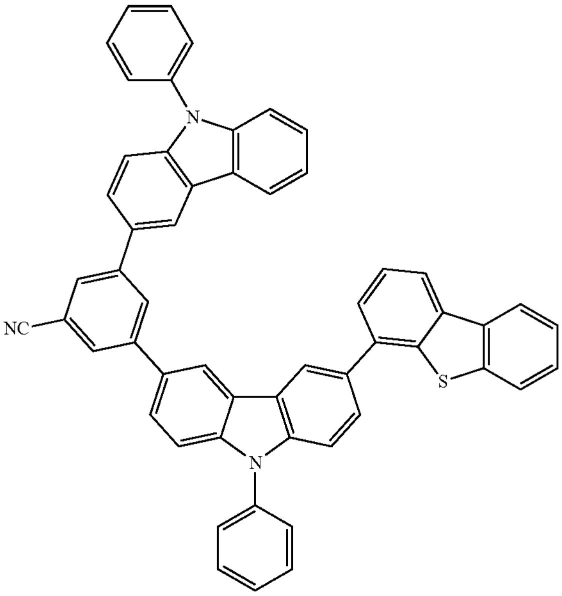
H1-358
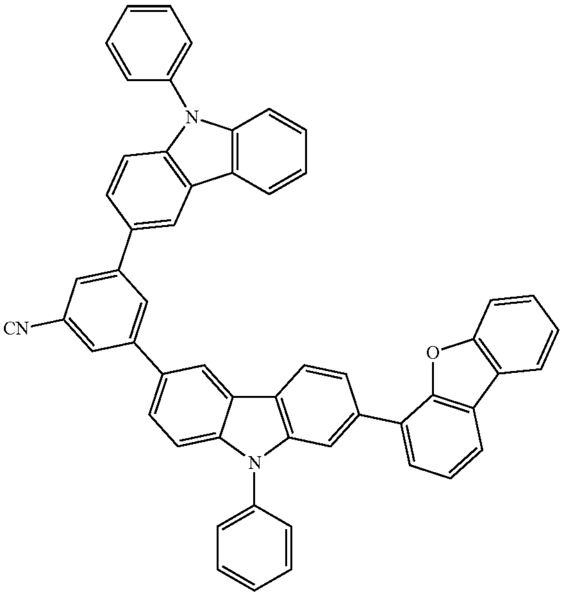

-continued
H1-359
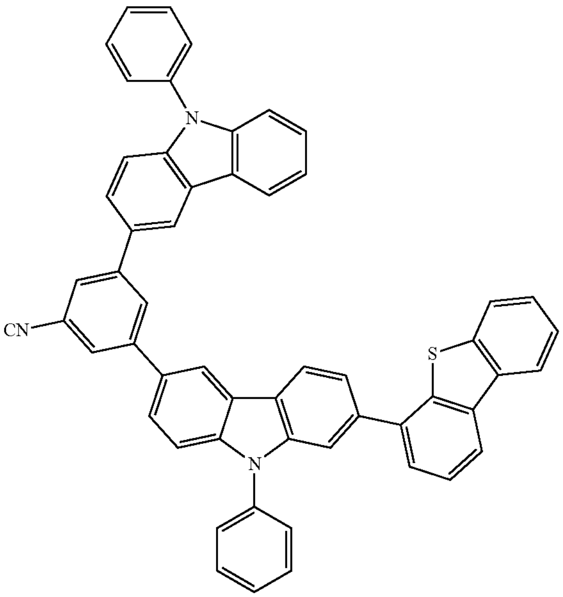
H1-368
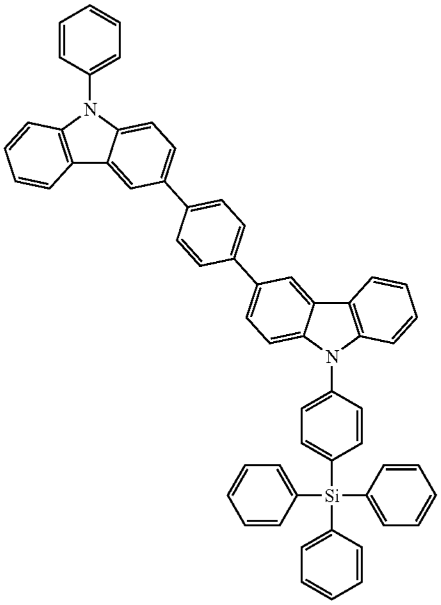
H1-369
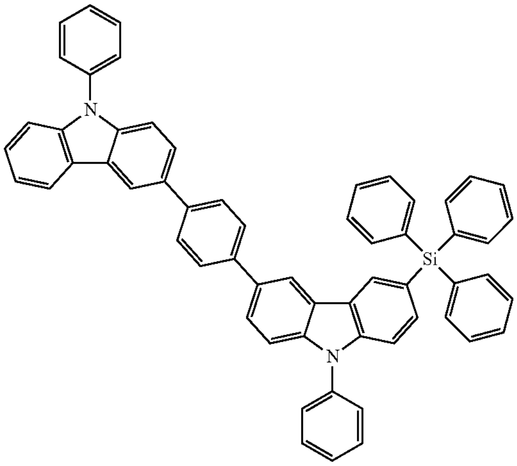
H1-371
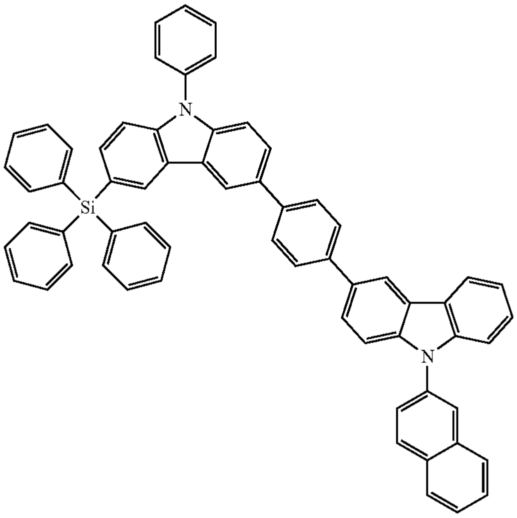
H1-372
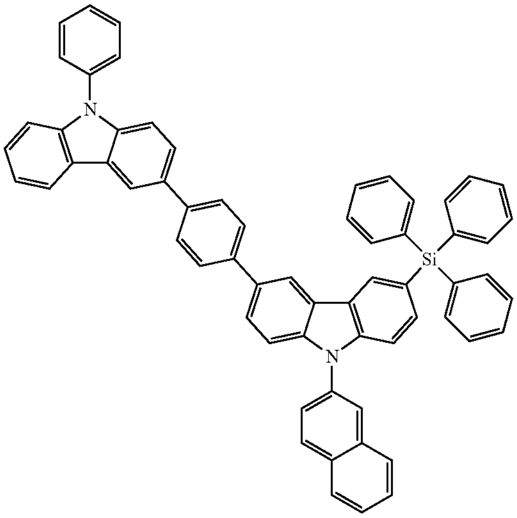

-continued
H1-375
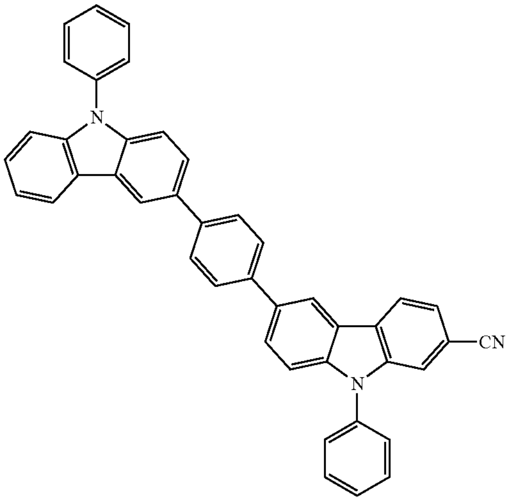
H1-376
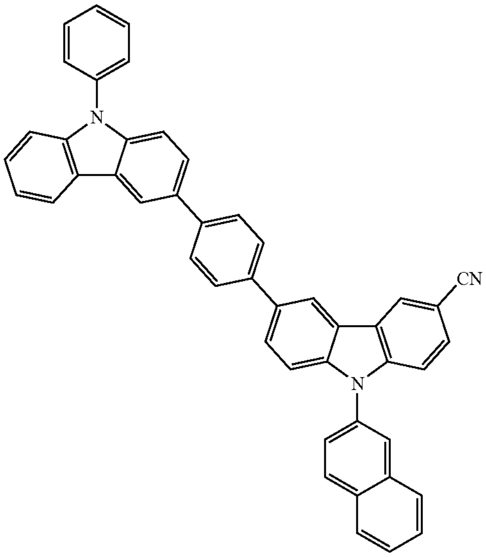
H1-377
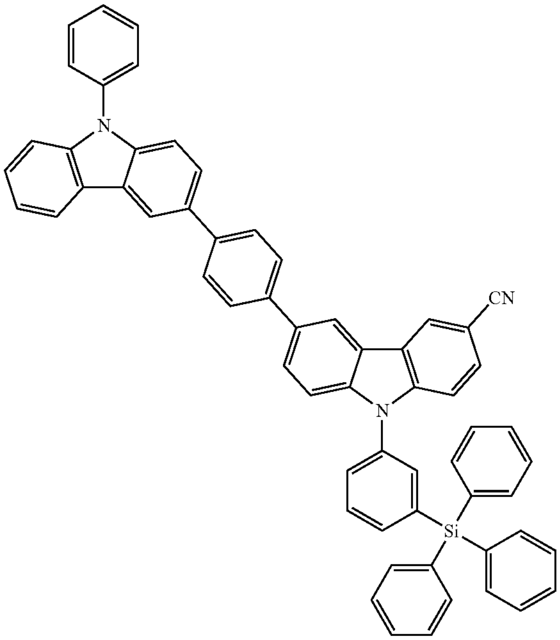

-continued
H1-378
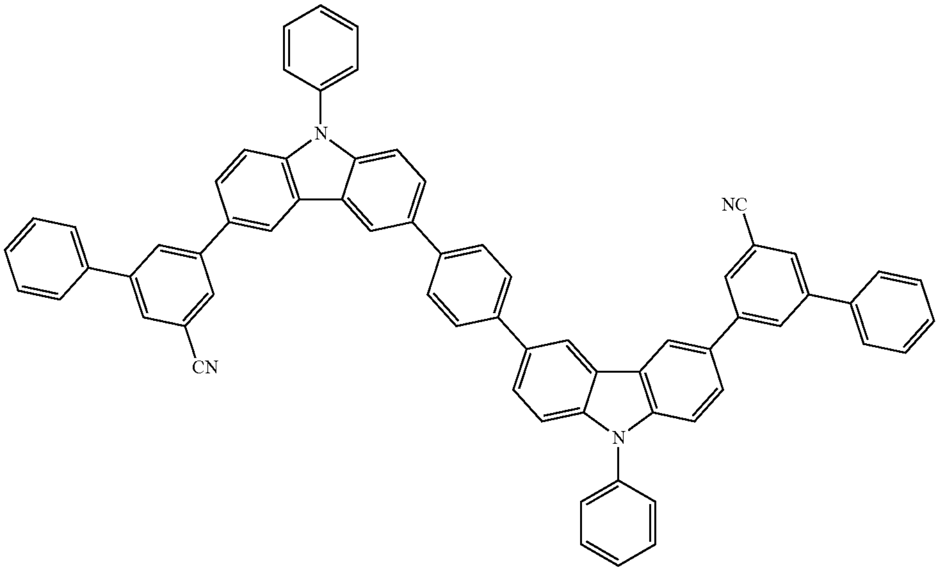
H1-379
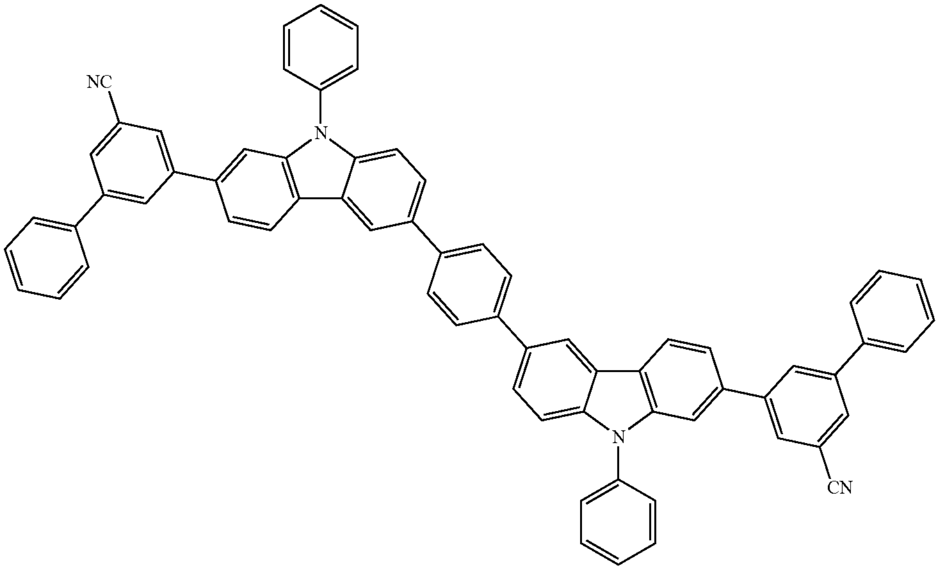
H1-380
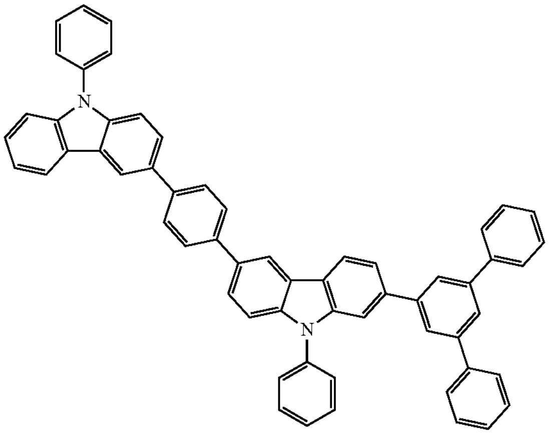
H1-381
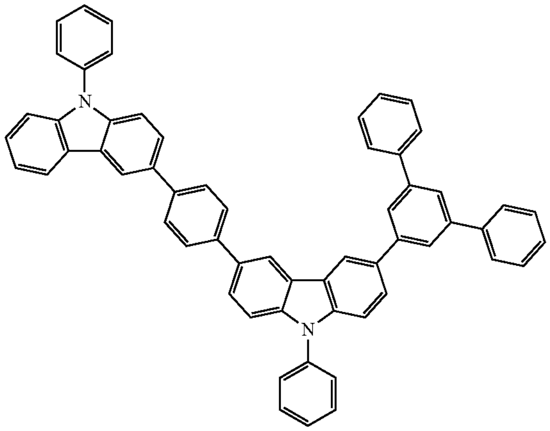

-continued
H1-382
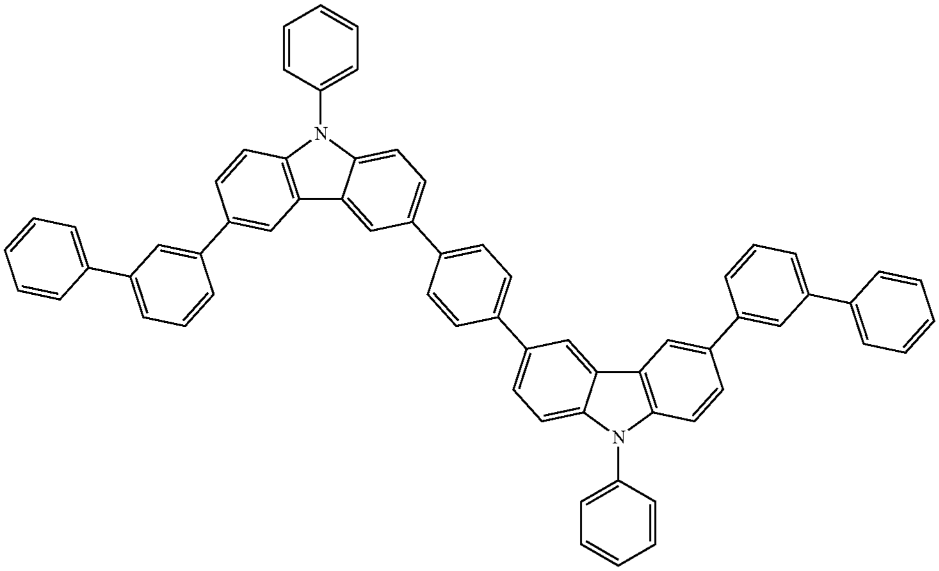
H1-383
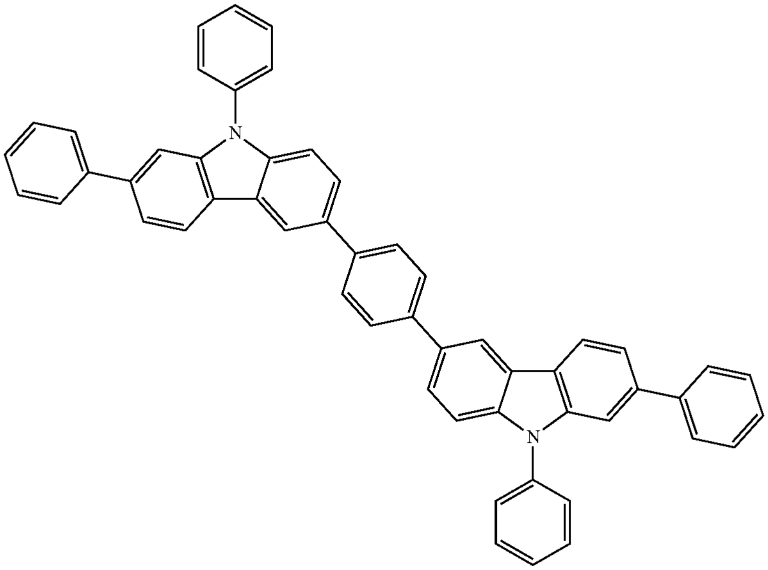

-continued
H1-384
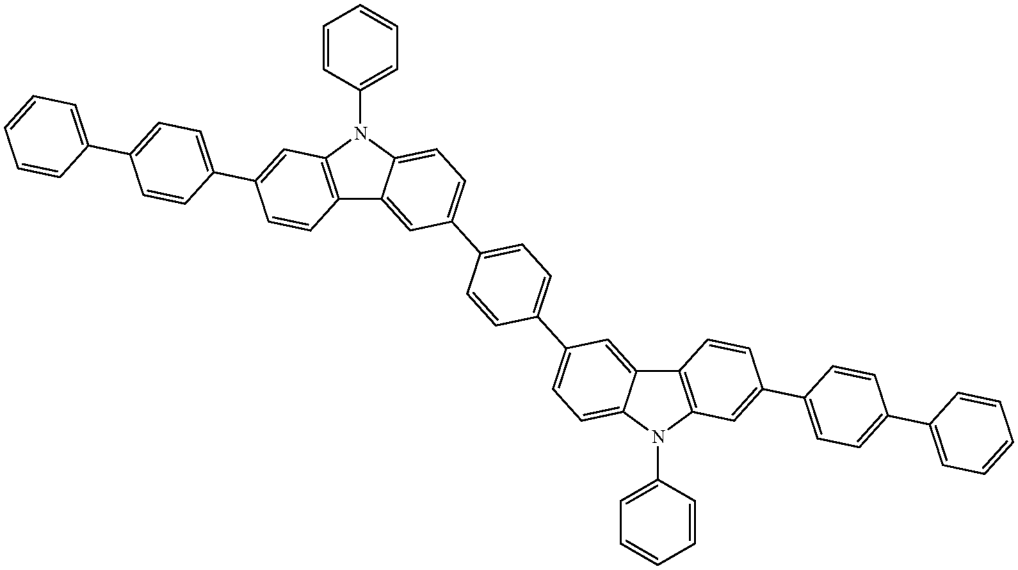
H1-385
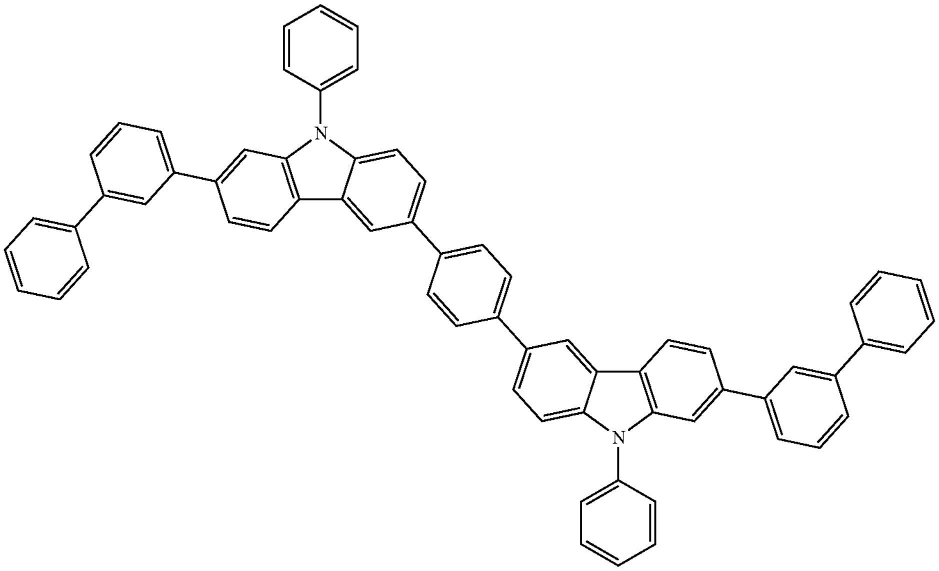
H1-386
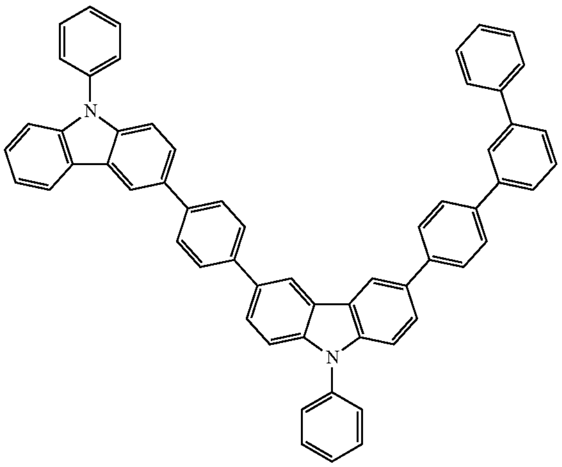
H1-387
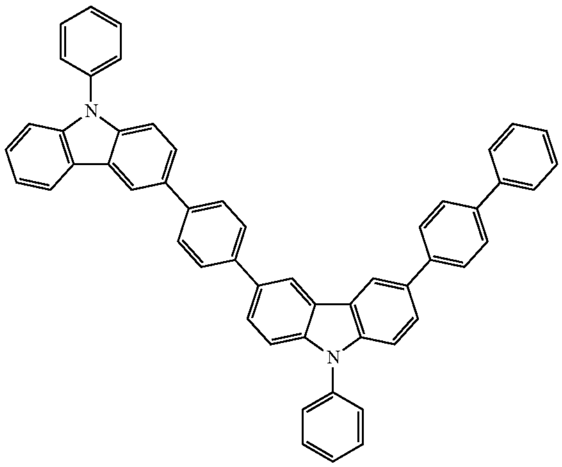

-continued
H1-388
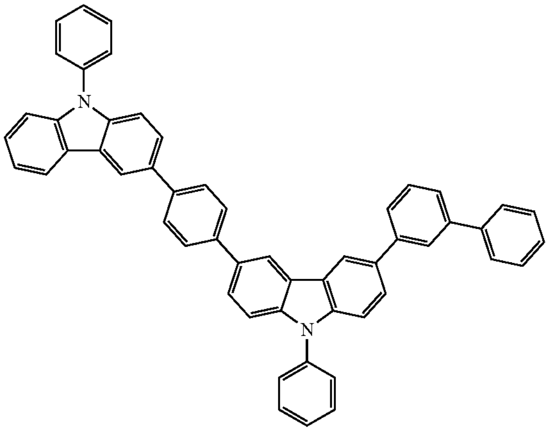
H1-389
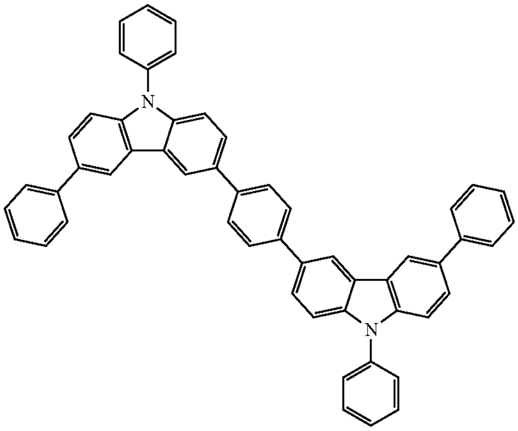
H1-390
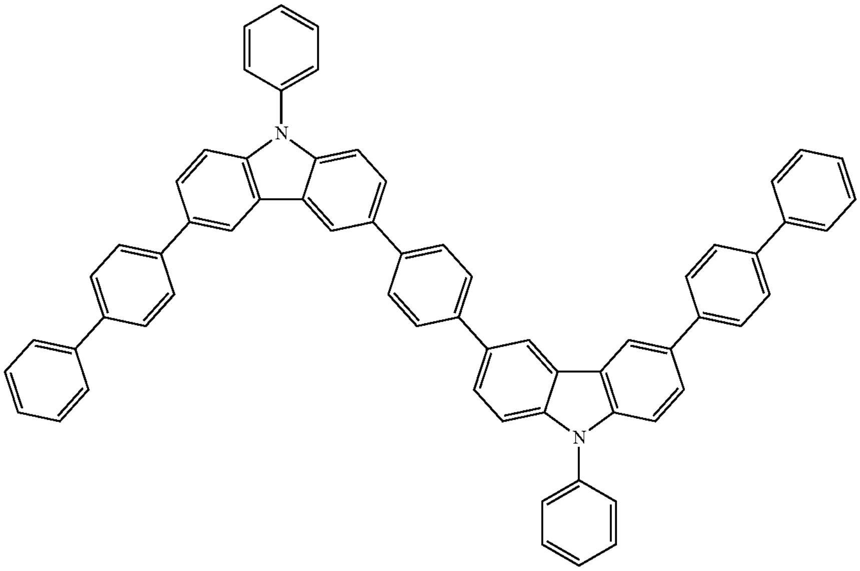
H1-391
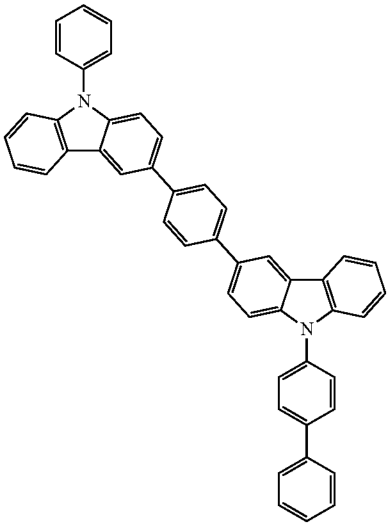
H1-392
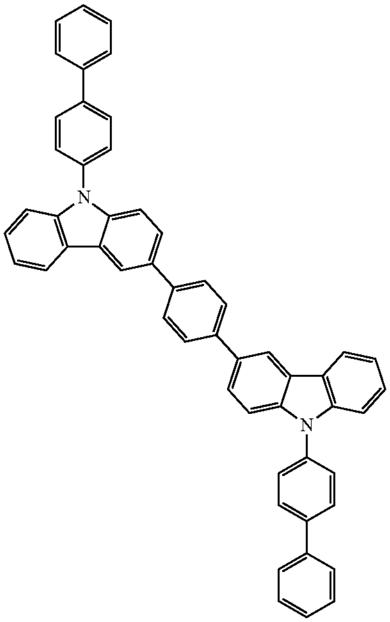

-continued
H1-393
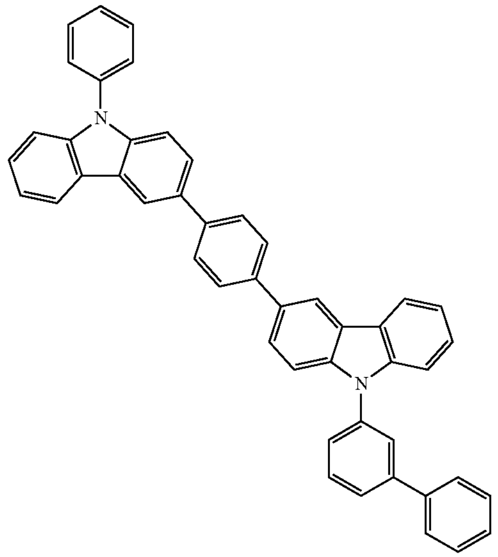
H1-394
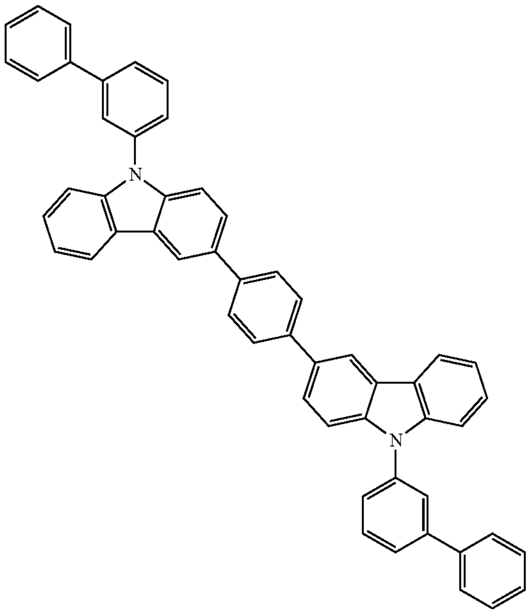
H1-395
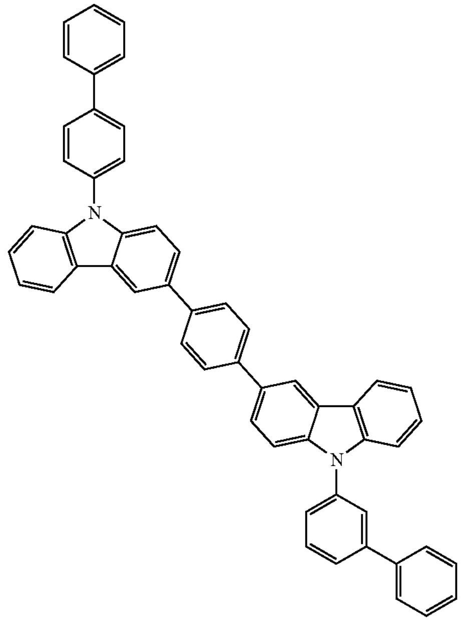
H1-405
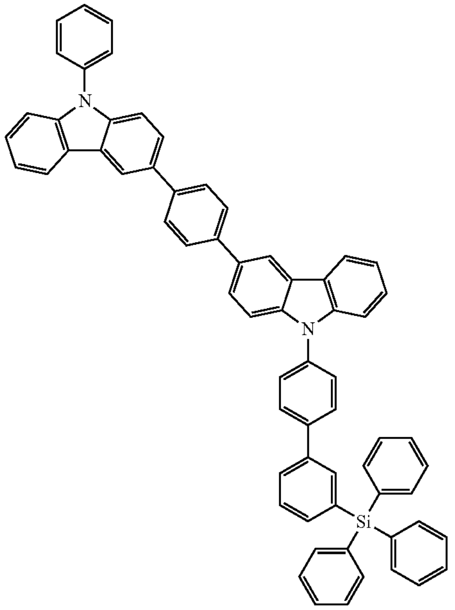

-continued
H1-407
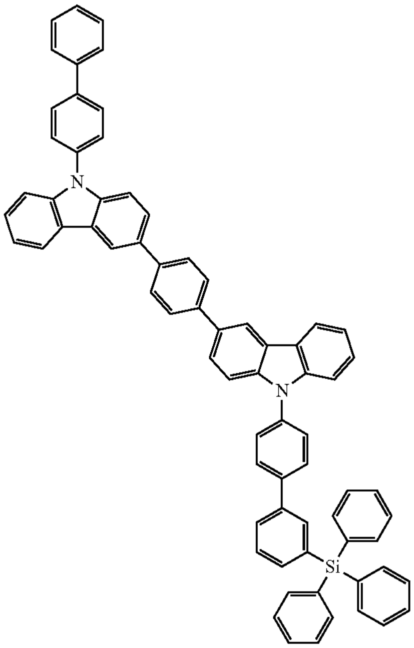
H1-408
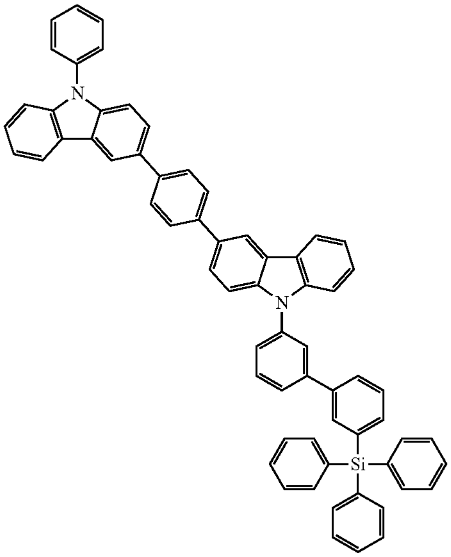
H1-409
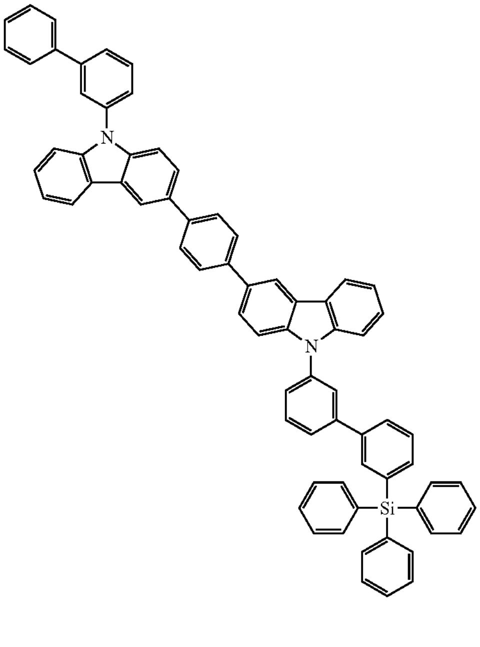
H1-410
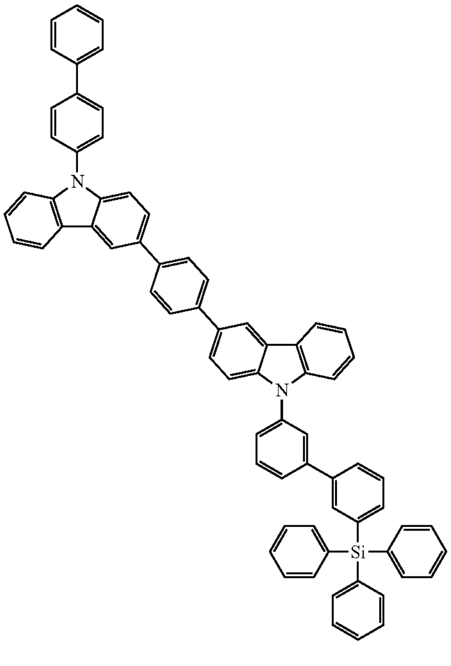

-continued
H1-411
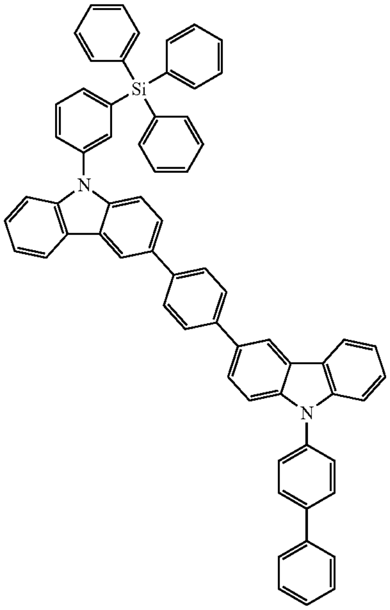
H1-412
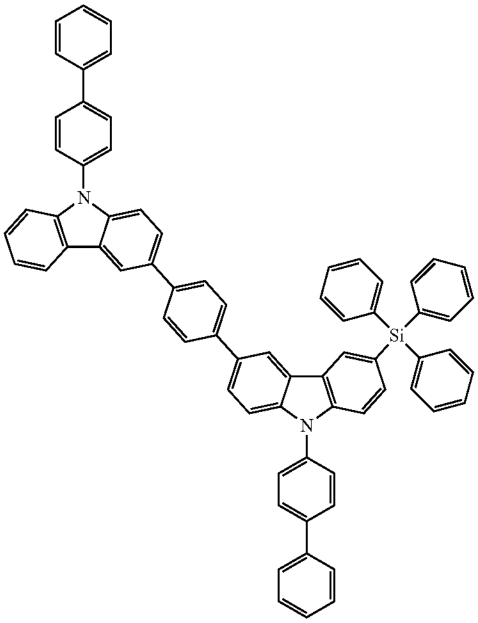
H1-413
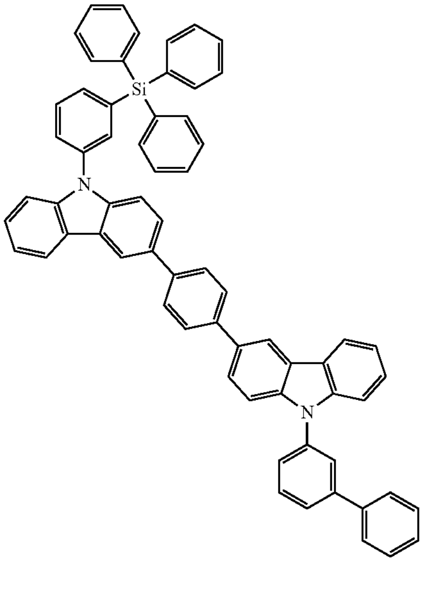
H1-414
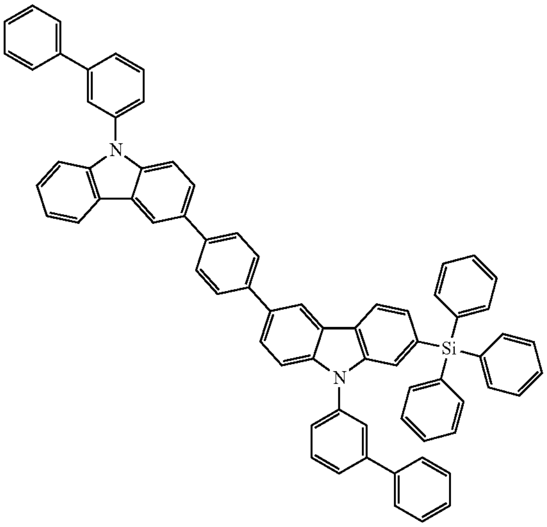

-continued
H1-415
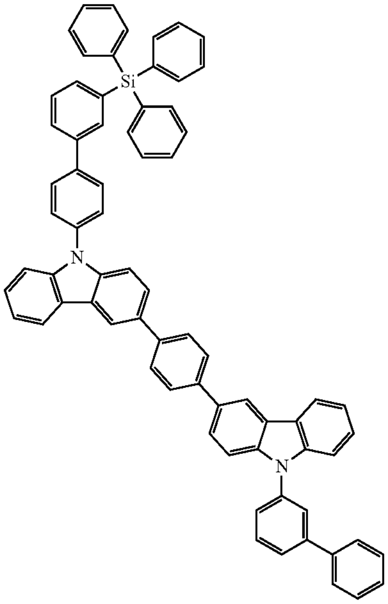
H1-416
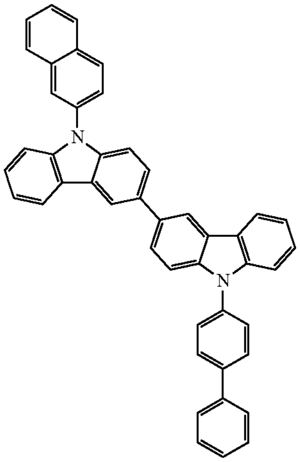
H1-417
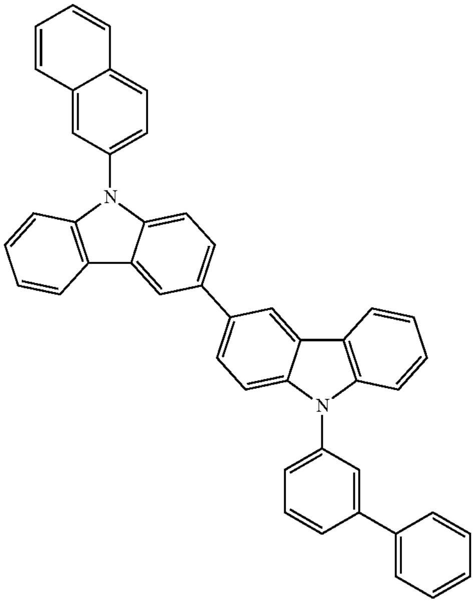
H1-418
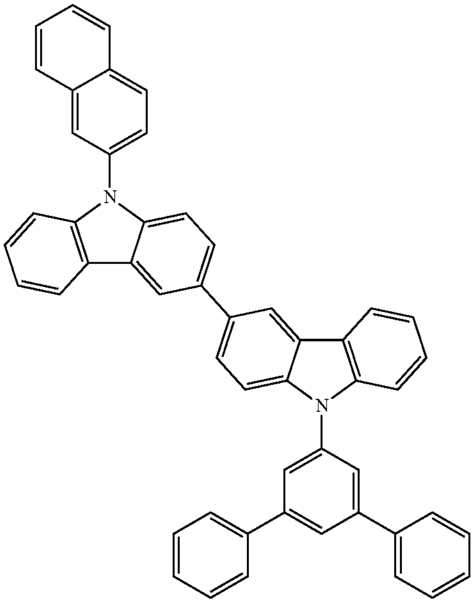

-continued
H1-419
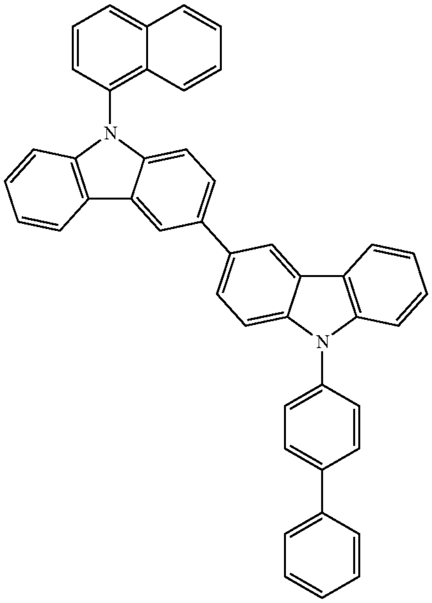
H1-420
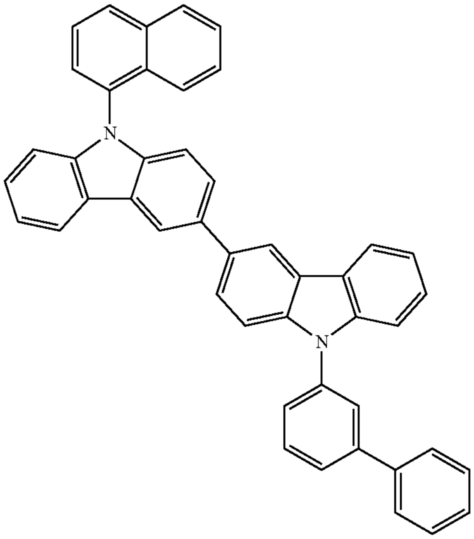
H1-421
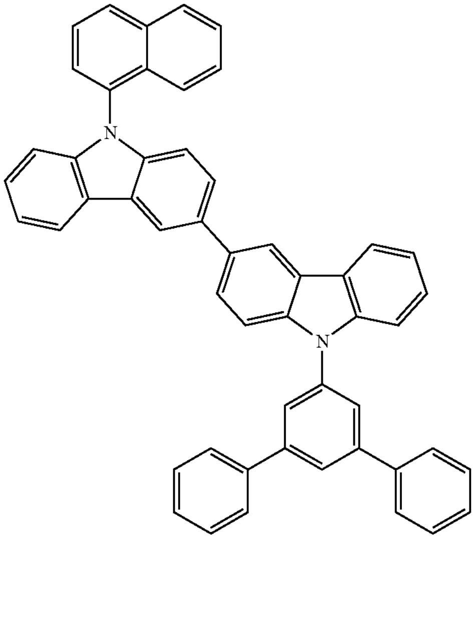
H1-422
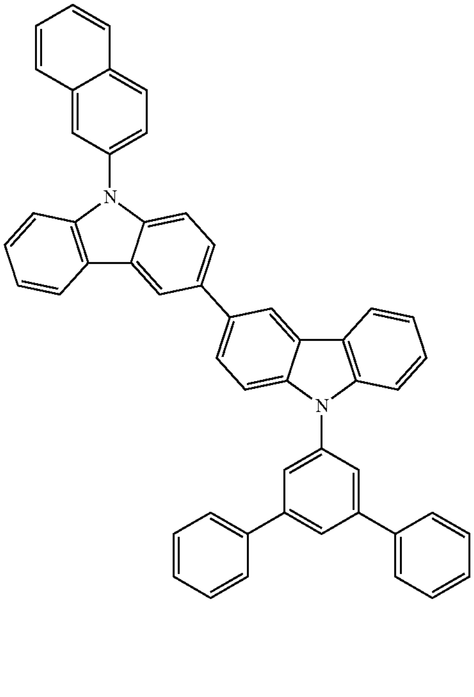
and -continued
H1-423
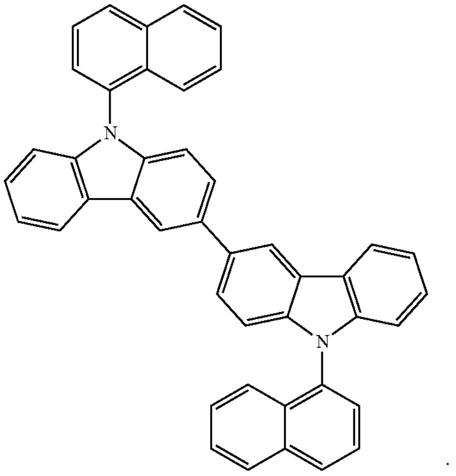
7. The organic electroluminescent device according to claim 1, wherein the compound represented by formula 2 is selected from the group consisting of:
A-1
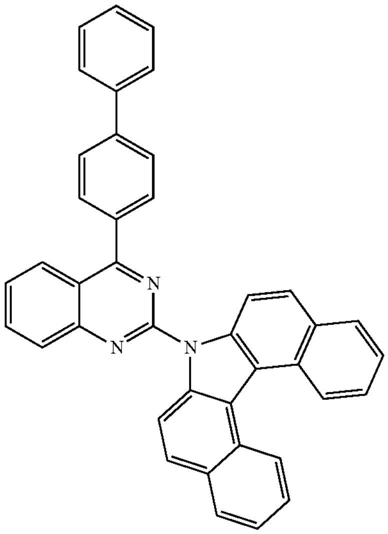
A-2
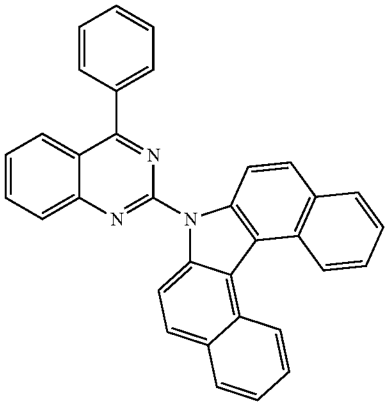
-continued
A-3
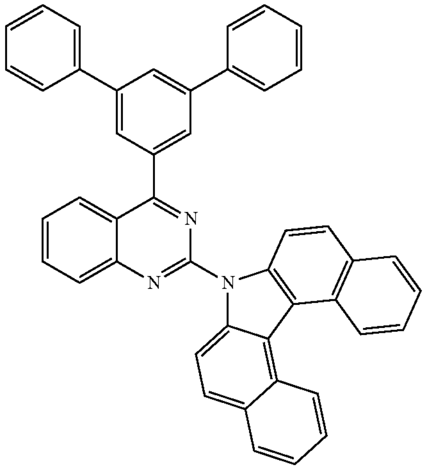
A-4
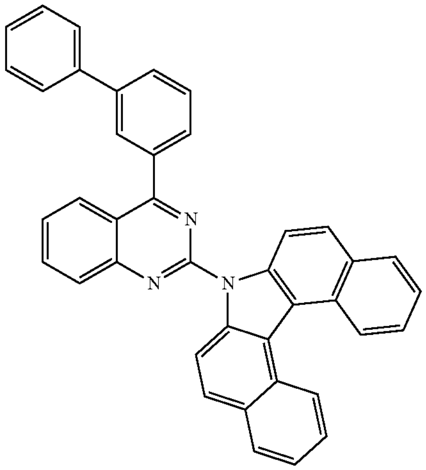

-continued
A-5
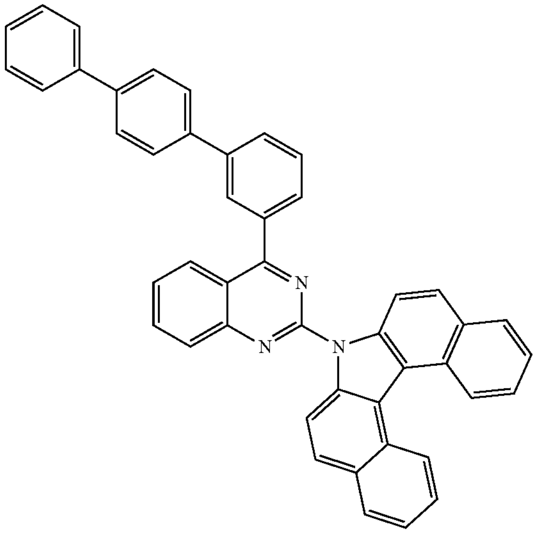
A-6
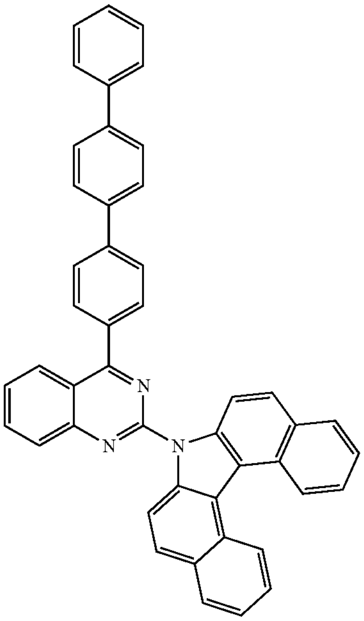
-continued
A-7
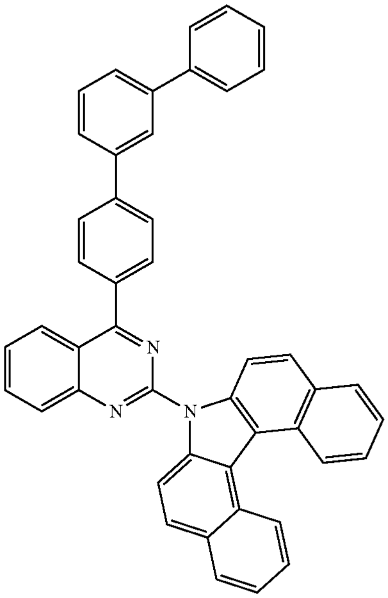
A-8
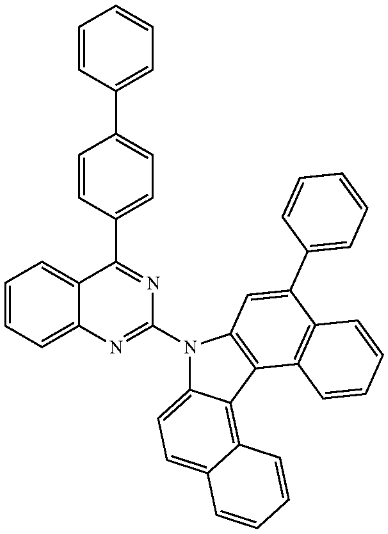
A-9
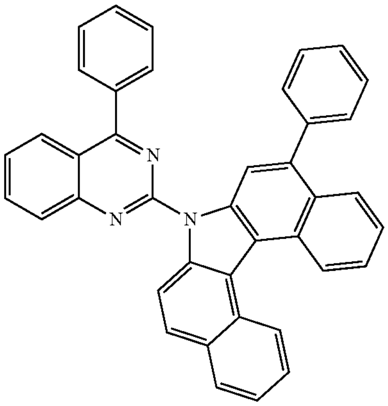

-continued
A-10
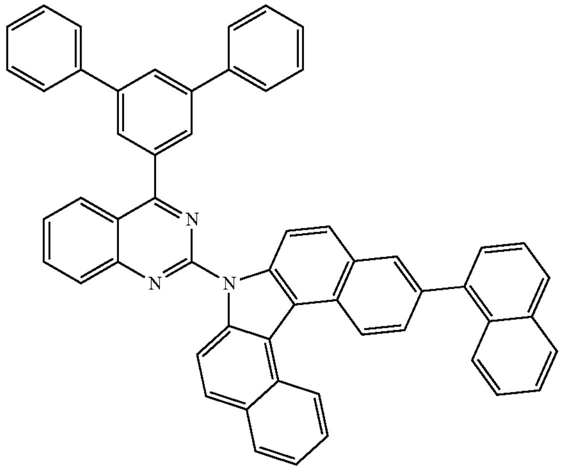
A-11
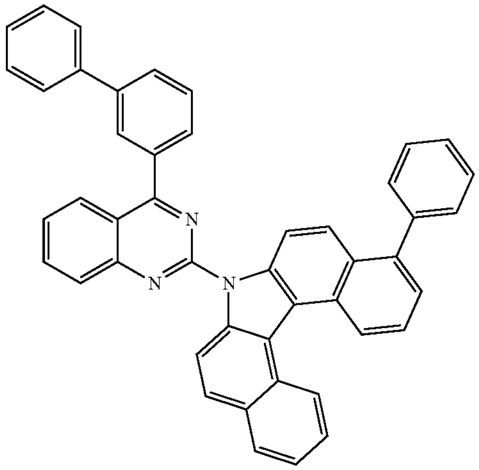
A-12
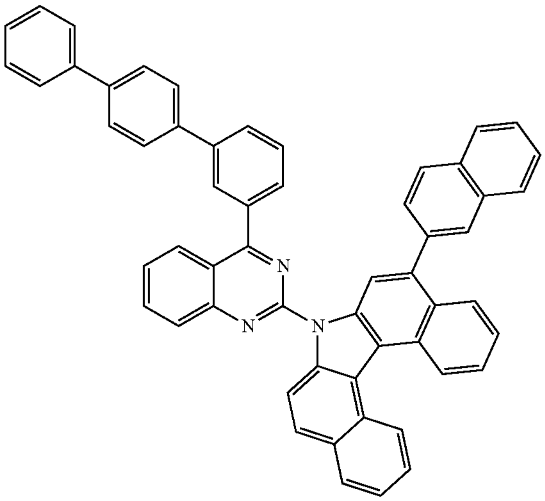
-continued
A-13
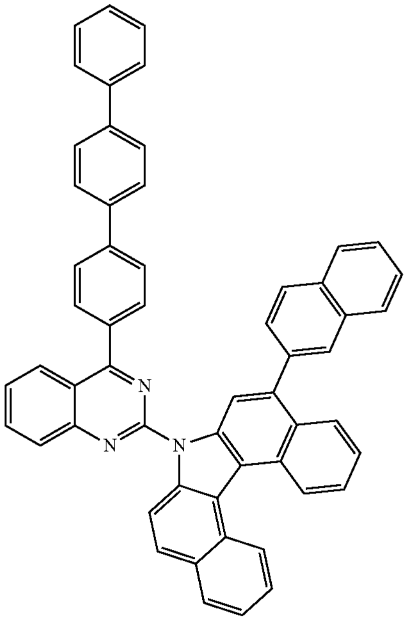
A-14
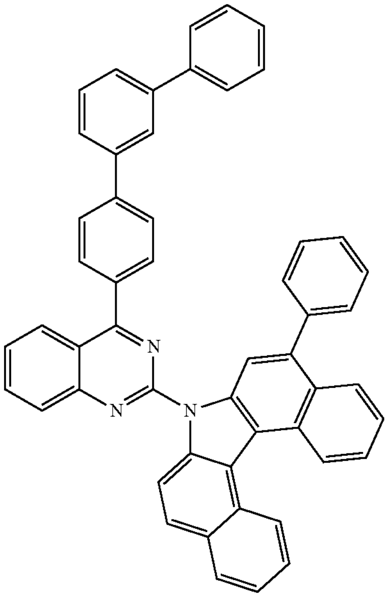

-continued
A-15
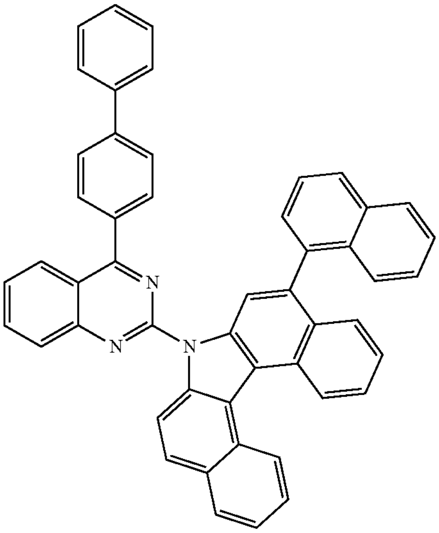
A-16
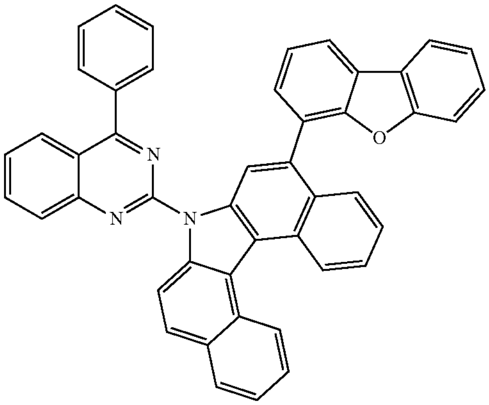
A-17
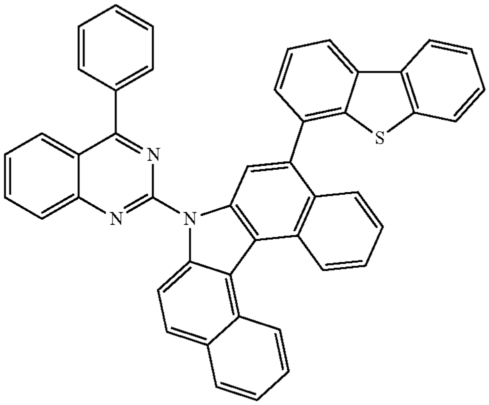
-continued
A-18
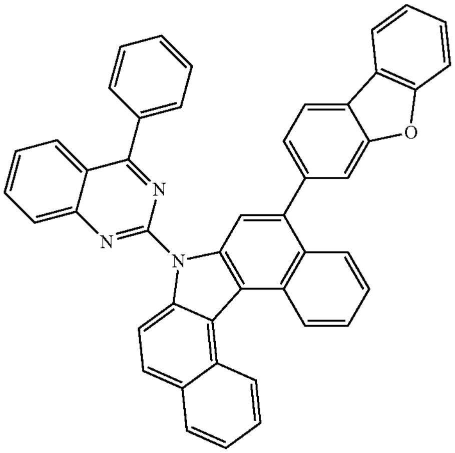
A-19
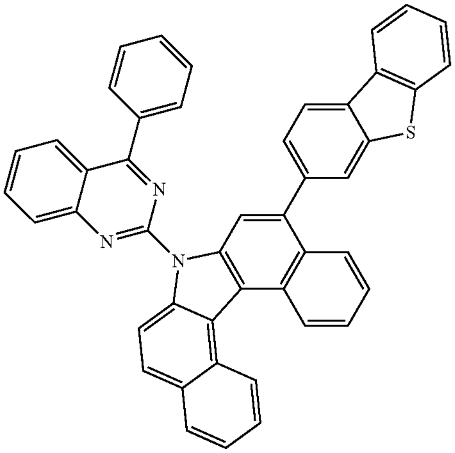
A-20
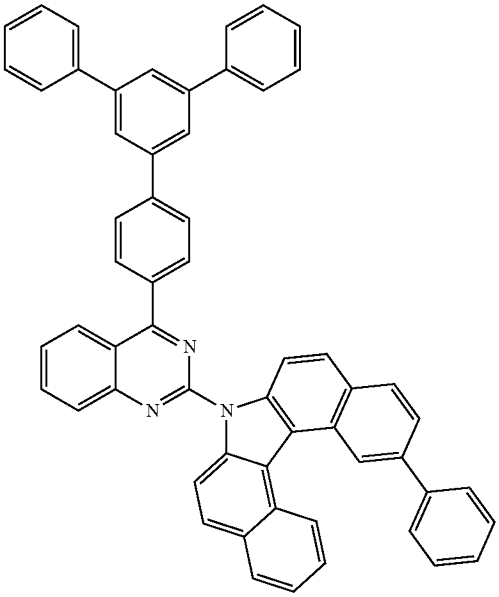

-continued
A-21
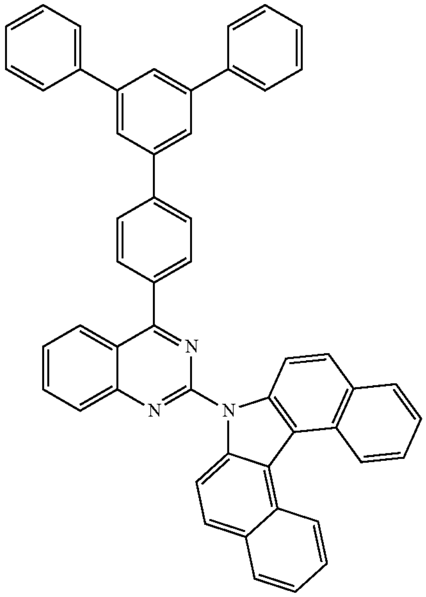
A-22
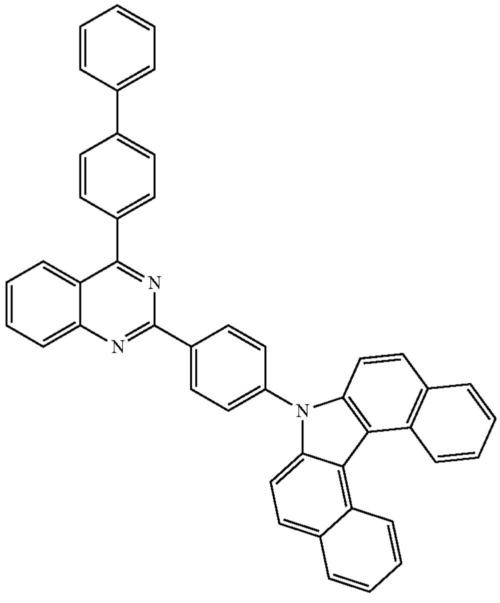
-continued
A-23
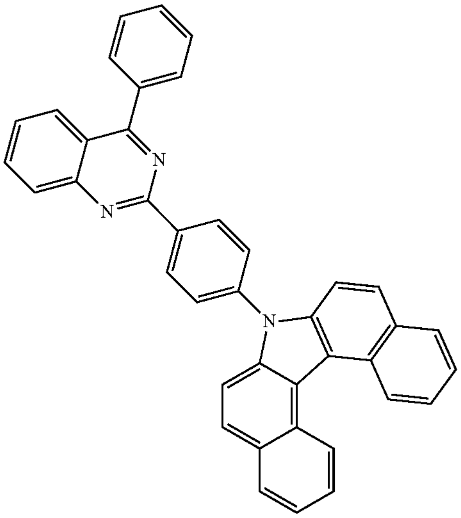
A-24
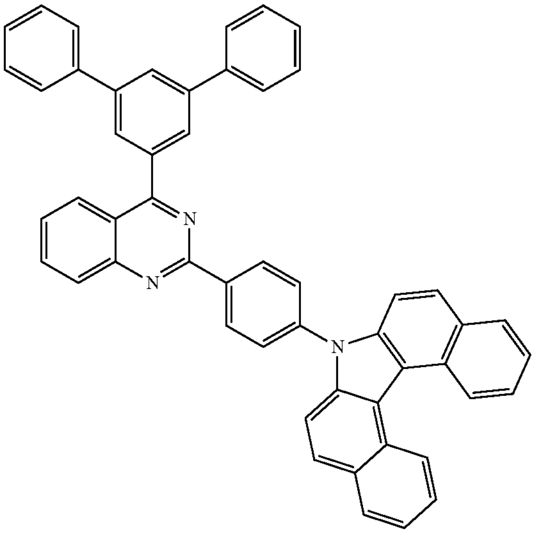
A-25
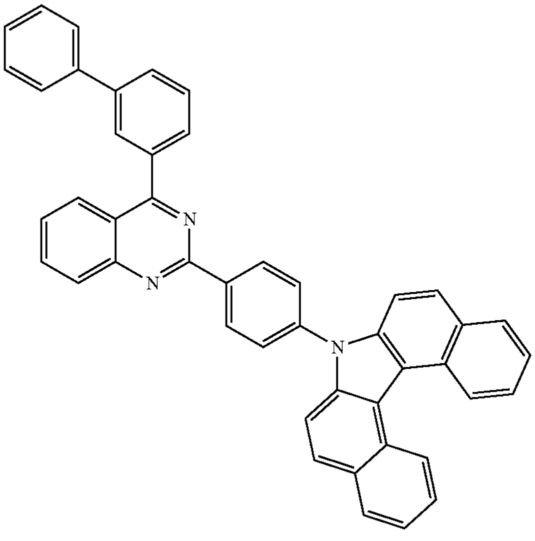

-continued
A-26
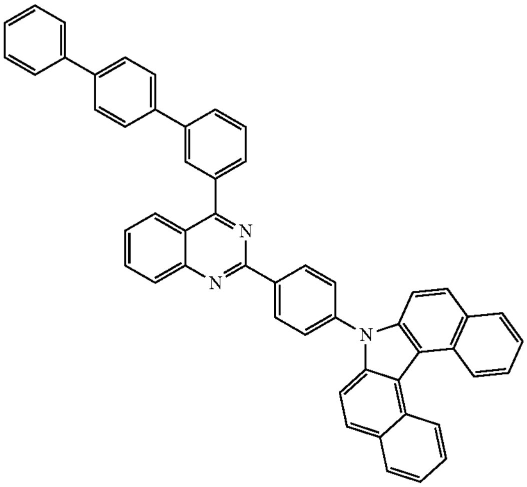
A-27
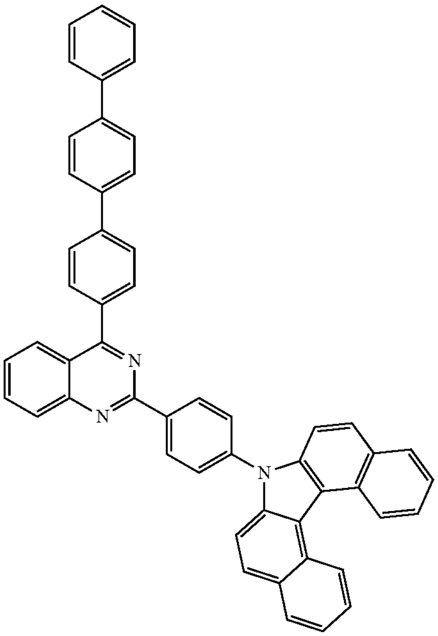
-continued
A-28
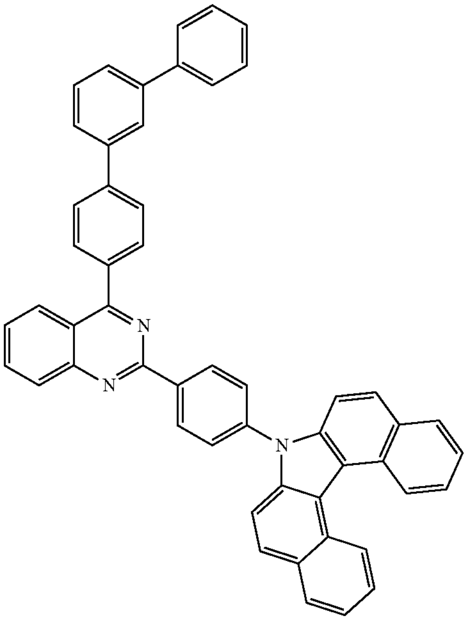
A-29
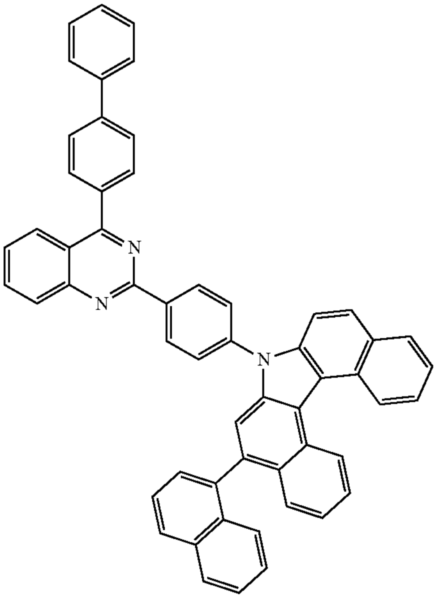

-continued
A-30
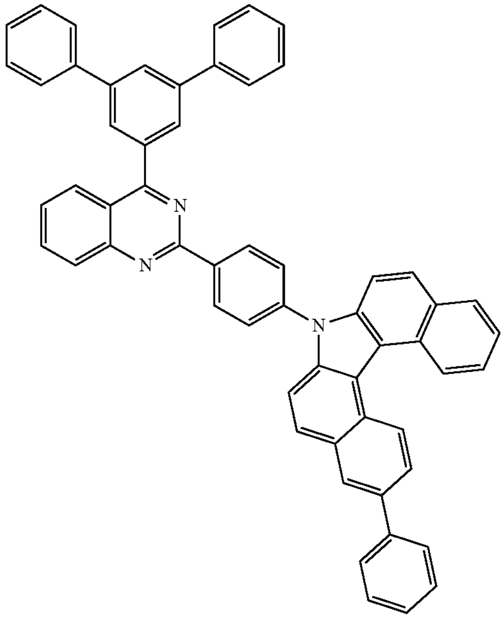
A-31
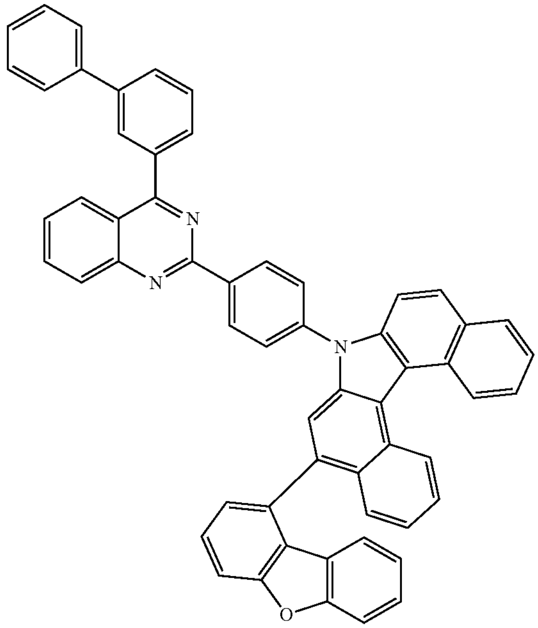
-continued
A-32
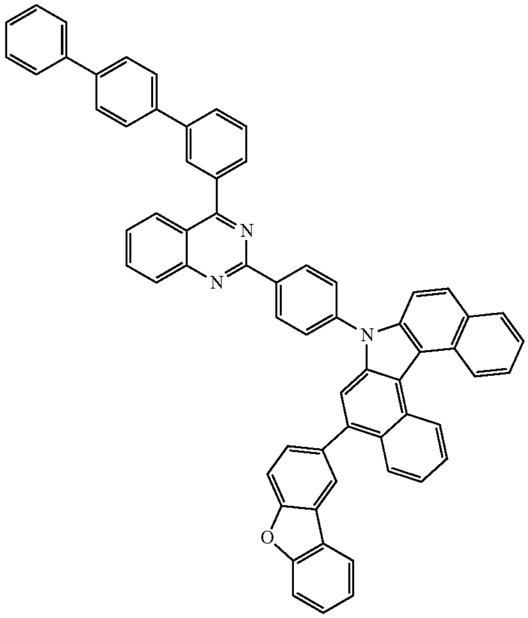
A-33
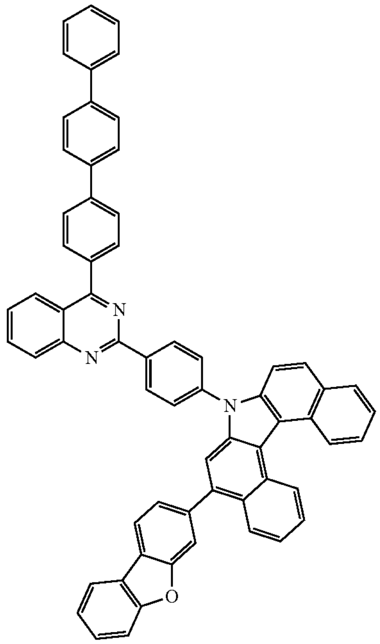

-continued
A-34
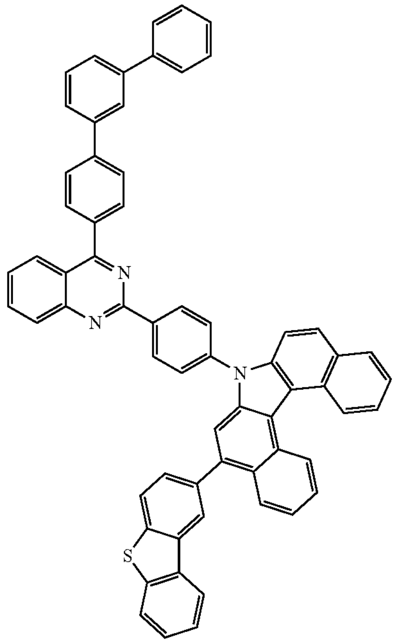
A-35
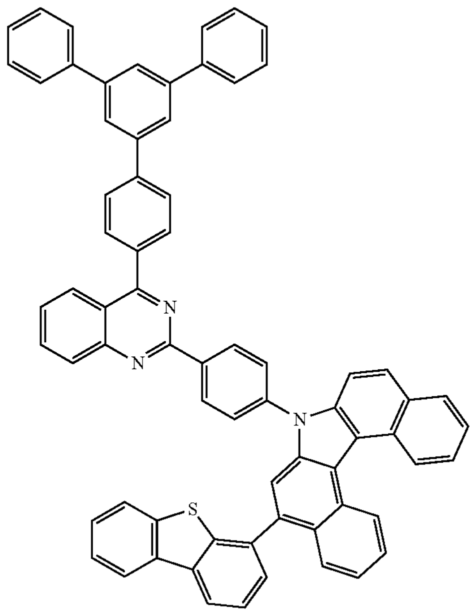
-continued
A-36
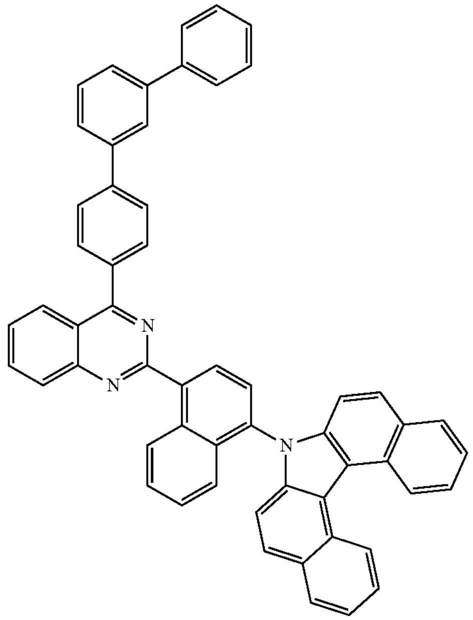
A-37
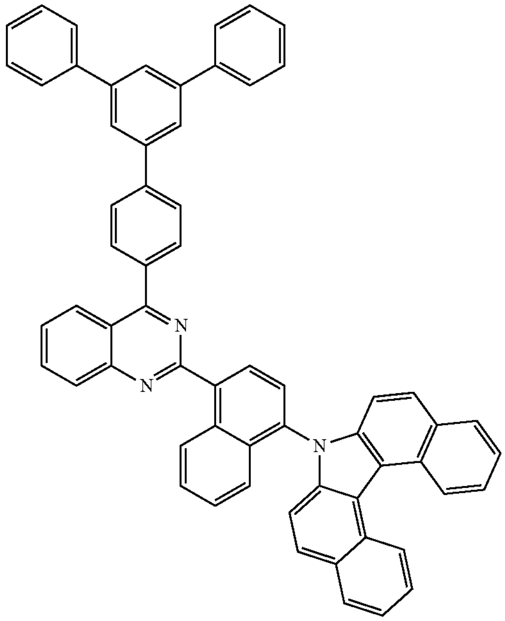

-continued
A-38
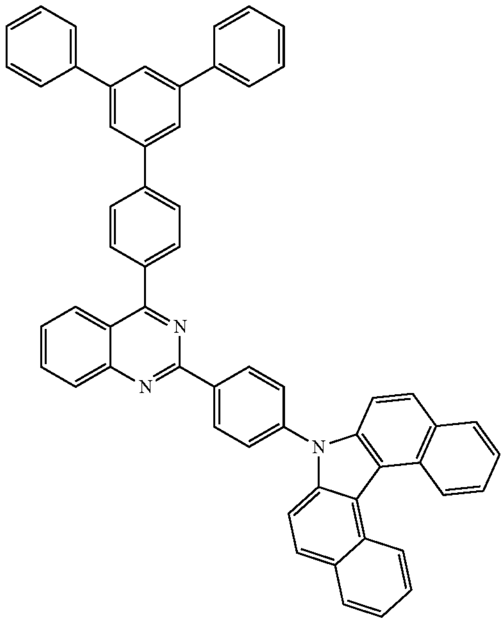
A-39
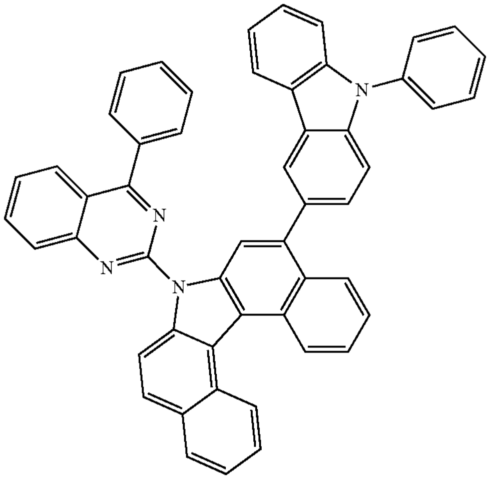
A-40
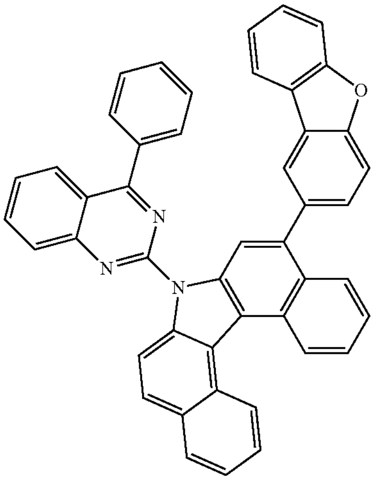
-continued
A-41
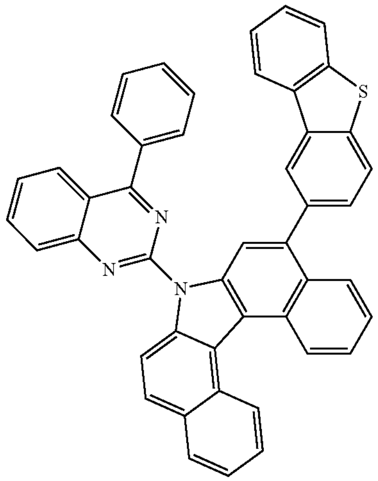
A-42
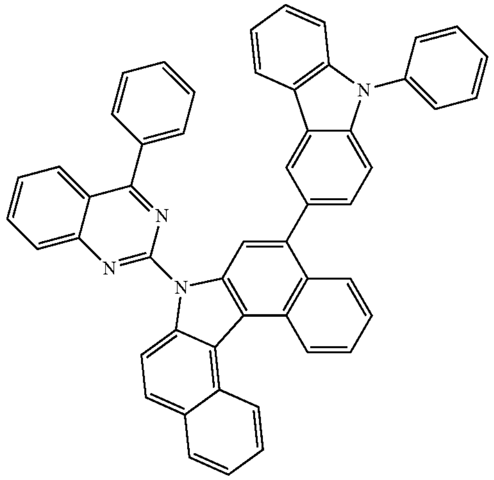
A-43
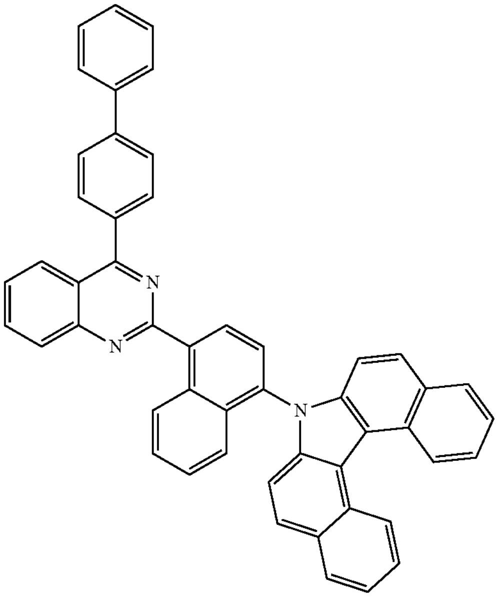

-continued
A-44
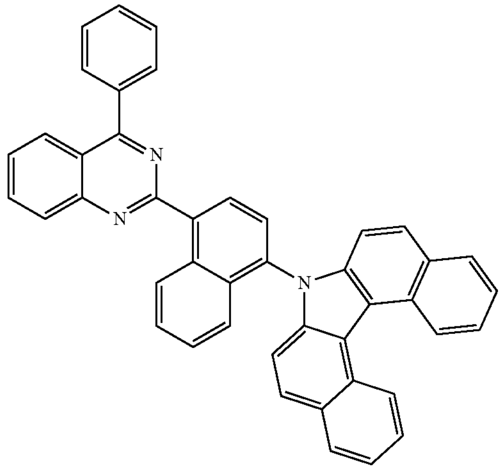
A-45
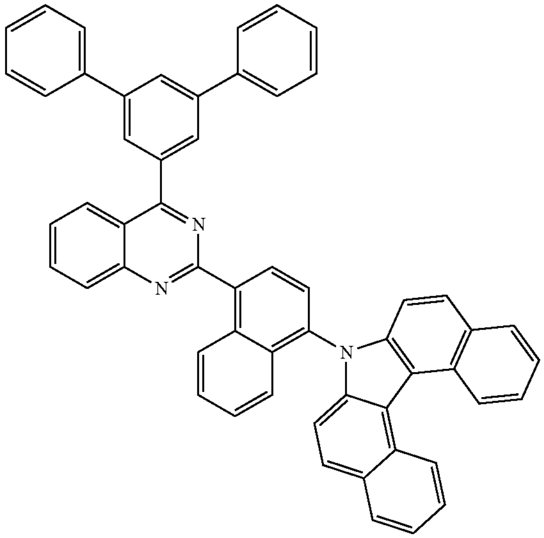
A-46
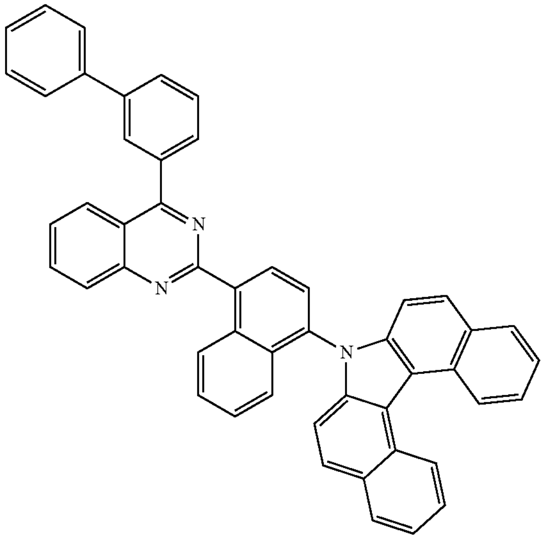
-continued
A-47
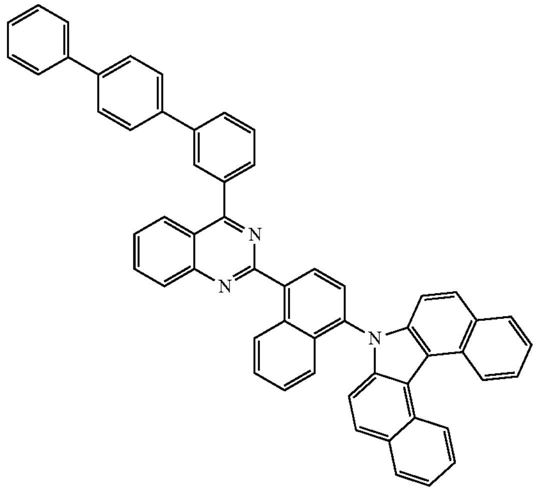
A-48
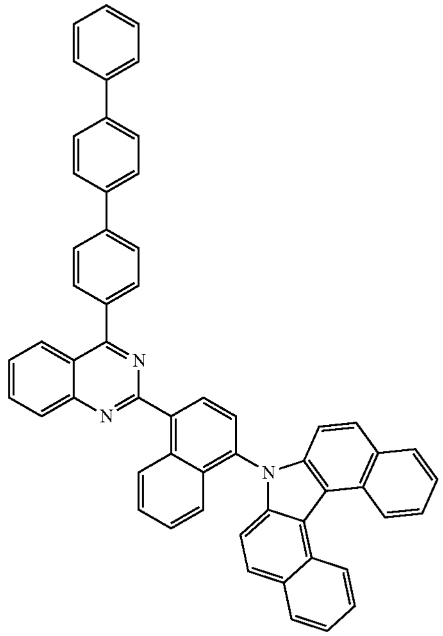

-continued
A-49
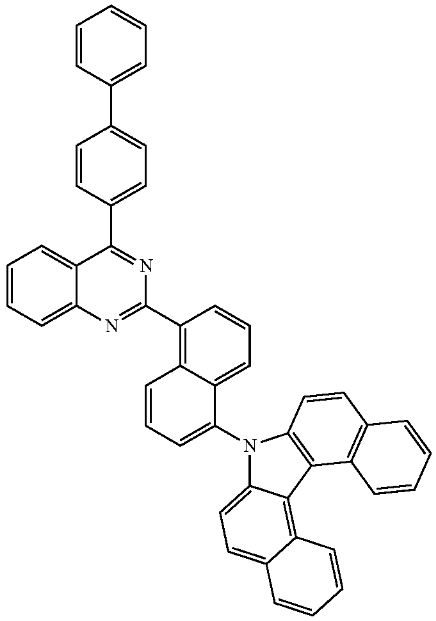
A-50
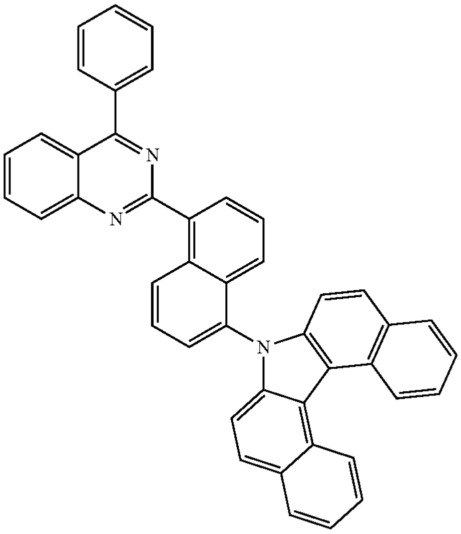
-continued
A-51
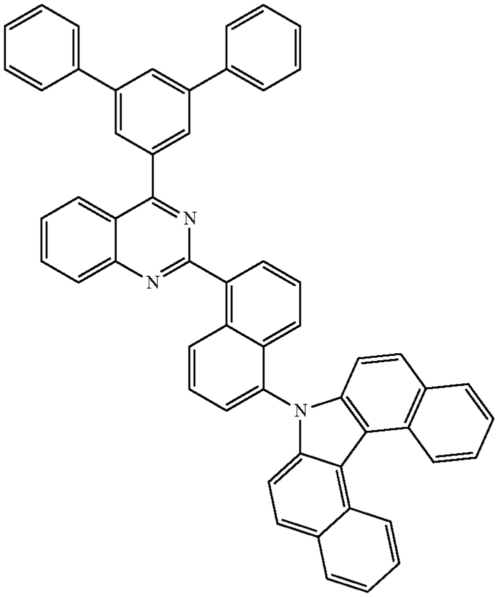
A-52
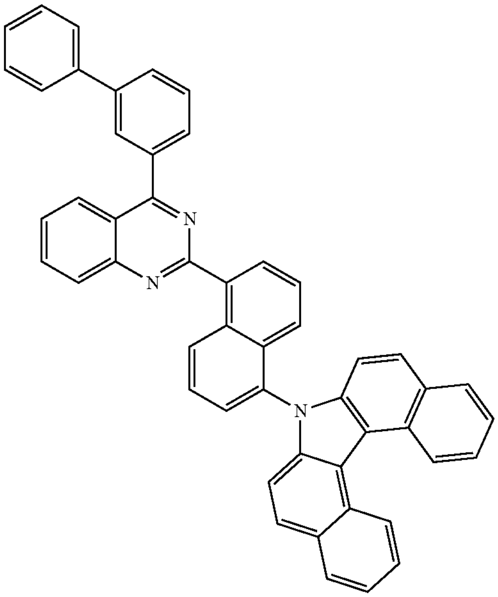

-continued
A-53
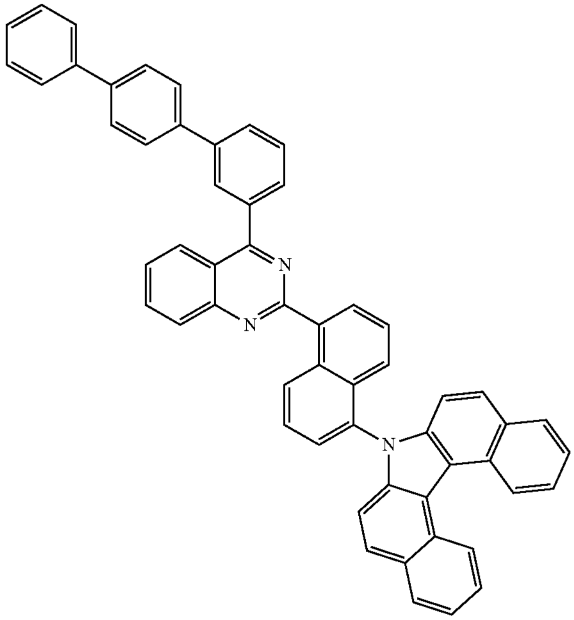
A-54
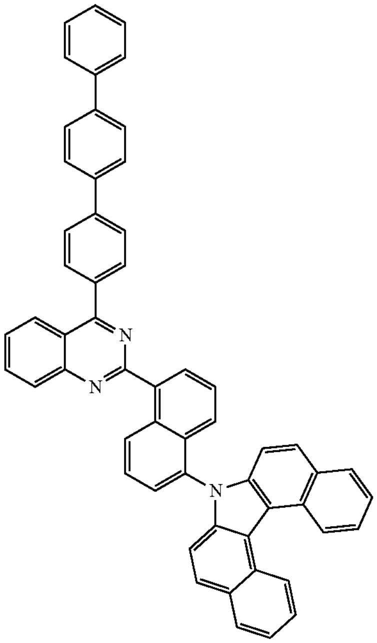
-continued
A-55
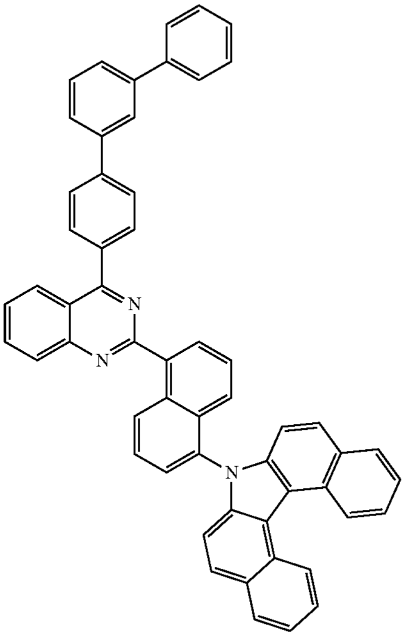
A-56
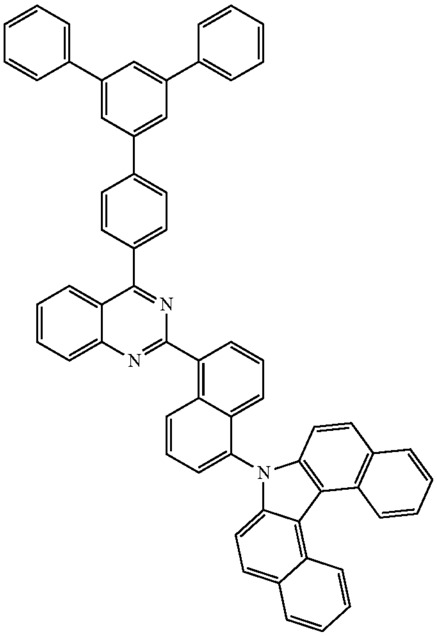

-continued
A-57
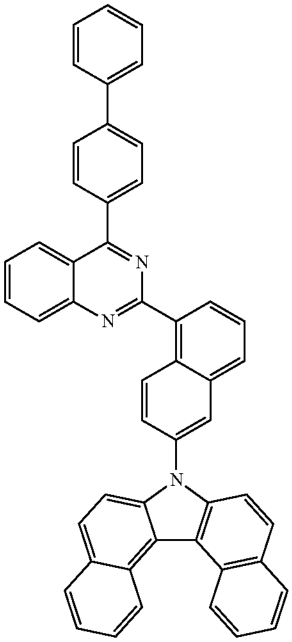
-continued
A-59
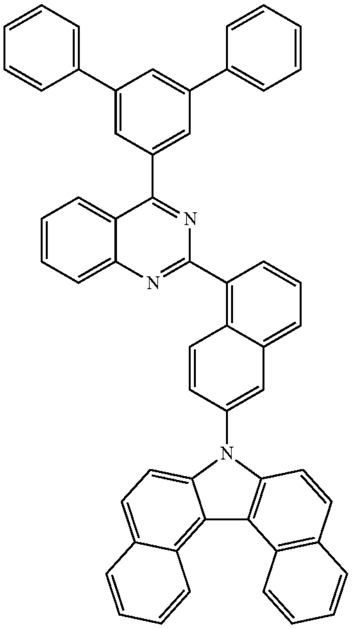
A-58
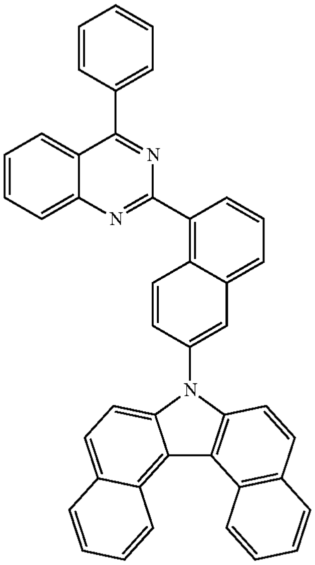
A-60
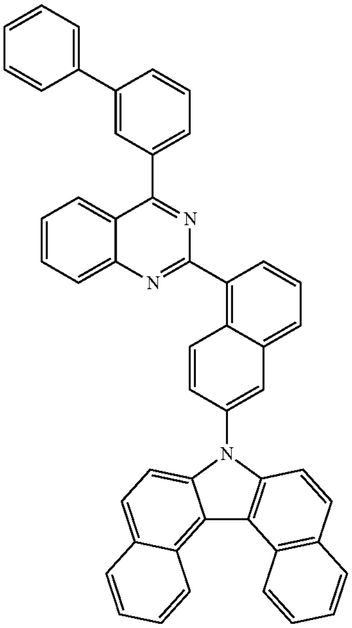

-continued
A-61
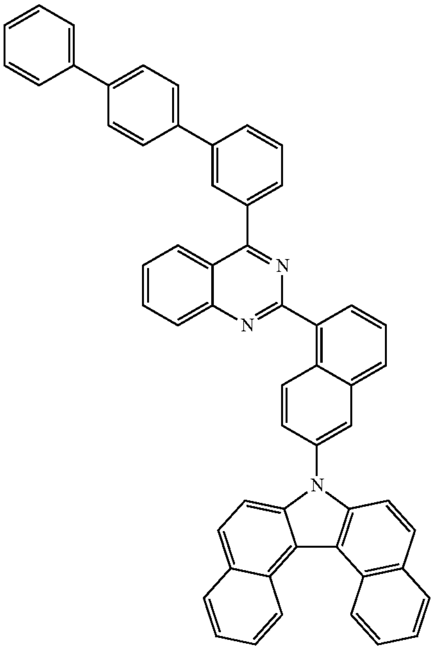
A-62
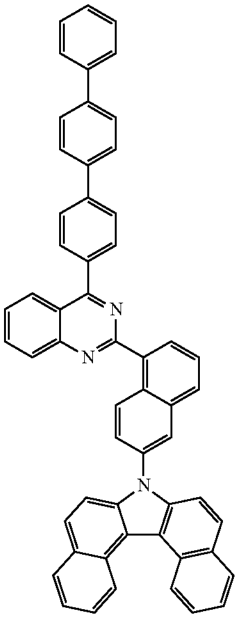
-continued
A-63
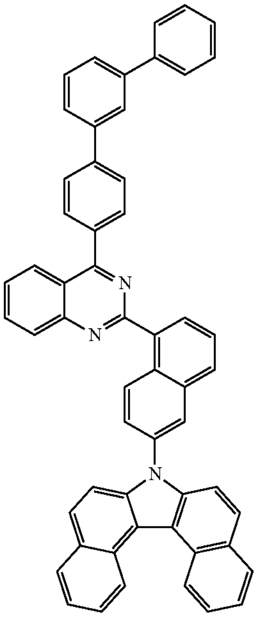
A-64
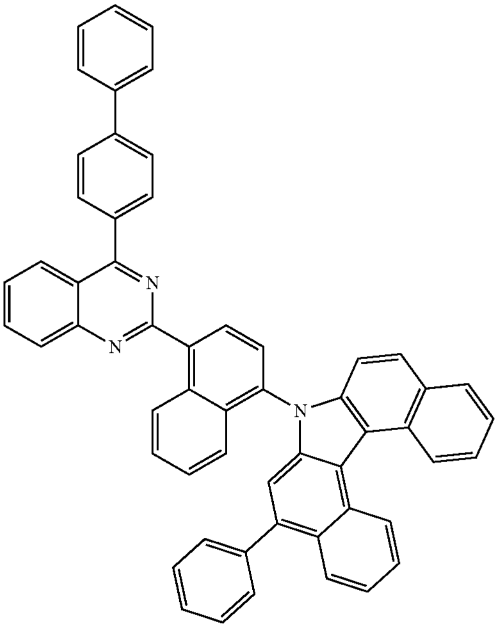

-continued
A-65
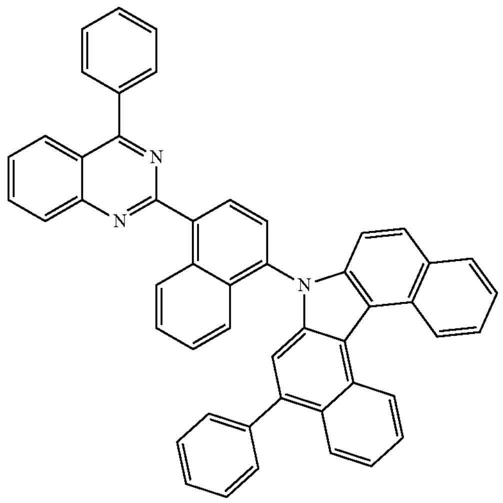
-continued
A-67
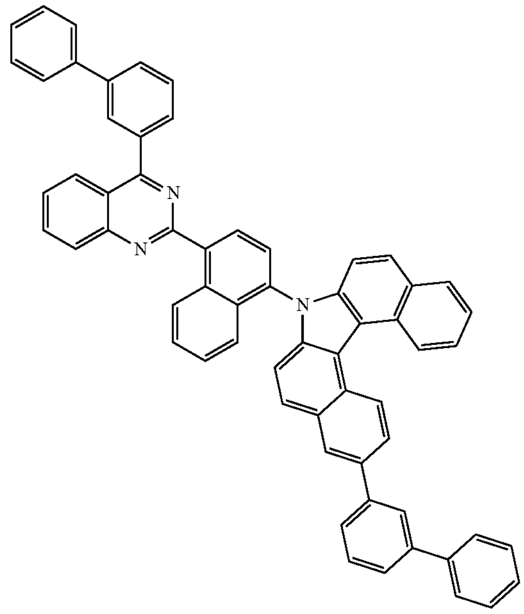
A-68
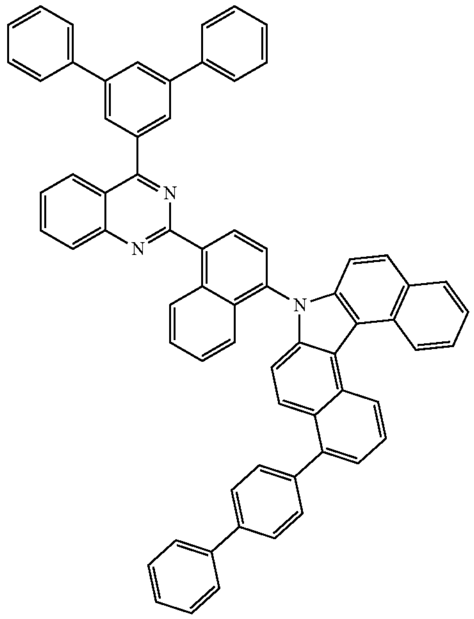
A-68
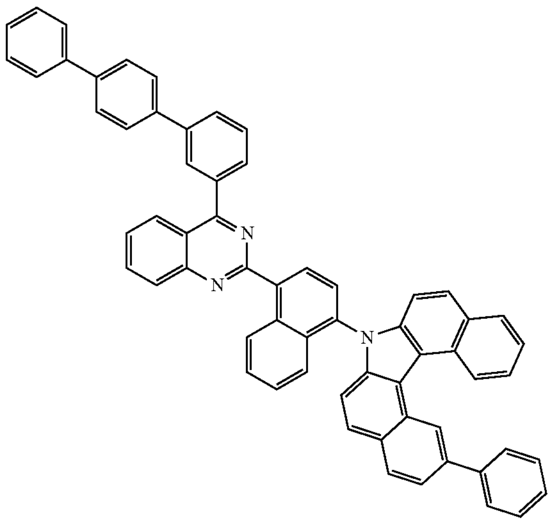

-continued
A-69
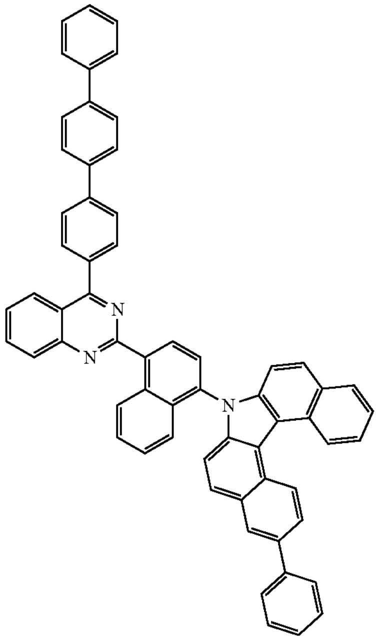
A-70
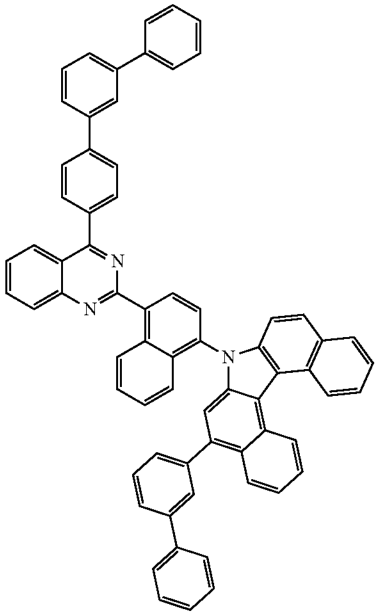
-continued
A-71
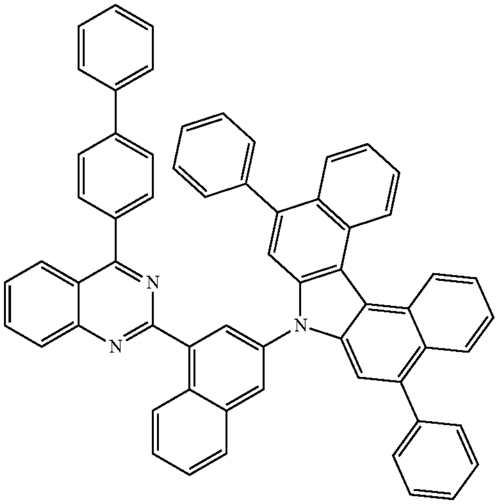
A-72
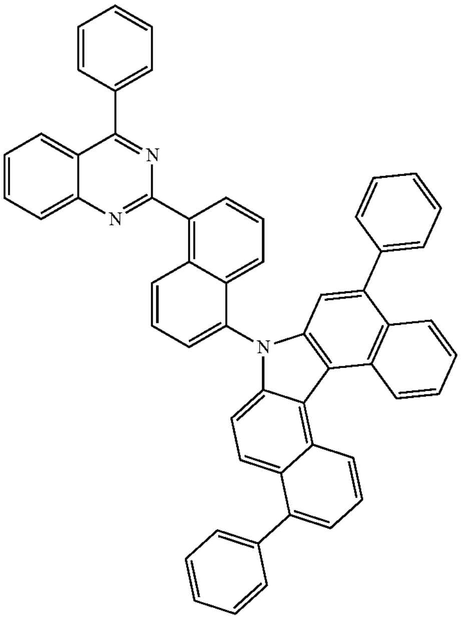

-continued
A-73
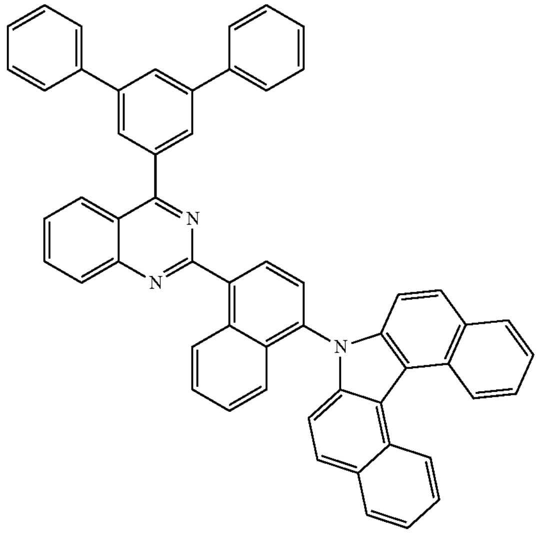
A-74
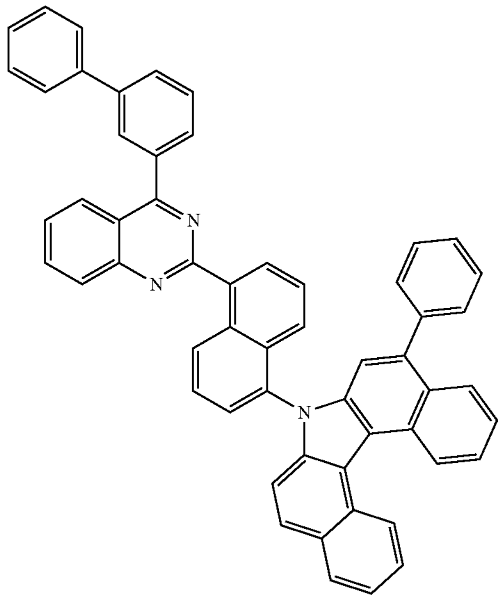
-continued
A-75
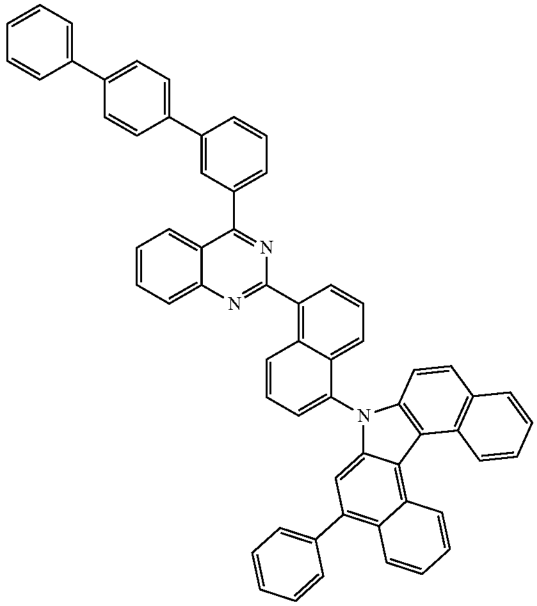
A-76
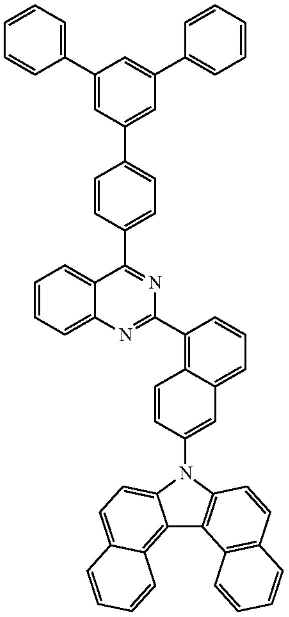

-continued
A-77
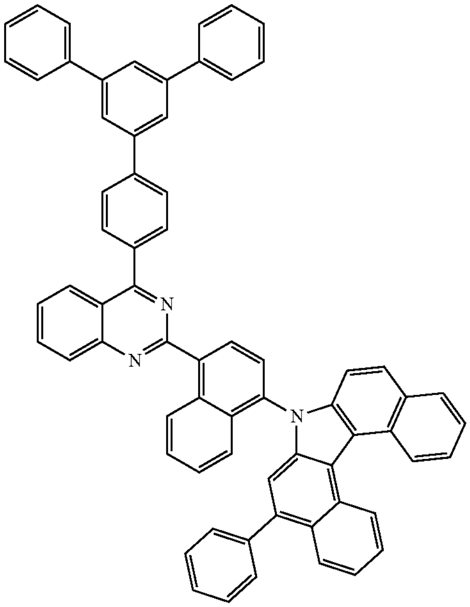
A-78
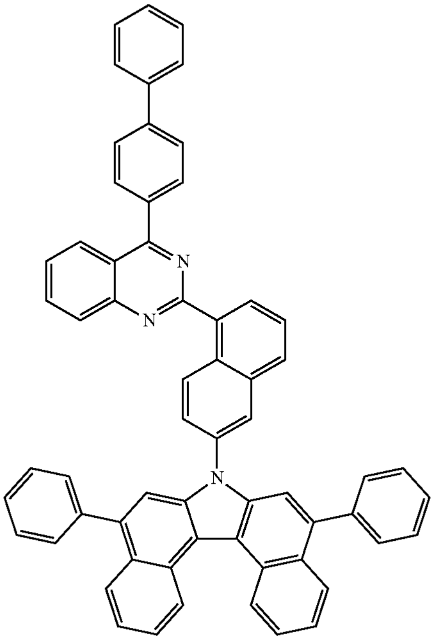
-continued
A-79
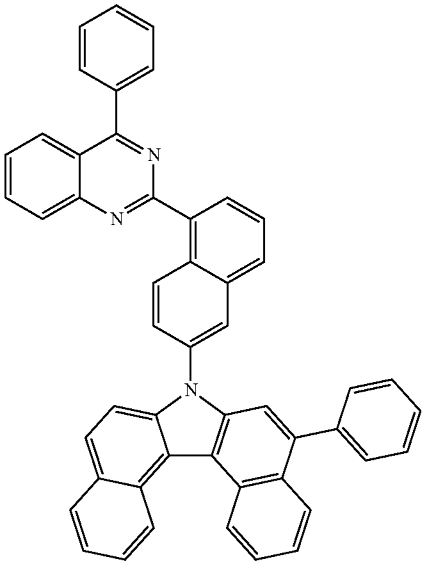
A-80
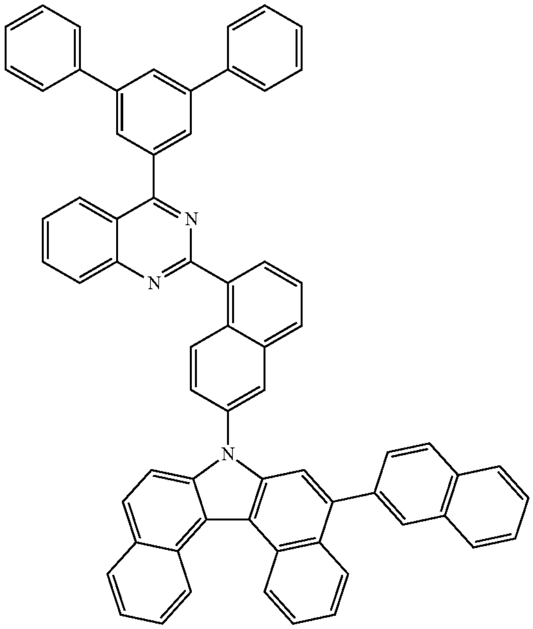

-continued
A-81
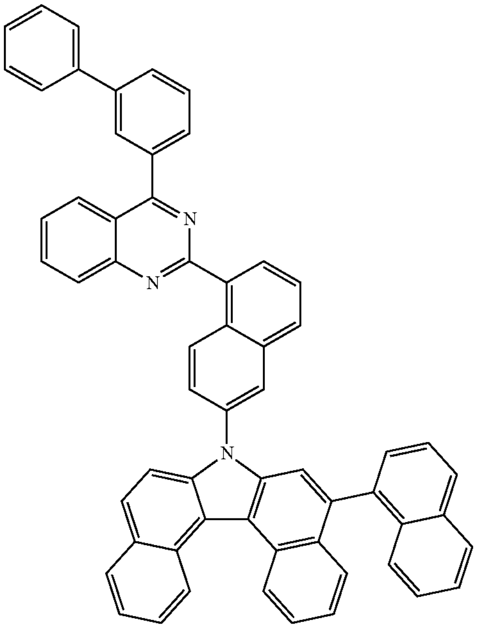
A-82
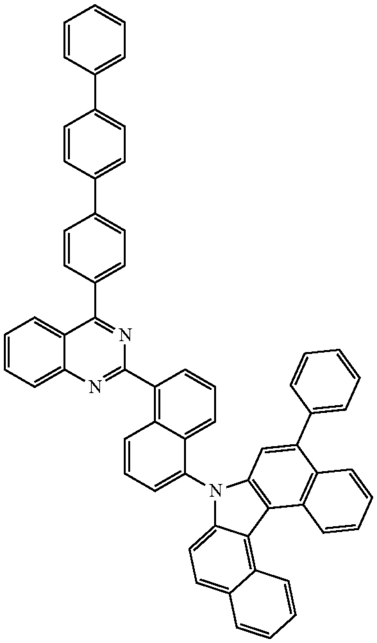
-continued
A-83
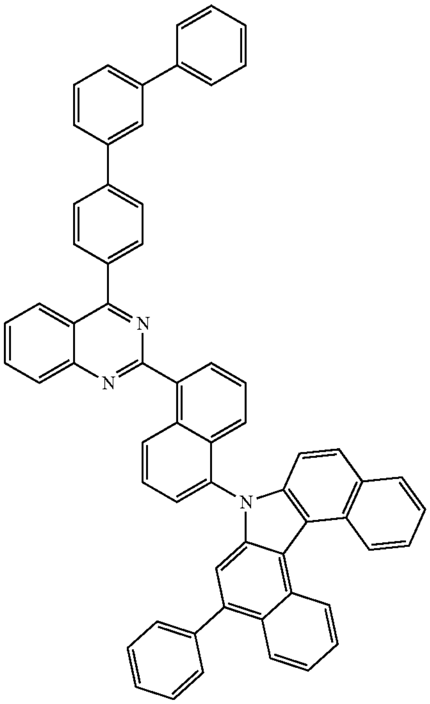
A-84
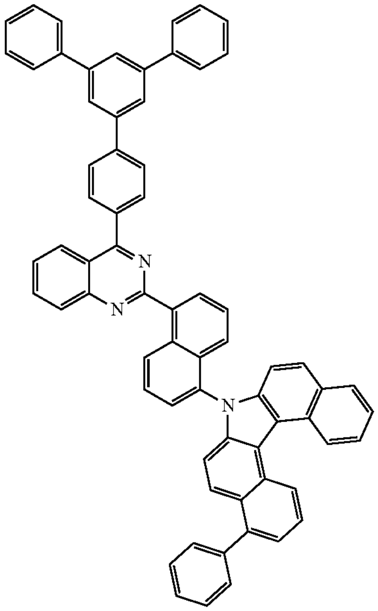

-continued
A-85
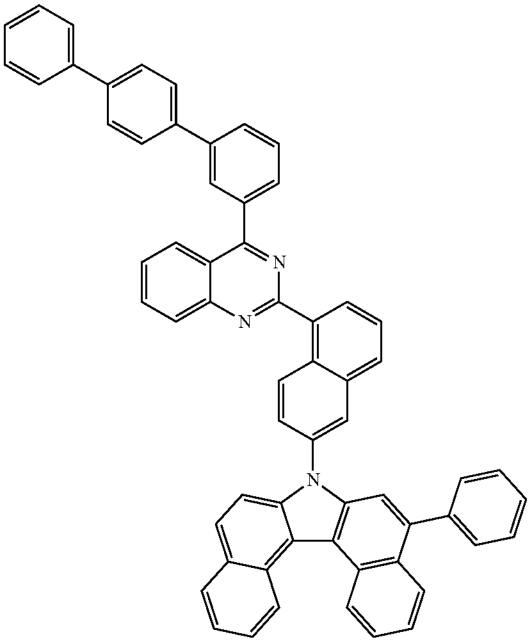
A-86
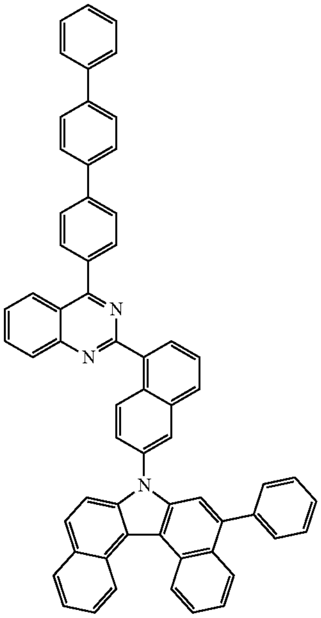
-continued
A-87
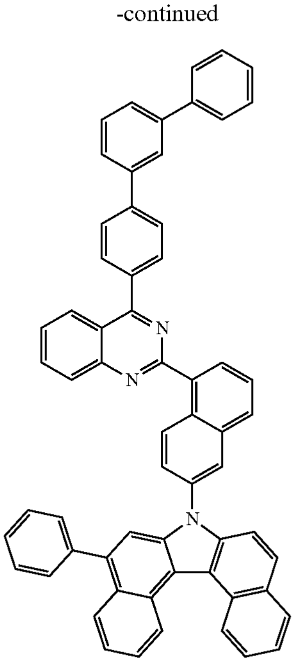
A-88
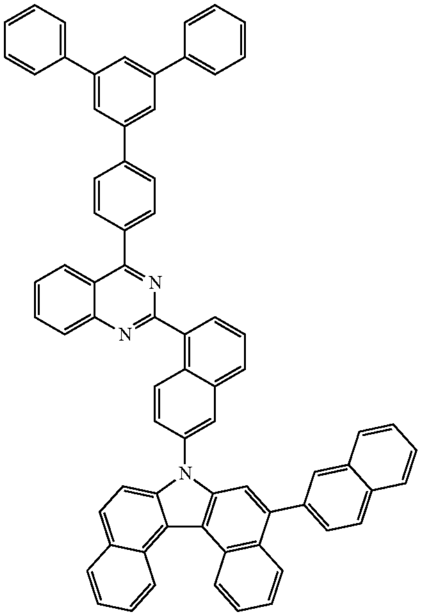

-continued
A-89
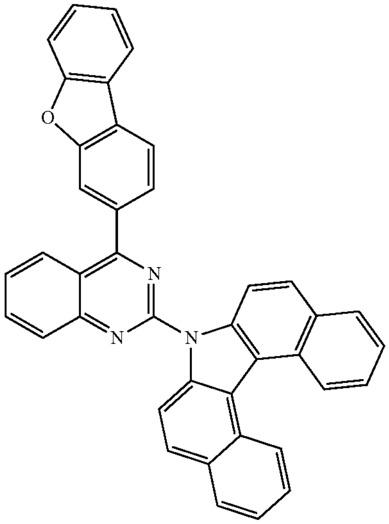
A-90
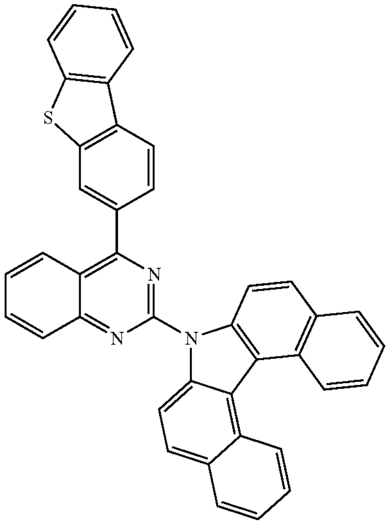
A-91
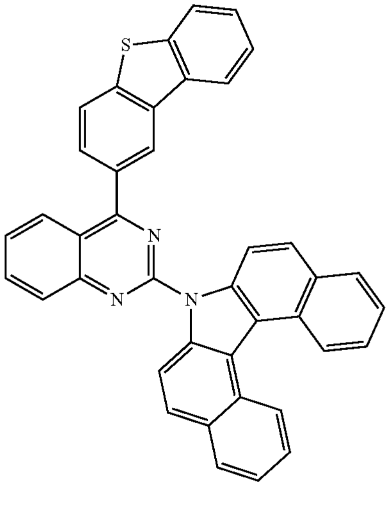
-continued
A-92
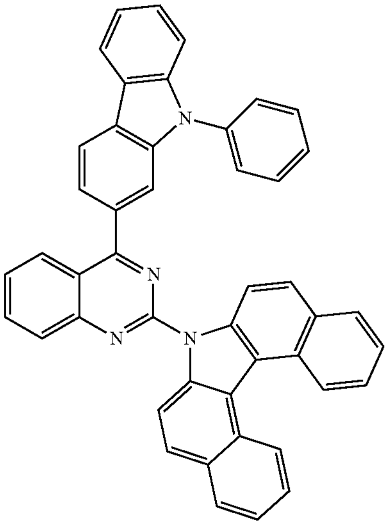
A-93
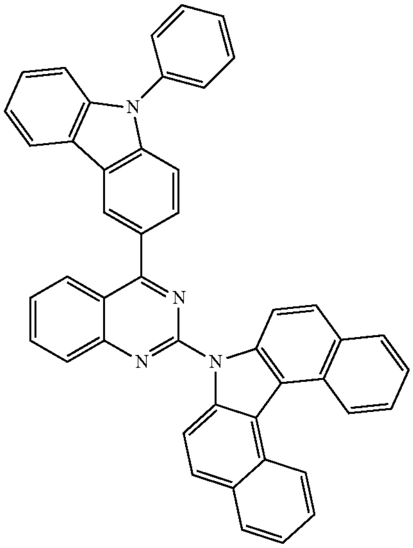
A-94
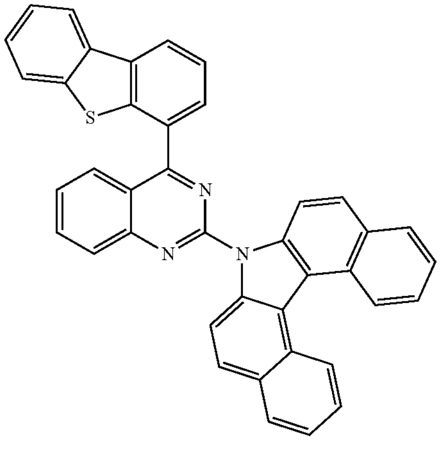

-continued
A-95
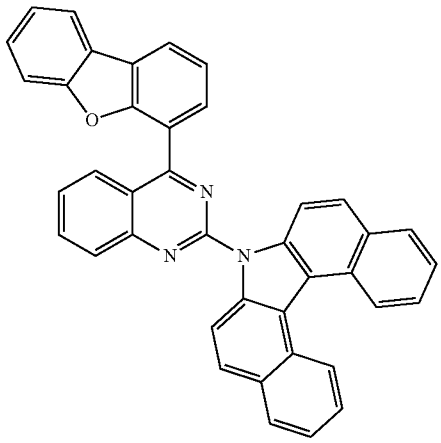
A-96
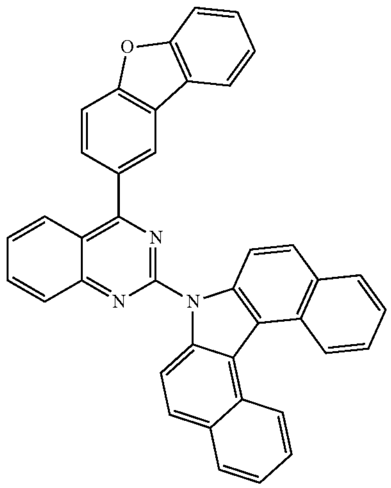
A-97
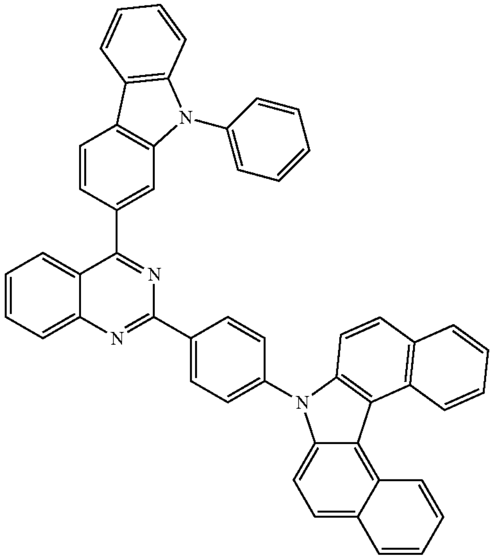
-continued
A-98
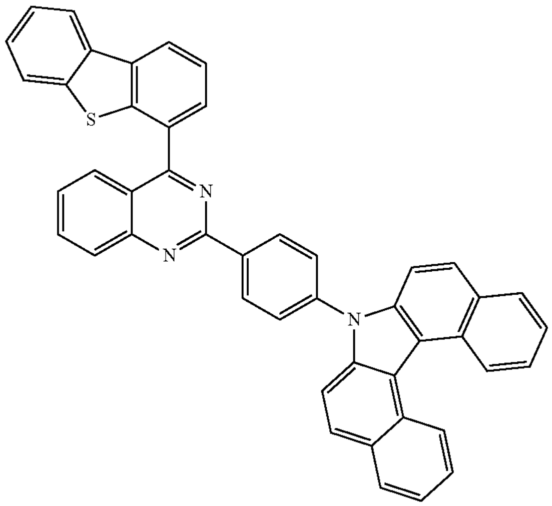
A-99
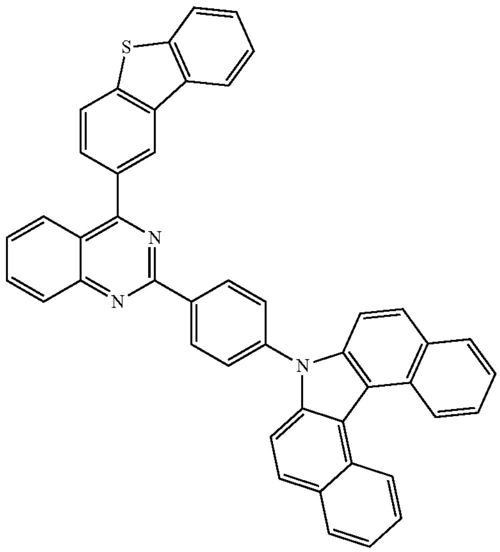
A-100
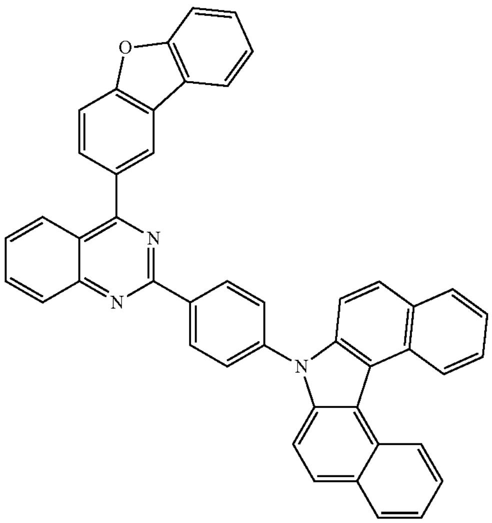

-continued
A-101
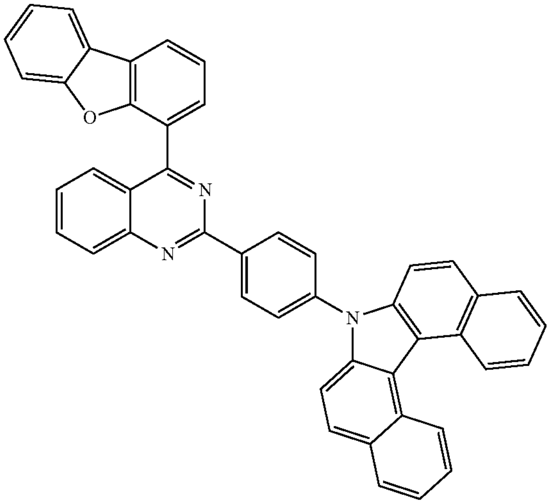
A-102
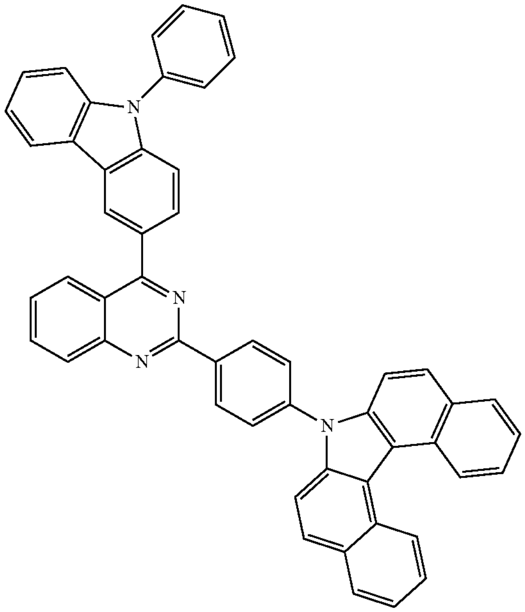
-continued
A-103
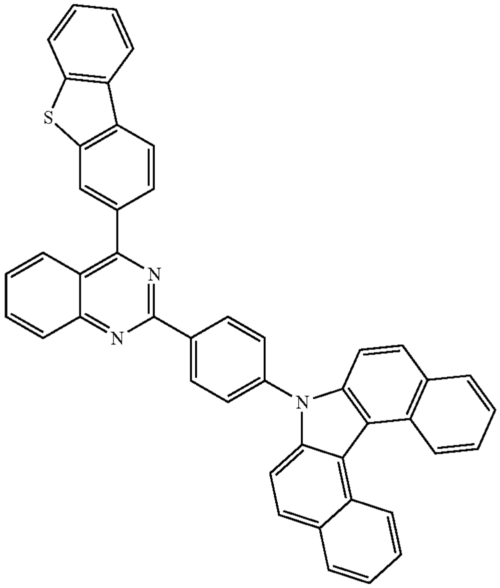
A-104
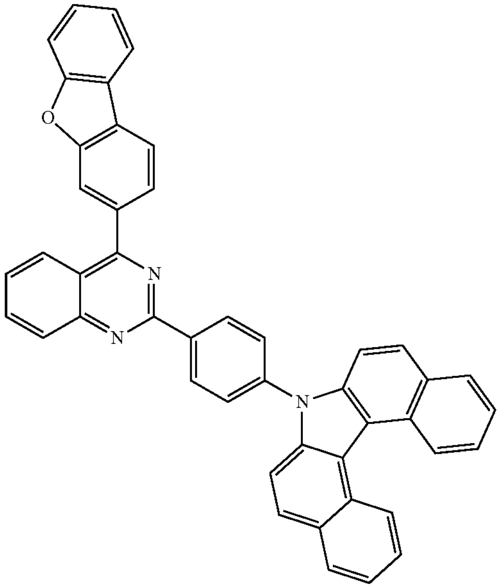

-continued
A-105
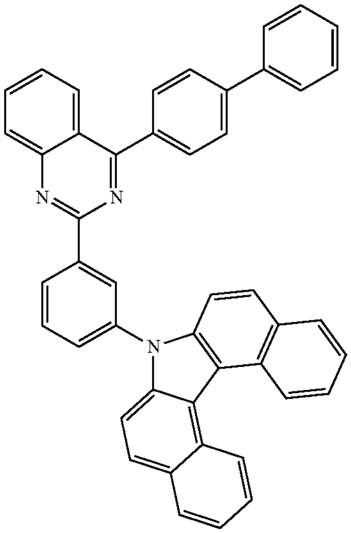
A-106
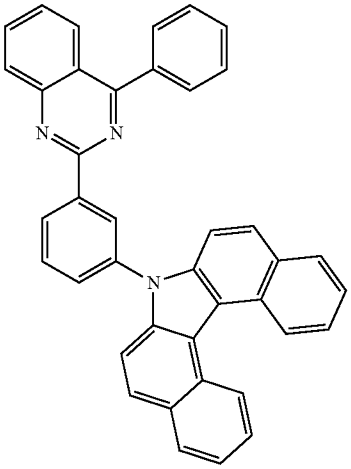
A-107
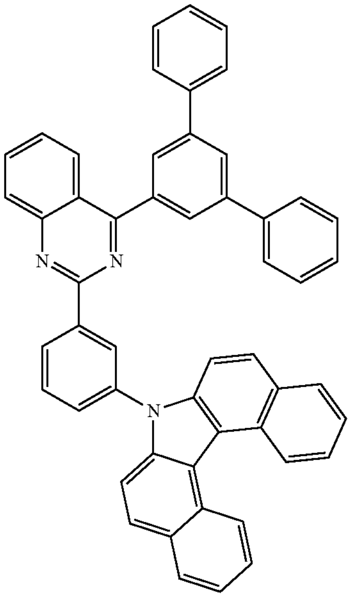
-continued
A-108
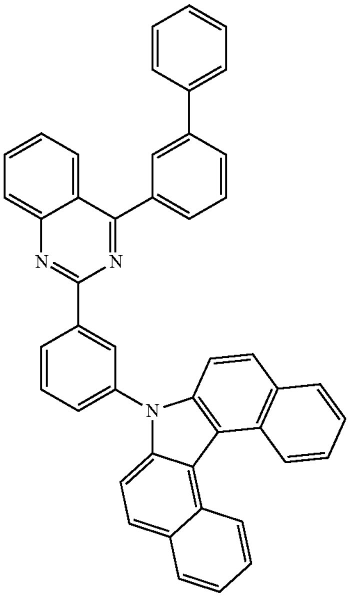
A-109
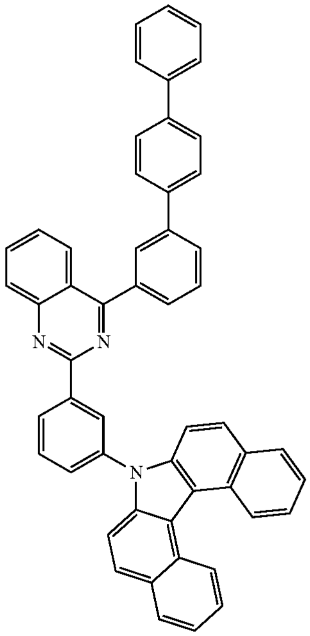

-continued
A-110
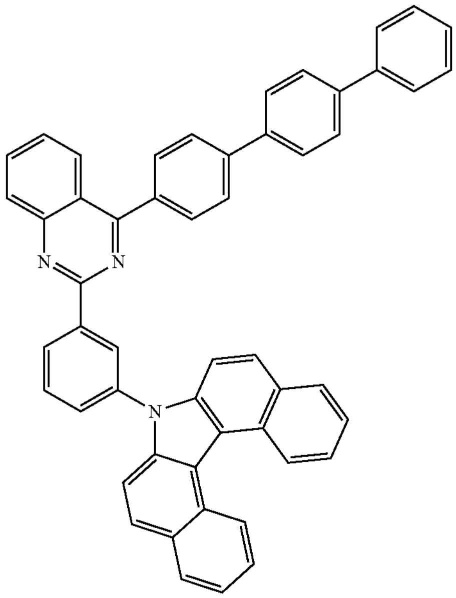
A-111
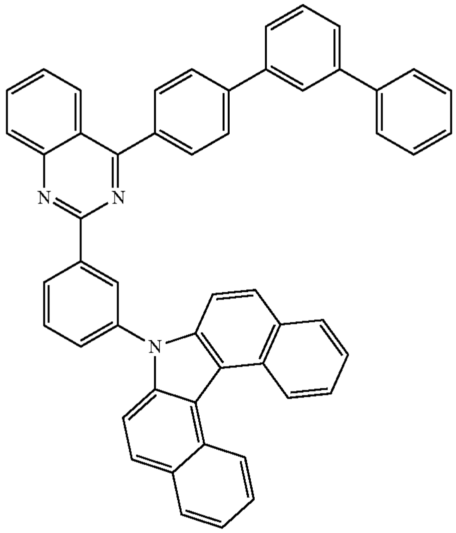
A-112
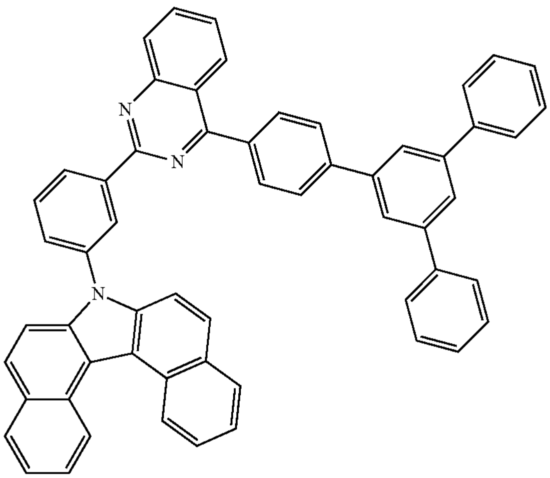
-continued
A-113
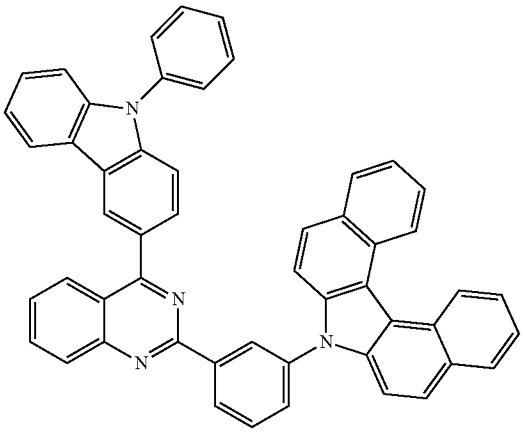
A-114
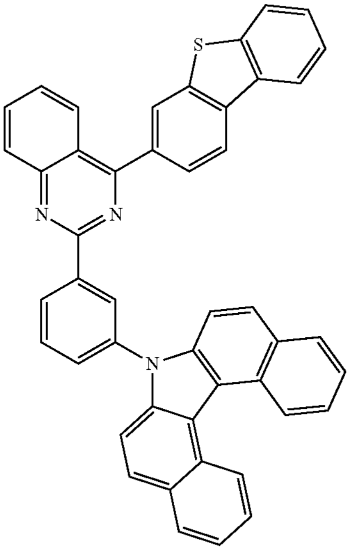
A-115
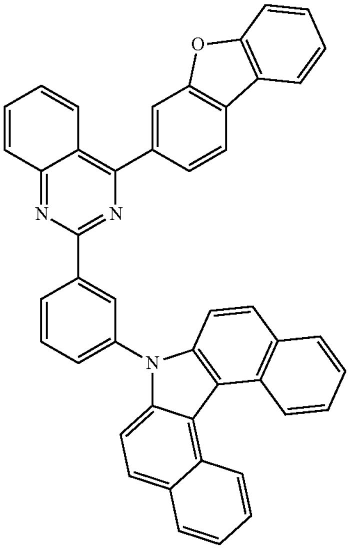

-continued
A-116
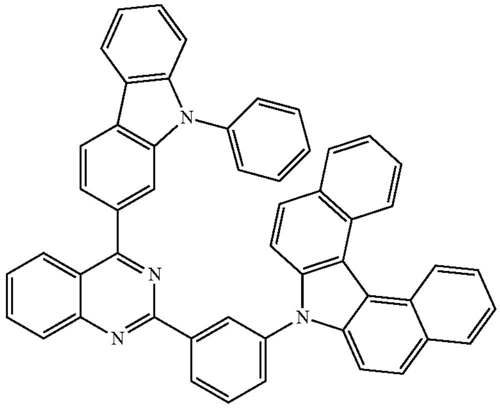
A-117
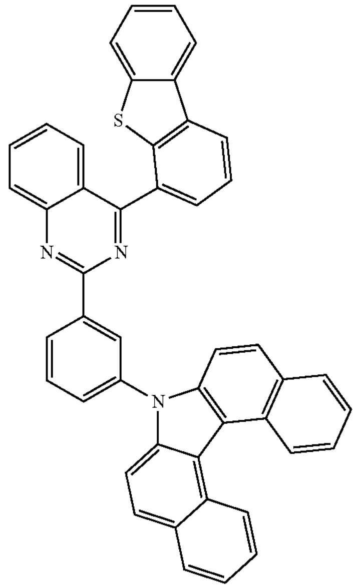
A-118
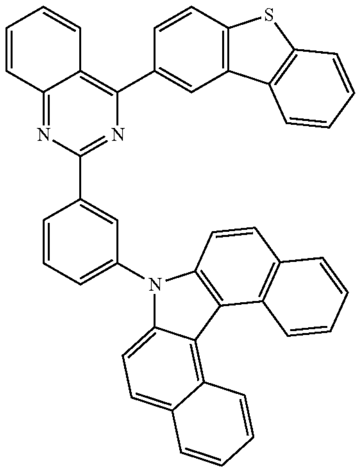
-continued
A-119
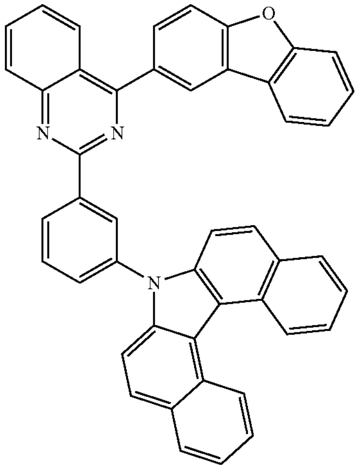
A-120
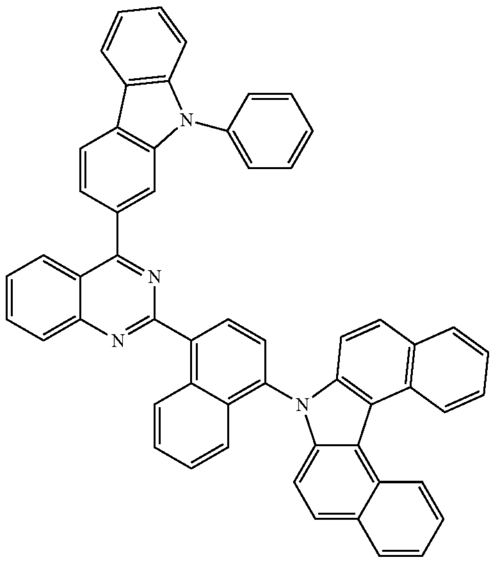
A-121
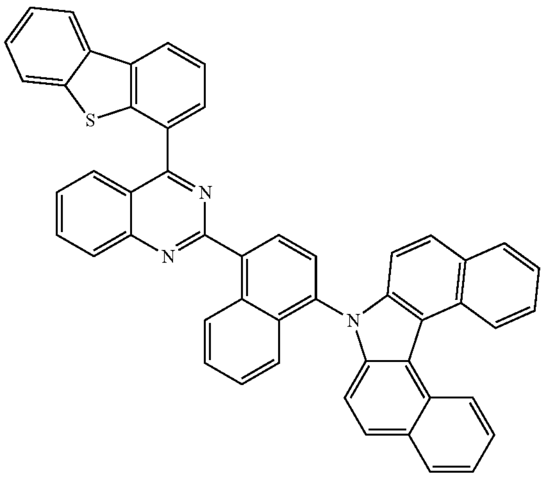

-continued
A-122
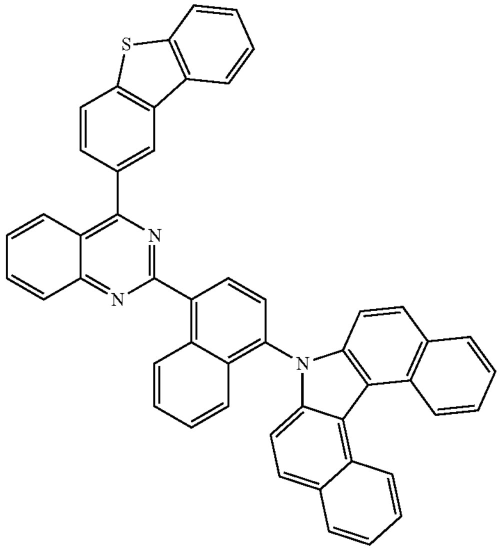
A-123
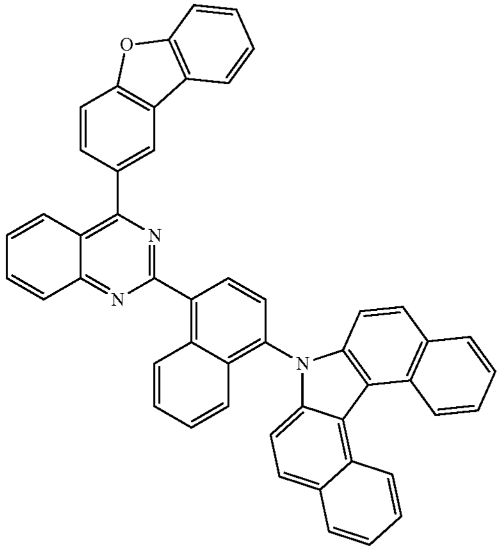
A-124
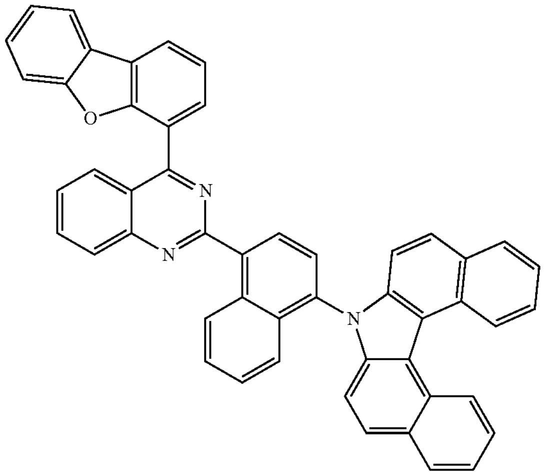
-continued
A-125
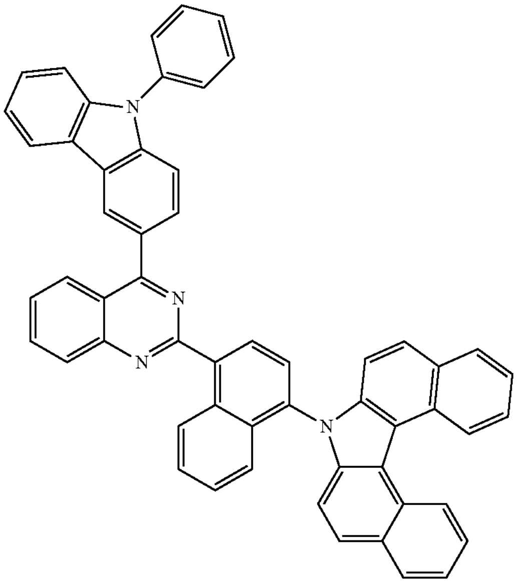
A-126
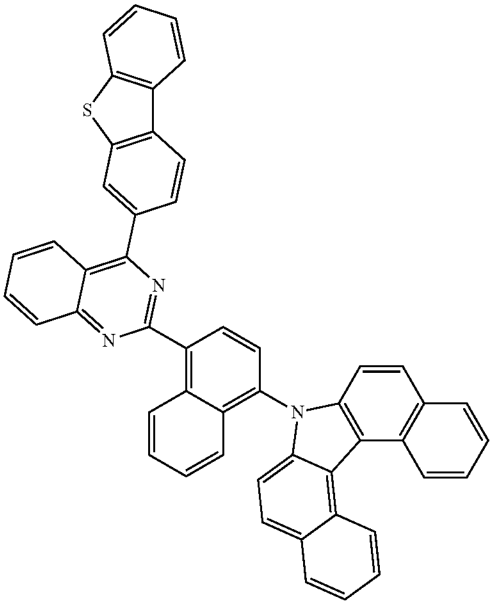

-continued
A-127
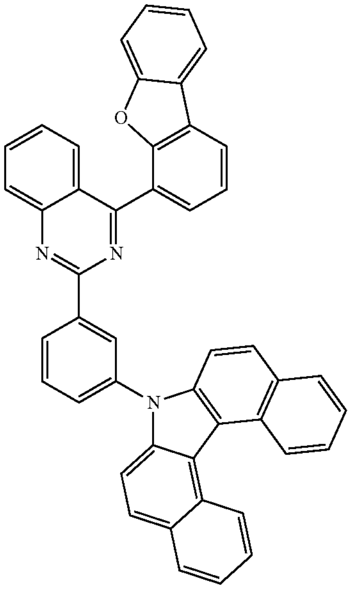
A-128
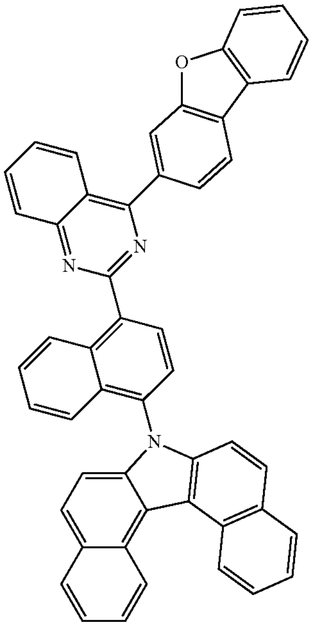
A-129
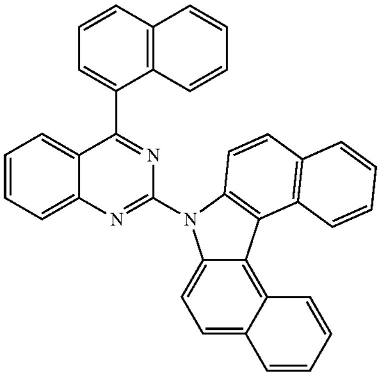
-continued
A-130
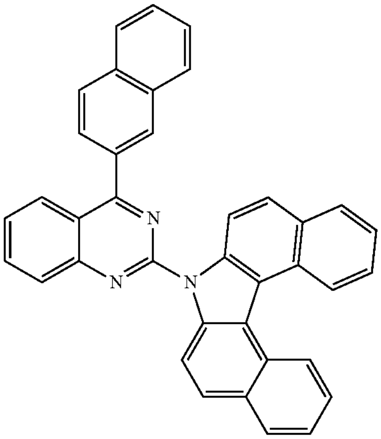
A-131
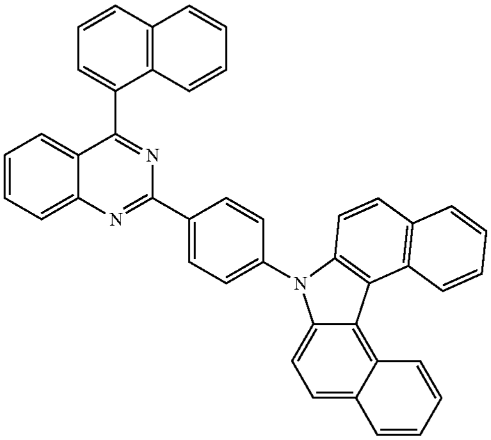
A-132
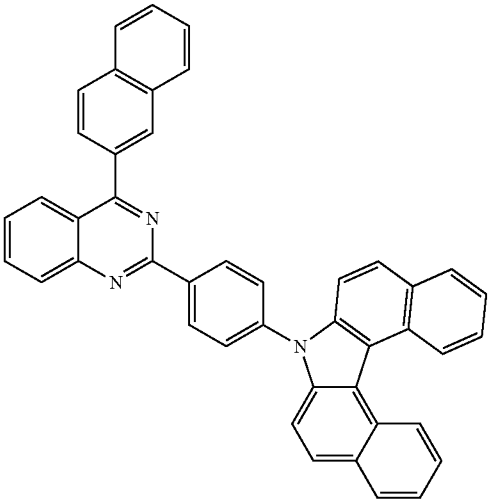

-continued
A-133
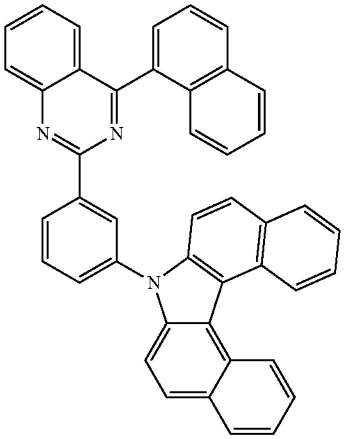
A-134
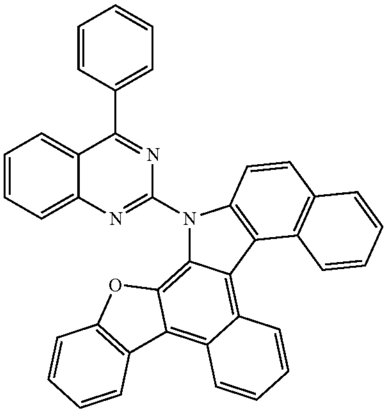
A-135
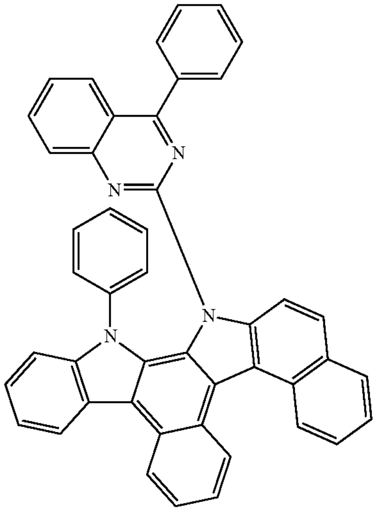
-continued
A-136
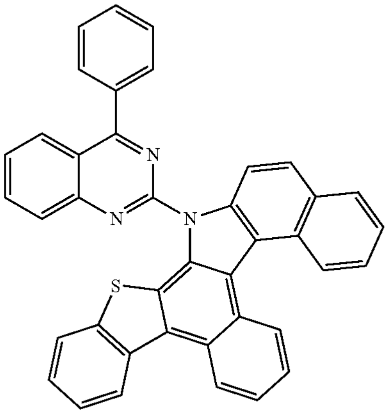
A-137
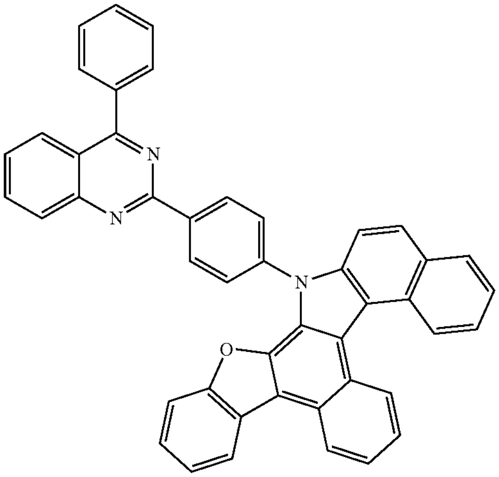
A-138
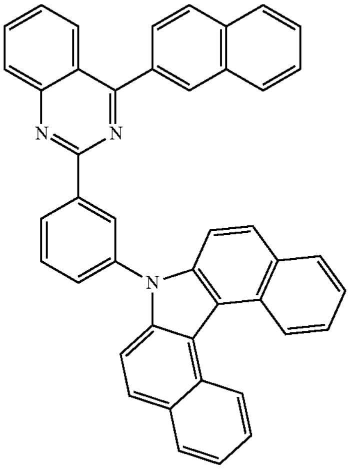

-continued
A-139
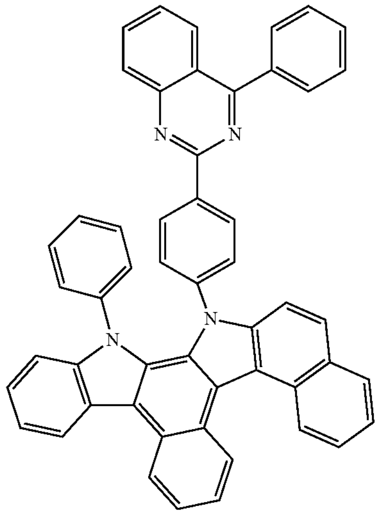
A-140
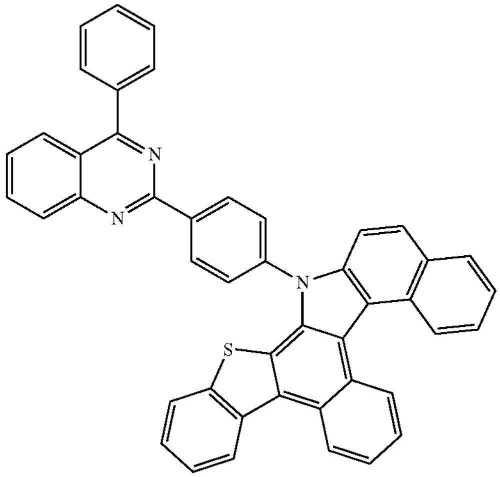
A-141
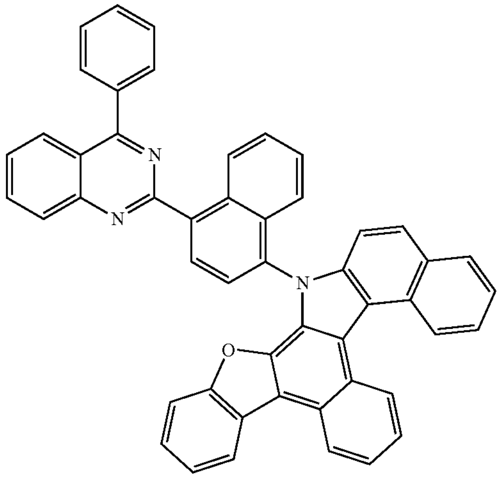
-continued
A-142
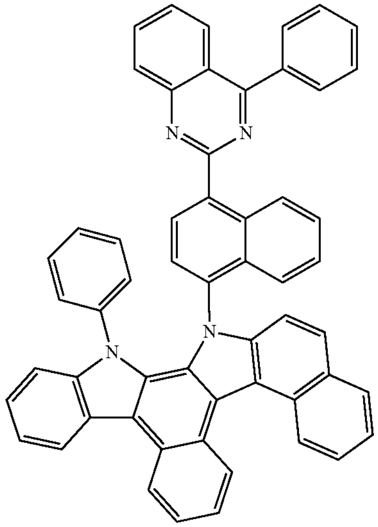
A-143
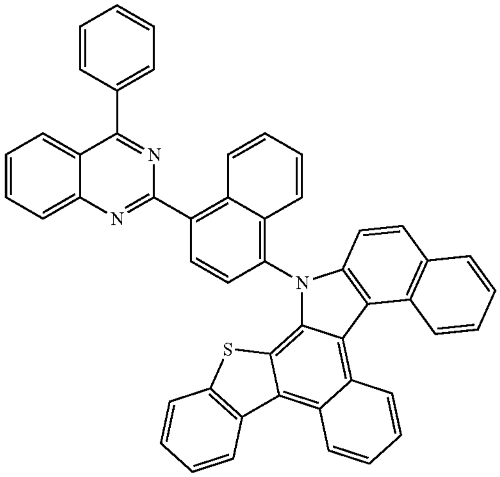
A-144
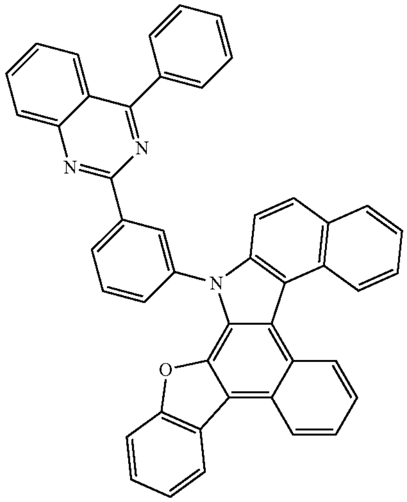

-continued
A-145
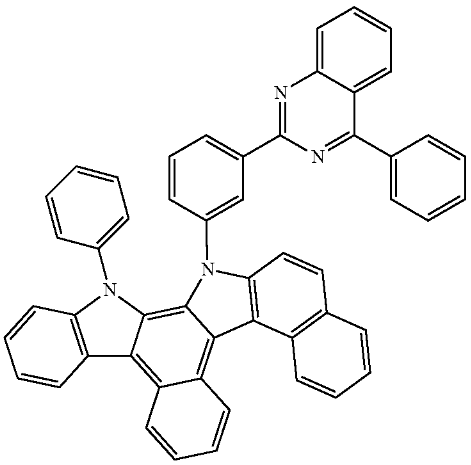
A-146
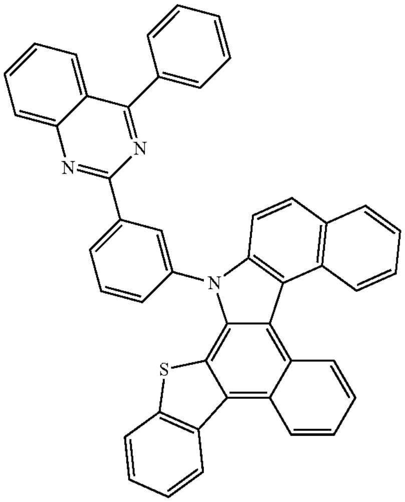
A-147
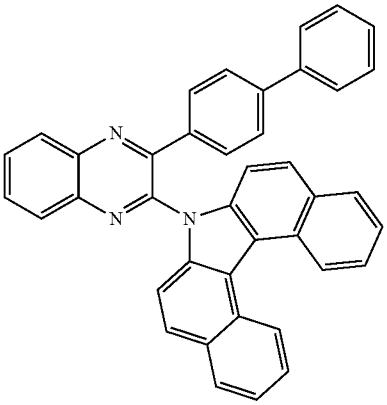
-continued
A-148
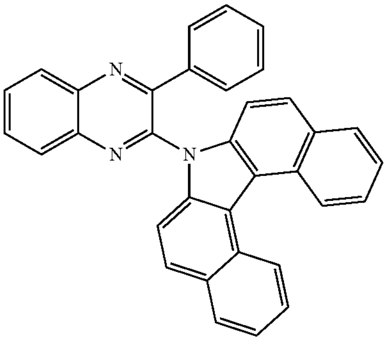
A-149
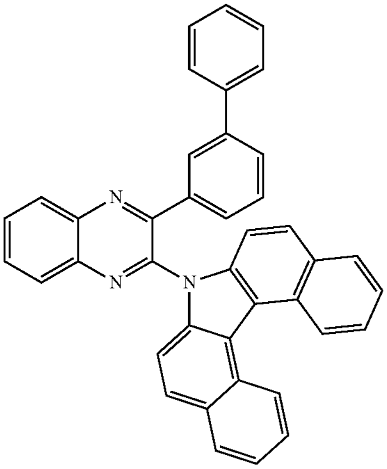
A-150
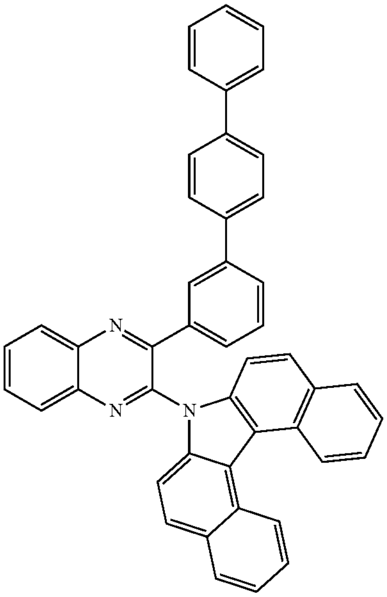

-continued
A-151
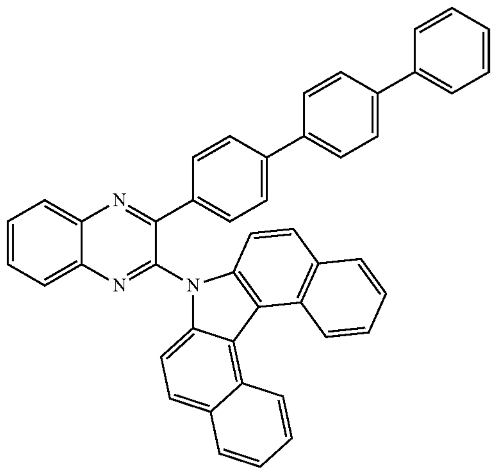
A-152
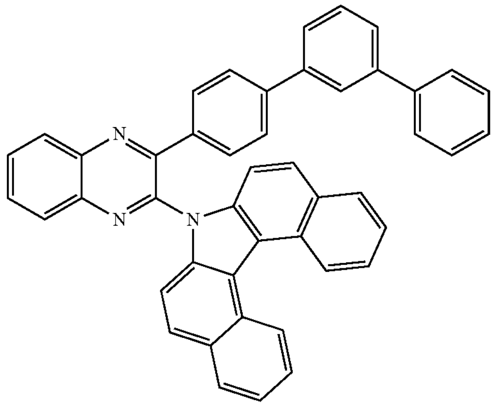
A-153
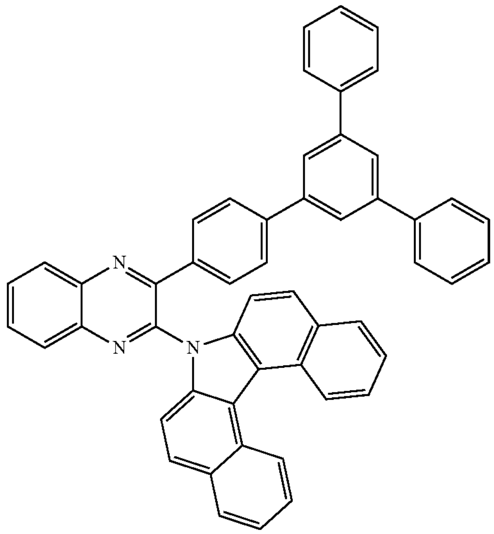
-continued
A-154
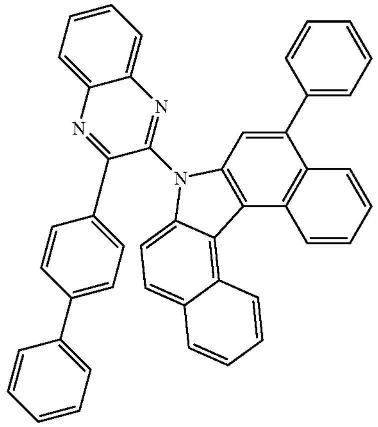
A-155
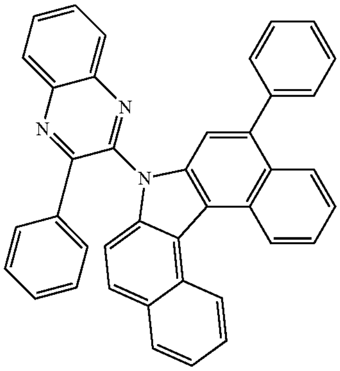
A-156
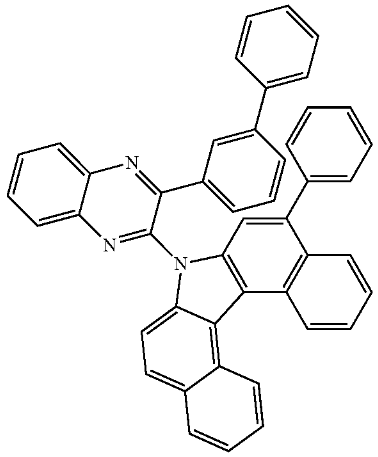
A-157
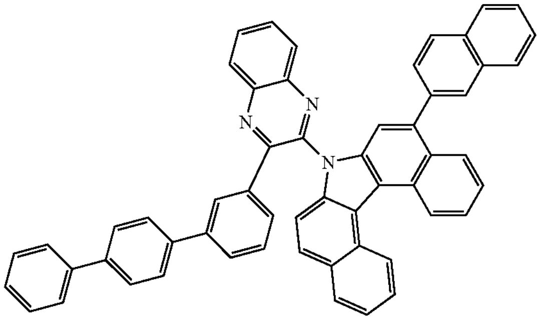

-continued
A-158
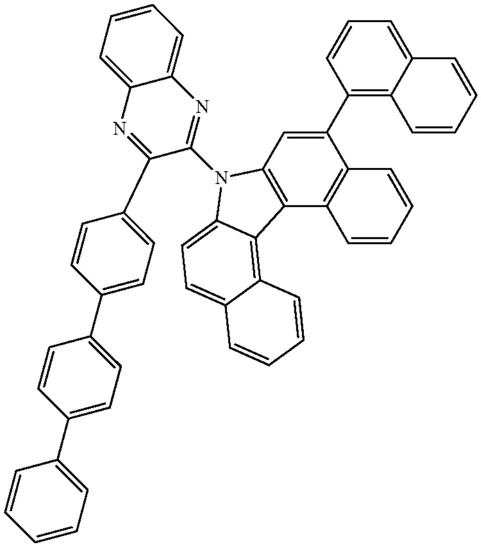
A-159
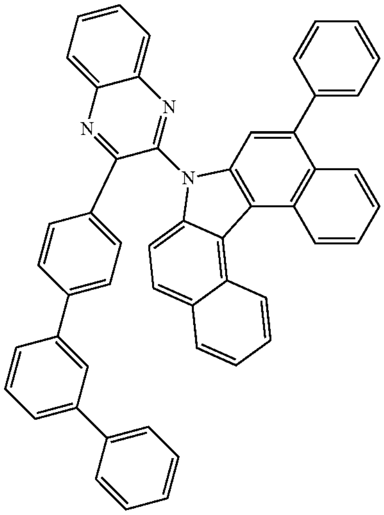
A-160
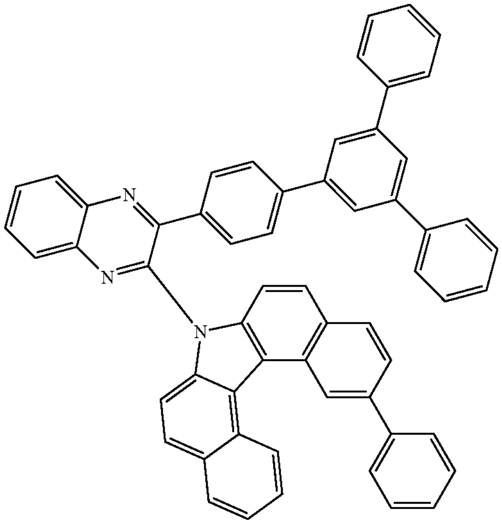
-continued
A-161
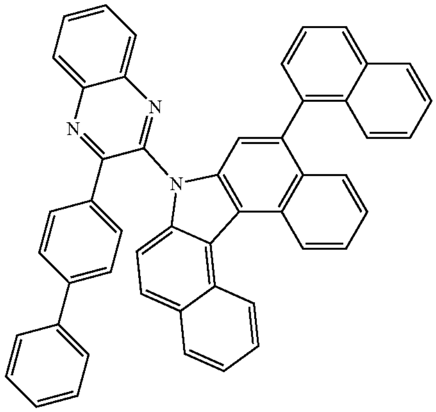
A-162
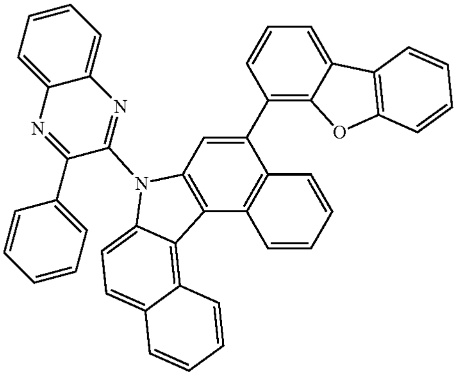
A-163
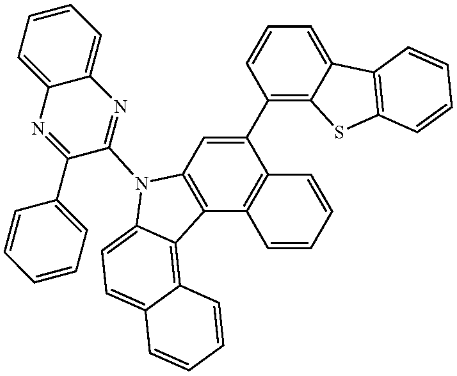
A-164
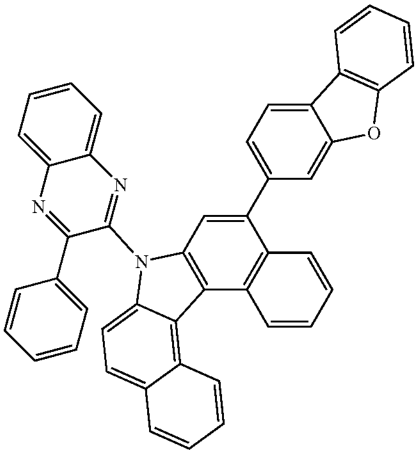

-continued
A-165
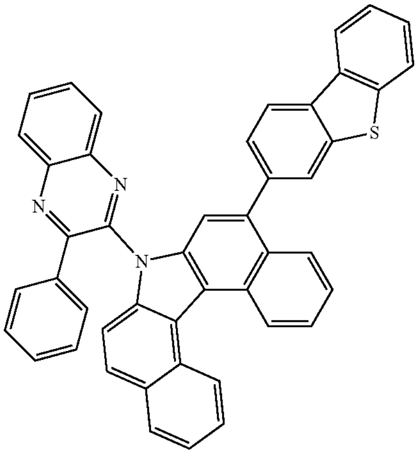
A-167
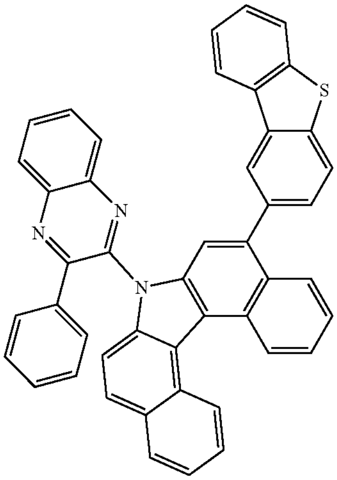
A-168
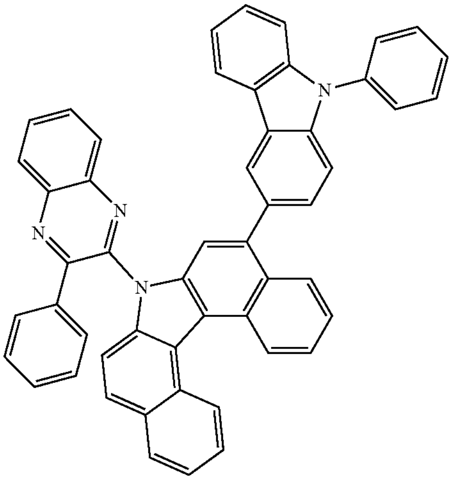
-continued
A-169
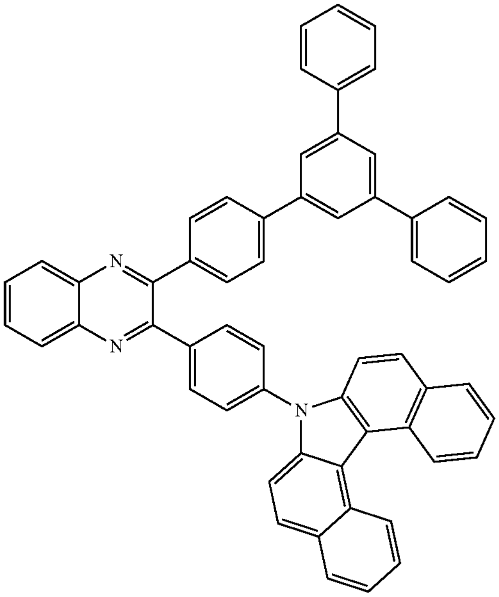
A-170
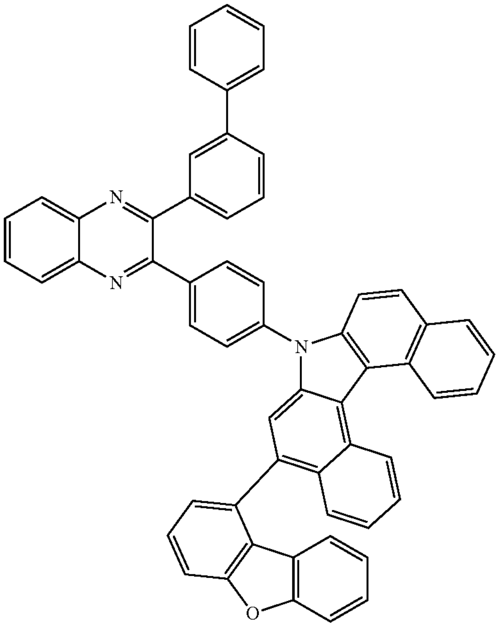

-continued
A-171
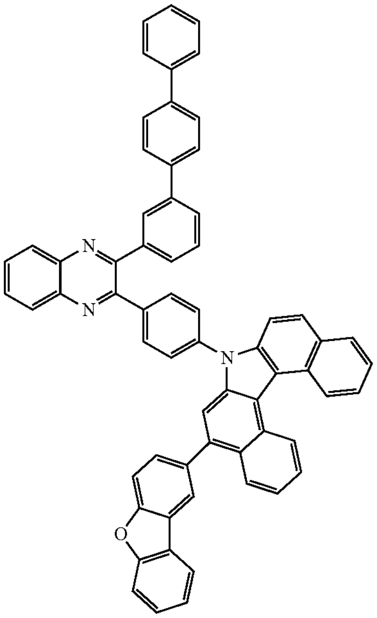
A-172
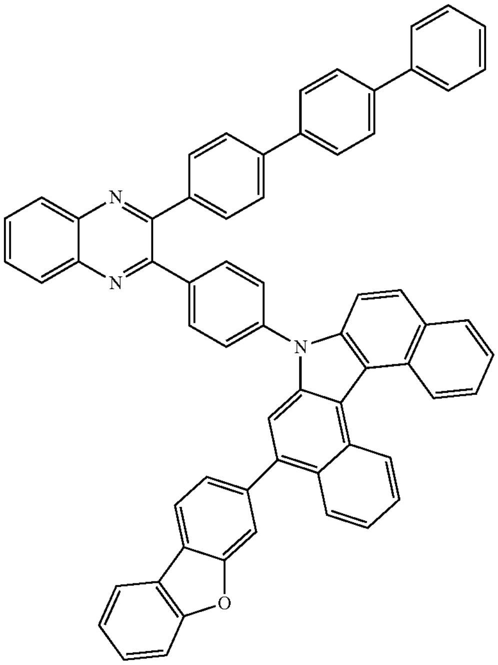
-continued
A-173
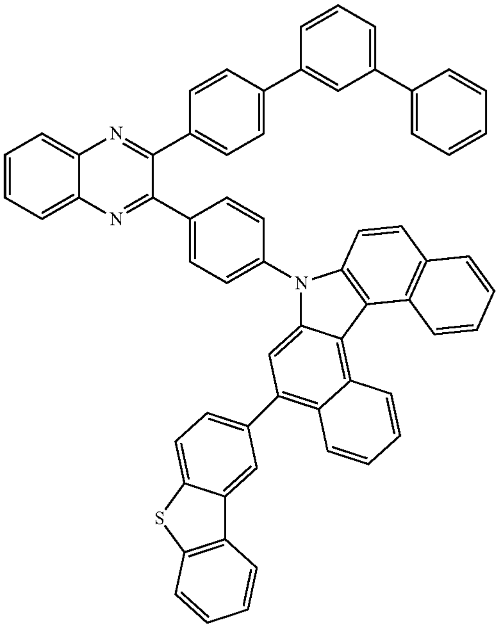
A-174
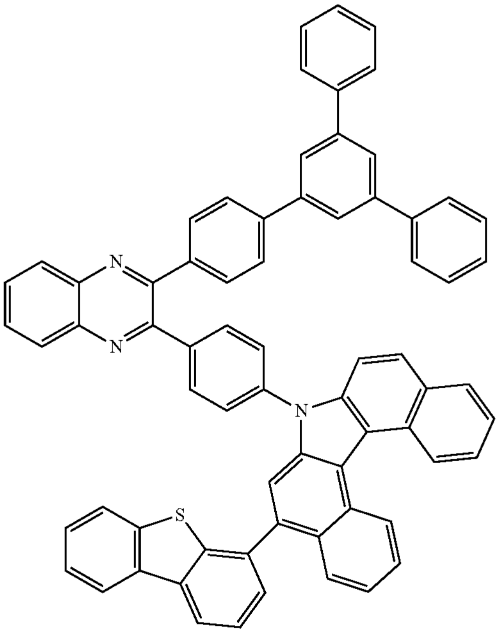

-continued
A-175
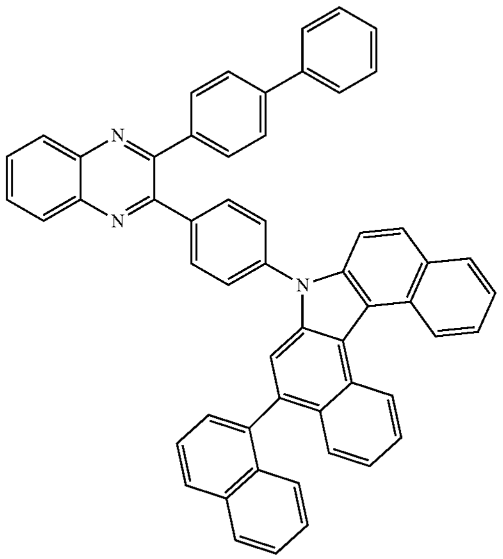
A-176
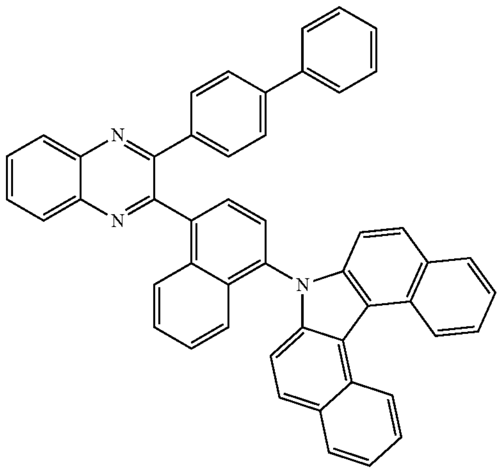
A-177
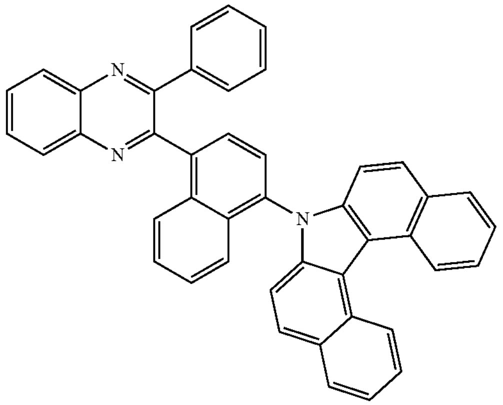
-continued
A-178
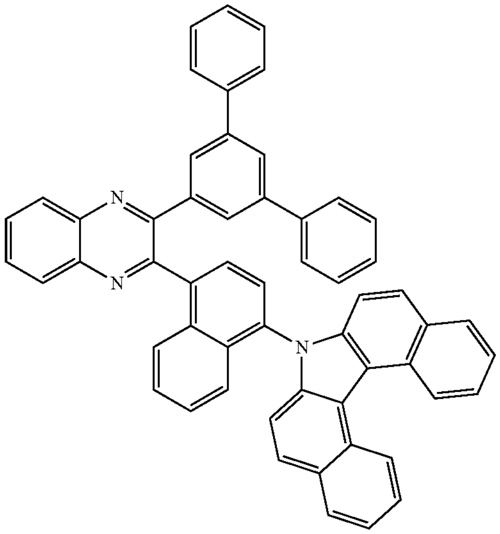
A-179
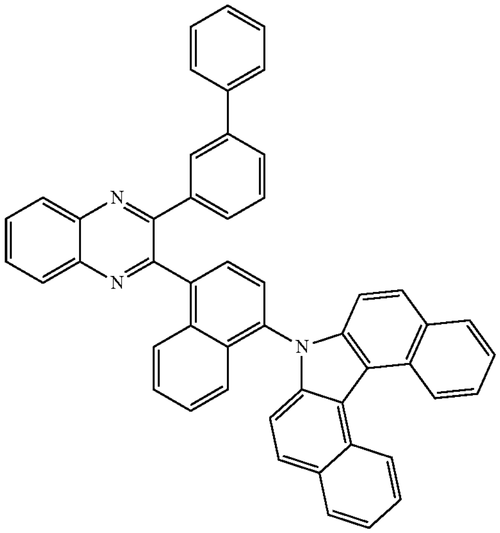

-continued
A-180
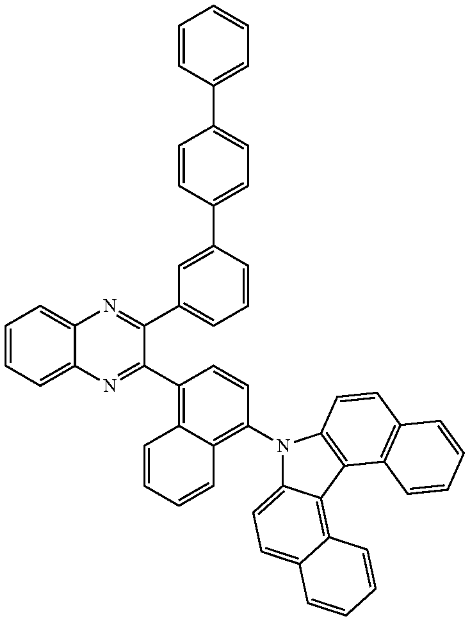
A-181
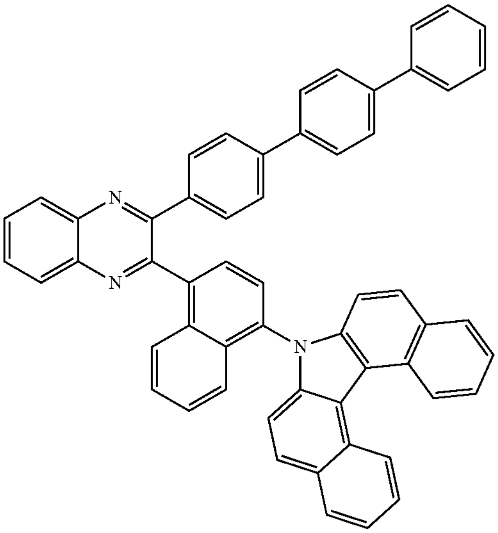
A-182
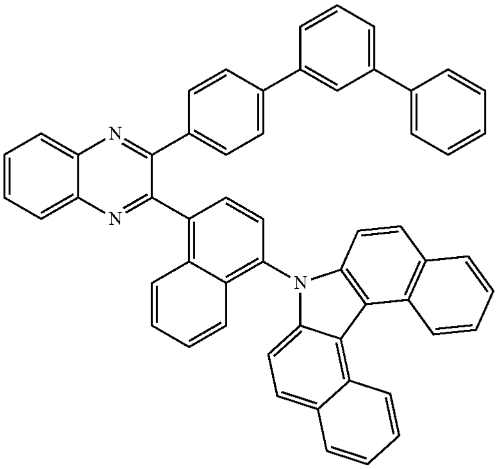
-continued
A-183
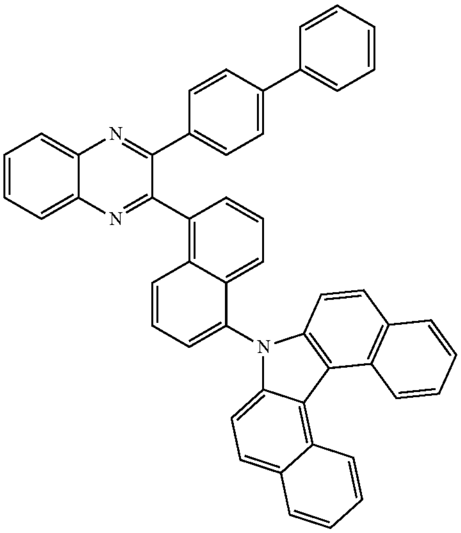
A-184
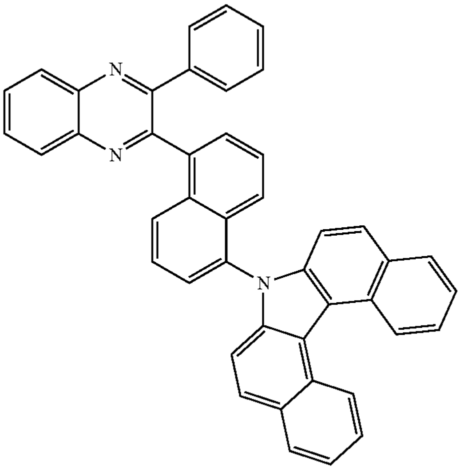
A-185
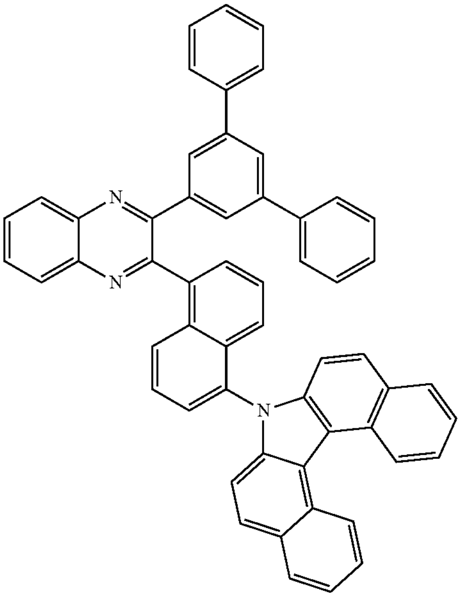

-continued
A-186
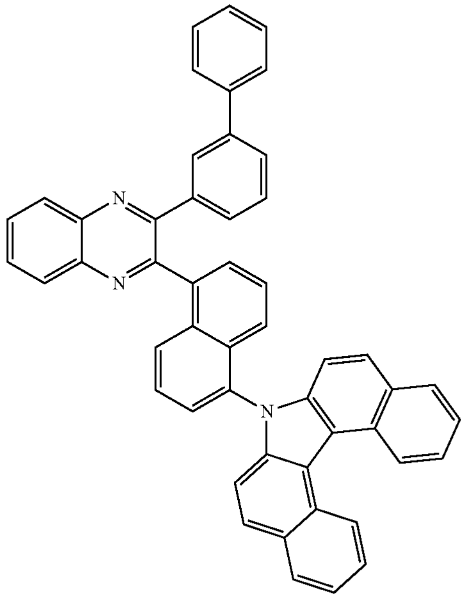
A-187
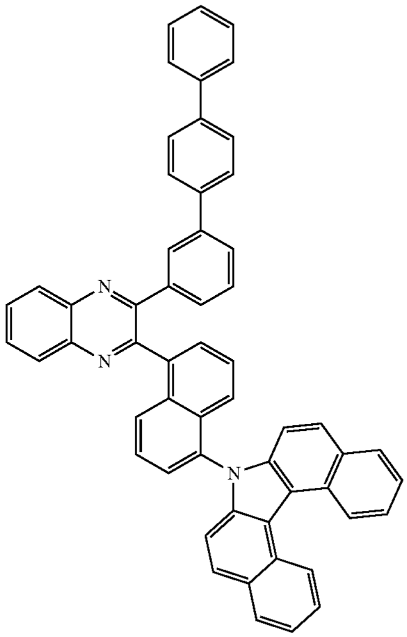
-continued
A-188
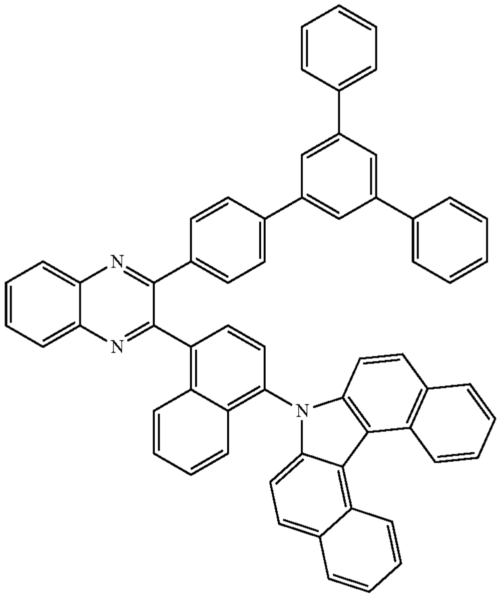
A-189
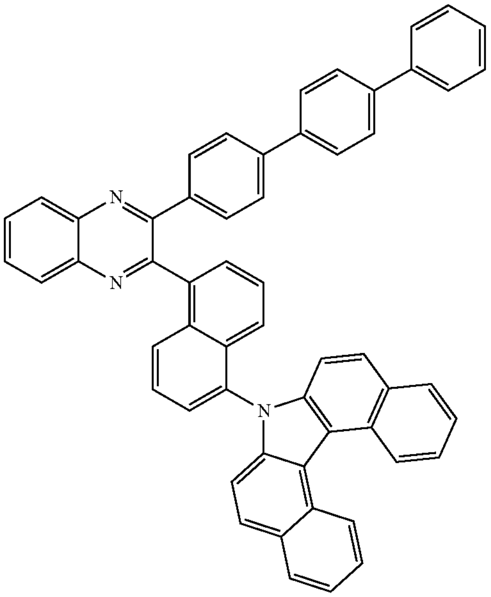

-continued
A-190
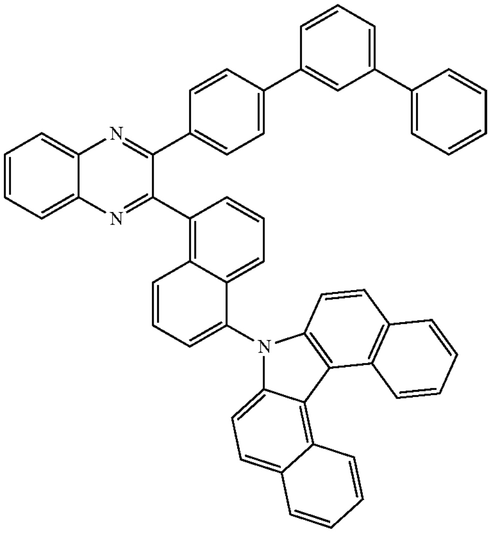
A-191
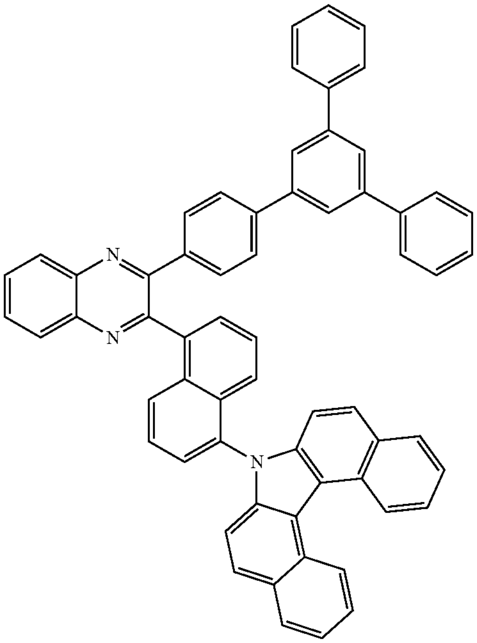
-continued
A-192
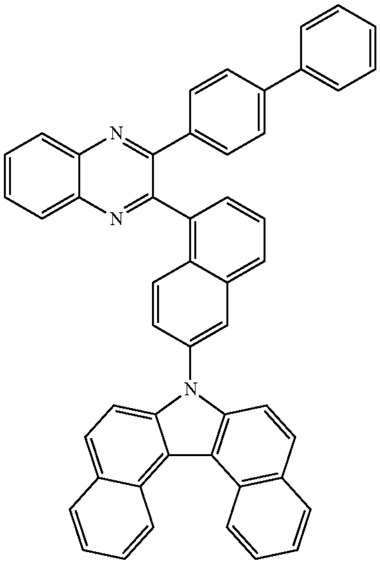
A-193
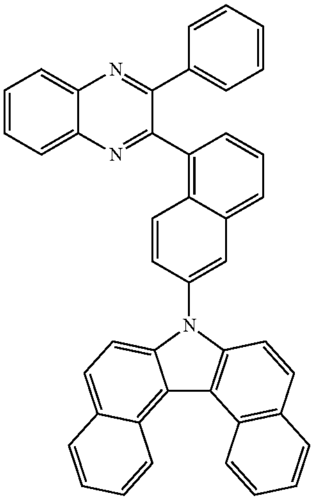

-continued
A-194
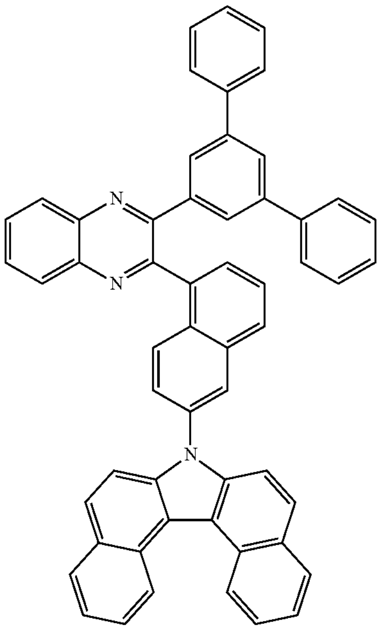
A-195
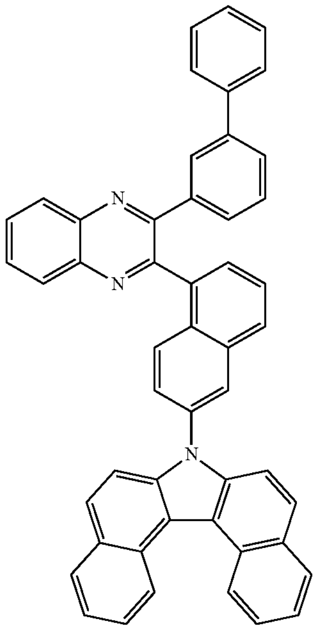
-continued
A-196
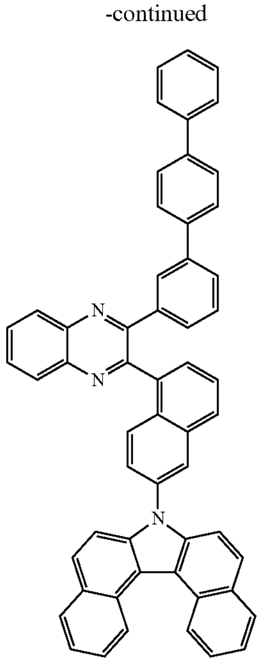
A-197
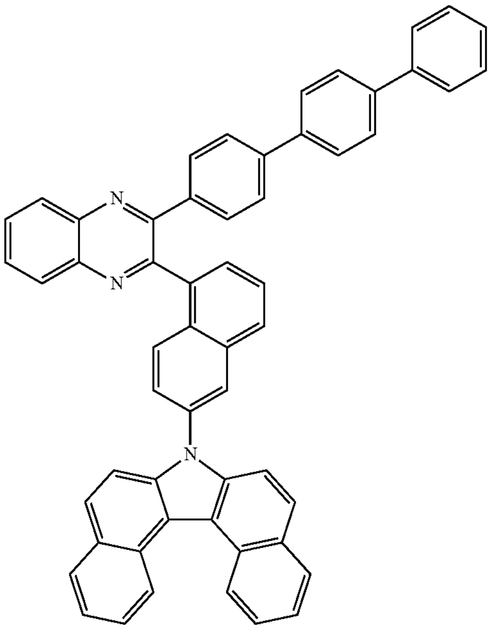

-continued
A-198
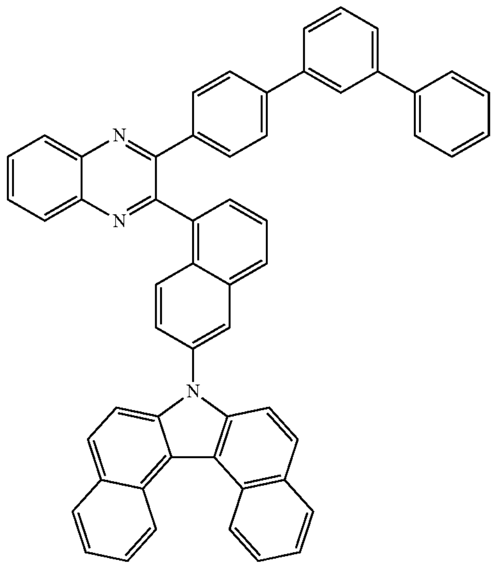
A-199
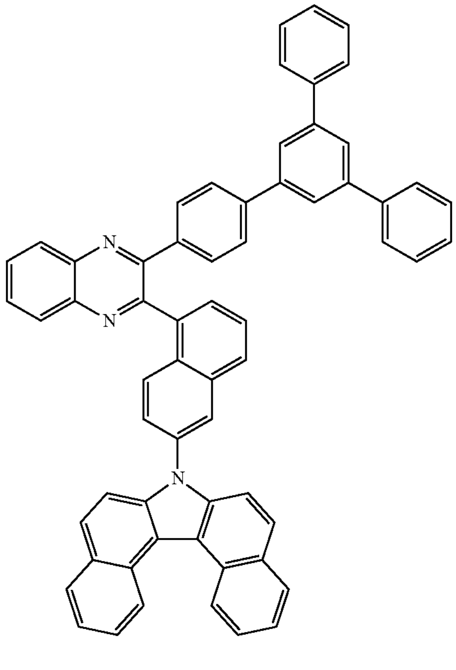
-continued
A-200
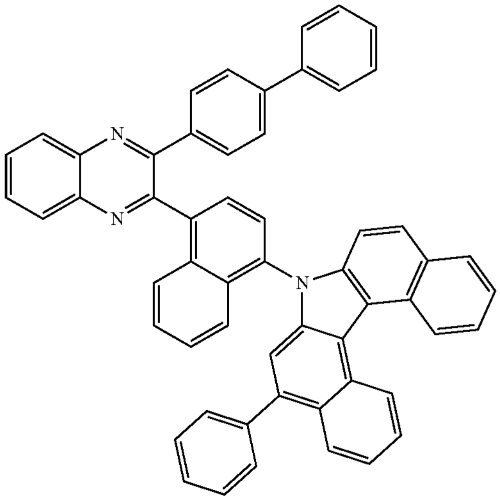
A-201
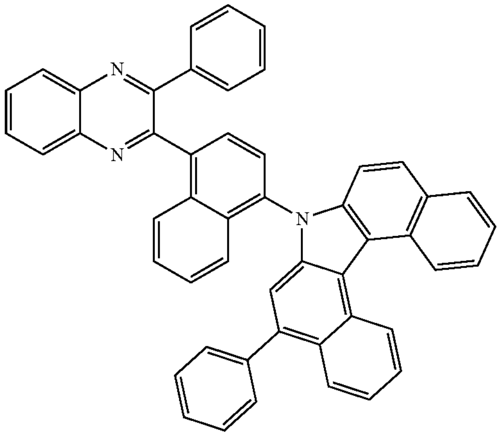
A-202
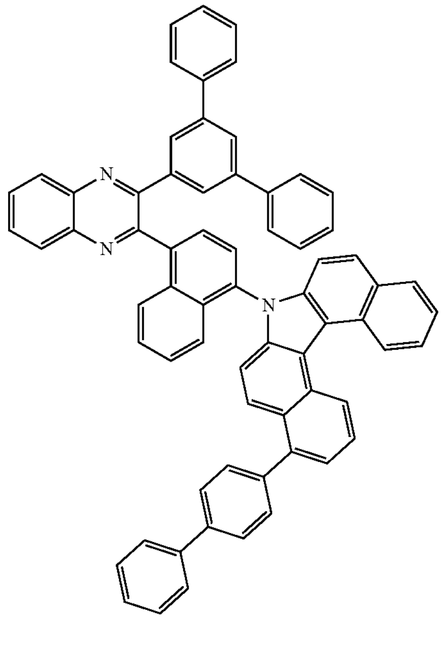

-continued
A-203
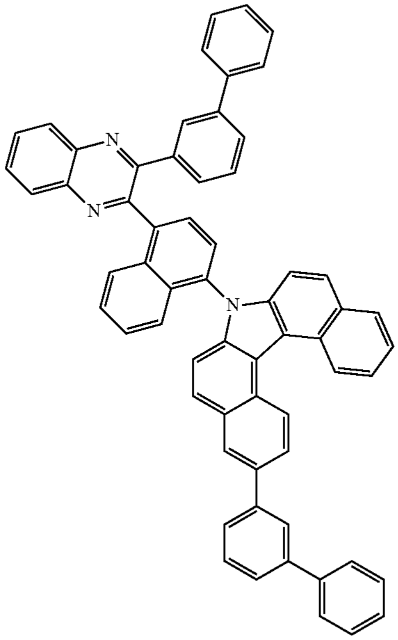
-continued
A-205
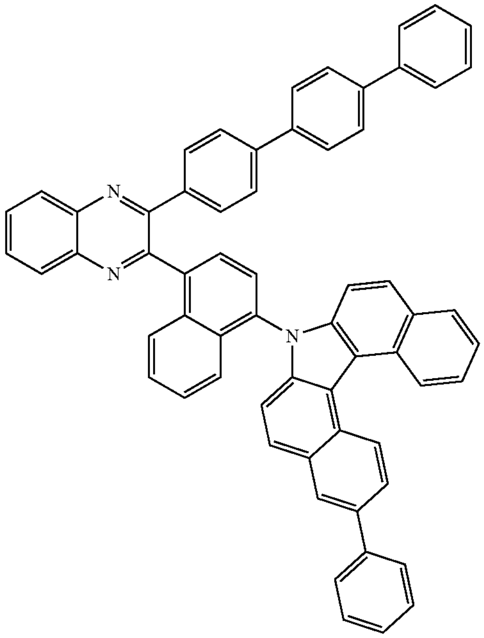
A-204
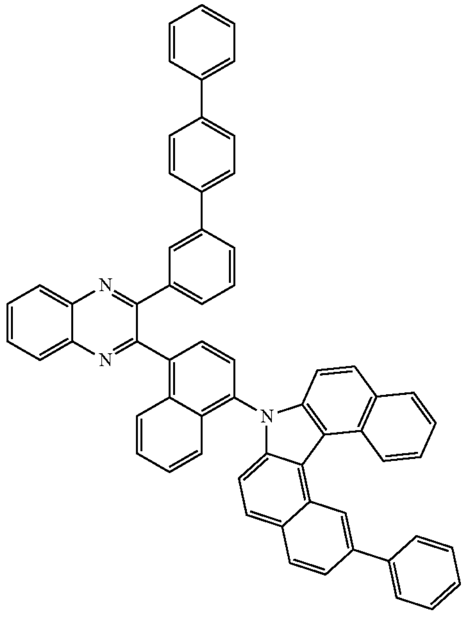
A-206
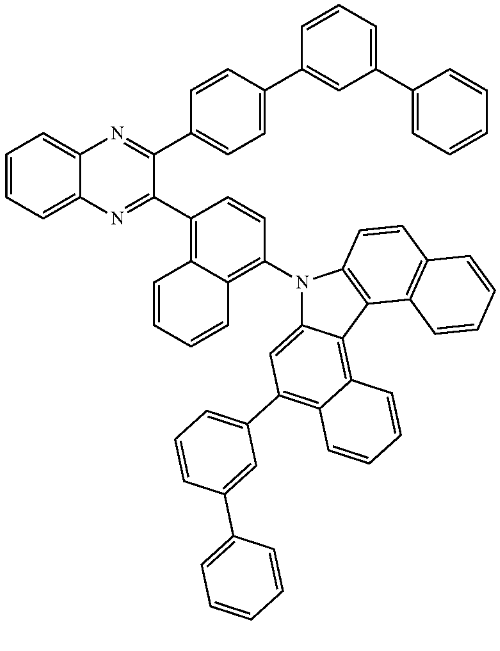

-continued
A-207
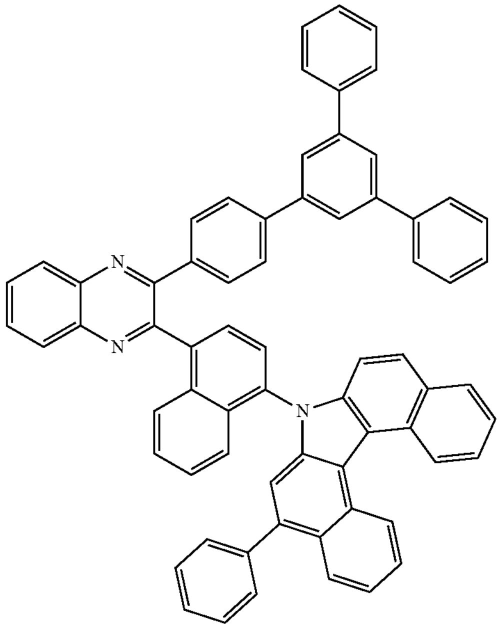
A-208
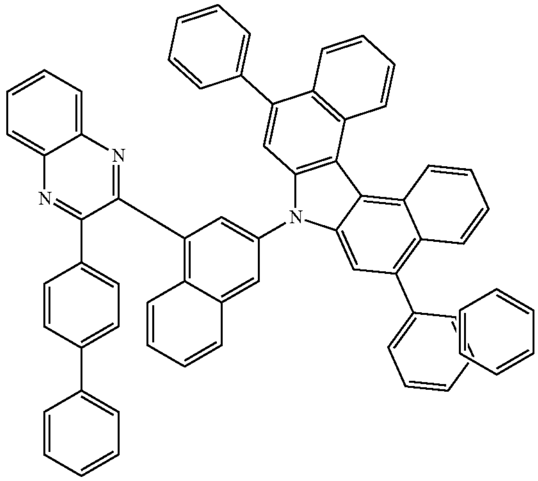
-continued
A-209
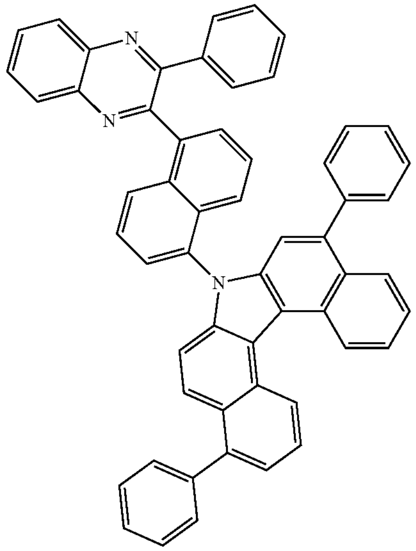
A-210
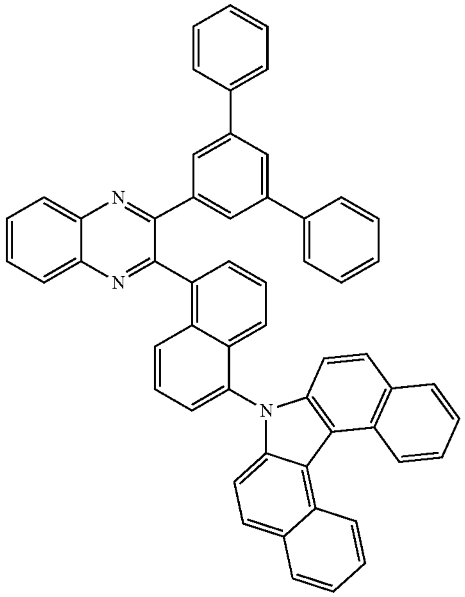

-continued
A-211
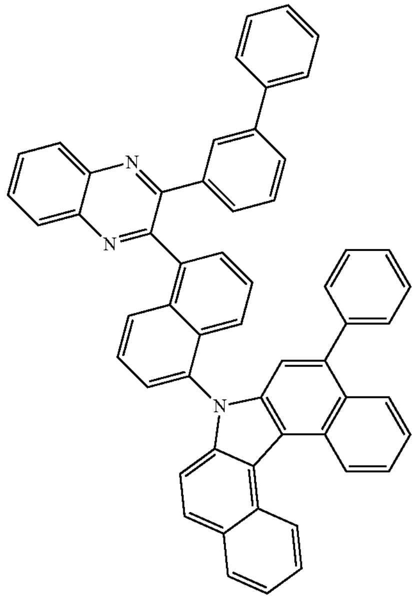
A-212
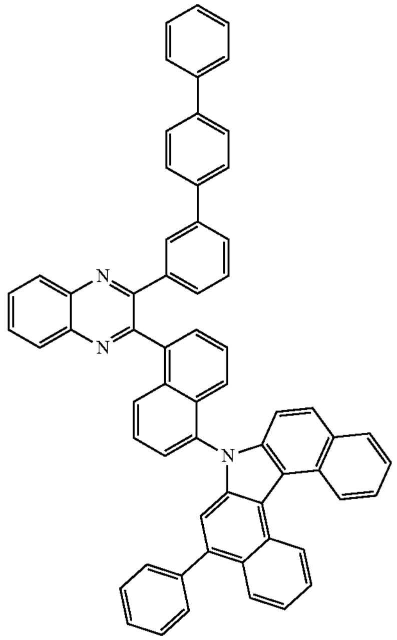
-continued
A-213
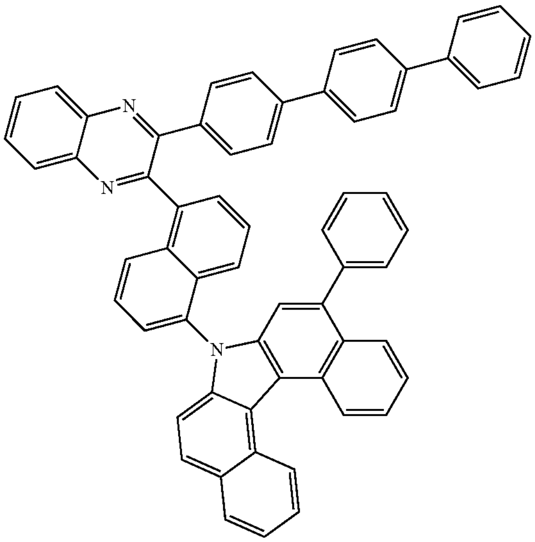
A-214
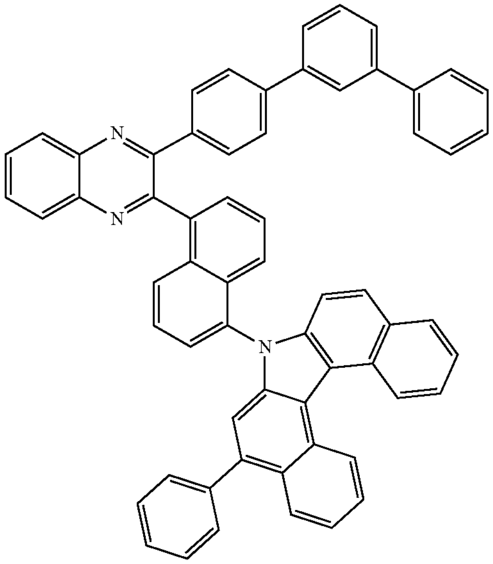

-continued
A-215
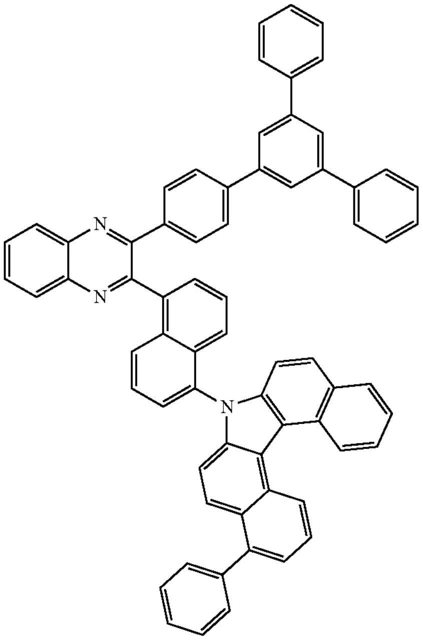
A-216
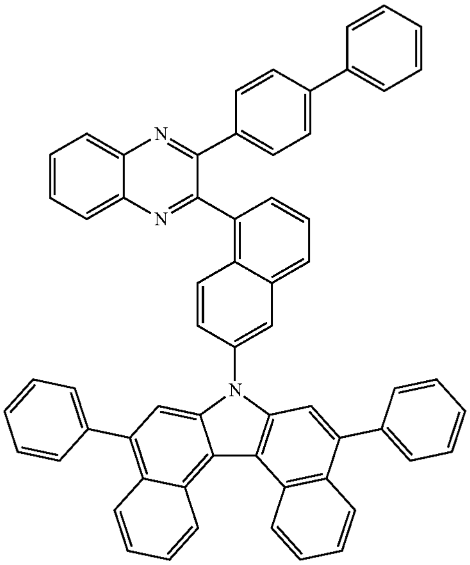
-continued
A-217
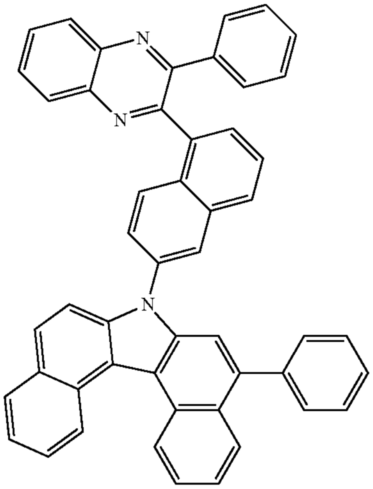
A-218
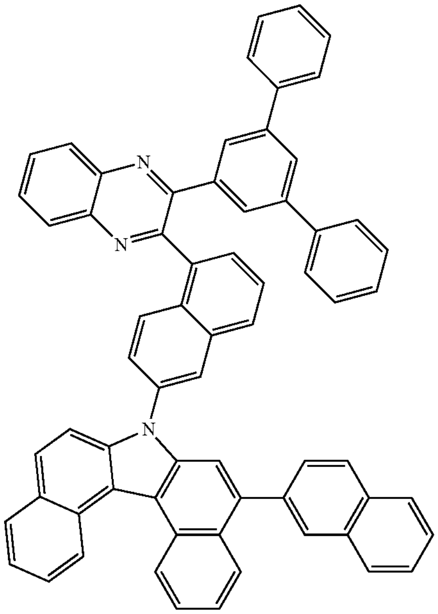

-continued
A-219
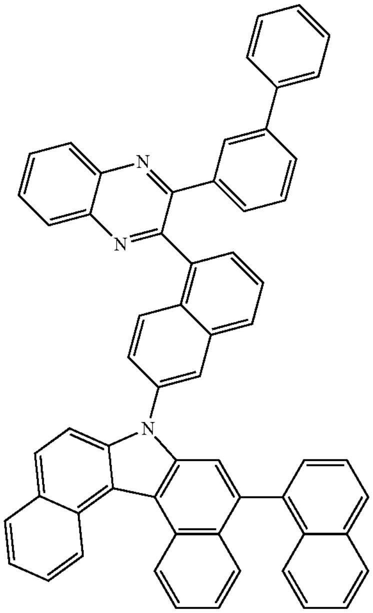
A-220
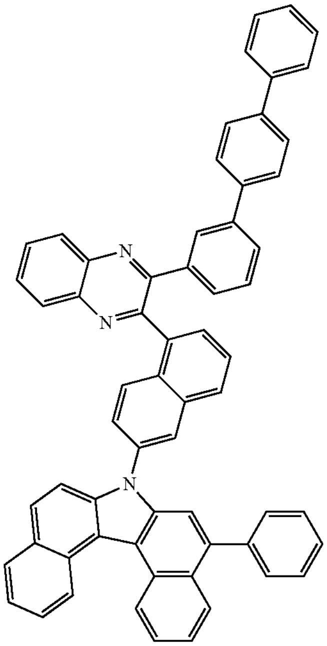
-continued
A-221
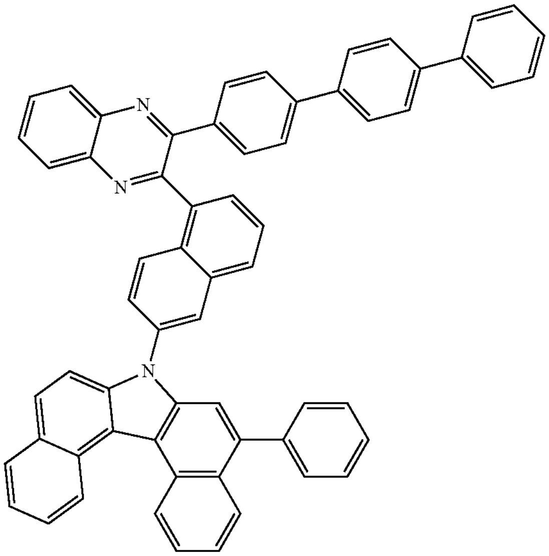
A-222
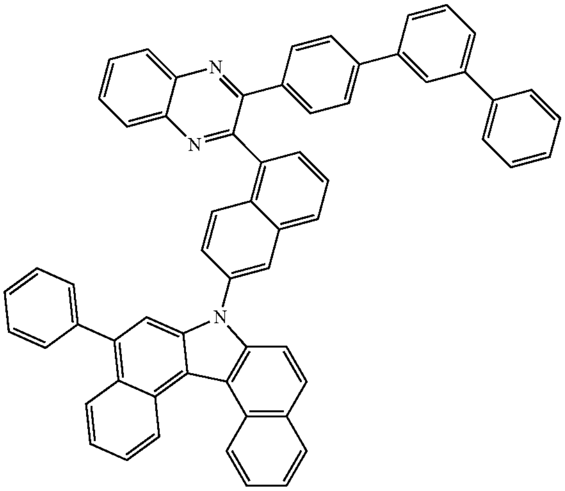
A-223
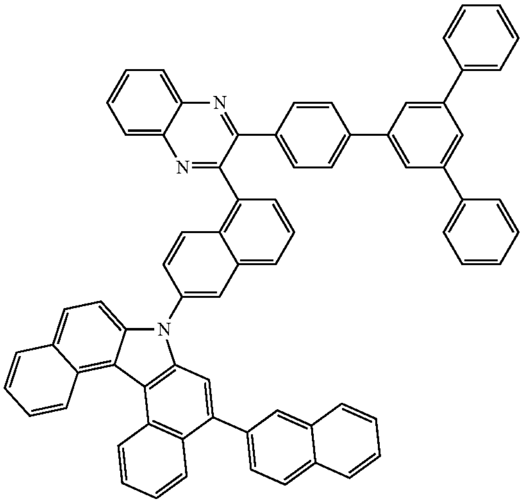

-continued
A-224
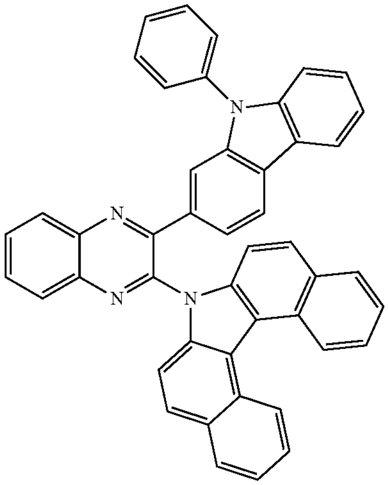
A-225
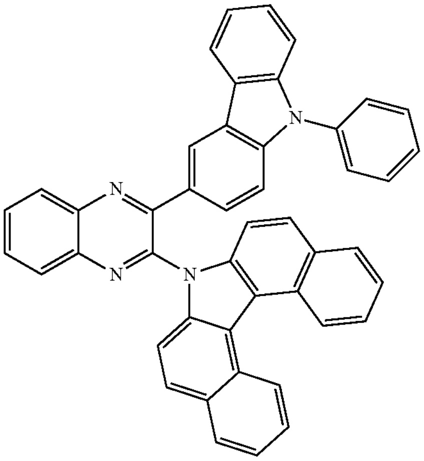
A-226
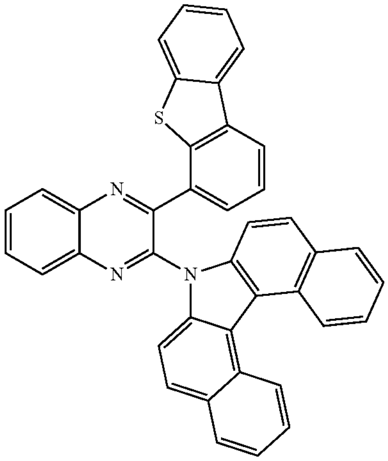
-continued
A-227
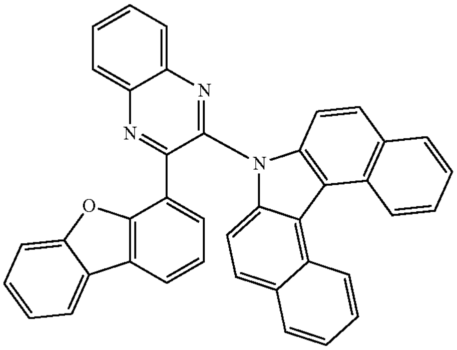
A-228
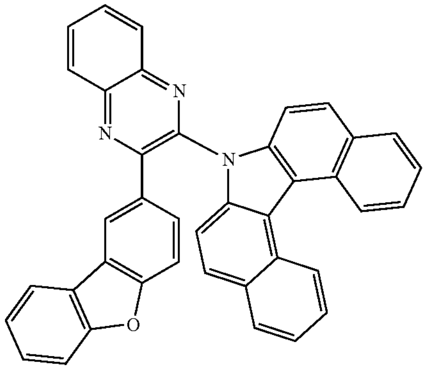
A-229
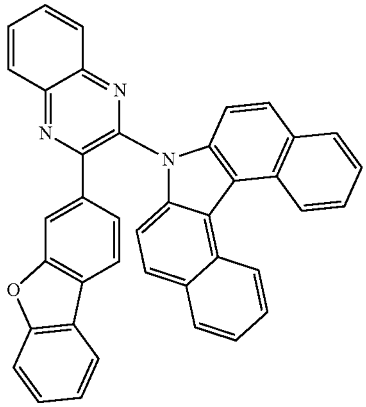
A-230
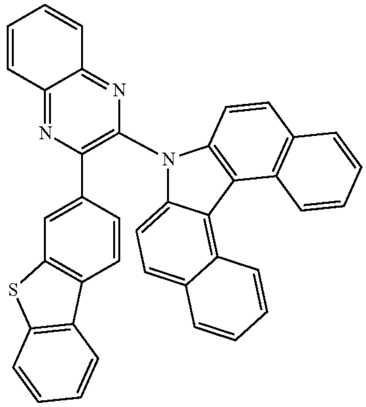

-continued
A-231
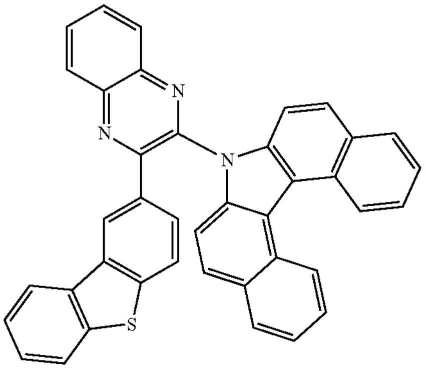
A-232
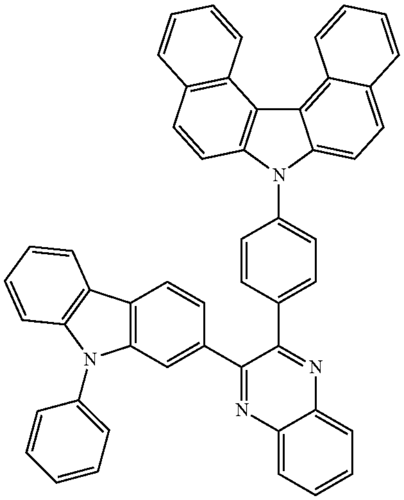
A-233
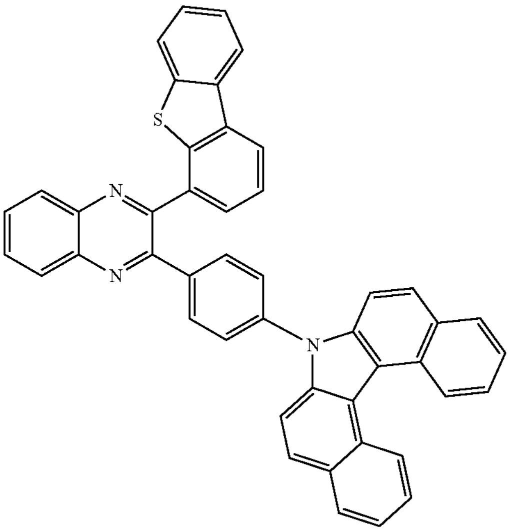
-continued
A-234
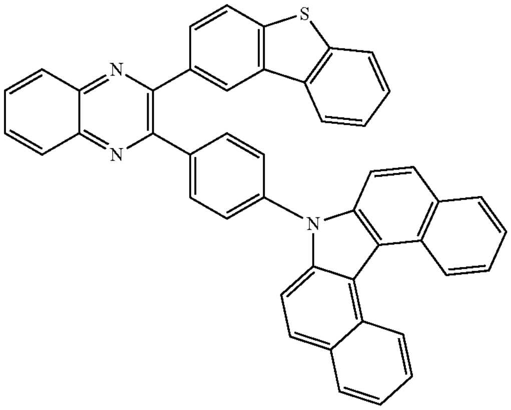
A-235
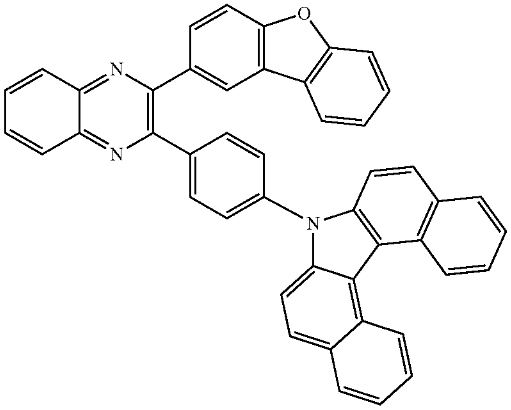
A-236
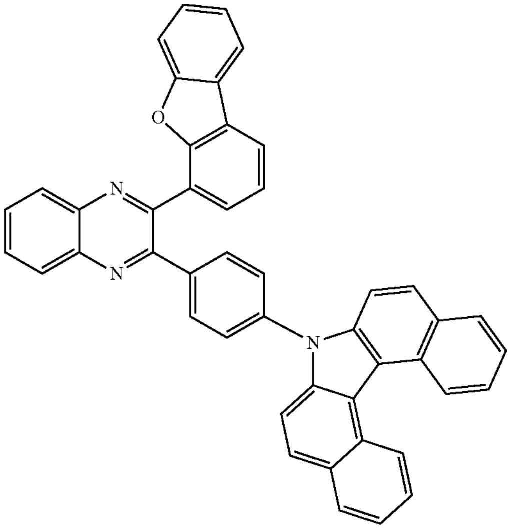

-continued
A-237
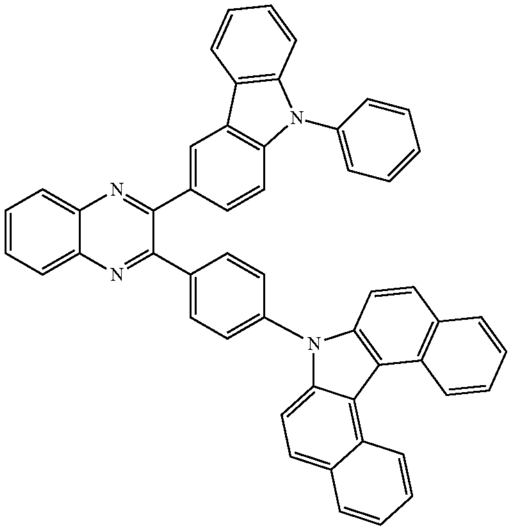
A-238
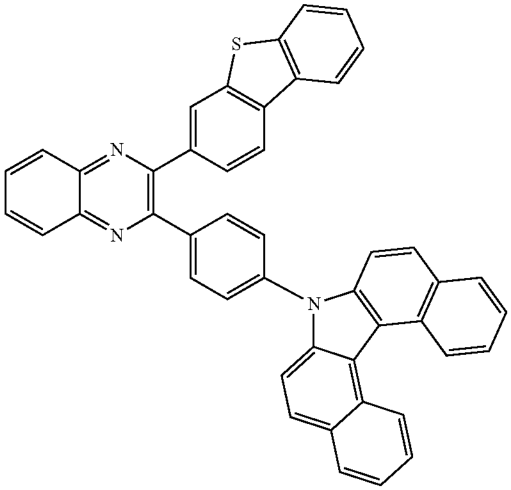
A-239
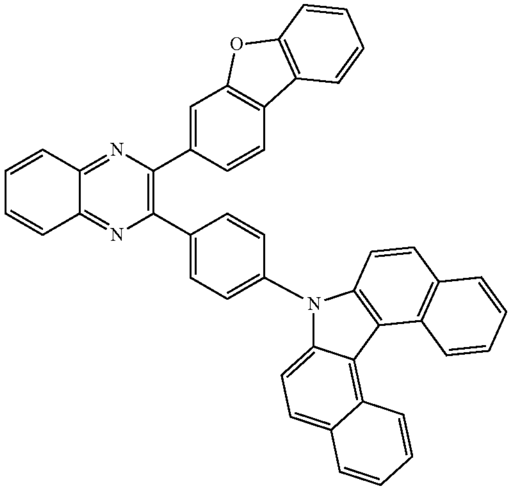
-continued
A-240
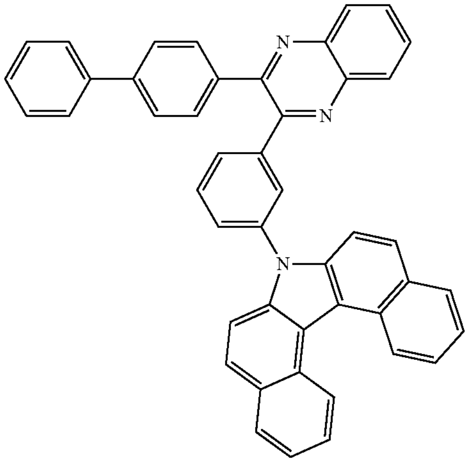
A-241
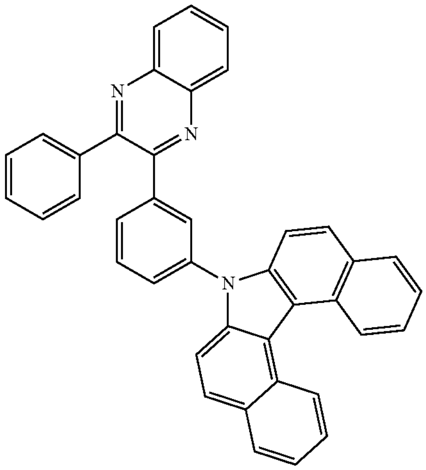
A-242
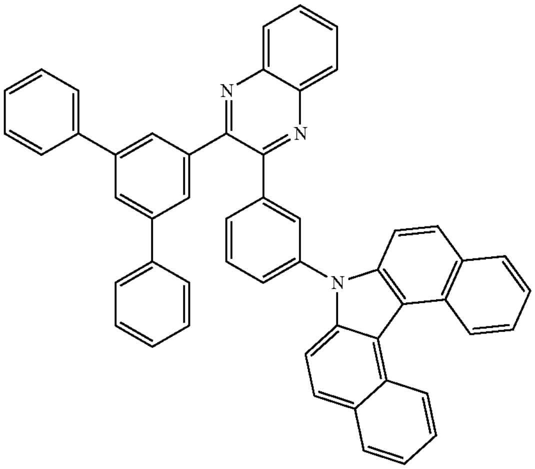

-continued
A-243
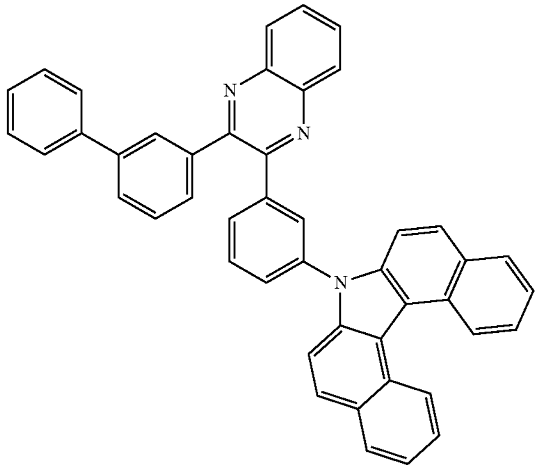
A-244
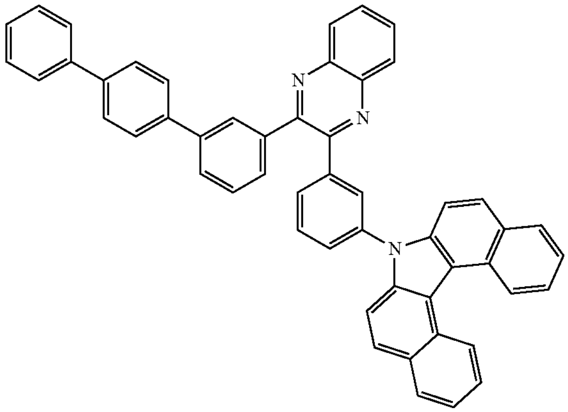
A-245
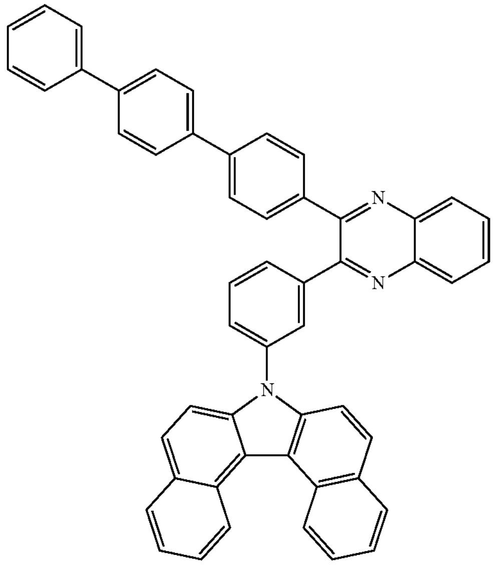
-continued
A-246
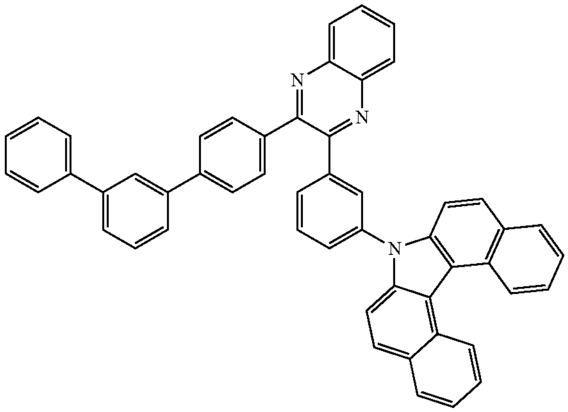
A-247
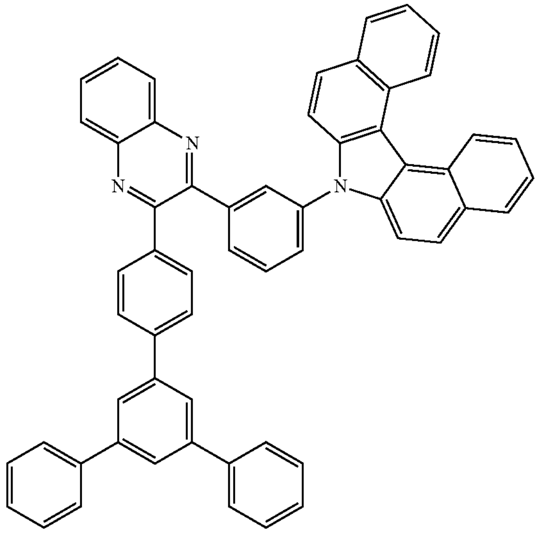
A-248
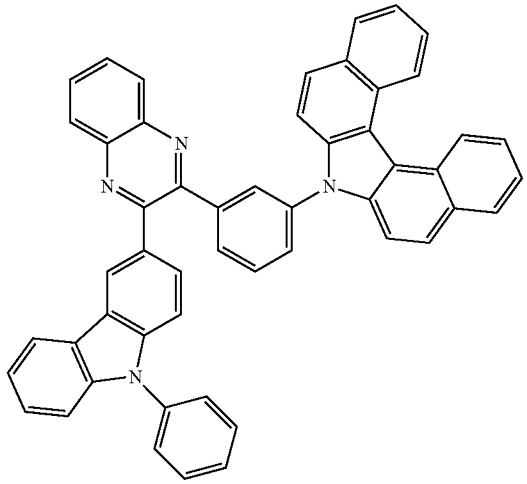

-continued
A-249
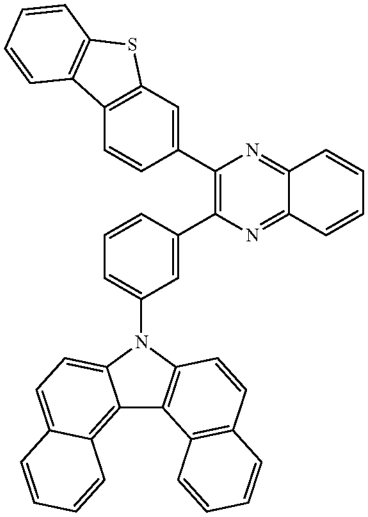
A-250
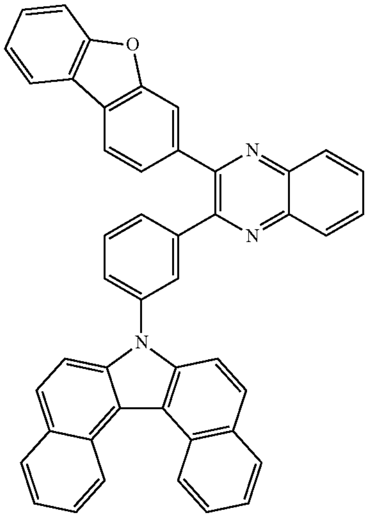
A-251
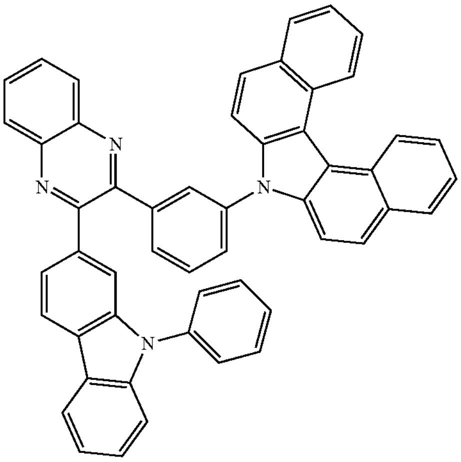
-continued
A-252
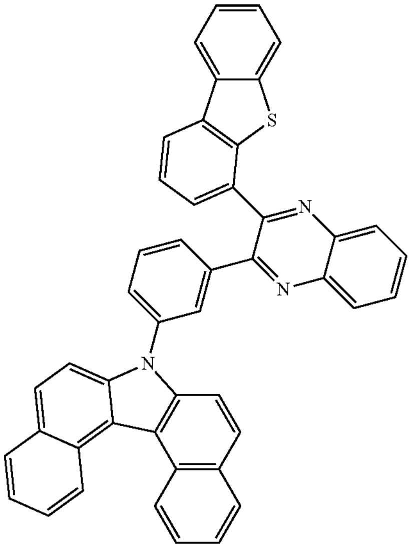
A-253
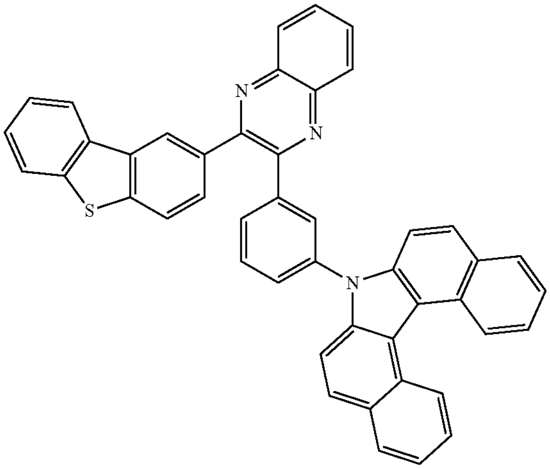
A-254
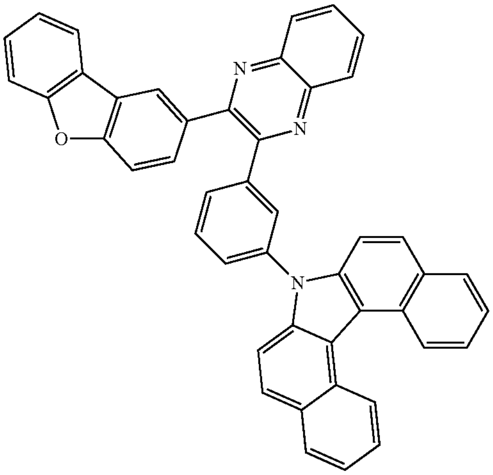

-continued
A-255
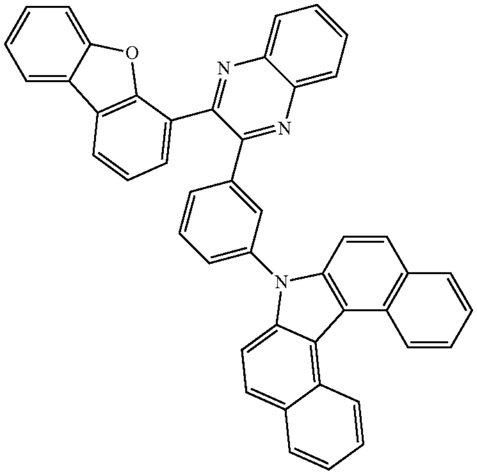
A-256
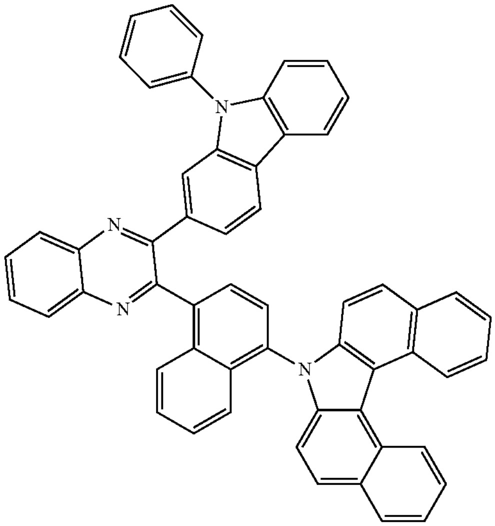
A-257
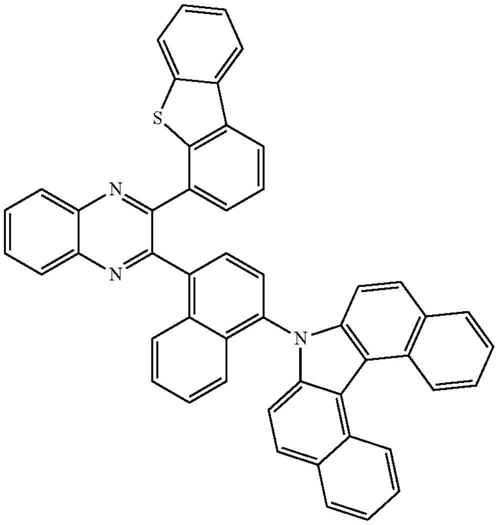
-continued
A-258
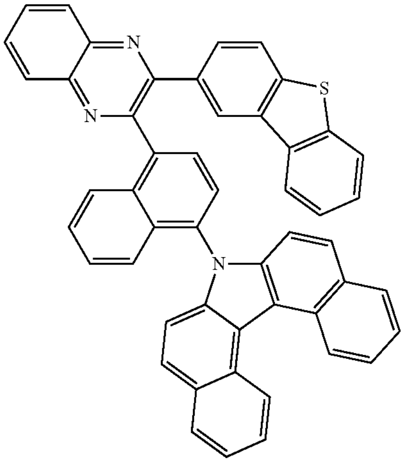
A-259
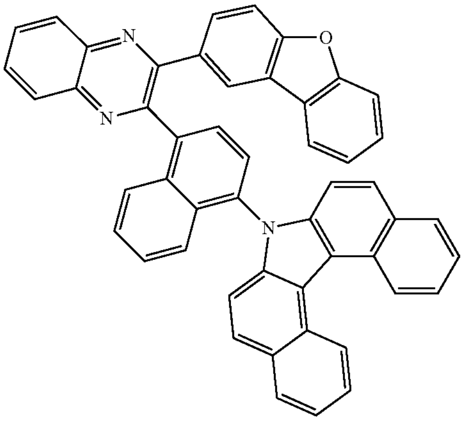
A-260
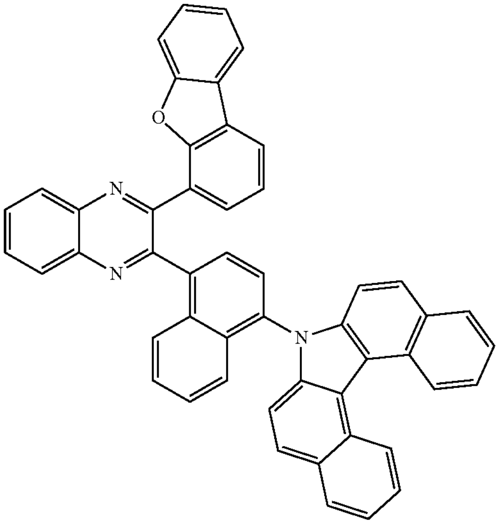

-continued
A-261
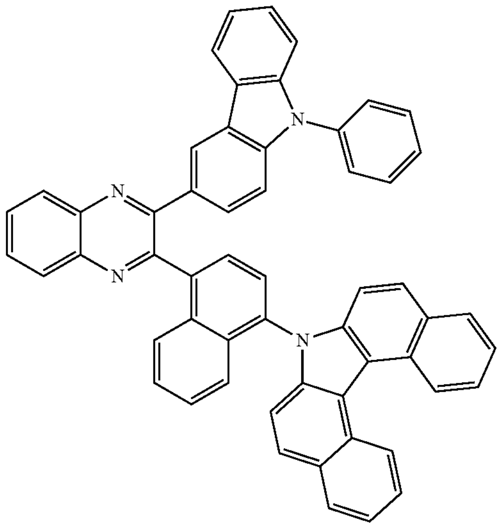
A-262
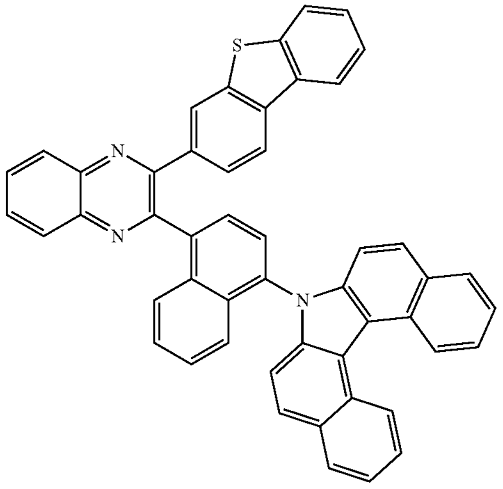
A-263
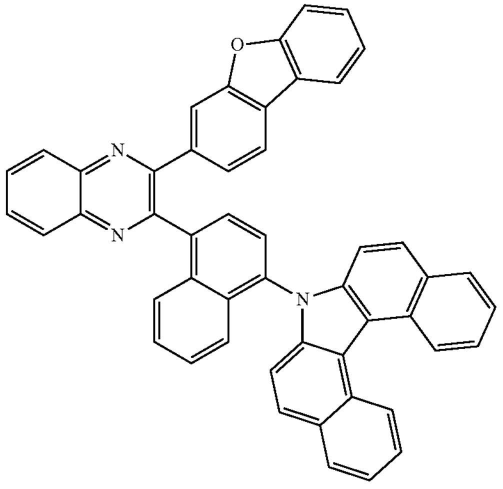
-continued
A-264
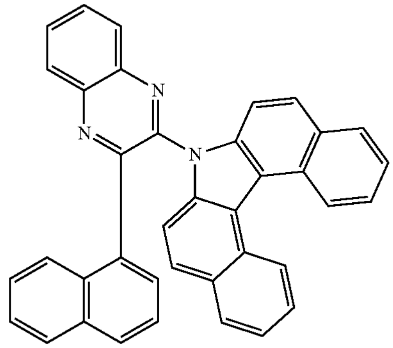
A-265
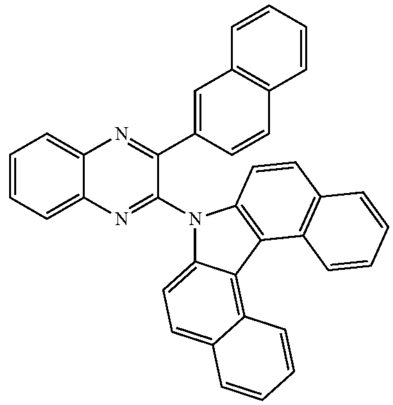
A-266
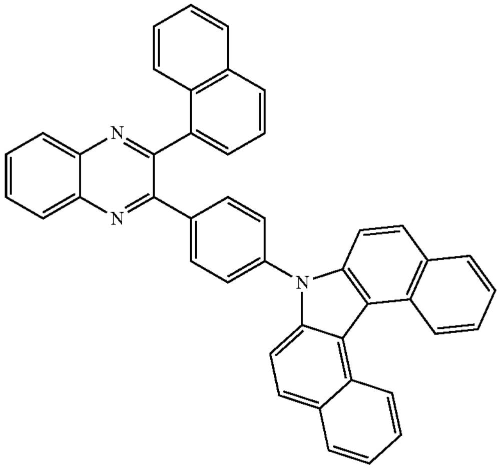

-continued
A-267
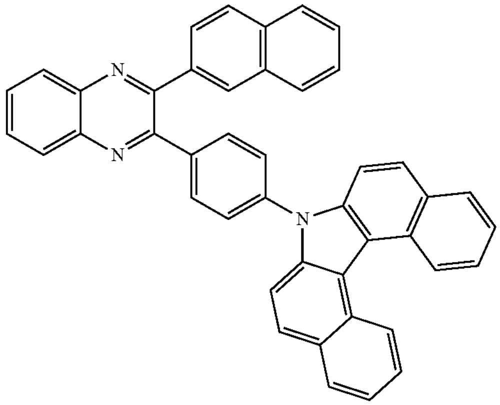
A-268
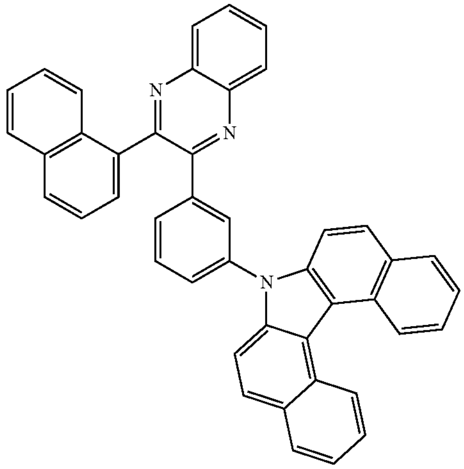
A-269
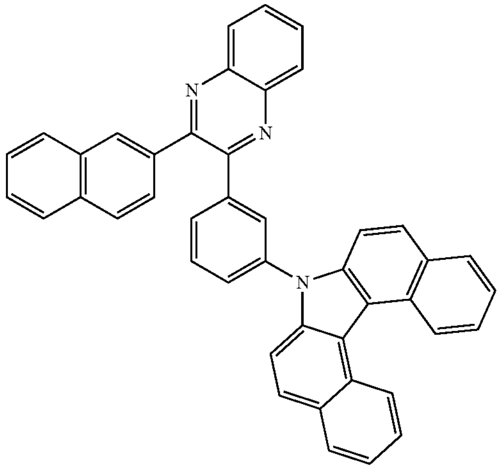
-continued
A-270
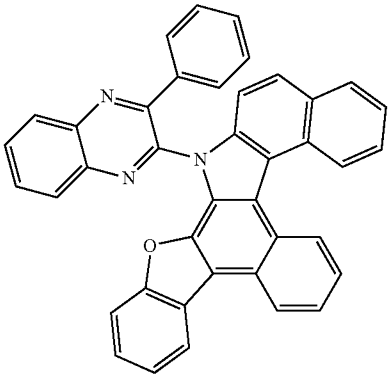
A-271
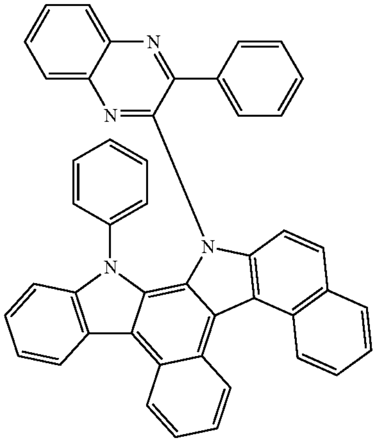
A-272
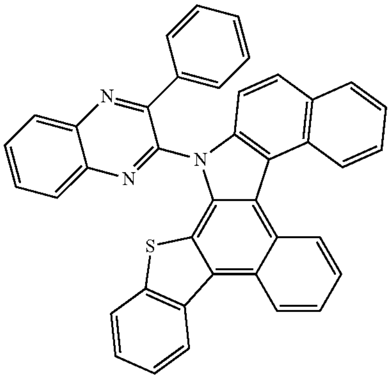
A-273
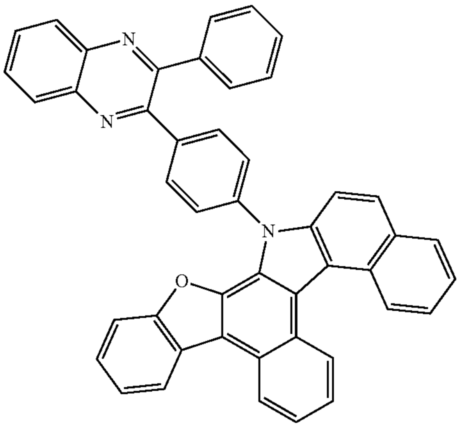

-continued
A-274
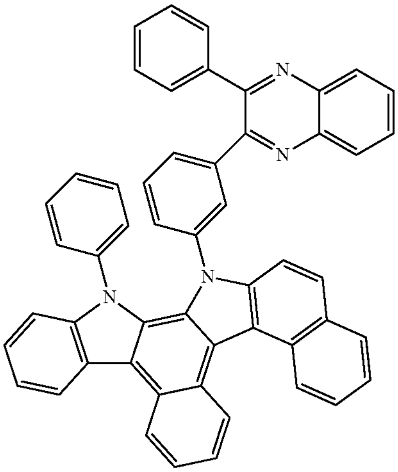
A-275
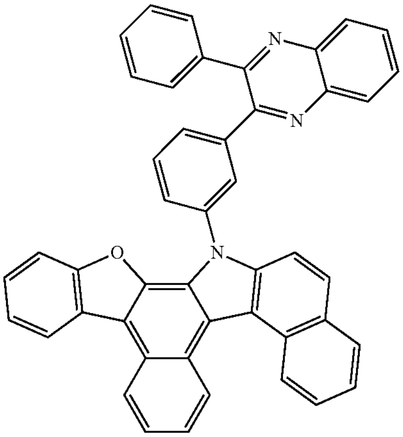
A-276
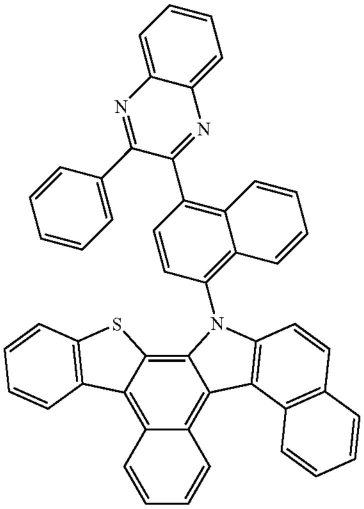
-continued
A-277
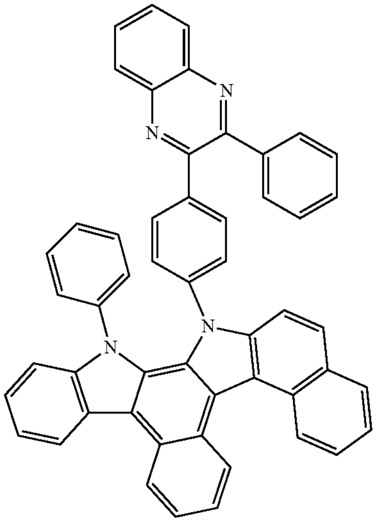
A-278
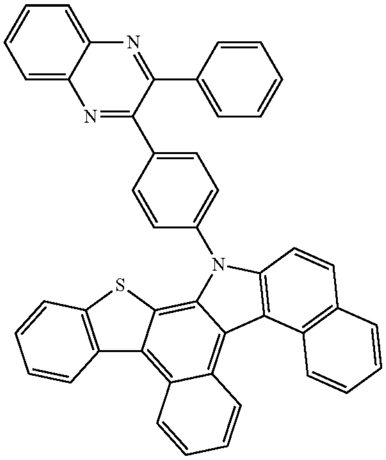
A-279
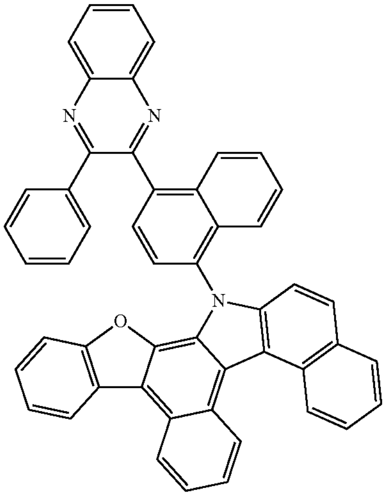

-continued
A-280
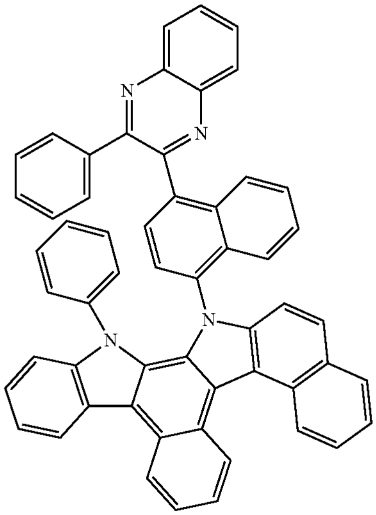
A-281
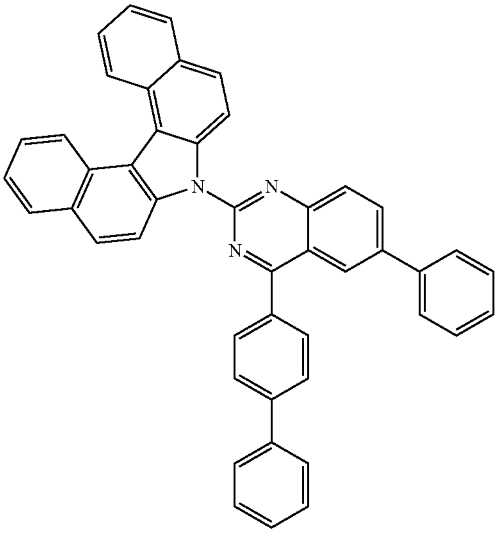
A-282
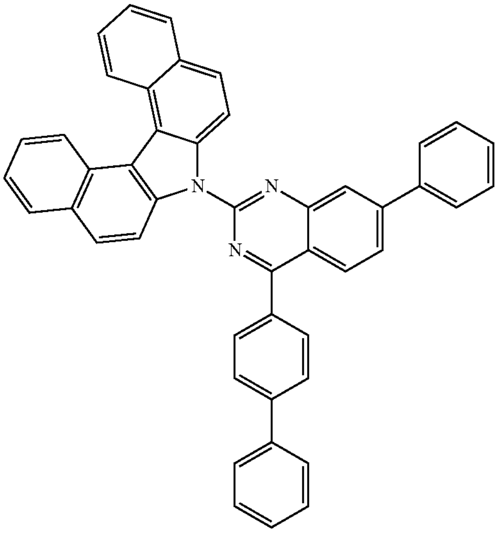
-continued
A-283
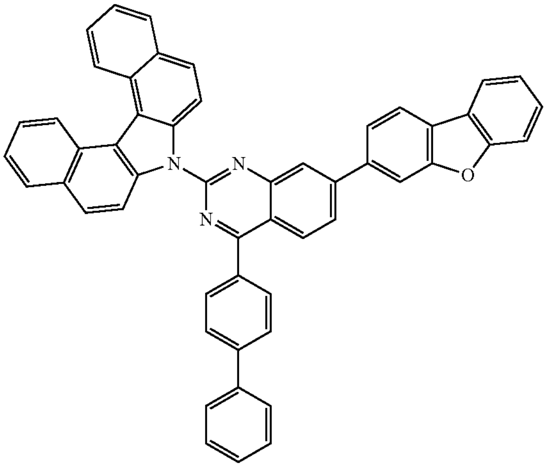
A-284
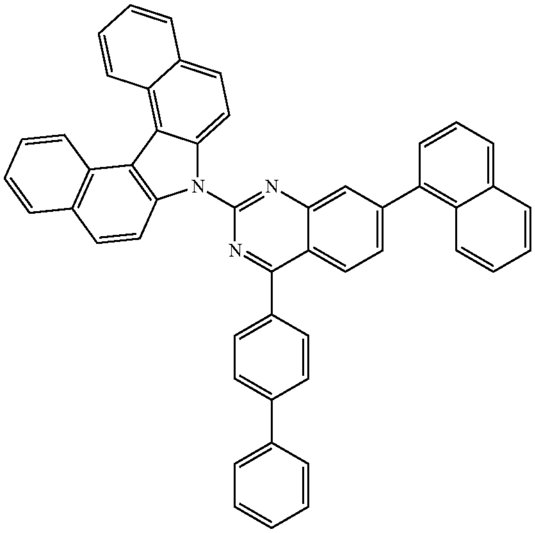
A-285
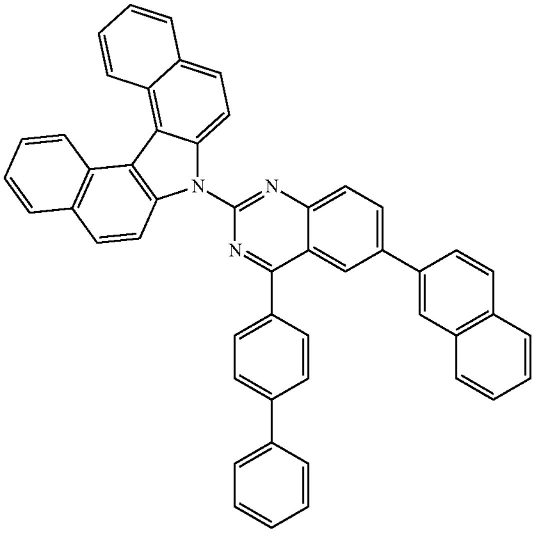

-continued
A-286
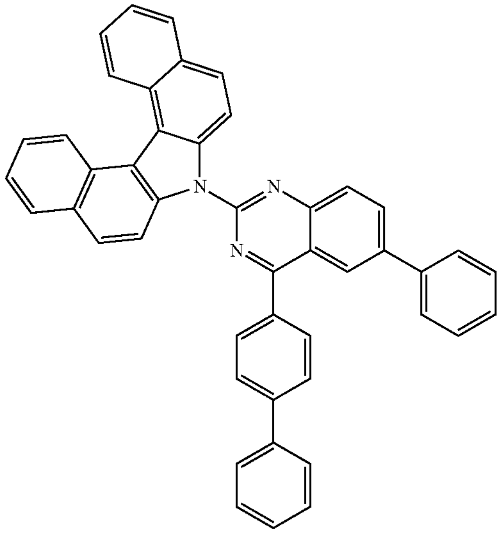
and
-continued
A-287
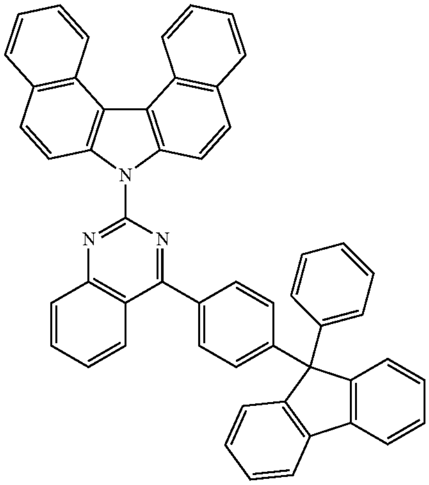
.
* * * * *